US012459922B2

(12) United States Patent
Chandrasekhar et al.

(10) Patent No.: US 12,459,922 B2
(45) Date of Patent: Nov. 4, 2025

(54) PARP7 INHIBITORS

(71) Applicant: Gilead Sciences, Inc., Foster City, CA (US)

(72) Inventors: Jayaraman Chandrasekhar, Redmond, WA (US); Jonah J. Chang, Woodinville, WA (US); Kevin S. Currie, North Bend, WA (US); Stephen D. Holmbo, Kirkland, WA (US); Jesse M. Jacobsen, Seattle, WA (US); David L Kukla, Newcastle, WA (US); Seung H. Lee, Sammamish, WA (US); Yasamin Moazami, Seattle, WA (US); Leena B. Patel, Seattle, WA (US); Thomas J. Paul, Snohomish, WA (US); Stephane Perreault, Brier, WA (US); Patrick J. Salvo, Burien, WA (US); Jennifer A. Treiberg, Redmond, WA (US); Heath A. Weaver, Seattle, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 18/160,082

(22) Filed: Jan. 26, 2023

(65) Prior Publication Data

US 2023/0365529 A1 Nov. 16, 2023

Related U.S. Application Data

(60) Provisional application No. 63/385,303, filed on Nov. 29, 2022, provisional application No. 63/378,647, filed on Oct. 6, 2022, provisional application No. 63/304,093, filed on Jan. 28, 2022.

(51) Int. Cl.

| | |
|---|---|
| ***C07D 401/14*** | (2006.01) |
| ***C07D 405/14*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |
| ***C07D 491/107*** | (2006.01) |
| ***C07D 495/04*** | (2006.01) |
| ***C07D 498/04*** | (2006.01) |

(52) U.S. Cl.

CPC ......... *C07D 401/14* (2013.01); *C07D 405/14* (2013.01); *C07D 413/14* (2013.01); *C07D 417/14* (2013.01); *C07D 471/04* (2013.01); *C07D 487/04* (2013.01); *C07D 491/107* (2013.01); *C07D 495/04* (2013.01); *C07D 498/04* (2013.01)

(58) Field of Classification Search

CPC .. C07D 401/14; C07D 405/14; C07D 413/14; C07D 417/14; C07D 471/04; C07D 487/04; C07D 491/107; C07D 495/04; C07D 498/04

See application file for complete search history.

(56) References Cited

U.S. PATENT DOCUMENTS

2020/0123134 A1* 4/2020 Vasbinder ............ C07D 403/14

FOREIGN PATENT DOCUMENTS

| | | |
|---|---|---|
| JP | 2021-523186 | 9/2021 |
| WO | WO 2019/055966 A2 | 3/2019 |
| WO | WO 2019/212937 A1 | 11/2019 |
| WO | WO 2020/223229 A1 | 11/2020 |
| WO | WO-2021/018948 A1 | 2/2021 |
| WO | WO 2021/087018 A1 | 5/2021 |
| WO | WO 2021/087025 A1 | 5/2021 |
| WO | WO 2022/156708 A1 | 7/2022 |
| WO | WO 2023/001296 A1 | 1/2023 |
| WO | WO 2023/076983 A1 | 5/2023 |

(Continued)

OTHER PUBLICATIONS

Curtin N. et al. (2020) "Poly(ADP-ribose) polymerase inhibition: past, present and future", Nature Reviews Drug Discovery 19(10): 711-736.

(Continued)

*Primary Examiner* — Clinton A Brooks

*Assistant Examiner* — Josmalen M. Ramos-Lewis

(74) *Attorney, Agent, or Firm* — Sheppard Mullin Richter & Hampton LLP

(57) ABSTRACT

Provided herein is a compound of Formula I:

(I)

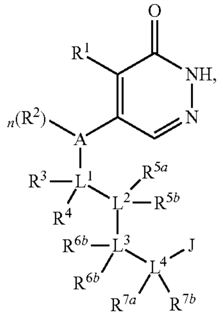

or a pharmaceutically acceptable salt, stereoisomer, mixture of stereoisomers, or deuterated analog thereof, a pharmaceutical composition comprising a compound of the present invention, together with a pharmaceutically acceptable excipient thereof, and a method of treating cancer with the same.

16 Claims, No Drawings

(56) References Cited

FOREIGN PATENT DOCUMENTS

| | | | |
|---|---|---|---|
| WO | WO 2023/147418 | A1 | 8/2023 |
| WO | WO 2025/024811 | A1 | 1/2025 |

OTHER PUBLICATIONS

Anonymous. (2022) "4 (3H)-Quinazolinone, 2-[[4-(5-chloro-1, 6-dihydro-6-oxo-4-pyridazinyl)-1-piperazinyl]methyl]-", Database Register [Online] Chemical Abstracts Service, 1 page.
Intl. Search Report—Written Opinion dated Apr. 24, 2023 for Intl. Appl. No. PCT/US2023/061372, 11 pages.
Office Action dated Jul. 2, 2024 for Taiwanese Appl. No. 112102850, 7 pages.
Pending U.S. Appl. No. 18/786,228, filed Jul. 26, 2024.
International Search Report and Written Opinion dated Oct. 30, 2024 for PCT/US2024/039885, 10 pages.

* cited by examiner

PARP7 INHIBITORS

CROSS REFERENCE TO RELATED APPLICATIONS

This application claims priority to U.S. Provisional Application No. 63/304,093, filed Jan. 28, 2022, U.S. Provisional Application No. 63/378,647, filed Oct. 6, 2022, and U.S. Provisional Application No. 63/385,303, filed Nov. 29, 2022, which are incorporated herein in their entireties for all purposes.

BACKGROUND OF THE INVENTION

Adenosine diphosphate (ADP)-ribosylation is a well conserved post-translational modification found in viruses, bacteria and eukaryotes. It is catalyzed by members of the ART superfamily of proteins, which transfer ADPr from nicotinamide adenine dinucleotide (NAD+) onto substrates via N-, O-, or S-glycosidic linkages on target molecules. One subset of ART's is the poly(adenosine diphosphate-ribose) polymerases (PARPs), that are members of a family of seventeen known enzymes that regulate fundamental cellular processes including gene Fexpression, protein degradation, and multiple cellular stress responses (M. S. Cohen, P. Chang, Insights into the biogenesis, function, and regulation of ADP-ribosylation. (Nat. Chem Biol 14, 236-243 (2018)). The ability of cancer cells to survive under stress is a fundamental cancer mechanism and an emerging approach for novel therapeutics.

Of particular interest is 2,3,7,8 tetrachlorodibenzo-p-dioxin (TCDD)-inducible poly(ADP ribose) polymerase (TIPARP), a CCCH-type zinc finger domain-containing protein. (Proc. Nat. Acad. Sci. 114 (10) 2681-2686 (2017)). TIPARP is also called PARP7 and ARTD14. PARP7 acts as negative regulator of certain aryl hydrocarbon receptor (AHR) transcriptional targets. AHR, in turn, is activated by many substrates, including cigarette smoke. PARP7 inhibitors have been shown to restore type I interferon (IFN) signaling responses to nucleic acids and causes tumor regression in a CT26 tumor-bearing, immunocompetent BALB/c mouse model. (Gozgit, et al., Cancer Cell 39, 1214-1226 (2021)).

There are currently no approved PARP7 inhibiting pharmaceuticals. Therefore, it would be useful to provide a PARP7 inhibiting compound with properties suitable for administration as a pharmaceutical agent to a mammal, particularly a human.

Thus, there is a need for improved PARP7 inhibitors for the treatment of cancer.

BRIEF SUMMARY OF THE INVENTION

Provided herein are compounds and pharmaceutical compositions useful as inhibitors of PARP7. Some compounds of the disclosure may find use in pharmaceutical compositions, together with at least one pharmaceutically acceptable excipient, for treating a subject in need thereof.

In one embodiment of the present invention, there is provided a compound of Formula (I):

(I)

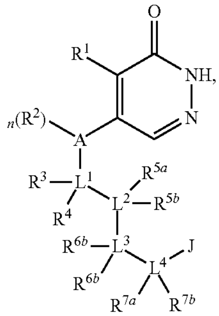

or a pharmaceutically acceptable salt, stereoisomer, mixture of stereoisomers, or deuterated analog thereof, J is

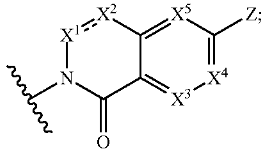

$X^1$ is N, C═O, C—$R^{10}$, or C—$(R^{10})_2$;

$X^2$ is N, N—$R^{11}$, C—$R^{12}$, or C—$(R^{12})_2$;

$X^3$ is N or C—$R^{13}$.

$X^4$ is N or C—$R^{13}$.

$X^5$ is N or C—$R^{13}$; or

A is Selected from:

C, O, N, 3-10 membered cycloalkyl optionally substituted with one or more $R^{15}$; or 4-11 membered heterocyclyl, optionally substituted with one or more $R^{15}$;

When A is 0, n is 0; when A is N, n is 1; and when A is C, n is 1 or 2;

When A is N, n is 0 or 1, and $L^1$ is C or N—$R^{17}$ and $L^2$, $L^3$ and $L^4$ are each C;

$L^1$, $L^2$, are each independently C, $C_{6-10}$ aryl, 5-12 membered heteroaryl or NH;

$L^3$ and $L^4$ are each C; or $L^1$ and $L^2$, together with the atoms to which they are attached, form a 3-12 membered cycloalkyl, $C_{6-10}$ aryl, 5-12 membered heteroaryl or a 4-12 membered heterocycle, each optionally substituted with one or more with $R^{15}$; wherein a 4-12 membered cycloalkyl or 4-12 membered heterocyclyl is monocyclic, bicyclic, fused bicyclic, spirocyclic or bridged, each optionally substituted with one or more $R^{15}$ and wherein the $C_{6-10}$ aryl, or 5-12 membered heteroaryl is monocyclic or bicyclic; or $L^1$ and $L^3$, together with the atoms to which they are attached, form a 3-12 membered cycloalkyl, $C_{6-10}$ aryl, 5-12 membered heteroaryl or a 4-12 membered heterocycle, each optionally substituted with one or more with $R^{15}$; wherein a 4-12 membered cycloalkyl or 4-12 membered heterocyclyl is monocyclic, bicyclic, fused bicyclic, spirocyclic or bridged, each optionally substituted with one or more $R^{15}$ and wherein the $C_{6-10}$ aryl, or 5-12 membered heteroaryl is monocyclic or bicyclic; or $L^2$ and $L^3$, together with the atoms to which they are attached, form a 3-12 membered cycloalkyl, $C_{6-10}$ aryl, 5-12 membered heteroaryl or a 4-12 membered heterocycle, each optionally substituted with one or more with $R^{15}$; wherein a 4-12 membered cycloalkyl or 4-12 membered heterocyclyl is monocyclic, bicyclic, fused bicyclic, spirocyclic or bridged, each optionally substituted with one or more $R^{15}$ and wherein the $C_{6-10}$ aryl, or 5-12 membered heteroaryl is monocyclic or bicyclic; or $L^3$ and $L^4$, together with the atoms to which they are attached, form a 3-12 membered cycloalkyl, $C_{6-10}$ aryl, 5-12 membered heteroaryl or a 4-12 membered heterocycle, each optionally substituted with one or more with $R^{15}$; wherein a 4-12 membered cycloalkyl or 4-12 membered heterocyclyl is monocyclic, bicyclic, fused bicyclic, spirocyclic or bridged, each optionally substituted with one or more $R^{15}$ and wherein the $C_{6-10}$ aryl, or 5-12 membered heteroaryl is monocyclic or bicyclic; or $L^2$ and $L^4$, together with the atoms to which they are attached, form a 3-12 membered cycloalkyl, $C_{6-10}$ aryl, 5-12 membered heteroaryl or a 4-12 membered heterocycle, each optionally substituted with one or more with $R^{15}$; wherein a 4-12 membered cycloalkyl or 4-12 membered heterocyclyl is monocyclic, bicyclic, fused bicyclic, spirocyclic or bridged, each optionally substituted with one or more $R^{15}$ and wherein the $C_{6-10}$ aryl, or 5-12 membered heteroaryl is monocyclic or bicyclic, each optionally substituted with one or more $R^{15}$;

$R^1$ is selected from H, halo, $CH_3$, $CH_2CH_3$, $CH_2F$, $CHF_2$, $CF_3$, $CH_2CF_3$, CN, O—$R^{14}$, C(O)—$R^{14}$, —$SF_5$; C(O)—N($R^{17}$)($R^{18}$), N($R^{17}$)($R^{18}$), N($R^{17}$)C(O)—$R^{15}$, N($R^{17}$)C(O)O—$R^{15}$, N($R^7$)S(O)$_2$($R^{15}$), N($R^{17}$)C(O)—N($R^{17}$)($R^{18}$), S(O)$_2R^{15}$, S(O)$_2$N($R^{17}$)($R^{18}$), S(O)(NH) $R^{17}$, S(O)(N$R^{17}$)N$R^{18}$, $C_{1-5}$ alkyl optionally substituted with one or more $R^{15}$; or $C_{3-10}$ cycloalkyl optionally substituted with one or more $R^{15}$; or 5-10 membered heteroaryl optionally substituted with one or more $R^{15}$; or $C_{6-10}$ aryl optionally substituted with one or more $R^{15}$; or 4-7 membered heterocyclyl optionally substituted with one or more $R^{15}$;

$R^2$ is selected from H, $C_{1-9}$ alkyl, $C_{2-9}$ alkenyl, or $C_{2-9}$ alkynyl, wherein any alkyl, alkenyl, and alkynyl are optionally substituted with one or more $R^{10}$;

$R^3$ and $R^4$ are each independently selected from H, $C_{1-9}$ alkyl, $C_{2-9}$ alkenyl, $C_{2-9}$ alkynyl, wherein any alkyl, alkenyl, and alkynyl are optionally substituted with one or more $R^{15}$, $C_{3-12}$ cycloalkyl optionally substituted with one or more $R^{15}$, $C_{6-10}$ aryl optionally substituted with one or more $R^{15}$, 4-11 membered heterocyclyl optionally substituted with one or more $R^5$, or 5-10 membered heteroaryl optionally substituted with one or more $R^5$; or $R^2$ and $R^3$, together with the atoms to which they are attached, form a 3-12 membered cycloalkyl, or a 4-12 membered heterocycle, optionally substituted with one or more with $R^{15}$;

wherein a 4-12 membered cycloalkyl or 4-12 membered heterocyclyl is monocyclic, bicyclic, fused bicyclic, spirocyclic or bridged optionally substituted with one or more $R^{15}$; or $R^3$ and $R^4$, together with the atoms to which they are attached, form a 3-12 membered cycloalkyl, or a 4-12 membered heterocycle, each optionally substituted with one or more with $R^{15}$; wherein a 3-12 membered cycloalkyl or 4-12 membered heterocyclyl is monocyclic, bicyclic, fused bicyclic, spirocyclic or bridged each optionally substituted with one or more $R^{15}$; or $R^2$ and $R^4$, together with the atoms to which they are attached, form a 3-12 membered cycloalkyl, or a 4-12 membered heterocycle, each optionally substituted with one or more with $R^{15}$; wherein a 3-12 membered cycloalkyl or 4-12 membered heterocyclyl is monocyclic, bicyclic, fused bicyclic, spirocyclic or bridged each optionally substituted with one or more $R^5$;

$R^{5a}$, $R^{5b}$ $R^{6a}$, $R^{6b}$, $R^{7a}$ $R^{7b}$ are each independently selected from H, halo, $NO_2$, CN, O—$R^{14}$, C(O)—$R^{16}$, C(O)—N($R^{17}$)($R^{18}$), N($R^{17}$)($R^{18}$), N($R^{17}$)C(O)—$R^{16}$, N($R^{17}$)C(O)O— $R^{14}$, N($R^{17}$)S(O)$_2$($R^{16}$), —N($R^{17}$)C(O)—N($R^{18}$)($R^{18}$), S(O)$_2R^{16}$, —$SF_5$, S(O)$_2$N($R^{17}$)($R^{18}$), S(O)(NH)$R^{17}$, S(O)(N$R^{17}$)N$R^{18}$ $C_{1-9}$ alkyl optionally substituted with one or more $R^{15}$;

$C_{2-9}$ alkynyl optionally substituted with one or more $R^{15}$;

$C_{2-9}$ alkenyl optionally substituted with one or more $R^{15}$;

5-12 membered heteroaryl optionally substituted with one or more $R^{15}$;

$C_{6-10}$ aryl optionally substituted with one or more $R^{15}$;

4-12 membered heterocyclyl optionally substituted with one or more $R^5$; or $C_{3-12}$ cycloalkyl optionally substituted with one or more $R^{15}$; or $R^{5a}$ and $R^{5b}$, together with the atoms to which they are attached, form a 3-12 membered cycloalkyl, or a 4-12 membered heterocycle, each optionally substituted with one or more with $R^{15}$; or $R^{6a}$ and $R^{6b}$ together with the atoms to which they are attached, form a 3-12 membered cycloalkyl, or a 4-12 membered heterocycle, each optionally substituted with one or more with $R^{15}$; or $R^{7a}$ and $R^{7b}$, together with the atoms to which they are attached, form a 3-12 membered cycloalkyl, or a 4-12 membered heterocycle, each optionally substituted with one or more with $R^{15}$ wherein a 3-12 membered cycloalkyl or 4-12 membered heterocyclyl is monocyclic, bicyclic, fused bicyclic, spirocyclic or bridged each optionally substituted with one or more $R^5$; or Z is selected from: H, —CN, $C_{1-9}$ alkyl, $C_{2-6}$ alkenyl, $C_{2-6}$ alkynyl, $C_{1-8}$ haloalkyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O($C_{6-10}$ aryl), —O(5-12 membered heteroaryl), —O(4-12 membered heterocyclyl), —OC(O) ($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-15}$ cycloalkyl), —OC(O)($C_{1-8}$ haloalkyl), —OC(O)($C_{6-10}$ aryl), —OC(O)(5-12 membered heteroaryl), —OC(O)(4-12 membered heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N($C_{6-10}$ aryl)$_2$, —N(5-12 membered heteroaryl)$_2$, —N(h4-12 membered heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)($C_{6-10}$ aryl), —N($C_{1-9}$ alkyl) (5-12 membered heteroaryl), —N($C_{1-9}$ alkyl)(4-12 membered heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)($C_{6-10}$ aryl), —C(O)(5-12 membered heteroaryl), —C(O)(4-12 membered heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O($C_{6-10}$ aryl), —C(O)O(5-12 membered heteroaryl), —C(O)O(4-12 membered heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH($C_{6-10}$ aryl), —C(O)NH(5-12 membered heteroaryl), —C(O)NH(4-12 membered heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N($C_{6-10}$ aryl)$_2$, —C(O)N(5-12 membered heteroaryl)$_2$, —C(O)N(4-12 membered heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH($C_{6-10}$ aryl), —NHC(O)NH(5-12 membered heteroaryl), —NHC(O)NH(4-12 membered heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S($C_{6-10}$ aryl), —S(5-12 membered heteroaryl), —S(4-12 membered heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)($C_{6-10}$ aryl), —S(O)(5-12 membered heteroaryl), —S(O)(4-12 membered heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$($C_{6-10}$ aryl), —S(O)$_2$(5-12 membered heteroaryl), —S(O)$_2$(4-12 membered heterocyclyl), —S(O)$_2$NH($C_{1-9}$ alkyl), or —S(O)$_2$N($C_{1-9}$ alkyl)$_2$; wherein any alkyl, cycloalkyl, aryl, heteroaryl, or heterocyclyl of $R^{15}$ is optionally substituted with one or more halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —S(O)(NH)($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$($C_{6-10}$ aryl), —S(O)$_2$(5-12 membered heteroaryl), —S(O)$_2$(4-12 membered heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O($C_{6-10}$ aryl), —O(5-12 membered heteroaryl), —O(4-12 membered heterocyclyl), or —O($C_{1-9}$ alkyl).

5-12 membered heteroaryl substituted with one or more $R^{13}$;

$C_{6-10}$ aryl optionally substituted with one or more $R^{15}$; $C_{3-12}$ cycloalkyl optionally substituted with one or more $R^{15}$; 4-12 membered heterocyclyl substituted with one or more $R^{15}$;

wherein any 5-12 membered heteroaryl, $C_{6-10}$ aryl, $C_{3-12}$ cycloalkyl, or 4-12 membered heterocyclyl, is monocyclic, bicyclic, substituted with one or more $R^{15}$ and 3-12 membered cycloalkyl or 4-12 membered heterocyclyl is monocyclic, bicyclic, fused bicyclic, spirocyclic or bridged each substituted with one or more $R^{15}$ $R^{10}$ is selected from: H, halo, $CH_3$, $CH_2F$, $CHF_2$, $CF_3$, $CH_2CF_3$, $OCH_3$, $OCF_3$, $OCHF_2$, $NO_2$, CN, O— $R^{14}$, C(O)—$R^{16}$, C(O)—N($R^{17}$)($R^{18}$), N($R^{17}$)($R^{18}$), N($R^{17}$)C(O)—$R^{16}$, N($R^{17}$)C(O)O— $R^{14}$, N($R^{17}$)S(O)$_2$($R^{16}$), —N($R^{17}$)C(O)—N($R^{18}$)($R^{18}$), S(O)$_2R^{16}$, —$SF_5$, S(O)$_2$N($R^{17}$)($R^{18}$), S(O)(NH)$R^{17}$, S(O)($NR^{17}$)$NR^{18}$, $C_{1-9}$ alkyl, $C_{2-6}$ alkenyl, $C_{2-6}$ alkynyl, $C_{3-15}$ cycloalkyl, $C_{6-10}$ aryl, 5-10 membered heteroaryl or 4-12 membered heterocyclyl, wherein any alkyl, alkenyl, alkenyl, cycloalkyl, aryl, heteroaryl, or heterocyclyl is optionally substituted with one or more with $R^{16}$;

$R^{11}$ is selected from: H, $C_{1-9}$ alkyl, $C_{2-9}$ alkenyl, $C_{2-9}$ alkynyl, $C_{3-12}$ cycloalkyl, $C_{6-10}$ aryl, 6-12 membered heteroaryl or 4-12 membered heterocyclyl, wherein any alkyl, alkenyl, alkenyl, cycloalkyl, aryl, heteroaryl, or heterocyclyl is optionally substituted with one or more with $R^{16}$;

$R^{12}$ is selected from: H, halo, $CH_3$, $CH_2F$, $CHF_2$, $CF_3$, $CH_2CF_3$, $OCH_3$, $OCF_3$, $OCHF_2$, $NO_2$, CN, O— $R^{14}$, C(O)—$R^{16}$, C(O)—N($R^{17}$)($R^{18}$), N($R^{17}$)($R^{18}$), N($R^{17}$)C(O)—$R^{16}$, N($R^{17}$)C(O)O— $R^{14}$, N($R^{17}$)S(O)$_2$($R^{16}$), —N($R^{17}$)C(O)—N($R^{18}$)($R^{18}$), S(O)$_2R^{16}$, S(O)$_2$N($R^{17}$)($R^{18}$), S(O)(NH)$R^{17}$, S(O)($NR^{17}$)$NR^{18}$, $C_{1-9}$ alkyl, $C_{2-9}$ alkenyl, $C_{2-9}$ alkynyl, $C_{3-12}$ cycloalkyl, $C_{6-10}$ aryl, 5-12 membered heteroaryl or 4-12 membered heterocyclyl, wherein any alkyl, alkenyl, alkenyl, cycloalkyl, aryl, heteroaryl, or heterocyclyl is optionally substituted with one or more with $R^{16}$;

$R^{13}$ is independently selected from: H, halo, $CH_3$, $CH_2F$, $CHF_2$, $CF_3$, $CH_2CF_3$, $OCH_3$, $OCF_3$, $OCHF_2$, $NO_2$, CN, O— $R^{14}$, C(O)—$R^{16}$, C(O)—N($R^{17}$)($R^{18}$), N($R^{17}$)($R^{18}$), N($R^{17}$)C(O)—$R^{16}$, N($R^{17}$)C(O)O— $R^{14}$, N($R^{17}$)S(O)$_2$($R^{16}$), —N($R^{17}$)C(O)—N($R^{18}$)($R^{18}$), —$SF_5$, S(O)$_2R^{16}$, S(O)$_2$N($R^{17}$)($R^{18}$), S(O)(NH)$R^{17}$, S(O)($NR^{17}$)$NR^{18}$, $C_{1-9}$ alkyl, $C_{2-9}$ alkenyl, $C_{2-9}$ alkynyl, $C_{3-12}$ cycloalkyl, $C_{6-10}$ aryl, 5-12 membered heteroaryl or 4-12 membered heterocyclyl, wherein any alkyl, alkenyl, alkenyl, cycloalkyl, aryl, heteroaryl, or heterocyclyl is optionally substituted with one or more with $R^{16}$;

$R^{15}$ is independently selected from: H, C═O, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, $C_{6-10}$ aryl, 5-12 membered heteroaryl, 4-12 membered heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O($C_{6-10}$ aryl), —O(5-12 membered heteroaryl), —O(4-12 membered heterocyclyl), —OC(O)($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-15}$ cycloalkyl), —OC(O)($C_{1-8}$ haloalkyl), —OC(O)($C_{6-10}$ aryl), —OC(O)(5-12 membered heteroaryl), —OC(O)

(4-12 membered heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ halo alkyl)$_2$, —N($C_{6-10}$ aryl)$_2$, —N(5-12 membered heteroaryl)$_2$, —N(h4-12 membered heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)($C_{6-10}$ aryl), —N($C_{1-9}$ alkyl) (5-12 membered heteroaryl), —N($C_{1-9}$ alkyl)(4-12 membered heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)($C_{6-10}$ aryl), —C(O)(5-12 membered heteroaryl), —C(O)(4-12 membered heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O($C_{6-10}$ aryl), —C(O)O(5-12 membered heteroaryl), —C(O)O(4-12 membered heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH($C_{6-10}$ aryl), —C(O)NH(5-12 membered heteroaryl), —C(O)NH(4-12 membered heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N($C_{6-10}$ aryl)$_2$, —C(O)N(5-12 membered heteroaryl)$_2$, —C(O)N(4-12 membered heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH($C_{6-10}$ aryl), —NHC(O)NH(5-12 membered heteroaryl), —NHC(O)NH(4-12 membered heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S($C_{6-10}$ aryl), —S(5-12 membered heteroaryl), —S(4-12 membered heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)($C_{6-10}$ aryl), —S(O)(5-12 membered heteroaryl), —S(O)(4-12 membered heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$($C_{6-10}$ aryl), —S(O)$_2$(5-12 membered heteroaryl), —S(O)$_2$(4-12 membered heterocyclyl), —S(O)$_2$NH($C_{1-9}$ alkyl), or —S(O)$_2$N($C_{1-9}$ alkyl)$_2$; wherein any alkyl, cycloalkyl, aryl, heteroaryl, or heterocyclyl of $R^{15}$ is optionally substituted with one or more halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —S(O)(NH)($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$($C_{6-10}$ aryl), —S(O)$_2$(5-12 membered heteroaryl), —S(O)$_2$(4-12 membered heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O($C_{6-10}$ aryl), —O(5-12 membered heteroaryl), —O(4-12 membered heterocyclyl), or —O($C_{1-9}$ alkyl).

$R^{16}$ is independently selected from: H, C═O, halo, —$NO_2$, —CN, $C_{1-9}$ alkyl, $C_{2-6}$ alkenyl, $C_{2-6}$ alkynyl, $C_{3-15}$ cycloalkyl, $C_{1-8}$ haloalkyl, $C_{6-10}$ aryl, 5-12 membered heteroaryl, 4-12 membered heterocyclyl, —OH, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O($C_{6-10}$ aryl), —O(5-12 membered heteroaryl), —O(4-12 membered heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N($C_{6-10}$ aryl)$_2$, —N(5-12 membered heteroaryl)$_2$, —N(4-12 membered heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)($C_{6-10}$ aryl), —N($C_{1-9}$ alkyl)(5-12 membered heteroaryl), —N($C_{1-9}$ alkyl)(4-12 membered heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)($C_{6-10}$ aryl), —C(O)(5-12 membered heteroaryl), —C(O)(4-12 membered heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O($C_{6-10}$ aryl), —C(O)O(5-12 membered heteroaryl), —C(O)O(4-12 membered heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH($C_{6-10}$ aryl), —C(O)NH(5-12 membered heteroaryl), —C(O)NH(4-12 membered heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N($C_{6-10}$ aryl)$_2$, —C(O)N(5-12 membered heteroaryl)$_2$, —C(O)N(4-12 membered heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH ($C_{3-15}$ cycloalkyl), —NHC(O)NH($C_{1-8}$ haloalkyl), —NHC(O)NH($C_{6-10}$ aryl), —NHC(O)NH(5-12 membered heteroaryl), —NHC(O)NH(4-12 membered heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S($C_{1-10}$ aryl), —S(5-12 membered heteroaryl), —S(4-12 membered heterocyclyl), —NHS (O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH) ($C_{1-9}$ alkyl), —S(O)(NH)($C_{3-9}$ cycloalkyl), —S(O)(N $C_{1-9}$ alkyl)($C_{1-9}$ alkyl), —S(O)(NH)($C_{1-10}$ aryl), —S(O)(NH)(5-12 membered heteroaryl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)($C_{6-10}$ aryl), —S(O)(5-12 membered heteroaryl), —S(O)(4-12 membered heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$($C_{6-10}$ aryl), —S(O)$_2$(5-12 membered heteroaryl), —S(O)$_2$(4-12 membered heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one or more halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O) O($C_{6-10}$ aryl), —NHC(O)O(5-12 membered heteroaryl), —NHC(O)O(4-12 membered heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$ ($C_{1-8}$ haloalkyl), —S(O)$_2$($C_{6-10}$ aryl), —S(O)$_2$(5-12 membered heteroaryl), —S(O)$_2$(4-12 membered heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O($C_{6-10}$ aryl), —O(5-12 membered heteroaryl), —O(4-12 membered heterocyclyl), or —O($C_{1-9}$ alkyl); and $R^{17}$ and $R^{18}$ are independently selected from: H, $C_{1-9}$ alkyl, $C_{2-6}$ alkenyl, $C_{2-6}$ alkynyl, $C_{3-15}$ cycloalkyl, $C_{6-10}$ aryl, 5-12 membered heteroaryl or 4-12 membered heterocyclyl wherein any alkyl, alkenyl, alkynyl, cycloalkyl, aryl, heteroaryl, or heterocyclyl is optionally substituted with one or more with $R^{16}$.

In one embodiment of the present invention, there is provided a compound represented by Formula (Ia):

(Ia)

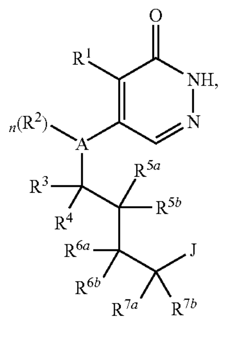

or a pharmaceutically acceptable salt, stereoisomer, mixture of stereoisomers, or deuterated analog thereof, J is

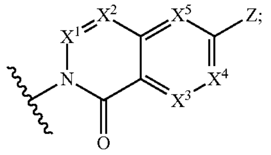

$X^1$ is N, C═O, C—$R^{10}$, or C—($R^{10}$)$_2$;

$X^2$ is N, N—$R^{11}$, C—$R^{12}$, or C—($R^{12}$)$_2$;

$X^3$ is N or C—$R^{13}$.

$X^4$ is N or C—$R^{13}$.

$X^5$ is N or C—$R^{13}$; or

A is Selected from:

C, O, N, 3-10 membered cycloalkyl optionally substituted with one or more $R^{15}$; or 4-11 membered heterocyclyl, optionally substituted with one or more $R^{15}$;

When A is 0, n is 0; when A is N, n is 1; and when A is C, n is 1 or 2;

$R^1$ is selected from H, halo, $CH_3$, $CH_2CH_3$, $CH_2F$, $CHF_2$, $CF_3$, $CH_2CF_3$, CN, O—$R^{14}$, C(O)—$R^{14}$, —$SF_5$; C(O)—N($R^{17}$)($R^{18}$), N($R^{17}$)($R^{18}$), N($R^{17}$)C(O)—$R^{15}$, N($R^{17}$)C(O)O—$R^{15}$, N($R^7$)S(O)$_2$($R^{15}$), N($R^{17}$)C(O)—N($R^{17}$)($R^{18}$), S(O)$_2R^{15}$, S(O)$_2$N($R^{17}$)($R^{18}$), S(O)(NH) $R^{17}$, S(O)(N$R^{17}$)N$R^{18}$ $C_{1-5}$ alkyl optionally substituted with one or more $R^{15}$; or $C_{3-10}$ cycloalkyl optionally substituted with one or more $R^{15}$;

5-10 membered heteroaryl optionally substituted with one or more $R^{15}$;

$C_{6-10}$ aryl optionally substituted with one or more $R^{15}$; or 4-7 membered heterocyclyl optionally substituted with one or more $R^{15}$ $R^2$ is selected from H, $C_{1-9}$ alkyl, $C_{2-9}$ alkenyl, or $C_{2-9}$ alkynyl, wherein any alkyl, alkenyl, and alkynyl are optionally substituted with one or more $R^{10}$;

$R^3$ and $R^4$ are each independently selected from H, $C_{1-9}$ alkyl, $C_{2-9}$ alkenyl, $C_{2-9}$ alkynyl, wherein any alkyl, alkenyl, and alkynyl are optionally substituted with one or more $R^{15}$, $C_{3-12}$ cycloalkyl optionally substituted with one or more $R^{15}$, $C_{6-10}$ aryl optionally substituted with one or more $R^{15}$, 4-11 membered heterocyclyl optionally substituted with one or more $R^{15}$, or 5-10 membered heteroaryl optionally substituted with one or more $R^{15}$; or $R^2$ and $R^3$, together with the atoms to which they are attached, form a 3-12 membered cycloalkyl, or a 4-12 membered heterocycle, optionally substituted with one or more with $R^{15}$;

wherein a 4-12 membered cycloalkyl or 4-12 membered heterocyclyl is monocyclic, bicyclic, fused bicyclic, spirocyclic or bridged optionally substituted with one or more $R^5$; or $R^3$ and $R^4$, together with the atoms to which they are attached, form a 3-12 membered cycloalkyl, or a 4-12 membered heterocycle, each optionally substituted with one or more with $R^{15}$; wherein a 3-12 membered cycloalkyl or 4-12 membered heterocyclyl is monocyclic, bicyclic, fused bicyclic, spirocyclic or bridged each optionally substituted with one or more $R^{15}$; or $R^{5a}$, $R^{5b}$ $R^{6a}$, $R^{6b}$, $R^{7a}R^{7b}$ are each independently selected from H, halo, $NO_2$, CN, O—$R^{14}$, C(O)—$R^{16}$, C(O)—N($R^{17}$)($R^{18}$), N($R^{17}$)($R^{18}$), N($R^{17}$)C(O)—$R^{16}$, N($R^{17}$)C(O)O—$R^{14}$, N($R^{17}$)$S(O)_2$($R^{16}$), —N($R^{17}$)C(O)—N($R^{18}$)($R^{18}$), $S(O)_2R^{16}$, —$SF_5$, $S(O)_2N(R^{17})(R^{18})$, S(O)(NH)$R^{17}$, S(O)($NR^{17}$)$NR^{18}$ $C_{1-9}$ alkyl optionally substituted with one or more $R^{15}$;

$C_{2-9}$ alkynyl optionally substituted with one or more $R^{15}$;

$C_{2-9}$ alkenyl optionally substituted with one or more $R^{15}$;

5-12 membered heteroaryl optionally substituted with one or more $R^{15}$;

$C_{6-10}$ aryl optionally substituted with one or more $R^{15}$;

4-12 membered heterocyclyl optionally substituted with one or more $R^5$; or $C_{3-12}$ cycloalkyl optionally substituted with one or more $R^{15}$; or $R^{5a}$ and $R^{5b}$, together with the atoms to which they are attached, form a 3-12 membered cycloalkyl, or a 4-12 membered heterocycle, each optionally substituted with one or more with $R^{15}$; or $R^{6a}$ and $R^{6b}$ together with the atoms to which they are attached, form a 3-12 membered cycloalkyl, or a 4-12 membered heterocycle, each optionally substituted with one or more with $R^{15}$; or $R^{7a}$ and $R^{7b}$, together with the atoms to which they are attached, form a 3-12 membered cycloalkyl, or a 4-12 membered heterocycle, each optionally substituted with one or more with $R^{15}$ wherein a 3-12 membered cycloalkyl or 4-12 membered heterocyclyl is monocyclic, bicyclic, fused bicyclic, spirocyclic or bridged each optionally substituted with one or more $R^{15}$; or Z is selected from: —CN, $C_{1-9}$ alkyl, $C_{2-6}$ alkenyl, $C_{2-6}$ alkynyl, $C_{1-8}$ haloalkyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O($C_{6-10}$ aryl), —O(5-12 membered heteroaryl), —O(4-12 membered heterocyclyl), —OC(O) ($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-15}$ cycloalkyl), —OC(O)($C_{1-8}$ haloalkyl), —OC(O)($C_{6-10}$ aryl), —OC(O)(5-12 membered heteroaryl), —OC(O)(4-12 membered heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N($C_{6-10}$ aryl)$_2$, —N(5-12 membered heteroaryl)$_2$, —N(h4-12 membered heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)($C_{6-10}$ aryl), —N($C_{1-9}$ alkyl) (5-12 membered heteroaryl), —N($C_{1-9}$ alkyl)(4-12 membered heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)($C_{6-10}$ aryl), —C(O)(5-12 membered heteroaryl), —C(O)(4-12 membered heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O($C_{6-10}$ aryl), —C(O)O(5-12 membered heteroaryl), —C(O)O(4-12 membered heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH($C_{6-10}$ aryl), —C(O)NH(5-12 membered heteroaryl), —C(O)NH(4-12 membered heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N($C_{6-10}$ aryl)$_2$, —C(O)N(5-12 membered heteroaryl)$_2$, —C(O)N(4-12 membered heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH($C_{6-10}$ aryl), —NHC(O)NH(5-12 membered heteroaryl), —NHC(O)NH(4-12 membered heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S($C_{6-10}$ aryl), —S(5-12 membered heteroaryl), —S(4-12 membered heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)($C_{6-10}$ aryl), —S(O)(5-12 membered heteroaryl), —S(O)(4-12 membered heterocyclyl), —$S(O)_2$($C_{1-9}$ alkyl), —$S(O)_2$($C_{2-6}$ alkenyl), —$S(O)_2$($C_{2-6}$ alkynyl), —$S(O)_2$($C_{3-15}$ cycloalkyl), —$S(O)_2$($C_{1-8}$ haloalkyl), —$S(O)_2$($C_{6-10}$ aryl), —$S(O)_2$(5-12 membered heteroaryl), —$S(O)_2$(4-12 membered heterocyclyl), —$S(O)_2$NH($C_{1-9}$ alkyl), or —$S(O)_2$N($C_{1-9}$ alkyl)$_2$; wherein any alkyl, cycloalkyl, aryl, heteroaryl, or heterocyclyl of $R^{15}$ is optionally substituted with one or more halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —S(O)(NH)($C_{1-9}$ alkyl), —$S(O)_2$($C_{1-9}$ alkyl), —$S(O)_2$($C_{3-15}$ cycloalkyl), —$S(O)_2$($C_{1-8}$ haloalkyl), —$S(O)_2$($C_{6-10}$ aryl), —$S(O)_2$(5-12 membered heteroaryl), —$S(O)_2$(4-12 membered heterocyclyl), —$S(O)_2$NH($C_{1-9}$ alkyl), —$S(O)_2$N($C_{1-9}$ alkyl)$_2$, —O($C_{3-15}$ cycloalkyl), —O($C_{1-8}$ haloalkyl), —O($C_{6-10}$ aryl), —O(5-12 membered heteroaryl), —O(4-12 membered heterocyclyl), or —O($C_{1-9}$ alkyl).

5-12 membered heteroaryl substituted with one or more $R^{13}$.

$C_{6-10}$ aryl optionally substituted with one or more $R^{15}$; $C_{3-12}$ cycloalkyl optionally substituted with one or more $R^{15}$; 4-12 membered heterocyclyl substituted with one or more $R^{15}$;

wherein any 5-12 membered heteroaryl, $C_{6-10}$ aryl, $C_{3-12}$ cycloalkyl, or 4-12 membered heterocyclyl, is monocyclic, bicyclic, substituted with one or more $R^{15}$ and 3-12 membered cycloalkyl or 4-12 membered heterocyclyl is monocyclic, bicyclic, fused bicyclic, spirocyclic or bridged each substituted with one or more $R^{15}$ $R^{10}$ is selected from: H, halo, $CH_3$, $CH_2F$, $CHF_2$, $CF_3$, $CH_2CF_3$, $OCH_3$, $OCF_3$, $OCHF_2$, $NO_2$, CN, O—$R^{14}$, C(O)—$R^{16}$, C(O)—N($R^{17}$)($R^{18}$), N($R^{17}$)($R^{18}$), N($R^{17}$)C(O)—$R^{16}$, N($R^{17}$)C(O)O—$R^{14}$, N($R^{17}$)S(O)$_2$($R^{16}$), —N($R^{17}$)C(O)—N($R^{18}$)($R^{18}$), S(O)$_2R^{16}$, —$SF_5$, S(O)$_2$N($R^{17}$)($R^{18}$), S(O)(NH)$R^{17}$, S(O)(N$R^{17}$)N$R^{18}$, $C_{1-9}$ alkyl, $C_{2-6}$ alkenyl, $C_{2-6}$ alkynyl, $C_{3-15}$ cycloalkyl, $C_{6-10}$ aryl, 5-10 membered heteroaryl or 4-12 membered heterocyclyl, wherein any alkyl, alkenyl, alkenyl, cycloalkyl, aryl, heteroaryl, or heterocyclyl is optionally substituted with one or more with $R^{16}$ $R^{11}$ is selected from: H, $C_{1-9}$ alkyl, $C_{2-9}$ alkenyl, $C_{2-9}$ alkynyl, $C_{3-12}$ cycloalkyl, $C_{6-10}$ aryl, 6-12 membered heteroaryl or 4-12 membered heterocyclyl wherein any alkyl, alkenyl, alkenyl, cycloalkyl, aryl, heteroaryl, or heterocyclyl is optionally substituted with one or more with $R^{16}$ $R^{12}$ is selected from: H, halo, $CH_3$, $CH_2F$, $CHF_2$, $CF_3$, $CH_2CF_3$, $OCH_3$, $OCF_3$, $OCHF_2$, $NO_2$, CN, O—$R^{14}$, C(O)—$R^{16}$, C(O)—N($R^{17}$)($R^{18}$), N($R^{17}$)($R^{18}$), N($R^{17}$)C(O)—$R^{16}$, N($R^{17}$)C(O)O—$R^{14}$, N($R^{17}$)S(O)$_2$($R^{16}$), —N($R^{17}$)C(O)—N($R^{18}$)($R^{18}$), S(O)$_2R^{16}$, S(O)$_2$N($R^{17}$)($R^{18}$), S(O)(NH)$R^{17}$, S(O)(N$R^{17}$)N$R^{18}$, $C_{1-9}$ alkyl, $C_{2-9}$ alkenyl, $C_{2-9}$ alkynyl, $C_{3-12}$ cycloalkyl, $C_{6-10}$ aryl, 5-12 membered heteroaryl or 4-12 membered heterocyclyl, wherein any alkyl, alkenyl, alkenyl, cycloalkyl, aryl, heteroaryl, or heterocyclyl is optionally substituted with one or more with $R^{16}$ $R^{13}$ is independently selected from: H, halo, $CH_3$, $CH_2F$, $CHF_2$, $CF_3$, $CH_2CF_3$, $OCH_3$, $OCF_3$, $OCHF_2$, $NO_2$, CN, O—$R^{14}$, C(O)—$R^{16}$, C(O)—N($R^{17}$)($R^{18}$), N($R^{17}$)($R^{18}$), N($R^{17}$)C(O)—$R^{16}$, N($R^{17}$)C(O)O—$R^{14}$, N($R^{17}$)S(O)$_2$($R^{16}$), —N($R^{17}$)C(O)—N($R^{18}$)($R^{18}$), —$SF_5$, S(O)$_2R^{16}$, S(O)$_2$N($R^{17}$)($R^{18}$), S(O)(NH)$R^{17}$, S(O)(N$R^{17}$)N$R^{18}$, $C_{1-9}$ alkyl, $C_{2-9}$ alkenyl, $C_{2-9}$ alkynyl, $C_{3-12}$ cycloalkyl, $C_{6-10}$ aryl, 5-12 membered heteroaryl or 4-12 membered heterocyclyl wherein any alkyl, alkenyl, alkenyl, cycloalkyl, aryl, heteroaryl, or heterocyclyl is optionally substituted with one or more with $R^{16}$;

$R^{15}$ is independently selected from: H, C═O, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, $C_{6-10}$ aryl, 5-12 membered heteroaryl, 4-12 membered heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O($C_{6-10}$ aryl), —O(5-12 membered heteroaryl), —O(4-12 membered heterocyclyl), —OC(O)($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-15}$ cycloalkyl), —OC(O)($C_{1-8}$ haloalkyl), —OC(O)($C_{6-10}$ aryl), —OC(O)(5-12 membered heteroaryl), —OC(O)(4-12 membered heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N($C_{6-10}$ aryl)$_2$, —N(5-12 membered heteroaryl)$_2$, —N(h4-12 membered heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)($C_{6-10}$ aryl), —N($C_{1-9}$ alkyl) (5-12 membered heteroaryl), —N($C_{1-9}$ alkyl)(4-12 membered heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)($C_{6-10}$ aryl), —C(O)(5-12 membered heteroaryl), —C(O)(4-12 membered heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O($C_{6-10}$ aryl), —C(O)O(5-12 membered heteroaryl), —C(O)O(4-12 membered heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH($C_{6-10}$ aryl), —C(O)NH(5-12 membered heteroaryl), —C(O)NH(4-12 membered heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N($C_{6-10}$ aryl)$_2$, —C(O)N(5-12 membered heteroaryl)$_2$, —C(O)N(4-12 membered heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH($C_{6-10}$ aryl), —NHC(O)NH(5-12 membered heteroaryl), —NHC(O)NH(4-12 membered heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S($C_{6-10}$ aryl), —S(5-12 membered heteroaryl), —S(4-12 membered heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)($C_{6-10}$ aryl), —S(O)(5-12 membered heteroaryl), —S(O)(4-12 membered heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$($C_{6-10}$ aryl), —S(O)$_2$(5-12 membered heteroaryl), —S(O)$_2$(4-12 membered heterocyclyl), —S(O)$_2$NH($C_{1-9}$ alkyl), or —S(O)$_2$N($C_{1-9}$ alkyl)$_2$;_wherein any alkyl, cycloalkyl, aryl, heteroaryl, or heterocyclyl of $R^{15}$ is optionally substituted with one or more halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH($C_{6-10}$ aryl), —NH(5-12 membered heteroaryl), —NH(4-12 membered heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)($C_{1-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —S(O)(NH)($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$($C_{6-10}$ aryl), —S(O)$_2$(5-12 membered heteroaryl), —$S(O)_2$(4-12 membered heterocyclyl), —$S(O)_2NH(C_{1-9}$ alkyl), —$S(O)_2N(C_{1-9}$ alkyl$)_2$, —$O(C_{3-15}$ cycloalkyl), —$O(C_{1-8}$ haloalkyl), —$O(C_{6-10}$ aryl), —O(5-12 membered heteroaryl), —O(4-12 membered heterocyclyl), or —$O(C_{1-9}$ alkyl).

$R^{16}$ is independently selected from: H, C═O, halo, —$NO_2$, —CN, $C_{1-9}$ alkyl, $C_{2-6}$ alkenyl, $C_{2-6}$ alkynyl, $C_{3-15}$ cycloalkyl, $C_{1-8}$ haloalkyl, $C_{6-10}$ aryl, 5-12 membered heteroaryl, 4-12 membered heterocyclyl, —OH, —$O(C_{1-9}$ alkyl), —$O(C_{2-6}$ alkenyl), —$O(C_{2-6}$ alkynyl), —$O(C_{3-15}$ cycloalkyl), —$O(C_{1-8}$ haloalkyl), —$O(C_{6-10}$ aryl), —O(5-12 membered heteroaryl), —O(4-12 membered heterocyclyl), —$NH_2$, —$NH(C_{1-9}$ alkyl), —$NH(C_{2-6}$ alkenyl), —$NH(C_{2-6}$ alkynyl), —$NH(C_{3-15}$ cycloalkyl), —$NH(C_{1-8}$ haloalkyl), —$NH(C_{6-10}$ aryl), —NH(5-12 membered heteroaryl), —NH(4-12 membered heterocyclyl), —$N(C_{1-9}$ alkyl$)_2$, —$N(C_{3-15}$ cycloalkyl$)_2$, —$N(C_{2-6}$ alkenyl$)_2$, —$N(C_{2-6}$ alkynyl$)_2$, —$N(C_{3-15}$ cycloalkyl$)_2$, —$N(C_{1-8}$ haloalkyl$)_2$, —$N(C_{6-10}$ aryl$)_2$, —N(5-12 membered heteroaryl$)_2$, —N(4-12 membered heterocyclyl$)_2$, —$N(C_{1-9}$ alkyl)($C_{3-15}$ cycloalkyl), —$N(C_{1-9}$ alkyl)($C_{2-6}$ alkenyl), —$N(C_{1-9}$ alkyl)($C_{2-6}$ alkynyl), —$N(C_{1-9}$ alkyl)($C_{3-15}$ cycloalkyl), —$N(C_{1-9}$ alkyl)($C_{1-8}$ haloalkyl), —$N(C_{1-9}$ alkyl)($C_{6-10}$ aryl), —$N(C_{1-9}$ alkyl)(5-12 membered heteroaryl), —$N(C_{1-9}$ alkyl)(4-12 membered heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)($C_{6-10}$ aryl), —C(O)(5-12 membered heteroaryl), —C(O)(4-12 membered heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O($C_{6-10}$ aryl), —C(O)O(5-12 membered heteroaryl), —C(O)O(4-12 membered heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH($C_{6-10}$ aryl), —C(O)NH(5-12 membered heteroaryl), —C(O)NH(4-12 membered heterocyclyl), —C(O)N($C_{1-9}$ alkyl$)_2$, —C(O)N($C_{3-15}$ cycloalkyl$)_2$, —C(O)N($C_{2-6}$ alkenyl$)_2$, —C(O)N($C_{2-6}$ alkynyl$)_2$, —C(O)N($C_{3-15}$ cycloalkyl$)_2$, —C(O)N($C_{1-8}$ haloalkyl$)_2$, —C(O)N($C_{6-10}$ aryl$)_2$, —C(O)N(5-12 membered heteroaryl$)_2$, —C(O)N(4-12 membered heterocyclyl$)_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH($C_{6-10}$ aryl), —NHC(O)NH(5-12 membered heteroaryl), —NHC(O)NH(4-12 membered heterocyclyl), —SH, —$S(C_{1-9}$ alkyl), —$S(C_{2-6}$ alkenyl), —$S(C_{2-6}$ alkynyl), —$S(C_{3-15}$ cycloalkyl), —$S(C_{1-8}$ haloalkyl), —$S(C_{6-10}$ aryl), —S(5-12 membered heteroaryl), —S(4-12 membered heterocyclyl), —NHS(O)($C_{1-9}$ alkyl), —$N(C_{1-9}$ alkyl)(S(O)($C_{1-9}$ alkyl), —S(O)N($C_{1-9}$ alkyl$)_2$, —S(O)($C_{1-9}$ alkyl), —S(O)(NH)($C_{1-9}$ alkyl), —S(O)(NH)($C_{3-9}$ cycloalkyl), —S(O)(N $C_{1-9}$ alkyl)($C_{1-9}$ alkyl), —S(O)(NH)($C_{1-10}$ aryl), —S(O)(NH)(5-12 membered heteroaryl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)($C_{6-10}$ aryl), —S(O)(5-12 membered heteroaryl), —S(O)(4-12 membered heterocyclyl), —$S(O)_2(C_{1-9}$ alkyl), —$S(O)_2(C_{2-6}$ alkenyl), —$S(O)_2(C_{2-6}$ alkynyl), —$S(O)_2(C_{3-15}$ cycloalkyl), —$S(O)_2(C_{1-8}$ haloalkyl), —$S(O)_2(C_{6-10}$ aryl), —$S(O)_2$(5-12 membered heteroaryl), —$S(O)_2$(4-12 membered heterocyclyl), —$S(O)_2NH(C_{1-9}$ alkyl), or —$S(O)_2N(C_{1-9}$ alkyl$)_2$;

wherein any alkyl, cycloalkyl, aryl, heteroaryl, or heterocyclyl is optionally substituted with one or more halo, $C_{1-9}$ alkyl, $C_{1-8}$ haloalkyl, —OH, —$NH_2$, —$NH(C_{1-9}$ alkyl), —$NH(C_{3-15}$ cycloalkyl), —$NH(C_{1-8}$ haloalkyl), —$NH(C_{6-10}$ aryl), —NH(5-12 membered heteroaryl), —NH(4-12 membered heterocyclyl), —$N(C_{1-9}$ alkyl$)_2$, —$N(C_{3-15}$ cycloalkyl$)_2$, —NHC(O)($C_{3-15}$ cycloalkyl), —NHC(O)($C_{1-8}$ haloalkyl), —NHC(O)($C_{6-10}$ aryl), —NHC(O)(5-12 membered heteroaryl), —NHC(O)(4-12 membered heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O($C_{6-10}$ aryl), —NHC(O)O(5-12 membered heteroaryl), —NHC(O)O(4-12 membered heterocyclyl), —NHC(O)NH($C_{1-9}$ alkyl), —S(O)(NH)($C_{1-9}$ alkyl), $S(O)_2(C_{1-9}$ alkyl), —$S(O)_2(C_{3-15}$ cycloalkyl), —$S(O)_2(C_{1-8}$ haloalkyl), —$S(O)_2(C_{6-10}$ aryl), —$S(O)_2$(5-12 membered heteroaryl), —$S(O)_2$(4-12 membered heterocyclyl), —$S(O)_2NH(C_{1-9}$ alkyl), —$S(O)_2N(C_{1-9}$ alkyl$)_2$, —$O(C_{3-15}$ cycloalkyl), —$O(C_{1-8}$ haloalkyl), —$O(C_{6-10}$ aryl), —O(5-12 membered heteroaryl), —O(4-12 membered heterocyclyl), or —$O(C_{1-9}$ alkyl); and $R^{17}$ and $R^{18}$ are independently selected from: H, $C_{1-9}$ alkyl, $C_{2-6}$ alkenyl, $C_{2-6}$ alkynyl, $C_{3-15}$ cycloalkyl, $C_{6-10}$ aryl, 5-12 membered heteroaryl or 4-12 membered heterocyclyl wherein any alkyl, alkenyl, alkynyl, cycloalkyl, aryl, heteroaryl, or heterocyclyl is optionally substituted with one or more with $R^{16}$.

There is also provided a pharmaceutical composition comprising a compound, or a pharmaceutically acceptable salt, stereoisomer, mixture of stereoisomers, or deuterated analog thereof, of the present invention, together with a pharmaceutically acceptable excipient.

Further, there is provided a method of treating cancer, in a subject in need thereof, comprising administering to said patient a compound of the present invention, or a pharmaceutical composition comprising a compound of the present invention.

DETAILED DESCRIPTION OF THE INVENTION

I. Definitions

The following description sets forth exemplary methods, parameters and the like. It should be recognized, however, that such description is not intended as a limitation on the scope of the present disclosure but is instead provided as a description of exemplary embodiments.

The following description sets forth exemplary methods, parameters and the like. It should be recognized, however, that such description is not intended as a limitation on the scope of the present disclosure but is instead provided as a description of exemplary embodiments.

A dash ("-") that is not between two letters or symbols is used to indicate a point of attachment for a substituent. For example, —C(O)$NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A wavy line (  ) indicates a point of attachment.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. $—(CH_2)_3CH_3$), sec-butyl (i.e. $—CH(CH_3)CH_2CH_3$), isobutyl (i.e. $—CH_2CH(CH_3)_2$) and tert-butyl (i.e. $—C(CH_3)_3$); and "propyl" includes n-propyl (i.e. $—(CH_2)_2CH_3$) and isopropyl (i.e. $—CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Amino" refers to the group $—NR^yR^y$ wherein each $R^y$ is independently selected from the group consisting of hydrogen, alkyl, alkenyl, alkynyl, aryl, heterocyclyl, cycloalkyl or heteroaryl, each of which is optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-10}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cyano" refers to the group —CN.

"Keto" refers to a group C=O.

"Carbamoyl" refers to both an "O-carbamoyl" group which refers to the group $—O—C(O)NR^yR^z$ and an "N-carbamoyl" group which refers to the group $—NR^yC(O)OR^z$, wherein $R^y$ and $R^z$ are independently selected from the group consisting of hydrogen, alkyl, aryl, haloalkyl, or heteroaryl; each of which may be optionally substituted.

"Carboxyl" refers to —C(O)OH.

"Ester" refers to both —OC(O)R and —C(O)OR, wherein R is a substituent; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl ($—CHF_2$) and trifluoromethyl ($—CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, $—S(O)_2—$, and the like, where R is H, alkyl, aryl, cycloalkyl, heteroalkyl, heteroaryl or heterocyclyl, each of which may be optionally substituted. Examples of heteroalkyl groups include $—OCH_3$, $—CH_2OCH_3$, $—SCH_3$, $—CH_2SCH_3$, $—NRCH_3$, and $—CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo [1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" or "heterocycle" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bicyclic heterocyclyl groups, bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring atoms (i.e., 4-20 membered heterocyclyl), 2 to ring atoms (i.e., 4-12 membered heterocyclyl), 4 to 10 ring atoms (i.e., 4-10 membered heterocyclyl), 4 to 8 ring atoms (i.e., 4-8 membered heterocyclyl), or 4 to 6 ring carbon atoms (i.e., 4-6 membered heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more C═O and/or thiC═O groups. Examples of heterocyclyl groups include pyrrolidinyl, piperidinyl, piperazinyl, oxetanyl, diC═Olanyl, azetidinyl, azetidinyl, morpholinyl, thiomorpholinyl, 4-7 membered sultam, 4-7 membered cyclic carbamate, 4-7 membered cyclic carbonate, 4-7 membered cyclic sulfide and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro [3.4]octanyl, and 6-oxa-1-azaspiro[3.3]heptanyl. Examples of the fused-heterocyclyl rings include, but are not limited to, 1,2,3,4-tetrahydroisoquinolinyl, 1-C═O-1,2,3,4-tetrahydroisoquinolinyl, 1-C═O-1,2-dihydroisoquinolinyl, 4,5,6,7-tetrahydrothieno[2,3-c]pyridinyl, indolinyl, and isoindolinyl, where the heterocyclyl can be bound via either ring of the fused system. As used herein, a bicyclic heterocyclyl group is a heterocyclyl group attached at two points to another cyclic group, wherein the other cyclic group may itself be a heterocyclic group, or a carbocyclic group.

As used herein, the term "nitrogen or sulfur containing heterocyclyl" means a heterocyclyl moiety that contains at least one nitrogen atom or at least one sulfur atom, or both a nitrogen atom and a sulfur atom within the ring structure. It is to be understood that other heteroatoms, including oxygen, may be present in addition to the nitrogen, sulfur, or combinations thereof. Examples of nitrogen or sulfur containing heterocyclyls include morpholinyl, thiomorpholinyl, thiazolyl, isothiazolyl, oxazolidinone 1,2 dithiolyl, piperidinyl, piperazinyl, and the like.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Nitro" refers to the group $—NO_2$.

"Sulfonyl" refers to the group $—S(O)_2R$, where R is a substituent, or a defined group.

"Alkylsulfonyl" refers to the group $—S(O)_2R$, where R is a substituent, or a defined group.

"Alkylsulfinyl" refers to the group —S(O)R, where R is a substituent, or a defined group.

"Thiocyanate"-SCN.

"Thiol" refers to the group —SR, where R is a substituent, or a defined group.

"ThiC═O" or "thione" refer to the group (═S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl,"

then the general term can refer to any antecedent specifically recited term, such as ($C_{1-3}$ alkyl), ($C_{4-6}$ alkyl), —O($C_{1-4}$ alkyl), ($C_{3-10}$ cycloalkyl), O—($C_{3-10}$ cycloalkyl) and the like. For example, "any aryl" includes both "aryl" and "—O(aryl) as well as examples of aryl, such as phenyl or naphthyl and the like. Also, the term "any heterocyclyl" includes both the terms "heterocyclyl" and O-(heterocyclyl)," as well as examples of heterocyclyls, such as oxetanyl, tetrahydropyranyl, morpholino, piperidinyl and the like. In the same manner, the term "any heteroaryl" includes the terms "heteroaryl" and "O-(heteroryl)," as well as specific heteroaryls, such as pyridine and the like.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds may exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN$(alkyl)_2$), trialkyl amines (i.e., N$(alkyl)_3$), substituted alkyl amines (i.e., $NH_2$(substituted alkyl)), di(substituted alkyl) amines (i.e., HN$(substituted\ alkyl)_2$), tri (substituted alkyl) amines (i.e., N$(substituted\ alkyl)_3$), alkenyl amines (i.e., $NH_2$(alkenyl)), dialkenyl amines (i.e., HN$(alkenyl)_2$), trialkenyl amines (i.e., N$(alkenyl)_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, C═O, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl," then the general term can refer to any antecedent specifically recited term, such as ($C_{1-3}$ alkyl), ($C_{4-6}$ alkyl), —O($C_{1-4}$ alkyl), ($C_{3-10}$ cycloalkyl), O—($C_{3-10}$ cycloalkyl) and the like. For example, "any aryl" includes both "aryl" and "—O(aryl) as well as examples of aryl, such as phenyl or naphthyl and the like. Also, the term "any heterocyclyl" includes both the terms "heterocyclyl" and O-(heterocyclyl)," as well as examples of heterocyclyls, such as oxetanyl, tetrahydropyranyl, morpholino, piperidinyl and the like. In the same manner, the term "any heteroaryl" includes the terms "heteroaryl" and "O-(heteroaryl)," as well as specific heteroaryls, such as pyridine and the like.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, C═O, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

II. Combinations

Patients being treated by administration of the PARP7 inhibitors of the disclosure often exhibit diseases or conditions that benefit from treatment with other therapeutic agents. These diseases or conditions can be of an oncology nature or can be related to Inflammation, metabolic disorders, gastrointestinal disorders and the like. Thus, one aspect of the disclosure is a method of treating cancer, comprising administering a compound of the in combination with one or more compounds useful for the treatment of such diseases to a subject, particularly a human subject, in need thereof.

In some embodiments, a compound of the present disclosure is co-formulated with the additional one or more active ingredients. In some embodiments, the other active ingredient is administered at approximately the same time, in a separate dosage form. In some embodiments, the other active ingredient is administered sequentially, and may be administered at different times in relation to a compound of the present disclosure.

In some embodiments, a compound, or pharmaceutical composition provided herein, is administered with one or more (e.g., one, two, three, or four) additional therapeutic agents. In some embodiments the additional therapeutic agent includes, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (e.g., a mono- and multi-specific antibody, or fragment thereof, in any format, such as DART®, Duobody®, BiTE®, BiKE, TriKE, XmAb®, TandAb®, scFv, Fab, Fab derivative), a bi-specific antibody, a non-immunoglobulin antibody mimetic (e.g., including adnectin, affibody, affilin, affimer, affitin, alphabody, anticalin, peptide aptamer, armadillo repeat protein (ARM), atrimer, avimer, designed ankyrin repeat protein (DARPin®), fynomer, knottin, Kunitz domain peptide, monobody, and nanoCLAMPs), an antibody-drug conjugate (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, e.g., an inhibitor, agonist, antagonist, ligand, modulator, stimulator, blocker, activator or suppressor of a target (e.g., polypeptide or polynucleotide), such as: 2'-5'-oligoadenylate synthetase (OAS1; NCBI Gene ID: 4938); 5'-3' exoribonuclease 1 (XRN1; NCBI Gene ID: 54464); 5'-nucleotidase ecto (NT5E, CD73; NCBI Gene ID: 4907); ABL proto-oncogene 1, non-receptor tyrosine kinase (ABL1, BCR-ABL, c-ABL, v-ABL; NCBI Gene ID: 25); absent in melanoma 2 (AIM2; NCBI Gene ID: 9447); acetyl-CoA acyltransferase 2 (ACAA2; NCBI Gene ID: 10499); acid phosphatase 3 (ACP3; NCBI Gene ID: 55); adenosine deaminase (ADA, ADA1; NCBI Gene ID: 100); adenosine receptors (e.g., ADORA1 (A1), ADORA2A (A2a, A2AR), ADORA2B (A2b, A2BR), ADORA3 (A3); NCBI Gene IDs: 134, 135, 136, 137); AKT serine/threonine kinase 1 (AKT1, AKT, PKB; NCBI Gene ID: 207); alanyl aminopeptidase, membrane (ANPEP, CD13; NCBI Gene ID: 290); ALK receptor tyrosine kinase (ALK, CD242; NCBI Gene ID: 238); alpha fetoprotein (AFP; NCBI Gene ID: 174); amine oxidase copper containing (e.g., AOC1 (DA01), AOC2, AOC3 (VAP1); NCBI Gene IDs: 26, 314, 8639); androgen receptor (AR; NCBI Gene ID: 367); angiopoietins (ANGPT1, ANGPT2; NCBI Gene IDs: 284, 285); angiotensin II receptor type 1 (AGTR1; NCBI Gene ID: 185); angiotensinogen (AGT; NCBI Gene ID: 183); apolipoprotein A1 (APOA1; NCBI Gene ID: 335); apoptosis inducing factor mitochondria associated 1 (AIFM1, AIF; NCBI Gene ID: 9131); arachidonate 5-lipoxygenase (ALOX5; NCBI Gene ID: 240); asparaginase (ASPG; NCBI Gene ID:

374569); asteroid homolog 1 (ASTE1; NCBI Gene ID: 28990); ATM serine/threonine kinase (ATM; NCBI Gene ID: 472); ATP binding cassette subfamily B member 1 (ABCB1, CD243, GP170; NCBI Gene ID: 5243); ATP-dependent Clp-protease (CLPP; NCBI Gene ID: 8192); ATR serine/threonine kinase (ATR; NCBI Gene ID: 545); AXL receptor tyrosine kinase (AXL; NCBI Gene ID: 558); B and T lymphocyte associated (BTLA, CD272; NCBI Gene ID: 151888); baculoviral IAP repeat containing proteins (BIRC2 (cIAP1), BIRC3 (cIAP2), XIAP (BIRC4, IAP3), BIRC5 (survivin); NCBI Gene IDs: 329, 330, 331, 332); basigin (Ok blood group) (BSG, CD147; NCBI Gene ID: 682); B-cell lymphoma 2 (BCL2; NCBI Gene ID: 596); BCL2 binding component 3 (BBC3, PUMA; NCBI Gene ID: 27113); BCL2 like (e.g., BCL2L1 (Bcl-x), BCL2L2 (BIM); Bcl-x; NCBI Gene IDs: 598, 10018); beta 3-adrenergic receptor (ADRB3; NCBI Gene ID: 155); bone gamma-carboxyglutamate protein (BGLAP; NCBI Gene ID: 632); bone morphogenetic protein-10 ligand (BMP10; NCBI Gene ID: 27302); bradykinin receptors (e.g., BDKRB1, BDKRB2; NCBI Gene IDs: 623, 624); B-RAF (BRAF; NCBI Gene ID: 273); breakpoint cluster region (BCR; NCBI Gene ID: 613); bromodomain and external domain (BET) bromodomain containing proteins (e.g., BRD2, BRD3, BRD4, BRDT; NCBI Gene IDs: 6046, 8019, 23476, 676); Bruton's tyrosine kinase (BTK; NCBI Gene ID: 695); cadherins (e.g., CDH3 (p-cadherin), CDH6 (k-cadherin); NCBI Gene IDs: 1001, 1004); cancer/testis antigens (e.g., CTAG1A, CTAG1B, CTAG2; NCBI Gene IDs: 1485, 30848, 246100); cannabinoid receptors (e.g., CNR1 (CB1), CNR2 (CB2); NCBI Gene IDs: 1268, 1269); carbohydrate sulfotransferase 15 (CHST15; NCBI Gene ID: 51363); carbonic anhydrases (e.g., CA1, CA2, CA3, CA4, CA5A, CA5B, CA6, CA7, CA8, CA9, CA10, CA11, CA12, CA13, CA14; NCBI Gene IDs: 759, 760, 761, 762, 763, 765, 766, 767, 768, 770, 771, 11238, 23632, 56934, 377677); carcinoembryonic antigen related cell adhesion molecules (e.g., CEACAM3 (CD66d), CEACAM5 (CD66e), CEACAM6 (CD66c); NCBI Gene IDs: 1048, 1084, 4680); casein kinases (e.g., CSNK1A1 (CK1), CSNK2A1 (CK2); NCBI Gene IDs: 1452, 1457); caspases (e.g., CASP3, CASP7, CASP8; NCBI Gene IDs: 836, 840, 841, 864); catenin beta 1 (CTNNB1; NCBI Gene ID: 1499); cathepsin G (CTSG; NCBI Gene ID: 1511); Cbl proto-oncogene B (CBLB, Cbl-b; NCBI Gene ID: 868); C—C motif chemokine ligand 21 (CCL21; NCBI Gene ID: 6366); C—C motif chemokine receptor 2 (CCR2; NCBI Gene ID: 729230); C—C motif chemokine receptors (e.g., CCR3 (CD193), CCR4 (CD194), CCR5 (CD195), CCR8 (CDw198); NCBI Gene IDs: 1232, 1233, 1234, 1237); CCAAT enhancer binding protein alpha (CEBPA, CEBP; NCBI Gene ID: 1050); cell adhesion molecule 1 (CADM1; NCBI Gene ID: 23705); cell division cycle 7 (CDC7; NCBI Gene ID: 8317); cellular communication network factor 2 (CCN2; NCBI Gene ID: 1490); cereblon (CRBN; NCBI Gene ID: 51185); checkpoint kinases (e.g., CHEK1 (CHK1), CHEK2 (CHK2); NCBI Gene IDs: 1111, 11200); cholecystokinin B receptor (CCKBR; NCBI Gene ID: 887); chorionic somatomammotropin hormone 1 (CSH1; NCBI Gene ID: 1442); claudins (e.g., CLDN6, CLDN18; NCBI Gene IDs: 9074, 51208); cluster of differentiation markers (e.g., CD1A, CD1C, CD1D, CD1E, CD2, CD3 alpha (TRA), CD beta (TRB), CD gamma (TRG), CD delta (TRD), CD4, CD8A, CD8B, CD19, CD20 (MS4A1), CD22, CD24, CD25 (IL2RA, TCGFR), CD28, CD33 (SIGLEC3), CD37, CD38, CD39 (ENTPD1), CD40 (TNFRSF5), CD44 (MIC4, PGP1), CD47 (IAP), CD48 (BLASTI), CD52, CD55 (DAF), CD58 (LFA3), CD74, CD79a, CD79b, CD80 (B7-1), CD84, CD86 (B7-2), CD96 (TACTILE), CD99 (MIC2), CD115 (CSF1R), CD116 (GMCSFR, CSF2RA), CD122 (IL2RB), CD123 (IL3RA), CD128 (IL8R1), CD132 (IL2RG), CD135 (FLT3), CD137 (TNFRSF9, 4-1BB), CD142 (TF, TFA), CD152 (CTLA4), CD160, CD182 (IL8R2), CD193 (CCR3), CD194 (CCR4), CD195 (CCR5), CD207, CD221 (IGF1R), CD222 (IGF2R), CD223 (LAG3), CD226 (DNAM1), CD244, CD247, CD248, CD276 (B7-H3), CD331 (FGFR1), CD332 (FGFR2), CD333 (FGFR3), CD334 (FGFR4); NCBI Gene IDs: 909, 911, 912, 913, 914, 919, 920, 923, 925, 926, 930, 931, 933, 940, 941, 942, 945, 951, 952, 953, 958,960, 961, 962, 965, 972, 973, 974, 1043, 1232, 1233, 1234, 1237, 1436, 1438, 1493, 1604, 2152, 2260, 2261, 2263, 2322, 3480, 3482, 3559, 3560, 3561, 3563, 3577, 3579, 3604, 3902, 4267, 6955, 6957, 6964, 6965, 8832, 10666, 11126, 50489, 51744, 80381, 100133941); clusterin (CLU; NCBI Gene ID: 1191); coagulation factors (e.g., F7, FXA; NCBI Gene IDs: 2155, 2159); collagen type IV alpha chains (e.g., COL4A1, COL4A2, COL4A3, COL4A4, COL4A5; NCBI Gene IDs: 1282, 1284, 1285, 1286, 1287); collectin subfamily member 10 (COLEC10; NCBI Gene ID: 10584); colony stimulating factors (e.g., CSF1 (MCSF), CSF2 (GMCSF), CSF3 (GCSF); NCBI Gene IDs: 1435, 1437, 1440); complement factors (e.g., C3, C5; NCBI Gene IDs: 718, 727); COP9 signalosome subunit 5 (COPS5; NCBI Gene ID: 10987); C-type lectin domain family member (e.g., CLEC4C (CD303), CLEC9A (CD370), CLEC12A (CD371); CD371; NCBI Gene ID: 160364, 170482, 283420); C—X—C motif chemokine ligand 12 (CXCL12; NCBI Gene ID: 6387); C—X—C motif chemokine receptors (CXCR1 (IL8R1, CD128), CXCR2 (IL8R2, CD182), CXCR3 (CD182, CD183, IP-10R), CXCR4 (CD184); NCBI Gene ID: 2833, 3577, 3579, 7852); cyclin D1 (CCND1, BCL1; NCBI Gene ID: 595); cyclin dependent kinases (e.g., CDK1, CDK2, CDK3, CDK4, CDK5, CDK6, CDK7, CDK8, CDK9, CDK10, CDK12; NCBI Gene ID: 983, 1017, 1018, 1019, 1020, 1021, 1022, 1024, 1025, 8558, 51755); cyclin G1 (CCNG1; NCBI Gene ID: 900); cytochrome P450 family members (e.g., CYP2D6, CYP3A4, CYP11A1, CYP11B2, CYP17A1, CYP19A1, CYP51A1; NCBI Gene IDs: 1565, 1576, 1583, 1585, 1586, 1588, 1595); cytochrome P450 oxidoreductase (POR; NCBI Gene ID: 5447); cytokine inducible SH2 containing protein (CISH; NCBI Gene ID: 1154); cytotoxic T-lymphocyte associated protein 4 (CTLA4, CD152; NCBI Gene ID: 1493); DEAD-box helicases (e.g., DDX5, DDX6, DDX58; NCBI Gene IDs: 1655, 1656, 23586); delta like canonical Notch ligands (e.g., DLL3, DLL4; NCBI Gene IDs: 10683, 54567); diablo IAP-binding mitochondrial protein (DIABLO, SMAC; NCBI Gene ID: 56616); diacylglycerol kinases (e.g., DGKA, DGKZ; NCBI Gene IDs: 1606, 8525); dickkopf WNT signaling pathway inhibitors (e.g., DKK1, DKK3; NCBI Gene ID: 22943, 27122); dihydrofolate reductase (DHFR; NCBI Gene ID: 1719); dihydropyrimidine dehydrogenase (DPYD; NCBI Gene ID: 1806); dipeptidyl peptidase 4 (DPP4; NCBI Gene ID: 1803); discoidin domain receptor tyrosine kinases (e.g., DDR1 (CD167), DDR2; CD167; NCBI Gene ID: 780, 4921); DNA dependent protein kinase (PRKDC; NCBI Gene ID: 5591); DNA topoisomerases (e.g., TOP1, TOP2A, TOP2B, TOP3A, TOP3B; NCBI Gene ID: 7150, 7153, 7155, 7156, 8940); dopachrome tautomerase (DCT; NCBI Gene ID: 1638); dopamine receptor D2 (DRD2; NCBI Gene ID: 1318); DOT1 like histone lysine methyltransferase (DOT1L; NCBI Gene ID: 84444); ectonucleotide pyrophosphatase/phosphodiesterase 3 (ENPP3, CD203c; NCBI Gene ID: 5169); EMAP like 4

(EML4; NCBI Gene ID: 27436); endoglin (ENG; NCBI Gene ID: 2022); endoplasmic reticulum aminopeptidases (e.g., ERAP1, ERAP2; NCBI Gene ID: 51752, 64167); enhancer of zeste 2 polycomb repressive complex 2 subunit (EZH2; NCBI Gene ID: 2146); ephrin receptors (e.g., EPHA1, EPHA2EPHA3, EPHA4, EPHA5, EPHA7, EPHB4; NCBIGene ID:1969, 2041, 2042, 2043, 2044, 2045, 2050); ephrins (e.g., EFNA1, EFNA4, EFNB2; NCBI Gene ID: 1942, 1945, 1948); epidermal growth factor receptors (e.g., ERBB1 (HER1, EGFR), ERBB1 variant III (EGFRvIII), ERBB2 (HER2, NEU, CD340), ERBB3 (HER3), ERBB4 (HER4); NCBI Gene ID: 1956, 2064, 2065, 2066); epithelial cell adhesion molecule (EPCAM; NCBI Gene ID: 4072); epithelial mitogen (EPGN; NCBI Gene ID: 255324); eukaryotic translation elongation factors (e.g., EEF1A2, EEF2; NCBI Gene ID: 1917, 1938); eukaryotic translation initiation factors (e.g., EIF4A1, EIF5A; NCBI Gene ID: 1973, 1984); exportin-1 (XPO1; NCBI Gene ID: 7514); farnesoid X receptor (NR1H4, FXR; NCBI Gene ID: 9971); Fas ligand (FASLG, FASL, CD95L, CD178, TNFSF6; NCBI Gene ID: 356); fatty acid amide hydrolase (FAAH; NCBI Gene ID: 2166); fatty acid synthase (FASN; FAS; NCBI Gene ID: 2194); Fc fragment of Ig receptors (e.g., FCER1A, FCGRT, FCGR3A (CD16); NCBI Gene IDs: 2205, 2214, 2217); Fc receptor like 5 (FCRL5, CD307; NCBI Gene ID: 83416); fibroblast activation protein alpha (FAP; NCBI Gene ID: 2191); fibroblast growth factor receptors (e.g., FGFR1 (CD331), FGFR2 (CD332), FGFR3 (CD333), FGFR4 (CD334); NCBI Gene IDs: 2260, 2261, 2263, 2264); fibroblast growth factors (e.g., FGF1 (FGF alpha), FGF2 (FGF beta), FGF4, FGF5; NCBI Gene IDs: 2246, 2247, 2249, 2250); fibronectin 1 (FN1, MSF; NCBI Gene ID: 2335); fms related receptor tyrosine kinases (e.g., FLT1 (VEGFR1), FLT3 (STK1, CD135), FLT4 (VEGFR2); NCBI Gene IDs: 2321, 2322, 2324); fms related receptor tyrosine kinase 3 ligand (FLT3LG; NCBI Gene ID: 2323); focal adhesion kinase 2 (PTK2, FAK1; NCBI Gene ID: 5747); folate hydrolase 1 (FOLH1, PSMA; NCBI Gene ID: 2346); folate receptor 1 (FOLR1; NCBI Gene ID: 2348); forkhead box protein M1 (FOXM1; NCBI Gene ID: 2305); FURIN (FURIN, PACE; NCBI Gene ID: 5045); FYN tyrosine kinase (FYN, SYN; NCBI Gene ID: 2534); galectins (e.g., LGALS3, LGALS8 (PCTA1), LGALS9; NCBI Gene ID: 3958, 3964, 3965); glucocorticoid receptor (NR3C1, GR; NCBI Gene ID: 2908); glucuronidase beta (GUSB; NCBI Gene ID: 2990); glutamate metabotropic receptor 1 (GRM1; NCBI Gene ID: 2911); glutaminase (GLS; NCBI Gene ID: 2744); glutathione S-transferase Pi (GSTP1; NCBI Gene ID: 2950); glycogen synthase kinase 3 beta (GSK3B; NCBI Gene ID: 2932); glypican 3 (GPC3; NCBI Gene ID: 2719); gonadotropin releasing hormone 1 (GNRH1; NCBI Gene ID: 2796); gonadotropin releasing hormone receptor (GNRHR; NCBI Gene ID: 2798); GPNMB glycoprotein nmb (GPNMB, osteoactivin; NCBI Gene ID: 10457); growth differentiation factor 2 (GDF2, BMP9; NCBI Gene ID: 2658); growth factor receptor-bound protein 2 (GRB2, ASH; NCBI Gene ID: 2885); guanylate cyclase 2C (GUCY2C, STAR, MECIL, MUCIL, NCBI Gene ID: 2984); H19 imprinted maternally expressed transcript (H19; NCBI Gene ID: 283120); HCK proto-oncogene, Src family tyrosine kinase (HCK; NCBI Gene ID: 3055); heat shock proteins (e.g., HSPA5 (HSP70, BIP, GRP78), HSPB1 (HSP27), HSP90B1 (GP96); NCBI Gene IDs: 3309, 3315, 7184); heme oxygenases (e.g., HMOX1 (HO1), HMOX2 (HO1); NCBI Gene ID: 3162, 3163); heparanase (HPSE; NCBI Gene ID: 10855); hepatitis A virus cellular receptor 2 (HAVCR2, TIM3, CD366; NCBI Gene ID: 84868); hepatocyte growth factor (HGF; NCBI Gene ID: 3082); HERV-H LTR-associating 2 (HHLA2, B7-H7; NCBI Gene ID: 11148); histamine receptor H2 (HRH2; NCBI Gene ID: 3274); histone deacetylases (e.g., HDAC1, HDAC7, HDAC9; NCBI Gene ID: 3065, 9734, 51564); HRas proto-oncogene, GTPase (HRAS; NCBI Gene ID: 3265); hypoxia-inducible factors (e.g., HIF1A, HIF2A (EPAS1); NCBI Gene IDs: 2034, 3091); I-Kappa-B kinase (IKK beta; NCBI Gene IDs: 3551, 3553); IKAROS family zinc fingers (IKZF1 (LYF1), IKZF3; NCBI Gene ID: 10320, 22806); immunoglobulin superfamily member 11 (IGSF11; NCBI Gene ID: 152404); indoleamine 2,3-dioxygenases (e.g., IDO1, ID02; NCBI Gene IDs: 3620, 169355); inducible T cell costimulator (ICOS, CD278; NCBI Gene ID: 29851); inducible T cell costimulator ligand (ICOSLG, B7-H2; NCBI Gene ID: 23308); insulin like growth factor receptors (e.g., IGF1R, IGF2R; NCBI Gene ID: 3480, 3482); insulin like growth factors (e.g., IGF1, IGF2; NCBI Gene IDs: 3479, 3481); insulin receptor (INSR, CD220; NCBI Gene ID: 3643); integrin subunits (e.g., ITGA5 (CD49e), ITGAV (CD51), ITGB1 (CD29), ITGB2 (CD18, LFA1, MAC1), ITGB7; NCBI Gene IDs: 3678, 3685, 3688, 3695, 3698); intercellular adhesion molecule 1 (ICAM1, CD54; NCBI Gene ID: 3383); interleukin 1 receptor associated kinase 4 (IRAK4; NCBI Gene ID: 51135); interleukin receptors (e.g., IL2RA (TCGFR, CD25), IL2RB (CD122), IL2RG (CD132), IL3RA, IL6R, IL13RA2 (CD213A2), IL22RA1; NCBI Gene IDs: 3598, 3559, 3560, 3561, 3563, 3570, 58985); interleukins (e.g., IL1A, IL1B, IL2, IL3, IL6 (HGF), IL7, IL8 (CXCL8), IL10 (TGIF), IL12A, IL12B, IL15, IL17A (CTLA8), IL18, IL23A, IL24, IL-29 (IFNL1); NCBI Gene IDs: 3552, 3553, 3558, 3562, 3565, 3569, 3574, 3586, 3592, 3593, 3600, 3605, 3606, 11009, 51561, 282618); isocitrate dehydrogenases ($NADP(+)_1$) (e.g., IDH1, IDH2; NCBI Gene IDs: 3417, 3418); Janus kinases (e.g., JAK1, JAK2, JAK3; NCBI Gene IDs: 3716, 3717, 3718); kallikrein related peptidase 3 (KLK3; NCBI Gene ID: 354); killer cell immunoglobulin like receptor, Ig domains and long cytoplasmic tails (e.g., KIR2DL1 (CD158A), KIR2DL2 (CD158B1), KIR2DL3 (CD158B), KIR2DL4 (CD158D), KIR2DL5A (CD158F), KIR2DL5B, KIR3DL1 (CD158E1), KIR3DL2 (CD158K), KIR3DP1 (CD158c), KIR2DS2 (CD158J); NCBI Gene IDs: 3802, 3803, 3804, 3805, 3811, 3812, 57292, 553128, 548594, 100132285); killer cell lectin like receptors (e.g., KLRC1 (CD159A), KLRC2 (CD159c), KLRC3, KLRRC4, KLRD1 (CD94), KLRG1, KLRK1 (NKG2D, CD314); NCBI Gene IDs: 3821, 3822, 3823, 3824, 8302, 10219, 22914); kinase insert domain receptor (KDR, CD309, VEGFR2; NCBI Gene ID: 3791); kinesin family member 11 (KIF11; NCBI Gene ID: 3832); KiSS-1 metastasis suppressor (KISS1; NCBI Gene ID: 3814); KIT proto-oncogene, receptor tyrosine kinase (KIT, C-KIT, CD117; NCBI Gene ID: 3815); KRAS proto-oncogene, GTPase (KRAS; NCBI Gene ID: 3845); lactotransferrin (LTF; NCBI Gene ID: 4057); LCK proto-oncogene, Src family tyrosine kinase (LCK; NCBI Gene ID: 3932); LDL receptor related protein 1 (LRP1, CD91, IGFBP3R; NCBI Gene ID: 4035); leucine rich repeat containing 15 (LRRC15; NCBI Gene ID: 131578); leukocyte immunoglobulin like receptors (e.g., LILRB1 (ILT2, CD85J), LILRB2 (ILT4, CD85D); NCBI Gene ID: 10288, 10859); leukotriene A4 hydrolase (LTA4H; NCBI Gene ID: 4048); linker for activation of T-cells (LAT; NCBI Gene ID: 27040); luteinizing hormone/choriogonadotropin receptor (LHCGR; NCBI Gene ID: 3973); LY6/PLAUR domain containing 3 (LYPD3; NCBI Gene ID: 27076); lymphocyte activating 3 (LAG3; CD223; NCBI Gene ID: 3902); lymphocyte antigens (e.g., LY9 (CD229), LY75 (CD205); NCBI Gene IDs: 4063, 17076); LYN proto-oncogene, Src family tyrosine kinase (LYN; NCBI Gene ID: 4067); lypmphocyte cytosolic protein 2 (LCP2; NCBI Gene ID: 3937); lysine demethylase 1A (KDM1A; NCBI Gene ID: 23028); lysophosphatidic acid receptor 1 (LPAR1, EDG2, LPA1, GPR26; NCBI Gene ID: 1902); lysyl oxidase (LOX; NCBI Gene ID: 4015); lysyl oxidase like 2 (LOXL2; NCBI Gene ID: 4017); macrophage migration inhibitory factor (MIF, GIF; NCBI Gene ID: 4282); macrophage stimulating 1 receptor (MST1R, CD136; NCBI Gene ID: 4486); MAGE family members (e.g., MAGEA1, MAGEA2, MAGEA2B, MAGEA3, MAGEA4, MAGEA5, MAGEA6, MAGEA10, MAGEA11, MAGEC1, MAGEC2, MAGED1, MAGED2; NCBI Gene IDs: 4100, 4101, 4102, 4103, 4104, 4105, 4109, 4110, 9500, 9947, 10916, 51438, 266740); major histocompatibility complexes (e.g., HLA-A, HLA-E, HLA-F, HLA-G; NCBI Gene IDs: 3105, 3133, 3134, 3135); major vault protein (MVP, VAULTI; NCBI Gene ID: 9961); MALT1 paracaspase (MALT1; NCBI Gene ID: 10892); MAPK activated protein kinase 2 (MAPKAPK2; NCBI Gene ID: 9261); MAPK interacting serine/threonine kinases (e.g., MKNK1, MKNK2; NCBI Gene IDs: 2872, 8569); matrix metallopeptidases (e.g., MMP1, MMP2, MMP3, MMP7, MMP8, MMP9, MMP10, MMP11, MMP12, MMP13, MMP14, MMP15, MMP16, MMP17, MMP19, MMP20, MMP21, MMP24, MMP25, MMP26, MMP27, MMP28; NCBI Gene IDs: 4312, 4313, 4314, 4316, 4317, 4318, 4319, 4320, 4321, 4322, 4323, 4324, 4325, 4326, 4327, 9313, 10893, 56547, 64066, 64386, 79148, 118856); MCL1 apoptosis regulator, BCL2 family member (MCL1; NCBI Gene ID: 4170); MDM2 proto-oncogene (MDM2; NCBI Gene ID: 4193); MDM4 regulator of p53 (MDM4; BMFS6; NCBI Gene ID: 4194); mechanistic target of rapamycin kinase (MTOR, FRAP1; NCBI Gene ID: 2475); melan-A (MLANA; NCBI Gene ID: 2315); melanocortin receptors (MC1R, MC2R; NCBI Gene IDs: 4157, 4148); MER proto-oncogene, tyrosine kinase (MERTK; NCBI Gene ID: 10461); mesothelin (MSLN; NCBI Gene ID: 10232); MET proto-oncogene, receptor tyrosine kinase (MET, c-Met, HGFR; NCBI Gene ID: 4233); methionyl aminopeptidase 2 (METAP2, MAP2; NCBI Gene ID: 10988); MHC class I polypeptide-related sequences (e.g., MICA, MICB; NCBI Gene IDs: 4277, 100507436); mitogen activated protein kinases (e.g., MAPK1 (ERK2), MAPK3 (ERK1), MAPK8 (JNK1), MAPK9 (JNK2), MAPK10 (JNK3), MAPK11 ($p^{38}$ beta), MAPK12; NCBI Gene IDs: 5594, 5595, 5599, 5600, 5601, 5602, 819251); mitogen-activated protein kinase kinase kinases (e.g., MAP3K5 (ASK1), MAP3K8 (TPL2, AURA2); NCBI Gene IDs: 4217, 1326); mitogen-activated protein kinase kinase kinase kinase 1 (MAP4K1, HPK1; NCBI Gene ID: 11184); mitogen-activated protein kinase kinases (e.g., MAP2K1 (MEK1), MAP2K2 (MEK2), MAP2K7 (MEK7); NCBI Gene IDs: 5604, 5605, 5609); MPL proto-oncogene, thrombopoietin receptor (MPL; NCBI Gene ID: 4352); mucins (e.g., MUC1 (including splice variants thereof (e.g., including MUC1/A, C, D, X, Y, Z and REP)), MUC5AC, MUC16 (CA125); NCBI Gene IDs: 4582, 4586, 94025); MYC proto-oncogene, bHLH transcription factor (MYC; NCBI Gene ID: 4609); myostatin (MSTN, GDF8; NCBI Gene ID: 2660); myristoylated alanine rich protein kinase C substrate (MARCKS; NCBI Gene ID: 4082); natriuretic peptide receptor 3 (NPR3; NCBI Gene ID: 4883); natural killer cell cytotoxicity receptor 3 ligand 1 (NCR3LG1, B7-H6; NCBI Gene ID: 374383); necdin, MAGE family member (NDN; NCBI Gene ID: 4692); nectin cell adhesion molecules (e.g., NECTIN2 (CD112, PVRL2), NECTIN4 (PVRL4); NCBI Gene IDs: 5819, 81607); neural cell adhesion molecule 1 (NCAM1, CD56; NCBI Gene ID: 4684); neuropilins (e.g., NRP1 (CD304, VEGF165R), NRP2 (VEGF165R2); NCBI Gene IDs: 8828, 8829); neurotrophic receptor tyrosine kinases (e.g., NTRK1 (TRKA), NTRK2 (TRKB), NTRK3 (TRKC); NCBI Gene IDs: 4914, 4915, 4916); NFKB activating protein (NKAP; NCBI Gene ID: 79576); NIMA related kinase 9 (NEK9; NCBI Gene ID: 91754); NLR family pyrin domain containing 3 (NLRP3, NALP3; NCBI Gene ID: 114548); notch receptors (e.g., NOTCH1, NOTCH2, NOTCH3, NOTCH4; NCBI Gene IDs: 4851, 4853, 4854, 4855); NRAS proto-oncogene, GTPase (NRAS; NCBI Gene ID: 4893); nuclear factor kappa B (NFKB1, NFKB2; NCBI Gene IDs: 4790, 4791); nuclear factor, erythroid 2 like 2 (NFE2L2; NRF2; NCBI Gene ID: 4780); nuclear receptor subfamily 4 group A member 1 (NR4A1; NCBI Gene ID: 3164); nucleolin (NCL; NCBI Gene ID: 4691); nucleophosmin 1 (NPM1; NCBI Gene ID: 4869); nucleotide binding oligomerization domain containing 2 (NOD2; NCBI Gene ID: 64127); nudix hydrolase 1 (NUDT1; NCBI Gene ID: 4521); O-6-methylguanine-DNA methyltransferase (MGMT; NCBI Gene ID: 4255); opioid receptor delta 1 (OPRD1; NCBI Gene ID: 4985); ornithine decarboxylase 1 (ODC1; NCBI Gene ID: 4953); C=Oglutarate dehydrogenase (OGDH; NCBI Gene ID: 4967); parathyroid hormone (PTH; NCBI Gene ID: 5741); PD-L1 (CD274; NCBI Gene ID: 29126); periostin (POSTN; NCBI Gene ID: 10631); peroxisome proliferator activated receptors (e.g., PPARA (PPAR alpha), PPARD (PPAR delta), PPARG (PPAR gamma); NCBI Gene IDs: 5465, 5467, 5468); phosphatase and tensin homolog (PTEN; NCBI Gene ID: 5728); phosphatidylinositol-4,5-bisphosphate 3-kinases (PIK3CA (PI3K alpha), PIK3CB (PI3K beta), PIK3CD (PI3K delta), PIK3CG (PI3K gamma); NCBI Gene IDs: 5290, 5291, 5293, 5294); phospholipases (e.g., PLA2G1B, PLA2G2A, PLA2G2D, PLA2G3, PLA2G4A, PLA2G5, PLA2G7, PLA2G10, PLA2G12A, PLA2G12B, PLA2G15; NCBI Gene IDs: 5319, 5320, 5321, 5322, 7941, 8399, 50487, 23659, 26279, 81579, 84647); Pim proto-oncogene, serine/threonine kinases (e.g., PIM1, PIM2, PIM3; NCBI Gene IDs: 5292, 11040, 415116); placenta growth factor (PGF; NCBI Gene ID: 5228); plasminogen activator, urokinase (PLAU, u-PA, ATF; NCBI Gene ID: 5328); platelet derived growth factor receptors (e.g., PDGFRA (CD140A, PDGFR2), FDGFRB (CD140B, PDGFR1); NCBI Gene IDs: 5156, 5159); plexin B1 (PLXNB1; NCBI Gene ID: 5364); poliovirus receptor (PVR) cell adhesion molecule (PVR, CD155; NCBI Gene ID: 5817); polo like kinase 1 (PLK1; NCBI Gene ID: 5347); poly(ADP-ribose) polymerases (e.g., PARP1, PARP2, PARP3; NCBI Gene IDs: 142, 10038, 10039); polycomb protein EED (EED; NCBI Gene ID: 8726); porcupine O-acyltransferase (PORCN; NCBI Gene ID: 64840); PRAME nuclear receptor transcriptional regulator (PRAME; NCBI Gene ID: 23532); premelanosome protein (PMEL; NCBI Gene ID: 6490); progesterone receptor (PGR; NCBI Gene ID: 5241); programmed cell death 1 (PDCD1, PD-1, CD279; NCBI Gene ID: 5133); programmed cell death 1 ligand 2 (PDCDILG2, CD273, PD-L2; NCBI Gene ID: 80380); prominin 1 (PROM1, CD133; NCBI Gene ID: 8842); promyelocytic leukemia (PML; NCBI Gene ID: 5371); prosaposin (PSAP; NCBI Gene ID: 5660); prostaglandin E receptor 4 (PTGER4; NCBI Gene ID: 5734); prostaglandin E synthase (PTGES; NCBI Gene ID: 9536); prostaglandin-endoperoxide synthases (PTGS1 (COX1), PTGS2 (COX2); NCBI Gene ID: 5742, 5743); proteasome 20S subunit beta 9 (PSMB9; NCBI Gene ID: 5698); protein arginine methyltransferases (e.g., PRMT1, PRMT5; NCBI Gene ID: 3276, 10419); protein kinase $N_3$ (PKN3; NCBI Gene ID: 29941); protein phosphatase 2A (PPP2CA; NCBI Gene ID: 5515); protein tyrosine kinase 7 (inactive) (PTK7; NCBI Gene ID: 5754); protein tyrosine phosphatase receptors (PTPRB (PTPB), PTPRC (CD45R); NCBI Gene ID: 5787, 5788); prothymosin alpha (PTMA; NCBI Gene ID: 5757); purine nucleoside phosphorylase (PNP; NCBI Gene ID: 4860); purinergic receptor P2X 7 (P2RX7; NCBI Gene ID: 5027); PVR related immunoglobulin domain containing (PVRIG, CD112R; NCBI Gene ID: 79037); Raf-1 proto-oncogene, serine/threonine kinase (RAF1, c-Raf; NCBI Gene ID: 5894); RAR-related orphan receptor gamma (RORC; NCBI Gene ID: 6097); ras homolog family member C (RHOC); NCBI Gene ID: 389); Ras homolog, mTORC1 binding (RHEB; NCBI Gene ID: 6009); RB transcriptional corepressor 1 (RB1; NCBI Gene ID: 5925); receptor-interacting serine/threonine protein kinase 1 (RIPK1; NCBI Gene ID: 8737); ret proto-oncogene (RET; NCBI Gene ID: 5979); retinoic acid early transcripts (e.g., RAET1E, RAET1G, RAET1L; NCBI Gene IDs: 135250, 154064, 353091); retinoic acid receptors alpha (e.g., RARA, RARG; NCBI Gene IDs: 5914, 5916); retinoid X receptors (e.g., RXRA, RXRB, RXRG; NCBI Gene IDs: 6256, 6257, 6258); Rho associated coiled-coil containing protein kinases (e.g., ROCK1, ROCK2; NCBI Gene IDs: 6093, 9475); ribosomal protein S6 kinase B1 (RPS6KB1, S6K-beta 1; NCBI Gene ID: 6198); ring finger protein 128 (RNF128, GRAIL; NCBI Gene ID: 79589); ROS proto-oncogene 1, receptor tyrosine kinase (ROS1; NCBI Gene ID: 6098); roundabout guidance receptor 4 (ROBO4; NCBI Gene ID: 54538); RUNX family transcription factor 3 (RUNX3; NCBI Gene ID: 864); S100 calcium binding protein A9 (S100A9; NCBI Gene ID: 6280); secreted frizzled related protein 2 (SFRP2; NCBI Gene ID: 6423); secreted phosphoprotein 1 (SPP1; NCBI Gene ID: 6696); secretoglobin family 1A member 1 (SCGB1A1; NCBI Gene ID: 7356); selectins (e.g., SELE, SELL (CD62L), SELP (CD62); NCBI Gene IDs: 6401, 6402, 6403); semaphorin 4D (SEMA4D; CD100; NCBI Gene ID: 10507); sialic acid binding Ig like lectins (SIGLEC7 (CD328), SIGLEC9 (CD329), SIGLEC10; NCBI Gene ID: 27036, 27180, 89790); signal regulatory protein alpha (SIRPA, CD172A; NCBI Gene ID: 140885); signal transducer and activator of transcription (e.g., STAT1, STAT3, STATSA, STATSB; NCBI Gene IDs: 6772, 6774, 6776, 6777); sirtuin-3 (SIRT3; NCBI Gene ID: 23410); signaling lymphocytic activation molecule (SLAM) family members (e.g., SLAMF1 (CD150), SLAMF6 (CD352), SLAMF7 (CD319), SLAMF8 (CD353), SLAMF9; NCBI Gene IDs: 56833, 57823, 89886, 114836); SLIT and NTRK like family member 6 (SLITRK6; NCBI Gene ID: 84189); smoothened, frizzled class receptor (SMO; NCBI Gene ID: 6608); soluble epoxide hydrolase 2 (EPHX2; NCBI Gene ID: 2053); solute carrier family members (e.g., SLC3A2 (CD98), SLC5A5, SLC6A2, SLC10A3, SLC34A2, SLC39A6, SLC43A2 (LAT4), SLC44A4; NCBI Gene IDs: 6520, 6528, 6530, 8273, 10568, 25800, 80736, 124935); somatostatin receptors (e.g., SSTR1, SSTR2, SSTR3, SSTR4, SSTR5; NCBI Gene IDs: 6751, 6752, 6753, 6754, 6755); sonic hedgehog signaling molecule (SHH; NCBI Gene ID: 6469); Sp1 transcription factor (SP1; NCBI Gene ID: 6667); sphingosine kinases (e.g., SPHK1, SPHK2; NCBI Gene IDs: 8877, 56848); sphingosine-1-phosphate receptor 1 (S1PR1, CD363; NCBI Gene ID: 1901); spleen associated tyrosine kinase (SYK; NCBI Gene ID: 6850); splicing factor 3B factor 1 (SF3B1; NCBI Gene ID: 23451); SRC proto-oncogene, non-receptor tyrosine kinase (SRC; NCBI Gene ID: 6714); stabilin 1 (STAB1, CLEVER-1; NCBI Gene ID: 23166); STEAP family member 1 (STEAPI; NCBI Gene ID: 26872); steroid sulfatase (STS; NCBI Gene ID: 412); stimulator of interferon response cGAMP interactor 1 (STINGI; NCBI Gene ID: 340061); superoxide dismutase 1 (SOD1, ALS1; NCBI Gene ID: 6647); suppressors of cytokine signaling (SOCS1 (CISH1), SOCS3 (CISH3); NCBI Gene ID: 8651, 9021); synapsin 3 (SYN3; NCBI Gene ID: 8224); syndecan 1 (SDC1, CD138, syndecan; NCBI Gene ID: 6382); synuclein alpha (SNCA, PARK1; NCBI Gene ID: 6622); T cell immunoglobulin and mucin domain containing 4 (TIMD4, SMUCKLER; NCBI Gene ID: 91937); T cell immunoreceptor with Ig and ITIM domains (TIGIT; NCBI Gene ID: 201633); tachykinin receptors (e.g., TACR1, TACR3; NCBI Gene ID: 6869, 6870); TANK binding kinase 1 (TBK1; NCBI Gene ID: 29110); tankyrase (TNKS; NCBI Gene ID: 8658); TATA-box binding protein associated factor, RNA polymerase I subunit B (TAF1B; NCBI Gene ID: 9014); T-box transcription factor T (TBXT; NCBI Gene ID: 6862); TCDD inducible poly(ADP-ribose) polymerase (TIPARP, PAPR7; NCBI Gene ID: 25976); tec protein tyrosine kinase (TEC; NCBI Gene ID: 7006); TEK receptor tyrosine kinase (TEK, CD202B, TIE2; NCBI Gene ID: 7010); telomerase reverse transcriptase (TERT; NCBI Gene ID: 7015); tenascin C (TNC; NCBI Gene ID: 3371); three prime repair exonucleases (e.g., TREX1, TREX2; NCBI Gene ID: 11277, 11219); thrombomodulin (THBD, CD141; NCBI Gene ID: 7056); thymidine kinases (e.g., TK1, TK2; NCBI Gene IDs: 7083, 7084); thymidine phosphorylase (TYMP; NCBI Gene ID: 1890); thymidylate synthase (TYMS; NCBI Gene ID: 7298); thyroid hormone receptor (THRA, THRB; NCBI Gene IDs: 7606, 7608); thyroid stimulating hormone receptor (TSHR; NCBI Gene ID: 7253); TNF superfamily members (e.g., TNFSF4 (OX40L, CD252), TNFSF5 (CD40L), TNFSF7 (CD70), TNFSF8 (CD153, CD30L), TNFSF9 (4-1BB-L, CD137L), TNFSF10 (TRAIL, CD253, APO2L), TNFSF11 (CD254, RANKL2, TRANCE), TNFSF13 (APRIL, CD256, TRAIL2), TNFSF13b (BAFF, BLYS, CD257), TNFSF14 (CD258, LIGHT), TNFSF18 (GITRL); NCBI Gene IDs: 944, 959, 970, 7292, 8600, 8740, 8741, 8743, 8744, 8995); toll like receptors (e.g., TLR1 (CD281), TLR2 (CD282), TLR3 (CD283), TLR4 (CD284), TLR5, TLR6 (CD286), TLR7, TLR8 (CD288), TLR9 (CD289), TLR10 (CD290); NCBI Gene IDs: 7096, 7097, 7098, 7099, 10333, 51284, 51311, 54106, 81793); transferrin (TF; NCBI Gene ID: 7018); transferrin receptor (TFRC, CD71; NCBI Gene ID: 7037); transforming growth factors (e.g., TGFA, TGFB1; NCBI Gene ID: 7039, 7040); transforming growth factor receptors (e.g., TGFBR1, TGFBR2, TGFBR3; NCBI Gene ID: 7046, 7048, 7049); transforming protein E7 (E7; NCBI Gene ID: 1489079); transglutaminase 5 (TGM5; NCBI Gene ID: 9333); transient receptor potential cation channel subfamily V member 1 (TRPV1, VR1; NCBI Gene ID: 7442); transmembrane and immunoglobulin domain containing 2 (TMIGD2, CD28H, IGPR1; NCBI Gene ID: 126259); triggering receptors expressed on myeloid cells (e.g., TREM1 (CD354), TREM2; NCBI Gene ID: 54209, 54210); trophinin (TRO, MAGED3; NCBI Gene ID: 7216); trophoblast glycoprotein (TPBG; NCBI Gene ID: 7162); tryptophan 2,3-dioxygenase (TDO2; NCBI Gene ID: 6999); tryptophan hydroxylases (e.g., TPH1, TPH2; NCBI Gene ID: 7166, 121278); tumor associated calcium signal transducer 2 (TACSTD2, TROP2, EGP1; NCBI Gene ID: 4070); tumor necrosis factor (TNF; NCBI Gene ID: 7124); tumor necrosis factor (TNF) receptor superfamily members (e.g., TNFRSF1A (CD120a), TNFRSF1B (CD120b), TNFRSF4 (OX40), TNFRSF5 (CD40), TNFRSF6 (CD95, FAS receptor), TNFRSF7 (CD27), TNFRSF8 (CD30), TNFRSF9 (CD137, 4-1BB), TNFRSF10A (CD261), TNFRSF10B (TRAIL, DR5, CD262), TNFRSF10C, TNFRSF10D, TNFRSF11A, TNFRSF11B (OPG), TNFRSF12A, TNFRSF13B, TNFR13C (CD268, BAFFR), TNFRSF14 (CD270, LIGHTR), TNFRSF16, TNFRSF17 (CD269, BCMA), TNFRSF18 (GITR, CD357), TNFRSF19, TNFRSF21, TNFRSF25; NCBI Gene IDs: 355, 608, 939, 943, 958, 3604, 4804, 4982, 7132, 7133, 7293, 8718, 8764, 8784, 8792, 8793, 8794, 8795, 8797, 23495, 27242, 51330, 55504); tumor protein p53 (TP53; NCBI Gene ID: 7157); tumor suppressor 2, mitochondrial calcium regulator (TUSC2; NCBI Gene ID: 11334); TYRO3 protein tyrosine kinase (TYRO3; BYK; NCBI Gene ID: 7301); tyrosinase (TYR; NCBI Gene ID: 7299); tyrosine hydroxylase (TH; NCBI Gene ID: 7054); tyrosine kinase with immunoglobulin like and EGF like domains 1 (e.g., TIE1, TIE1; NCBI Gene ID: 7075); tyrosine-protein phosphatase non-receptor type 11 (PTPN11, SHP2; NCBI Gene ID: 5781); ubiquitin conjugating enzyme E2 I (UBE2I, UBC9; NCBI Gene ID: 7329); ubiquitin C-terminal hydrolase L5 (UCHL5; NCBI Gene ID: 51377); ubiquitin specific peptidase 7 (USP7; NCBI Gene ID: 7874); ubiquitin-like modifier activating enzyme 1 (UBA1; NCBI Gene ID: 7317); UL16 binding proteins (e.g., ULBP1, ULBP2, ULBP3; NCBI Gene ID: 79465, 80328, 80328); valosin-containing protein (VCP, CDC48; NCBI Gene ID: 7415); vascular cell adhesion molecule 1 (VCAM1, CD106; NCBI Gene ID: 7412); vascular endothelial growth factors (e.g., VEGFA, VEGFB; NCBI Gene ID: 7422, 7423); vimentin (VIM; NCBI Gene ID: 7431); vitamin D receptor (VDR; NCBI Gene ID: 7421); V-set domain containing T cell activation inhibitor 1 (VTCN1, B7-H4; NCBI Gene ID: 79679); V-set immunoregulatory receptor (VSIR, VISTA, B7-H5; NCBI Gene ID: 64115); WEE1 G2 checkpoint kinase (WEE1; NCBI Gene ID: 7465); WRN RecQ like helicase (WRN; RECQ3; NCBI Gene ID: 7486); WT1 transcription factor (WT1; NCBI Gene ID: 7490); WW domain containing transcription regulator 1 (WWTR1; TAZ; NCBI Gene ID: 25937); X—C motif chemokine ligand 1 (XCL1, ATAC; NCBI Gene ID: 6375); X—C motif chemokine receptor 1 (XCR1, GPR5, CCXCR1; NCBI Gene ID: 2829); Yesl associated transcriptional regulator (YAP1; NCBI Gene ID: 10413); zeta chain associated protein kinase 70 (ZAP70; NCBI Gene ID: 7535).

In some embodiments, the one or more additional therapeutic agents include, e.g., an agent targeting 5'-nucleotidase ecto (NT5E or CD73; NCBI Gene ID: 4907); adenosine $A_{2A}$ receptor (ADORA2A; NCBI Gene ID: 135); adenosine $A_{2B}$ receptor (ADORA2B; NCBI Gene ID: 136); C—C motif chemokine receptor 8 (CCR8, CDw198; NCBI Gene ID: 1237); cytokine inducible SH2 containing protein (CISH; NCBI Gene ID: 1154); diacylglycerol kinase alpha (DGKA, DAGK, DAGK1 or DGK-alpha; NCBI Gene ID: 1606); fms like tyrosine kinase 3 (FLT3, CD135; NCBI Gene ID: 2322); integrin associated protein (IAP, CD47; NCBI Gene ID: 961); interleukine-2 (IL2; NCBI Gene ID:3558); interleukine 2 receptor (IL2RA, IL2RB, IL2RG; NCBI Gene IDs: 3559, 3560, 3561); Kirsten rat sarcoma virus (KRAS; NCBI Gene ID: 3845; including mutations, such as KRAS G12C or G12D); mitogen-activated protein kinase kinase kinase kinase 1 (MAP4K1) (also called Hematopoietic Progenitor Kinase 1 (HPK1), NCBI Gene ID: 11184); myeloid cell leukemia sequence 1 apoptosis regulator (MCL1; NCBI Gene ID: 4170); phosphatidylinositol-4,5-bisphosphate 3-kinase, catalytic subunit delta (PIK3CD; NCBI Gene ID: 5293); programmed death-ligand 1 (PD-L1, CD274; NCBI Gene ID 29126); programmed cell death protein 1 (PD-1, CD279; NCBI Gene ID: 5133); proto-oncogen c-KIT (KIT, CD117; NCBI Gene ID: 3815); signal-regulatory protein alpha (SIRPA, CD172A; NCBI Gene ID: 140885); TCDD inducible poly(ADP-ribose) polymerase (TIPARP, PARP7; NCBI Gene ID: 25976); T cell immunoreceptor with Ig and ITIM domains (TIGIT; NCBI Gene ID: 201633); triggering receptor expressed on myeloid cells 1 (TREM1; NCBI Gene ID: 54210); triggering receptor expressed on myeloid cells 2 (TREM2; NCBI Gene ID: 54209); tumor-associated calcium signal transducer 2 (TACSTD2, TROP2, EGP1; NCBI Gene ID: 4070); tumor necrosis factor receptor superfamily, member 4 (TNFRSF4, CD134, OX40; NCBI Gene ID:7293); tumor necrosis factor receptor superfamily, member 9 (TNFRSF9, 4-IBB, CD137; NCBI Gene ID: 3604); tumor necrosis factor receptor superfamily, member 18 (TNFRSF18, CD357, GITR; NCBI Gene ID: 8784); WRN RecQ like helicase (WRN; NCBI Gene ID: 7486); zinc finger protein Helios (IKZF2; NCBI Gene ID: 22807).

Illustrative Mechanisms of Action

Immune Checkpoint Modulators

In some embodiments an antibody and/or fusion protein provided herein is administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Clin Cancer Res.* (2018) 37:110). In some embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688). Inhibition of regulatory T-cells (Treg) or Treg depletion can alleviate their suppression of antitumor immune responses and have anti-cancer effects (e.g., reviewed in Plitas and Rudensky, *Annu. Rev. Cancer Biol.* (2020) 4:459-77; Tanaka and Sakaguchi, *Eur. J. Immunol.* (2019) 49:1140-1146).

Examples of immune checkpoint proteins or receptors include CD27 (NCBI Gene ID: 939), CD70 (NCBI Gene ID: 970); CD40 (NCBI Gene ID: 958), CD40LG (NCBI Gene ID: 959); CD47 (NCBI Gene ID: 961), SIRPA (NCBI Gene ID: 140885); CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941), CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBP5; NCBI Gene ID: 353091); retinoic acid early transcript 1L (RAET1L; ULBP6; NCBI Gene ID: 154064); killer cell immunoglobulin like receptor, three Ig domains and long cytoplasmic tail 1 (KIR, CD158E1; NCBI Gene ID: 3811, e.g., lirilumab (IPH-2102, IPH-4102)); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1); killer cell lectin like receptor D1 (KLRD1; NCBI Gene ID: 3824); killer cell lectin like receptor G1 (KLRG1; CLEC15A, MAFA, 2F1; NCBI Gene ID: 10219); sialic acid binding Ig like lectin 7 (SIGLEC7; NCBI Gene ID: 27036); and sialic acid binding Ig like lectin 9 (SIGLEC9; NCBI Gene ID: 27180).

In some embodiments an antibody and/or fusion protein provided herein is administered with one or more blockers or inhibitors of one or more T-cell inhibitory immune checkpoint proteins or receptors. Illustrative T-cell inhibitory immune checkpoint proteins or receptors include CD274 (CD274, PDL1, PD-L1); programmed cell death 1 ligand 2 (PDCDILG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSFI4 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the antibody and/or fusion protein provided herein is administered with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In some embodiments the antibody and/or fusion protein provided herein is administered with one or more blockers or inhibitors of one or more NK-cell inhibitory immune checkpoint proteins or receptors. Illustrative NK-cell inhibitory immune checkpoint proteins or receptors include killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments the antibody and/or fusion protein provided herein is administered with one or more agonist or activators of one or more NK-cell stimulatory immune checkpoint proteins or receptors. Illustrative NK-cell stimulatory immune checkpoint proteins or receptors include CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In some embodiments the one or more immune checkpoint inhibitors comprises a proteinaceous (e.g., antibody or fragment thereof, or antibody mimetic) inhibitor of PD-L1 (CD274), PD-1 (PDCD1), CTLA4, or TIGIT. In some embodiments the one or more immune checkpoint inhibitors comprises a small organic molecule inhibitor of PD-L1 (CD274), PD-1 (PDCD1), CTLA4, or TIGIT. In some embodiments the one or more immune checkpoint inhibitors comprises a proteinaceous (e.g., antibody or fragment thereof, or antibody mimetic) inhibitor of LAG3.

Examples of inhibitors of CTLA4 that can be co-administered include ipilimumab, tremelimumab, BMS-986218, AGEN1181, zalifrelimab (AGEN1884), BMS-986249, MK-1308, REGN-4659, ADU-1604, CS-1002 (ipilimumab biosimilar), BCD-145, APL-509, JS-007, BA-3071, ONC-392, AGEN-2041, HBM-4003, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include pembrolizumab, nivolumab, cemiplimab, pidilizumab, AMP-224, MEDI0680 (AMP-514), spartalizumab, atezolizumab, avelumab, durvalumab, BMS-936559, cosibelimab (CK-301), sasanlimab (PF-06801591), tislelizumab (BGB-A317), GLS-010 (WBP-3055), AK-103 (HX-008), AK-105, CS-1003, HLX-10, retifanlimab (MGA-012), BI-754091, balstilimab (AGEN-2034), AMG-404, toripalimab (JS-001), cetrelimab (JNJ-63723283), genolimzumab (CBT-501), LZM-009, prolgolimab (BCD-100), lodapolimab (LY-3300054), SHR-1201, camrelizumab (SHR-1210), Sym-021, budigalimab (ABBV-181), PD1-PIK, BAT-1306, avelumab (MSB0010718C), CX-072, CBT-502, dostarlimab (TSR-042), MSB-2311, JTX-4014, BGB-A333, SHR-1316, CS-1001 (WBP-3155, envafolimab (KN-035), sintilimab (IBI-308), HLX-20, KL-A167, STI-A1014, STI-A1015 (IMC-001), BCD-135, FAZ-053, TQB-2450, MDX1105-01, GS-4224, GS-4416, INCB086550, MAX10181, zimberelimab (AB122), spartalizumab (PDR-001), and compounds disclosed in WO2018195321, WO2020014643, WO2019160882, or WO2018195321, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1), RO-7247669 (PD-1/LAG-3), MGD-019 (PD-1/CTLA4), KN-046 (PD-1/CTLA4), MEDI-5752 (CTLA4/PD-1), RO-7121661 (PD-1/TIM-3), RG7769 (PD-1/TIM-3), TAK-252 (PD-1/OX40L), XmAb-20717 (PD-1/CTLA4), AK-104 (CTLA4/PD-1), FS-118 (LAG-3/PD-L1), FPT-155 (CTLA4/PD-L1/CD28), GEN-1046 (PD-L1/4-1BB), bintrafusp alpha (M7824; PD-L1/TGFD-EC domain), CA-170 (PD-L1/VISTA), CDX-527 (CD27/PD-L1), LY-3415244 (TIM3/PDL1), and INBRX-105 (4-1BB/PDL1). In some embodiments the PD-L1 inhibitor is a small molecule inhibitor, such as CA-170, GS-4224, GS-4416 and lazertinib (GNS-1480; PD-L1/EGFR).

Examples of inhibitors of TIGIT that can be co-administered include tiragolumab (RG-6058), vibostolimab, domvanalimab, domvanalimab (AB154), AB308, BMS-986207, AGEN-1307, COM-902, or etigilimab.

Examples of inhibitors of LAG3 that can be co-administered include leramilimab (LAG525).

Inhibition of regulatory T-cell (Treg) activity or Treg depletion can alleviate their suppression of antitumor immune responses and have anticancer effects. See, e.g., Plitas and Rudensky, *Annu. Rev. Cancer Biol.* (2020) 4:459-77; Tanaka and Sakaguchi, *Eur. J. Immunol.* (2019) 49:1140-1146. In some embodiments, an antibody and/or fusion protein provided herein is administered with one or more inhibitors of Treg activity or a Treg depleting agent. Treg inhibition or depletion can augment the effect of immune checkpoint inhibitors in cancer therapeutics.

In some embodiments an antibody and/or fusion protein provided herein is administered with one or more Treg inhibitors. In some embodiments the Treg inhibitor can suppress the migration of Tregs into the tumor microenvironment. In some embodiments Treg inhibitor can reduce the immunosuppressive function of Tregs. In some embodiments, the Treg inhibitor can modulate the cellular phenotype and induce production of proinflammatory cytokines. Exemplary Treg inhibitors include without limitation, CCR4 (NCBI Gene ID: 1233) antagonists and degraders of Ikaros zinc-finger proteins (e.g., Ikaros (IKZF1; NCBI Gene ID: 10320), Helios (IKZF2; NCBI Gene ID: 22807), Aiolos (IKZF3; NCBI Gene ID: 22806), and Eos (IKZF4; NCBI Gene ID: 64375).

Examples of Helios Degraders that can be Co-Administered Include without Limitation I-57 (Novartis) and compounds disclosed in WO2019038717, WO2020012334, WO20200117759, and WO2021101919.

In some embodiments an antibody and/or fusion protein provided herein is administered with one or more Treg depleting agents. In some embodiments the Treg depleting agent is an antibody. In some embodiments the Treg depleting antibody has antibody-dependent cytotoxic (ADCC) activity. In some embodiments, the Treg depleting antibody is Fc-engineered to possess an enhanced ADCC activity. In some embodiments the Treg depleting antibody is an antibody-drug conjugate (ADC). Illustrative targets for Treg depleting agents include without limitation CD25 (IL2RA; NCBI Gene ID: 3559), CTLA4 (CD152; NCBI Gene ID: 1493); GITR (TNFRSF18; NCBI Gene ID: 8784); 4-1BB (CD137; NCBI Gene ID: 3604), OX-40 (CD134; NCBI Gene ID: 7293), LAG3 (CD223; NCBI Gene ID: 3902), TIGIT (NCBI Gene ID: 201633), CCR4 (NCBI Gene ID: 1233), and CCR8 (NCBI Gene ID: 1237).

In some embodiments the Treg inhibitor or Treg depleting agent that can be co-administered comprises an antibody or antigen-binding fragment thereof that selectively binds to a cell surface receptor selected from the group consisting of C—C motif chemokine receptor 4 (CCR4), C—C motif chemokine receptor 7 (CCR7), C—C motif chemokine receptor 8 (CCR8), C—X—C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis x (CD15s), CD27, ectonucleoside triphosphate diphosphohydrolase 1 (ENTPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL2RA (CD25) or a combination thereof.

Examples of Treg depleting anti-CCR8 antibodies that can be administered include without limitation JTX-1811 (GS-1811) (Jounce Therapeutics, Gilead Sciences), BMS-986340 (Bristol Meyers Squibb), S-531011 (Shionogi), FPA157 (Five Prime Therapeutics), SRF-114 (Surface Oncology), HBM1022 (Harbor BioMed), IO-1 (Oncurious), and antibodies disclosed in WO2021163064, WO2020138489, and WO2021152186.

Examples of Treg depleting anti-CCR4 antibodies that can be administered include mogamulizumab.

Inhibiting, depleting, or reprogramming of non-stimulatory myeloid cells in the tumor microenvironment can enhance anti-cancer immune responses (see, e.g., Binnewies et al., *Nat. Med.* (2018) 24(5): 541-550; WO2016049641). Illustrative targets for depleting or reprogramming non-stimmulatory myeloid cells include triggering receptors expressed on myeloid cells, TREM-1 (CD354, NCBI Gene ID: 54210) and TREM-2 (NCBI Gene ID: 54209). In some embodiments an antibody and/or fusion protein provided herein is administered with one or more myeloid cell depleting or reprogramming agents, such as an anti-TREM-1 antibody (e.g. PY159; antibodies disclosed in WO2019032624) or an anti-TREM-2 antibody (e.g., PY314; antibodies disclosed in WO2019118513).

Cluster of Differentiation Agonists or Activators

In some embodiments, the antibody and/or fusion protein provided herein is administered with agents targeting a cluster of differentiation (CD) marker. Exemplary CD marker targeting agents that can be co-administered include without limitation A6, AD-IL24, neratinib, tucatinib (ONT 380), mobocertinib (TAK-788), tesevatinib, trastuzumab (HERCEPTIN®), trastuzumab biosimimar (HLX-02), margetuximab, BAT-8001, pertuzumab (Perjeta), pegfilgrastim, RG6264, zanidatamab (ZW25), cavatak, AIC-100, tagraxofusp (SL-401), HLA-A2402/HLA-A0201 restricted epitope peptide vaccine, dasatinib, imatinib, nilotinib, sorafenib, lenvatinib mesylate, ofranergene obadenovec, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, olverembatinib dimesylate (HQP-1351), cabozantinib, ponatinib, and famitinib L-malate, CX-2029 (ABBV-2029), SCB-313, CA-170, COM-701, CDX-301, GS-3583, asunercept (APG-101), APO-010, and compounds disclosed in WO2016196388, WO2016033570, WO2015157386, WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, PCT/US2019/063091, WO19173692, WO2016179517, WO2017096179, WO2017096182, WO2017096281, WO2018089628, WO2017096179, WO2018089628, WO2018195321, WO2020014643, WO2019160882, WO2018195321, WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, WO2020068752, Cancer Discov. 2019 Jan. 9(1):8; and Gariepy J., et al. 106th Annu Meet Am Assoc Immunologists (AAI) (May 9-13, San Diego, 2019, Abst 71.5).

In some embodiments the CD marker targeting agent that can be co-administered include small molecule inhibitors, such as PBF-1662, BLZ-945, pemigatinib (INCB-054828), rogaratinib (BAY-1163877), AZD4547, roblitinib (FGF-401), quizartinib dihydrochloride, SX-682, AZD-5069, PLX-9486, avapritinib (BLU-285), ripretinib (DCC-2618), imatinib mesylate, JSP-191, BLU-263, CD117-ADC, AZD3229, telatinib, vorolanib, GO-203-2C, AB-680, PSB-12379, PSB-12441, PSB-12425, CB-708, HM-30181A, motixafortide (BL-8040), LY2510924, burixafor (TG-0054), X4P-002, mavorixafor (X4P-001-IO), plerixafor, CTX-5861, or REGN-5678 (PSMA/CD28).

In some embodiments the CD marker targeting agent that can be co-administered include small molecule agonists, such as interleukin 2 receptor subunit gamma, eltrombopag, rintatolimod, poly-ICLC (NSC-301463), Riboxxon, Apoxxim, RIBOXXIM@, MCT-465, MCT-475, G100, PEPA-10, eftozanermin alfa (ABBV-621), E-6887, motolimod, resiquimod, selgantolimod (GS-9688), VTX-1463, NKTR-262, AST-008, CMP-001, cobitolimod, tilsotolimod, litenimod, MGN-1601, BB-006, IMO-8400, IMO-9200, agatolimod, DIMS-9054, DV-1079, lefitolimod (MGN-1703), CYT-003, and PUL-042.

In some embodiments the CD marker targeting agent that can be co-administered include antibodies, such as tafasitamab (MOR208; MorphoSys AG), Inebilizumab (MEDI-551), obinutuzumab, IGN-002, rituximab biosimilar (PF-05280586), varlilumab (CDX-1127), AFM-13 (CD16/CD30), AMG330, otlertuzumab (TRU-016), isatuximab, felzartamab (MOR-202), TAK-079, TAK573, daratumumab (DARZALEX®), TTX-030, selicrelumab (RG7876), APX-005M, ABBV-428, ABBV-927, mitazalimab (JNJ-64457107), lenziluma, alemtuzuma, emactuzumab, AMG-820, FPA-008 (cabiralizumab), PRS-343 (CD-137/Her2), AFM-13 (CD16/CD30), belantamab mafodotin (GSK-2857916), AFM26 (BCMA/CD16A), simlukafusp alfa (RG7461), urelumab, utomilumab (PF-05082566), AGEN2373, ADG-106, BT-7480, PRS-343 (CD-137/HER2), FAP-4-IBBL (4-1BB/FAP), ramucirumab, CDX-0158, CDX-0159 and FSI-174, relatlimab (ONO-4482), LAG-525, MK-4280, fianlimab (REGN-3767), INCAGN2385, encelimab (TSR-033), atipotuzumab, BrevaRex (Mab-AR-20.5), MEDI-9447 (oleclumab), CPX-006, IPH-53, BMS-986179, NZV-930, CPI-006, PAT-SC1, lirilumab (IPH-2102), lacutamab (IPH-4102), monalizumab, BAY-1834942, NEO-201 (CEACAM 5/6), Iodine (131I) apamistamab (131I-BC8 (lomab-B)), MEDI0562 (tavolixizumab), GSK-3174998, INCAGN1949, BMS-986178, GBR-8383, ABBV-368, denosumab, BION-1301, MK-4166, INCAGN-1876, TRX-518, BMS-986156, MK-1248, GWN-323, CTB-006, INBRX-109, GEN-1029, pepinemab (VX-15), vopratelimab (JTX-2011), GSK3359609, cobolimab (TSR-022), MBG-453, INCAGN-2390, and compounds disclosed in WO 2017096179, WO2017096276, WO2017096189, and WO2018089628.

In some embodiments the CD marker targeting agent that can be co-administered include cell therapies, such as CD19-ARTEMIS, TBI-1501, CTL-119 huCART-19 T cells, 1 iso-cel, lisocabtagene maraleucel (JCAR-017), axicabtagene ciloleucel (KTE-C19, Yescarta®), axicabtagene ciloleucel (KTE-X19), U.S. Pat. Nos. 7,741,465, 6,319,494, UCART-19, tabelecleucel (EBV-CTL), T tisagenlecleucel-T (CTL019), CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110, anti-CD19 CAR T-cell therapy (B-cell acute lymphoblastic leukemia, Universiti Kebangsaan Malaysia), anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem, UCAR-011, ICTCAR-014, GC-007F, PTG-01, CC-97540, GC-007G, TC-310, GC-197, tisagenlecleucel-T, CART-19, tisagenlecleucel (CTL-019)), anti-CD20 CAR T-cell therapy (non-Hodgkin's lymphoma), MB-CART2019.1 (CD19/CD20), WZTL-002 dual anti-CD19/anti-CD20 CAR-T cells, ICG-132 (CD19/CD20), ACTR707 ATTCK-20, PBCAR-20A, LB-1905, CIK-CAR.CD33, CD33CART, dual anti-BCMA/anti-CD38 CAR T-cell therapy, CART-ddBCMA, MB-102, IM-23, JEZ-567, UCART-123, PD-1 knockout T cell therapy (esophageal cancer/NSCLC), ICTCAR-052, Tn MUC-1 CAR-T, ICTCAR-053, PD-1 knockout T cell therapy (esophageal cancer/NSCLC), AUTO-2, anti-BCMA CAR T-cell therapy, Descartes-011, anti-BCMA/anti-CD38 CAR T-cell therapy, CART-ddBCMA, BCMA-CS1 cCAR, CYAD-01 (NKG2D LIGAND MODULATOR), KD-045, PD-L1 t-haNK, BCMA-CS1 cCAR, MEDI5083, anti-CD276 CART, and therapies disclosed in WO2012079000 or WO2017049166.

Cluster of Differentiation 47 (CD47) Inhibitors

In some embodiments the antibody and/or fusion protein provided herein is administered with an inhibitor of CD47 (IAP, MER6, OA3; NCBI Gene ID: 961). Examples of CD47 inhibitors include anti-CD47 mAbs (Vx-1004), anti-human CD47 mAbs (CNTO-7108), CC-90002, CC-90002-ST-001, humanized anti-CD47 antibody or a CD47-blocking agent, NI-1701, NI-1801, RCT-1938, ALX148, SG-404, SRF-231, and TTI-621. Additional exemplary anti-CD47 antibodies include CC-90002, magrolimab (Hu5F9-G4), AO-176 (Vx-1004), letaplimab (IBI-188) (letaplimab), lemzoparlimab (TJC-4), SHR-1603, HLX-24, LQ-001, IMC-002, ZL-1201, IMM-01, B6H12, GenSci-059, TAY-018, PT-240, 1F8-GMCSF, SY-102, KD-015, ALX-148, AK-117, TTI-621, TTI-622, or compounds disclosed in WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, and WO2020009725. In some embodiments, the CD47 inhibitor is RRx-001, DSP-107, VT-1021, IMM-02, SGN-CD47M, or SIRPa-Fc-CD40L (SL-172154). In some embodiments the CD47 inhibitor is magrolimab.

In some embodiments, the CD47 inhibitor is a bispecific antibodies targeting CD47, such as IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33), TG-1801 (NI-1701), or NI-1801.

SIRPα Targeting Agents

In some embodiments the antibody and/or fusion protein provided herein is administered with a SIRPα targeting agent (NCBI Gene ID: 140885; UniProt P78324). Examples of SIRPα targeting agents include SIRPα inhibitors, such as AL-008, RRx-001, and CTX-5861, and anti-SIRPα antibodies, such as FSI-189 (GS-0189), ES-004, BI-765063, ADU1805, CC-95251, Q-1801 (SIRPa/PD-L1). Additional SIRPu-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

FLT3R Agonists

In some embodiments the antibody and/or fusion protein provided herein is administered with a FLT3R agonist. In some embodiments, the antibody and/or fusion protein provided herein is administered with a FLT3 ligand. In some embodiments, the antibody and/or fusion protein provided herein is administered with a FLT3L-Fc fusion protein, e.g., as described in WO2020263830. In some embodiments the antibody and/or fusion protein provided herein is administered with GS-3583 or CDX-301. In some embodiments the antibody and/or fusion protein provided herein is administered with GS-3583.

TNF Receptor Superfamily (TNFRSF) Member Agonists or Activators

In some embodiments, the antibody and/or fusion protein provided herein is administered with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include MEDI6469, MEDI6383, tavolixizumab (MEDI0562), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include RG7876, SEA-CD40, APX-005M, and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include urelumab, utomilumab (PF-05082566), AGEN-2373, and ADG-106.

In some embodiments the anti-TNFRSF17 (BCMA) antibody GSK-2857916 is co-administered.

Example anti-TNFRSF18 (GITR) antibodies that can be co-administered include MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi-specific antibodies targeting TNFRSF family members that can be co-administered include PRS-343 (CD-137/HER2), AFM26 (BCMA/CD16A), AFM-13 (CD16/CD30), odronextamab (REGN-1979; CD20/CD3), AMG-420 (BCMA/CD3), INHIBRX-105 (4-1BB/PDL1), FAP-4-IBBL (4-1BB/FAP), plamotamab (XmAb-13676; CD3/CD20), RG-7828 (CD20/CD3), CC-93269 (CD3/BCMA), REGN-5458 (CD3/BCMA), and IMM-0306 (CD47/CD20).

Bi-Specific T-Cell Engagers

In some embodiments antibody and/or fusion protein provided herein is administered with a bi-specific T-cell engager (e.g., not having an Fc) or an anti-CD3 bi-specific antibody (e.g., having an Fc). Illustrative anti-CD3 bi-specific antibodies or BiTEs that can be co-administered include duvortuxizumab (JNJ-64052781; CD19/CD3), AMG-211 (CEA/CD3), AMG-160 (PSMA/CD3), RG7802 (CEA/CD3), ERY-974 (CD3/GPC3), PF-06671008 (Cadherins/CD3), APVO436 (CD123/CD3), flotetuzumab (CD123/CD3), odronextamab (REGN-1979; CD20/CD3), MCLA-117 (CD3/CLEC12A), JNJ-0819 (heme/CD3), JNJ-7564 (CD3/heme), AMG-757 (DLL3-CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), AMG-211 (CEA/CD3), blinatumomab (CD19/CD3), huGD2-BsAb (CD3/GD2), ERY974 (GPC3/CD3), GEMoab (CD3/PSCA), RG6026 (CD20/CD3), RG6194 (HER2/CD3), PF-06863135 (BCMA/CD3), SAR440234 (CD3/CDw123), JNJ-9383 (MGD-015), AMG-424 (CD38/CD3), tidutamab (XmAb-18087 (SSTR2/CD3)), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), tidutamab (XmAb-18087; SSTR2/CD3), catumaxomab (CD3/EpCAM), REGN-4018 (MUC16/CD3), mosunetuzumab (RG-7828; CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology*. (2017) May 17; 6(7): e1326437); PD-L1 (Horn, et al., *Oncotarget*. 2017 Aug. 3; 8(35):57964-57980); and EGFRvIII (Yang, et al., *Cancer Lett*. 2017 Sep. 10; 403:224-230).

Bi- and Tri-Specific Natural Killer (NK)-Cell Engagers

In some embodiments the antibody and/or fusion protein provided herein is administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol*. (2016) 1441:333-346; Fang, et al., *Semin Immunol*. (2017) 31:37-54.

MCL1 apoptosis regulator, BCL2 family member (MCL1) Inhibitors

In some embodiments the antibody and/or fusion protein provided herein is administered with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include tapotoclax (AMG-176), AMG-397, S-64315, AZD-5991, 483-LM, A-1210477, UMI-77, JKY-5-037, PRT-1419, GS-9716, and those described in WO2018183418, WO2016033486, and WO2017147410.

SHP2 Inhibitors

In some embodiments antibody and/or fusion protein provided herein is administered with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, and those described in WO2018172984 and WO2017211303.

Hematopoietic Progenitor Kinase 1 (HPK1) Inhibitors and Degraders

In some embodiments, the antibody and/or fusion protein provided herein is administered with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO2020092621, WO2018183956, WO2018183964, WO2018167147, WO2018049152, WO2020092528, WO2016205942, WO2016090300, WO2018049214, WO2018049200, WO2018049191, WO2018102366, WO2018049152, and WO2016090300.

Apoptosis Signal-Regulating Kinase (ASK) Inhibitors

In some embodiments the antibody and/or fusion protein provided herein is administered with an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include those described in WO2011008709 (Gilead Sciences) and WO 2013112741 (Gilead Sciences).

Bruton Tyrosine Kinase (BTK) Inhibitors

In some embodiments the antibody and/or fusion protein provided herein is administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include (S)-6-amino-9-(1-(but-2-ynoyl)pyrrolidin-3-yl)-7-(4-phenoxyphenyl)-7H-purin-8(9H)-one, acalabrutinib (ACP-196), zanubrutinib (BGB-3111), CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, PCI-32765, and TAS-5315.

Cyclin-Dependent Kinase (CDK) Inhibitors

In some embodiments the antibody and/or fusion protein provided herein is administered with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022), or cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include abemaciclib, alvocidib (HMR-1275, flavopiridol), AT-7519, dinaciclib, ibrance, FLX-925, LEE001, palbociclib, samuraciclib, ribociclib, rigosertib, selinexor, UCN-01, SY1365, CT-7001, SY-1365, G1T38, milciclib, trilaciclib, simurosertib hydrate (TAK931), and TG-02.

Discoidin Domain Receptor (DDR) Inhibitors

In some embodiments the antibody and/or fusion protein provided herein is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In some embodiments the antibody and/or fusion protein provided herein is administered with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In some embodiments the targeted E3 ligase ligand conjugates comprise a targeting or binding moiety that targets or binds a protein described herein, and an E3 ligase ligand or binding moiety. In some embodiments the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In some embodiments the targeted E3 ligase ligand conjugates comprise a kinase inhibitor (e.g., a small molecule kinase inhibitor, e.g., of BTK and an E3 ligase ligand or binding moiety. See, e.g., WO2018098280. In some embodiments the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208, and WO2018144649.

Histone Deacetylase (HDAC) Inhibitors

In some embodiments the antibody and/or fusion protein provided herein is administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat.

Indoleamine-pyrrole-2,3-dioxygenase (IDO1) Inhibitors

In some embodiments the antibody and/or fusion protein provided herein is administered with an inhibitor of indoleamine 2,3-dioxygenase 1 (IDO1; NCBI Gene ID: 3620). Examples of IDO1 inhibitors include BLV-0801, epacadostat, linrodostat (F-001287, BMS-986205), GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST, EOS-200271, KHK-2455, and LY-3381916.

Janus Kinase (JAK) Inhibitors

In some embodiments, the antibody and/or fusion protein provided herein is administered with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include AT9283, AZD1480, baricitinib, BMS-911543, fedratinib, filgotinib (GLPG0634), gandotinib (LY2784544), INCB039110 (itacitinib), lestaurtinib, momelotinib (CYT0387), ilginatinib maleate (NS-018), pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In some embodiments the antibody and/or fusion protein provided herein is administered with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL2 inhibitors include the antibodies described in WO 2009017833 (Arresto Biosciences), WO 2009035791 (Arresto Biosciences), and WO 2011097513 (Gilead Biologics).

Matrix Metalloprotease (MMP) Inhibitors

In some embodiments the antibody and/or fusion protein provided herein is administered with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include marimastat (BB-2516), cipemastat (Ro 32-3555), GS-5745 (andecaliximab), and those described in WO 2012027721 (Gilead Biologics).

RAS and RAS Pathway Inhibitors

In some embodiments the antibody and/or fusion protein provided herein is administered with an inhibitor of KRAS proto-oncogene, GTPase (KRAS; a.k.a., NS; NS3; CFC2; RALD; K-Ras; KRAS1; KRAS2; RASK2; KI-RAS; C—K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893) or HRAS proto-oncogene, GTPase (HRAS; a.k.a., CTLO; KRAS; HAMSV; HRAS1; KRAS2; RASH1; RASK2; Ki-Ras; p21ras; C—H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C—Raf), MEK (MEK1, MEK2), ERK, PI3K, AKT and mTOR. Illustrative K-Ras inhibitors that can be co-administered include sotorasib (AMG-510), COTI-219, ARS-3248, WDB-178, BI-3406, BI-1701963, SML-8-73-1 (G12C), adagrasib (MRTX-849), ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 and KRpep-2d. Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered include BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, inavolisib (RG6114), ASN-003. Illustrative AKT inhibitors that can be co-administered include capivasertib and GSK2141795. Illustrative PI3K/mTOR inhibitors that can be co-administered include dactolisib, omipalisib, voxtalisib. gedatolisib, GSK2141795, GSK-2126458, inavolisib (RG6114), sapanisertib, ME-344, sirolimus (oral nanoamorphous formulation, cancer), racemetyrosine (TYME-88 (mTOR/cytochrome P450 3A4)), temsirolimus (TORISEL®, CCI-779), CC-115, onatasertib (CC-223), SF-1126, and PQR-309 (bimiralisib). In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

Mitogen-Activated Protein Kinase (MEK) Inhibitors

In some embodiments the antibody and/or fusion protein provided herein is administered with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib.

Phosphatidylinositol 3-Kinase (PI3K) Inhibitors

In some embodiments antibody and/or fusion protein provided herein is administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, $p^1$10D, NCBI Gene ID: 5293). In some embodiments the PI3K inhibitor is a pan-PI3K inhibitor. Examples of PI3K inhibitors include ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO2005113556 (ICOS), WO 2013/052699 (Gilead Calistoga), WO2013116562 (Gilead Calistoga), WO2014100765 (Gilead Calistoga), WO2014100767 (Gilead Calistoga), and WO2014201409 (Gilead Sciences).

Spleen Tyrosine Kinase (SYK) Inhibitors

In some embodiments the antibody and/or fusion protein provided herein is administered with an inhibitor of spleen associated tyrosine kinase (SYK, p72-Syk, NCBI Gene ID: 6850). Examples of SYK inhibitors include 6-(1H-indazol- 6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib ($R^{406}$), gusacitinib (ASN-002), and those described in U.S. Pat. No. 8,450,321 (Gilead Connecticut) and US20150175616.

Toll-Like Receptor (TLR) Agonists

In some embodiments antibody and/or fusion protein provided herein is administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include DS-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, BDB-001, DSP-0509, and the compounds disclosed in US20100143301 (Gilead Sciences), US20110098248 (Gilead Sciences), and US20090047249 (Gilead Sciences), US20140045849 (Janssen), US20140073642 (Janssen), WO2014056953 (Janssen), WO2014076221 (Janssen), WO2014128189 (Janssen), US20140350031 (Janssen), WO2014023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Tyrosine-Kinase Inhibitors (TKIs)

In some embodiments the antibody and/or fusion protein provided herein is administered with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody). Exemplary EGFR targeting agents include neratinib, tucatinib (ONT-380), tesevatinib, mobocertinib (TAK-788), DZD-9008, varlitinib, abivertinib (ACEA-0010), EGF816 (nazartinib), olmutinib (BI-1482694), osimertinib (AZD-9291), AMG-596 (EGFRvIII/CD3), lifirafenib (BGB-283), vectibix, lazertinib (LECLAZA@), and compounds disclosed in Booth, et al., Cancer Biol Ther. 2018 Feb. 1; 19(2):132-137. Antibodies targeting EGFR include without limitation modotuximab, cetuximab sarotalocan (RM-1929), seribantumab, necitumumab, depatuxizumab mafodotin (ABT-414), tomuzotuximab, depatuxizumab (ABT-806), and cetuximab.

Chemotherapeutic Agents

In some embodiments the antibody and/or fusion protein provided herein is administered with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8;dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carminomycin, carzinophilin, chromomycins, dactinomycin, daunorubicin, detorubicin, 6-diazo-5-C═O-L-norleucine, dC═Orubicin (including morpholino-dC═Orubicin, cyanomorpholino-dC═Orubicin, 2-pyrrolino-dC═Orubicin, and deoxydC═Orubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; sabizabulin (Veru-111); platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204, enobosarm (GTX-024), darolutamide, and IONIS-AR-2.5Rx (antisense).

An example progesterone receptor antagonist includes onapristone. Additional progesterone targeting agents include TRI-CYCLEN LO (norethindrone+ethinyl estradiol), norgestimate+ethinylestradiol (Tri-Cyclen) and levonorgestrel.

Anti-Angiogenic Agents

In some embodiments the antibody and/or fusion protein provided herein is administered with an anti-angiogenic agent. Anti-angiogenic agents that can be co-administered include retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2. Examples for anti-VEGFA antibodies that can be co-administered include bevacizumab, vanucizumab, faricimab, dilpacimab (ABT-165; DLL4/VEGF), or navicixizumab (OMP-305B83; DLL4/VEGF).

Anti-Fibrotic Agents

In some embodiments the antibody and/or fusion protein provided herein is administered with an anti-fibrotic agent. Anti-fibrotic agents that can be co-administered include the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 20040248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments the antibody and/or fusion protein provided herein is administered with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include mofezolac, GLY-230, and TRK-700.

Examples of inhibitors of prostaglandin-endoperoxide synthase 2 (PTGS2, COX-2; NCBI Gene ID: 5743) that can be co-administered include diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, NS-398, pamicogrel, parecoxib, robenacoxib, rofecoxib, rutecarpine, tilmacoxib, and zaltoprofen. Examples of dual COX1/COX2 inhibitors that can be co-administered include HP-5000, lornoxicam, ketorolac tromethamine, bromfenac sodium, ATB-346, HP-5000. Examples of dual COX-2/carbonic anhydrase (CA) inhibitors that can be co-administered include polmacoxib and imrecoxib.

Examples of inhibitors of secreted phospholipase A2, prostaglandin E synthase (PTGES, PGES; Gene ID: 9536) that can be co-administered include LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., *Oncotarget.* (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include meclofenamate sodium, zileuton.

Examples of inhibitors of soluble epoxide hydrolase 2 (EPHX2, SEH; NCBI Gene ID: 2053) that can be co-administered include compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include GS-4875, GS-5290, BHM-078 and those described in WO2006124944, WO2006124692, WO2014064215, WO2018005435, Teli, et al., *J Enzyme Inhib Med Chem.* (2012) 27(4):558-70; Gangwall, et al., *Curr Top Med Chem.* (2013) 13(9):1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In some embodiments the antibody and/or fusion protein provided herein is administered with an agent that promotes or increases tumor oxygenation or reoxygenation, or prevents or reduces tumor hypoxia. Illustrative agents that can be co-administered include, e.g., Hypoxia inducible factor-1 alpha (HIF-lu) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO2007137767, WO2007139791, WO2014107171, and WO2016149562.

Immunotherapeutic Agents

In some embodiments the antibody and/or fusion protein provided herein is administered with an immunotherapeutic agent. In some embodiments the immunotherapeutic agent is an antibody. Example immunotherapeutic agents that can be co-administered include abagovomab, AB308, ABP-980, adecatumumab, afutuzumab, alemtuzumab, altumomab, amatuximab, anatumomab, arcitumomab, atezolizumab, bavituximab, bectumomab, bevacizumab, bivatuzumab, blinatumomab, brentuximab, camidanlumab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, zimberelimab, and 3F8. Rituximab can be used for treating indolent B-cell cancers, including marginal-zone lymphoma, WM, CLL, and small lymphocytic lymphoma. A combination of rituximab and chemotherapy agents is especially effective.

The exemplified therapeutic antibodies can be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include gemtuzumab, brentuximab, belantamab (e.g., belantamab mafodotin), camidanlumab (e.g., camidanlumab tesirine), trastuzumab (e.g., trastuzumab deruxtecan; trasuzumab emtansine), inotuzumab, glembatumumab, anetumab, mirvetuximab (e.g., mirvetuximab soravtansine), depatuxizumab, vadastuximab, labetuzumab, ladiratuzumab (e.g., ladiratuzumab vedotin), loncastuximab (e.g., loncastuximab tesirine), sacituzumab (e.g., sacituzumab govitecan), datopotamab (e.g., datopotamab deruxtecan; DS-1062; Dato-DXd), patritumab (e.g., patritumab deruxtecan), lifastuzumab, indusatumab, polatuzumab (e.g., polatuzumab vedotin), pinatuzumab, coltuximab, upifitamab (e.g., upifitamab rilsodotin), indatuximab, milatuzumab, rovalpituzumab (e.g., rovalpituzumab tesirine), enfortumab (e.g., enfortumab vedotin), tisotumab (e.g., tisotumab vedotin), tusamitamab (e.g., tusamitamab ravtansine), disitamab (e.g., disitamab vedotin), telisotuzumab vedotin (ABBV-399), AGS-16C3F, ASG-22ME, AGS67E, AMG172, AMG575, BAY1129980, BAY1187982, BAY94-9343, GSK2857916, Humax-TF-ADC, IMGN289, IMGN151, IMGN529, IMGN632, IMGN853, IMGC936, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A, SYD985, DS-7300, XMT-1660, IMMU-130, and IMMU-140. ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., dC═Orubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein. In some embodiments, the therapeutic agent conjugated to the drug-conjugated antibody is a topoisomerase I inhibitor (e.g., a camptothecin analog, such as irinotecan or its active metabolite SN38). In some embodiments, the therapeutic agents (e.g., anticancer or antineoplastic agents) that can be conjugated to the drug-conjugated antibodies, fragments thereof, or antibody mimetics include an immune checkpoint inhibitor. In some embodiments the conjugated immune checkpoint inhibitor is a conjugated small molecule inhibitor of CD274 (PDL1, PD-L1), programmed cell death 1 (PDCD1, PD1, PD-1) or CTLA4. In some embodiments the conjugated small molecule inhibitor of CD274 or PDCD1 is selected from the group consisting of GS-4224, GS-4416, INCB086550 and MAX10181. In some embodiments the conjugated small molecule inhibitor of CTLA4 comprises BPI-002.

In some embodiments the ADCs that can be co-administered include an antibody targeting tumor-associated calcium signal transducer 2 (TROP-2; TACSTD2; EGP-1; NCBI Gene ID: 4070). Illustrative anti-TROP-2 antibodies include without limitation TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius BioTech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Klus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (*Mediterranea* Theranostic, LegoChem Biosciences), KD-065 (Nanjing KAEDI Biotech), and those described in WO2020016662

(Abmart), WO2020249063 (Bio-Thera Solutions), US20190048095 (Bio-Thera Solutions), WO2013077458 (LivTech/Chiome), EP20110783675 (Chiome), WO2015098099 (Daiichi Sankyo), WO2017002776 (Daiichi Sankyo), WO2020130125 (Daiichi Sankyo), WO2020240467 (Daiichi Sankyo), US2021093730 (Daiichi Sankyo), U.S. Pat. No. 9,850,312 (Daiichi Sankyo), CN112321715 (Biosion), US2006193865 (Immunomedics/Gilead), WO2011068845 (Immunomedics/Gilead), US2016296633 (Immunomedics/Gilead), US2017021017 (Immunomedics/Gilead), US2017209594 (Immunomedics/Gilead), US2017274093 (Immunomedics/Gilead), US2018110772 (Immunomedics/Gilead), US2018185351 (Immunomedics/Gilead), US2018271992 (Immunomedics/Gilead), WO2018217227 (Immunomedics/Gilead), US2019248917 (Immunomedics/Gilead), CN111534585 (Immunomedics/Gilead), US2021093730 (Immunomedics/Gilead), US2021069343 (Immunomedics/Gilead), U.S. Pat. No. 8,435,539 (Immunomedics/Gilead), U.S. Pat. No. 8,435,529 (Immunomedics/Gilead), U.S. Pat. No. 9,492,566 (Immunomedics/Gilead), WO2003074566 (Gilead), WO2020257648 (Gilead), US2013039861 (Gilead), WO2014163684 (Gilead), U.S. Pat. No. 9,427,464 (LivTech/Chiome), U.S. Ser. No. 10/501,555 (Abruzzo Theranostic/Oncoxx), WO2018036428 (Sichuan Kelun Pharma), WO2013068946 (Pfizer), WO2007095749 (Roche), and WO2020094670 (SynAffix). In some embodiments, the anti-Trop-2 antibody is selected from hRS7, Trop-2-XPAT, and BAT-8003. In some embodiments, the anti-Trop-2 antibody is hRS7. In some embodiments, hRS7 is as disclosed in U.S. Pat. Nos. 7,238,785; 7,517,964 and 8,084,583, which are incorporated herein by reference. In some embodiments, the antibody-drug conjugate comprises an anti-Trop-2 antibody and an anticancer agent linked by a linker. In some embodiments, the linker includes the linkers disclosed in U.S. Pat. No. 7,999,083. In some embodiments, the linker is CL2A. In some embodiments, the drug moiety of antibody-drug conjugate is a chemotherapeutic agent. In some embodiments, the chemotherapeutic agent is selected from dC═Orubcin (DOX), epirubicin, morpholinodC═Orubicin (morpholino-DOX), cyanomorpholino-dC═Orubicin (cyanomorpholinoDOX), 2-pyrrolino-dC═Orubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic moiety is SN-38. In some embodiments the antibody and/or fusion protein provided herein is administered with sacituzumab govitecan.

In some embodiments the ADCs that can be co-administered include an antibody targeting carcinoembryonic antigen-related cell adhesion molecule 1 (CEACAM1; CD66a; NCBI Gene ID: 634). In some embodiments the CEACAM1 antibody is hMN-14 (e.g., as described in WO1996011013). In some embodiments the CEACAM1-ADC is as described in WO2010093395 (anti-CEACAM-1-CL2A-SN38). In some embodiments the antibody and/or fusion protein provided herein is administered with the CEACAM1-ADC IMMU-130.

In some embodiments the ADCs that can be co-administered include an antibody targeting MHC class II cell surface receptor encoded by the human leukocyte antigen complex (HLA-DR). In some embodiments the HLA-DR antibody is hL243 (e.g., as described in WO2006094192). In some embodiments the HLA-DR-ADC is as described in WO2010093395 (anti-HLA-DR-CL2A-SN38). In some embodiments the antibody and/or fusion protein provided herein is administered with the HLA-DR-ADC IMMU-140.

Cancer Gene Therapy and Cell Therapy

In some embodiments the antibody and/or fusion protein provided herein is administered with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments the antibody and/or fusion protein provided herein is administered with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/

RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD160, CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvIII); ganglioside G2 (GD2); ganglioside GD3 (αNeuSAc(2-8)αNeuSAc(2-3)βDGaip(1-4)bDGIcp(1-1) Cer); ganglioside GM3 (αNeuSAc(2-3)βDGalp(1-4)DDGlcp(1-1)Cer); TNF receptor superfamily member 17 (TNFRSF17, BCMA); Tn antigen ((Tn Ag) or (GaINAcu-Ser/Thr)); prostate-specific membrane antigen (PSMA); receptor tyrosine kinase-like orphan receptor 1 (ROR1); tumor-associated glycoprotein 72 (TAG72); CD38; CD44v6; Carcinoembryonic antigen (CEA); epithelial cell adhesion molecule (EPCAM); B7H3 (CD276); KIT (CD117); interleukin-13 receptor subunit alpha-2 (IL-13Ra2 or CD213A2); mesothelin; interleukin 11 receptor alpha (IL-11Ra); prostate stem cell antigen (PSCA); protease serine 21 (Testisin or PRSS21); vascular endothelial growth factor receptor 2 (VEGFR2); Lewis(Y)antigen; CD24; platelet-derived growth factor receptor beta (PDGFR-beta); stage-specific embryonic antigen-4 (SSEA-4); CD20; delta like 3 (DLL3); folate receptor alpha; receptor tyrosine-protein kinase, ERBB2 (Her2/neu); mucin 1, cell surface associated (MUC1); epidermal growth factor receptor (EGFR); neural cell adhesion molecule (NCAM); prostase; prostatic acid phosphatase (PAP); elongation factor 2 mutated (ELF2M); ephrin B2; fibroblast activation protein alpha (FAP); insulin-like growth factor 1 receptor (IGF-I receptor), carbonic anhydrase IX (CAIX); proteasome (Prosome, Macropain) subunit, beta type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); fucosyl GM1; sialyl Lewis adhesion molecule (sLe); transglutaminase 5 (TGS5); high molecular weight-melanomaassociatedantigen (HMW-MAA); o-acetyl-GD2 ganglioside (OAcGD2); folate receptor beta; tumor endothelial marker 1 (TEM1/CD248); tumor endothelial marker 7-related (TEM7R); six transmembrane epithelial antigen of the prostate I (STEAPI); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); polysialic acid; placenta-specific 1 (PLAC1); hexasaccharide portion of globoH glycoceramide (GloboH); mammary gland differentiation antigen (NY—BR-1); uroplakin 2 (UPK2); hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); olfactory receptor 51E2 (ORS IE2); TCR Gamma Alternate Reading Frame Protein (TARP); Wilms tumor protein (WT1); cancer/testis antigen 1 (NY-ESO-1); cancer/testis antigen 2 (LAGE-1a); melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); androgen receptor; cyclin BI; v-myc avian myelocytomatosis viral oncogene neuroblastoma derived homolog (MYCN); ras homolog family member C (RhoC); tyrosinase-related protein 2 (TRP-2); cytochrome P450 1B1(CYP IBI); CCCTC-Binding Factor (Zinc Finger Protein)-Like (BORIS or Brother of the Regulator of Imprinted Sites), squamous cell carcinoma antigen recognized by T-cells 3 (SART3); paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); receptor for advanced glycation endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; leukocyte-associated immunoglobulin-like receptor 1 (LAIRI); Fc fragment of IgA receptor (FCAR or CD89); leukocyte immunoglobulin-like receptor subfamily A member 2 (LILRA2); CD300 molecule-like family member f (CD300LF); C-type lectin domain family 12 member A (CLECI2A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, Ll-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-$R^1$, TRAIL-$R^1$ (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15QI4, CASC5, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen 1A (CTAGIA; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ES02, LAGE-1, LAGE2B; NCBI Gene ID: 30848), CCCTC-binding factor like (CTCFL; BORIS, CT27, CTCF-T, HMGBIL1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMADI; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPS1L1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., *Proc Nat Acad Sci USA.* 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

Examples of cell therapies include: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments the one or more additional co-administered therapeutic agents can be categorized by their mechanism of action, e.g., into the following groups:

- agents targeting adenosine deaminase, such as pentostatin or cladribine;
- agents targeting ATM, such as AZD1390;
- agents targeting MET, such as savolitinib, capmatinib, tepotinib, ABT-700, AG213, JNJ-38877618 (OMO-1), merestinib, HQP-8361, BMS-817378, or TAS-115;
- agents targeting mitogen-activated protein kinase, such as antroquinonol, binimetinib, cobimetinib, selumetinib, trametinib, uprosertib, mirdametinib (PD-0325901), pimasertib, refametinib, or compounds disclosed in WO2011008709, WO2013112741, WO2006124944, WO2006124692, WO2014064215, WO2018005435, Zhou, et al., Cancer Lett. 2017 Nov. 1, 408:130-137, Teli, et al., J Enzyme Inhib Med Chem. (2012) 27(4): 558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42, or Hu, et al., Bioorg Med Chem Lett. (2011) 21(16):4758-61;
- agents targeting thymidine kinase, such as aglatimagene besadenovec (ProstAtak, PancAtak, GliAtak, GMCI, or AdV-tk);
- agents targeting targeting an interleukin pathway, such as pegilodecakin (AM-0010) (pegylated IL10), CA-4948 (IRAK4 inhibitor);
- agents targeting cytochrome P450 family members, such as letrozole, anastrozole, aminoglutethimide, megestrol acetate (MEGACE®), exemestane, formestane, fadrozole, vorozole (RIVISOR®), letrozole (FEMARA®), or anastrozole (ARIMIDEX®);
- agents targeting CD73, such as a CD73 inhibitor (e.g., quemliclustat (AB680)) or an anti-CD73 antibody (e.g., oleclumab);
- agents targeting DKK3, such as MTG-201;
- agents targeting EEF1A2, such as plitidepsin;
- agents targeting EIF4A1, such as rohinitib;
- agents targeting endoglin, such as TRC105 (carotuximab);
- agents targeting exportin-1, such as eltanexor;
- agents targeting fatty acid amide hydrolase, such as compounds disclosed in WO2017160861;
- agents targeting heat shock protein 90 beta family member 1, such as anlotinib;
- agents targeting lactotransferrin, such as ruxotemitide (LTX-315);
- agents targeting lysyl oxidase, such as compounds disclosed in U.S. Pat. Nos. 4,965,288, 4,997,854, 4,943,593, 5,021,456, 5,059,714, 5,120,764, 5,182,297, 5,252,608, or US20040248871;
- agents targeting MAGE family members, such as KITE-718, MAGE-A10C796T, or MAGE-A10 TCR;
- agents targeting MDM2, such as ALRN-6924, CMG-097, milademetan monotosylate monohydrate (DS-3032b), or AMG-232;
- agents targeting MDM4, such as ALRN-6924;
- agents targeting melan-A, such as MART-1 F5 TCR engineered PBMCs;
- agents targeting mesothelin, such as CSG-MESO or TC-210;
- agents targeting METAP2, such as M8891 or APL-1202;
- agents targeting NLRP3, such as BMS-986299;
- agents targeting C═Oglutarate dehydrogenase, such as devimistat (CPI-613);
- agents targeting placenta growth factor, such as aflibercept;
- agents targeting SLC10A3, such as compounds disclosed in WO2015148954, WO2012082647, or WO2017160861;
- agents targeting transforming growth factor alpha (TGFα), such as compounds disclosed in WO2019103203;
- agents targeting tumor protein p53, such as kevetrin (stimulator);
- agents targeting vascular endothelial growth factor A, such as aflibercept;
- agents targeting vascular endothelial growth factor receptor, such as fruquintinib or MP0250;
- agents targeting VISTA, such as CA-170, or HMBD-002;
- agents targeting WEE1, such as adavosertib (AZD-1775);
- small molecule inhibitors targeting ABL1, such as imatinib, rebastinib, asciminib, or ponatinib (ICLUSIG®);
- small molecule antagonists targeting adenosine receptor, such as CPI-444, AZD-4635, preladenant, etrumadenant (AB928), or PBF-509;
- small molecule inhibitors targeting arachidonate 5-lipoxygenase, such as meclofenamate sodium or zileuton;
- small molecule inhibitors targeting ATR serine/threonine kinase, such as BAY-937, ceralasertib (AZD6738), AZD6783, VX-803, or VX-970 (berzosertib);
- small molecule inhibitors targeting AXL receptor tyrosine kinase, such as bemcentinib (BGB-324), SLC-0211, or gilteritinib (Axl/Flt3);

small molecule inhibitors targeting Bruton's tyrosine kinase (BTK), such as (S)-6-amino-9-(1-(but-2-ynoyl) pyrrolidin-3-yl)-7-(4-phenoxyphenyl)-7H-purin-8 (9H)-one, acalabrutinib (ACP-196), zanubrutinib (BGB-3111), CB988, poseltinib (HM71224), ibrutinib (Imbruvica), M-2951 (evobrutinib), tirabrutinib (ONO-4059), rilzabrutinib (PRN-1008), spebrutinib (CC-292), vecabrutinib, ARQ-531 (MK-1026), SHR-1459, DTRMWXHS-12, or TAS-5315;

small molecule inhibitors targeting neurotrophic receptor tyrosine kinase such as larotrectinib, entrectinib, or selitrectinib (LOXO-195);

small molecule inhibitors targeting ROS proto-oncogene 1, receptor tyrosine kinase, such as entrectinib, repotrectinib (TPX-0005), or lorlatinib;

small molecule inhibitors targeting SRC proto-oncogene, non-receptor tyrosine kinase, such as VAL-201, tirbanibulin (KX2-391), or ilginatinib maleate (NS-018);

small molecule inhibitors targeting B-cell lymphoma 2, such as navitoclax (ABT-263), venetoclax (ABT-199, RG-7601), or AT-101 (gossypol);

small molecule inhibitors targeting bromodomain and external domain (BET) bromodomain containing protein, such as ABBV-744, INCB-054329, INCB057643, AZD-5153, ABT-767, BMS-986158, CC-90010, NHWD-870, ODM-207, ZBC246, ZEN3694, CC-95775 (FT-1101), mivebresib, BI-894999, PLX-2853, PLX-51107, CPI-0610, or GS-5829;

small molecule inhibitors targeting carbohydrate sulfotransferase 15, such as STNM-01;

small molecule inhibitors targeting carbonic anhydrase, such as polmacoxib, acetazolamide, or methazolamide;

small molecule inhibitors targeting catenin beta 1, such as CWP-291, or PRI-724;

small molecule antagonists targeting a C—C motif chemokine receptor, such as CCX-872, BMS-813160 (CCR2/CCR5) or MK-7690 (vicriviroc);

small molecule antagonists targeting a C—X—C motif chemokine receptor (e.g., CXCR4), blixafortide;

small molecule inhibitors targeting cereblon, such as avadomide (CC-122), CC-92480, CC-90009, or iberdomide;

small molecule inhibitors targeting checkpoint kinase 1, such as SRA737;

small molecule inhibitors targeting a complement component, such as Imprime PGG (Biothera Pharmaceuticals);

small molecule inhibitor targeting a C—X—C motif chemokine ligand (e.g., CXCL12), such as olaptesed pegol (NOX-A12);

small molecule inhibitors targeting cytochrome P450 family, such as ODM-209, LAE-201, seviteronel (VT-464), CFG920, abiraterone, or abiraterone acetate;

small molecule inhibitors targeting DEAD-box helicase 5, such as supinoxin (RX-5902);

small molecule inhibitors targeting DGKα, e.g., such as described in WO2021130638;

small molecule inhibitors targeting diablo IAP-binding mitochondrial protein, such as BI-891065;

small molecule inhibitors targeting dihydrofolate reductase, such as pralatrexate or pemetrexed disodium;

small molecule inhibitors targeting DNA dependent protein kinase, such as MSC2490484A (nedisertib), VX-984, AsiDNA (DT-01), LXS-196, or sotrastaurin;

small molecule inhibitors targeting MARCKS, such as BIO-11006;

small molecule inhibitors targeting RIPK1, such as GSK-3145094;

small molecule inhibitors targeting Rho associated coiled-coil containing protein kinase, such as AT13148 or KD025;

small molecule inhibitors targeting DNA topoisomerase, such as irinotecan, firtecan pegol, or amrubicin;

small molecule inhibitors targeting dopamine receptor D2, such as ONC-201;

small molecule inhibitors targeting DOT1 like histone lysine methyltransferase, such as pinometostat (EPZ-5676);

small molecule inhibitors targeting EZH2, such as tazemetostat, CPI-1205, or PF-06821497;

small molecule inhibitors targeting fatty acid synthase, such as TVB-2640 (Sagimet Biosciences);

small molecule inhibitors targeting fibroblast growth factor receptor 2 (FGFR2), such as bemarituzumab (FPA144);

small molecule inhibitors targeting focal adhesion kinase (FAK, PTK2), such as VS-4718, defactinib, or GSK2256098;

small molecule inhibitors targeting folate receptor 1, such as pralatrexate;

small molecule inhibitors targeting FOXM1, such as thiostrepton;

small molecule inhibitors targeting galectin 3, such as belapectin (GR-MD-02);

small molecule antagonists targeting glucocorticoid receptor, such as relacorilant (CORT-125134);

small molecule inhibitors targeting glutaminase include without limitation CB-839 (telaglenastat), or bis-2-(5-phenylacetamido-1,3,4-thiadiazol-2-yl)ethyl sulfide (BPTES);

small molecule inhibitors targeting GNRHR, such as elagolix, relugolix, or degarelix;

small molecule inhibitors targeting EPAS1, such as belzutifan (PT-2977 (Merck & Co.));

small molecule inhibitors targeting isocitrate dehydrogenase (NADP(+)), such as limitation ivosidenib (AG-120), vorasidenib (AG-881) (IDH1 and IDH2), IDH-305, or enasidenib (AG-221);

small molecule inhibitors targeting lysine demethylase 1A, such as CC-90011;

small molecule inhibitors targeting MAPK interacting serine/threonine kinase, such as tomivosertib (eFT-508);

small molecule inhibitors targeting notch receptor, such as AL-101 (BMS-906024);

small molecule inhibitors targeting polo like kinase 1 (PLK1), such as volasertib or onvansertib;

small molecule inhibitors targeting poly(ADP-ribose) polymerase (PARP), such as olaparib (MK7339), rucaparib, veliparib, talazoparib, ABT-767, pamiparib (BGB-290), fluazolepali (SHR-3162), niraparib (JNJ-64091742), stenoparib (2X-121 (e-7499)), simmiparib, IMP-4297, SC-10914, IDX-1197, HWH-340, CEP 9722, CEP-8983, E7016, 3-aminobenzamide, or CK-102;

small molecule inhibitors targeting polycomb protein EED, such as MAK683;

small molecule inhibitors targeting porcupine O-acyltransferase, such as WNT-974;

small molecule inhibitors targeting prostaglandin-endoperoxide synthase, such as HP-5000, lornoxicam, ketorolac tromethamine, bromfenac sodium, otenaproxesul (ATB-346), mofezolac, GLY-230, TRK-700, diclofenac, meloxicam, parecoxib, etoricoxib, celecoxib, AXS-06, diclofenac potassium, reformulated celecoxib (DRGT-46), AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, pamicogrel, parecoxib, robenacoxib, rofecoxib, rutecarpine, tilmacoxib, zaltoprofen, or imrecoxib;

small molecule inhibitors targeting protein arginine N methyltransferase, such as MS203, PF-06939999, GSK3368715, or GSK3326595;

small molecule inhibitors targeting PTPN11, such as TNO155 (SHP-099), RMC-4550, JAB-3068, RMC-4630 (SAR442720), or compounds disclosed in WO2018172984 or WO2017211303;

small molecule antagonist targeting retinoic acid receptor, such as tamibarotene (SY-1425);

small molecule inhibitors targeting ribosomal protein S6 kinase B1, such as MSC2363318A;

small molecule inhibitors targeting S100 calcium binding protein A9, such as tasquinimod;

small molecule inhibitors targeting selectin E, such as uproleselan sodium (GMI-1271);

small molecule inhibitors targeting SF3B1, such as H3B-8800;

small molecule inhibitors targeting Sirtuin-3, such as YC8-02;

small molecule inhibitors targeting SMO, such as sonidegib (Odomzo®, formerly LDE-225), vismodegib (GDC-0449), glasdegib (PF-04449913), itraconazole, or patidegib, taladegib;

small molecule antagonists targeting somatostatin receptor, such as OPS-201;

small molecule inhibitors targeting sphingosine kinase 2, such as opaganib (Yeliva®, ABC294640);

small molecule inhibitors targeting STAT3, such as napabucasin (BBI-608);

small molecule inhibitors targeting tankyrase, such as G007-LK or stenoparib (2X-121 (e-7499));

small molecule inhibitors targeting TFGBR1, such as galunisertib, PF-06952229;

small molecule inhibitors targeting thymidylate synthase, such as idetrexed (ONX-0801);

small molecule inhibitors targeting tumor protein p53, such as CMG-097;

small molecule inhibitors targeting valosin-containing protein, such as CB-5083;

small molecule inhibitors targeting WT1, such as ombipepimut-S(DSP-7888);

small molecule agonists targeting adenosine receptor, such as namodenoson (CF102);

small molecule agonist(s) targeting asparaginase, such as crisantaspase (Erwinase®), GRASPA (ERY-001, ERY-ASP), calaspargase pegol, or pegaspargase;

small molecule agonists targeting CCAAT enhancer binding protein alpha, such as MTL-501;

small molecule agonists targeting cytochrome P450 family, such as mitotane;

small molecule agonists targeting DExD/H-box helicase 58, such as RGT-100;

small molecule agonists targeting GNRHR, such as leuprorelin acetate, leuprorelin acetate sustained release depot (ATRIGEL), triptorelin pamoate, or goserelin acetate;

small molecule agonists targeting GRB2, such as prexigebersen (BP1001);

small molecule agonists targeting NFE2L2, such as omavelC═Olone (RTA-408);

small molecule agonists targeting NOD2, such as mifamurtide (liposomal);

small molecule agonists targeting RAR-related orphan receptor gamma, such as cintirorgon (LYC-55716);

small molecule agonists targeting retinoic acid receptor (RAR), such as tretinoin;

small molecule agonists targeting STINGI, such as ADU-S100 (MIW-815), SB-11285, MK-1454, SR-8291, AdVCA0848, GSK-532, SYN-STING, MSA-1, SR-8291, cyclic-GAMP (cGAMP), or cyclic-di-AMP;

small molecule agonists targeting thyroid hormone receptor beta, such as levothyroxine sodium;

small molecule agonists targeting tumor necrosis factor, such as tasonermin;

antisense agents targeting baculoviral IAP repeat containing 5, such as EZN-3042;

antisense agents targeting GRB2, such as prexigebersen;

antisense agents targeting heat shock protein 27, such as apatorsen;

antisense agents targeting STAT3, such as danvatirsen (IONIS-STAT3-2.5Rx);

gene therapies targeting a C—C motif chemokine receptor, such as SB-728-T;

gene therapies targeting an interleukin, such as EGENE-001, tavokinogene telseplasmid, nogapendekin alfa (ALT-803), NKTR-255, NIZ-985 (hetIL-15), SAR441000, or MDNA-55;

antibodies targeting claudin 18, such as claudiximab;

antibodies targeting clusterin, such as AB-16B5;

antibodies targeting a complement component, such as ravulizumab (ALXN-1210);

antibodies targeting a C—X—C motif chemokine ligand, such as BMS-986253 (HuMax-Inflam);

antibodies targeting delta like canonical Notch ligand 4 (DLL4), such as demcizumab, navicixizumab (DLL4/VEGF);

antibodies targeting EPH receptor A3, such as fibatuzumab (KB-004);

antibodies targeting epithelial cell adhesion molecule, such as oportuzumab monatox (VB4-845);

antibodies targeting fibroblast growth factor, such as GAL-F2, B-701 (vofatamab);

antibodies targeting hepatocyte growth factor, such as MP-0250;

antibodies targeting an interleukin, such as canakinumab (ACZ885), gevokizumab (VPM087), CJM-112, guselkumab, talacotuzumab (JNJ-56022473), siltuximab, or tocilizumab;

antibodies targeting LRRC15, such as ABBV-085 or cusatuzumab (ARGX-110);

antibodies targeting mesothelin, such as BMS-986148, SEL-403, or anti-MSLN-MMAE;

antibodies targeting myostatin, such as landogrozumab;

antibodies targeting notch receptor, such as tarextumab;

antibodies targeting TGFB1 (TGF$1), such as SAR439459, ABBV-151, NIS793, SRK-181, XOMA089, or compounds disclosed in WO2019103203;

vaccines targeting fms related receptor tyrosine kinase, such as HLA-A2402/HLA-A0201 restricted epitope peptide vaccine;

vaccines targeting heat shock protein 27, such as PSV-AML (PhosphoSynVax);

vaccines targeting PD-L1, such as IO-120+IO-103 (PD-L1/PD-L2 vaccines) or IO-103;

vaccines targeting tumor protein p53, such as MVA-p53;
vaccines targeting WT1, such as WT-1 analog peptide vaccine (WT1-CTL);
cell therapies targeting baculoviral IAP repeat containing 5, such as tumor lysate/MUC1/survivin PepTivator-loaded dendritic cell vaccine;
cell therapies targeting carbonic anhydrase, such as DC-Ad-GMCAIX;
cell therapies targeting C—C motif chemokine receptor, such as CCR5-SBC-728-HSPC;
cell therapies targeting folate hydrolase 1, such as CIK-CAR.PSMA or CART-PSMA-TGFβRDN;
cell therapies targeting GSTP1, such as CPG3-CAR (GLYCAR);
cell therapies targeting HLA-A, such as FH-MCVA2TCR or NeoTCR-P1;
cell therapies targeting an interleukin, such as CST-101;
cell therapies targeting KRAS, such as anti-KRAS G12D mTCR PBL;
cell therapies targeting MET, such as anti-cMet RNA CAR T;
cell therapies targeting MUC16, such as JCAR-020;
cell therapies targeting PD-1, such as PD-1 knockout T cell therapy (esophageal cancer/NSCLC);
cell therapies targeting PRAME, such as BPX-701;
cell therapies targeting transforming protein E7, such as KITE-439;
cell therapies targeting WT1, such as WT1-CTL, ASP-7517, or JTCR-016.

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, dC═Orubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, dC═Orubicin, dC═Orubicin hydrochloride, DT-PACE (dexamethasone, thalidomide, cisplatin, dC═Orubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, dC═Orubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID@, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal dC═Orubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R—CHOP (rituximab and CHOP), R—CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus ($CC_{1-77}9$), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, dC═Orubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including Rituximab® and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R—CHOP (rituximab, cyclophosphamide, dC═Orubicin, vincristine, and prednisone), R-FCM, R—CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R—CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, $CC_{1-779}$), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, dC═Orubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal dC═Orubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma (DLBCL) Combination Therapy

Therapeutic agents used to treat diffuse large B-cell lymphoma (DLBCL) include cyclophosphamide, dC═Orubicin, vincristine, prednisone, anti-CD20 monoclonal antibodies, etoposide, bleomycin, many of the agents listed for WM, and any combination thereof, such as ICE and RICE. In some embodiments therapeutic agents used to treat DLBCL include rituximab (Rituxan®), cyclophosphamide, dC═Orubicin hydrochloride (hydroxydaunorubicin), vincristine sulfate (Oncovin®), prednisone, bendamustine, ifosfamide, carboplatin, etoposide, ibrutinib, polatuzumab vedotin piiq, bendamustine, copanlisib, lenalidomide (Revlimid®), dexamethasone, cytarabine, cisplatin, Yescarta®, Kymriah®, Polivy® (polatuzumab vedotin), BR (bendamustine (Treanda®), gemcitabine, oxiplatin, oxaliplatin, tafasitamab, polatuzumab, cyclophosphamide, or combinations thereof. In some embodiments therapeutic agents used to treat DLBCL include R—CHOP (rituximab+cyclophosphamide+dC═Orubicin hydrochloride (hydroxydaunorubicin)+vincristine sulfate (Oncovin®), +prednisone), rituximab+bendamustine, R-ICE (Rituximab+Ifosfamide+Carboplatin+Etoposide), rituximab+lenalomide, R-DHAP (rituximab+dexamethasone+high-dose cytarabine (Ara C)+cisplatin), Polivy® (polatuzumab vedotin)+BR (bendamustine (Treanda®) and rituximab (Rituxan®), R-GemOx (Gemcitabine+oxaliplatin+rituximab), Tafa-Len (tafasitamab+lenalidomide), Tafasitamab+Revlimid®, polatuzumab+bendamustine, Gemcitabine+oxaliplatin, R-EPOCH (rituximab+etoposide phosphate+prednisone+vincristine sulfate (Oncovin®)+cyclophosphamide+dC═Orubicin hydrochloride (hydroxydaunorubicin)), or CHOP (cyclophosphamide+dC═Orubicin hydrochloride (hydroxydaunorubicin)+vincristine sulfate (Oncovin®)+prednisone). In some embodiments therapeutic agents used to treat DLBCL include tafasitamab, glofitamab, epcoritamab, Lonca-T (loncastuximab tesirine), Debio-1562, polatuzumab, Yescarta, JCAR017, ADCT-402, brentuximab vedotin, MT-3724, odronextamab, Auto-03, Allo-501A, or TAK-007.

Chronic Lymphocytic Leukemia Combination Therapy

Therapeutic agents used to treat chronic lymphocytic leukemia (CLL) include chlorambucil, cyclophosphamide, fludarabine, pentostatin, cladribine, dC═Orubicin, vincristine, prednisone, prednisolone, alemtuzumab, many of the agents listed for WM, and combination chemotherapy and chemoimmunotherapy, including the following common combination regimens: CVP, R—CVP, ICE, R-ICE, FCR, and FR.

High Risk Myelodysplastic Syndrome (HR MDS) Combination Therapy

Therapeutic agents used to treat HR MDS include azacitidine (Vidaza®), decitabine (Dacogen®), lenalidomide (Revlimid®), cytarabine, idarubicin, daunorubicin, and combinations thereof. In some embodiments combinations include cytarabine+daunorubicin and cytarabine+idarubicin. In some embodiments therapeutic agents used to treat HR MDS include pevonedistat, venetoclax, sabatolimab, guadecitabine, rigosertib, ivosidenib, enasidenib, selinexor, BGB324, DSP-7888, or SNS-301.

Low Risk Myelodysplastic Syndrome (LR MDS) Combination Therapy

Therapeutic agents used to treat LR MDS include lenalidomide, azacytidine, and combinations thereof. In some embodiments therapeutic agents used to treat LR MDS include roxadustat, luspatercept, imetelstat, LB-100, or rigosertib.

Acute Myeloid Leukemia (AML) Combination Therapy

Therapautic agents used to treat AML include cytarabine, idarubicin, daunorubicin, midostaurin (Rydapt®), venetoclax, azacitidine, ivasidenib, gilteritinib, enasidenib, low-dose cytarabine (LoDAC), mitoxantrone, fludarabine, granulocyte-colony stimulating factor, idarubicin, gilteritinib (Xospata®), enasidenib (Idhifa®), ivosidenib (Tibsovo®), decitabine (Dacogen®), mitoxantrone, etoposide, Gemtuzumab ozogamicin (Mylotarg®), glasdegib (Daurismo®), and combinations thereof. In some embodiments therapeutic agents used to treat AML include FLAG-Ida (fludarabine, cytarabine (Ara-C), granulocyte-colony stimulating factor (G-CSF) and idarubicin), cytarabine+idarubicin, cytarabine+daunorubicin+midostaurin, venetoclax+azacitidine, cytarabine+daunorubicin, or MEC (mitoxantrone, etoposide, and cytarabine). In some embodiments, therapeutic agents used to treat AML include pevonedistat, venetoclax, sabatolimab, eprenetapopt, or lemzoparlimab.

Multiple Myeloma (MM) Combination Therapy

Therapeutic agents used to treat MM include lenalidomide, bortezomib, dexamethasone, daratumumab (Darzalex®), pomalidomide, Cyclophosphamide, Carfilzomib (Kyprolis®), Elotuzumab (Empliciti), and combinations thereof. In some embodiments therapeutic agents used to treat MM include RVS (lenalidomide+bortezomib+dexamethasone), RevDex (lenalidomide plus dexamethasone), CYBORD (Cyclophosphamide+Bortezomib+Dexamethasone), Vel/Dex (bortezomib plus dexamethasone), or PomDex (Pomalidomide+low-dose dexamethasone). In some embodiments therapeutic agents used to treat MM include JCARH125, TAK-573, belantamab-m, ide-cel (CAR-T).

Breast Cancer Combination Therapy

Therapeutic agents used to treat breast cancer include albumin-bound paclitaxel, anastrozole, atezolizumab, capecitabine, carboplatin, cisplatin, cyclophosphamide, docetaxel, dC═Orubicin, epirubicin, everolimus, exemestane, fluorouracil, fulvestrant, gemcitabine, Ixabepilone, lapatinib, letrozole, methotrexate, mitoxantrone, paclitaxel, pegylated liposomal dC═Orubicin, pertuzumab, tamoxifen, toremifene, trastuzumab, vinorelbine, and any combinations thereof. In some embodiments therapeutic agents used to treat breast cancer (e.g., HR+/−/HER2+/−) include trastuzumab (Herceptin®), pertuzumab (Perjeta®), docetaxel, carboplatin, palbociclib (Ibrance®), letrozole, trastuzumab emtansine (Kadcyla®), fulvestrant (Faslodex®), olaparib (Lynparza®), eribulin, tucatinib, capecitabine, lapatinib, everolimus (Afinitor®), exemestane, eribulin mesylate (Halaven®), and combinations thereof. In some embodiments therapeutic agents used to treat breast cancer include trastuzumab+pertuzumab+docetaxel, trastuzumab+pertuzumab+docetaxel+carboplatin, palbociclib+letrozole, tucatinib+capecitabine, lapatinib+capecitabine, palbociclib+fulvestrant, or everolimus+exemestane. In some embodiments therapeutic agents used to treat breast cancer include trastuzumab deruxtecan (Enhertu®), datopotamab deruxtecan (DS-1062), enfortumab vedotin (Padcev®), balixafortide, elacestrant, or a combination thereof. In some embodiments therapeutic agents used to treat breast cancer include balixafortide+eribulin.

Triple Negative Breast Cancer (TNBC) Combination Therapy

Therapeutic agents used to treat TNBC include atezolizumab, cyclophosphamide, docetaxel, dC═Orubicin, epirubicin, fluorouracil, paclitaxel, and combinations thereof. In some embodiments therapeutic agents used to treat TNBC include olaparib (Lynparza®), atezolizumab (Tecentriq®), paclitaxel (Abraxane®), eribulin, bevacizumab (Avastin®), carboplatin, gemcitabine, eribulin mesylate (Halaven®), sacituzumab govitecan (Trodelvy®), pembrolizumab (Keytruda®), cisplatin, dC═Orubicin, epirubicin, or a combination thereof. In some embodiments therapeutic agents to treat TNBC include atezolizumab+paclitaxel, bevacizumab+paclitaxel, carboplatin+paclitaxel, carboplatin+gemcitabine, or paclitaxel+gemcitabine. In some embodiments therapeutic agents used to treat TNBC include eryaspase, capivasertib, alpelisib, rucaparib+nivolumab, atezolumab+paclitaxel+gemcitabine+capecitabine+carboplatin, ipatasertib+paclitaxel, ladiratuzumab vedotin+pembrolimab, durvalumab+DS-8201a, trilaciclib+gemcitabine+carboplatin. In some embodiments therapeutic agents used to treat TNBC include trastuzumab deruxtecan (Enhertu®), datopotamab deruxtecan (DS-1062), enfortumab vedotin (Padcev®), balixafortide, adagloxad simolenin, nelipepimut-s (NeuVax®), nivolumab (Opdivo®), rucaparib, toripalimab (Tuoyi®), camrelizumab, capivasertib, durvalumab (Imfinzi®), and combinations thereof. In some embodiments therapeutic agents use to treat TNBC include nivolumab+rucaparib, bevacizumab (Avastin®)+chemotherapy, toripalimab+paclitaxel, toripalimab+albumin-bound paclitaxel, camrelizumab+chemotherapy, pembrolizumab+chemotherapy, balixafortide+eribulin, durvalumab+trastuzumab deruxtecan, durvalumab+paclitaxel, or capivasertib+paclitaxel.

Bladder Cancer Combination Therapy

Therapeutic agents used to treat bladder cancer include datopotamab deruxtecan (DS-1062), trastuzumab deruxtecan (Enhertu®), erdafitinib, eganelisib, lenvatinib, bempegaldesleukin (NKTR-214), or a combination thereof. In some embodiments therapeutic agents used to treat bladder cancer include eganelisib+nivolumab, pembrolizumab (Keytruda®)+enfortumab vedotin (Padcev®), nivolumab+ipilimumab, duravalumab+tremelimumab, lenvatinib+pembrolizumab, enfortumab vedotin (Padcev®)+pembrolizumab, and bempegaldesleukin+nivolumab.

Colorectal Cancer (CRC) Combination Therapy

Therapeutic agents used to treat CRC include bevacizumab, capecitabine, cetuximab, fluorouracil, irinotecan, leucovorin, oxaliplatin, panitumumab, ziv-aflibercept, and any combinations thereof. In some embodiments therapeutic agents used to treat CRC include bevacizumab (Avastin®), leucovorin, 5-FU, oxaliplatin (FOLFOX), pembrolizumab (Keytruda®), FOLFIRI, regorafenib (Stivarga®), aflibercept (Zaltrap®), cetuximab (Erbitux®), Lonsurf (Orcantas®), XELOX, FOLFOXIRI, or a combination thereof. In some embodiments therapeutic agents used to treat CRC include bevacizumab+leucovorin+5-FU+oxaliplatin (FOLFOX), bevacizumab+FOLFIRI, bevacizumab+FOLFOX, aflibercept+FOLFIRI, cetuximab+FOLFIRI, bevacizumab+XELOX, and bevacizumab+FOLFOXIRI. In some embodiments therapeutic agents used to treat CRC include binimetinib+encorafenib+cetuximab, trametinib+dabrafenib+panitumumab, trastuzumab+pertuzumab, napabucasin+FOLFIRI+bevacizumab, nivolumab+ipilimumab.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof. In some embodiments therapeutic agents used to treat gastroesophageal junction cancer (GEJ) include herceptin, cisplatin, 5-FU, ramicurimab, or paclitaxel. In some embodiments therapeutic agents used to treat GEJ cancer include ALX-148, AO-176, or IBI-188.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Therapeutic agents used to treat head and neck squamous cell carcinoma (HNSCC) include pembrolizumab, carboplatin, 5-FU, docetaxel, cetuximab (Erbitux®), cisplatin, nivolumab (Opdivo®), and combinations thereof. In some embodiments therapeutic agents used to treat HNSCC include pembrolizumab+carboplatin+5-FU, cetuximab+cisplatin+5-FU, cetuximab+carboplatin+5-FU, cisplatin+5-FU, and carboplatin+5-FU. In some embodiments therapeutic agents used to treat HNSCC include durvalumab, durvalumab+tremelimumab, nivolumab+ipilimumab, rovaluecel, pembrolizumab, pembrolizumab+epacadostat, GSK3359609+pembrolizumab, lenvatinib+pembrolizumab, retifanlimab, retifanlimab+enobituzumab, ADU-S100+pembrolizumab, epacadostat+nivolumab+ipilimumab/lirilumab.

Non-Small Cell Lung Cancer Combination Therapy

Therapeutic agents used to treat non-small cell lung cancer (NSCLC) include afatinib, albumin-bound paclitaxel, alectinib, atezolizumab, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof. In some embodiments therapeutic agents used to treat NSCLC include alectinib (Alecensa®), dabrafenib (Tafinlar®), trametinib (Mekinist®), osimertinib (Tagrisso®), entrectinib (Tarceva®), crizotinib (Xalkori®), pembrolizumab (Keytruda®), carboplatin, pemetrexed (Alimta®), nab-paclitaxel (Abraxane®), ramucirumab (Cyramza®), docetaxel, bevacizumab (Avastin®), brigatinib, gemcitabine, cisplatin, afatinib (Gilotrif®), nivolumab (Opdivo®), gefitinib (Iressa®), and combinations thereof. In some embodiments therapeutic agents used to treat NSCLC include dabrafenib+trametinib, pembrolizumab+carboplatin+pemetrexed, pembrolizumab+carboplatin+nab-paclitaxel, ramucirumab+docetaxel, bevacizumab+carboplatin+pemetrexed, pembrolizumab+pemetrexed+carboplatin, cisplatin+pemetrexed, bevacizumab+carboplatin+nab-paclitaxel, cisplatin+gemcitabine, nivolumab+docetaxel, carboplatin+pemetrexed, carboplatin+nab-paclitaxel, or pemetrexed+cisplatin+carboplatin. In some embodiments therapeutic agents used to NSCLC include datopotamab deruxtecan (DS-1062), trastuzumab deruxtecan (Enhertu®), enfortumab vedotin (Padcev®), durvalumab, canakinumab, cemiplimab, nogapendekin alfa, avelumab, tiragolumab, domvanalimab, vibostolimab, ociperlimab, or a combination thereof. In some embodiments therapeutic agents used to treat NSCLC include datopotamab deruxtecan+pembrolizumab, datopotamab deruxtecan+durvalumab, durvalumab+tremelimumab, pembrolizumab+lenvatinib+pemetrexed, pembrolizumab+olaparib, nogapendekin alfa (N-803)+pembrolizumab, tiragolumab+atezolizumab, vibostolimab+pembrolizumab, or ociperlimab+tislelizumab.

Small Cell Lung Cancer Combination Therapy

Therapeutic agents used to treat small cell lung cancer (SCLC) include atezolizumab, bendamustime, carboplatin, cisplatin, cyclophosphamide, docetaxel, dC═Orubicin, etoposide, gemcitabine, ipillimumab, irinotecan, nivolumab, paclitaxel, temozolomide, topotecan, vincristine, vinorelbine, and any combinations thereof. In some embodiments therapeutic agents used to treat SCLC include atezolizumab, carboplatin, cisplatin, etoposide, paclitaxel, topotecan, nivolumab, durvalumab, trilaciclib, or combinations thereof. In some embodiments therapeutic agents used to treat SCLC include atezolizumab+carboplatin+etoposide, atezolizumab+carboplatin, atezolizumab+etoposide, or carboplatin+paclitaxel.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, dC═Orubicin, etoposide, exemestane, gemcitabine, ifosfamide, irinotecan, letrozole, leuprolide acetate, liposomal dC═Orubicin, megestrol acetate, melphalan, olaparib, oxaliplatin, paclitaxel, pazopanib, pemetrexed, tamoxifen, topotecan, vinorelbine, and any combinations thereof.

Pancreatic Cancer Combination Therapies

Therapeutic agents used to treat pancreatic cancer include 5-FU, leucovorin, oxaliplatin, irinotecan, gemcitabine, nab-paclitaxel (Abraxane®), FOLFIRINOX, and combinations thereof. In some embodiments therapeutic agents used to treat pancreatic cancer include 5-FU+leucovorin+oxaliplatin+irinotecan, 5-FU+nanoliposomal irinotecan, leucovorin+nanoliposomal irinotecan, and gemcitabine+nab-paclitaxel.

Prostate Cancer Combination Therapies

Therapeutic agents used to treat prostate cancer include enzalutamide (Xtandi®), leuprolide, trifluridine, tipiracil (Lonsurf), cabazitaxel, prednisone, abiraterone (Zytiga®), docetaxel, mitoxantrone, bicalutamide, LHRH, flutamide, ADT, sabizabulin (Veru-111), and combinations thereof. In some embodiments therapeutic agents used to treat prostate cancer include enzalutamide+leuprolide, trifluridine+tipiracil (Lonsurf), cabazitaxel+prednisone, abiraterone+prednisone, docetaxel+prednisone, mitoxantrone+prednisone, bicalutamide+LHRH, flutamide+LHRH, leuprolide+flutamide, and abiraterone+prednisone+ADT.

Additional Exemplified Combination Therapies

In some embodiments the antibody and/or fusion protein provided herein is administered with one or more therapeutic agents selected from a PI3K inhibitor, a Trop-2 binding agent, CD47 antagonist, a SIRPα antagonist, a FLT3R agonist, a PD-1 antagonist, a PD-L1 antagonist, an MCL1 inhibitor, a CCR8 binding agent, an HPK1 antagonist, a DGKα inhibitor, a CISH inhibitor, a PARP-7 inhibitor, a Cbl-b inhibitor, a KRAS inhibitor (e.g., a KRAS G12C or G12D inhibitor), a KRAS degrader, a beta-catenin degrader, a helios degrader, a CD73 inhibitor, an adenosine receptor antagonist, a TIGIT antagonist, a TREM1 binding agent, a TREM2 binding agent, a CD137 agonist, a GITR binding agent, an OX40 binding agent, and a CAR-T cell therapy.

In some embodiments the antibody and/or fusion protein provided herein is administered with one or more therapeutic agents selected from a PI3K6 inhibitor (e.g., idealisib), an anti-Trop-2 antibody drug conjugate (e.g., sacituzumab govitecan, datopotamab deruxtecan (DS-1062)), an anti-CD47 antibody or a CD47-blocking agent (e.g., magrolimab, DSP-107, AO-176, ALX-148, letaplimab (IBI-188), lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab, avelumab), a small molecule MCL1 inhibitor (e.g., GS-9716), a small molecule HPK1 inhibitor (e.g., GS-6451), a HPK1 degrader (PROTAC; e.g., ARV-766), a small molecule DGKa inhibitor, a small molecule CD73 inhibitor (e.g., quemliclustat (AB680)), an anti-CD73 antibody (e.g., oleclumab), a dual $A_{2a}/A_{2b}$ adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a CD137 agonist (e.g., AGEN-2373), a GITR/OX40 binding agent (e.g., AGEN-1223) and a CAR-T cell therapy (e.g., axicabtagene ciloleucel, brexucabtagene autoleucel, tisagenlecleucel).

In some embodiments the antibody and/or fusion protein provided herein is administered with one or more therapeutic agents selected from idealisib, sacituzumab govitecan, magrolimab, GS-0189, GS-3583, zimberelimab, GS-4224, GS-9716, GS-6451, quemliclustat (AB680), etrumadenant (AB928), domvanalimab, AB308, PY159, PY314, AGEN-1223, AGEN-2373, axicabtagene ciloleucel and brexucabtagene autoleucel.

III. Pharmaceutical Compositions

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, PA). Such methods include the step of bringing into association the active ingredient with inactive ingredients (e.g., a carrier, pharmaceutical excipient, etc.) which constitutes one or more accessory ingredients. In general the formulations are prepared by uniformly and intimately bringing into association the active ingredient with liquid carriers or finely divided solid carriers or both, and then, if necessary, shaping the product.

In certain embodiments, formulations suitable for oral administration are presented as discrete units such as capsules, cachets or tablets each containing a predetermined amount of the active ingredient.

In certain embodiments, the pharmaceutical formulations include one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight). In some embodiments, the pharmaceutical compositions described herein contain about 1 to 800 mg, 1 to 600 mg, 1 to 400 mg, 1 to 200 mg, 1 to 100 mg or 1 to 50 mg of the compound of Formula I, or a pharmaceutically acceptable salt thereof. In some embodiments, the pharmaceutical compositions described herein contain not more than about 400 mg of the compound of Formula I. In some embodiments, the pharmaceutical compositions described herein contain about 100 mg of the compound of Formula I, or a pharmaceutically acceptable salt thereof.

It should be understood that in addition to the ingredients particularly mentioned above the formulations disclosed herein may include other agents conventional in the art having regard to the type of formulation in question, for example those suitable for oral administration may include flavoring agents.

Veterinary compositions comprising at least one active ingredient as above defined together with a veterinary carrier are further provided.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

IV. Routes of Administration

One or more compounds of Formula I (herein referred to as the active ingredients), or a pharmaceutically acceptable salt thereof, are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally. Accordingly, in one embodiment, the pharmaceutical compositions described herein are oral dosage forms. In certain embodiments, the pharmaceutical compositions described herein are oral solid dosage forms.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

Formulation Example 2

A tablet Formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone | |
| (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Formulation Example 5

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 6

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) | |
| Microcrystalline cellulose (89%) | 50.0 mg |

-continued

| Ingredient | Amount |
|---|---|
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Formulation Example 7

A subcutaneous formulation may be prepared as follows:

| Ingredient | Quantity |
|---|---|
| Active Ingredient | 5.0 mg |
| Corn Oil | 1.0 mL |

Formulation Example 8

An injectable preparation is prepared having the following composition:

| Ingredients | Amount |
|---|---|
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Formulation Example 9

A topical preparation is prepared having the following composition:

| Ingredients | grams |
|---|---|
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to100 |

All of the above ingredients, except water, are combined and heated to 60° C. with stirring. A sufficient quantity of water at 60° C. is then added with vigorous stirring to emulsify the ingredients and water then added q.s. 100 g.

Formulation Example 10

Sustained Release Composition

| Ingredient | Weight Range % |
|---|---|
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

Sustained release formulations of this disclosure may be prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols). The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Formulation Example 11

A tablet Formula Is prepared using the ingredients below:

| Ingredient | Quantity (mg/tablet) |
|---|---|
| Active Ingredient | 300.0 |
| Cellulose, microcrystalline | 100.0 |
| Colloidal silicon dioxide | 10.0 |
| Stearic acid | 5.0 |

The components are blended and compressed to form tablets.

V. List of Abbreviations and Acronyms

| Abbreviation | Meaning |
|---|---|
| ° C. | Degree Celsius |
| Ac | Acetyl |
| AD-H | Adipic acid dihydrazide |
| ADP | Adenosine diphosphate |
| aq | Aqueous |
| ATP | Adenosine triphosphate |
| D | Doublet |
| DCM | Dichloromethane |
| dd | Doublet of doublets |
| ddd | Doublet of doublet of doublets |
| DIEA | N,N-Diisopropylethyamine |
| DIPEA | N,N-Diisopropylethylamine (Hunig's Base) |
| DMA | Dimethylacetamide |
| DME | 1,2-Dimethoxyethane |
| DMF | Dimethylformamide |
| DMP | Dess-Martin periodinane |
| DMSO | Dimethylsulfoxide |
| Dt | Doublet-triplet |
| EC50 | The half maximal effective concentration |
| EDC | 1-(3-dimethylaminopropyl)-3-ethylcarbodiimide |
| EDTA | Ethylenediaminetetraacetic acid |
| Eq | Equivalents |
| ES/MS | Electrospray mass spectrometry |
| Et | Ethyl |
| EtOAc | Ethyl acetate |
| EtOH | Ethanol (Ethyl alcohol) |
| FBS | Fetal bovine serum |
| G | Grams |
| h | hours |
| HATU | 1-[Bis(dimethylamino)methylene]-1H-1,2,3-triazolo[4,5-b]pyridinium 3-oxid hexafluorophosphate |
| HEPES | 2-[4-(2-hydroxyethyl)piperazin-1-yl]ethanesulfonic acid |
| HCl | Hydrochloric acid |
| HOAc | Acetic acid |
| HPLC | High performance liquid chromatography |
| Hrs | Hours |
| Hz | Hertz |
| $IC_{50}$ | Half-maximal inhibitory concentration |
| i-pr | Isopropyl |
| Isolute ® | polystyrene-divinylbenzene copolymer |
| J | Coupling constant (MHz) |
| Li HMDS | Lithium bis(trimethylsilyl)amide |
| LiOH | Lithium hydroxide |
| LiI | Lithium iodide |
| M | Molar |
| M | multiplet |
| M+ | Mass peak |
| M + H+ | Mass peak plus hydrogen |
| Me | Methyl |
| MeCN | Acetonitrile |
| MeOH | Methanol (Methyl alcohol) |
| $Me_6Sn_2$ | Hexamethyldistannane (hexamethylditin) |
| Mg | Milligram |
| $MgSO_4$ | Magnesium sulfate |
| MHz | Megahertz |
| Min | Minute |
| ml/mL | Milliliter |
| mM | Millimolar |
| Mmol | Millimole |
| $NaHCO_3$ | Sodium bicarbonate |
| NBS | N-Bromosuccinimide |
| n- | Normal |
| nBu/Bu | n-Butyl (normal Butyl) |
| NaH | Sodium hydride |
| $NaHCO_3$ | Sodium bicarbonate |
| nL | Nanoliter |
| Nm | Nanometer |
| NMP | 1-methylpyrrolidin-2-one |
| NMR | Nuclear magnetic resonance |
| Ph | Phenyl |
| psi | Pounds per square inch |
| Q | Quartet |

-continued

V. List of Abbreviations and Acronyms

| Abbreviation | Meaning |
|---|---|
| q.s. | Quantity sufficient to achieve a stated |
| rac-BINAP Pd G3 | Methanesulfonato[2,2'-bis(diphenylphosphino)-1,1'-binaphthyl](2'-amino-1,1'-biphenyl-2-yl)palladium(II) |
| RP | Reverse phase |
| Rt | Room temperature |
| RuPhos ® | Methanesulfonato-2'-methylamino-1,1'-biphenyl-2-yl- Palladacycles $4^{th}$ generation |
| S | Singlet |
| T | Triplet |
| t-BuBrettPhos Pd G3 | 2-(Di-tert-butylphosphino)-2',4',6'- triisopropyl-3,6-dimethoxy-1,1'-biphenyl)-2-(2'-amino-1,1'-biphenyl)]palladium(II) methanesulfonate |
| TEA | Trimethylamine |
| THF | Tetrahydrofuran |
| TFA | Trifluoroacetic acid |
| XPhos Pd G4 ® | dicyclohexyl-[2-[2,4,6-tri(propan-2-yl)phenyl]phenyl]phosphanium;methanesulfonic acid;N-methyl-2-phenylaniline;palladium General Scheme |

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

i. General scheme A

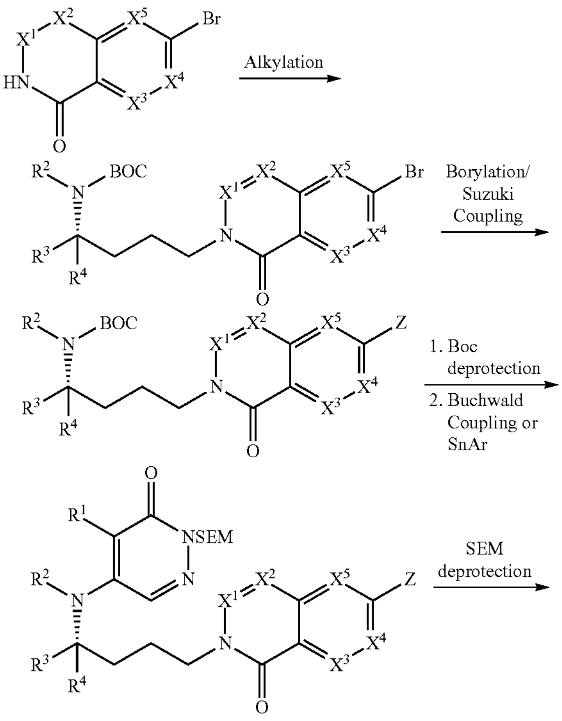

-continued
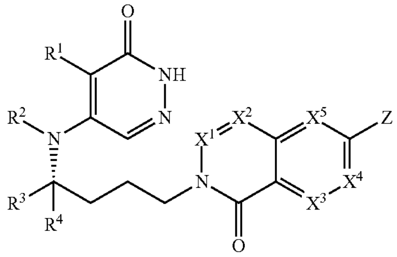
ii. General scheme B
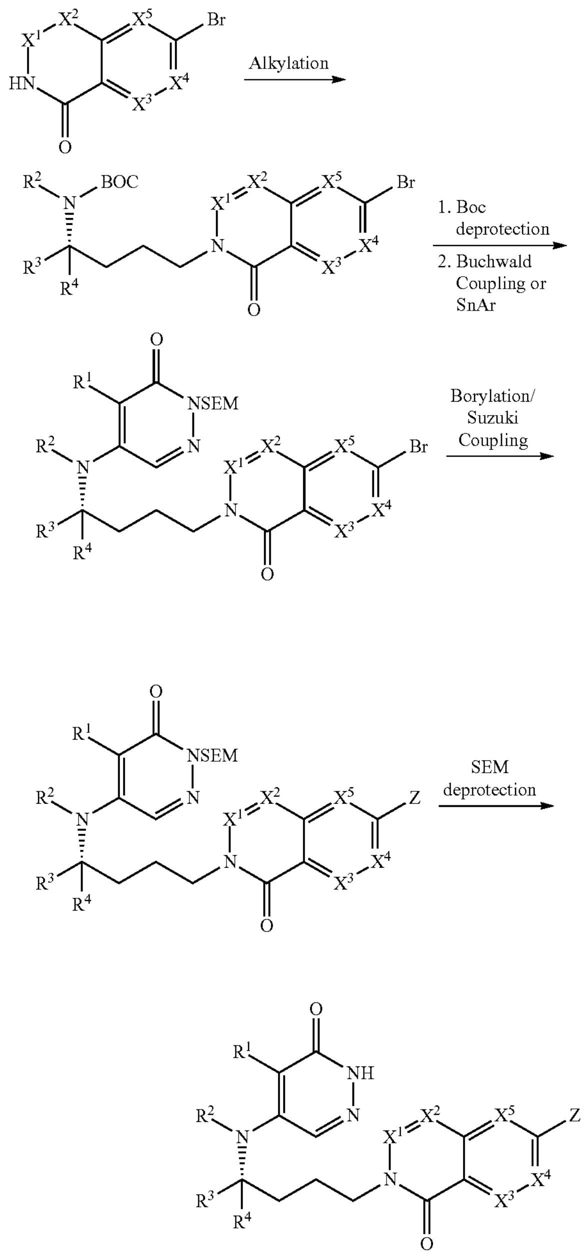
iii. General scheme C
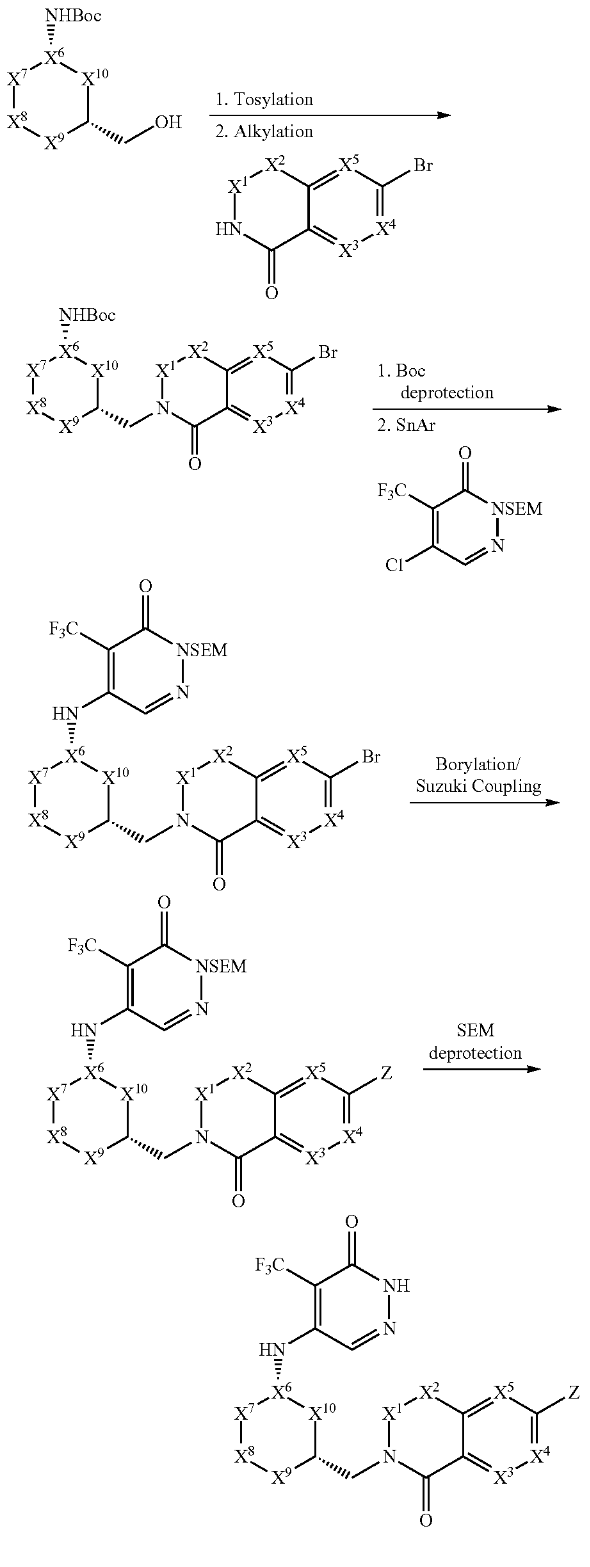
Examples
The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

iv. General scheme A

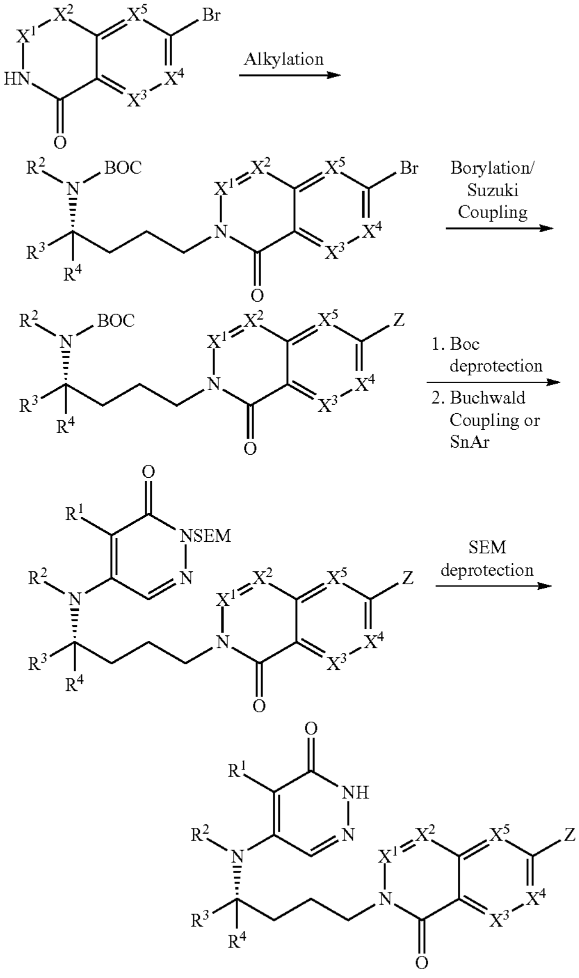

v. General scheme B

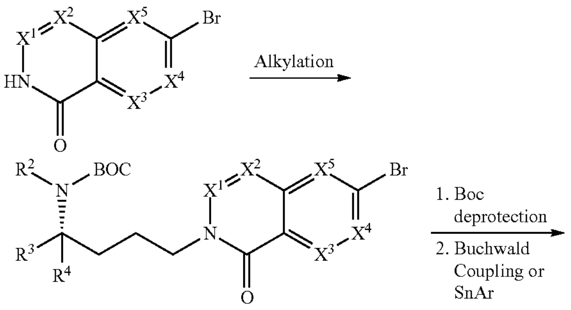

-continued

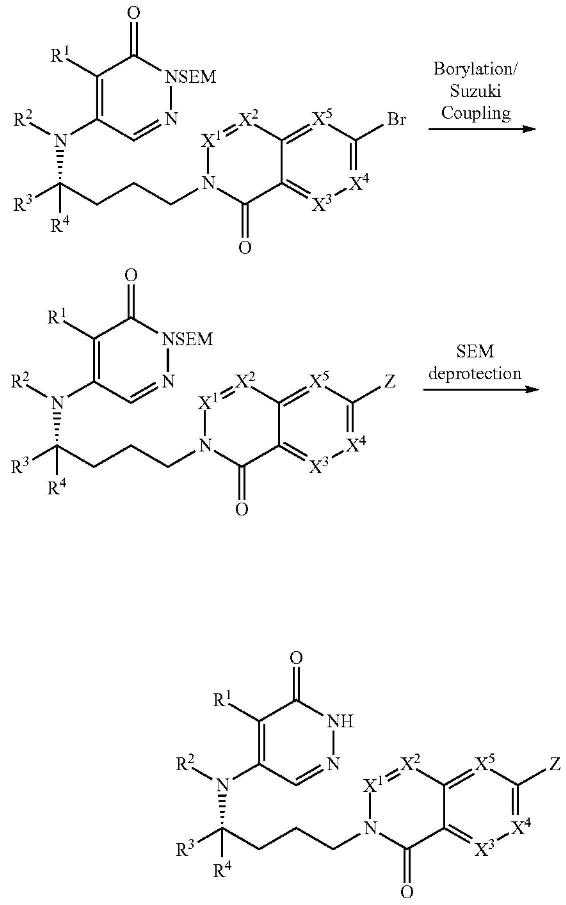

iii. General scheme C

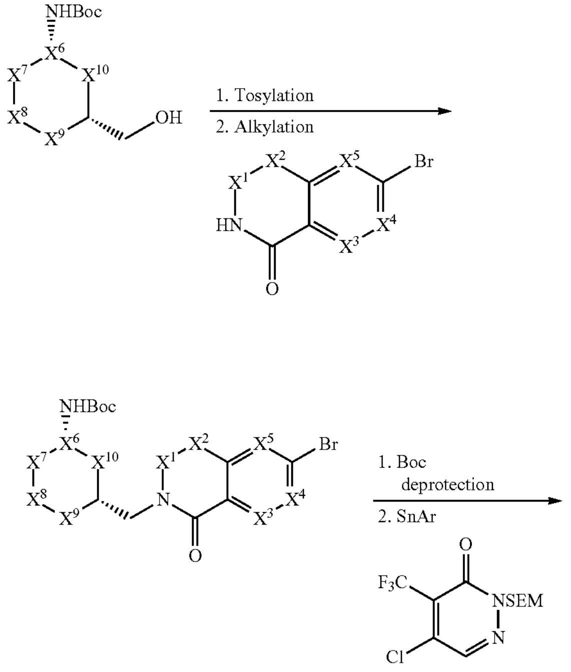

-continued

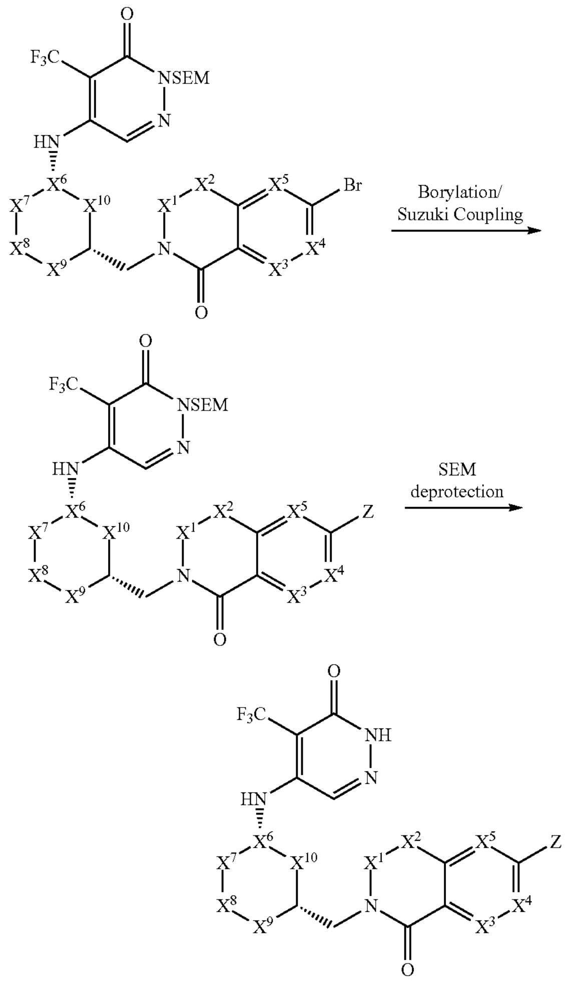

ii. Synthetic Examples

Example 1 Preparation of 2-(4-((6-oxo-5-(trifluoromethyl)-1,6-dihydropyridazin-4-yl)amino)pentyl)-6-(5-(trifluoromethyl)pyridin-2-yl)isoquinolin-1(2H)-one

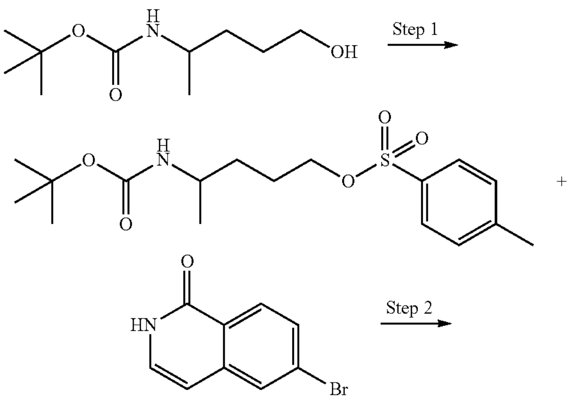

-continued

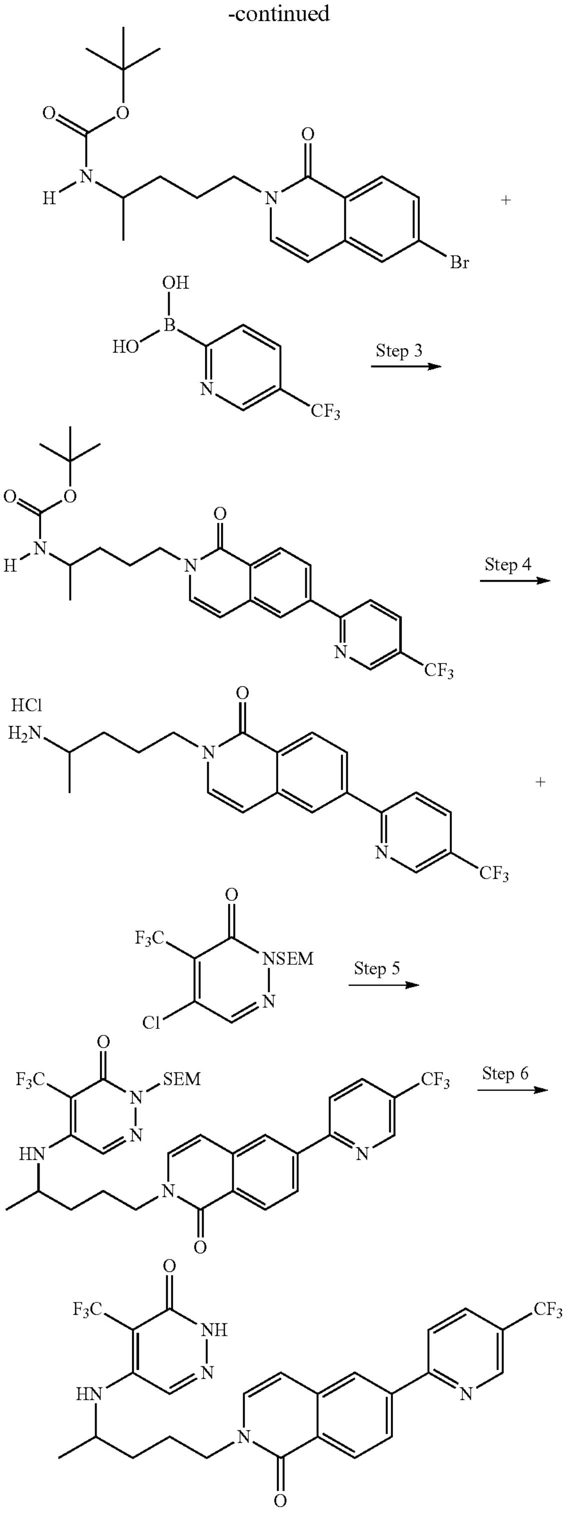

Example 1

Step 1. To a stirred solution of tert-butyl N-[(1S,3R)-3-hydroxycyclopentyl]carbamate (200 mg, 0.984 mmol) and triethylamine (199 mg, 1.97 mmol) in dichloromethane (4.50 mL) at 0° C. was added p-Toluenesulfonyl chloride (188 mg, 0.984 mmol) dropwise and the mixture was warmed to room temperature and stirred for 2 h. Upon completion, the mixture was diluted with water and extracted with dicholoromethane. The combined organic layers were washed with brine, dried over $Na_2SO_4$ and concentrated in vacuo to give the crude product. The crude residue was purified using column chromatography eluting with EtOAc in hexanes 0-100% to afford 4-(tert-butoxycarbonylamino)pentyl 4-methylbenzenesulfonate. ES/MS: m/z 380.4 $[M+Na]^+$.

Step 2. To a mixture of 6-bromo-2H-isoquinolin-1-one (55.0 mg, 0.245 mmol) and 4-(tert-butoxycarbonylamino) pentyl 4-methylbenzenesulfonate (102 mg, 0.285 mmol) in DMF (0.70 mL) was added $Cs_2CO_3$ (160 mg, 0.491 mmol) and the reaction was stirred at room temperature for 18 h. Upon completion, the mixture was diluted with EtOAc, washed with water, washed with brine, dried over $Na_2SO_4$ and concentrated in vacuo to give the crude product. The crude residue was purified using column chromatography eluting with EA in hexanes 0-100% to afford tert-butyl N-[4-(6-bromo-1-oxo-2-isoquinolyl)-1-methyl-butyl]carbamate. ES/MS: m/z 411.2 $[M+H]^+$.

Step 3. A solution of tert-butyl N-[4-(6-bromo-1-oxo-2-isoquinolyl)-1-methyl-butyl]carbamate (106 mg, 0.259 mmol), [5-(trifluoromethyl)-2-pyridyl]boronic acid (148 mg, 0.777 mmol), Pd(dppf)$Cl_2$ (21.4 mg, 0.026 mmol), and KOAc (76.2 mg, 0.777 mmol) in dioxane (2.0 mL) and water (0.30 mL) was purged with nitrogen gas for 5 minutes and heated at 90° C. for 18 hrs. Upon cooling, the mixture was filtered through a pad of Celite®, concentrated in vacuo to give the crude product. The crude residue was purified using column chromatography eluting with EtOAc in hexanes 0-100% to afford tert-butyl N-[1-methyl-4-[1-oxo-6-[5-(trifluoromethyl)-2-pyridyl]-2-isoquinolyl]butyl]carbamate. ES/MS: m/z 476.6 $[M+H]^+$.

Step 4. To a solution of tert-butyl N-[1-methyl-4-[1-oxo-6-[5-(trifluoromethyl)-2-pyridyl]-2-isoquinolyl]butyl]carbamate (54.2 mg, 0.114 mmol) in dichloromethane (1.10 mL) was added trifluoroacetic acid (0.19 mL, 5.70 mmol) at room temperature and the mixture was stirred for 1 hr. Upon completion, the solvent was removed under reduced pressure to afford 2-(4-aminopentyl)-6-[5-(trifluoromethyl)-2-pyridyl]isoquinolin-1-one hydrochloride. ES/MS: m/z 376.3 $[M+H]^+$.

Step 5. A mixture of 2-(4-aminopentyl)-6-[5-(trifluoromethyl)-2-pyridyl]isoquinolin-1-one hydrochloride (47 mg, 0.11 mmol), 5-chloro-4-(trifluoromethyl)-2-(2-trimethylsilylethoxymethyl)pyridazin-3-one (45 mg, 0.14 mmol), and N,N-diisopropylethylamine (0.10 mL, 0.57 mmol) in DMF (2.0 mL) was heated at 80° C. for 15 minutes. Upon completion, the reaction was diluted with EtOAc, washed with water, washed with brine, dried over $Na_2SO_4$ and concentrated in vacuo to give the crude product. The crude residue was purified using column chromatography eluting with EtOAc in hexanes 0-100% to provide 2-[4-[[6-oxo-5-(trifluoromethyl)-1-(2-trimethylsilylethoxymethyl) pyridazin-4-yl]amino]pentyl]-6-[5-(trifluoromethyl)-2-pyridyl]isoquinolin-1-one. ES/MS: m/z 668.1 $[M+H]^+$.

Step 6. To a solution of 2-[4-[[6-oxo-5-(trifluoromethyl)-1-(2-trimethylsilylethoxymethyl)pyridazin-4-yl]amino]pentyl]-6-[5-(trifluoromethyl)-2-pyridyl]isoquinolin-1-one (59.6 mg, 0.084 mmol) in dichloromethane (1.0 mL) was added trifluoroacetic acid (0.078 mL, 1.02 mmol) at room temperature and the mixture was stirred for 45 minutes. The excess trifluoroacetic acid and solvent was removed under reduced pressure and the residue was dissolved in MeOH (1.0 mL). To this was added ethylenediamine (0.057 mL, 0.84 mmol) and the resulting mixture was stirred at room temperature for 1 hr. Upon completion, the mixture was concentrated in vacuo and purified via reverse phase prep-HPLC (5-100% MeCN in water, 0.1% TFA) to afford 2-[4-[[6-oxo-5-(trifluoromethyl)-1H-pyridazin-4-yl]amino] pentyl]-6-[5-(trifluoromethyl)-2-pyridyl]isoquinolin-1-one. 1H NMR (400 MHz, DMSO-d6) δ 12.43 (s, 1H), 9.12 (s, 1H), 8.48 (s, 1H), 8.40-8.33 (m, 3H), 8.26 (d, J=8.1 Hz, 1H), 7.92 (s, 1H), 7.54 (d, J=7.2 Hz, 1H), 6.79-6.75 (m, 1H), 6.39-6.31 (m, 1H), 4.03-3.96 (m, 3H), 1.77-1.63 (m, 3H), 1.52 (s, 1H), 1.17 (d, J=6.2 Hz, 3H). ES/MS m/z=538.1 $[M+H]^+$.

Example 2 and Example 3 Preparation of 2-[(4R)-4-[[6-oxo-5-(trifluoromethyl)-1H-pyridazin-4-yl] amino]pentyl]-6-[5-(trifluoromethyl)-2-pyridyl]isoquinolin-1-one and 2-[(4S)-4-[[6-oxo-5-(trifluoromethyl)-1H-pyridazin-4-yl]amino]pentyl]-6-[5-(trifluoromethyl)-2-pyridyl]isoquinolin-1-one

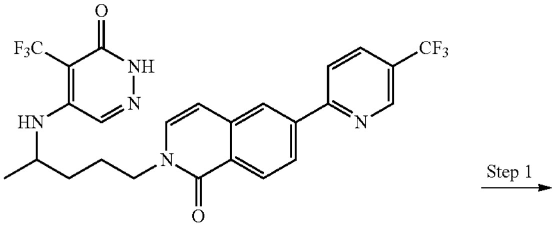

Example 1

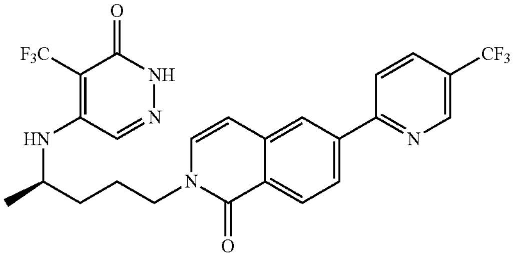

Example 2

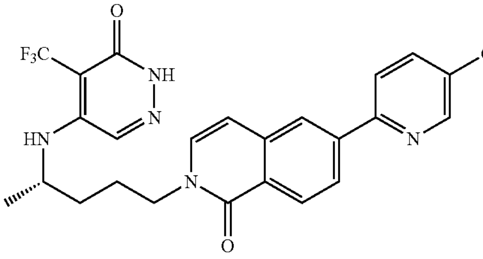

Example 3

Step 1. Examples 2 and Example 3 were separated via chiral SFC (AD-H, 5 □m, 21×250 mm column; 35% EtOH as co-solvent; 100 bar; 40° C.). The first eluting peak was assigned as the (R)-configuration (Example 2), and the second eluting peak was assigned as the (S)-configuration (Example 3). The final compounds were free of TFA.

Example 2: 1H NMR (400 MHz, DMSO-d6) δ 12.43 (s, 1H), 9.12 (s, 1H), 8.48 (s, 1H), 8.40-8.33 (m, 3H), 8.26 (d, J=8.1 Hz, 1H), 7.92 (s, 1H), 7.54 (d, J=7.2 Hz, 1H), 6.79-6.75 (m, 1H), 6.39-6.31 (m, 1H), 4.03-3.96 (m, 3H), 1.77-1.63 (m, 3H), 1.52 (s, 1H), 1.17 (d, J=6.2 Hz, 3H). ES/MS m/z: 538.1 $[M+H]^+$.

Example 3: 1H NMR (400 MHz, DMSO-d6) δ 12.43 (s, 1H), 9.12 (s, 1H), 8.48 (s, 1H), 8.40-8.33 (m, 3H), 8.26 (d, J=8.1 Hz, 1H), 7.92 (s, 1H), 7.54 (d, J=7.2 Hz, 1H), 6.79-6.75 (m, 1H), 6.39-6.31 (m, 1H), 4.03-3.96 (m, 3H), 1.77-1.63 (m, 3H), 1.52 (s, 1H), 1.17 (d, J=6.2 Hz, 3H). ES/MS m/z: 538.1 [M+H]$^+$.

Example 4: 2-[(4S)-4-[[6-oxo-5-(trifluoromethyl)-1H-pyridazin-4-yl]amino]pentyl]-6 [5-(trifluoromethyl)pyrimidin-2-yl]phthalazin-1-one Example 4

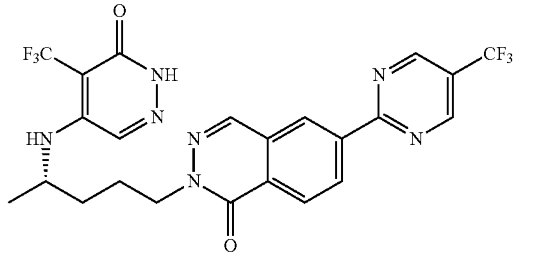

The title compound was synthesized as described in Example 1, using 6-bromo-2H-phthalazin-1-one in place of 6-bromoisoquinolin-1(2H)-one. 1H NMR (400 MHz, DMSO-d6) δ 12.41 (s, 1H), 9.48 (s, 2H), 9.02 (d, J=1.2 Hz, 1H), 8.85 (dd, J=8.4, 1.6 Hz, 1H), 8.68 (s, 1H), 8.45 (d, J=8.4 Hz, 1H), 7.91 (s, 1H), 6.35 (dd, J=8.5, 3.1 Hz, 1H), 4.17 (t, J=6.8 Hz, 2H), 3.98 (d, J=12.0 Hz, 1H), 1.86-1.76 (m, 2H), 1.75-1.64 (m, 1H), 1.55 (d, J=19.6 Hz, 1H), 1.17 (d, J=6.3 Hz, 3H). ES/MS m/z: 540.1 [M+H]$^+$.

Example 5 Preparation of 2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one

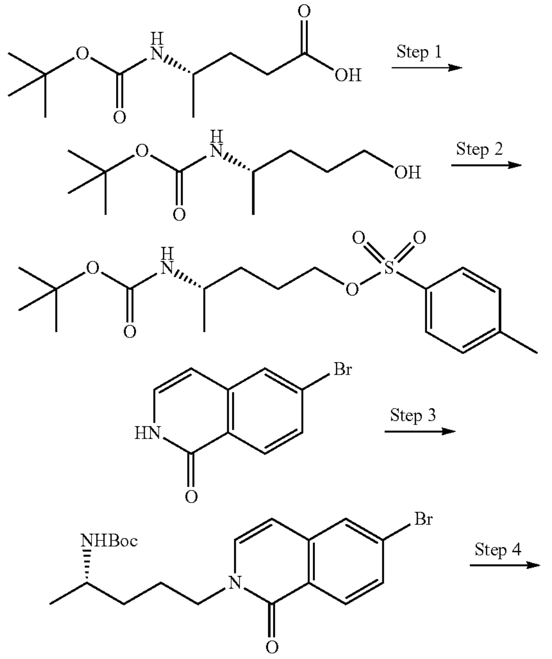

-continued

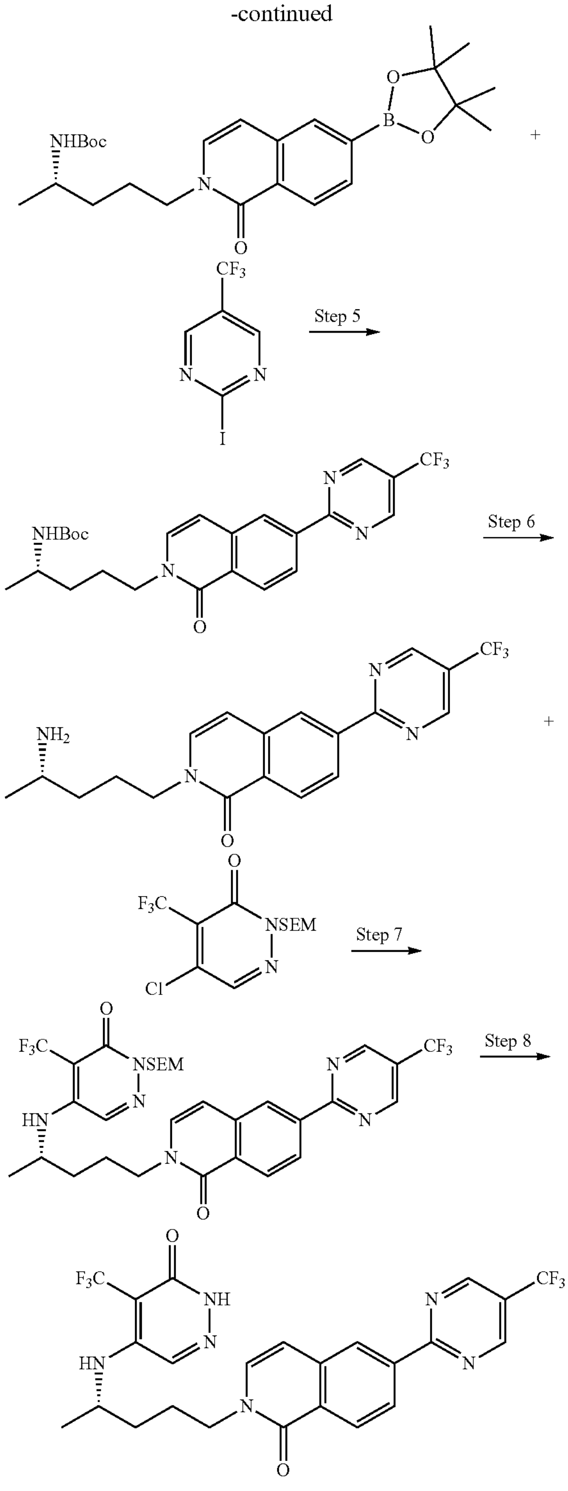

Example 5

Step 1. In a vial were placed (4S)-4-(tert-butoxycarbonylamino)pentanoic acid (1000 mg, 4.6 mmol), and triethylamine (0.642 mL, 4.6 mmol) in THF (44.4 mL). The mixture was cool to 0° C. and placed under nitrogen atmosphere. To this solution was added ethyl chloroformate (0.44 mL, 4.6 mmol) and the reaction was stirred for 30 minutes at 0° C. The mixture was then filtered to remove the precipitated triethylamine hydrochloride. The filtrate containing the mixed anhydride was slowly added to a stirred suspension of sodium borohydride (522 mg, 13.8 mmol) in 20% aqueous THF (10.0 mL) maintained at 10° C. After the mixture was stirred for 30 minutes, it was acidified with 1N HCl to pH~4. The mixture was then extracted with EtOAc, washed with 2M NaOH solution, washed with brine, dried ($Na_2SO_4$), and purified by flash chromatography (100% hexanes to 100% EtOAc) to give tert-butyl N-[(1S)-4-hydroxy-1-methyl-butyl]carbamate. ES/MS: m/z 204.498 [M+H].

Step 2. In a vial were placed tert-butyl N-[(1S)-4-hydroxy-1-methyl-butyl]carbamate (450 mg, 2.21 mmol), and triethylamine (0.62 mL, 4.43 mmol) in DCM (10.1 mL). The mixture was cooled to 0° C. and p-toluenesulfonyl chloride (422 mg, 2.21 mmol) was added. After mixture was warmed to room temperature and stirred for 2 h, it was quenched with water and extracted with EtOAc (×3). The combined organic layers were washed with brine, dried ($Na_2SO_4$), and purified by flash chromatography (100% hexanes to 100% EtOAc) to give [(4S)-4-(tert-butoxycarbonylamino)pentyl]4-methylbenzenesulfonate. ES/MS m/z: 358.551 [M+H].

Step 3. In a vial were placed 6-bromo-2H-isoquinolin-1-one (175 mg, 0.94 mmol), [(4S)-4-(tert-butoxycarbonylamino)pentyl]4-methylbenzenesulfonate (335 mg, 0.94 mmol), and cesium carbonate in DMF (3.7 mL). After the mixture was stirred at room temperature for 16 h, it was quenched with water and extracted with EtOAc (×3). The combined organic layers were washed with water and brine, dried ($Na_2SO_4$), and purified by flash chromatography (100% hexanes to 100% EtOAc) to give tert-butyl N-[(1S)-4-(6-bromo-1-oxo-2-isoquinolyl)-1-methyl-butyl]carbamate. ES/MS m/z: 411.125 [M+H].

Step 4. In a vial were placed tert-butyl N-[(1S)-4-(6-bromo-1-oxo-2-isoquinolyl)-1-methyl-butyl]carbamate (314 mg, 0.77 mmol), 1,1'-Bis(diphenylphosphino)ferrocene-palladium(II)dichloride dichloromethane complex (63 mg, 0.077 mmol), potassium acetate (226 mg, 2.30 mmol), and bis(pinacolato)diboron (292 mg, 1.15 mmol) in dioxane (3.19 mL). The mixture was heated to 100° C. for 1 hr. Upon completion, the reaction was quenched with water and extracted with EtOAc. The combined organic layers were washed with water and brine, dried ($Na_2SO_4$), filtered through Celite, and concentrated to give tert-butyl N-[(1S)-1-methyl-4-[1-oxo-6-(4,4,5,5-tetramethyl-1,3,2-dioxaborolan-2-yl)-2-isoquinolyl]butyl]carbamate. ES/MS: m/z 457.26 [M+H].

Step 5. In a vial were placed tert-butyl N-[(1S)-1-methyl-4-[1-oxo-6-(4,4,5,5-tetramethyl-1,3,2-dioxaborolan-2-yl)-2-isoquinolyl]butyl]carbamate (175 mg, 0.38 mmol), 2-iodo-5-(trifluoromethyl)pyrimidine (158 mg, 0.575 mmol), [1,1'-Bis(di-tert-butylphosphino)ferrocene]dichloropalladium(II) (12.5 mg, 0.019 mmol), and 2M aqueous sodium carbonate (0.58 mL, 1.15 mmol) in dioxane (3.5 mL). The mixture was heated to 80° C. for 2 h, and was then quenched with water and extracted with EtOAc (×3). The combined organic layers were washed with water, washed with brine, dried ($Na_2SO_4$), and purified by flash chromatography (100% hexanes to 100% EtOAc) to afford tert-butyl N-[(1S)-1-methyl-4-[1-oxo-6-[5-(trifluoromethyl)pyrimidin-2-yl]-2-isoquinolyl]butyl]carbamate. ES/MS: m/z 477.247 [M+H].

Step 6. In a vial were placed tert-butyl N-[(1S)-1-methyl-4-[1-oxo-6-[5-(trifluoromethyl)pyrimidin-2-yl]-2-isoquinolyl]butyl]carbamate (120 mg, 0.25 mmol), and trifluoroacetic acid (0.19 mL, 2.5 mmol) in DCM (2.2 mL) and the mixture was stirred for 1 h, and concentrated under vacuum to give 2-[(4S)-4-aminopentyl]-6-[5-(trifluoromethyl)pyrimidin-2-yl]isoquinolin-1-one. ES/MS: m/z 377.702 [M+H].

Step 7. In a vial were placed 5-chloro-4-(trifluoromethyl)-2-(2-trimethylsilylethoxymethyl)pyridazin-3-one (123 mg, 0.38 mmol), 2-[(4S)-4-aminopentyl]-6-[5-(trifluoromethyl)pyrimidin-2-yl]isoquinolin-1-one (94 mg, 0.25 mmol), and N,N-Diisopropylethylamine (0.22 mL, 1.25 mmol) in DMF (0.71 mL). The mixture was heated to 80° C. and stirred for 1 hr. Upon completion, the reaction was quenched with water and extracted with EtOAc (×3). The combined organic layers were washed with water and brine, dried ($Na_2SO_4$), and purified by flash chromatography (100% hexanes to 100% EtOAc) to give 2-[(4S)-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one. ES/MS m/z: 669.33 [M+H].

Step 8. In a vial were placed 2-[(4S)-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one (163 mg, 0.24 mmol), and trifluoroacetic acid (0.16 mL, 2.4 mmol) in DCM (10.7 mL). The mixture was stirred for 1 hr, and then was concentrated under vacuum. The resulting crude product was dissolved in methanol (4.0 mL) and ethylenediamine (0.16 mL, 2.44 mmol) was added and the mixture was stirred for 15 minutes and then concentrated under vacuum. The resulting crude product was purified by reverse phase prep-HPLC (5-100% MeCN in water, 0.1% TFA) to afford 2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one. 1H NMR (400 MHz, DMSO-d6) δ 12.44 (s, 1H), 9.43 (s, 2H), 8.75 (s, 1H), 8.50 (dd, J=8.5, 1.6 Hz, 1H), 8.40 (d, J=8.5 Hz, 1H), 7.93 (s, 1H), 7.56 (d, J=7.3 Hz, 1H), 6.86 (d, J=7.3 Hz, 1H), 6.36 (dq, J=6.8, 3.3 Hz, 1H), 4.03-3.96 (m, 3H), 1.86-1.62 (m, 3H), 1.52 (dq, J=13.2, 6.3 Hz, 1H), 1.18 (d, J=6.3 Hz, 3H). ES/MS m/z: 539.062.

Example 6: 6-(2-(3-oxo-3-(4-(5-(trifluoromethyl)pyrimidin-2-yl)piperazin-1-yl)propyl)phenyl)-4-(trifluoromethyl)pyridazin-3(2H)-one Example 6

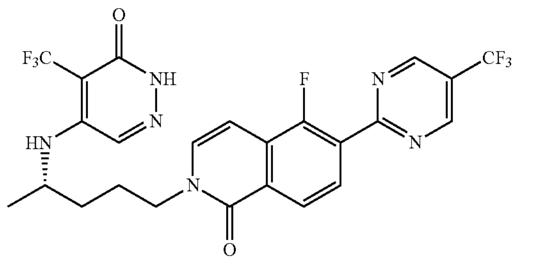

The title compound was synthesized as described in Example 5, using 6-bromo-5-fluoroisoquinolin-1(2H)-one instead of 6-bromoisoquinolin-1(2H)-one to give 5-fluoro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one. 1H NMR (400 MHz, DMSO-d6) δ 12.43 (s, 1H), 9.48 (s, 2H), 8.26-8.10 (m, 2H), 7.92 (s, 1H), 7.66 (d, J=7.5 Hz, 1H), 6.81 (d, J=7.5 Hz, 1H), 6.35 (dd, J=8.6, 3.9 Hz, 1H), 4.02 (q, J=8.4, 7.4 Hz, 3H), 1.71 (ddt, J=21.7, 13.9, 6.6 Hz, 3H), 1.51 (dq, J=12.9, 6.1 Hz, 1H), 1.17 (d, J=6.3 Hz, 3H). ES/MS m/z: 557.002.

Example 7: 8-fluoro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one Example 7

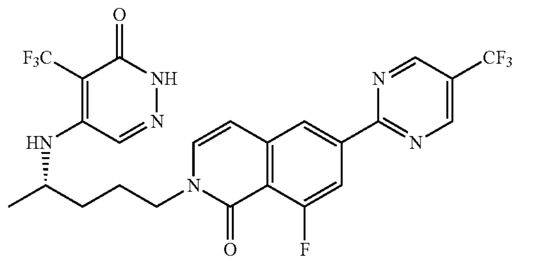

The title compound was synthesized as described in Example 5, using 6-bromo-8-fluoroisoquinolin-1(2H)-one instead of 6-bromoisoquinolin-1(2H)-one to give 8-fluoro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one. 1H NMR (400 MHz, DMSO-d6) δ 12.43 (s, 1H), 9.45 (s, 2H), 8.55 (s, 1H), 8.07 (d, J=12.8 Hz, 1H), 7.92 (s, 1H), 7.60 (d, J=7.3 Hz, 1H), 6.87 (dd, J=7.4, 1.9 Hz, 1H), 6.35 (dd, J=8.8, 3.9 Hz, 1H), 3.96 (t, J=6.6 Hz, 3H), 1.70 (tq, J=15.1, 7.8, 7.0 Hz, 3H), 1.51 (dq, J=13.1, 6.7 Hz, 1H), 1.17 (d, J=6.2 Hz, 3H). ES/MS m/z: 557.041.

Example 8: 7-fluoro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one Example 8

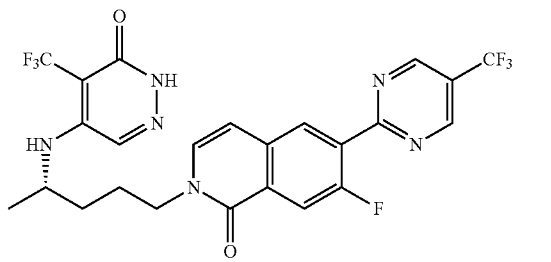

The title compound was synthesized as described in Example 5, using 6-bromo-7-fluoroisoquinolin-1(2H)-one instead of 6-bromoisoquinolin-1(2H)-one to give 7-fluoro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one. 1H NMR (400 MHz, DMSO-d6) δ 12.44 (s, 1H), 9.48 (s, 2H), 8.44 (d, J=7.1 Hz, 1H), 8.03 (d, J=11.3 Hz, 1H), 7.92 (s, 1H), 7.53 (d, J=7.3 Hz, 1H), 6.85 (d, J=7.3 Hz, 1H), 6.36 (dq, J=7.1, 3.5 Hz, 1H), 4.01 (t, J=6.8 Hz, 3H), 1.71 (ddt, J=21.7, 13.8, 6.5 Hz, 3H), 1.52 (tt, J=13.2, 6.5 Hz, 1H), 1.18 (d, J=6.2 Hz, 3H). ES/MS: m/z 557.0.

Example 9: 7-fluoro-2-[(4S)-4-[[6-oxo-5-(trifluoromethyl)-1H-pyridazin-4-yl]amino]pentyl]-6-[5-(trifluoromethyl)-2-pyridyl]isoquinolin-1-one Example 9

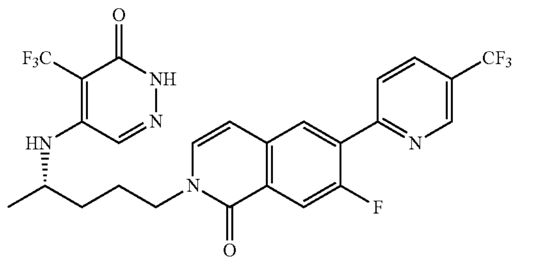

The title compound was synthesized as described in Example 5, using 2-bromo-5-(trifluoromethyl)pyridine instead of 2-iodo-5-(trifluoromethyl)pyrimidine to give 7-fluoro-2-[(4S)-4-[[6-oxo-5-(trifluoromethyl)-1H-pyridazin-4-yl]amino]pentyl]-6-[5-(trifluoromethyl)-2-pyridyl]isoquinolin-1-one. 1H NMR (400 MHz, DMSO-d6) δ 12.43 (s, 1H), 9.17 (d, J=2.3 Hz, 1H), 8.41 (dd, J=8.5, 2.3 Hz, 1H), 8.30 (d, J=7.3 Hz, 1H), 8.12 (d, J=8.2 Hz, 1H), 8.03 (d, J=11.6 Hz, 1H), 7.92 (s, 1H), 7.52 (d, J=7.3 Hz, 1H), 6.81 (d, J=7.3 Hz, 1H), 6.35 (dq, J=7.0, 3.3 Hz, 1H), 4.00 (t, J=6.8 Hz, 3H), 1.71 (dtq, J=22.4, 15.2, 6.9 Hz, 3H), 1.51 (tt, J=13.3, 6.7 Hz, 1H), 1.17 (d, J=6.2 Hz, 3H). ES/MS: m/z 556.0.

Example 10: 5-fluoro-2-[(4S)-4-[[6-oxo-5-(trifluoromethyl)-1H-pyridazin-4-yl]amino]pentyl]-6-[5-(trifluoromethyl)-2-pyridyl]isoquinolin-1-one Example 10

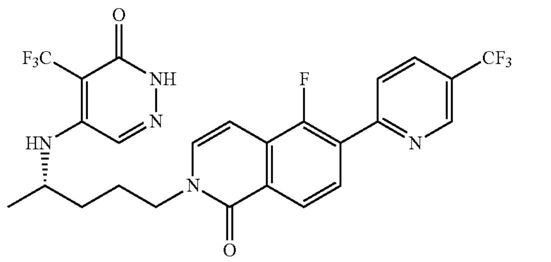

The title compound was synthesized as described in Example 5, using 6-bromo-5-fluoroisoquinolin-1(2H)-one instead of 6-bromo-7-fluoroisoquinolin-1(2H)-one to give 5-fluoro-2-[(4S)-4-[[6-oxo-5-(trifluoromethyl)-1H-pyridazin-4-yl]amino]pentyl]-6-[5-(trifluoromethyl)-2-pyridyl]isoquinolin-1-one. 1H NMR (400 MHz, DMSO-d6) δ 12.45 (s, 1H), 9.17 (d, J=2.3 Hz, 1H), 8.40 (dd, J=8.5, 2.3 Hz, 1H), 8.17 (dd, J=8.5, 3.8 Hz, 2H), 8.03 (t, J=7.8 Hz, 1H), 7.93 (s, 1H), 7.65 (d, J=7.5 Hz, 1H), 6.79 (d, J=7.4 Hz, 1H), 6.36 (dq, J=7.0, 3.4 Hz, 1H), 4.02 (q, J=6.7 Hz, 3H), 1.72 (dddd, J=22.5, 15.2, 10.8, 6.4 Hz, 3H), 1.53 (tt, J=13.0, 6.5 Hz, 1H), 1.18 (d, J=6.2 Hz, 3H). ES/MS: m/z 556.0.

Example 11: 8-fluoro-2-[(4S)-4-[[6-oxo-5-(trifluoromethyl)-1H-pyridazin-4-yl]amino]pentyl]-6-[5-(trifluoromethyl)-2-pyridyl]isoquinolin-1-one Example 11

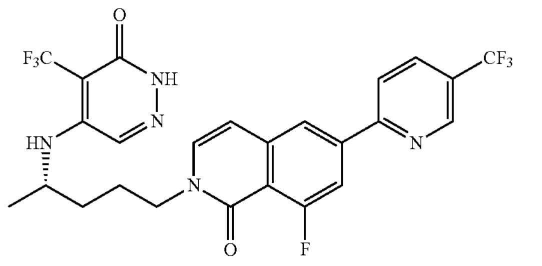

The title compound was synthesized as described in Example 5, using 6-bromo-8-fluoroisoquinolin-1(2H)-one instead of 6-bromo-7-fluoroisoquinolin-1(2H)-one to give 8-fluoro-2-[(4S)-4-[[6-oxo-5-(trifluoromethyl)-1H-pyridazin-4-yl]amino]pentyl]-6-[5-(trifluoromethyl)-2-pyridyl]isoquinolin-1-one. 1H NMR (400 MHz, DMSO-d6) δ 12.43 (s, 1H), 9.19-9.05 (m, 1H), 8.46-8.34 (m, 2H), 8.32 (d, J=1.6 Hz, 1H), 7.97 (dd, J=13.2, 1.7 Hz, 1H), 7.92 (s, 1H), 7.58 (d, J=7.4 Hz, 1H), 6.77 (dd, J=7.4, 2.0 Hz, 1H), 6.36 (dt, J=8.4, 3.6 Hz, 1H), 3.95 (t, J=6.6 Hz, 2H), 1.81-1.59 (m, 3H), 1.51 (dq, J=12.6, 6.5 Hz, 1H), 1.17 (d, J=6.3 Hz, 3H). ES/MS: m/z 556.235.

Example 12: 7-[(4S)-4-[[6-oxo-5-(trifluoromethyl)-1H-pyridazin-4-yl]amino]pentyl]-3-[5-(trifluoromethyl)pyrimidin-2-yl]-1,7-naphthyridin-8-one Example 12

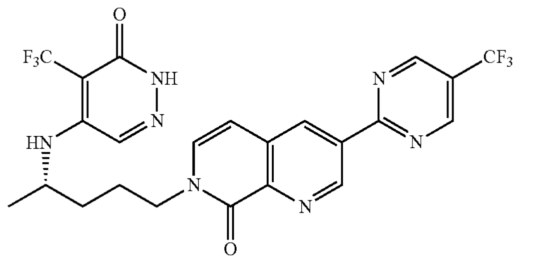

The title compound was synthesized as described in Example 5, using 3-bromo-7H-1,7-naphthyridin-8-one instead of 6-bromo-2H-isoquinolin-1-one and 2-bromo-5-(trifluoromethyl)pyrimidine instead of 2-iodo-5-(trifluoromethyl)pyrimidine. 1H NMR (400 MHz, DMSO-d6) δ 12.43 (s, 1H), 9.69 (d, J=2.0 Hz, 1H), 9.49 (s, 2H), 9.09 (d, J=2.0 Hz, 1H), 7.92 (s, 1H), 7.67 (d, J=7.3 Hz, 1H), 6.87 (d, J=7.3 Hz, 1H), 6.41-6.31 (m, 1H), 4.07-3.96 (m, 3H), 1.82-1.63 (m, 3H), 1.60-1.46 (m, 1H), 1.17 (d, J=6.3 Hz, 3H). ES/MS: m/z 540.0 [M+H]+.

Example 13: 2-[(4S)-4-[[6-oxo-5-(trifluoromethyl)-1H-pyridazin-4-yl]amino]pentyl]-6-[5 (trifluoromethyl)-2-pyridyl]-2,7-naphthyridin-1-one Example 13

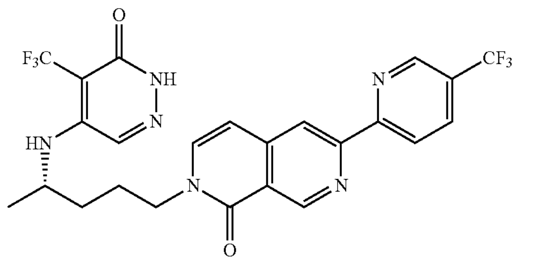

The title compound was synthesized as described in Example 1 using 6-bromo-2H-2,7-naphthyridin-1-one instead of 6-bromo-2H-isoquinolin-1-one and [(4S)-4-(tert-butoxycarbonylamino)pentyl]4-methylbenzenesulfonate. 1H NMR (400 MHz, DMSO-d6) δ 12.43 (s, 1H), 9.47 (s, 1H), 9.13 (d, J=2.2 Hz, 1H), 8.69 (d, J=8.3 Hz, 1H), 8.65 (s, 1H), 8.42 (dd, J=8.2, 2.3 Hz, 1H), 7.92 (s, 1H), 7.81 (d, J=7.3 Hz, 1H), 6.87 (d, J=7.3 Hz, 1H), 6.41-6.30 (m, 1H), 4.07-3.93 (m, 3H), 1.81-1.60 (m, 3H), 1.60-1.46 (m, 1H), 1.17 (d, J=6.2 Hz, 3H). ES/MS m/z: 539.0 [M+H]+.

Example 14: 2-[(4S)-4-[[6-oxo-5-(trifluoromethyl)-1H-pyridazin-4-yl]amino]pentyl]-6-[5-(trifluoromethyl)-2-pyridyl]-2,7-naphthyridin-1-one Example 14

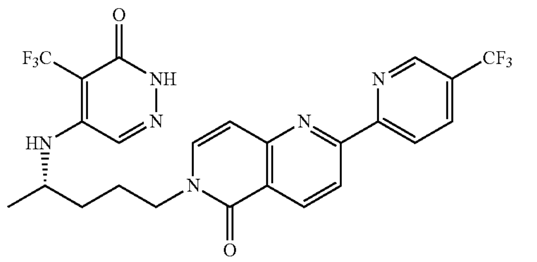

The title compound was synthesized as described in Example 1 using 2-bromo-6H-1,6-naphthyridin-5-one instead of 6-bromo-2H-isoquinolin-1-one and [(4S)-4-(tert-butoxycarbonylamino)pentyl]4-methylbenzenesulfonate. 1H NMR (400 MHz, DMSO-d6) δ 12.43 (s, 1H), 9.16 (s, 1H), 8.78-8.68 (m, 2H), 8.53 (d, J=8.4 Hz, 1H), 8.48-8.40 (m, 1H), 7.92 (s, 1H), 7.83 (d, J=7.6 Hz, 1H), 6.83 (d, J=7.5 Hz, 1H), 6.40-6.31 (m, 1H), 4.07-3.93 (m, 3H), 1.81-1.62 (m, 3H), 1.60-1.46 (m, 1H), 1.17 (d, J=6.2 Hz, 3H). ES/MS m/z: 539.1 [M+H]+.

Example 15 Preparation of (S)-2-(4-((5-acetyl-6-oxo-1,6-dihydropyridazin-4-yl)amino)pentyl)-7-fluoro-6-(5-(trifluoromethyl)pyrimidin-2-yl)isoquinolin-1(2H)-one

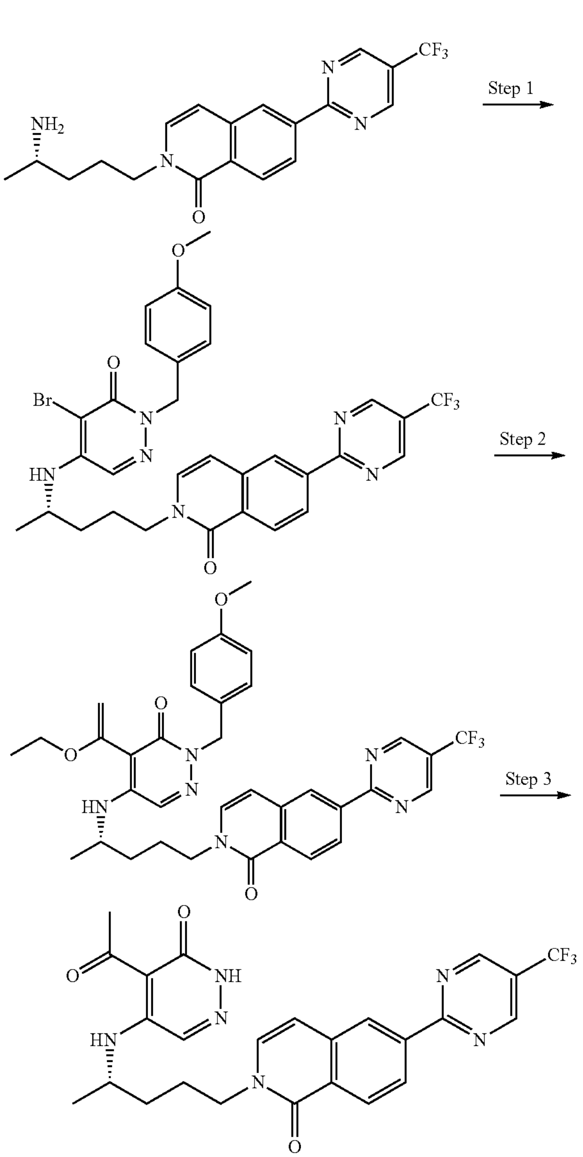

Example 15

Step 1. In a vial were placed 2-[(4S)-4-aminopentyl]-6-[5-(trifluoromethyl)pyrimidin-2-yl]isoquinolin-1-one (200 mg, 0.53 mmol), 4-bromo-5-chloro-2-((2-(trimethylsilyl)ethoxy)methyl)pyridazin-3(2H)-one (175 mg, 0.53 mmol), and DIPEA (0.47 mL, 2.7 mmol) in DMF (2.5 mL). After the mixture was stirred at 110° C. for 16 hr, it was loaded onto the Silica pre-packed cartridge and purified by flash chromatography (100% DCM to 100% EtOAc then 100% DCM to 100% MeOH) to give 2-[(4S)-4-[[5-bromo-1-[(4-methoxyphenyl)methyl]-6-oxo-pyridazin-4-yl]amino]pentyl]-6-[5-(trifluoromethyl)pyrimidin-2-yl]isoquinolin-1-one. ES/MS m/z: 669.2 $[M+H]^+$.

Step 2. In a microwave reaction vial were placed (S)-2-(4-((5-bromo-6-oxo-1-((2-(trimethylsilyl)ethoxy)methyl)-1,6-dihydropyridazin-4-yl)amino)pentyl)-7-fluoro-6-(5-(trifluoromethyl)pyrimidin-2-yl)isoquinolin-1(2H)-one (100 mg, 0.15 mmol), tributyl(1-ethoxyvinyl)tin (108 mg, 0.30 mmol), and tetrakis(triphenylphosphine)palladium (17 mg, 0.015 mmol), and dioxane (1.5 mL). The mixture was sonicated for 20 seconds, purged with nitrogen gas for 5 minutes, and heated at 130° C. in a microwave reactor for 1 hr. The reaction was then filtered through a pad of Celite®, concentrated in vacuo, and used in the next step without further purification.

Step 3. The title compound was synthesized following the procedure described in the step 8 of Example 5, using 2-[(4S)-4-[(5-acetyl-6-oxo-1H-pyridazin-4-yl)amino]pentyl]-6-[5-(trifluoromethyl)pyrimidin-2-yl]isoquinolin-1-one instead of (S)-2-(4-((6-oxo-5-(trifluoromethyl)-1-((2-(trimethylsilyl)ethoxy)methyl)-1,6-dihydropyridazin-4-yl)amino)pentyl)-6-(5-(trifluoromethyl)pyrimidin-2-yl)isoquinolin-1(2H)-one. 1H NMR (400 MHz, Methanol-d4) δ 9.15 (d, J=0.9 Hz, 2H), 8.72 (d, J=1.6 Hz, 1H), 8.53 (dd, J=8.5, 1.7 Hz, 1H), 8.34 (d, J=8.5 Hz, 1H), 7.81 (s, 1H), 7.35 (d, J=7.4 Hz, 1H), 6.74 (d, J=7.3 Hz, 1H), 3.99 (dt, J=19.4, 6.7 Hz, 3H), 2.48 (s, 3H), 1.94-1.72 (m, 2H), 1.61 (q, J=7.2 Hz, 2H), 1.20 (d, J=6.4 Hz, 3H). ES/MS m/z: 513.2 $[M+H]^+$.

Example 16 Preparation of (S)-2-(4-((5-acetyl-6-oxo-1,6-dihydropyridazin-4-yl)amino)pentyl)-7-fluoro-6-(5-(trifluoromethyl)pyrimidin-2-yl)isoquinolin-1(2H)-one

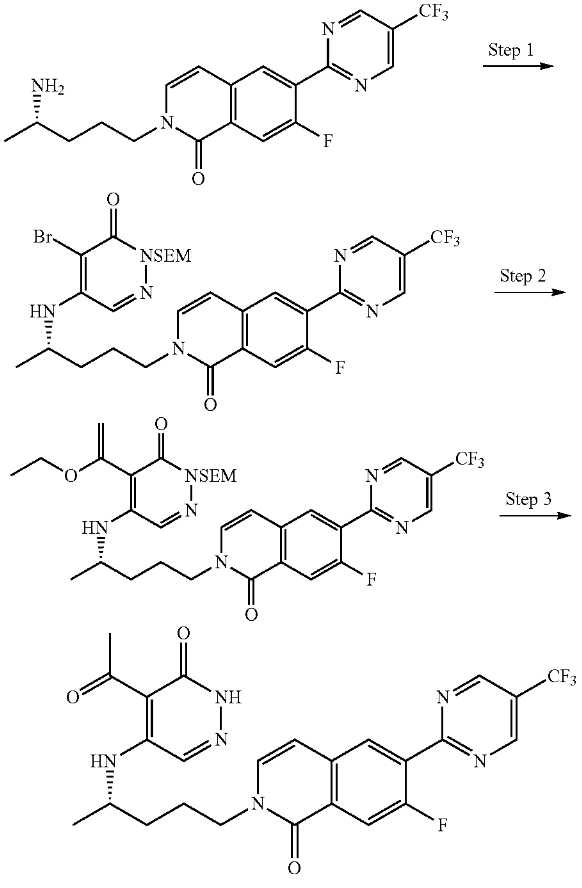

Example 16

Step 1. In a vial were placed (S)-2-(4-aminopentyl)-7-fluoro-6-(5-(trifluoromethyl)pyrimidin-2-yl)isoquinolin-1(2H)-one (117 mg, 0.30 mmol), 4-bromo-5-chloro-2-((2-(trimethylsilyl)ethoxy)methyl)pyridazin-3(2H)-one (202 mg, 0.59 mmol), and DIPEA (0.52 mL, 3.0 mmol) in ACN (2.0 mL). After the mixture was stirred at 110° C. for 16 hr, it was loaded onto a Silica pre-packed cartridge and purified by flash chromatography (100% DCM to 100% EtOAc then 100% DCM to 100% MeOH) to give (S)-2-(4-((5-bromo-6-oxo-1-((2-(trimethylsilyl)ethoxy)methyl)-1,6-dihydropyridazin-4-yl)amino)pentyl)-7-fluoro-6-(5-(trifluoromethyl)pyrimidin-2-yl)isoquinolin-1(2H)-one. ES/MS m/z: 697.3 $[M+H]^+$.

Step 2. In a microwave reaction vial were placed (S)-2-(4-((5-bromo-6-oxo-1-((2-(trimethylsilyl)ethoxy)methyl)-1,6-dihydropyridazin-4-yl)amino)pentyl)-7-fluoro-6-(5-(trifluoromethyl)pyrimidin-2-yl)isoquinolin-1(2H)-one (6.0 mg, 0.0086 mmol), tributyl(1-ethoxyvinyl)tin (35 mg, 0.095 mmol), and tetrakis(triphenylphosphine)palladium (4.0 mg, 0.0036 mmol), and dioxane (1.0 mL). The mixture was sonicated for 20 seconds, purged with $N_2$ gas for 5 minutes, and placed in the microwave reactor, and stirred at 130° C. for 1.5 hr. The mixture was filtered through a pad of Celite®, concentrated in vacuo to afford (S)-2-(4-((5-(1-ethoxyvinyl)-6-oxo-1-((2-(trimethylsilyl)ethoxy)methyl)-1,6-dihydropyridazin-4-yl)amino)pentyl)-7-fluoro-6-(5-(trifluoromethyl)pyrimidin-2-yl)isoquinolin-1(2H)-one.

Step 3. The title compound was synthesized following the procedure described in the step 8 of Example 5, using (S)-2-(4-((5-(1-ethoxyvinyl)-6-oxo-1-((2-(trimethylsilyl)ethoxy)methyl)-1,6-dihydropyridazin-4-yl)amino)pentyl)-7-fluoro-6-(5-(trifluoromethyl)pyrimidin-2-yl)isoquinolin-1(2H)-one instead of (S)-2-(4-((6-oxo-5-(trifluoromethyl)-1-((2-(trimethylsilyl)ethoxy)methyl)-1,6-dihydropyridazin-4-yl)amino)pentyl)-6-(5-(trifluoromethyl)pyrimidin-2-yl)isoquinolin-1(2H)-one. 1H NMR (400 MHz, DMSO-d6) δ 12.28 (s, 1H), 10.61 (d, J=8.7 Hz, 1H), 9.48 (s, 2H), 8.44 (d, J=7.2 Hz, 1H), 8.03 (d, J=11.4 Hz, 1H), 7.96 (s, 1H), 7.66-7.50 (m, 2H), 6.84 (m, 1H), 4.04 (m, 3H), 3.46 (m, 2H), 1.76 (m, 2H), 1.63-1.48 (m, 2H), 1.20 (m, 3H), 0.89 (m, 1H). ES/MS m/z: 531.2 $[M+H]^+$.

Example 17: Preparation of (S)-6-(5-(difluoromethoxy)pyridin-2-yl)-8-fluoro-2-(4-((6-oxo-5-(trifluoromethyl)-1,6-dihydropyridazin-4-yl)amino)pentyl)isoquinolin-1(2H)-one

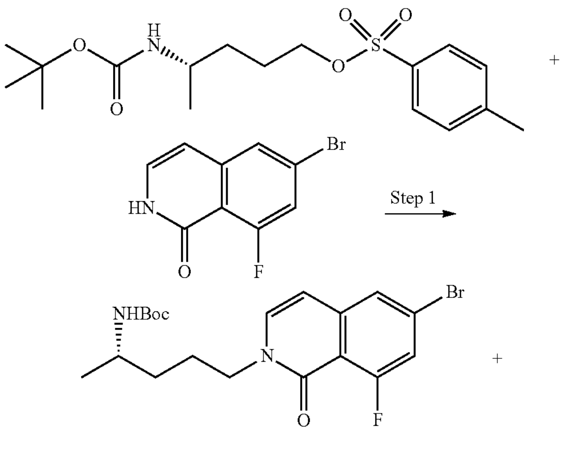

-continued

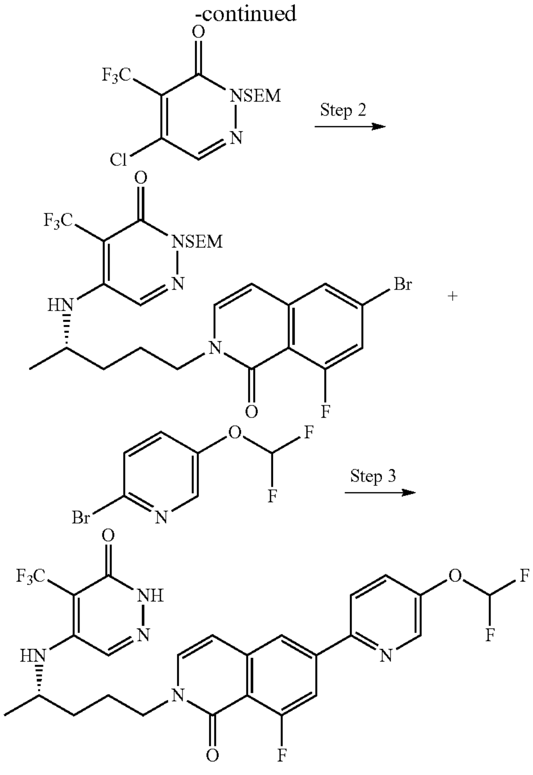

Example 17

Step 1. In a vial were placed 6-Bromo-8-fluoro-1,2-dihydroisoquinolin-1-one (1.00 g, 4.13 mmol), [(4S)-4-(tert-butoxycarbonylamino)pentyl]4-methylbenzenesulfonate (1.77 g, 4.96 mmol), and cesium carbonate (2.69 g, 8.26 mmol) in DMF (14.0 mL). After mixture was stirred at room temperature for 16 hr, it was quenched with water and extracted with EtOAc (x3). The combined organic layers were washed with water and brine, dried ($Na_2SO_4$), and purified by flash chromatography (100% hexanes to 100% EtOAc) to give tert-butyl N-[(1S)-4-(6-bromo-8-fluoro-1-oxo-2-isoquinolyl)-1-methyl-butyl]carbamate. ES/MS m/z: 429.1 $[M+2+H]^+$+.

Step 2. In a vial were placed tert-butyl N-[(1S)-4-(6-bromo-8-fluoro-1-oxo-2-isoquinolyl)-1-methyl-butyl]carbamate (591 mg, 1.38 mmol), and trifluoroacetic acid (1.06 mL, 13.8 mmol) in DCM (14.0 mL). After the mixture was stirred for 1 hr, it was concentrated under vacuum. To the same vial was then added 5-chloro-4-(trifluoromethyl)-2-(2-trimethylsilylethoxymethyl)pyridazin-3-one (682 mg, 2.07 mmol) and N,N-Diisopropylethylamine (1.20 mL, 6.92 mmol) in DMF (7.00 mL). The mixture was heated to 80° C. and stirred for 1 hr, and then quenched with water and extracted with EtOAc (x3). The combined organic layers were washed with water and brine, dried ($MgSO_4$), and purified by flash chromatography (100% hexanes to 100% EtOAc) to give 6-bromo-8-fluoro-2-[(4S)-4-[[6-oxo-5-(trifluoromethyl)-1-(2-trimethylsilylethoxymethyl)pyridazin-4-yl]amino]pentyl]isoquinolin-1-one. ES/MS m/z: 621.105 $[M+H]^+$.

Step 3. In a vial were placed 6-bromo-8-fluoro-2-[(4S)-4-[[6-oxo-5-(trifluoromethyl)-1-(2-trimethylsilylethoxymethyl)pyridazin-4-yl]amino]pentyl]isoquinolin-1-one (165 mg, 0.267 mmol), 1,1'-Bis(diphenylphosphino)ferrocene-palladium(II)dichloride dichloromethane complex (44 mg, 0.054 mmol), potassium acetate (79 mg, 0.80 mmol), and bis(pinacolato)diboron (101 mg, 0.40 mmol) in dioxane (3.00 mL). The mixture was heated to 80° C. and stirred for 1 hr, followed by the addition of 2 M aqueous sodium carbonate (0.25 mL, 0.495 mmol) and 2-bromo-5-(difluoromethoxy)pyridine (55.4 mg, 0.248 mmol). The reaction was then stirred for an additional hour at 80° C. Upon completion, the mixture was filtered through Celite® and concentrated under vacuum. To the crude product was then added trifluoroacetic acid (1.65 mL) and the mixture was stirred for 1 hr at room temperature and concentrated under vacuum. The resulting product was dissolved in methanol (4.0 mL) and ethylenediamine (0.16 mL, 2.44 mmol) was added and stirred for 15 minutes, and then was concentrated under vacuum. The crude product was purified by reverse phase prep-HPLC (5-100% MeCN in water, 0.1% TFA) to afford 6-[5-(difluoromethoxy)-2-pyridyl]-8-fluoro-2-[(4S)-4-[[6-oxo-5-(trifluoromethyl)-1H-pyridazin-4-yl]amino]pentyl]isoquinolin-1-one. $^{1}$H NMR (400 MHz, DMSO-d6) δ 12.44 (s, 1H), 8.64 (d, J=2.8 Hz, 1H), 8.27-8.21 (m, 1H), 8.21-8.17 (m, 1H), 7.94-7.88 (m, 1H), 7.88-7.81 (m, 1H), 7.57-7.51 (m, 1H), 7.62-7.23 (m, 1H), 6.77-6.67 (m, 1H), 6.38-6.30 (m, 1H), 4.02-3.90 (m, 3H), 1.78-1.44 (m, 4H), 1.18 (d, J=6.3 Hz, 3H). ES/MS m/z: 554.2 105 $[M+H]^+$.

Example 18: (S)-6-(8-fluoro-1-oxo-2-(4-((6-oxo-5-(trifluoromethyl)-1,6-dihydropyridazin-4-yl)amino)pentyl)-1,2-dihydroisoquinolin-6-yl)nicotinonitrile Example 18

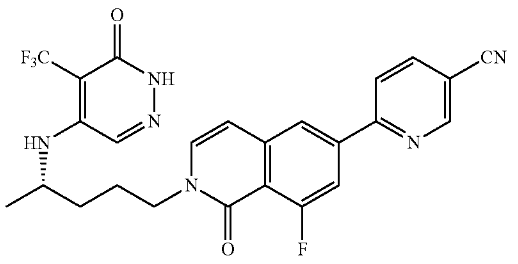

The title compound was synthesized as described in Example 17, using 2-bromo-5-cyanopyridine instead of 2-bromo-5-(difluoromethoxy)pyridine. 1H NMR (400 MHz, DMSO-d6) δ 12.43 (s, 1H), 9.21-9.11 (m, 1H), 8.55-8.47 (m, 1H), 8.43-8.35 (m, 1H), 8.34-8.30 (m, 1H), 8.01-7.93 (m, 1H), 7.93-7.90 (m, 1H), 7.58 (d, J=7.3 Hz, 1H), 6.88-6.60 (m, 1H), 6.45-6.18 (m, 1H), 4.18-3.88 (m, 5H), 1.89-1.39 (m, 4H), 1.20-1.12 (m, 3H). ES/MS m/z: 513.3 $[M+H]^+$.

Example 19: (S)-8-fluoro-6-(5-fluoropyridin-2-yl)-2-(4-((6-oxo-5-(trifluoromethyl)-1,6-dihydropyridazin-4-yl)amino)pentyl)isoquinolin-1(2H)-one Example 19

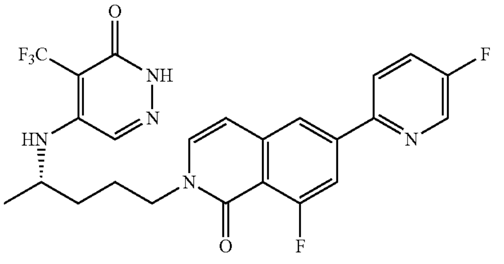

The title compound was synthesized as described in Example 17, using 2-bromo-5-fluoropyridine instead of 2-bromo-5-(difluoromethoxy)pyridine. 1H NMR (400 MHz, DMSO-d6) δ 12.44 (s, 1H), 8.73 (d, J=2.9 Hz, 1H), 8.28-8.21 (m, 1H), 8.18 (d, J=1.7 Hz, 1H), 7.97-7.83 (m, 3H), 7.54 (d, J=7.4 Hz, 1H), 6.78-6.65 (m, 1H), 6.44-6.27 (m, 1H), 4.05-3.86 (m, 4H), 1.82-1.43 (m, 5H), 1.32-1.06 (m, 3H). ES/MS m/z: 506.2 $[M+H]^+$.

Intermediate 1 Preparation of 6-bromo-7,8-difluoroisoquinolin-1(2H)-one

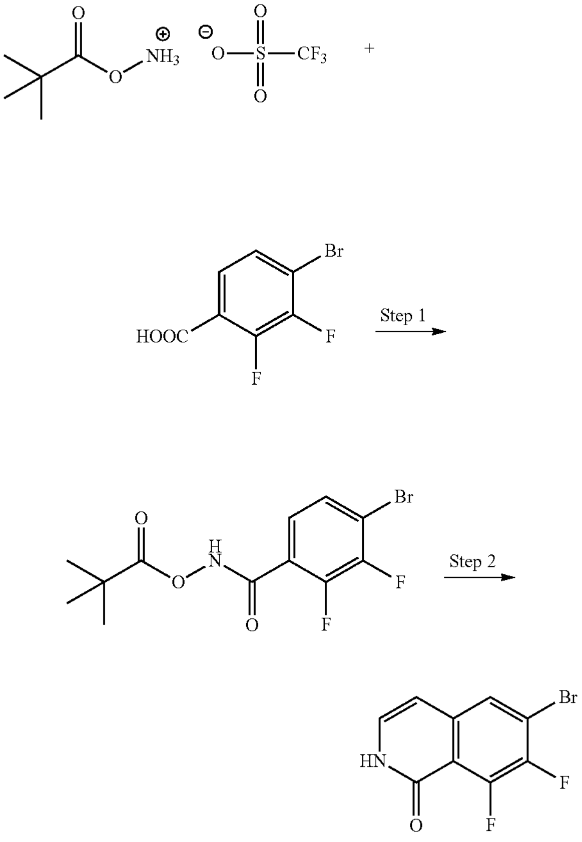

Intermediate 1

Step 1. To a vial was added 4-bromo-2,3-difluoro-benzoic acid (1.03 g, 4.36 mmol), amino 2,2-dimethylpropanoate; trifluoromethanesulfonic acid (1.17 g, 4.36 mmol), HATU (1.74 g, 4.58 mmol), and N,N-Diisopropylethylamine (2.28 mL, 13.1 mmol) in DMF (11.0 mL). The reaction was stirred at 25° C. for 1 hour and then quenched with water and extracted with EtOAc (x3). The organic layers were dried ($MgSO_4$) and purified by flash chromatography (100% hexanes to 100% EtOAc to give 4-bromo-2,3-difluoro-N-(pivaloyloxy)benzamide. ES/MS m/z: 337.907 $[M+H]^+$+.

Step 2. To a vial was added [(4-bromo-2,3-difluoro-benzoyl)amino]2,2-dimethylpropanoate (459 mg, 1.37 mmol), vinyl acetate (0.252 mL, 2.73 mmol), cesium acetate (131 mg, 0.683 mmol), and (pentamethylcyclopentadienyl) rhodium(III) dichloride dimer (65 mg, 0.137 mmol) in methanol (7.00 mL). The reaction is stirred at 45° C. for 8 hours, and then concentrated under vacuum to give 6-bromo-7,8-difluoroisoquinolin-1(2H)-one which was used directly in the alkylation step. ES/MS m/z: 261.890 $[M+H]^+$+.

Example 20: (S)-8-fluoro-6-(5-fluoropyridin-2-yl)-2-(4-((6-oxo-5-(trifluoromethyl)-1,6-dihydropyridazin-4-yl)amino)pentyl)isoquinolin-1(2H)-one Example 20

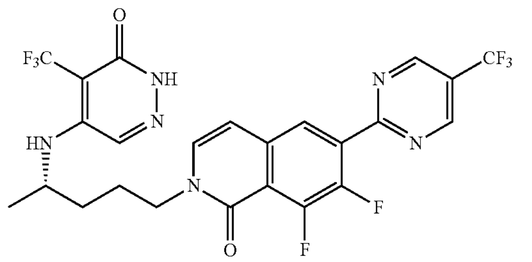

The title compound was synthesized as described in Example 17, using 2-iodo-5-(trifluoromethyl)pyrimidine instead of 2-bromo-5-(difluoromethoxy)pyridine and 2-bromo-7,8-difluoroisoquinolin-1(2H)-one instead of 6-Bromo-8-fluoro-1,2-dihydroisoquinolin-1-one. 1H NMR (400 MHz, DMSO-d6) δ 12.43 (s, 1H), 9.56-9.44 (m, 2H), 8.31-8.17 (m, 1H), 7.92 (s, 1H), 7.56 (d, J=7.4 Hz, 1H), 6.87-6.75 (m, 1H), 6.40-6.29 (m, 1H), 4.07-3.89 (m, 3H), 1.77-1.45 (m, 5H), 1.18 (d, J=6.3 Hz, 3H). ES/MS m/z: 575.3 $[M+H]^+$.

Example 21: 7-fluoro-2-[(4S)-4-[[6-oxo-5-(trifluoromethyl)-1H-pyridazin-4-yl]amino]pentyl]-6-[5-(trifluoromethyl)pyrazin-2-yl]isoquinolin-1-one Example 21

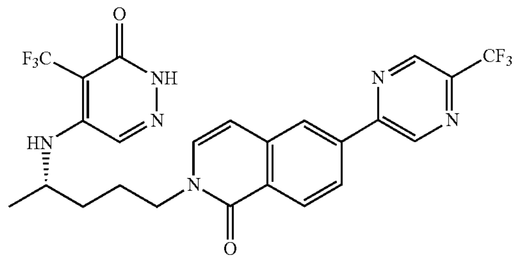

The title compound was synthesized as described in Example 5 with the following changes:

Step 3. 6-Bromo-7-fluoro-2H-isoquinolin-1-one was used instead of 6-bromo-2H-isoquinolin-1-one.

Step 4. The reaction was allowed to proceed for 18 hours rather than 1 hour. The reaction was filtered through Celite© and the filtrate was used directly in the next step.

Step 5. 2-Bromo-5-(trifluoromethyl)pyrazine was used instead of 2-iodo-5-(trifluoromethyl)pyrimidine and the aqueous workup was omitted. 1H NMR (400 MHz, DMSO-d6) δ 12.42 (s, 1H), 9.40 (d, J=1.4 Hz, 1H), 9.34 (t, J=1.9 Hz, 1H), 8.35 (d, J=7.2 Hz, 1H), 8.08 (d, J=11.5 Hz, 1H), 7.91 (s, 1H), 7.54 (d, J=7.4 Hz, 1H), 6.83 (d, J=7.4 Hz, 1H), 6.39-6.31 (m, 1H), 4.05-3.94 (m, 3H), 1.81-1.59 (m, 3H), 1.56-1.46 (m, 1H), 1.17 (d, J=6.3 Hz, 3H). ES/MS m/z: 557.3 $[M+H]^+$.

Example 22: Preparation of (S)-7-fluoro-6-(5-methoxypyrimidin-2-yl)-2-(4-((6-oxo-5-(trifluoromethyl)-1,6-dihydropyridazin-4-yl)amino)pentyl)isoquinolin-1(2H)-one Example 22

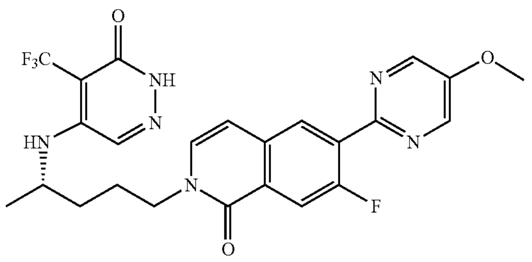

The title compound was synthesized as described in Example 5, with the following changes:

Step 3. 6-Bromo-7-fluoro-2H-isoquinolin-1-one was used instead of 6-bromo-2H-isoquinolin-1-one.

Step 4. The reaction was stirred for 3 hrs rather than 1 hr The reaction was filtered through Celite© and the filtrate was used directly in the next step.

Step 5. 2-Bromo-5-methoxy-pyrimidine was used instead of 2-iodo-5-(trifluoromethyl)pyrimidine and the aqueous workup was omitted. 1H NMR (400 MHz, DMSO-d6) δ 12.43 (s, 1H), 7.91 (t, J=5.7 Hz, 2H), 7.83 (d, J=7.6 Hz, 1H), 7.46 (d, J=7.4 Hz, 1H), 7.15 (t, J=1.9 Hz, 1H), 7.12 (dt, J=8.3, 1.9 Hz, 1H), 7.00 (d, J=8.3 Hz, 1H), 6.69 (d, J=7.4 Hz, 1H), 6.39-6.30 (m, 1H), 4.35-4.26 (m, 4H), 4.04-3.94 (m, 3H), 1.80-1.58 (m, 3H), 1.55-1.42 (m, 1H), 1.16 (d, J=6.3 Hz, 3H). ES/MS m/z: 545.3 $[M+H]^+$.

Example 23: (S)-5-(7-fluoro-1-oxo-2-(4-((6-oxo-5-(trifluoromethyl)-1,6-dihydropyridazin-4-yl)amino)pentyl)-1,2-dihydroisoquinolin-6-yl)pyrazine-2-carbonitrile Example 23

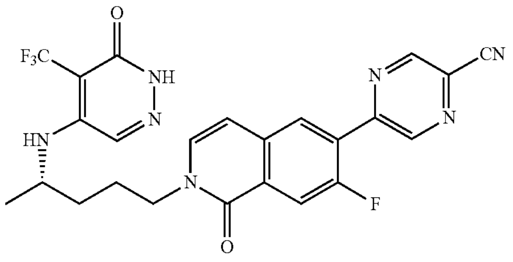

The title compound was synthesized as described in Example 5, with the following changes:

Step 3. 6-Bromo-7-fluoro-2H-isoquinolin-1-one was used instead of 6-bromo-2H-isoquinolin-1-one.

Step 4. The reaction was allowed to proceed for 3 hours rather than 1 hour. The reaction was filtered through Celite© and the filtrate was used directly in the next step.

Step 5. 5-Bromopyrazine-2-carbonitrile was used instead of 2-iodo-5-(trifluoromethyl)pyrimidine and the aqueous workup was omitted. 1H NMR (400 MHz, DMSO-d6) δ 12.42 (s, 1H), 9.42 (d, J=1.5 Hz, 1H), 9.32 (t, J=1.9 Hz, 1H), 8.36 (d, J=7.2 Hz, 1H), 8.07 (d, J=11.6 Hz, 1H), 7.90 (s, 1H), 7.54 (d, J=7.4 Hz, 1H), 6.83 (d, J=7.2 Hz, 1H), 6.38-6.30 (m, 1H), 4.04-3.91 (m, 3H), 1.80-1.59 (m, 3H), 1.56-1.45 (m, 1H), 1.16 (d, J=6.3 Hz, 3H). ES/MS m/z: 514.3 [M+H]$^+$.

Example 24: (S)-2-(7-fluoro-1-oxo-2-(4-((6-oxo-5-(trifluoromethyl)-1,6-dihydropyridazin-4-yl)amino)pentyl)-1,2-dihydroisoquinolin-6-yl)pyrimidine-5-carbonitrile Example 24

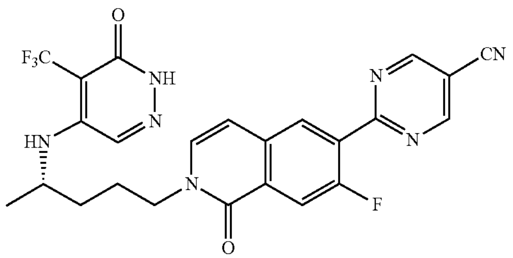

The title compound was synthesized as described in Example 5, with the following changes:

Step 3. 6-Bromo-7-fluoro-2H-isoquinolin-1-one was used instead of 6-bromo-2H-isoquinolin-1-one.

Step 4. The reaction was allowed to proceed for 3 hours rather than 1 hour. The reaction was filtered through Celite© and the filtrate was used directly in the next step.

Step 5. 2-Bromopyrimidine-5-carbonitrile was used instead of 2-iodo-5-(trifluoromethyl)pyrimidine and the aqueous workup was omitted. 1H NMR (400 MHz, DMSO-d6) δ 12.43 (s, 1H), 9.50 (s, 2H), 8.46 (d, J=7.2 Hz, 1H), 8.02 (d, J=11.5 Hz, 1H), 7.92 (s, 1H), 7.53 (d, J=7.4 Hz, 1H), 6.85 (d, J=7.3 Hz, 1H), 6.40-6.31 (m, 1H), 4.04-3.96 (m, 3H), 1.84-1.59 (m, 3H), 1.51 (dt, J=18.8, 6.2 Hz, 1H), 1.17 (d, J=6.3 Hz, 3H). ES/MS m/z: 513.3 [M+H]$^+$.

Example 25: (S)-6-(7-fluoro-1-oxo-2-(4-((6-oxo-5-(trifluoromethyl)-1,6-dihydropyridazin-4-yl)amino)pentyl)-1,2-dihydroisoquinolin-6-yl)nicotinonitrile Example 25

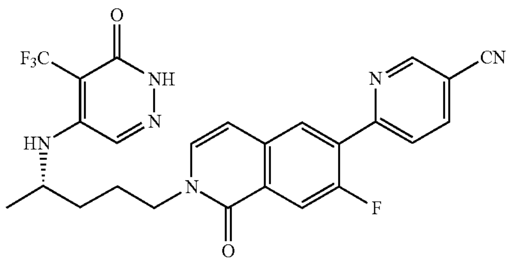

The title compound was synthesized as described in Example 5, with the following changes:

Step 3. 6-bromo-7-fluoro-2H-isoquinolin-1-one was used instead of 6-bromo-2H-isoquinolin-1-one.

Step 4. The reaction was allowed to proceed for 3 hours rather than 1 hour. The reaction was filtered through Celite© and the filtrate was used directly in the next step.

Step 5. 6-bromopyridine-3-carbonitrile was used instead of 2-iodo-5-(trifluoromethyl)pyrimidine and the aqueous workup was omitted. 1H NMR (400 MHz, DMSO-d6) δ 12.42 (s, 1H), 9.22 (dd, J=2.2, 0.9 Hz, 1H), 8.50 (dd, J=8.3, 2.2 Hz, 1H), 8.31 (d, J=7.4 Hz, 1H), 8.12-8.08 (m, 1H), 8.03 (d, J=11.7 Hz, 1H), 7.91 (s, 1H), 7.52 (d, J=7.4 Hz, 1H), 6.81 (d, J=7.3 Hz, 1H), 6.39-6.31 (m, 1H), 4.04-3.91 (m, 3H), 1.82-1.59 (m, 3H), 1.56-1.45 (m, 1H), 1.16 (d, J=6.3 Hz, 3H). ES/MS m/z: 513.3 [M+H]$^+$.

Example 26: (S)-6-(2,3-dihydrobenzofuran-7-yl)-7-fluoro-2-(4-((6-oxo-5-(trifluoromethyl)-1,6-dihydropyridazin-4-yl)amino)pentyl)isoquinolin-1(2H)-one Example 26

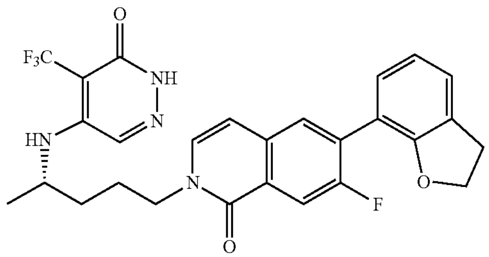

The title compound was synthesized as described in Example 1, with the following changes:

Step 1. 6-Bromo-7-fluoro-2H-isoquinolin-1-one was used instead of 6-bromo-2H-isoquinolin-1-one.

Step 2. 2,3-dihydrobenzofuran-7-ylboronic acid was used instead of [5-(trifluoromethyl)-2-pyridyl]boronic acid.

Example 27: (S)-6-(2,3-dihydrobenzo[b][1,4]dioxin-5-yl)-7-fluoro-2-(4-((6-oxo-5-(trifluoromethyl)-1,6-dihydropyridazin-4-yl)amino)pentyl)isoquinolin-1(2H)-one Example 27

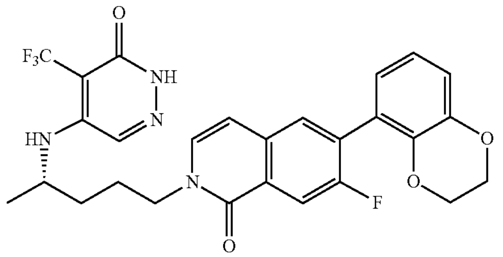

The title compound was synthesized as described in Example 1, with the following changes:

Step 2. 6-Bromo-7-fluoro-2H-isoquinolin-1-one was used instead of 6-bromo-2H-isoquinolin-1-one.

Step 3. 2,3-Dihydro-1,4-benzodioxin-5-ylboronic acid was used instead of [5-(trifluoromethyl)-2-pyridyl]boronic acid. 1H NMR (400 MHz, DMSO-d6) δ 12.44 (s, 1H), 7.95-7.87 (m, 2H), 7.71 (d, J=6.9 Hz, 1H), 7.47 (d, J=7.4 Hz, 1H), 6.98 (dd, J=8.1, 2.1 Hz, 1H), 6.94 (t, J=7.6 Hz, 1H), 6.88 (dd, J=7.2, 2.1 Hz, 1H), 6.68 (d, J=7.3 Hz, 1H), 6.40-6.30 (m, 1H), 4.31-4.18 (m, 4H), 4.04-3.93 (m, 3H), 1.82-1.58 (m, 3H), 1.57-1.43 (m, 1H), 1.17 (d, J=6.3 Hz, 3H). ES/MS m/z: 545.3 $[M+H]^+$.

Example 28: (S)-6-(2,3-dihydrobenzo[b][1,4]dioxin-6-yl)-7-fluoro-2-(4-((6-oxo-5-(trifluoromethyl)-1,6-dihydropyridazin-4-yl)amino)pentyl)isoquinolin-1(2H)-one Example 28

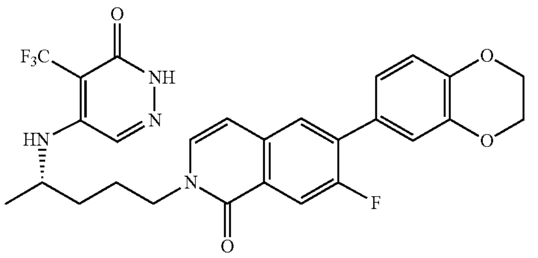

The title compound was synthesized as described in Example 1, with the following changes:

Step 2. 6-Bromo-7-fluoro-2H-isoquinolin-1-one was used instead of 6-bromo-2H-isoquinolin-1-one.

Step 3. 2-(2,3-Dihydro-1,4-benzodioxin-6-yl)-4,4,5,5-tetramethyl-1,3,2-dioxaborolane was used instead of [5-(trifluoromethyl)-2-pyridyl]boronic acid. 1H NMR (400 MHz, DMSO-d6) δ 12.43 (s, 1H), 7.91 (t, J=5.7 Hz, 2H), 7.83 (d, J=7.6 Hz, 1H), 7.46 (d, J=7.4 Hz, 1H), 7.15 (t, J=1.9 Hz, 1H), 7.12 (dt, J=8.3, 1.9 Hz, 1H), 7.00 (d, J=8.3 Hz, 1H), 6.69 (d, J=7.4 Hz, 1H), 6.39-6.30 (m, 1H), 4.35-4.26 (m, 4H), 4.04-3.94 (m, 3H), 1.80-1.58 (m, 3H), 1.55-1.42 (m, 1H), 1.16 (d, J=6.3 Hz, 3H). ES/MS m/z: 545.3 $[M+H]^+$.

Example 29: (S)-6-fluoro-3-(4-((6-oxo-5-(trifluoromethyl)-1,6-dihydropyridazin-4-yl)amino)pentyl)-7-(5-(trifluoromethyl)pyrimidin-2-yl)quinazolin-4(3H)-one Example 29

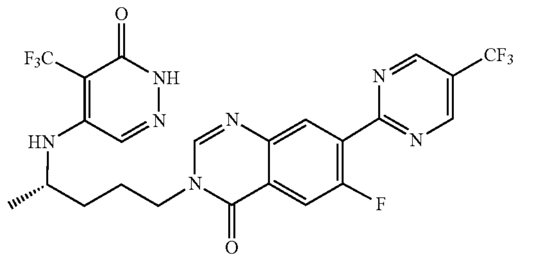

The title compound was synthesized as described in Example 5, using 7-bromo-6-fluoro-1H-quinazolin-4-one instead of 6-bromoisoquinolin-1(2H)-one to give (S)-6-fluoro-3-(4-((6-oxo-5-(trifluoromethyl)-1,6-dihydropyridazin-4-yl)amino)pentyl)-7-(5-(trifluoromethyl)pyrimidin-2-yl)quinazolin-4(3H)-one as a white solid. 1H NMR (400 MHz, DMSO-d6) δ 12.44 (s, 1H), 9.50 (d, J=1.0 Hz, 2H), 8.46 (s, 1H), 8.35 (d, J=6.7 Hz, 1H), 8.01 (d, J=10.6 Hz, 1H), 7.92 (s, 1H), 6.41-6.26 (m, 1H), 4.11-3.88 (m, 3H), 1.83-1.62 (m, 3H), 1.62-1.42 (m, 1H), 1.17 (d, J=6.3 Hz, 3H). ES/MS m/z: 558.20 $[M+H]^+$.

Example 30 Preparation of 6-fluoro-3-[(4S)-4-[[6-oxo-5-(trifluoromethyl)-1H-pyridazin-4-yl]amino]pentyl]-7-[5-(trifluoromethyl)pyrimidin-2-yl]-1H-quinazoline-2,4-dione

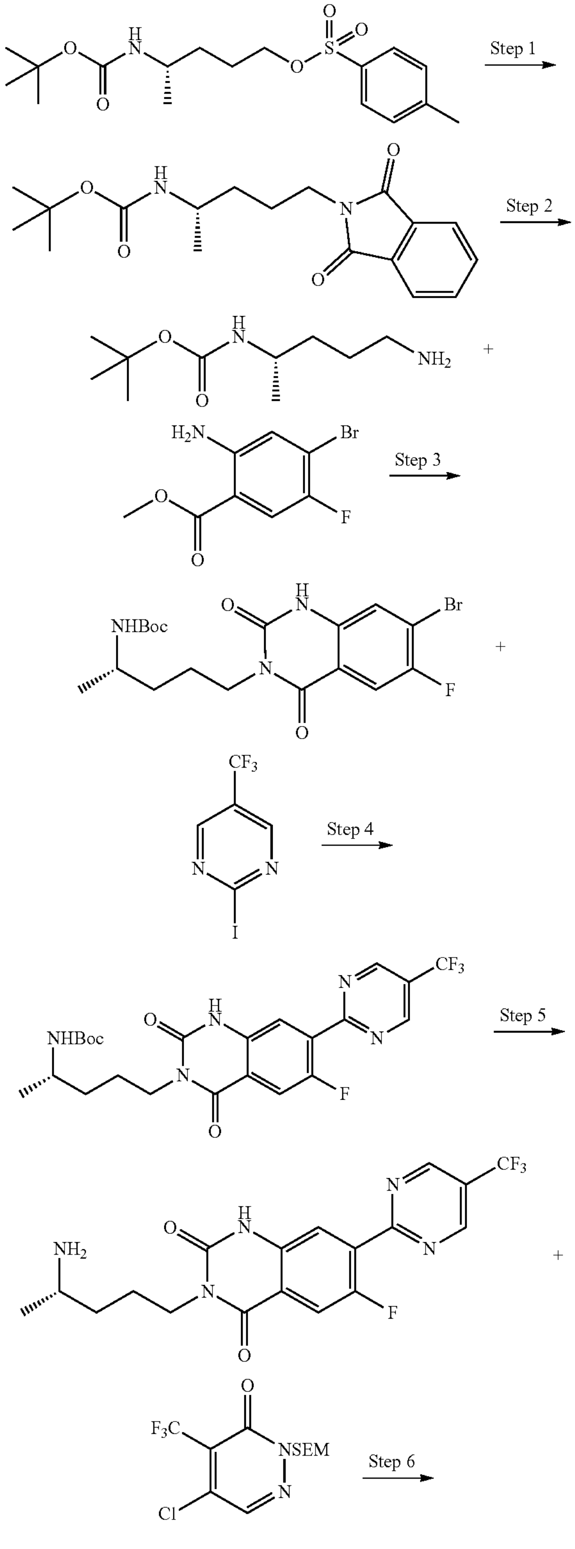

-continued

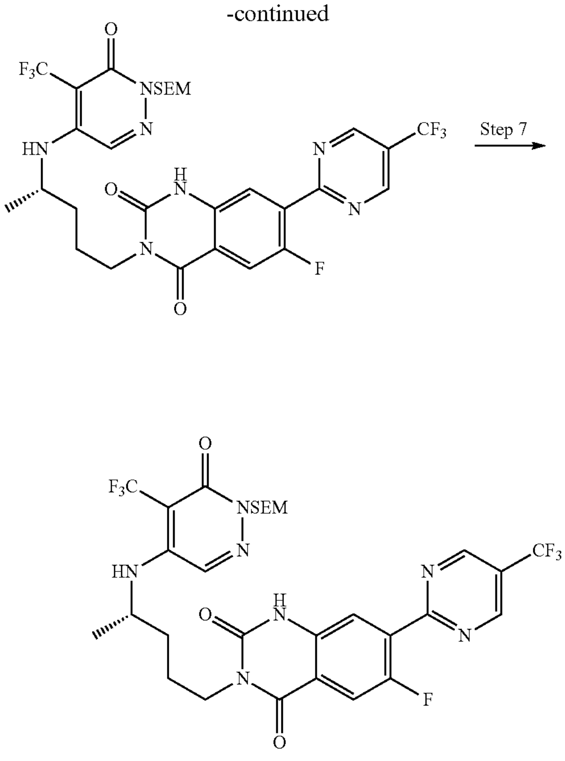

Example 30

Step 1. Phthalimide potassium salt (0.995 g, 5.37 mmol) was added to a solution of [(4S)-4-(tert-butoxycarbonylamino)pentyl]4-methylbenzenesulfonate (1.60 g, 4.48 mmol) in DMF (17.8 mL) and the resulting solution was heated to 80° C. for 2.5 hr. The reaction mixture was then diluted with water (ca. 100 mL) and the resulting white precipitate was collected by filtration to afford tert-butyl N-[(1S)-4-(1,3-dioxoisoindolin-2-yl)-1-methyl-butyl]carbamate. ES/MS m/z: 333.08 $[M+H]^+$.

Step 2. Hydrazine (0.378 mL, 12.0 mmol) was added slowly to a solution of tert-butyl N-[(1S)-4-(1,3-dioxoisoindolin-2-yl)-1-methyl-butyl]carbamate (0.8 g, 2.41 mmol) in EtOH (11.0 mL) and the resulting solution was heated to 80° C. for 45 min, at which time the formation of a significant amount of white precipitate hindered stirring. The suspension was then diluted with MeOH (10.0 mL) and a large excess of $Et_2O$, and the white precipitate was removed by filtration. The filtrate was concentrated in vacuo to afford tert-butyl (S)-(5-aminopentan-2-yl)carbamate. ES/MS m/z: 203.15 $[M+H]^+$.

Step 3. Triethylamine (1.75 mL, 12.6 mmol) was added to a solution of triphosgene (0.822 g, 2.77 mmol) and methyl 2-amino-4-bromo-5-fluoro-benzoate (624 mg, 2.52 mmol) in DCM (20.0 mL). The resulting solution was stirred at room temperature for 2 hr, followed by the addition of tert-butyl N-[(1S)-4-amino-1-methyl-butyl]carbamate (390 mg, 1.93 mmol) as a solution in DCM (20.0 mL). The reaction mixture was stirred at room temperature for 3.5 hr, followed by the addition of NaOMe (1.67 mL, 25% in MeOH, 7.29 mmol). After an additional 30 minutes of stirring at room temperature the reaction mixture was poured into saturated aqueous $NH_4Cl$, extracted with EtOAc, washed with brine, dried ($MgSO_4$), and concentrated in vacuo. To the crude oil was added DCM (2.00 mL) and PhMe (20 mL), and the resulting white precipitate was collected by filtration to afford tert-butyl N-[(1S)-4-(7-bromo-6-fluoro-2,4-dioxo-1H-quinazolin-3-yl)-1-methyl-butyl]carbamate. ES/MS m/z: 444.033 $[M+H]^+$.

Step 4. Dioxane (5.00 mL) was added to a vial charged with tert-butyl N-[(1S)-4-(7-bromo-6-fluoro-2,4-dioxo-1H-quinazolin-3-yl)-1-methyl-butyl]carbamate (124 mg, 0.279 mmol), potassium acetate (82 mg, 0.837 mmol), bis(pinacolato)diboron (106 mg, 0.419 mmol), and (1,1'-bis(diphenylphosphino)ferrocene)-dichloropalladium(II) (20.4 mg, 0.028 mmol). The resulting suspension was sparged with nitrogen for 5 minutes, then heated to 80° C. for 16 hr. To the reaction mixture was then added 2-iodo-5-(trifluoromethyl)pyrimidine (153 mg, 0.558 mmol) and $Na_2CO_3$ (0.419 mL, 2N in $H_2O$, 0.837 mmol) and the resulting solution was then heated to 80° C. for 2 hr, then cooled to room temperature, filtered through a pad of Celite©, concentrated in vacuo, and purified by flash chromatography (100% hexanes to 100% EtOAc) to afford tert-butyl N-[(1S)-4-[6-fluoro-2,4-dioxo-7-[5-(trifluoromethyl)pyrimidin-2-yl]-1H-quinazolin-3-yl]-1-methyl-butyl]carbamate. ES/MS m/z: 512.11 $[M+H]^+$.

Step 5. In a vial were placed tert-butyl N-[(1S)-4-[6-fluoro-2,4-dioxo-7-[5-(trifluoromethyl)pyrimidin-2-yl]-1H-quinazolin-3-yl]-1-methyl-butyl]carbamate (135 mg, 0.264 mmol), and trifluoroacetic acid (2.00 mL) in DCM (10.0 mL). After the mixture was allowed to stir for 1 hr, it was concentrated under vacuum to give 3-[(4S)-4-aminopentyl]-6-fluoro-7-[5-(trifluoromethyl)pyrimidin-2-yl]-1H-quinazoline-2,4-dione. ES/MS m/z: 412.119 $[M+H]^+$.

Step 6. In a vial were placed 5-chloro-4-(trifluoromethyl)-2-(2-trimethylsilylethoxymethyl)pyridazin-3-one (138 mg, 0.419 mmol), 3-[(4S)-4-aminopentyl]-6-fluoro-7-[5-(trifluoromethyl)pyrimidin-2-yl]-1H-quinazoline-2,4-dione (115 mg, 0.279 mmol), and N,N-Diisopropylethylamine (0.486 mL, 2.79 mmol) in DMF (10.0 mL). After the mixture was stirred at room temperature for 16 h, it was quenched with water and extracted with EtOAc. The combined organic layers were washed with water and brine, dried ($Na_2SO_4$), and purified by flash chromatography (100% hexanes to 100% EtOAc) to give 6-fluoro-3-[(4S)-4-[[6-oxo-5-(trifluoromethyl)-1-(2-trimethylsilylethoxymethyl)pyridazin-4-yl]amino]pentyl]-7-[5-(trifluoromethyl)pyrimidin-2-yl]-1H-quinazoline-2,4-dione. ES/MS m/z: 704.29 $[M+H]^+$.

Step 7. In a vial were placed 6-fluoro-3-[(4S)-4-[[6-oxo-5-(trifluoromethyl)-1-(2-trimethylsilylethoxymethyl)pyridazine-4-yl]amino]pentyl]-7-[5-(trifluoromethyl)pyrimidin-2-yl]-1H-quinazoline-2,4-dione (136 mg, 0.193 mmol), and trifluoroacetic acid (1.48 mL, 19.3 mmol) in DCM (10.0 mL). After the mixture was allowed to stir for 1 hr, it was concentrated in vacuo. The resulting crude product was dissolved in methanol (5.00 mL) and ethylenediamine (0.258 mL, 3.86 mmol) was added. The resulting solution was stirred at room temperature for 10 minutes, then concentrated in vacuo. The resulting crude product was purified by reverse phase prep-HPLC (5-100% MeCN in water, 0.1% TFA) to afford 6-fluoro-3-[(4S)-4-[[6-oxo-5-(trifluoromethyl)-1H-pyridazin-4-yl]amino]pentyl]-7-[5-(trifluoromethyl)pyrimidin-2-yl]-1H-quinazoline-2,4-dione. 1H NMR (400 MHz, DMSO-d6) δ 12.42 (s, 1H), 11.68 (s, 1H), 9.48 (d, J=0.9 Hz, 2H), 7.98-7.88 (m, 2H), 7.81 (d, J=10.5 Hz, 1H), 6.41-6.28 (m, 1H), 4.03-3.95 (m, 1H), 3.92 (t, J=6.8 Hz, 2H), 1.76-1.56 (m, 3H), 1.59-1.47 (m, 1H), 1.17 (d, J=6.3 Hz, 3H). ES/MS m/z: 574.20 $[M+H]^+$.

Example 31: 7-fluoro-2-[(4S)-4-[[6-oxo-5-(trifluoromethyl)-1H-pyridazin-4-yl]amino]pentyl]-6-(2-pyridyl)isoquinolin-1-one Example 31

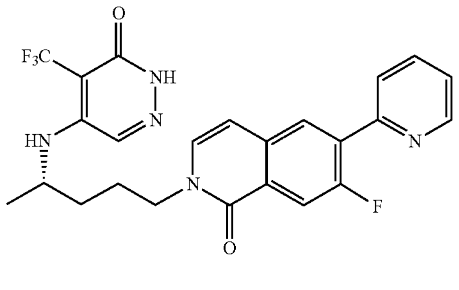

The title compound was synthesized as described in Example 5, using 2-bromopyridine in place of 6-bromoisoquinolin-1(2H)-one to give 7-fluoro-2-[(4S)-4-[[6-oxo-5-(trifluoromethyl)-1H-pyridazin-4-yl]amino]pentyl]-6-(2-pyridyl)isoquinolin-1-one (15 mg, 48%) as an off-white solid. 1H NMR (400 MHz, DMSO-d6) δ 12.43 (s, 1H), 8.78 (ddd, J=4.8, 1.8, 1.0 Hz, 1H), 8.24 (d, J=7.4 Hz, 1H), 8.04-7.95 (m, 2H), 7.94-7.86 (m, 2H), 7.54-7.46 (m, 2H), 6.79 (d, J=7.3 Hz, 1H), 6.35 (dd, J=8.6, 3.7 Hz, 1H), 3.99 (t, J=6.2 Hz, 3H), 1.71 (ddq, J=24.2, 15.8, 8.8, 7.7 Hz, 3H), 1.50 (dq, J=12.9, 6.7, 6.3 Hz, 1H), 1.17 (d, J=6.3 Hz, 3H). ES/MS m/z: 488.2 $[M+H]^+$.

Example 32: 7-fluoro-2-[(4S)-4-[[6-oxo-5-(trifluoromethyl)-1H-pyridazin-4-yl]amino]pentyl]-6-[5-(trifluoromethoxy)-2-pyridyl]isoquinolin-1-one Example 32

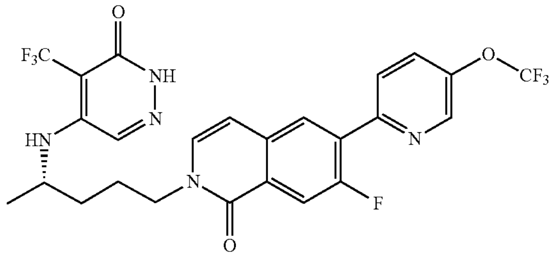

The title compound was synthesized as described in Example 8, using 2-bromo-5-(trifluoromethoxy)pyridine in place of 2-iodo-5-(trifluoromethyl)pyrimidine to give 7-fluoro-2-[(4S)-4-[[6-oxo-5-(trifluoromethyl)-1H-pyridazin-4-yl]amino]pentyl]-6-[5-(trifluoromethoxy)-2-pyridyl]isoquinolin-1-one. 1H NMR (400 MHz, DMSO-d6) δ 12.43 (s, 1H), 8.88 (dt, J=2.8, 0.8 Hz, 1H), 8.25 (d, J=7.4 Hz, 1H), 8.13-7.97 (m, 3H), 7.91 (s, 1H), 7.50 (d, J=7.4 Hz, 1H), 6.79 (d, J=7.3 Hz, 1H), 6.35 (dd, J=8.7, 3.8 Hz, 1H), 3.99 (t, J=6.7 Hz, 3H), 1.70 (ddt, J=24.5, 15.7, 7.3 Hz, 3H), 1.55-1.45 (m, 1H), 1.17 (d, J=6.3 Hz, 3H). ES/MS m/z: 572.2 $[M+H]^+$.

Example 33: 6-[5-(difluoromethyl)-2-pyridyl]-7-fluoro-2-[(4S)-4-[[6-oxo-5-(trifluoromethyl)-1H-pyridazin-4-yl]amino]pentyl]isoquinolin-1-one Example 33

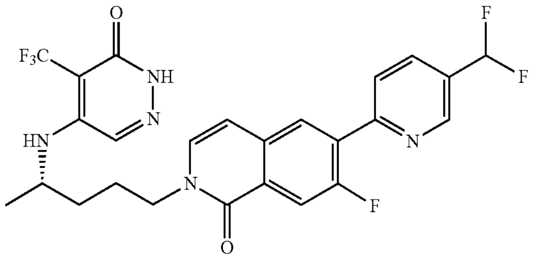

The title compound was synthesized as described in Example 8, using 2-bromo-5-(difluoromethyl)pyridine in place of 2-iodo-5-(trifluoromethyl)pyrimidine to give 6-[5-(difluoromethyl)-2-pyridyl]-7-fluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.43 (s, 1H), 8.98 (p, J=1.2 Hz, 1H), 8.28 (d, J=7.4 Hz, 1H), 8.20 (ddd, J=8.3, 2.4, 1.3 Hz, 1H), 8.07-7.99 (m, 2H), 7.91 (s, 1H), 7.51 (d, J=7.4 Hz, 1H), 7.25 (t, J=55.2 Hz, 1H), 6.81 (d, J=7.4 Hz, 1H), 6.35 (dq, J=6.7, 3.3 Hz, 1H), 3.99 (q, J=6.4 Hz, 3H), 1.82-1.58 (m, 3H), 1.51 (dt, J=8.9, 6.1 Hz, 1H), 1.17 (d, J=6.3 Hz, 3H). ES/MS m/z:538.2 $[M+H]^+$.

Example 34: 7-fluoro-6-(5-fluoropyrimidin-2-yl)-2-[(4S)-4-[[6-oxo-5-(trifluoromethyl)-1H-pyridazin-4-yl]amino]pentyl]isoquinolin-1-one Example 34

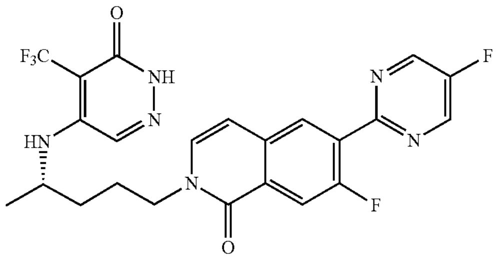

The title compound was synthesized as described in Example 8, using 2-bromo-5-fluoro-pyrimidine in place of 2-iodo-5-(trifluoromethyl)pyrimidine to give 7-fluoro-6-(5-fluoropyrimidin-2-yl)-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.43 (s, 1H), 9.11 (d, J=0.8 Hz, 2H), 8.32 (d, J=7.2 Hz, 1H), 8.00 (d, J=11.3 Hz, 1H), 7.92 (s, 1H), 7.51 (d, J=7.4 Hz, 1H), 6.82 (d, J=7.3 Hz, 1H), 6.35 (dd, J=8.7, 3.7 Hz, 1H), 3.99 (t, J=6.4 Hz, 3H), 1.71 (dtd, J=22.2, 14.8, 13.7, 7.1 Hz, 3H), 1.50 (dq, J=12.9, 6.3 Hz, 1H), 1.17 (d, J=6.3 Hz, 3H). ES/MS m/z: 507.2 $[M+H]^+$.

Example 35: 7-fluoro-6-(5-fluoro-2-pyridyl)-2-[(4S)-4-[[6-oxo-5-(trifluoromethyl)-1H-pyridazin-4-yl]amino]pentyl]isoquinolin-1-one Example 35

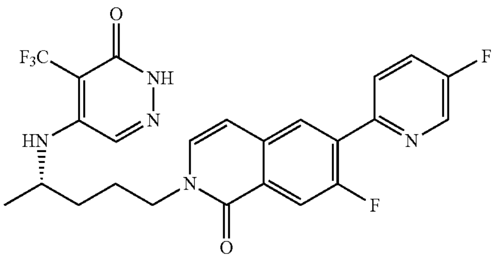

The title compound was synthesized as described in Example 8, using 2-bromo-5-fluoro-pyridine in place of 2-iodo-5-(trifluoromethyl)pyrimidine to give 7-fluoro-6-(5-fluoro-2-pyridyl)-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.43 (s, 1H), 8.79 (d, J=2.9 Hz, 1H), 8.21 (d, J=7.4 Hz, 1H), 8.05-7.87 (m, 4H), 7.49 (d, J=7.4 Hz, 1H), 6.79 (d, J=7.3 Hz, 1H), 6.46-6.22 (m, 1H), 3.99 (t, J=6.1 Hz, 3H), 1.69 (ddp, J=22.3, 15.6, 6.7 Hz, 3H), 1.50 (dq, J=13.0, 6.2 Hz, 1H), 1.17 (d, J=6.3 Hz, 3H). ES/MS m/z: 506.2 $[M+H]^+$.

Example 36: 2-[(4R)-4-cyclopropyl-4-[[6-oxo-5-(trifluoromethyl)-1H-pyridazin-4-yl]amino]butyl]-7-fluoro-6-[5-(trifluoromethyl)pyrimidin-2-yl]isoquinolin-1-one

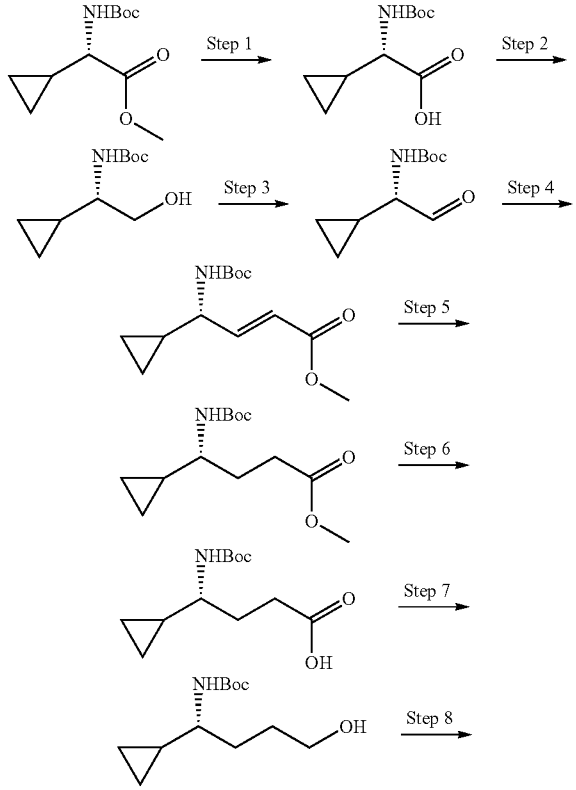

-continued

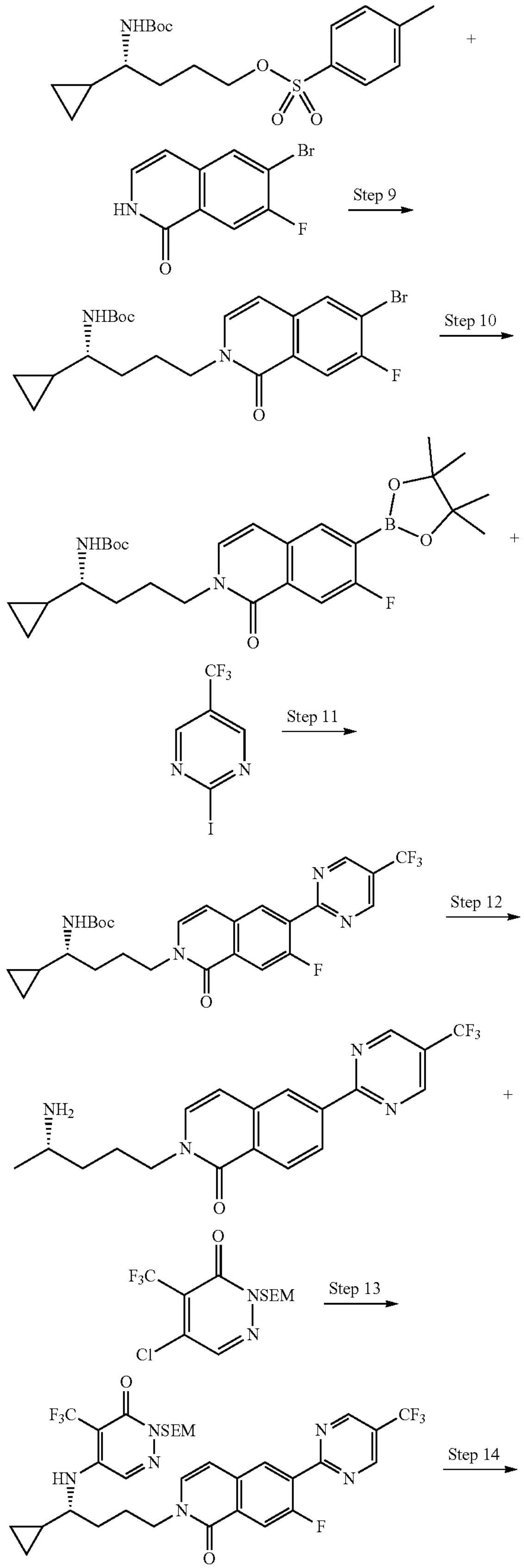

-continued

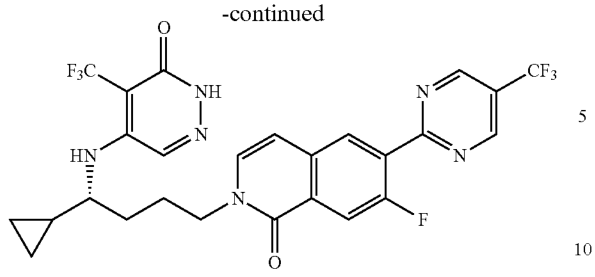

Example 36

Step 1. In a vial were placed methyl (2S)-2-(tert-butoxycarbonylamino)-2-cyclopropyl-acetate (500 mg, 2.18 mmol) and 1N lithium hydroxide solution (aq.) (5.45 mL, 5.45 mmol) in THF (17 mL). The mixture was stirred at room temperature for 4 h. Upon completion, the reaction was diluted with ethyl acetate, washed with 1 N HCl solution (aq.), washed with brine, dried over $Na_2SO_4$ and concentrated to give (2S)-2-(tert-butoxycarbonylamino)-2-cyclopropyl-acetic acid. ES/MS m/z 159.701 [M-tert-butyl]$^-$.

Step 2. In a vial were placed (2S)-2-(tert-butoxycarbonylamino)-2-cyclopropyl-acetic acid (468 mg, 2.17 mmol), triethylamine (0.303 mL, 2.17 mmol), and THF (21.0 mL). The mixture was cool to 0° C. and placed under nitrogen atmosphere. To this solution was added ethyl chloroformate (0.208 mL, 2.17 mmol) and stirred for 30 min at 0° C. The reaction was then filtered to remove the precipitated triethylamine hydrochloride. The filtrate containing the mixed anhydride was slowly added to a stirred suspension of sodium borohydride (247 mg, 6.52 mmol) in 20% aqueous THF (10.0 mL) maintained at 10° C. After mixture stirred for 30 minutes, it was acidified with 1N HCl to pH~4. The mixture was then extracted with EtOAc (×3), washed with 2M NaOH solution, washed with brine, dried ($Na_2SO_4$), and purified by flash chromatography (100% hexanes to 100% EtOAc) to give tert-butyl N-[(1S)-1-cyclopropyl-2-hydroxy-ethyl]carbamate. ES/MS: m/z 145.8 [M-tert-butyl]$^-$.

Step 3. In a vial was placed tert-butyl N-[(1S)-1-cyclopropyl-2-hydroxy-ethyl]carbamate (378 mg, 1.88 mmol) in DCM (16.0 mL). The mixture was cooled to 0° C. and Dess-Martin Periodinane (1590 mg, 3.76 mmol) was added. Reaction was warmed to room temperature and stirred for 1 h. Upon complete conversion the reaction mixture was diluted with DCM, washed with saturated sodium bicarbonate solution, washed with brine, dried over $Na_2SO_4$ and concentrated to give tert-butyl N-[(1S)-1-cyclopropyl-2-oxo-ethyl]carbamate. ES/MS: m/z 143.8 [M-tert-butyl]$^-$.

Step 4. In a vial were placed tert-butyl N-[(1S)-1-cyclopropyl-2-oxo-ethyl]carbamate (374 mg, 1.88 mmol), and methyl(triphenylphosphoranylidene)acetate (941 mg, 2.82 mmol) in THF (15.0 mL). Reaction was stirred at room temperature for 12 h, concentrated in vacuo, and purified via flash chromatography (100% hexanes to 100% EtOAc) to give methyl (E,4S)-4-(tert-butoxycarbonylamino)-4-cyclopropyl-but-2-enoate. ES/MS: m/z 278.2 [M+Na]$^+$.

Step 5. In a pressure vial were placed methyl (E,4S)-4-(tert-butoxycarbonylamino)-4-cyclopropyl-but-2-enoate (255 mg, 0.999 mmol), p-toluenesulfonhydrazide (2790 mg, 15 mmol), and sodium acetate trihydrate (2718 mg, 20 mmol) in THF:$H_2O$ (1:1, 12.9 mL). Mixture was heated to 80° C. and stirred for 8 h. Upon complete conversion the reaction was diluted with EtOAc, washed with saturated sodium bicarbonate solution, washed with brine, dried over $Na_2SO_4$, and purified via flash chromatography (100% hexanes to 100% EtOAc) to give methyl (4R)-4-(tert-butoxycarbonylamino)-4-cyclopropyl-butanoate. ES/MS: m/z 257.6 [M+H]$^+$.

Step 6. In a vial were placed methyl (4R)-4-(tert-butoxycarbonylamino)-4-cyclopropyl-butanoate (233 mg, 0.905 mmol), and 1N lithium hydroxide solution (aq.) (2.26 mL, 2.26 mmol) in THF (7.06 mL). The mixture was stirred at room temperature for 4 h. Upon complete conversion reaction diluted with ethyl acetate, washed with 1N HCl solution (aq.), washed with brine, organic layer was dried over $Na_2SO_4$ and concentrated to give (4R)-4-(tert-butoxycarbonylamino)-4-cyclopropyl-butanoic acid. ES/MS m/z 187.761 [M-tert-butyl]$^-$.

Step 7. In a vial were placed (4R)-4-(tert-butoxycarbonylamino)-4-cyclopropyl-butanoic acid (220 mg, 0.904 mmol), and triethylamine (0.126 mL, 0.904 mmol) in THF (8.73 mL). The mixture was cool to 0° C. and placed under nitrogen atmosphere. To this solution was added ethyl chloroformate (0.087 mL, 0.904 mmol). After mixture stirred for 30 min at 0° C., it was filtered to remove the precipitated triethylamine hydrochloride. The filtrate containing the mixed anhydride was slowly added to a stirred suspension of sodium borohydride (103 mg, 2.71 mmol) in 20% aqueous THF (10.0 mL) maintained at 10° C. After mixture was stirred for 30 minutes, it was acidified with 1N HCl to pH~4. The mixture was then extracted with EtOAc, washed with 2M NaOH solution, washed with brine, dried ($Na_2SO_4$), and purified by flash chromatography (100% hexanes to 100% EtOAc) to give tert-butyl N-[(1R)-1-cyclopropyl-4-hydroxy-butyl]carbamate. ES/MS: m/z 229.6 [M+H]$^+$.

Step 8. In a vial were placed tert-butyl N-[(1R)-1-cyclopropyl-4-hydroxy-butyl]carbamate (193 mg, 0.842 mmol), and triethylamine (0.235 mL, 1.68 mmol) in DCM (3.85 mL). The mixture was cooled to 0° C. and p-toluenesulfonyl chloride (160 mg, 0.842 mmol) was added. The mixture was warmed to room temperature and stirred for 2 h and was then quenched with water and extracted with EtOAc (×3). The combined organic layers were washed with brine, dried ($Na_2SO_4$), and purified by flash chromatography (100% hexanes to 100% EtOAc) to give [(4R)-4-(tert-butoxycarbonylamino)-4-cyclopropyl-butyl]4-methylbenzenesulfonate. ES/MS m/z: 406.1 [M+Na]

Step 9. In a vial were placed 6-bromo-7-fluoro-2H-isoquinolin-1-one (110 mg, 0.454 mmol), [(4R)-4-(tert-butoxycarbonylamino)-4-cyclopropyl-butyl]4-methylbenzenesulfonate (209 mg, 0.545 mmol), and cesium carbonate (296 mg, 0.909 mmol) in DMF (2.20 mL). After mixture was stirred at room temperature for 16 h, it was quenched with water and extracted with EtOAc (×3). The combined organic layers were washed with water and brine, dried ($Na_2SO_4$), and purified by flash chromatography (100% hexanes to 100% EtOAc) to give tert-butyl N-[(1R)-4-(6-bromo-7-fluoro-1-oxo-2-isoquinolyl)-1-cyclopropyl-butyl]carbamate. ES/MS m/z: 455.0 [M+H]$^+$.

Step 10. In a vial were placed tert-butyl N-[(1R)-4-(6-bromo-7-fluoro-1-oxo-2-isoquinolyl)-1-cyclopropyl-butyl] carbamate (181 mg, 0.399 mmol), 1,1'-Bis(diphenylphosphino)ferrocene-palladium(II)dichloride dichloromethane complex (33 mg, 0.0399 mmol), potassium acetate (118 mg, 1.2 mmol), and bis(pinacolato)diboron (152 mg, 0.599 mmol) in dioxane (1.70 mL). The mixture was heated to 100° C. and stirred for 1 h. Upon completion, the reaction was quenched with water and extracted with EtOAc (×3). The combined organic layers were washed with water and brine, dried ($Na_2SO_4$), filtered through Celite©, and concentrated to give tert-butyl N-[(1R)-1-cyclopropyl-4-[7-fluoro-1-oxo-6-(4,4,5,5-tetramethyl-1,3,2-dioxaborolan-2-yl)-2-isoquinolyl]butyl]carbamate. ES/MS: m/z 501.3 [M+H]$^+$.

Step 11. In a vial were placed tert-butyl N-[(1R)-1-cyclopropyl-4-[7-fluoro-1-oxo-6-(4,4,5,5-tetramethyl-1,3,2-dioxaborolan-2-yl)-2-isoquinolyl]butyl]carbamate (200 mg, 0.4 mmol), 2-iodo-5-(trifluoromethyl)pyrimidine (164 mg, 0.6 mmol), [1,1'-Bis(di-tert-butylphosphino)ferrocene] dichloropalladium(II) (13 mg, 0.02 mmol), and 2M aqueous sodium carbonate (0.6 mL, 1.2 mmol) in dioxane (3.61 mL). After the mixture was heated to 80° C. and allowed to stir for 2 h, it was quenched with water and extracted with EtOAc (×3). The combined organic layers were washed with water and brine, dried ($Na_2SO_4$), and purified by flash chromatography (100% hexanes to 100% EtOAc) to give tert-butyl N-[(1R)-1-cyclopropyl-4-[7-fluoro-1-oxo-6-[5-(trifluoromethyl)pyrimidin-2-yl]-2-isoquinolyl]butyl]carbamate. ES/MS: m/z 521.2 [M+H]$^+$.

Step 12. In a vial were placed tert-butyl N-[(1R)-1-cyclopropyl-4-[7-fluoro-1-oxo-6-[5-(trifluoromethyl)pyrimidin-2-yl]-2-isoquinolyl]butyl]carbamate (196 mg, 0.377 mmol), and trifluoroacetic acid (0.288 mL, 3.77 mmol) in DCM (3.30 mL). After the mixture was allowed to stir for 1 h, it was concentrated under vacuum to give 2-[(4R)-4-amino-4-cyclopropyl-butyl]-7-fluoro-6-[5-(trifluoromethyl)pyrimidin-2-yl]isoquinolin-1-one. ES/MS: m/z 421.1 [M+H]$^+$.

Step 13. In a vial were placed 5-chloro-4-(trifluoromethyl)-2-(2-trimethylsilylethoxymethyl)pyridazin-3-one (185 mg, 0.564 mmol), 2-[(4R)-4-amino-4-cyclopropyl-butyl]-7-fluoro-6-[5-(trifluoromethyl)pyrimidin-2-yl]isoquinolin-1-one (158 mg, 0.376 mmol), and N,N-Diisopropylethylamine (0.327 mL, 1.88 mmol) in DMF (1.10 mL). After the mixture was heated to 80° C. and allowed to stir for 1 h, it was quenched with water and extracted with EtOAc (×3). The combined organic layers were washed with water and brine, dried ($Na_2SO_4$), and purified by flash chromatography (100% hexanes to 100% EtOAc) to give 2-[(4R)-4-cyclopropyl-4-[[6-oxo-5-(trifluoromethyl)-1-(2-trimethylsilylethoxymethyl)pyridazin-4-yl]amino]butyl]-7-fluoro-6-[5-(trifluoromethyl)pyrimidin-2-yl]isoquinolin-1-one. ES/MS m/z: 713.3 [M+H]$^+$.

Step 14. In a vial were placed 2-[(4R)-4-cyclopropyl-4-[[6-oxo-5-(trifluoromethyl)-1-(2-trimethylsilylethoxymethyl)pyridazin-4-yl]amino]butyl]-7-fluoro-6-[5-(trifluoromethyl)pyrimidin-2-yl]isoquinolin-1-one (169 mg, 0.237 mmol), and trifluoroacetic acid (0.181 mL, 2.7 mmol) in DCM (10.4 mL). After the mixture was allowed to stir for 1 h, it was concentrated under vacuum. The resulting crude product was dissolved in methanol (4.0 mL) and ethylenediamine (0.159 mL, 2.437 mmol) was added. The mixture was stirred for 15 minutes and was concentrated under vacuum. The resulting crude product was purified by reverse phase prep-HPLC (5-100% MeCN in water, 0.1% TFA) to afford 2-[(4R)-4-cyclopropyl-4-[[6-oxo-5-(trifluoromethyl)-1H-pyridazin-4-yl]amino]butyl]-7-fluoro-6-[5-(trifluoromethyl)pyrimidin-2-yl]isoquinolin-1-one. 1H NMR (400 MHz, DMSO-d6) δ 12.40 (s, 1H), 9.48 (d, J=1.0 Hz, 2H), 8.44 (d, J=7.2 Hz, 1H), 8.04 (d, J=11.4 Hz, 1H), 7.89 (s, 1H), 7.54 (d, J=7.4 Hz, 1H), 6.85 (d, J=7.3 Hz, 1H), 6.51 (dd, J=9.0, 3.8 Hz, 1H), 4.01 (t, J=6.3 Hz, 2H), 3.36 (s, 1H), 1.72 (d, J=40.1 Hz, 4H), 1.10 (tt, J=8.2, 3.4 Hz, 1H), 0.50 (dp, J=8.4, 4.2 Hz, 1H), 0.38 (tt, J=8.9, 4.1 Hz, 1H), 0.25 (ddq, J=18.6, 9.3, 4.6 Hz, 2H). ES/MS m/z: 508.3 [M+H]$^+$.

Example 37: 7-fluoro-2-[(4S)-4-[[6-oxo-5-(trifluoromethyl)-1H-pyridazin-4-yl]amino]hexyl]-6-[5-(trifluoromethyl)pyrimidin-2-yl]isoquinolin-1-one Example 37

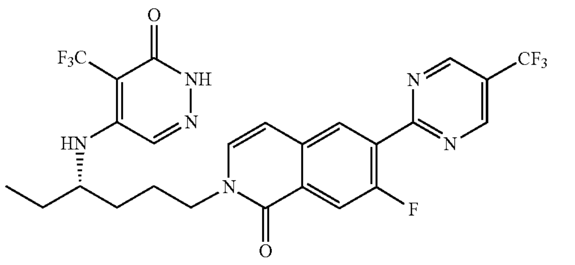

The title compound was synthesized as described in Example 6, using tert-butyl N-[(1S)-1-formylpropyl]carbamate in place of tert-butyl N-[(1S)-1-cyclopropyl-2-oxo-ethyl]carbamate to give 7-fluoro-2-[(4S)-4-[[6-oxo-5-(trifluoromethyl)-1H-pyridazin-4-yl]amino]hexyl]-6-[5-(trifluoromethyl)pyrimidin-2-yl]isoquinolin-1-one. 1H NMR (400 MHz, DMSO-d6) δ 12.42 (s, 1H), 9.48 (d, J=0.9 Hz, 2H), 8.44 (d, J=7.1 Hz, 1H), 8.03 (d, J=11.4 Hz, 1H), 7.96 (s, 1H), 7.53 (d, J=7.3 Hz, 1H), 6.85 (d, J=7.2 Hz, 1H), 6.28 (dd, J=9.1, 3.9 Hz, 1H), 4.00 (t, J=6.8 Hz, 2H), 3.85 (d, J=7.7 Hz, 1H), 1.83-1.66 (m, 2H), 1.57 (tt, J=14.4, 8.0 Hz, 4H), 0.82 (t, J=7.3 Hz, 3H). ES/MS m/z: 571.3 [M+H]$^+$.

Example 38: 1-[6-[8-fluoro-1-oxo-2-[(4S)-4-[[6-oxo-5-(trifluoromethyl)-1H-pyridazin-4-yl]amino]pentyl]-6-isoquinolyl]-3-pyridyl]cvclopropanecarbonitrile

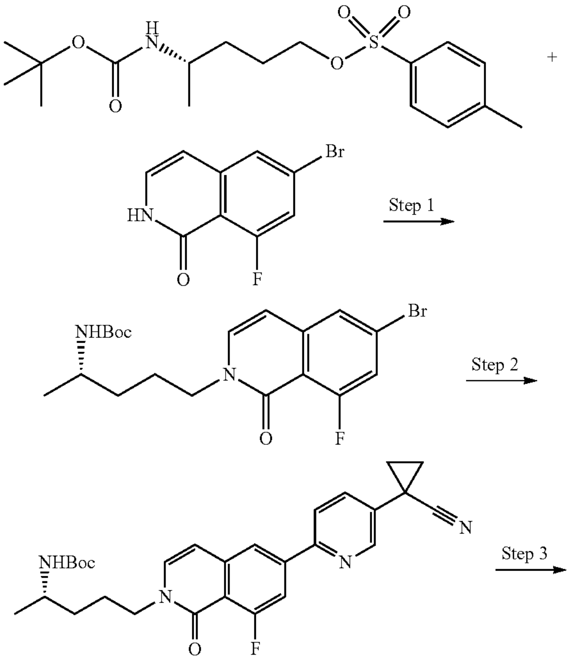

-continued

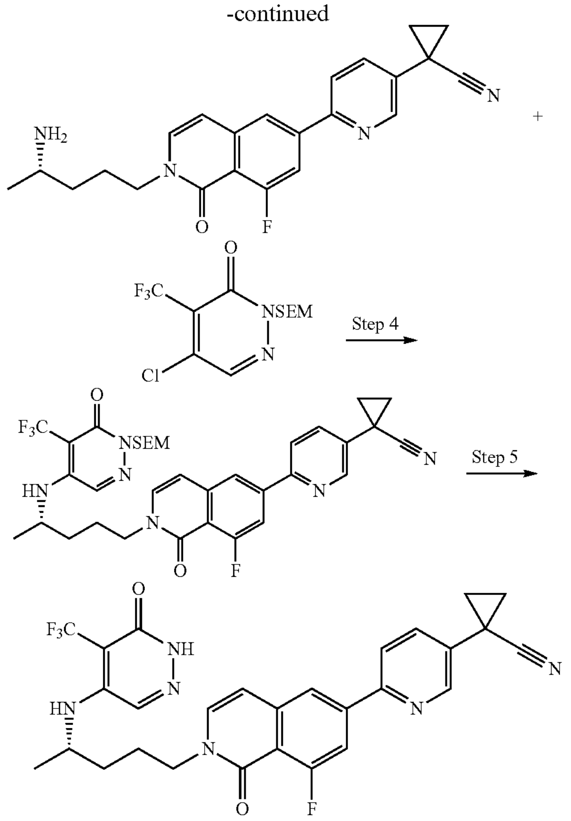

Example 38

Step 1. In a vial were placed 6-bromo-8-fluoro-2H-isoquinolin-1-one (500 mg, 2.48 mmol), [(4S)-4-(tert-butoxycarbonylamino)pentyl]4-methylbenzenesulfonate (886 mg, 2.48 mmol), and cesium carbonate (1346 mg, 4.13 mmol) in DMF (9.76 mL). After mixture was stirred at room temperature for 16 h, it was quenched with water and extracted with EtOAc (x3). The combined organic layers were washed with water and brine, dried over $Na_2SO_4$, and purified via flash chromatography (100% hexanes to 100% EtOAc) to give tert-butyl N-[(1S)-4-(6-bromo-8-fluoro-1-oxo-2-isoquinolyl)-1-methyl-butyl]carbamate. ES/MS m/z: 429.047 $[M+2+H]^+$+.

Step 2. In a vial were placed tert-butyl N-[(1S)-4-(6-bromo-8-fluoro-1-oxo-2-isoquinolyl)-1-methyl-butyl]carbamate (100 mg, 0.234 mmol), tetrahydroxydiboron (62.9 mg, 0.702 mmol), chloro(2-dicyclohexylphosphino-2',4',6'-triisopropyl-1,1'-biphenyl)[2-(2'-amino-1,1'-biphenyl)]palladium(II) (9.21 mg, 0.0117 mmol), 2-Dicyclohexylphosphino-2',4',6'-triisopropylbiphenyl (11.2 mg, 0.0234 mmol), and potassium acetate (68.9 mg, 0.702 mmol) in EtOH (3.9 mL). Mixture was purged with nitrogen gas for 5 minutes and stirred at 80° C. until full conversion to boronic acid was observed. Following full conversion to the boronic acid, 1.8 M aqueous potassium carbonate solution (0.39 mL, 0.702 mmol) was added followed by 1-(6-bromo-3-pyridyl)cyclopropanecarbonitrile (57.4 mg, 0.257 mmol). Reaction was stirred at 80° C. for 3 h. Upon completion, it was diluted with EtOAc, washed with water, washed with brine, dried over $Na_2SO_4$, concentrated and purified via flash chromatography (100% hexanes to 100% EtOAc) to give tert-butyl N-[(1S)-4-[6-[5-(1-cyanocyclopropyl)-2-pyridyl]-8-fluoro-1-oxo-2-isoquinolyl]-1-methyl-butyl]carbamate. ES/MS m/z: 491.249 $[M+H]^+$.

Step 3. In a vial were placed tert-butyl N-[(1S)-4-[6-[5-(1-cyanocyclopropyl)-2-pyridyl]-8-fluoro-1-oxo-2-isoquinolyl]-1-methyl-butyl]carbamate (34 mg, 0.069 mmol), and trifluoroacetic acid (0.053 mL, 0.69 mmol) in DCM (0.89 mL). After the mixture was allowed to stir for 1 h, it was concentrated under vacuum to give 1-[6-[2-[(4S)-4-aminopentyl]-8-fluoro-1-oxo-6-isoquinolyl]-3-pyridyl]cyclopropanecarbonitrile. ES/MS: m/z 391.1 $[M+H]^+$.

Step 4. In a vial were placed 5-chloro-4-(trifluoromethyl)-2-(2-trimethylsilylethoxymethyl)pyridazin-3-one (34.1 mg, 0.104 mmol), 1-[6-[2-[(4S)-4-aminopentyl]-8-fluoro-1-oxo-6-isoquinolyl]-3-pyridyl]cyclopropanecarbonitrile (27 mg, 0.069 mmol), and N,N-Diisopropylethylamine (0.06 mL, 0.35 mmol) in DMF (2.04 mL). After the mixture was heated to 80° C. and allowed to stir for 1 h, it was quenched with water and extracted with EtOAc. The combined organic layers were washed with water and brine, dried ($Na_2SO_4$), and purified by flash chromatography (100% hexanes to 100% EtOAc) to give 1-[6-[8-fluoro-1-oxo-2-[(4S)-4-[[6-oxo-5-(trifluoromethyl)-1-(2-trimethylsilylethoxymethyl) pyridazin-4-yl]amino]pentyl]-6-isoquinolyl]-3-pyridyl]cyclopropanecarbonitrile. ES/MS m/z: 683.4 $[M+H]^+$.

Step 5. In a vial were placed 1-[6-[8-fluoro-1-oxo-2-[(4S)-4-[[6-oxo-5-(trifluoromethyl)-1-(2-trimethylsilylethoxymethyl)pyridazin-4-yl]amino]pentyl]-6-isoquinolyl]-3-pyridyl]cyclopropanecarbonitrile (34 mg, 0.05 mmol), and trifluoroacetic acid (0.038 mL, 0.5 mmol) in DCM (2.2 mL). After the mixture was allowed to stir for 1 h, it was concentrated under vacuum. The resulting crude product was dissolved in methanol (4.0 mL) and ethylenediamine (0.033 mL, 0.5 mmol) was added. After the mixture was allowed to stir for 15 min, it was concentrated under vacuum. The resulting oil was purified by reverse phase prep-HPLC (5-100% MeCN in water, 0.1% TFA) to afford 1-[6-[8-fluoro-1-oxo-2-[(4S)-4-[[6-oxo-5-(trifluoromethyl)-1H-pyridazin-4-yl]amino]pentyl]-6-isoquinolyl]-3-pyridyl] cyclopropanecarbonitrile. 1H NMR (400 MHz, DMSO-d6) δ 12.43 (s, 1H), 8.73 (dd, J=2.5, 0.8 Hz, 1H), 8.34-8.08 (m, 2H), 8.02-7.81 (m, 3H), 7.54 (d, J=7.4 Hz, 1H), 6.74 (dd, J=7.4, 2.0 Hz, 1H), 6.36 (dt, J=8.5, 3.5 Hz, 1H), 4.03-3.91 (m, 3H), 1.93-1.84 (m, 2H), 1.79-1.60 (m, 4H), 1.50 (dq, J=12.7, 6.5 Hz, 1H), 1.17 (d, J=6.3 Hz, 3H). ES/MS m/z: 553.3 $[M+H]^+$.

Example 39: 8-fluoro-2-[(4S)-4-[[6-oxo-5-(trifluoromethyl)-1H-pyridazin-4-yl]amino]pentyl]-6-[5-[1-(trifluoromethyl)cyclopropyl]-2-pyridyl]isoquinolin-1-one Example 39

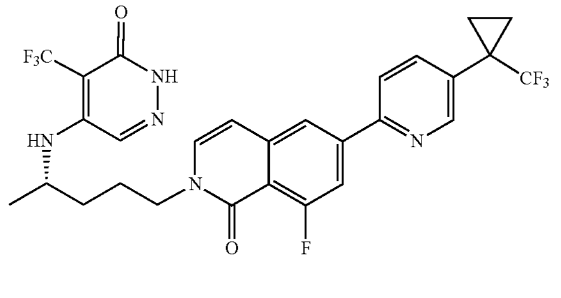

The title compound was synthesized as described in Example 8, using 2-chloro-5-[1-(trifluoromethyl)cyclopropyl]pyridine in place of 1-(6-bromo-3-pyridyl)cyclopropanecarbonitrile to give 8-fluoro-2-[(4S)-4-[[6-oxo-5-(trifluoromethyl)-1H-pyridazin-4-yl]amino]pentyl]-6-[5-[1-(trifluoromethyl)cyclopropyl]-2-pyridyl]isoquinolin-1-one. 1H NMR (400 MHz, DMSO-d6) δ 12.43 (s, 1H), 8.81 (d, J=2.2 Hz, 1H), 8.23 (d, J=1.6 Hz, 1H), 8.18 (dd, J=8.3, 0.8 Hz, 1H), 8.05 (dd, J=8.2, 2.3 Hz, 1H), 7.90 (dd, J=13.3, 1.5 Hz, 2H), 7.55 (d, J=7.4 Hz, 1H), 6.74 (dd, J=7.4, 2.0 Hz, 1H), 6.36 (dt, J=8.5, 3.6 Hz, 1H), 3.96 (dt, J=13.2, 7.1 Hz, 3H), 1.69 (tt, J=16.3, 7.4 Hz, 3H), 1.51 (dt, J=11.4, 6.1 Hz, 1H), 1.43 (t, J=3.5 Hz, 2H), 1.31-1.25 (m, 2H), 1.17 (d, J=6.3 Hz, 3H). ES/MS m/z: 596.3 $[M+H]^+$.

Example 40: 8-fluoro-6-[5-(methylsulfonimidoyl)-2-pyridyl]-2-[(4S)-4-[[6-oxo-5-(trifluoromethyl)-1H-pyridazin-4-yl]amino]pentyl]isoquinolin-1-one Example 40

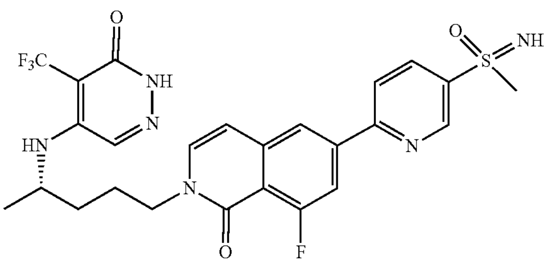

The title compound was synthesized as described in Example 8, using Intermediate 2 in place of 1-(6-bromo-3-pyridyl)cyclopropanecarbonitrile to give 8-fluoro-6-[5-(methylsulfonimidoyl)-2-pyridyl]-2-[(4S)-4-[[6-oxo-5-(trifluoromethy)-1H-pyridazin-4-yl]amino]pentyl]isoquinolin-1-one. NMR (400 MHz, DMSO-d6) δ 12.43 (s, 1H), 9.19 (dd, J=2.4, 0.8 Hz, 1H), 8.45 (dd, J=8.4, 2.3 Hz, 1H), 8.40 (dd, J=8.4, 0.9 Hz, 1H), 8.32 (d, J=1.6 Hz, 1H), 7.97 (dd, J=13.1, 1.7 Hz, 1H), 7.92 (s, 1H), 7.58 (d, J=7.3 Hz, 1H), 6.77 (dd, J=7.4, 2.0 Hz, 1H), 6.35 (dd, J=8.7, 3.7 Hz, 1H), 3.95 (t, J=6.5 Hz, 2H), 3.31 (s, 3H), 1.68 (td, J=13.8, 6.9 Hz, 3H), 1.51 (dt, J=11.5, 6.2 Hz, 1H), 1.17 (d, J=6.3 Hz, 3H). ES/MS m/z: 565.3 $[M+H]^+$.

Intermediate 2: Preparation of tert-butyl N-[(6-chloro-3-pyridyl)-methyl-oxo-lambda6-sulfanylidene]carbamate

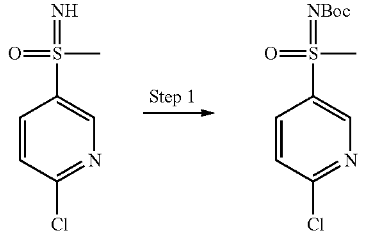

Intermediate 2

Step 1. In a vial were placed (6-chloro-3-pyridyl)-imino-methyl-oxo-lambda6-sulfane (300 mg, 1.57 mmol), and 1M potassium t-butoxide (THF solution, 1.89 mL, 1.89 mmol) in THF (3.65 mL). Reaction allowed to stir at room temperature for 30 min. After stirring, di-tert-butyl decarbonate (687 mg, 3.15 mmol) was added. Reaction allowed to stir for 4 h, diluted with EtOAc, washed with water, washed with brine, dried over $Na_2SO_4$, and purified via flash chromatography (100% hexanes to 100% EtOAc) to give tert-butyl N-[(6-chloro-3-pyridyl)-methyl-oxo-lambda6-sulfanylidene]carbamate. ES/MS m/z: 290.965 $[M+H]^+$.

Example 41: 8-fluoro-2-[(4S)-4-[[6-oxo-5-(trifluoromethyl)-1H-pyridazin-4-yl]amino]pentyl]-6-[5-(2,2,2-trifluoroethyl)-2-pyridyl]isoquinolin-1-one Example 41

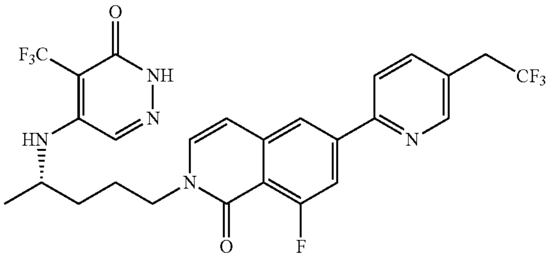

The title compound was synthesized as described in Example 8, using 2-chloro-5-(2,2,2-trifluoroethyl)pyridine in place of 1-(6-bromo-3-pyridyl)cyclopropanecarbonitrile to give 8-fluoro-2-[(4S)-4-[[6-oxo-5-(trifluoromethyl)-1H-pyridazin-4-yl]amino]pentyl]-6-[5-(2,2,2-trifluoroethyl)-2-pyridyl]isoquinolin-1-one. 1H NMR (400 MHz, DMSO-d6) δ 12.43 (s, 1H), 8.72 (d, J=2.1 Hz, 1H), 8.26-8.15 (m, 2H), 8.02-7.95 (m, 1H), 7.94-7.86 (m, 2H), 7.55 (d, J=7.4 Hz, 1H), 6.73 (dd, J=7.5, 2.0 Hz, 1H), 6.35 (d, J=8.6 Hz, 1H), 3.95 (q, J=9.4, 6.8 Hz, 3H), 3.84 (q, J=11.5 Hz, 2H), 1.79-1.59 (m, 3H), 1.59-1.44 (m, 1H), 1.17 (d, J=6.3 Hz, 3H). ES/MS m/z: 570.3 $[M+H]^+$.

Example 42: 6-[5-(difluoromethoxy)pyrimidin-2-yl]-7-fluoro-2-[(4S)-4-[[6-oxo-5-(trifluoromethyl)-1H-pyridazin-4-yl]amino]pentyl]isoquinolin-1-one Example 42

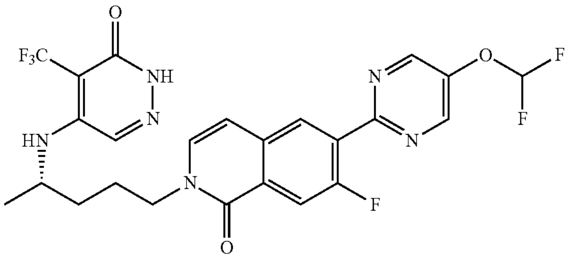

The title compound was synthesized as described in Example 8, using 2-chloro-5-(difluoromethoxy)pyrimidine in place of 2-iodo-5-(trifluoromethyl)pyrimidine to give 6-[5-(difluoromethoxy)pyrimidin-2-yl]-7-fluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.43 (s, 1H), 8.99 (s, 2H), 8.33 (d, J=7.2 Hz, 1H), 8.00 (d, J=11.3 Hz, 1H), 7.92 (s, 1H), 7.70-7.29 (m, 2H), 6.82 (d, J=7.4 Hz, 1H), 6.35 (dd, J=8.6, 3.9 Hz, 1H), 3.99 (t, J=6.3 Hz, 3H), 1.83-1.62 (m, 3H), 1.52 (q, J=5.2, 4.5 Hz, 1H), 1.17 (d, J=6.3 Hz, 3H). ES/MS m/z: 555.3 $[M+H]^+$.

Example 43: 6-[5-(difluoromethoxy)-2-pyridyl]-7-fluoro-2-[(4S)-4-[[6-oxo-5-(trifluoromethyl)-1H-pyridazin-4-yl]amino]pentyl]isoquinolin-1-one Example 43

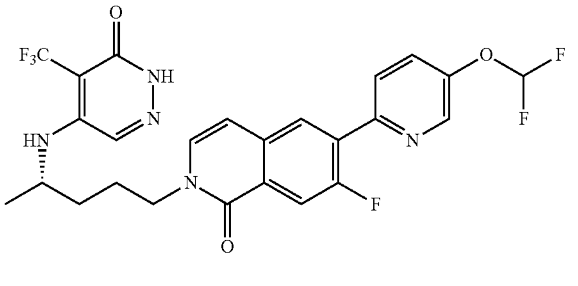

The title compound was synthesized as described in Example 8, using 2-bromo-5-(difluoromethoxy)pyridine in place of 2-iodo-5-(trifluoromethyl)pyrimidine to give 6-[5-(difluoromethoxy)-2-pyridyl]-7-fluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.43 (s, 1H), 8.69 (d, J=2.9 Hz, 1H), 8.23 (d, J=7.5 Hz, 1H), 8.03-7.95 (m, 2H), 7.91 (s, 1H), 7.85 (dd, J=8.7, 2.9 Hz, 1H), 7.63-7.23 (m, 2H), 6.79 (d, J=7.3 Hz, 1H), 6.35 (dd, J=8.9, 3.7 Hz, 1H), 3.99 (t, J=6.2 Hz, 3H), 1.85-1.58 (m, 3H), 1.56-1.38 (m, 1H), 1.17 (d, J=6.3 Hz, 3H). ES/MS m/z: 554.3 $[M+H]^+$.

Example 44: Preparation of 7-chloro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one Example 44

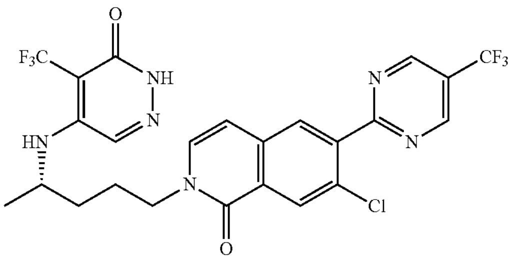

The title compound was synthesized as described in Example 5, using 6-bromo-7-chloroisoquinolin-1(2H)-one instead of 6-bromoisoquinolin-1(2H)-one to give 7-chloro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one. 1H NMR (400 MHz, DMSO-d6) δ 12.44 (s, 1H), 9.53-9.48 (m, 3H), 8.33 (s, 1H), 8.13 (s, 1H), 7.93 (s, 1H), 7.59 (d, J=7.4 Hz, 1H), 6.79 (d, J=7.2 Hz, 1H), 6.41-6.30 (m, 1H), 4.06-3.93 (m, 3H), 1.80-1.61 (m, 3H), 1.58-1.46 (m, 1H), 1.17 (d, J=6.3 Hz, 3H). ES/MS m/z: 573.3 $[M+H]^+$.

Example 45: Preparation of 3-methyl-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one Example 45

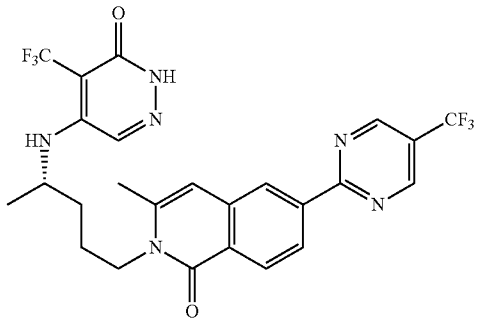

The title compound was synthesized as described in Example 5, using 6-bromo-3-methylisoquinolin-1(2H)-one instead of 6-bromoisoquinolin-1(2H)-one to give 3-methyl-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one. 1H NMR (400 MHz, DMSO-d6) δ 12.43 (s, 1H), 9.42 (d, J=1.0 Hz, 2H), 8.62 (d, J=1.6 Hz, 1H), 8.43 (dd, J=8.5, 1.7 Hz, 1H), 8.33 (d, J=8.5 Hz, 1H), 7.94 (s, 1H), 6.73 (s, 1H), 6.44-6.37 (m, 1H), 4.13-3.95 (m, 3H), 2.46 (s, 3H), 1.80-1.54 (m, 4H), 1.19 (d, J=6.3 Hz, 3H). ES/MS m/z: 553.3 $[M+H]^+$.

Example 46: Preparation of 4-methyl-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one

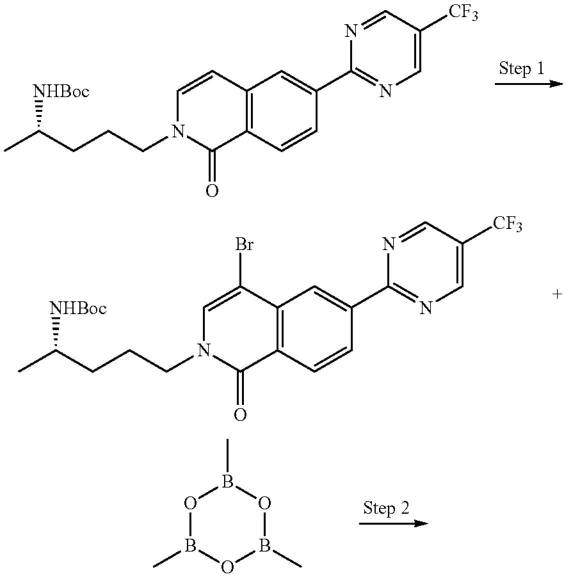

-continued

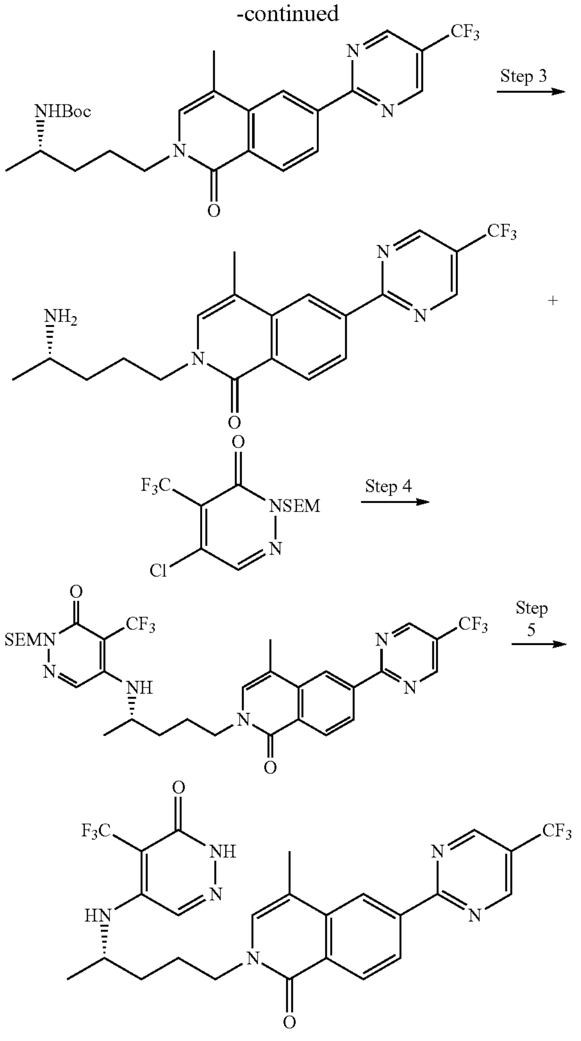

Example 46

Step 1. tert-butyl N-[(1S)-1-methyl-4-[1-oxo-6-[5-(trifluoromethyl)pyrimidin-2-yl]-2-isoquinolyl]butyl]carbamate (300 mg, 0.60 mmol) was dissolved in THF (3.0 mL) and the solution stirred at ambient temperature. N-bromosuccinimide (160 mg, 0.9 mmol) was added and the reaction stirred for 1 h. The solvent was removed in vacuo and the residue purified via column chromatography eluting with EtOAc in hexanes 0-70% to provide tert-butyl N-[(1S)-4-[4-bromo-1-oxo-6-[5-(trifluoromethyl)pyrimidin-2-yl]-2-isoquinolyl]-1-methyl-butyl]carbamate. ES/MS: m/z 555.13/557.08 $[M+H]^+$.

Step 2. To a vial was charged tert-butyl N-[(1S)-4-[4-bromo-1-oxo-6-[5-(trifluoromethyl)pyrimidin-2-yl]-2-isoquinolyl]-1-methyl-butyl]carbamate (102 mg, 0.17 mmol) and [1,1'-Bis(di-tert-butylphosphino)ferrocene]dichloropalladium(II) (6.0 mg, 0.009 mmol). The vial was purged with dry nitrogen and charged with dioxane (1.0 mL), 1.8 M aqueous potassium carbonate (0.19 mL, 0.35 mmol), and trimethylboroxine (0.05 mL, 0.35 mmol). The reaction was then stirred at 100° C. for 16 hours before being diluted with EtOAc and filtered through a plug of Celite. The filtrate was evaporated and purified twice using column chromatography eluting with EtOAc in hexanes 0-70% then MeCN in hexanes 0-35% to yield tert-butyl N-[(1S)-1-methyl-4-[4-methyl-1-oxo-6-[5-(trifluoromethyl)pyrimidin-2-yl]-2-isoquinolyl]butyl]carbamate. ES/MS: m/z 491.2 $[M+H]^+$.

Step 3. In a vial were placed tert-butyl N-[(1S)-1-methyl-4-[4-methyl-1-oxo-6-[5-(trifluoromethyl)pyrimidin-2-yl]-2-isoquinolyl]butyl]carbamate (61 mg, 0.12 mmol), and trifluoroacetic acid (0.09 mL, 1.2 mmol) in DCM (2.0 mL). After the mixture was allowed to stir for 1 h, it was concentrated under vacuum to give 2-[(4S)-4-aminopentyl]-4-methyl-6-[5-(trifluoromethyl)pyrimidin-2-yl]isoquinolin-1-one that was used directly in the next step.

Step 4. In a vial were placed 5-chloro-4-(trifluoromethyl)-2-(2-trimethylsilylethoxymethyl)pyridazin-3-one (46 mg, 0.14 mmol), 2-[(4S)-4-aminopentyl]-4-methyl-6-[5-(trifluoromethyl)pyrimidin-2-yl]isoquinolin-1-one (46 mg, 0.12 mmol), and N,N-Diisopropylethylamine (0.13 mL, 0.73 mmol) in ACN (0.50 mL). After the mixture was heated to 60° C. and allowed to stir for 18 h, it was quenched with 10% aqueous potassium hydrogensulfate and extracted with EtOAc. The combined organic layers were dried ($Na_2SO_4$), filtered, and the solvent removed in vacuo to give 4-methyl-2-[(4S)-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one that was used directly in the next step.

Step 5. In a vial were placed 4-methyl-2-[(4S)-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one (80 mg, 0.12 mmol) and trifluoroacetic acid (0.09 mL, 1.2 mmol) in DCM (2.0 mL). After the mixture was allowed to stir for 1 hr, it was concentrated under vacuum. The resulting oil was dissolved in methanol (1.0 mL) and ethylenediamine (0.08 mL, 1.2 mmol) was added. After the mixture was allowed to stir for 1 hr, it was concentrated under vacuum. The resulting crude product was purified by reverse phase prep-HPLC (5-100% MeCN in water, 0.1% TFA) to afford 4-methyl-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one. 1H NMR (400 MHz, DMSO-d6) δ 12.43 (s, 1H), 9.45 (d, J=0.9 Hz, 2H), 8.73 (d, J=1.6 Hz, 1H), 8.55 (dd, J=8.5, 1.6 Hz, 1H), 8.44 (d, J=8.4 Hz, 1H), 7.92 (s, 1H), 7.42 (d, J=1.3 Hz, 1H), 6.40-6.32 (m, 1H), 4.06-3.92 (m, 3H), 2.34 (s, 3H), 1.81-1.61 (m, 3H), 1.58-1.46 (m, 1H), 1.17 (d, J=6.3 Hz, 3H). ES/MS m/z: 553.3 $[M+H]^+$.

Intermediate 3: Preparation of tert-butyl (1R,2R,5S)-2-[3-(p-tolylsulfonyloxy)propyl]-3-azabicyclo[3.1.0]hexane-3-carboxylate

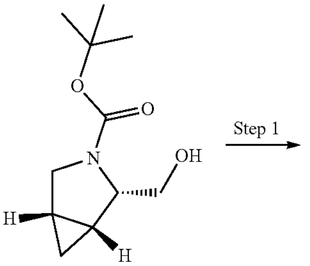

-continued

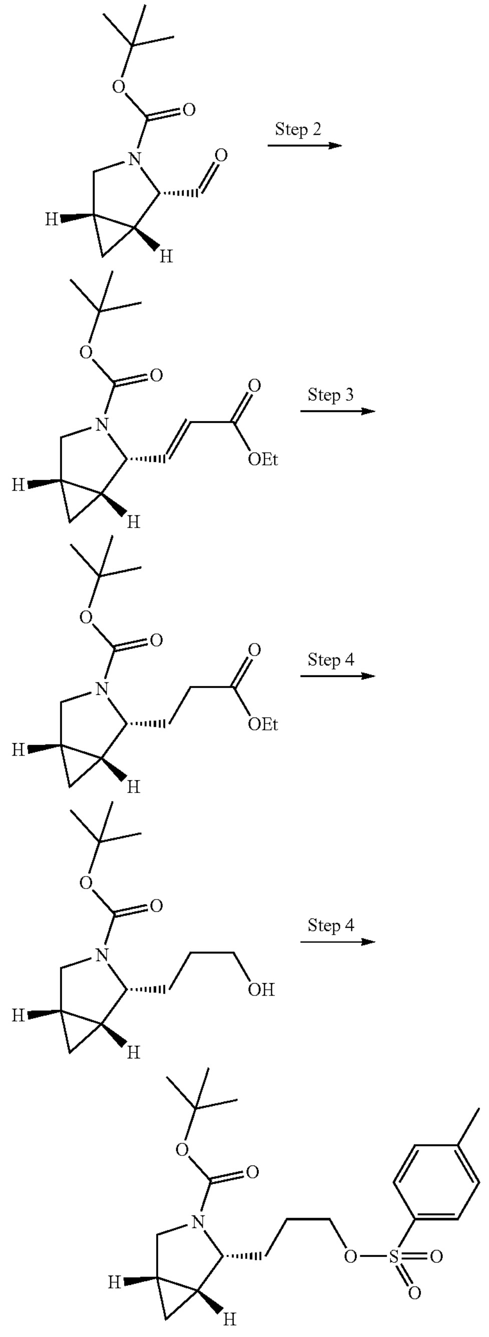

Intermediate 3

Step 1. tert-butyl (1R,2S,5S)-2-(hydroxymethyl)-3-azabicyclo[3.1.0]hexane-3-carboxylate (750 mg, 3.5 mmol) was dissolved in DCM (18.0 mL) and the solution was stirred at 0° C. DMP (2.99 g, 7.0 mmol) was added and the reaction was allowed to warm to ambient temperature and stir for 2.5 hr at which point saturated aqueous sodium bicarbonate was added. The mixture was stirred for 10 minutes and the solids were removed via filtration. The phases were then separated, and the aqueous layer extracted twice more with DCM. The combined organic layers were dried over $Na_2SO_4$, filtered, and evaporated to a white solid. The crude was purified by flash chromatography (100% hexanes to 100% EtOAc) to give tert-butyl (1R,2S,5S)-2-formyl-3-azabicyclo[3.1.0]hexane-3-carboxylate. ES/MS m/z: 156.28 $[M-tBu]^-$.

Step 2. tert-butyl (1R,2S,5S)-2-formyl-3-azabicyclo[3.1.0]hexane-3-carboxylate (580 mg, 2.6 mmol) was dissolved in DCM (15.0 mL) and the solution was stirred at ambient temperature. Ethyl (triphenylphosphoranylidene) acetate (1.37 g, 3.90 mmol) was added and the reaction was stirred for 24 h at which point saturated aqueous ammonium chloride was added and the mixture was extracted three times with DCM. The combined organic layers were dried over $MgSO_4$, filtered, and evaporated to a provide the crude product. The crude product was purified by flash chromatography (100% hexanes to 70% EtOAc) to give tert-butyl (1R,2R,5S)-2-[(E)-3-ethoxy-3-oxo-prop-1-enyl]-3-azabicyclo[3.1.0]hexane-3-carboxylate. ES/MS m/z: 282.12 $[M+H]^+$.

Step 3. tert-butyl (1R,2R,5S)-2-[(E)-3-ethoxy-3-oxo-prop-1-enyl]-3-azabicyclo[3.1.0]hexane-3-carboxylate (710 mg, 2.4 mmol) and 10% Pd/C (wet, 70 mg) were carefully flushed with nitrogen and then suspended in EtOH (10.0 mL). The reaction was purged with nitrogen and then stirred under a balloon of hydrogen at ambient temperature. After 1.5 h, the reaction was purged with nitrogen and filtered through a plug of Celite®. The filtrate was evaporated to yield a grey oil. The crude was purified by flash chromatography (100% hexanes to 30% EtOAc) to give tert-butyl (1R,2R,5S)-2-(3-ethoxy-3-oxo-propyl)-3-azabicyclo[3.1.0]hexane-3-carboxylate. ES/MS m/z: 306.20 $[M+H+Na]^+$.

Step 4. tert-butyl (1R,2R,5S)-2-(3-ethoxy-3-oxo-propyl)-3-azabicyclo[3.1.0]hexane-3-carboxylate (440 mg, 1.5 mmol) was dissolved in THF (8.0 mL) and MeOH (0.06 mL, 1.5 mmol) was added. The solution was then cooled to 0° C. and a suspension of lithium borohydride (94.0 mg, 4.5 mmol) in THF (8.0 mL) was added slowly. The reaction was stirred at ambient temperature for 4 h at which point an additional portion of solid lithium borohydride (160 mg, 7.4 mmol) was added. The reaction was stirred for an additional 16 h and was then quenched by the careful addition of 10% aqueous potassium hydrogen sulfate. The mixture was extracted three times with EtOAc, and the combined organic layers were dried over $MgSO_4$. The organic layers were filtered and evaporated and the crude product was purified by flash chromatography (100% hexanes to 60% EtOAc) to give tert-butyl (1R,2R,5S)-2-(3-hydroxypropyl)-3-azabicyclo[3.1.0]hexane-3-carboxylate. ES/MS m/z: 242.10 $[M+H]^+$.

Step 5. tert-butyl (1R,2R,5S)-2-(3-hydroxypropyl)-3-azabicyclo[3.1.0]hexane-3-carboxylate (170 mg, 0.70 mmol) was dissolved in DCM (5.0 mL) and treated with TEA (0.22 mL, 1.6 mmol). The solution was cooled to 0° C. and then p-toluenesulfonyl chloride (160 mg, 0.84 mmol) was added. The reaction was left to stir at ambient temperature for 20 h at which point 10% aqueous potassium hydrogen sulfate was added and the mixture extracted three times with DCM. The combined organics were washed with brine, dried over $MgSO_4$, filtered, and evaporated to yield an amber oil. The crude product was purified by flash chromatography (100% hexanes to 60% EtOAc) to give tert-butyl (1R,2R,5S)-2-[3-(p-tolylsulfonyloxy)propyl]-3-azabicyclo[3.1.0]hexane-3-carboxylate. ES/MS m/z: 396.15 $[M+H]^+$.

Example 47: Preparation of 6-[3-[(1R,2R,5S)-3-[6-oxo-5-(trifluoromethyl)-1H-pyridazin-4-yl]-3-azabicyclo[3.1.0]hexan-2-yl]propyl]-2-[5-(trifluoromethyl)-2-pyridyl]-1,6-naphthyridin-5-one Example 47

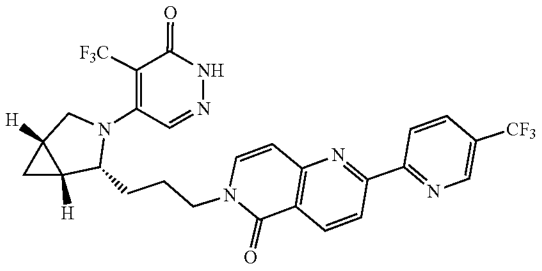

The title compound was synthesized as described in Example 1 using 2-bromo-6H-1,6-naphthyridin-5-one instead of 6-bromo-2H-isoquinolin-1-one and tert-butyl (1R,2R,5S)-2-[3-(p-tolylsulfonyloxy)propyl]-3-azabicyclo[3.1.0]hexane-3-carboxylate instead of 4-(tert-butoxycarbonylamino)pentyl 4-methylbenzenesulfonate (Intermediate 3) to give 6-[3-[(1R,2R,5S)-3-[6-oxo-5-(trifluoromethyl)-1H-pyridazin-4-yl]-3-azabicyclo[3.1.0]hexan-2-yl]propyl]-2-[5-(trifluoromethyl)-2-pyridyl]-1,6-naphthyridin-5-one. 1H NMR (400 MHz, DMSO-d6) δ 12.70 (s, 1H), 9.19-9.13 (m, 1H), 8.74 (d, J=8.4 Hz, 1H), 8.71 (d, J=8.3 Hz, 1H), 8.54 (d, J=8.4 Hz, 1H), 8.45 (dd, J=8.6, 2.4 Hz, 1H), 7.93 (s, 1H), 7.86 (d, J=7.6 Hz, 1H), 6.84 (d, J=7.5 Hz, 1H), 4.37-4.26 (m, 1H), 4.18-4.06 (m, 1H), 4.06-3.95 (m, 1H), 3.68 (d, J=10.2 Hz, 1H), 3.37 (dd, J=10.4, 4.6 Hz, 1H), 2.01-1.79 (m, 3H), 1.79-1.64 (m, 2H), 1.30-1.16 (m, 1H), 0.68-0.58 (m, 1H), 0.40-0.30 (m, 1H). ES/MS m/z: 577.3 $[M+H]^+$.

Example 48: 8-fluoro-2-[3-[(1R,2R,5S)-3-[6-oxo-5-(trifluoromethyl)-1H-pyridazin-4-yl]-3-azabicyclo[3.1.0]hexan-2-yl]propyl]-6-[5-(trifluoromethyl)-2-pyridyl]isoquinolin-1-one Example 48

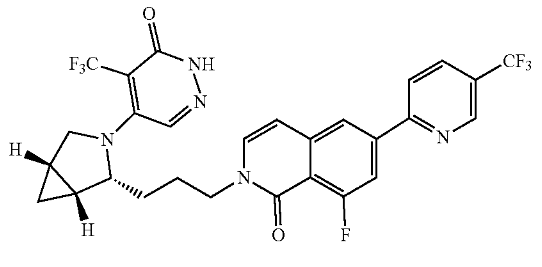

The title compound was synthesized as described in Example 8, using 2-bromo-5-(trifluoromethyl)pyridine in place of 1-(6-bromo-3-pyridyl)cyclopropanecarbonitrile and tert-butyl (1R,2R,5S)-2-[3-(p-tolylsulfonyloxy)propyl]-3-azabicyclo[3.1.0]hexane-3-carboxylate (Intermediate 3) in place of [(4S)-4-(tert-butoxycarbonylamino)pentyl]4-methylbenzenesulfonate to give 8-fluoro-2-[3-[(1R,2R,5S)-3-[6-oxo-5-(trifluoromethyl)-1H-pyridazin-4-yl]-3-azabicyclo[3.1.0]hexan-2-yl]propyl]-6-[5-(trifluoromethyl)-2-pyridyl]isoquinolin-1-one. 1H NMR (400 MHz, DMSO-d6) δ 12.70 (s, 1H), 9.12 (dt, J=2.1, 1.1 Hz, 1H), 8.45-8.36 (m, 2H), 8.32 (d, J=1.6 Hz, 1H), 8.01-7.89 (m, 2H), 7.61 (d, J=7.4 Hz, 1H), 6.77 (dd, J=7.4, 2.0 Hz, 1H), 4.31 (dt, J=8.9, 3.9 Hz, 1H), 4.09-3.87 (m, 3H), 3.68 (d, J=10.2 Hz, 1H), 3.37 (dd, J=10.3, 4.5 Hz, 1H), 1.86 (tt, J=8.0, 4.4 Hz, 2H), 1.70 (td, J=9.0, 8.6, 4.6 Hz, 2H), 1.22 (qd, J=10.5, 4.8 Hz, 1H), 0.63 (td, J=7.8, 4.8 Hz, 1H), 0.35 (q, J=4.3 Hz, 1H). ES/MS m/z: 594.3 $[M+H]^+$.

Example 49: 6-[4-amino-5-(trifluoromethyl)-2-pyridyl]-7-fluoro-2-[(4S)-4-[[6-oxo-5(trifluoromethyl)-1H-pyridazin-4-yl]amino]pentyl]isoquinolin-1-one Example 49

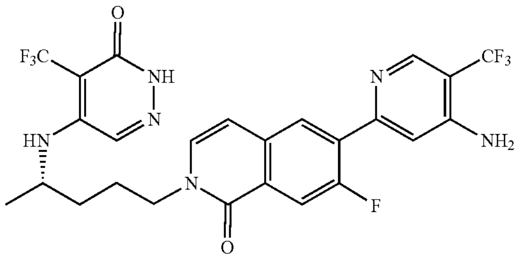

The title compound was synthesized as described in Example 5, using 6-bromo-7-fluoroisoquinolin-1(2H)-one instead of 6-bromoisoquinolin-1(2H)-one and 2-chloro-5-(trifluoromethyl)pyridin-4-amine instead of 2-iodo-5-(trifluoromethyl)pyrimidine to give 6-[4-amino-5-(trifluoromethyl)-2-pyridyl]-7-fluoro-2-[(4S)-4-[[6-oxo-5-(trifluoromethyl)-1H-pyridazin-4-yl]amino]pentyl] isoquinolin-1-one. 1H NMR (400 MHz, DMSO-d6) δ 12.43 (s, 1H), 8.60 (s, 1H), 8.21-8.11 (m, 1H), 8.02 (d, J=11.5 Hz, 1H), 7.93 (d, J=12.4 Hz, 1H), 7.52 (d, J=7.4 Hz, 1H), 7.28 (s, 1H), 6.77 (d, J=7.4 Hz, 1H), 6.35 (dd, J=9.2, 3.9 Hz, 1H), 4.00 (t, J=6.7 Hz, 4H), 1.84-1.41 (m, 5H), 1.18 (t, J=6.4 Hz, 4H). ES/MS: m/z 571.3 $[M+H]^+$.

Example 50: 6-[5-(1-amino-2,2,2-trifluoro-ethyl)-2-pyridyl]-7-fluoro-2-[(4S)-4-[[6-oxo-5-(trifluoromethyl)-1H-pyridazin-4-yl]amino]pentyl]isoquinolin-1-one Example 50

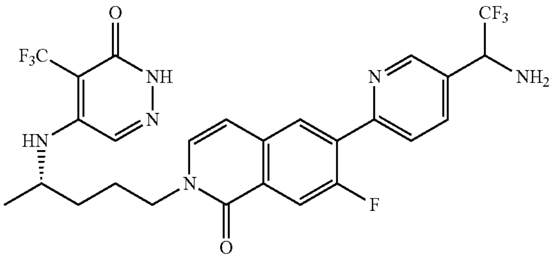

The title compound was synthesized as described in Example 5, using 6-bromo-7-fluoroisoquinolin-1(2H)-one instead of 6-bromoisoquinolin-1(2H)-one and 1-(6-chloro-3-pyridyl)-2,2,2-trifluoro-ethanamine instead of 2-iodo-5-(trifluoromethyl)pyrimidine to give 6-[5-(1-amino-2,2,2-tri-fluoro-ethyl)-2-pyridyl]-7-fluoro-2-[(4S)-4-[[6-oxo-5-(trifluoromethyl)-1H-pyridazin-4-yl]amino]pentyl] isoquinolin-1-one. 1H NMR (400 MHz, DMSO-d6) δ 12.43 (s, 1H), 8.93 (d, J=2.3 Hz, 1H), 8.26 (d, J=7.4 Hz, 1H), 8.20-8.10 (m, 1H), 8.02 (dd, J=10.2, 7.0 Hz, 2H), 7.91 (s, 1H), 7.51 (d, J=7.4 Hz, 1H), 6.79 (d, J=7.3 Hz, 1H), 6.35 (dd, J=8.6, 3.8 Hz, 1H), 4.00 (t, J=6.7 Hz, 4H), 1.83-1.41 (m, 5H), 1.17 (d, J=6.3 Hz, 3H). ES/MS: m/z 585.3 $[M+H]^+$.

Example 51 (S)-6-(5-(difluoromethyl)pyridin-2-yl)-7,8-difluoro-2-(4-((6-oxo-5-(trifluoromethyl)-1,6-dihydropyridazin-4-yl)amino)pentyl)isoquinolin-1(2H)-one Example 51

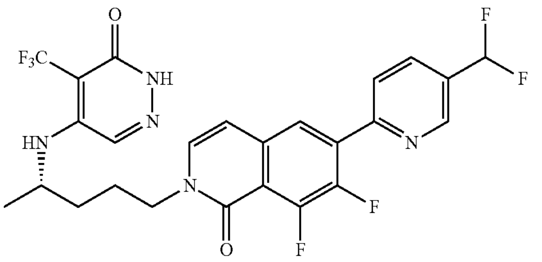

The title compound was synthesized as described in Example 17, 2-iodo-5-(trifluoromethyl)pyrimidine instead of 2-bromo-5-(difluoromethyl)pyridine and 2-bromo-7,8-difluoroisoquinolin-1(2H)-one instead of 6-Bromo-8-fluoro-1,2-dihydroisoquinolin-1-one to give (S)-6-(5-(difluoromethyl)pyridin-2-yl)-7,8-difluoro-2-(4-((6-oxo-5-(trifluoromethyl)-1,6-dihydropyridazin-4-yl)amino)pentyl) isoquinolin-1(2H)-one. 1H NMR (400 MHz, DMSO-d6) δ 12.43 (s, 1H), 9.02-8.96 (m, 1H), 8.26-8.17 (m, 1H), 8.10-8.01 (m, 2H), 7.91 (s, 1H), 7.56-7.50 (m, 1H), 7.26 (t, J=55.2 Hz, 1H), 6.81-6.74 (m, 1H), 6.44-6.26 (m, 1H), 2.48-2.51 (m, 3H), 1.82-1.60 (m, 2H), 1.60-1.42 (m, 1H), 1.17 (d, J=6.3 Hz, 3H). ES/MS: m/z 556.1 $[M+H]^+$.

Example 52 (S)-7,8-difluoro-6-(5-fluoropyridin-2-yl)-2-(4-((6-oxo-5-(trifluoromethyl)-1,6-dihydropyridazin-4-yl)amino)pentyl)isoquinolin-1(2H)-one Example 52

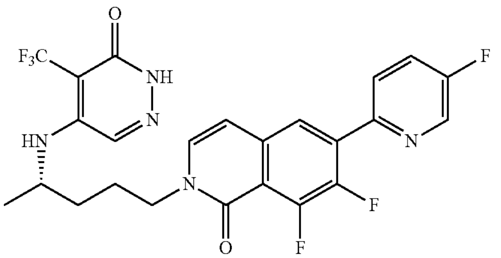

The title compound was synthesized as described in Example 17, using 2-iodo-5-(trifluoromethyl)pyrimidine instead of 2-bromo-5-fluoropyridine and 2-bromo-7,8-difluoroisoquinolin-1(2H)-one instead of 6-Bromo-8-fluoro-1,2-dihydroisoquinolin-1-one to give (S)-7,8-difluoro-6-(5-fluoropyridin-2-yl)-2-(4-((6-oxo-5-(trifluoromethyl)-1,6-dihydropyridazin-4-yl)amino)pentyl)isoquinolin-1(2H)-one. 1H NMR (400 MHz, DMSO-d6) δ12.43 (s, 1H), 8.89-8.71 (m, 1H), 8.08-7.78 (m, 5H), 7.51 (d, J=7.4 Hz, 1H), 6.85-6.67 (m, 1H), 6.43-6.25 (m, 1H), 4.04-3.91 (m, 2H), 3.13-2.98 (m, 1H), 1.79-1.60 (m, 3H), 1.59-1.44 (m, 1H), 1.17 (d, J=6.3 Hz, 3H). ES/MS: m/z 524.2 $[M+H]^+$.

Example 53 (S)-6-(5-(difluoromethyl)pyrimidin-2-yl)-7,8-difluoro-2-(4-((6-oxo-5-(trifluoromethyl)-1,6-dihydropyridazin-4-yl)amino)pentyl)isoquinolin-1(2H)-one Example 53

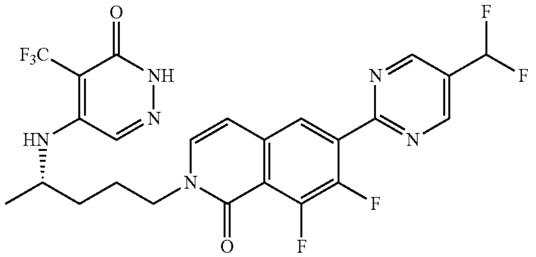

The title compound was synthesized as described in Example 17 using 2-iodo-5-(trifluoromethyl)pyrimidine instead of 2-chloro-5-(difluoromethyl)pyrimidine and 2-bromo-7,8-difluoroisoquinolin-1(2H)-one instead of 6-Bromo-8-fluoro-1,2-dihydroisoquinolin-1-one to give (S)-6-(5-(difluoromethyl)pyrimidin-2-yl)-7,8-difluoro-2-(4-((6-oxo-5-(trifluoromethyl)-1,6-dihydropyridazin-4-yl)amino) pentyl)isoquinolin-1(2H)-one. 1H NMR (400 MHz, DMSO-d6) δ 12.43 (s, 1H), 9.35-9.20 (m, 2H), 8.25-8.17 (m, 1H), 7.92 (s, 1H), 7.84 (s, 1H), 7.58-7.51 (m, 1H), 7.31 (t, J=54.7 Hz, 1H), 6.86-6.77 (m, 1H), 6.47-6.27 (m, 1H), 3.96 (t, J=6.4 Hz, 2H), 3.08-2.96 (m, 1H), 1.79-1.61 (m, 3H), 1.57-1.46 (m, 1H), 1.18 (d, J=6.3 Hz, 3H). ES/MS: m/z 557.1 $[M+H]^+$.

Example 54 (S)-7,8-difluoro-6-(5-fluoropyrimidin-2-yl)-2-(4-((6-oxo-5-(trifluoromethyl)-1,6-dihydropyridazin-4-yl)amino)pentyl)isoquinolin-1(2H)-one Example 54

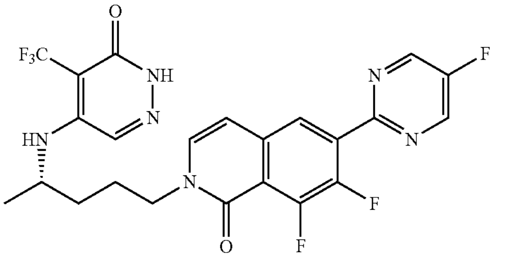

The title compound was synthesized as described in Example 17, using 2-iodo-5-(trifluoromethyl)pyrimidine instead of 2-bromo-5-fluoropyrimidine and 2-bromo-7,8-difluoroisoquinolin-1(2H)-one instead of 6-Bromo-8-fluoro-1,2-dihydroisoquinolin-1-one to give (S)-7,8-difluoro-6-(5-fluoropyrimidin-2-yl)-2-(4-((6-oxo-5-(trifluoromethyl)-1,6-dihydropyridazin-4-yl)amino)pentyl)isoquinolin-1(2H)- one. 1H NMR (400 MHz, DMSO-d6) δ 12.43 (s, 1H), 9.13 (s, 1H), 8.15-8.10 (m, 1H), 7.92 (s, 1H), 7.83 (s, 1H), 7.53 (d, J=7.4 Hz, 1H), 6.84-6.74 (m, 1H), 6.40-6.27 (m, 1H), 4.04-3.90 (m, 2H), 3.06-2.97 (m, 1H), 1.79-1.60 (m, 3H), 1.51 (dt, J=11.1, 6.3 Hz, 1H), 1.17 (d, J=6.3 Hz, 3H). ES/MS: m/z 523.5 [M+H]$^+$.

Example 55 (S)-7,8-difluoro-2-(4-((6-oxo-5-(trifluoromethyl)-1,6-dihydropyridazin-4-yl)amino)pentyl)-6-(5-(trifluoromethyl)pyridin-2-yl)isoquinolin-1(2H)-one Example 55

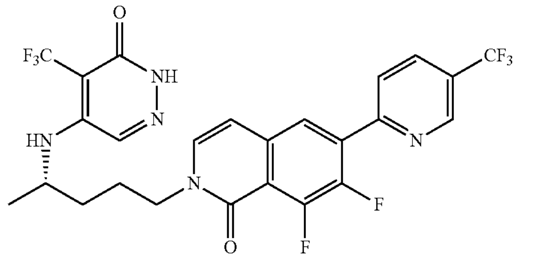

The title compound was synthesized as described in Example 17 using 2-iodo-5-(trifluoromethyl)pyrimidine instead of 2-bromo-5-(trifluoromethyl)pyridine and 2-bromo-7,8-difluoroisoquinolin-1(2H)-one instead of 6-Bromo-8-fluoro-1,2-dihydroisoquinolin-1-one to give 56 (S)-7,8-difluoro-2-(4-((6-oxo-5-(trifluoromethyl)-1,6-dihydropyridazin-4-yl)amino)pentyl)-6-(5-(trifluoromethyl)pyridin-2-yl)isoquinolin-1(2H)-one. 1H NMR (400 MHz, DMSO-d6) δ 12.43 (s, 1H), 9.24-9.09 (m, 1H), 8.49-8.38 (m, 1H), 8.18-8.11 (m, 1H), 8.09-8.02 (m, 1H), 7.91 (s, 1H), 7.56-7.51 (m, 1H), 6.82-6.71 (m, 1H), 6.41-6.26 (m, 1H), 4.02-3.91 (m, 2H), 3.08-2.99 (m, 1H), 1.80-1.60 (m, 3H), 1.58-1.45 (m, 1H), 1.18 (d, J=6.3 Hz, 3H). ES/MS: m/z 574.2 [M+H]$^+$.

Example 56 (S)-6-(5-(difluoromethoxy)pyrimidin-2-yl)-7,8-difluoro-2-(4-((6-oxo-5-(trifluoromethyl)-1,6-dihydropyridazin-4-yl)amino)pentyl)isoquinolin-1(2H)-one Example 56

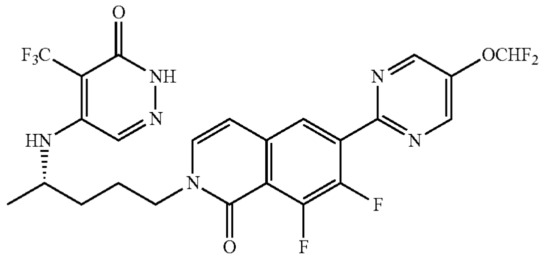

The title compound was synthesized as described in Example 17, 2-chloro-5-(difluoromethoxy)pyrimidine instead of 2-iodo-5-(trifluoromethyl)pyrimidine and 2-bromo-7,8-difluoroisoquinolin-1(2H)-one instead of 6-Bromo-8-fluoro-1,2-dihydroisoquinolin-1-one to give (S)-6-(5-(difluoromethoxy)pyrimidin-2-yl)-7,8-difluoro-2-(4-((6-oxo-5-(trifluoromethyl)-1,6-dihydropyridazin-4-yl)amino)pentyl)isoquinolin-1(2H)-one. 1H NMR (400 MHz, DMSO-d6) δ 12.43 (s, 1H), 9.01 (s, 2H), 8.20-8.08 (m, 1H), 7.92 (s, 1H), 7.56-7.51 (m, 1H), 7.50 (t, J=72.6 Hz, 1H), 6.83-6.73 (m, 1H), 6.40-6.29 (m, 1H), 4.04-3.90 (m, 3H), 1.78-1.59 (m, 3H), 1.58-1.45 (m, 1H), 1.17 (d, J=6.3 Hz, 3H). ES/MS: m/z 573.3 [M+H]$^+$.

Example 57: (S)-6-(5-(difluoromethoxy)pyridin-2-yl)-7,8-difluoro-2-(4-((6-oxo-5-(trifluoromethyl)-1,6-dihydropyridazin-4-yl)amino)pentyl)isoquinolin-1(2H)-one Example 57

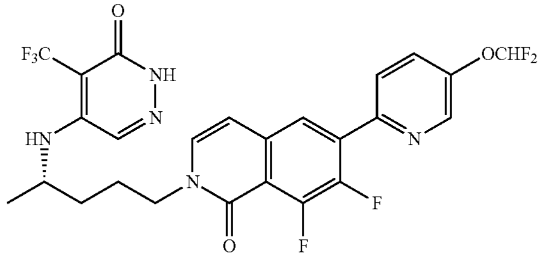

The title compound was synthesized as described in Example 17, using 2-bromo-5-(difluoromethoxy)pyridine instead of 2-bromo-5-(trifluoromethyl)pyridine and 2-bromo-7,8-difluoroisoquinolin-1(2H)-one instead of 6-Bromo-8-fluoro-1,2-dihydroisoquinolin-1-one to give (S)-6-(5-(difluoromethoxy)pyridin-2-yl)-7,8-difluoro-2-(4-((6-oxo-5-(trifluoromethyl)-1,6-dihydropyridazin-4-yl)amino)pentyl)isoquinolin-1(2H)-one. 1H NMR (400 MHz, DMSO-d6) δ 12.43 (s, 1H), 8.70 (d, J=2.9 Hz, 1H), 8.04-7.96 (m, 2H), 7.95-7.82 (m, 2H), 7.55-7.48 (m, 1H), 7.44 (t, J=73.1 Hz, 1H), 6.81-6.65 (m, 1H), 6.48-6.22 (m, 1H), 4.10-3.80 (m, 3H), 1.79-1.59 (m, 3H), 1.57-1.44 (m, 1H), 1.17 (d, J=6.3 Hz, 3H). ES/MS: m/z 572.3 [M+H]$^+$.

Example 58: (S)-6-fluoro-3-(4-((6-oxo-5-(trifluoromethyl)-1,6-dihydropyridazin-4-yl)amino)pentyl)-7-(5-(trifluoromethyl)pyridin-2-yl)quinazolin-4(3H)-one Example 58

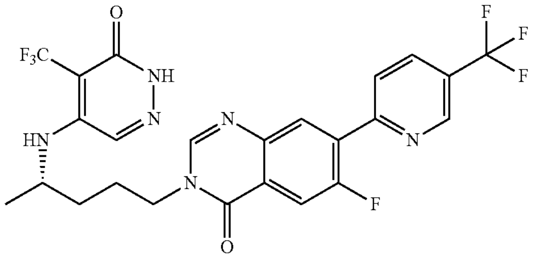

The title compound was synthesized as described in Example 17, using 2-bromo-5-(trifluoromethyl)pyridine instead of 2-bromo-5-(difluoromethoxy)pyridine and 7-bromo-6-fluoro-1H-quinazolin-4-one instead of 6-Bromo-8-fluoro-1,2-dihydroisoquinolin-1-one to give (S)-6-fluoro-3-(4-((6-oxo-5-(trifluoromethyl)-1,6-dihydropyridazin-4-yl)amino)pentyl)-7-(5-(trifluoromethyl)pyridin-2-yl)quinazolin-4(3H)-one. 1H NMR (400 MHz, DMSO-d6) δ 12.44 (s, 1H), 9.19 (dd, J=2.4, 1.2 Hz, 1H), 8.45 (s, 1H), 8.42 (dd, J=8.5, 2.4 Hz, 1H), 8.24 (d, J=6.9 Hz, 1H), 8.14 (d, J=8.1 Hz, 1H), 8.00 (d, J=10.8 Hz, 1H), 7.92 (s, 1H), 6.43-6.24 (m, 1H), 4.04-3.99 (m, 3H), 1.83-1.61 (m, 3H), 1.59-1.46 (m, 1H), 1.17 (d, J=6.3 Hz, 3H). ES/MS m/z: 557.30 $[M+H]^+$.

Example 59: (S)-6-fluoro-7-(5-fluoropyridin-2-yl)-3-(4-((6-oxo-5-(trifluoromethyl)-1,6-dihydropyridazin-4-yl)amino)pentyl)quinazolin-4(3H)-one Example 59

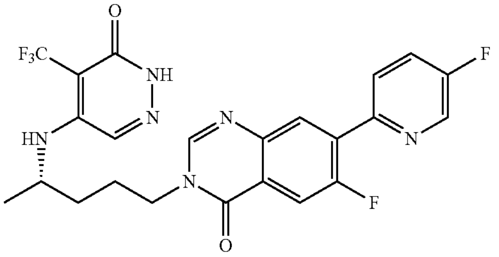

The title compound was synthesized as described in Example 17, using 2-bromo-5-fluoro-pyridine instead of 2-bromo-5-(difluoromethoxy)pyridine and 7-bromo-6-fluoro-1H-quinazolin-4-one instead of 6-Bromo-8-fluoro-1,2-dihydroisoquinolin-1-one to give (S)-6-fluoro-7-(5-fluoropyridin-2-yl)-3-(4-((6-oxo-5-(trifluoromethyl)-1,6-dihydropyridazin-4-yl)amino)pentyl)quinazolin-4(3H)-one. 1H NMR (400 MHz, DMSO-d6) δ 12.44 (s, 1H), 8.80 (d, J=2.9 Hz, 1H), 8.43 (s, 1H), 8.15 (d, J=7.0 Hz, 1H), 8.00 (ddd, J=8.9, 4.6, 1.8 Hz, 1H), 7.98-7.89 (m, 3H), 6.40-6.28 (m, 1H), 4.05-3.94 (m, 3H), 1.80-1.62 (m, 3H), 1.59-1.45 (m, 1H), 1.17 (d, J=6.3 Hz, 3H). ES/MS m/z: 507.30 $[M+H]^+$.

Example 60: 6-fluoro-7-(5-fluoropyrimidin-2-yl)-3-[(4S)-4-[[6-oxo-5-(trifluoromethyl)-1H-pyridazin-4-yl]amino]pentyl]quinazolin-4-one Example 60

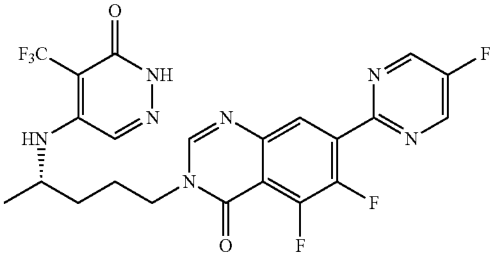

The title compound was synthesized as described in Example 17, using 2-bromo-5-fluoro-pyrimidine instead of 2-bromo-5-(difluoromethoxy)pyridine and 7-bromo-6-fluoro-1H-quinazolin-4-one instead of 6-Bromo-8-fluoro-1,2-dihydroisoquinolin-1-one to give 6-fluoro-7-(5-fluoropyrimidin-2-yl)-3-[(4S)-4-[[6-oxo-5-(trifluoromethyl)-1H-pyridazin-4-yl]amino]pentyl]quinazolin-4-one. 1H NMR (400 MHz, DMSO-d6) δ 12.44 (s, 1H), 9.12 (d, J=0.7 Hz, 2H), 8.44 (s, 1H), 8.24 (d, J=6.8 Hz, 1H), 7.97 (d, J=10.6 Hz, 1H), 7.92 (s, 1H), 6.40-6.28 (m, 1H), 4.05-3.93 (m, 3H), 1.84-1.62 (m, 3H), 1.59-1.46 (m, 1H), 1.17 (d, J=6.3 Hz, 3H). ES/MS m/z: 508.20 $[M+H]^+$.

Intermediate 4: Preparation of tert-butyl (1-(3-(7-fluoro-1-oxo-6-(4,4,5,5-tetramethyl-1,3,2-dioxaborolan-2-yl)isoquinolin-2(1H)-yl)propyl)cyclopropyl) carbamate Intermediate 4

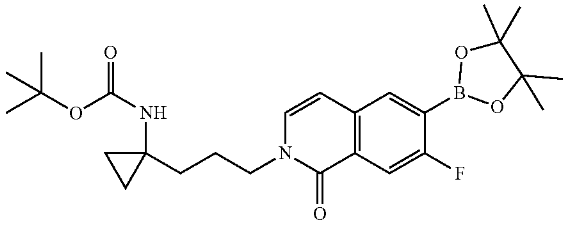

The title compound was synthesized as described in Example 5, using tert-butyl (1-(3-hydroxypropyl)cyclopropyl)carbamate and 6-bromo-7-fluoroisoquinolin-1(2H)-one instead of tert-butyl N-[(1S)-4-hydroxy-1-methyl-butyl]carbamate in step 2 and 6-bromoisoquinolin-1(2H)-one in step 3, respectively, to give tert-butyl (1-(3-(7-fluoro-1-oxo-6-(4,4,5,5-tetramethyl-1,3,2-dioxaborolan-2-yl)isoquinolin-2(1H)-yl)propyl)cyclopropyl)carbamate. ES/MS: m/z 487.2 $[M+H]^+$.

Intermediate 5: Preparation of tert-butyl (1-(3-(7-fluoro-1-oxo-6-(5-(trifluoromethyl)pyrimidin-2-yl)isoquinolin-2(1H)-yl)propyl)cyclopropyl)carbamate Intermediate 5

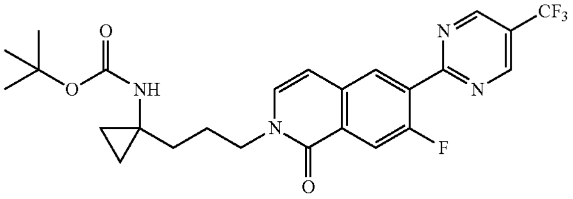

In a vial were placed tert-butyl (1-(3-(7-fluoro-1-oxo-6-(4,4,5,5-tetramethyl-1,3,2-dioxaborolan-2-yl)isoquinolin-2(1H)-yl)propyl)cyclopropyl)carbamate (66 mg, 0.14 mmol), 2-chloro-5-(trifluoromethyl)pyrimidine (37 mg, 0.20 mmol), and $Pd(PPh_3)_4$(16 mg, 0.014 mmol) in dioxane (1.0 mL) and $Na_2CO_3$ aq. (2M, 0.3 mL). The mixture was sonicated for 20 seconds, purged with $N_2$ for 20 seconds, and stirred at 110° C. for 16 h. Upon completion, the mixture was cooled to room temperature and concentrated in vacuo. The crude product was purified using silica flash chromatography (100% hexanes to 10% EtOAc) to give tert-butyl (1-(3-(7-fluoro-1-oxo-6-(5-(trifluoromethyl)pyrimidin-2-yl)isoquinolin-2(1H)-yl)propyl)cyclopropyl)carbamate (45 mg, 66%). ES/MS: m/z 507.2 $[M+H]^+$.

Example 61: 7-fluoro-2-(3-(1-((6-oxo-5-(trifluoromethyl)-1,6-dihydropyridazin-4-yl)amino)cyclopropyl)propyl)-6-(5-(trifluoromethyl)pyrimidin-2-yl) isoquinolin-1(2H)-one Example 61

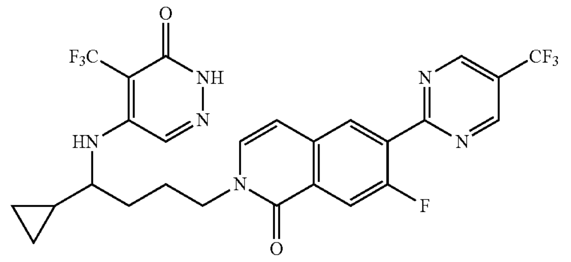

The title compound was synthesized as described in Example 5, using tert-butyl (1-(3-(7-fluoro-1-oxo-6-(5-(trifluoromethyl)pyrimidin-2-yl)isoquinolin-2(1H)-yl)propyl) cyclopropyl)carbamate instead of tert-butyl N-[(1S)-1-methyl-4-[1-oxo-6-[5-(trifluoromethyl)pyrimidin-2-yl]-2-isoquinolyl]butyl]carbamate to give 7-fluoro-2-(3-(1-((6-oxo-5-(trifluoromethyl)-1,6-dihydropyridazin-4-yl)amino) cyclopropyl)propyl)-6-(5-(trifluoromethyl)pyrimidin-2-yl) isoquinolin-1(2H)-one. 1H NMR (400 MHz, DMSO-d6) δ 12.54 (s, 1H), 9.48 (s, 2H), 8.43 (d, J=7.2 Hz, 1H), 8.24-7.92 (m, 2H), 7.54 (d, J=7.4 Hz, 1H), 7.34 (m, 1H), 6.84 (d, J=7.4 Hz, 1H), 3.99 (t, J=7.1 Hz, 2H), 1.92-1.33 (m, 4H), 0.85 (m, 4H). ES/MS: m/z 569.1 $[M+H]^+$.

Example 62: 6-fluoro-3-[(4S)-4-[[6-oxo-5-(trifluoromethyl)-1H-pyridazin-4-yl]amino]pentyl]-7-(7H-pyrrolo[2,3-d]pyrimidin-2-yl)quinazolin-4-one Example 62

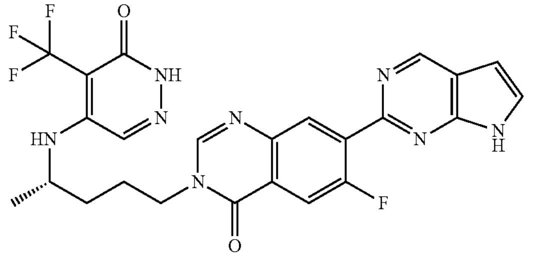

The title compound was synthesized as described in Example 17 with the following changes:

Step 1. 6-Bromo-7-fluoro-2H-isoquinolin-1-one was used instead of 6-bromo-2H-isoquinolin-1-one.

Step 3. 2-Chloro-7H-pyrrolo[2,3-d]pyrimidine is used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 1H NMR (400 MHz, DMSO-d6) δ 12.55-12.27 (m, 2H), 9.22 (s, 1H), 8.43 (s, 1H), 8.32 (d, J=6.9 Hz, 1H), 7.99-7.87 (m, 2H), 7.77-7.69 (m, 1H), 6.77-6.64 (m, 1H), 6.40-6.31 (m, 1H), 4.07-3.92 (m, 3H), 1.85-1.62 (m, 3H), 1.60-1.43 (m, 1H), 1.17 (d, J=6.3 Hz, 3H). ES/MS m/z: 529.2 $[M+H]^+$.

Example 63: 6-fluoro-7-(5-methyl-7H-pyrrolo[2,3-d]pyrimidin-2-yl)-3-[(4S)-4-[[6-oxo-5-(trifluoromethyl)-1H-pyridazin-4-yl]amino]pentyl]quinazolin-4-one Example 63

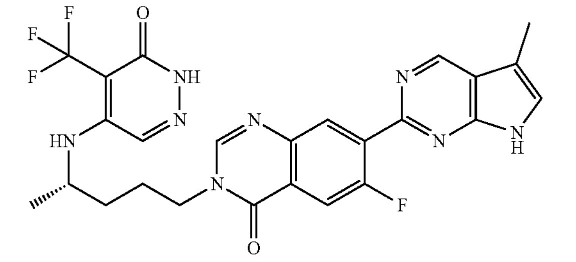

The title compound was synthesized as described in Example 17 with the following changes:

Step 1. 6-Bromo-7-fluoro-2H-isoquinolin-1-one was used instead of 6-bromo-2H-isoquinolin-1-one.

Step 3. 2-chloro-5-methyl-7H-pyrrolo[2,3-d]pyrimidine is used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 1H NMR (400 MHz, DMSO-d6) δ 1H NMR (400 MHz, DMSO-d6) δ 12.44 (s, 1H), 12.15 (s, 1H), 9.20 (s, 1H), 8.43 (s, 1H), 8.30 (d, J=6.8 Hz, 1H), 8.07-7.81 (m, 2H), 7.55-7.40 (m, 1H), 6.40-6.31 (m, 1H), 4.06-3.95 (m, 3H), 2.37 (s, 3H), 1.82-1.61 (m, 3H), 1.59-1.47 (m, 1H), 1.18 (d, J=6.3 Hz, 3H). ES/MS m/z: 543.2 $[M+H]^+$.

Example 64: 6-fluoro-7-(5-fluoro-7H-pyrrolo[2,3-d] pyrimidin-2-yl)-3-[(4S)-4-[[6-oxo-5-(trifluoromethyl)-1H-pyridazin-4-yl]amino]pentyl]quinazolin-4-one Example 64

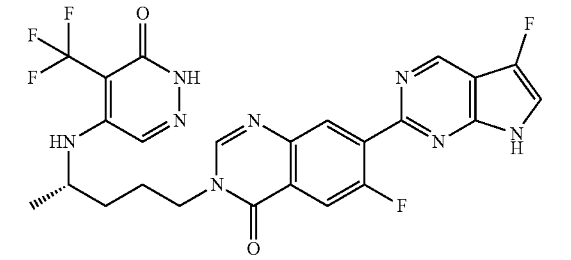

The title compound was synthesized as described in Example 17 with the following changes:

Step 1. 6-Bromo-7-fluoro-2H-isoquinolin-1-one was used instead of 6-bromo-2H-isoquinolin-1-one.

Step 3. -chloro-5-fluoro-7H-pyrrolo[2,3-d]pyrimidine is used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 1H NMR (400 MHz, DMSO-d6) δ 12.44 (s, 1H), 12.32 (s, 1H), 9.30 (s, 1H), 8.43 (s, 1H), 8.32 (d, J=6.9 Hz, 1H), 7.98-7.90

(m, 2H), 7.72 (t, J=2.5 Hz, 1H), 6.39-6.32 (m, 1H), 4.05-3.98 (m, 3H), 1.79-1.65 (m, 3H), 1.58-1.50 (m, 1H), 1.17 (d, J=6.3 Hz, 3H). ES/MS m/z: 547.2 [M+H]$^+$.

Example 65: 7-(4-amino-5-cyclopropyl-pyrimidin-2-yl)-6-fluoro-3-[(4S)-4-[[6-oxo-5-(trifluoromethyl)-1H-pyridazin-4-yl]amino]pentyl]quinazolin-4-one Example 65

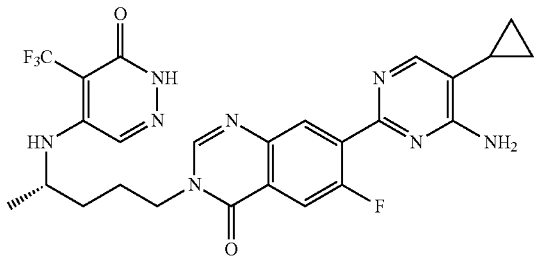

The title compound was synthesized as described in Example 17 with the following changes:

Step 1. 6-Bromo-7-fluoro-2H-isoquinolin-1-one was used instead of 6-bromo-2H-isoquinolin-1-one.

Step 3. 2-chloro-5-cyclopropyl-pyrimidin-4-amine is used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 1H NMR (400 MHz, DMSO-d6) δ 1H NMR (400 MHz, DMSO-d6) δ 12.44 (s, 1H), 8.46 (s, 1H), 8.13 (d, J=6.5 Hz, 1H), 8.09 (d, J=1.0 Hz, 1H), 8.00 (d, J=10.2 Hz, 1H), 7.92 (s, 1H), 6.38-6.27 (m, 1H), 4.03-3.97 (m, 2H), 1.81-1.63 (m, 4H), 1.60-1.45 (m, 1H), 1.17 (d, J=6.3 Hz, 3H), 1.02-0.94 (m, 2H), 0.84-0.69 (m, 2H). ES/MS m/z: 545.2 [M+H]$^+$.

Example 66: 7-(4-amino-5-methoxy-pyrimidin-2-yl)-6-fluoro-3-[(4S)-4-[[6-oxo-5-(trifluoromethyl)-1H-pyridazin-4-yl]amino]pentyl]quinazolin-4-one Example 66

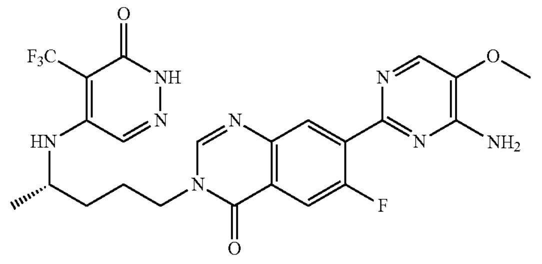

The title compound was synthesized as described in Example 17 with the following changes:

Step 1. 6-Bromo-7-fluoro-2H-isoquinolin-1-one was used instead of 6-bromo-2H-isoquinolin-1-one.

Step 3. 2-chloro-5-methoxy-pyrimidin-4-amine is used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 12.44 (s, 1H), 8.44 (s, 1H), 8.11 (d, J=6.6 Hz, 1H), 8.08 (s, 1H), 7.97 (d, J=10.2 Hz, 1H), 7.92 (s, 1H), 6.40-6.28 (m, 1H), 4.03-3.98 (m, 2H), 3.96 (s, 3H), 1.91-1.62 (m, 3H), 1.61-1.44 (m, 1H), 1.17 (d, J=6.3 Hz, 3H). ES/MS m/z: 535.2 [M+H]$^+$.

Example 67: 7-(4-amino-5-fluoro-pyrimidin-2-yl)-6-fluoro-3-[(4S)-4-[[6-oxo-5-(trifluoromethyl)-1H-pyridazin-4-yl]amino]pentyl]quinazolin-4-one Example 67

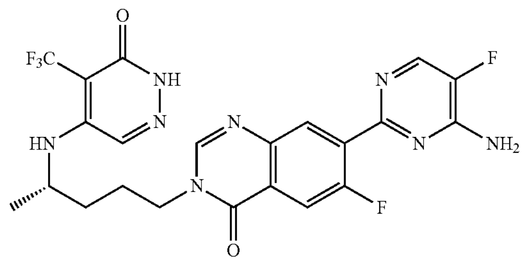

The title compound was synthesized as described in Example 17 with the following changes:

Step 1. 6-Bromo-7-fluoro-2H-isoquinolin-1-one was used instead of 6-bromo-2H-isoquinolin-1-one.

Step 3. 2-chloro-5-fluoro-pyrimidin-4-amine is used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 1H NMR (400 MHz, DMSO-d6) δ 12.44 (s, 1H), 8.41 (s, 1H), 8.36 (d, J=3.7 Hz, 1H), 8.10 (d, J=6.8 Hz, 1H), 7.92 (s, 1H), 7.88 (d, J=10.4 Hz, 1H), 7.58 (s, 2H), 6.39-6.31 (m, 1H), 4.03-3.97 (m, 2H), 1.84-1.60 (m, 3H), 1.59-1.42 (m, 1H), 1.17 (d, J=6.3 Hz, 3H). ES/MS m/z: 523.2 [M+H]$^+$.

Example 68: Preparation of 7-fluoro-2-[[(1R,2R)-2-[(1S)-1-[[6-oxo-5-(trifluoromethyl)-1H-pyridazin-4-yl]amino]ethyl]cyclopropyl]methyl]-6-[5-(trifluoromethyl)pyrimidin-2-yl]isoquinolin-1-one

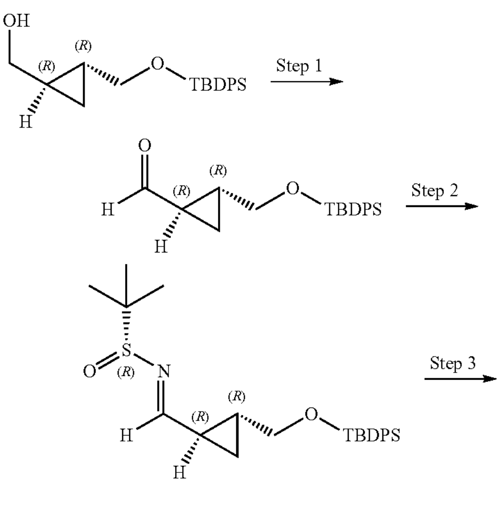

-continued

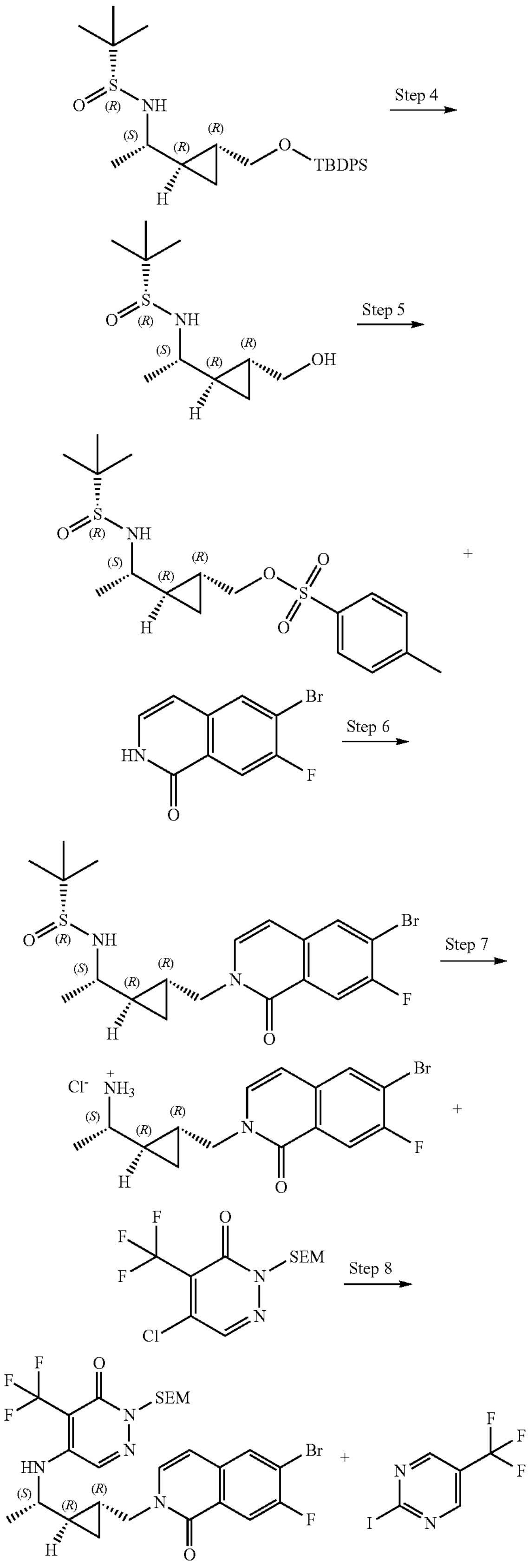

-continued

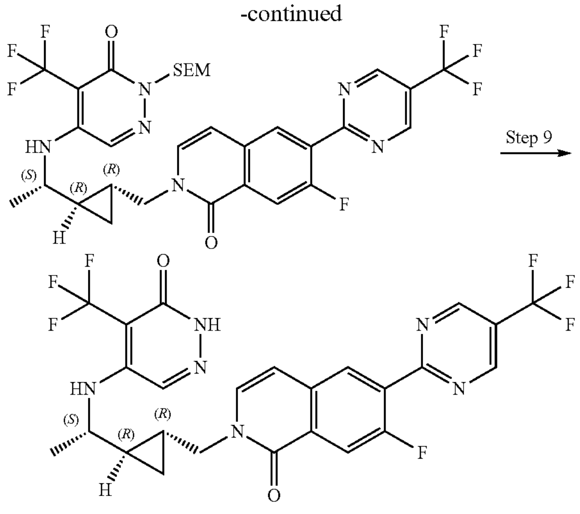

Example 68

Step 1. To a stirred solution of [(1R,2R)-2-[[tert-butyl(diphenyl)silyl]oxymethyl]cyclopropyl]methanol (2.08 g, 6.11 mmol) and sodium carbonate (646 mg, 7.33 mmol) in dichloromethane (61.0 mL) at 0° C. was added Dess Martin periodinane (3.11 g, 7.33 mmol) and the mixture was warmed to room temperature and stirred for 2 hr. Upon completion, the mixture was filtered through Celite© and concentrated in vacuo to give the crude product. The crude residue was purified using column chromatography eluting with EtOAc in hexanes 0-100% to afford (1R,2R)-2-[[tert butyl(diphenyl)silyl]oxymethyl]cyclopropanecarbaldehyde ES/MS: m/z 339.4 $[M+H]^+$.

Step 2. To a stirred solution (1R,2R)-2-[[tert-butyl(diphenyl)silyl]oxymethyl]cyclopropanecarbaldehyde (2.15 g, 6.36 mmol) and anhydrous copper sulfate (4.06 g, 25.5 mmol) in dichloromethane (61.0 mL) was added (R)-2-methylpropane-2-sulfinamide (1.16 g, 9.54 mmol) and the mixture was stirred for 18 h. Upon completion, the mixture was filtered through Celite® and concentrated in vacuo to give the crude product. The crude residue was purified using column chromatography eluting with EtOAc in hexanes 0-100% to afford (NE,R)—N-[[(1R,2R)-2-[[tert-butyl(diphenyl)silyl]oxymethyl]cyclopropyl]methylene]-2-methyl-propane-2-sulfinamide ES/MS: m/z 447.1 $[M+H]^+$.

Step 3. To a mixture of (NE,R)—N-[[(1R,2R)-2-[[tert-butyl(diphenyl)silyl]oxymethyl]cyclopropyl]methylene]-2-methyl-propane-2-sulfinamide (2.59 g, 5.87 mmol) in dichloromethane (28.0 mL) cooled to −78° C. was added 3.0 M Methyl magnesium bromide in diethyl ether (2.15 ml, 6.46 mmol). The solution was stirred at −78° C. for 1 hr then warmed to room temperature and stirred for an additional 2 hr. Reaction mixture was quenched by the addition of saturated aqueous ammonium chloride and extracted with dichloromethane. The combined organic layers were washed with brine, dried over $MgSO_4$ and concentrated in vacuo to give the crude product (R)—N-[(1S)-1-[(1R,2R)-2-[[tert-butyl(diphenyl)silyl]oxymethyl]cyclopropyl]ethyl]-2-methyl-propane-2-sulfinamide ES/MS: m/z 458.2 $[M+H]^+$.

Step 4. To a stirred solution (R)—N-[(1S)-1-[(1R,2R)-2-[[tert-butyl(diphenyl)silyl]oxymethyl]cyclopropyl]ethyl]-2-methyl-propane-2-sulfinamide (2.75 g, 6.01 mmol) in tetrahydrofuran was added 1.0 M tetrabutylammonium fluoride in tetrahydrofuran (10.5 ml, 10.5 mmol) and the mixture was stirred for 2 hr. Upon completion the reaction mixture was poured into saturated aqueous ammonium chloride and extracted with ethyl acetate. The combined organic layers were washed with brine, dried over $MgSO_4$ and concentrated in vacuo to give the crude product (R)—N-[(1S)-1-[(1R,2R)-2-(hydroxymethyl)cyclopropyl]ethyl]-2-methyl-propane-2-sulfinamide ES/MS: m/z 220.4 $[M+H]^+$.

Step 5. To a stirred solution of (R)—N-[(1S)-1-[(1R,2R)-2-(hydroxymethyl)cyclopropyl]ethyl]-2-methyl-propane-2-sulfinamide (345 mg, 1.57 mmol) and triethylamine (477 mg, 4.72 mmol) in dichloromethane (15 mL) at 0° C. was added p-Toluenesulfonyl chloride (480 mg, 2.52 mmol) and the mixture was warmed to room temperature and stirred for 18 hr. Upon completion, the mixture was diluted with water and extracted with dichloromethane. The combined organic layers were washed with brine, dried over $MgSO_4$ and concentrated in vacuo to give the crude product. The crude residue was purified using column chromatography eluting with MeOH in DCM 0-20% to afford [(1R,2R)-2-[(1S)-1-[[(R)-tert-butylsulfinyl]amino]ethyl]cyclopropyl]methyl 4-methylbenzenesulfonate ES/MS: m/z 374.4 $[M+H]^+$.

Step 6. To a mixture of 6-bromo-7-fluoro-2H-isoquinolin-1-one (95.7 mg, 0.396 mmol) and [(1R,2R)-2-[(1S)-1-[[(R)-tert-butylsulfinyl]amino]ethyl]cyclopropyl]methyl 4-methylbenzenesulfonate (98.5 mg, 0.264 mmol) in DMF (7.0 mL) was added $Cs_2CO_3$ (172 mg, 0.527 mmol) and the reaction was stirred at room temperature for 18 hr. Upon completion, the mixture was diluted with EtOAc, washed with water, washed with brine, dried over $MgSO_4$ and concentrated in vacuo to give the crude product. The crude residue was purified using column chromatography eluting with MeOH in DCM 0-20% to afford (R)—N-[(1S)-1-[(1R,2R)-2-[(6-bromo-7-fluoro-1-oxo-2-isoquinolyl)methyl]cyclopropyl]ethyl]-2-methyl-propane-2-sulfinamide ES/MS: m/z 444.9 $[M+H]^+$.

Step 7. To a solution of (R)—N-[(1S)-1-[(1R,2R)-2-[(6-bromo-7-fluoro-1-oxo-2-isoquinolyl)methyl]cyclopropyl]ethyl]-2-methyl-propane-2-sulfinamide (93.8 mg, 0.212 mmol) in methanol (2.50 mL) was added a solution of 4.0 M hydrogen chloride in dioxane (0.212 mL, 0.846 mmol) at room temperature and the mixture was stirred for 10 min. Upon completion, the solvent was removed under reduced pressure to afford 2-(((1R,2R)-2-((S)-1-aminoethyl)cyclopropyl)methyl)-6-bromo-7-fluoroisoquinolin-1(2H)-one hydrochloride. ES/MS: m/z 340.9 $[M+H]^+$.

Step 8. A mixture of 2-(((1R,2R)-2-((S)-1-aminoethyl)cyclopropyl)methyl)-6-bromo-7-fluoroisoquinolin-1(2H)-one hydrochloride (79.5 mg, 2.12 mmol), 5-chloro-4-(trifluoromethyl)-2-(2-trimethylsilylethoxymethyl)pyridazin-3-one (186 mg, 0.565 mmol), and N,N-diisopropylethylamine (0.435 mL, 2.50 mmol) in DMF (2.0 mL) was stirred at room temperature for 4 hr. Upon completion, the reaction was diluted with EtOAc, washed with water, washed with brine, dried over $MgSO_4$ and concentrated in vacuo to give the crude product. The crude residue was purified using column chromatography eluting with EtOAc in hexanes 0-100% to afford 6-bromo-7-fluoro-2-[[(1R,2R)-2-[(1S)-1-[[6-oxo-5-(trifluoromethyl)-1-(2-trimethylsilylethoxymethyl)pyridazin-4-yl]amino]ethyl]cyclopropyl]methyl]isoquinolin-1-one. ES/MS: m/z 633.0 $[M+H]^+$.

Step 9. In a vial were placed 6-bromo-7-fluoro-2-[[(1R,2R)-2-[(1S)-1-[[6-oxo-5-(trifluoromethyl)-1-(2-trimethylsilylethoxymethyl)pyridazin-4-yl]amino]ethyl]cyclopropyl]methyl]isoquinolin-1-one (123 mg, 0.195 mmol), 1,1'-Bis(diphenylphosphino)ferrocene-palladium(II)dichloride dichloromethane complex (16.1 mg, 0.0195 mmol), potassium acetate (57.3 mg, 0.584 mmol), and bis(pinacolato)diboron (74.2 mg, 0.292 mmol) in dioxane (1.84 mL). The mixture was heated to 80° C. and stirred for 16 hr, followed by the addition of 2 M aqueous sodium carbonate (0.21 mL, 0.427 mmol) and 2-iodo-5-(trifluoromethyl)pyrimidine (80.1 mg, 0.292 mmol). The reaction was then stirred for an additional hour at 80° C. Upon completion, the mixture was filtered through Celite© and concentrated under vacuum to afford the crude product which was then taken up in a solution of trifluoroacetic acid (1.5 mL) in dichloromethane (5 ml) and stirred for 1 hr at room temperature. Upon completion, the reaction was concentrated under vacuum and the resulting product was dissolved in methanol (5.0 mL) and ethylenediamine (0.16 mL, 2.42 mmol) was added and stirred for 15 minutes, and then concentrated under vacuum. The crude product was purified by reverse phase prep-HPLC (5-100% MeCN in water, 0.1% TFA) to afford 7-fluoro-2-[[(1R,2R)-2-[(1S)-1-[[6-oxo-5-(trifluoromethyl)-1H-pyridazin-4-yl]amino]ethyl]cyclopropyl]methyl]-6-[5-(trifluoromethyl)pyrimidin-2-yl]isoquinolin-1-one. $^1H$ NMR (400 MHz, DMSO-d6) δ 12.28 (s, 1H), 9.60-9.31 (m, 2H), 8.41 (d, J=7.2 Hz, 1H), 7.98 (d, J=11.5 Hz, 1H), 7.74 (s, 1H), 7.51 (d, J=7.4 Hz, 1H), 6.73 (d, J=7.4 Hz, 1H), 6.49-6.18 (m, 2H), 3.68-3.57 (m, 1H), 3.47-3.34 (m, 1H), 1.44-1.27 (m, 2H), 1.21 (d, J=6.3 Hz, 3H), 0.75-0.62 (m, 1H), 0.58-0.45 (m, 1H). ES/MS: m/z 569.1 $[M+H]^+$.

Intermediate 6: Preparation of 6-(5-chloropyrimidin-2-yl)-7-fluoro-2-[(4S)-4-[[6-oxo-5-(trifluoromethyl)-1-(2-trimethylsilylethoxymethyl)pyridazin-4-yl]amino]pentyl]isoquinolin-1-one Intermediate 6

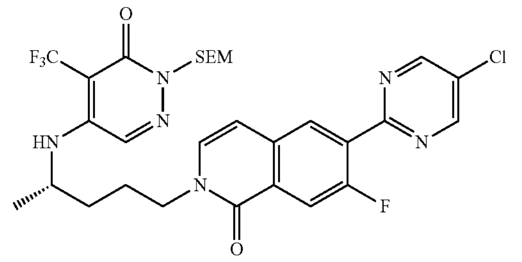

The title compound was synthesized as described in Example 17 with the following changes:

Step 1. 6-Bromo-7-fluoro-2H-isoquinolin-1-one was used instead of 6-bromo-2H-isoquinolin-1-one.

Step 3. 5-chloro-2-iodo-pyrimidine is used instead of 2-bromo-5-(difluoromethoxy)pyridine and 20 mol % of cataCXium Pd G4 and 2 M aqueous sodium carbonate (1.9 equiv.) were added following the completion of the borylation step.

Example 69: Preparation of 7-fluoro-6-[5-[3-hydroxy-3-(trifluoromethyl)azetidin-1-yl]pyrimidin-2-yl]-2-[(4S)-4-[[6-oxo-5-(trifluoromethyl)-1H-pyridazin-4-yl]amino]pentyl]isoquinolin-1-one

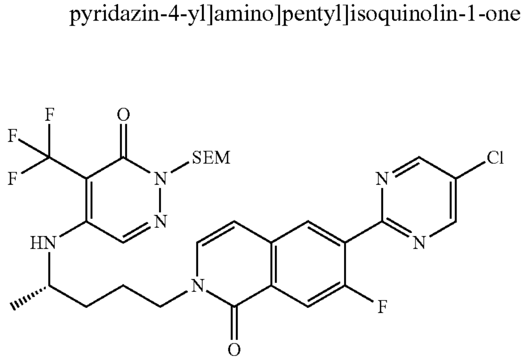

+

-continued

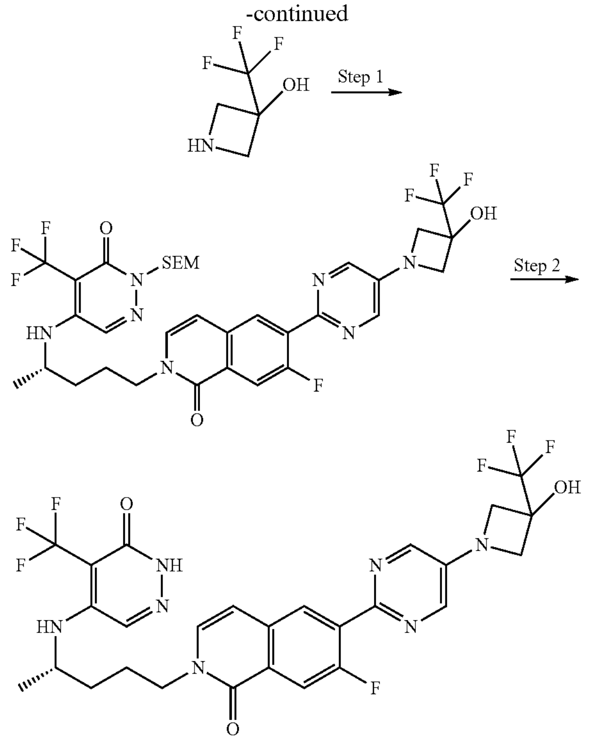

Example 69

Step 1. In a vial were placed 6-(5-chloropyrimidin-2-yl)-7-fluoro-2-[(4S)-4-[[6-oxo-5-(trifluoromethyl)-1-(2-trimethylsilylethoxymethyl)pyridazin-4-yl]amino]pentyl]isoquinolin-1-one Intermediate 6 (73 mg, 0.115 mmol), RuPhos Pd G4 (9.5 mg, 0.0112 mmol), cesium carbonate (146 mg, 0.447 mmol), and 3-(trifluoromethyl)azetidin-3-ol hydrochloride (21.8 mg, 0.123 mmol) in toluene (2.00 mL). The mixture was heated to 70° C. and stirred for 16 hr. Upon completion, the mixture was filtered through Celite® and concentrated under vacuum to afford the crude product which was then purified using column chromatography eluting with EtOAc in hexanes 0-100% to afford 7-fluoro-6-[5-[3-hydroxy-3-(trifluoromethyl)azetidin-1-yl]pyrimidin-2-yl]-2-[(4S)-4-[[6-oxo-5-(trifluoromethyl)-1-(2-trimethylsilylethoxymethyl)pyridazin-4-yl]amino]pentyl]isoquinolin-1-one. ES/MS: m/z 758.2 $[M+H]^+$.

Step 2. In a vial containing 7-fluoro-6-[5-[3-hydroxy-3-(trifluoromethyl)azetidin-1-yl]pyrimidin-2-yl]-2-[(4S)-4-[[6-oxo-5-(trifluoromethyl)-1-(2-trimethylsilylethoxymethyl)pyridazin-4-yl]amino]pentyl]isoquinolin-1-one (20.5 mg, 0.0271 mmol was added a solution of trifluoroacetic acid (1.5 mL) in dichloromethane (5 ml) which was stirred for 1 hr at room temperature. Upon completion, the mixture was concentrated under vacuum the resulting product was dissolved in methanol (5.0 mL) and ethylenediamine (0.06 mL, 0.947 mmol) was added and stirred for 15 minutes, and then was concentrated under vacuum. The crude product was purified by reverse phase prep-HPLC (5-100% MeCN in water, 0.1% TFA) to afford 7-fluoro-6-[5-[3-hydroxy-3-(trifluoromethyl)azetidin-1-yl]pyrimidin-2-yl]-2-[(4S)-4-[[6-oxo-5-(trifluoromethyl)-1H-pyridazin-4-yl]amino]pentyl]isoquinolin-1-one. $^1$H NMR (400 MHz, DMSO-d6) δ 1H NMR (400 MHz, DMSO-d6) δ 12.43 (s, 1H), 8.33 (s, 1H), 8.25 (d, J=7.4 Hz, 1H), 8.01-7.86 (m, 2H), 7.56-7.36 (m, 2H), 6.78 (d, J=7.3 Hz, 1H), 6.43-6.21 (m, 1H), 4.42-4.34 (m, 3H), 4.11-4.03 (m, 2H), 3.98 (t, J=6.5 Hz, 3H), 1.88-1.58 (m, 3H), 1.56-1.44 (m, 1H), 1.17 (d, J=6.3 Hz, 3H). ES/MS: m/z 628.1 $[M+H]^+$.

Example 70: 4-amino-2-[7-fluoro-1-oxo-2-[(4S)-4-[[6-oxo-5-(trifluoromethyl)-1H-pyridazin-4-yl]amino]hexyl]-6-isoquinolyl]pyrimidine-5-carbonitrile Example 70

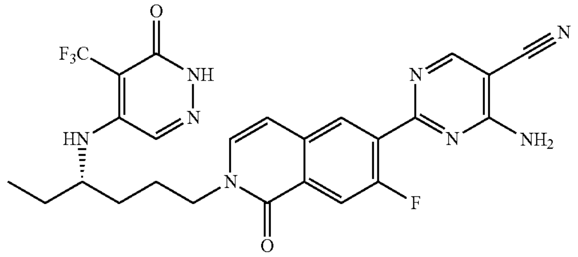

The title compound was synthesized as described in Example 37 with the following changes:

Step 5. 4-amino-2-chloro-pyrimidine-5-carbonitrile was used instead of 2-iodo-5-(trifluoromethyl)pyrimidine and 20 mol % of cataCXium Pd G4 and 2 M aqueous sodium carbonate (1.9 equiv.) were used to afford 4-amino-2-[7-fluoro-1-oxo-2-[(4S)-4-[[6-oxo-5-(trifluoromethyl)-1H-pyridazin-4-yl]amino]hexyl]-6-isoquinolyl]pyrimidine-5-carbonitrile. $^1$H NMR (400 MHz, DMSO-d6) δ 12.41 (s, 1H), 8.80 (s, 1H), 8.21 (d, J=7.1 Hz, 1H), 8.03-7.84 (m, 2H), 7.49 (d, J=7.4 Hz, 1H), 6.77 (d, J=7.4 Hz, 1H), 6.28 (dd, J=8.9, 3.9 Hz, 1H), 3.98 (t, J=6.8 Hz, 2H), 3.85 (d, J=7.3 Hz, 1H), 1.85-1.39 (m, 4H), 0.81 (t, J=7.3 Hz, 3H). ES/MS: m/z 543.3 $[M+H]^+$.

Example 71: 6-[4-amino-5-(trifluoromethyl)pyrimidin-2-yl]-7-fluoro-2-[(4S)-4-[[6-oxo-5-(trifluoromethyl)-1H-pyridazin-4-yl]amino]hexyl]isoquinolin-1-one Example 71

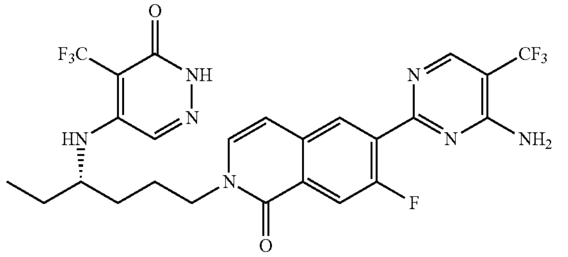

The title compound was synthesized as described in Example 37 with the following changes:

Step 5. 2-chloro-5-(trifluoromethyl)pyrimidin-4-amine was used instead of 2-iodo-5-(trifluoromethyl)pyrimidine and 20 mol % of cataCXium Pd G4 and 2 M aqueous sodium carbonate (1.9 equiv.) were used to afford 6-[4-amino-5-(trifluoromethyl)pyrimidin-2-yl]-7-fluoro-2-[(4S)-4-[[6-oxo-5-(trifluoromethyl)-1H-pyridazin-4-yl]amino]hexyl]isoquinolin-1-one. $^1$H NMR (400 MHz, DMSO-d6) δ 1H NMR (400 MHz, DMSO-d6) δ 1H NMR (400 MHz, DMSO-d6) δ 12.42 (s, 1H), 8.64 (d, J=1.1 Hz, 1H), 8.19 (d, J=7.0 Hz, 1H), 8.06-7.85 (m, 2H), 7.49 (d, J=7.4 Hz, 1H), 6.76 (d, J=7.3 Hz, 1H), 6.28 (dd, J=8.5, 3.9 Hz, 1H), 3.98 (t, J=6.8 Hz, 2H), 3.85 (d, J=8.8 Hz, 1H), 1.87-1.41 (m, 5H), 0.82 (t, J=7.3 Hz, 3H). ES/MS: m/z 586.3 $[M+H]^+$.

Example 72: 7-fluoro-2-[3-[1-[6-oxo-5-(trifluoromethyl)-1H-pyridazin-4-yl]azetidin-2-yl]propyl]-6-[5-(trifluoromethyl)pyrimidin-2-yl]isoquinolin-1-one Example 72

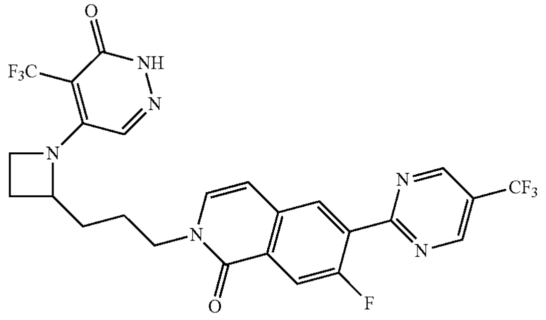

The title compound was synthesized as described in Example 5 with the following changes:

Step 1. 3-(1-tert-butoxycarbonylazetidin-2-yl)propanoic acid was used instead of (4S)-4-(tert-butoxycarbonylamino)pentanoic acid.

Step 5. 20 mol % of cataCXium Pd G4 and 2 M aqueous sodium carbonate (1.9 equiv.) were used to give 7-fluoro-2-[3-[1-[6-oxo-5-(trifluoromethyl)-1H-pyridazin-4-yl]azetidin-2-yl]propyl]-6-[5-(trifluoromethyl)pyrimidin-2-yl]isoquinolin-1-one. $^1$H NMR (400 MHz, DMSO-d6) δ 12.35 (s, 1H), 9.48 (d, J=0.9 Hz, 2H), 8.44 (d, J=7.1 Hz, 1H), 8.04 (d, J=11.4 Hz, 1H), 7.56 (d, J=7.9 Hz, 2H), 6.86 (d, J=7.4 Hz, 1H), 4.70 (s, 1H), 4.43-4.20 (m, 1H), 4.19-3.82 (m, 3H), 2.06-1.63 (m, 6H). ES/MS: m/z 569.3 $[M+H]^+$.

Example 73: 7-fluoro-2-[(4R)-5-hydroxy-5-methyl-4-[[6-oxo-5-(trifluoromethyl)-1H-pyridazin-4-yl]amino]hexyl]-6-[5-(trifluoromethyl)pyrimidin-2-yl]isoquinolin-1-one Example 73

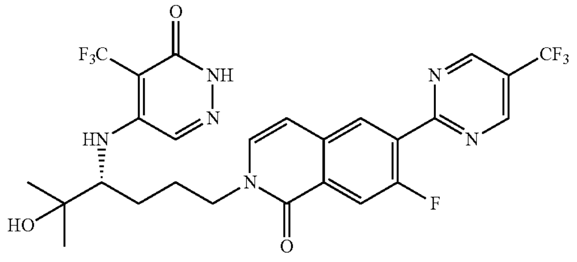

The title compound was synthesized as described in Example 36, beginning at Step 2, with the following changes:

Step 2. tert-Butyl N-[(1R)-2-hydroxy-1-(hydroxymethyl)-2-methyl-propyl]carbamate was used instead of (2S)-2-(tert-butoxycarbonylamino)-2-cyclopropyl-acetic acid.

Step 11. 20 mol % of cataCXium Pd G4 and 2 M aqueous sodium carbonate (1.9 equiv.) were added following the completion of the borylation step to give 7-fluoro-2-[(4R)-5-hydroxy-5-methyl-4-[[6-oxo-5-(trifluoromethyl)-1H-pyridazin-4-yl]amino]hexyl]-6-[5-(trifluoromethyl)pyrimidin-2-yl]isoquinolin-1-one. $^1$H NMR (400 MHz, DMSO-d6) δ 12.43 (s, 1H), 9.48 (d, J=1.0 Hz, 2H), 8.43 (d, J=7.1 Hz, 1H), 8.10-7.91 (m, 2H), 7.53 (d, J=7.4 Hz, 1H), 6.84 (d, J=7.4 Hz, 1H), 6.02 (dt, J=10.0, 4.8 Hz, 1H), 4.00 (tt, J=9.5, 4.6 Hz, 2H), 3.86 (t, J=9.9 Hz, 1H), 1.87-1.63 (m, 3H), 1.56 (dd, J=14.4, 9.1 Hz, 1H), 1.09 (d, J=16.6 Hz, 6H). ES/MS: m/z 601.3 $[M+H]^+$.

Example 74: 7-fluoro-6-[5-(1-hydroxy-1-methyl-ethyl)pyrimidin-2-yl]-2-[(4S)-4-[[6-oxo-5-(trifluoromethyl)-1H-pyridazin-4-yl]amino]pentyl]isoquinolin-1-one Example 74

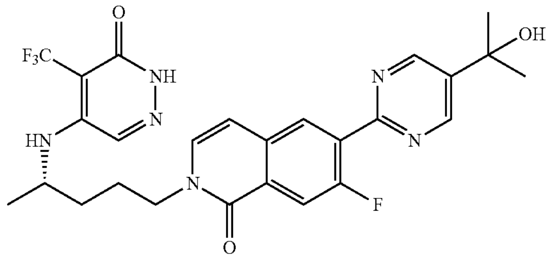

The title compound was synthesized as described in Example 9 with the following changes:

Step 5. 2-(2-chloropyrimidin-5-yl)propan-2-ol was used instead of 2-iodo-5-(trifluoromethyl)pyrimidine and 20 mol % of cataCXium Pd G4 and 2 M aqueous sodium carbonate (1.9 equiv.) were added following the completion of the borylation step to give 7-fluoro-6-[5-(1-hydroxy-1-methyl-ethyl)pyrimidin-2-yl]-2-[(4S)-4-[[6-oxo-5-(trifluoromethyl)-1H-pyridazin-4-yl]amino]pentyl]isoquinolin-1-one. $^1$H NMR (400 MHz, DMSO-d6) δ 12.43 (s, 1H), 9.06 (s, 2H), 8.32 (d, J=7.2 Hz, 1H), 7.98 (d, J=11.3 Hz, 1H), 7.92 (s, 1H), 7.50 (d, J=7.4 Hz, 1H), 6.81 (d, J=7.4 Hz, 1H), 6.36 (dd, J=8.8, 3.8 Hz, 1H), 3.99 (t, J=5.9 Hz, 3H), 1.80-1.60 (m, 3H), 1.55 (s, 7H), 1.17 (d, J=6.3 Hz, 3H). ES/MS: m/z 547.3 $[M+H]^+$.

Intermediate 7: Preparation of 2-(6-chloro-3-pyridyl)-2,2-difluoro-ethanol

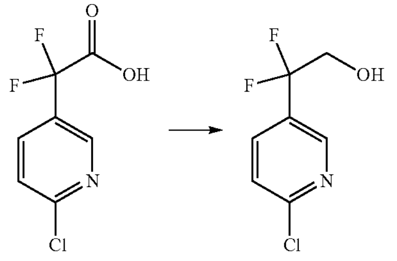

Intermediate 7

To a stirred solution of 2-(6-chloro-3-pyridyl)-2,2-difluoro-acetic acid (565 mg, 2.72 mmol) and triethylamine (0.379 mL, 2.72 mmol) in THF (26.3 mL) at 0° C. under $N_2$ atmosphere was added ethyl chloroformate (0.261 mL, 2.72 mmol). The solution was allowed to stir for 30 min at 0° C. and then was filtered to remove precipitated triethylamine hydrochloride. The filtrate containing the mixed anhydride was slowly added to a stirred suspension of $NaBH_4$ (309 mg, 8.17 mmol) in 20% aqueous THF (10.0 mL) maintained at 10° C. and allowed to stir for 30 min, then acidified with a aqueous solution of 1N HCl to pH~4. The mixture was extracted with EtOAc, washed with a solution of 2M NaOH, washed with brine, dried over $Na_2SO_4$ and concentrated. The crude residue was purified using column chromatography eluting with EtOAc in hexanes 0-100% to afford of 2-(6-chloro-3-pyridyl)-2,2-difluoro-ethanol. ES/MS m/z: 193.97 $[M+H]^+$+.

Example 75: 6-[5-(1,1-difluoro-2-hydroxy-ethyl)-2-pyridyl]-7-fluoro-2-[(4S)-4-[[6-oxo-5-(trifluoromethyl)-1H-pyridazin-4-yl]amino]pentyl]isoquinolin-1-one Example 75

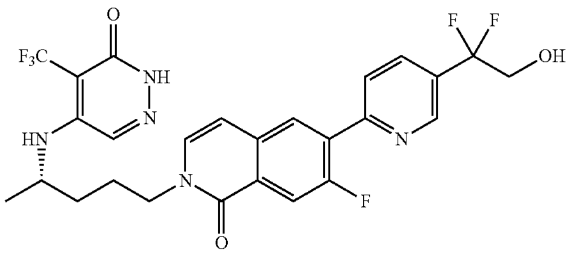

The title compound was synthesized as described in Example 9 with the following changes:

Step 5. 2-(6-chloro-3-pyridyl)-2,2-difluoro-ethanol was used instead of 2-iodo-5-(trifluoromethyl)pyrimidine to give and 20 mol % of cataCXium Pd G4 and 2 M aqueous sodium carbonate (1.9 equiv.) were added following the completion of the borylation step to give 6-[5-(1,1-difluoro-2-hydroxy-ethyl)-2-pyridyl]-7-fluoro-2-[(4S)-4-[[6-oxo-5-(trifluoromethyl)-1H-pyridazin-4-yl]amino]pentyl]isoquinolin-1-one. $^1$H NMR (400 MHz, DMSO-d6) δ 12.43 (s, 1H), 8.95-8.88 (m, 1H), 8.27 (d, J=7.4 Hz, 1H), 8.13 (dd, J=8.4, 2.4 Hz, 1H), 8.07-7.97 (m, 2H), 7.91 (s, 1H), 7.51 (d, J=7.4 Hz, 1H), 6.81 (d, J=7.3 Hz, 1H), 6.35 (d, J=7.2 Hz, 1H), 4.11-3.87 (m, 6H), 1.69 (d, J=26.8 Hz, 3H), 1.52 (d, J=9.3 Hz, 1H), 1.17 (d, J=6.3 Hz, 3H). ES/MS: m/z 568.3 $[M+H]^+$.

Example 76: 6-[5-(difluoromethyl)pyrimidin-2-yl]-7-fluoro-2-[(4S)-4-[[6-oxo-5-(trifluoromethyl)-1H-pyridazin-4-yl]amino]pentyl]isoquinolin-1-one Example 76

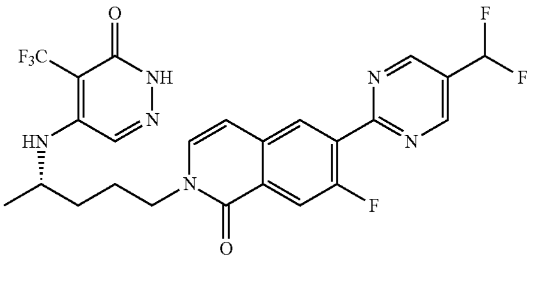

The title compound was synthesized as described in Example 9 with the following changes:

Step 5. 2-Chloro-5-(difluoromethyl)pyrimidine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-[5-(difluoromethyl)pyrimidin-2-yl]-7-fluoro-2-[(4S)-4-[[6-oxo-5-(trifluoromethyl)-1H-pyridazin-4-yl]amino]pentyl]isoquinolin-1-one. $^1$H NMR (400 MHz, DMSO-d6) δ 12.43 (s, 1H), 8.33 (s, 1H), 8.25 (d, J=7.4 Hz, 1H), 8.01-7.86 (m, 2H), 7.56-7.36 (m, 2H), 6.78 (d, J=7.3 Hz, 1H), 6.43-6.21 (m, 1H), 4.42-4.34 (m, 3H), 4.11-4.03 (m, 2H), 3.98 (t, J=6.5 Hz, 3H), 1.88-1.58 (m, 3H), 1.56-1.44 (m, 1H), 1.17 (d, J=6.3 Hz, 3H). ES/MS: m/z 539.1 $[M+H]^+$.

Example 77: (S)-6-(4-amino-5-methylpyrimidin-2-yl)-7,8-difluoro-2-(4-((6-oxo-5-(trifluoromethyl)-1,6-dihydropyridazin-4-yl)amino)pentyl)isoquinolin-1(2H)-one Example 77

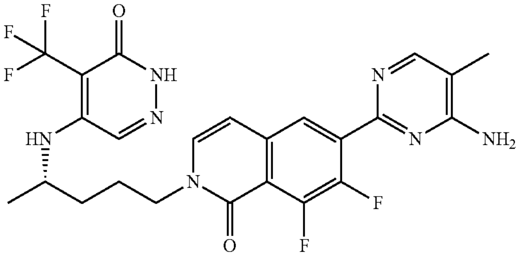

The title compound was synthesized as described in Example 17 with the following changes:

Step 1. 2-bromo-7,8-difluoroisoquinolin-1(2H)-one was used instead of 6-bromo-8-fluoro-1,2-dihydroisoquinolin-1-one Step 3. 2-Chloro-5-methylpyrimidin-4-amine was used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 1H NMR (400 MHz, DMSO-d6) δ 12.43 (s, 1H), 8.22 (s, 1H), 7.94-7.89 (m, 2H), 7.53 (d, J=7.4 Hz, 1H), 6.72 (dd, J=7.6, 1.9 Hz, 1H), 6.35 (d, J=5.3 Hz, 1H), 4.03-3.88 (m, 2H), 2.10 (s, 3H), 1.79-1.59 (m, 3H), 1.53 (d, J=9.5 Hz, 1H), 1.17 (d, J=6.3 Hz, 3H). ES/MS: m/z 536.3 $[M+H]^+$.

Example 78: (S)-7-(4-amino-5-methylpyrimidin-2-yl)-6-fluoro-3-(4-((6-oxo-5-(trifluoromethyl)-1,6-dihydropyridazin-4-yl)amino)pentyl)quinazolin-4(3H)-one Example 78

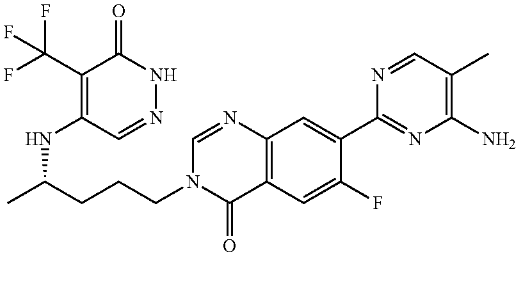

The title compound was synthesized as described in Example 17 with the following changes:

Step 1. 7-bromo-6-fluoro-1H-quinazolin-4-one was used instead of 6-bromo-8-fluoro-1,2-dihydroisoquinolin-1-one Step 3. 2-chloro-5-methylpyrimidin-4-amine was used instead of 2-bromo-5-(difluoromethoxy)pyridine and 20 mol % of cataCXium Pd G4 and 2 M aqueous sodium carbonate (1.9 equiv.) were added following the completion of the borylation step. $^{1}$H NMR (400 MHz, DMSO-d6) δ 1H NMR (400 MHz, DMSO-d6) δ 12.44 (s, 1H), 8.45 (s, 1H), 8.25 (s, 1H), 8.14 (d, J=6.6 Hz, 1H), 8.00 (d, J=10.2 Hz, 1H), 7.92 (s, 1H), 6.42-6.26 (m, 2H), 4.07-3.89 (m, 2H), 2.12 (s, 3H), 1.83-1.64 (m, 3H), 1.60-1.46 (m, 1H), 1.17 (d, J=6.3 Hz, 4H). ES/MS: m/z 519.3 [M+H]$^{+}$.

Example 79: (S)-7-(2-amino-5-methylpyrimidin-4-yl)-6-fluoro-3-(4-((6-oxo-5-(trifluoromethyl)-1,6-dihydropyridazin-4-yl)amino)pentyl)quinazolin-4(3H)-one Example 79

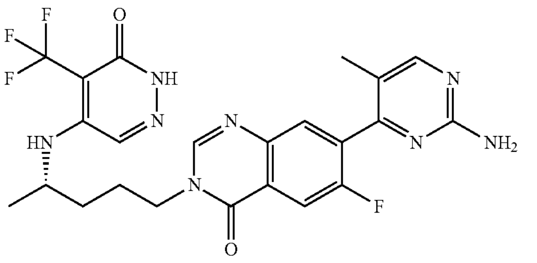

The title compound was synthesized as described in Example 17 with the following changes:

Step 1. 7-bromo-6-fluoro-1H-quinazolin-4-one was used instead of 6-bromo-8-fluoro-1,2-dihydroisoquinolin-1-one.

Step 3. 4-bromo-5-methylpyrimidin-2-amine was used instead of 2-bromo-5-(difluoromethoxy)pyridine and 20 mol % of cataCXium Pd G4 and 2 M aqueous sodium carbonate (1.9 equiv.) were added following the completion of the borylation step. $^{1}$H NMR (400 MHz, DMSO-d6) δ 1H NMR (400 MHz, DMSO-d6) δ 1H NMR (400 MHz, DMSO-d6) δ 12.44 (s, 1H), 8.42 (s, 1H), 8.25 (s, 1H), 7.94 (d, J=9.5 Hz, 1H), 7.92 (s, 1H), 7.72 (d, J=6.4 Hz, 1H), 6.62 (s, 2H), 6.39-6.31 (m, 1H), 4.05-3.92 (m, 3H), 1.94 (s, 3H), 1.82-1.60 (m, 3H), 1.60-1.46 (m, 1H), 1.17 (d, J=6.3 Hz, 3H). ES/MS: m/z 519.3 [M+H]$^{+}$.

Example 80: (S)-6-(2-amino-5-methylpyrimidin-4-yl)-7,8-difluoro-2-(4-((6-oxo-5-(trifluoromethyl)-1,6-dihydropyridazin-4-yl)amino)pentyl)isoquinolin-1(2H)-one Example 80

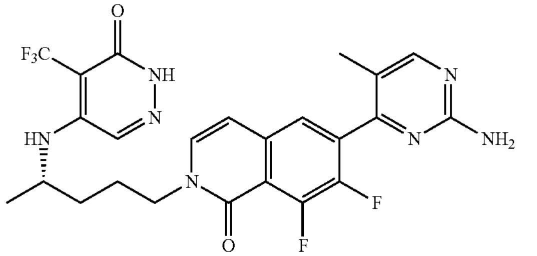

The title compound was synthesized as described in Example 17 with the following changes:

Step 1. 2-bromo-7,8-difluoroisoquinolin-1(2H)-one was used instead of 6-bromo-8-fluoro-1,2-dihydroisoquinolin-1-one Step 3. 4-Bromo-5-methylpyrimidin-2-amine was used instead of 2-bromo-5-(difluoromethoxy)pyridine and 20 mol % of cataCXium Pd G4 and 2 M aqueous sodium carbonate (1.9 equiv.) were added following the completion of the borylation step. $^{1}$H NMR (400 MHz, DMSO-d6) δ 12.44 (s, 1H), 8.28 (s, 1H), 7.92 (s, 1H), 7.56 (d, J=6.2 Hz, 1H), 7.52 (d, J=7.4 Hz, 1H), 6.68 (d, J=7.3 Hz, 1H), 6.35 (d, J=5.3 Hz, 1H), 4.02-3.90 (m, 3H), 1.96 (s, 3H), 1.77-1.62 (m, 3H), 1.57-1.46 (m, 1H), 1.17 (d, J=6.3 Hz, 3H). ES/MS: m/z 536.3 [M+H]$^{+}$.

Example 81: (S)-6-(4-amino-5-(trifluoromethyl)pyrimidin-2-yl)-7,8-difluoro-2-(4-((6-oxo-5-(trifluoromethyl)-1,6-dihydropyridazin-4-yl)amino)pentyl)isoquinolin-1(2H)-one Example 81

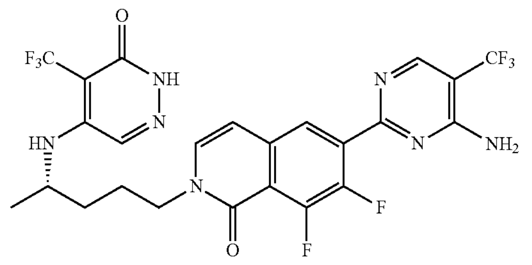

The title compound was synthesized as described in Example 17 with the following changes:

Step 1. 2-bromo-7,8-difluoroisoquinolin-1(2H)-one was used instead of 6-bromo-8-fluoro-1,2-dihydroisoquinolin-1-one Step 3. 2-chloro-5-(trifluoromethyl)pyrimidin-4-amine was used instead of 2-bromo-5-(difluoromethoxy)pyridine and 20 mol % of cataCXium Pd G4 and 2 M aqueous sodium carbonate (1.9 equiv.) were added following the completion of the borylation step. $^{1}$H NMR (400 MHz, DMSO-d6) δ 12.44 (s, 1H), 8.71-8.60 (m, 1H), 8.06-7.95 (m, 1H), 7.92 (s, 1H), 7.52 (d, J=7.4 Hz, 1H), 6.79-6.68 (m, 1H), 6.42-6.26 (m, 1H), 4.06-3.86 (m, 3H), 1.80-1.60 (m, 3H), 1.59-1.45 (m, 1H), 1.21-1.14 (m, 3H). ES/MS: m/z 590.3 [M+H]$^{+}$.

Example 82: (S)-7-(5-(difluoromethyl)pyrimidin-2-yl)-6-fluoro-3-(4-((6-oxo-5-(trifluoromethyl)-1,6-dihydropyridazin-4-yl)amino)pentyl)quinazolin-4(3H)-one Example 82

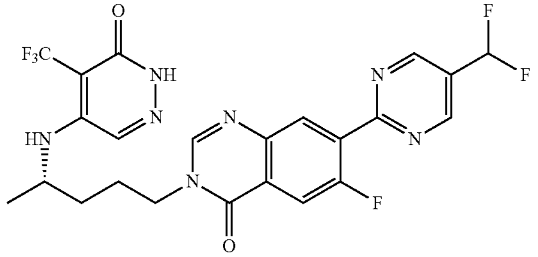

The title compound was synthesized as described in Example 17 with the following changes:

Step 1. 7-bromo-6-fluoro-1H-quinazolin-4-one was used instead of 6-bromo-8-fluoro-1,2-dihydroisoquinolin-1-one Step 3. 2-chloro-5-(difluoromethyl)pyrimidine was used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 12.44 (s, 1H), 9.26 (s, 2H), 8.45 (s, 1H), 8.32 (d, J=6.8 Hz, 1H), 7.99 (d, J=10.5 Hz, 1H), 7.92 (s, 1H), 7.31 (t, J=54.7 Hz, 1H), 6.43-6.27 (m, 1H), 4.07-3.91 (m, 3H), 1.82-1.62 (m, 3H), 1.59-1.48 (m, 1H), 1.17 (d, J=6.3 Hz, 3H). ES/MS: m/z 540.3 $[M+H]^+$.

Example 83: (S)-7-(5-cyclopropylpyrimidin-2-yl)-6-fluoro-3-(4-((6-oxo-5-(trifluoromethyl)-1,6-dihydropyridazin-4-yl)amino)pentyl)quinazolin-4(3H)-one Example 83

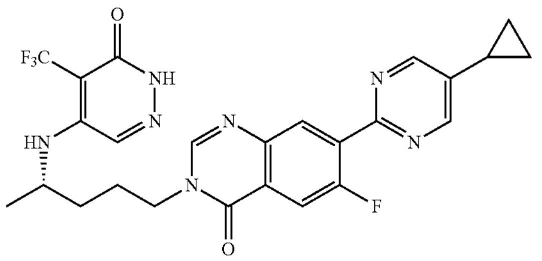

The title compound was synthesized as described in Example 17 with the following changes:

Step 1. 7-bromo-6-fluoro-1H-quinazolin-4-one was used instead of 6-bromo-8-fluoro-1,2-dihydroisoquinolin-1-one Step 3. 2-bromo-5-cyclopropylpyrimidine was used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 12.44 (s, 1H), 8.78 (s, 2H), 8.43 (s, 1H), 8.23 (d, J=6.8 Hz, 1H), 7.94 (d, J=10.8 Hz, 2H), 6.39-6.31 (m, 1H), 4.01 (t, J=6.6 Hz, 3H), 2.10-1.99 (m, 1H), 1.82-1.61 (m, 3H), 1.59-1.46 (m, 1H), 1.17 (d, J=6.3 Hz, 3H), 1.15-1.08 (m, 2H), 1.00-0.92 (m, 2H). ES/MS: m/z 530.3 $[M+H]^+$.

Example 84: (S)-7-fluoro-6-(5-(methylsulfonyl)pyrimidin-2-yl)-2-(4-((6-oxo-5-(trifluoromethyl)-1,6-dihydropyridazin-4-yl)amino)pentyl)isoquinolin-1(2H)-one Example 84

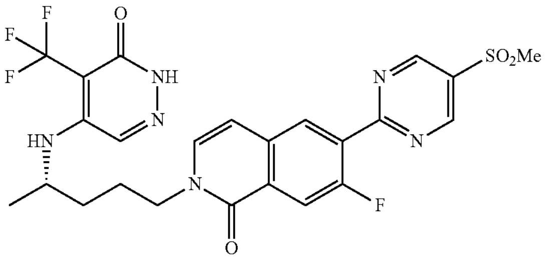

The title compound was synthesized as described in Example 17 with the following changes:

Step 1. 6-bromo-7-fluoro-1,2-dihydroisoquinolin-1-one was used instead of 6-bromo-8-fluoro-1,2-dihydroisoquinolin-1-one Step 3. 2-chloro-5-(methylsulfonyl)pyrimidine was used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 12.43 (s, 1H), 9.46 (s, 2H), 8.46 (d, J=7.1 Hz, 1H), 8.04 (d, J=11.4 Hz, 1H), 7.92 (s, 1H), 7.54 (d, J=7.4 Hz, 1H), 6.86 (d, J=7.4 Hz, 1H), 6.43-6.27 (m, 1H), 4.05-3.97 (m, 3H), 3.49 (s, 3H), 1.80-1.59 (m, 3H), 1.58-1.45 (m, 1H), 1.17 (d, J=6.3 Hz, 3H). ES/MS: m/z 567.3 $[M+H]^+$.

Intermediate 8: Preparation of 7,8-difluoro-6-(5-(trifluoromethyl)pyrimidin-2yl)isoquinolin-1(2H)-one

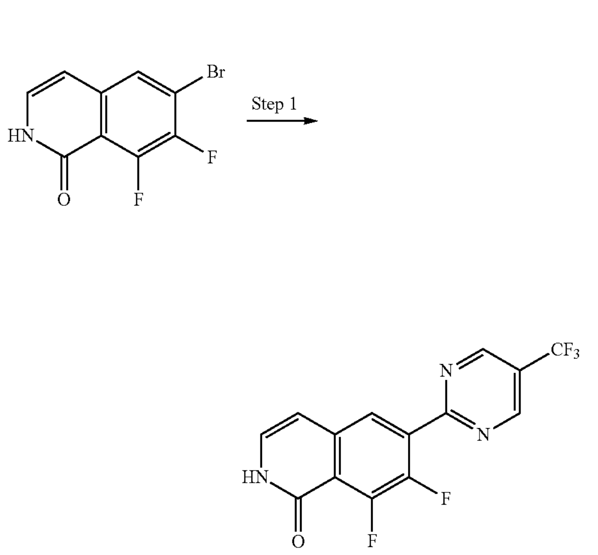

Intermediate 8

Step 1. To a vial was added 6-bromo-7,8-difluoroisoquinolin-1(2H)-one (1.00 g, 3.85 mmol), bis(pinocolato)diboron (1.47 g, 5.77 mmol), 1,1'-Bis(diphenylphosphino)ferrocene-palladium(II)dichloride dichloromethane complex (314 mg, 0.385 mmol), potassium acetate (1.13 g, 11.5 mmol), and 1,4-dioxane (39.0 mL). The reaction was stirred at 90° C. for 1 hr, cooled to room temperature, and then 2-iodo-5-(trifluoromethyl)pyrimidine (0.983 g, 3.59 mmol), cataCXium Pd G4 (0.533 g, 0.72 mmol), and aqueous sodium carbonate solution (5.38 mL, 2.0 M) were added. The reaction was stirred at 90° C. for 1 hour, cooled, and filtered over a fritted funnel to give 7,8-difluoro-6-(5-(trifluoromethyl)pyrimidin-2-yl)isoquinolin-1(2H)-one which was sufficiently pure for the next step. ES/MS m/z: 327.93 $[M+H]^+$.

Example 85: 7,8-difluoro-2-(4-((6-oxo-5-(trifluoromethyl)-1,6-dihydropyridazin-4-yl)amino)butyl)-6-(5-(trifluoromethyl)pyrimidin-2-yl)isoquinolin-1(2H)-one Example 85

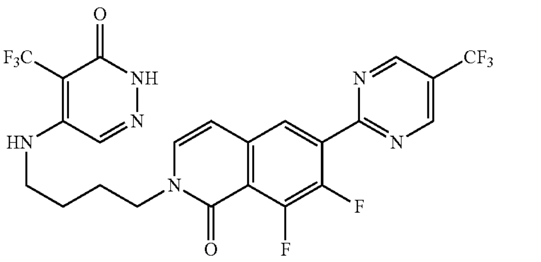

The title compound was synthesized as described in Example 1 with the following changes:

Step 1. Omitted

Step 2. 7,8-Difluoro-6-(5-(trifluoromethyl)pyrimidin-2-yl)isoquinolin-1(2H)-one (Intermediate 8) was used instead of 6-bromo-7-fluoro-1,2-dihydroisoquinolin-1-one and 4-((tert-butoxycarbonyl)amino)butyl 4-methylbenzenesulfonate was used instead of 4-(tert-butoxycarbonylamino)pentyl 4-methylbenzenesulfonate Step 3. Omitted Step 4. tert-Butyl (4-(7,8-difluoro-1-oxo-6-(5-(trifluoromethyl)pyrimidin-2-yl)isoquinolin-2(1H)-yl)butyl)carbamate was used instead of tert-butyl N-[1-methyl-4-[1-oxo-6-[5-(trifluoromethyl)-2-pyridyl]-2-isoquinolyl]butyl] carbamate Step 5. 2-(4-Aminobutyl)-7,8-difluoro-6-(5-(trifluoromethyl)pyrimidin-2-yl)isoquinolin-1(2H)-one hydrochloride was used instead of 2-(4-aminopentyl)-6-[5-(trifluoromethyl)-2-pyridyl]isoquinolin-1-one hydrochloride.

Step 6. 7,8-Dluoro-2-(4-((6-oxo-5-(trifluoromethyl)-1-((2-(trimethylsilyl)ethoxy)methyl)-1,6-dihydropyridazin-4-yl)amino)butyl)-6-(5-(trifluoromethyl)pyrimidin-2-yl)isoquinolin-1(2H)-one was used instead of 2-[4-[[6-oxo-5-(trifluoromethyl)-1-(2-trimethylsilylethoxymethyl)pyridazin-4-yl]amino]pentyl]-6-[5-(trifluoromethyl)-2-pyridyl]isoquinolin-1-one. $^1$H NMR (400 MHz, DMSO-d6) δ 12.42 (s, 1H), 9.51 (s, 2H), 8.30-8.18 (m, 1H), 7.89 (s, 1H), 7.57 (d, J=7.4 Hz, 1H), 7.17-7.07 (m, 1H), 6.87-6.77 (m, 1H), 4.04-3.92 (m, 3H), 1.78-1.65 (m, 3H), 1.63-1.48 (m, 3H). ES/MS: m/z 561.2 [M+H]$^+$.

Examples 86 and Example 87: (S)-7,8-difluoro-2-(4-((6-oxo-5-(trifluoromethyl)-1,6-dihydropyridazin-4-yl)amino)pentyl-4-d)-6-(5-(trifluoromethyl)pyrimidin-2-yl)isoquinolin-1(2H)-one and (R)-7,8-difluoro-2-(4-((6-oxo-5-(trifluoromethyl)-1,6-dihydropyridazin-4-yl)amino)pentyl-4-d)-6-(5-(trifluoromethyl)pyrimidin-2-yl)isoquinolin-1(2H)-one

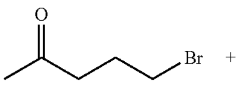

-continued

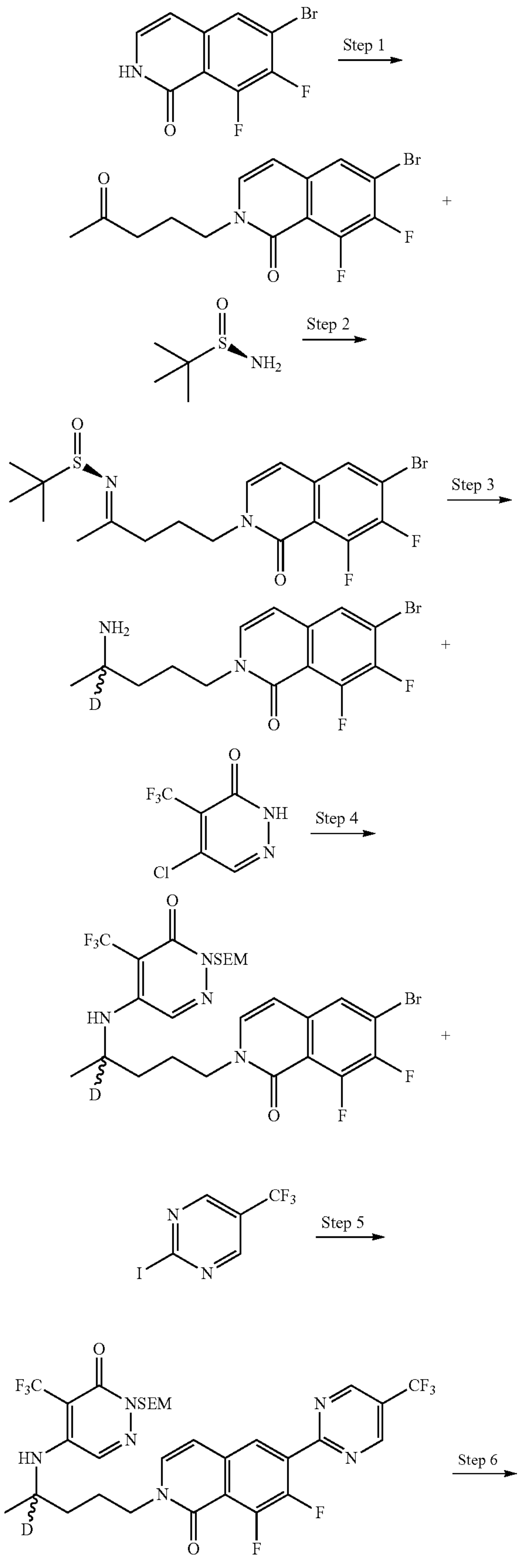

-continued

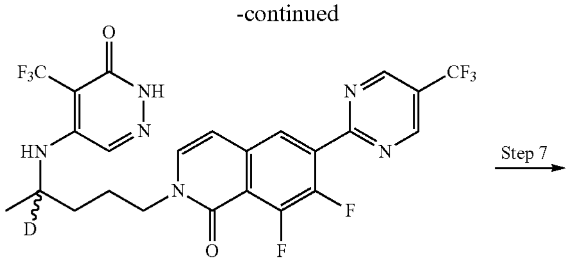

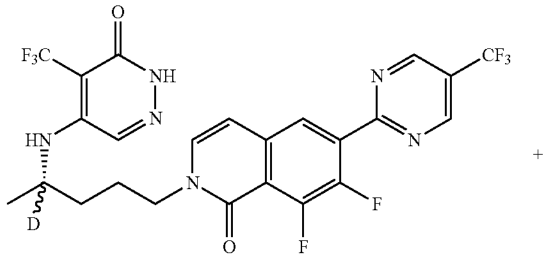

Example 86

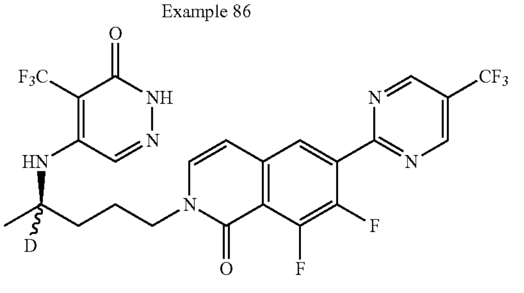

Example 87

Step 1. In a vial were placed 6-bromo-7,8-difluoro-2H-isoquinolin-1-one (2.00 g, 7.69 mmol), 5-bromo-pentan-2-one (1.52 g, 9.23 mmol), and cesium carbonate (5.01 g, 15.4 mmol) in DMF (40.0 mL). After the mixture was stirred at room temperature for 16 h, it was quenched with water and extracted with EtOAc (x3). The combined organic layers were washed with water and brine, dried ($Na_2SO_4$), and purified by flash chromatography (100% hexanes to 100% EtOAc) to give 6-bromo-7,8-difluoro-2-(4-oxopentyl)isoquinolin-1-one. ES/MS m/z: 343.886 [M+H].

Step 2. In a vial were placed 6-bromo-7,8-difluoro-2H-isoquinolin-1-one (685 mg, 1.99 mmol), (S)-(−)-2-methyl-2-propanesulfinamide (265 mg, 2.19 mmol), titanium(IV) ethoxide (0.835 mL, 3.98 mmol), and THF (20.0 mL). The reaction is heated to 65° C. for 8 h and afterward it was quenched with water and extracted with EtOAc (x3). The combined organic layers were washed with water and brine, dried ($MgSO_4$), and purified by flash chromatography (100% hexanes to 100% EtOAc) to give (S)—N-[4-(6-bromo-7,8-difluoro-1-oxo-2-isoquinolyl)-1-methyl-butylidene]-2-methyl-propane-2-sulfinamide. ES/MS m/z: 446.985 [M+H].

Step 3. In a vial were placed (S)—N-[4-(6-bromo-7,8-difluoro-1-oxo-2-isoquinolyl)-1-methyl-butylidene]-2-methyl-propane-2-sulfinamide (300 mg, 0.671 mmol) and methanol (6.70 mL). The reaction mixture was cooled to 0° C. and then sodium borodeuteride (28.1 mg, 0.671 mmol) was added in one portion. The reaction was stirred until completed by LCMS and then quenched with saturated ammonium chloride solution and extracted with EtOAc (x3). The combined organic layers were washed with water and brine, dried ($MgSO_4$), and concentrated. A solution of HCl (4N in dioxane, 0.671 mmol) was added and stirred for 1 h and concentrated to give 2-(4-amino-4-deuterio-pentyl)-6-bromo-7,8-difluoro-isoquinolin-1-one. ES/MS m/z: 345.937 [M+H].

Step 4. In a vial were placed 2-(4-amino-4-deuterio-pentyl)-6-bromo-7,8-difluoro-isoquinolin-1-one (232 mg, 0.670 mmol), 5-chloro-4-(trifluoromethyl)-2-(2-trimethylsilylethoxymethyl)pyridazin-3-one (331 mg, 1.01 mmol) and N,N-diisopropylethylamine (0.584 mL, 3.35 mmol) in DMF (7.00 mL). The mixture was heated to 80° C. and stirred for 1 hr, and then quenched with water and extracted with EtOAc (x3). The combined organic layers were washed with water and brine, dried (MgSO4), and purified by flash chromatography (100% hexanes to 100% EtOAc) to give 6-bromo-2-[4-deuterio-4-[[6-oxo-5-(trifluoromethyl)-1-(2-trimethylsilylethoxymethyl)pyridazin-4-yl]amino]pentyl]-7,8-difluoro-isoquinolin-1-one. ES/MS m/z: 638.061 [M+H].

Step 5. In a vial were placed 6-bromo-2-[4-deuterio-4-[[6-oxo-5-(trifluoromethyl)-1-(2-trimethylsilylethoxymethyl)pyridazin-4-yl]amino]pentyl]-7,8-difluoro-isoquinolin-1-one (171 mg, 0.268 mmol), 1,1'-Bis(diphenylphosphino)ferrocene-palladium(II)dichloride dichloromethane complex (43.7 mg, 0.054 mmol), potassium acetate (78.8 mg, 0.803 mmol), and bis(pinacolato)diboron (102 mg, 0.402 mmol) in dioxane (3.0 mL). The mixture was heated to 80° C. and stirred for 1 h, cooled, and then followed by the addition of 2 M aqueous sodium carbonate (0.403 mL, 0.805 mmol), cataCXium Pd G4 (39.8 mg, 0.054 mmol) and 2-iodo-5-(trifluoromethyl)pyrimidine (110 mg, 0.403 mmol). The reaction was then stirred for an additional hour at 80° C. Upon completion, the mixture was filtered through Celite® and concentrated under vacuum and then purified by flash chromatography (100% hexanes to 100% EtOAc) to give 2-[4-deuterio-4-[[6-oxo-5-(trifluoromethyl)-1-(2-trimethylsilylethoxymethyl)pyridazin-4-yl]amino]pentyl]-7,8-difluoro-6-[5-(trifluoromethyl)pyrimidin-2-yl]isoquinolin-1-one. ES/MS m/z: 706.137 [M+H].

Step 6. In a vial was placed 2-[4-deuterio-4-[[6-oxo-5-(trifluoromethyl)-1-(2-trimethylsilylethoxymethyl)pyridazin-4-yl]amino]pentyl]-7,8-difluoro-6-[5-(trifluoromethyl)pyrimidin-2-yl]isoquinolin-1-one (135 mg, 0.191 mmol), trifluoroacetic acid (0.366 mL, 4.78 mmol), and methylene chloride (5.0 mL). The reaction was stirred until completion as indicated by LCMS, concentrated, and purified by flash chromatography (100% DCM to 100% MeCN) to give 7,8-difluoro-2-(4-((6-oxo-5-(trifluoromethyl)-1,6-dihydropyridazin-4-yl)amino)pentyl-4-d)-6-(5-(trifluoromethyl)pyrimidin-2-yl)isoquinolin-1(2H)-one. ES/MS m/z: 576.2 [M+H].

Step 7. Examples 86 and Example 87 were separated via chiral SFC (AD-H, 5 μm, 21×250 mm column; 40% EtOH as co-solvent; 100 bar; 40° C.). The first eluting peak was assigned as the (S)-configuration (Example 2), and the second eluting peak was assigned as the (R)-configuration (Example 3). The final compounds were free of TFA.

Example 86: 2-[(4R)-4-deuterio-4-[[6-oxo-5-(trifluoromethyl)-1H-pyridazin-4-yl]amino]pentyl]-7,8-difluoro-6-[5-(trifluoromethyl)pyrimidin-2-yl]isoquinolin-1-one. $^1H$ NMR (400 MHz, DMSO-d6) δ 1H NMR (400 MHz, DMSO-d6) δ 12.43 (s, 1H), 9.57-9.42 (m, 2H), 8.26-8.21 (m, 1H), 7.92 (s, 1H), 7.56 (d, J=7.4 Hz, 1H), 6.85-6.78 (m, 1H), 6.35 (d, J=3.7 Hz, 1H), 4.01-3.90 (m, 2H), 1.80-1.60 (m, 3H), 1.57-1.43 (m, 1H), 1.17 (s, 3H). ES/MS: m/z 576.2 $[M+H]^+$.

Example 87: 2-[(4S)-4-deuterio-4-[[6-oxo-5-(trifluoromethyl)-1H-pyridazin-4-yl]amino]pentyl]-7,8-difluoro-6-[5-(trifluoromethyl)pyrimidin-2-yl]isoquinolin-1-one. $^1H$ NMR (400 MHz, DMSO-d6) δ 1H NMR (400 MHz, DMSO-d6) δ 12.43 (s, 1H), 9.57-9.42 (m, 2H), 8.26-8.21 (m, 1H), 7.92 (s, 1H), 7.56 (d, J=7.4 Hz, 1H), 6.85-6.78 (m, 1H), 6.35 (d, J=3.7 Hz, 1H), 4.01-3.90 (m, 2H), 1.80-1.60 (m, 3H), 1.57-1.43 (m, 1H), 1.17 (s, 3H). ES/MS: m/z 576.2 $[M+H]^+$.

Intermediate 9: Preparation of methyl(2R)-5-(6-bromo-7-fluoro-1-oxo-2-isoquinolyl)-2-(tert-butoxycarbonylamino)pentanoate Intermediate 9

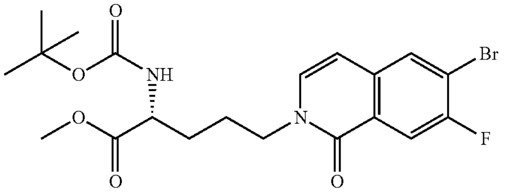

The title compound was synthesized as described in Steps 1-3 of Example 5 with the following changes:

Step 1. (4R)-4-(tert-butoxycarbonylamino)-5-methoxy-5-oxo-pentanoic acid was utilized as the starting material.

Step 3. 6-bromo-7-fluoro-2H-isoquinolin-1-one was used instead of 6-bromo-2H-isoquinolin-1-one. ES/MS m/z: 470.2 $[M+H]^+$.

Example 88: Preparation of 7-fluoro-2-[(4R)-5-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one

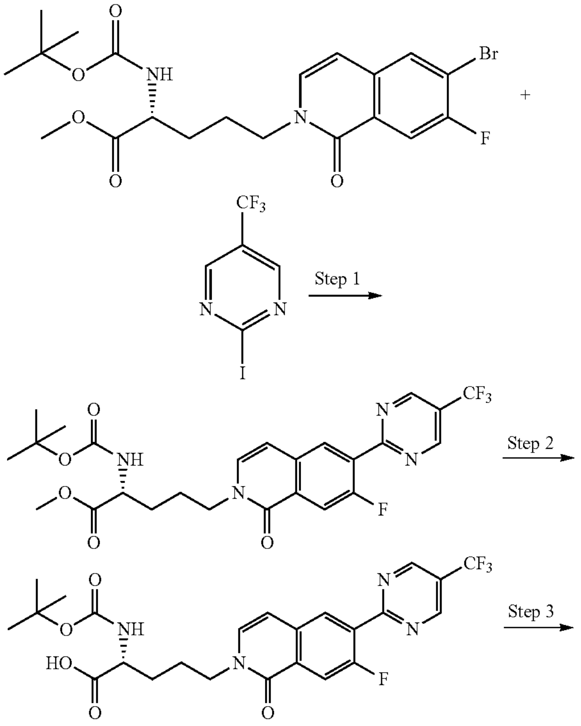

-continued

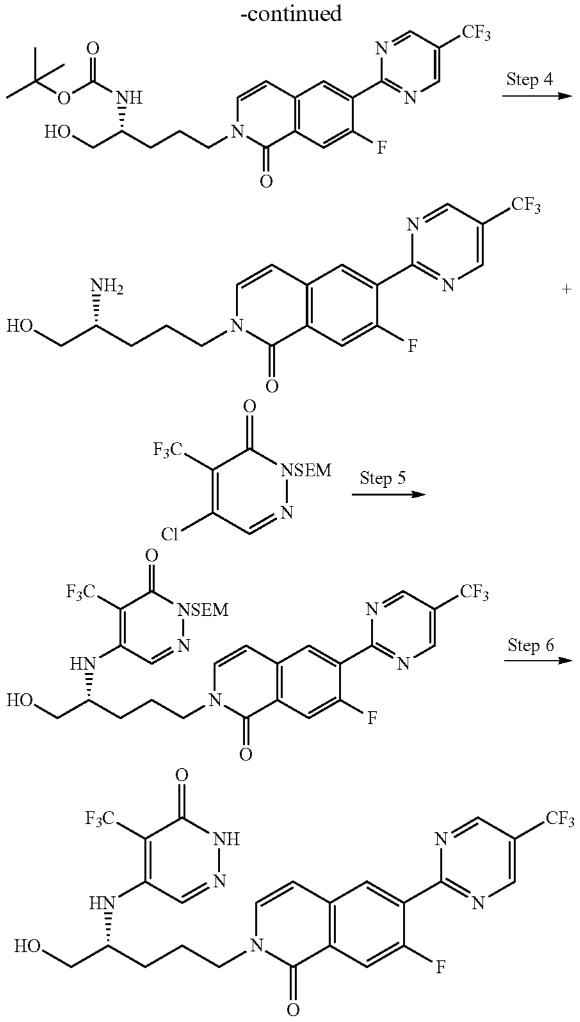

Example 88

Step 1. In a vial were placed methyl (2R)-5-(6-bromo-7-fluoro-1-oxo-2-isoquinolyl)-2-(tert-butoxycarbonylamino) pentanoate (782 mg, 1.6 mmol), 1,1'-Bis(diphenylphosphino)ferrocene-palladium(II)dichloride dichloromethane complex (58 mg, 0.07 mmol), potassium acetate (464 mg, 4.7 mmol), and bis(pinacolato)diboron (1.2 g, 4.7 mmol) in dioxane (14.0 mL). The mixture was bubbled with dry Nitrogen and stirred at 100° C. for 18 hr at which point LC/MS indicated complete conversion of the bromide. The reaction was cooled to ambient and 2 M aqueous sodium carbonate (2.4 mL, 4.7 mmol), 2-iodo-5-(trifluoromethyl) pyrimidine (518 mg, 1.9 mmol), and CataCXIum Pd G4 (59 mg, 0.079 mmol) were added. The mixture was bubbled with dry nitrogen gas and stirred at 80° C. 1 hr before additional 2-iodo-5-(trifluoromethyl)pyrimidine (108 mg, 0.39 mmol) was added. Stirred for 2 hr at 80° C. The reaction was then cooled, diluted with EtOAc and filtered through a plug of Celite©. The volatiles were evaporated in vacuo and the residue purified via flash chromatography (100% hexanes to 100% EtOAc) to give methyl (2R)-2-(tert-butoxycarbonylamino)-5-[7-fluoro-1-oxo-6-[5-(trifluoromethyl)pyrimidin-2-yl]-2-isoquinolyl]pentanoate. ES/MS m/z: 539.2 $[M+H]^+$.

Step 2. Methyl (2R)-2-(tert-butoxycarbonylamino)-5-[7-fluoro-1-oxo-6-[5-(trifluoromethyl)pyrimidin-2-yl]-2-isoquinolyl]pentanoate (758 mg, 1.1 mmol) was dissolved in THF (5.0 mL), MeOH (2.0 mL), and Water (1.0 mL). This was stirred rapidly at ambient temperature and treated with lithium hydroxide (33 mg, 1.4 mmol). After 90 minutes, LC/MS indicated partial conversion and additional Lithium hydroxide (17 mg, 0.70 mmol) was added. The reaction was stirred for an additional 90 minutes and then quenched with 10% aq. $KHSO_4$ and extracted 3× with EtOAc. The organics were washed with brine, dried over $MgSO_4$, filtered, and evaporated to yield (2R)-2-(tert-butoxycarbonylamino)-5-[7-fluoro-1-oxo-6-[5-(trifluoromethyl)pyrimidin-2-yl]-2-isoquinolyl]pentanoic acid which was used directly in the next step.

Step 3. (2R)-2-(tert-butoxycarbonylamino)-5-[7-fluoro-1-oxo-6-[5-(trifluoromethyl)pyrimidin-2-yl]-2-isoquinolyl] pentanoic acid (319 mg, 0.55 mmol) was dissolved in THF (6.4 mL) and was treated with TEA (0.15 mL, 1.1 mmol). The solution was then cooled to 0° C. and stirred rapidly. Isobutyl chloroformate (85 µL, 0.66 mmol) was added and the reaction maintained at 0° C. for 30 minutes at which point precipitated solids were filtered off and rinsed with minimal THF. The filtrate was slowly added to a rapidly stirred mixture of sodium borohydride (41 mg, 1.1 mmol) in THF (6.4 mL) and water (3.2 mL) that was held at 0° C. The reaction was stirred for a further hour at 0° C. and then was quenched with 10% aq. $KHSO_4$ and extracted 3× with EtOAc. The organics were dried over $MgSO_4$, filtered, and evaporated to yield crude material which was purified via flash column chromatography (100% hexanes to 100% EtOAc) to give tert-butyl N-[(1R)-4-[7-fluoro-1-oxo-6-[5-(trifluoromethyl)pyrimidin-2-yl]-2-isoquinolyl]-1-(hydroxymethyl)butyl]carbamate. ES/MS m/z: 511.1 $[M+H]^+$.

Step 4. tert-butyl N-[(1R)-4-[7-fluoro-1-oxo-6-[5-(trifluoromethyl)pyrimidin-2-yl]-2-isoquinolyl]-1-(hydroxymethyl)butyl]carbamate (124 mg, 0.22 mmol) was dissolved in DCM (2.0 mL) and stirred at ambient temperature. TFA (0.17 mL, 2.2 mmol) was added and the reaction stirred for 90 minutes before removing the volatiles in vacuo. This gave crude 2-[(4R)-4-amino-5-hydroxy-pentyl]-7-fluoro-6-[5-(trifluoromethyl)pyrimidin-2-yl]isoquinolin-1-one which was carried forward directly into the next step assuming quantitative yield.

Step 5. 2-[(4R)-4-amino-5-hydroxy-pentyl]-7-fluoro-6-[5-(trifluoromethyl)pyrimidin-2-yl]isoquinolin-1-one (90 mg, 0.22 mmol) and 5-chloro-4-(trifluoromethyl)-2-(2-trimethylsilylethoxymethyl)pyridazin-3-one (79 mg, 0.24 mmol) were dissolved in ACN (2.0 mL) and treated with DIPEA (0.38 mL, 2.2 mmol). The reaction was then stirred at 60° C. for 1 hour before cooling. 10% aq. $KHSO_4$ was added and the mixture extracted 3× with EtOAc. The organics were dried over $Na_2SO_4$, filtered, and evaporated to yield crude material which was purified via flash column chromatography (100% hexanes to 100% EtOAc) to give 7-fluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one. ES/MS m/z: 703.2 $[M+H]^+$.

Step 6. 7-fluoro-2-[(4R)-5-hydroxy-4-[[6-oxo-5-(trifluoromethyl)-1-(2-trimethylsilylethoxymethyl)pyridazin-4-yl] amino]pentyl]-6-[5-(trifluoromethyl)pyrimidin-2-yl]isoquinolin-1-one (65 mg, 0.093 mmol) was dissolved in DCM (2.0 mL) and stirred at ambient temperature. TFA (71 µL, 0.93 mmol) was added and the reaction stirred for 1 hour before being evaporated to dryness. The residue was then dissolved in MeOH (1.0 mL) and treated with ethylenediamine (62 µL, 0.93 mmol). After 30 minutes, the reaction was evaporated and the residue purified via reverse phase prep-HPLC (5-100% MeCN in water, 0.1% TFA) to afford 7-fluoro-2-[(4R)-5-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one. 1H NMR (400 MHz, DMSO-d6) δ 12.41 (s, 1H), 9.48 (d, J=1.0 Hz, 2H), 8.44 (d, J=7.1 Hz, 1H), 8.03 (d, J=11.4 Hz, 1H), 7.94 (s, 1H), 7.53 (d, J=7.4 Hz, 1H), 6.85 (d, J=7.4 Hz, 1H), 6.30-6.22 (m, 1H), 4.00 (t, J=6.9 Hz, 2H), 3.96-3.87 (m, 1H), 3.46 (d, J=4.9 Hz, 2H), 1.83-1.69 (m, 2H), 1.63-1.54 (m, 2H). ES/MS m/z: 573.3 $[M+H]^+$.

Example 89: Preparation of 2-[(4S)-2,2-difluoro-4-[[6-oxo-5-(trifluoromethyl)-1H-pyridazin-4-yl] amino]pentyl]-7-fluoro-6-[5-(trifluoromethyl)pyrimidin-2-yl]isoquinolin-1-one

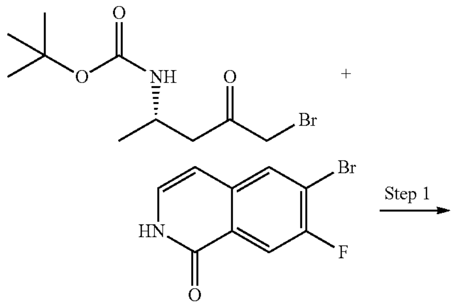

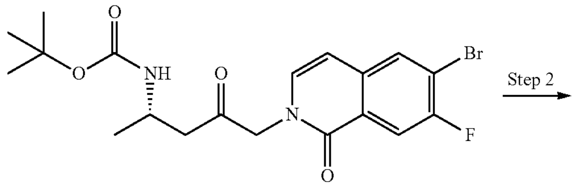

Intermediate 10

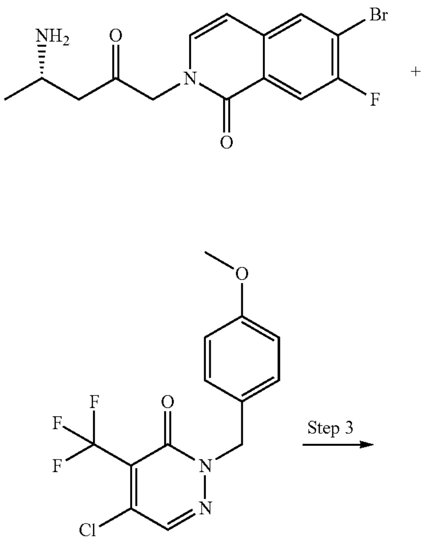

-continued

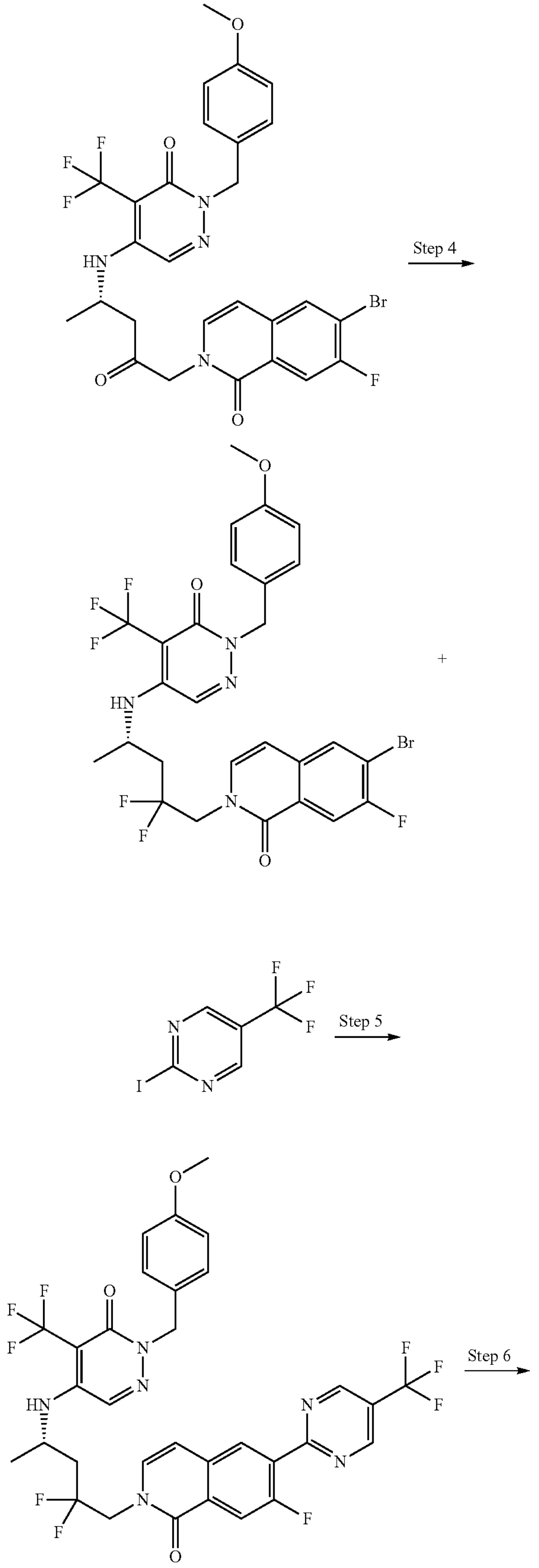

-continued

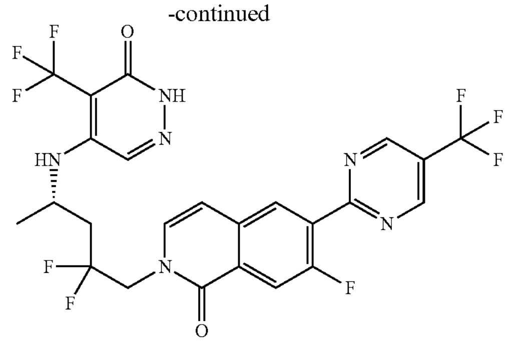

Example 89

Step 1. In a vial were placed 6-bromo-7-fluoro-2H-isoquinolin-1-one (900 mg, 3.72 mmol), tert-butyl N-[(1S)-4-bromo-1-methyl-3-oxo-butyl]carbamate (1.04 g, 3.72 mmol), and cesium carbonate (2.42 g, 7.44 mmol) in DMF (20.0 mL). After mixture was stirred at room temperature for 16 hr, it was filtered through a pad of celite with EtOAc and concentrated. Purified by flash chromatography (100% hexanes to 100% EtOAc) to give tert-butyl N-[(1S)-4-(6-bromo-7-fluoro-1-oxo-2-isoquinolyl)-1-methyl-3-oxo-butyl]carbamate, intermediate 10. ES/MS m/z: 442.9 $[M+H]^+$.

Step 2. In a vial were placed intermediate 10 (982 mg, 2.23 mmol), trifluoroacetic acid (4.40 mL) and DCM (4.40 mL). The mixture was stirred at room temperature for 2 hours before being concentrated to give 2-[(4S)-4-amino-2-oxo-pentyl]-6-bromo-7-fluoro-isoquinolin-1-one. ES/MS m/z: 342.8 $[M+H]^+$.p Step 3. In a vial were placed 2-[(4S)-4-amino-2-oxo-pentyl]-6-bromo-7-fluoro-isoquinolin-1-one (759 mg, 2.22 mmol), 5-chloro-2-[(4-methoxyphenyl)methyl]-4-(trifluoromethyl)pyridazin-3-one (1.06 g, 3.34 mmol), triethylamine (1.55 mL, 11.1 mmol) and DMF (8.80 mL). The mixture was heated to 85° C. and stirred for 3 hours before being concentrated. Purified by flash chromatography (100% hexanes to 100% EtOAc) to give 6-bromo-7-fluoro-2-[(4S)-4-[[1-[(4-methoxyphenyl)methyl]-6-oxo-5-(trifluoromethyl)pyridazin-4-yl]amino]-2-oxo-pentyl]isoquinolin-1-one. ES/MS m/z: 624.9 $[M+H]^+$.

Step 4. In a vial were placed 6-bromo-7-fluoro-2-[(4S)-4-[[1-[(4-methoxyphenyl)methyl]-6-oxo-5-(trifluoromethyl)pyridazin-4-yl]amino]-2-oxo-pentyl]isoquinolin-1-one (100 mg, 0.16 mmol) and diethylaminosulfur trifluoride (0.06 mL, 0.48 mmol) in DCM (1.6 mL) at 0° C. After stirring overnight, the reaction is cooled to 0° C. and diethylaminosulfur trifluoride (0.11 mL, 0.80 mmol) is added dropwise. After 1 hour, the reaction is heated to 40° C. After stirring overnight, the reaction is purified by flash chromatography (100% hexanes to 100% EtOAc) to give 6-bromo-2-[(4S)-2,2-difluoro-4-[[1-[(4-methoxyphenyl)methyl]-6-oxo-5-(trifluoromethyl)pyridazin-4-yl]amino]pentyl]-7-fluoro-isoquinolin-1-one. ES/MS m/z: 646.9 $[M+H]^+$.

Step 5. In a vial were placed 6-bromo-2-[(4S)-2,2-difluoro-4-[[1-[(4-methoxyphenyl)methyl]-6-oxo-5-(trifluoromethyl)pyridazin-4-yl]amino]pentyl]-7-fluoro-isoquinolin-1-one (35 mg, 0.05 mmol), 1,1'-Bis(diphenylphosphino)ferrocene-palladium(II)dichloride dichloromethane complex (8.8 mg, 0.01 mmol), potassium acetate (16 mg, 0.16 mmol), and bis(pinacolato)diboron (41 mg, 0.16 mmol) in dioxane (1.0 mL). The mixture was heated to 100° C. and stirred for 3 hours, followed by the addition of cesium carbonate (52 mg, 0.16 mmol), cataCXium Pd G4 (4 mg, 0.005 mmol), 2-iodo-5-(trifluoromethyl)pyrimidine (22 mg, 0.08 mmol), and water (0.2 mL). The reaction was then stirred for an additional hour at 90° C. Upon completion, the mixture was directly purified by flash chromatography (100% hexanes to 100% EtOAc) to give 2-[(4S)-2,2-difluoro-4-[[1-[(4-methoxyphenyl)methyl]-6-oxo-5-(trifluoromethyl)pyridazin-4-yl]amino]pentyl]-7-fluoro-6-[5-(trifluoromethyl)pyrimidin-2-yl]isoquinolin-1-one. ES/MS m/z: 713.7 $[M+H]^+$.

Step 6. In a vial were placed 7-fluoro-2-[(4S)-4-[[1-[(4-methoxyphenyl)methyl]-6-oxo-5-(trifluoromethyl) pyridazin-4-yl]amino]-2-oxo-pentyl]-6-[5-(trifluoromethyl) pyrimidin-2-yl]isoquinolin-1-one (50 mg, 0.72 mmol), trifluoroacetic acid (1.0 mL), and sulfuric acid (0.2 mL). The reaction was heated to 50° C. and stirred for 5 hours and purified by prep HPLC to give 2-[(4S)-2,2-difluoro-4-[[6-oxo-5-(trifluoromethyl)-1H-pyridazin-4-yl]amino]pentyl]-7-fluoro-6-[5-(trifluoromethyl)pyrimidin-2-yl]isoquinolin-1-one. $^1$H NMR (400 MHz, DMSO-d6) δ 12.47 (s, 1H), 9.49 (d, J=1.0 Hz, 2H), 8.46 (d, J=7.1 Hz, 1H), 8.07 (d, J=11.3 Hz, 1H), 7.96 (s, 1H), 7.43 (d, J=7.5 Hz, 1H), 6.88 (d, J=7.5 Hz, 1H), 6.67-6.53 (m, 1H), 4.70-4.46 (m, 2H), 4.40 (s, 1H), 2.58 (dq, J=15.1, 8.2, 7.3 Hz, 1H), 2.37-2.13 (m, 1H), 1.25 (d, J=6.4 Hz, 3H). ES/MS m/z: 593.3 $[M+H]^+$.

Example 90: Preparation of 7-fluoro-2-[(4S)-2-oxo-4-[[6-oxo-5-(trifluoromethyl)-1H-pyridazin-4-yl]amino]pentyl]-6-[5-(trifluoromethyl)pyrimidin-2-yl]isoquinolin-1-one

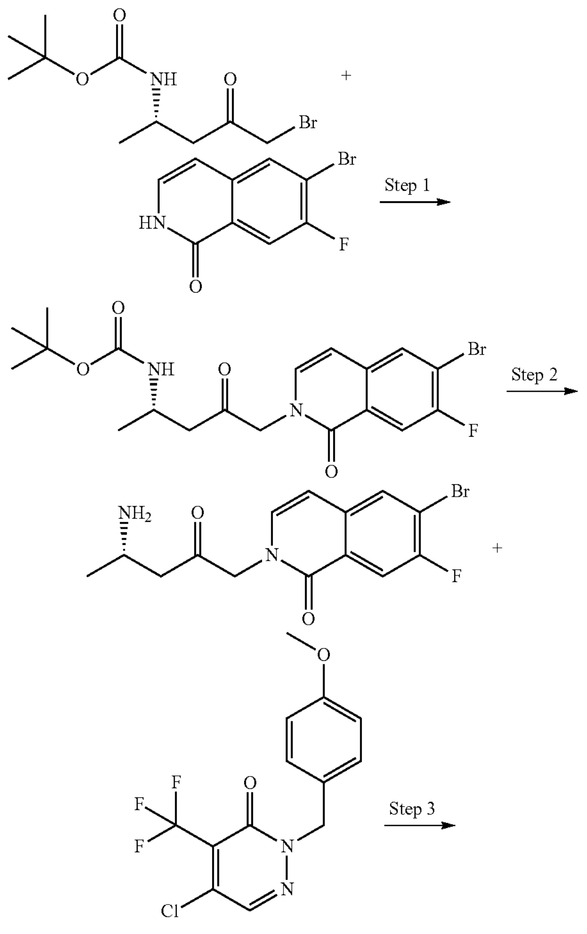

-continued

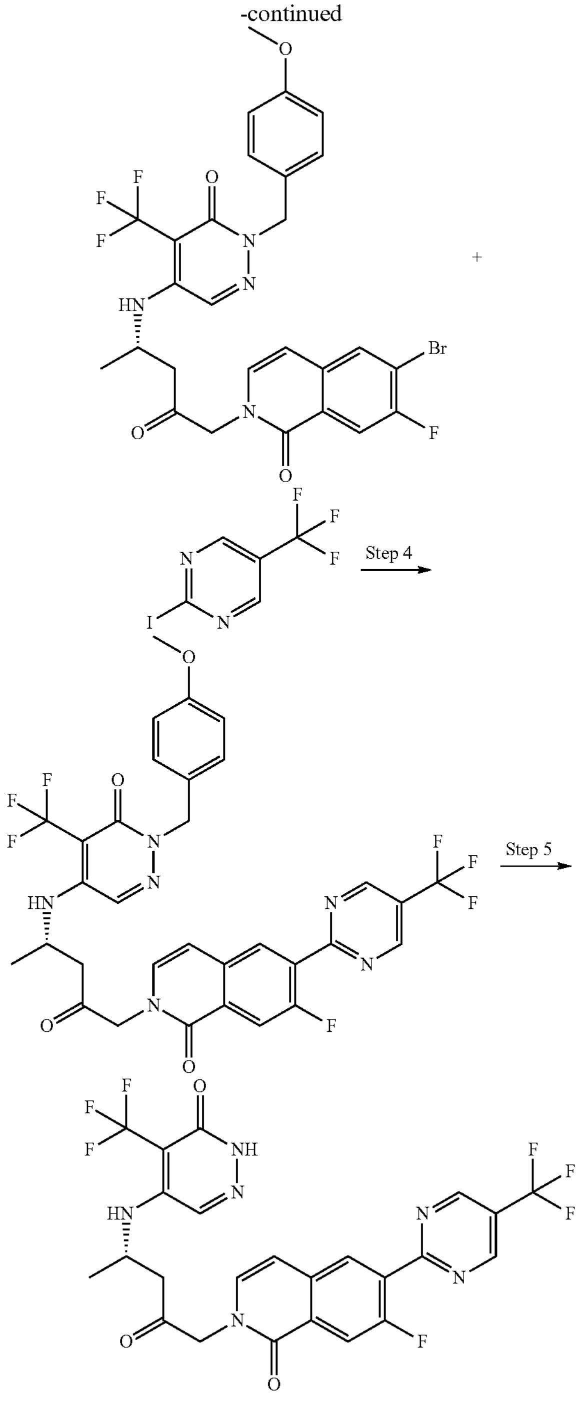

Example 90

Step 1. In a vial were placed 6-bromo-7-fluoro-2H-isoquinolin-1-one (900 mg, 3.72 mmol), tert-butyl N-[(1S)-4-bromo-1-methyl-3-oxo-butyl]carbamate (1.04 g, 3.72 mmol), and cesium carbonate (2.42 g, 7.44 mmol) in DMF (20.0 mL). After mixture was stirred at room temperature for 16 hr, it was filtered through a pad of Celite® with EtOAc and concentrated. Purified by flash chromatography (100% hexanes to 100% EtOAc) to give tert-butyl N-[(1S)-4-(6-bromo-7-fluoro-1-oxo-2-isoquinolyl)-1-methyl-3-oxo-butyl]carbamate. ES/MS m/z: 442.9 $[M+H]^+$.

Step 2. In a vial were placed tert-butyl N-[(1S)-4-(6-bromo-7-fluoro-1-oxo-2-isoquinolyl)-1-methyl-3-oxo-butyl]carbamate (982 mg, 2.23 mmol), trifluoroacetic acid (4.40 mL) and DCM (4.40 mL). The mixture was stirred at room temperature for 2 hours before being concentrated to give 2-[(4S)-4-amino-2-oxo-pentyl]-6-bromo-7-fluoro-isoquinolin-1-one. ES/MS m/z: 342.8 $[M+H]^+$.p Step 3. In a vial were placed 2-[(4S)-4-amino-2-oxo-pentyl]-6-bromo-7-fluoro-isoquinolin-1-one (759.0 mg, 2.22 mmol), 5-chloro-2-[(4-methoxyphenyl)methyl]-4-(trifluoromethyl)pyridazin-3-one (1.06 g, 3.34 mmol), triethylamine (1.55 mL, 11.1 mmol) and DMF (8.80 mL). The mixture was heated to 85° C. and stirred for 3 hrs before being concentrated. Purified by flash chromatography (100% hexanes to 100% EtOAc) to give 6-bromo-7-fluoro-2-[(4S)-4-[[1-[(4-methoxyphenyl)methyl]-6-oxo-5-(trifluoromethyl)pyridazin-4-yl]amino]-2-oxo-pentyl]isoquinolin-1-one. ES/MS m/z: 624.9 $[M+H]^+$.

Step 4. In a vial were placed 6-bromo-7-fluoro-2-[(4S)-4-[[1-[(4-methoxyphenyl)methyl]-6-oxo-5-(trifluoromethyl)pyridazin-4-yl]amino]-2-oxo-pentyl]isoquinolin-1-one (662 mg, 1.06 mmol), 1,1'-Bis(diphenylphosphino)ferrocene-palladium(II)dichloride dichloromethane complex (173 mg, 0.21 mmol), potassium acetate (313 mg, 3.19 mmol), and bis(pinacolato)diboron (809 mg, 3.19 mmol) in dioxane (10.0 mL). The mixture was heated to 100° C. and stirred for 3 hours, followed by the addition of cesium carbonate (1.04 g, 3.19 mmol), cataCXium Pd G4 (79 mg, 0.11 mmol), 2-iodo-5-(trifluoromethyl)pyrimidine (436 mg, 1.59 mmol), and water (2.5 mL). The reaction was then stirred for an additional hour at 80° C. Upon completion, the mixture was directly purified by flash chromatography (100% hexanes to 100% EtOAc) to give 7-fluoro-2-[(4S)-4-[[1-[(4-methoxyphenyl)methyl]-6-oxo-5-(trifluoromethyl)pyridazin-4-yl]amino]-2-oxo-pentyl]-6-[5-(trifluoromethyl)pyrimidin-2-yl]isoquinolin-1-one. ES/MS m/z: 691.1 $[M+H]^+$.

Step 5. In a vial were placed 7-fluoro-2-[(4S)-4-[[1-[(4-methoxyphenyl)methyl]-6-oxo-5-(trifluoromethyl)pyridazin-4-yl]amino]-2-oxo-pentyl]-6-[5-(trifluoromethyl)pyrimidin-2-yl]isoquinolin-1-one (50 mg, 0.72 mmol), trifluoroacetic acid (1.0 mL), and sulfuric acid (0.2 mL). The reaction was heated to 50° C. and stirred for 4 hours and purified by prep HPLC to give 7-fluoro-2-[(4S)-2-oxo-4-[[6-oxo-5-(trifluoromethyl)-1H-pyridazin-4-yl]amino]pentyl]-6-[5-(trifluoromethyl)pyrimidin-2-yl]isoquinolin-1-one. $^1$H NMR (400 MHz, DMSO-d6) δ 12.47 (s, 1H), 9.49 (s, 2H), 8.46 (d, J=7.1 Hz, 1H), 8.08-7.89 (m, 2H), 7.38 (d, J=7.3 Hz, 1H), 6.86 (d, J=7.4 Hz, 1H), 6.57 (dd, J=9.0, 4.2 Hz, 1H), 4.40 (q, J=7.1, 6.6 Hz, 1H), 3.00 (ddd, J=98.8, 17.5, 6.1 Hz, 2H), 1.23 (dd, J=13.3, 6.4 Hz, 3H). ES/MS m/z: 571.3 $[M+H]^+$.

Example 91: Preparation of 7-fluoro-2-[[3-[[6-oxo-5-(trifluoromethyl)-1H-pyridazin-4-yl]amino]phenyl]methyl]-6-[5-(trifluoromethyl)pyrimidin-2-yl]isoquinolin-1-one

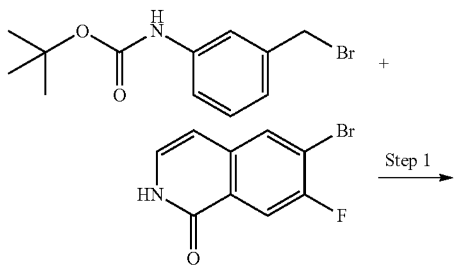

-continued

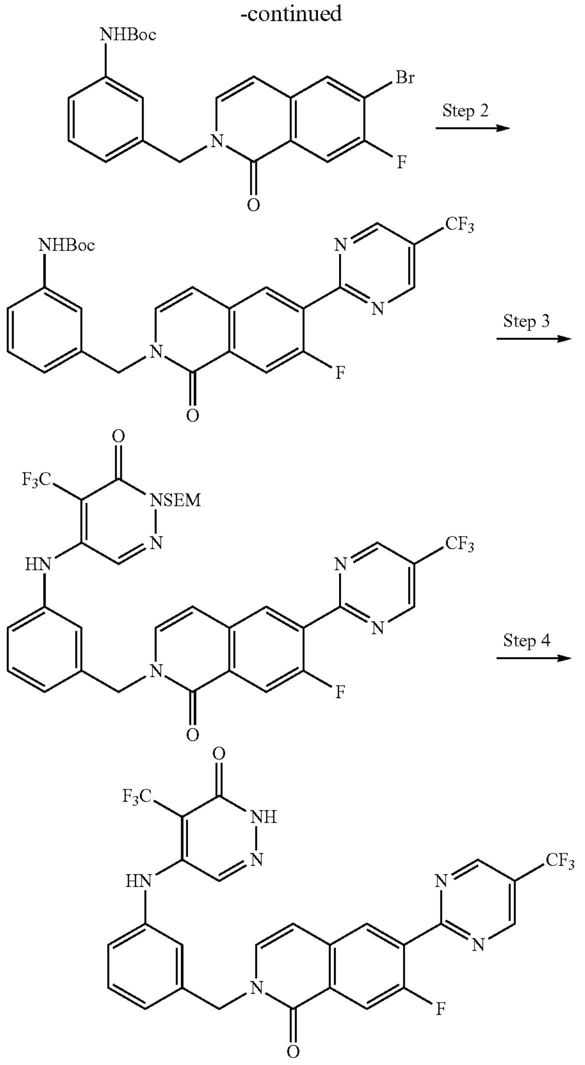

Example 91

Step 1. In a vial were placed 6-Bromo-7-fluoro-1,2-dihydroisoquinolin-1-one (300 mg, 1.24 mmol), tert-butyl N-[3-(bromomethyl)phenyl]carbamate (355 mg, 1.24 mmol), and cesium carbonate (1.21 g, 3.72 mmol) in DMF (10.0 mL). After mixture was stirred at room temperature for 16 hr, it was quenched with water and extracted with EtOAc (×3). The combined organic layers were washed with water and brine, dried ($Na_2SO_4$), and purified by flash chromatography (100% hexanes to 100% EtOAc) to give tert-butyl N-[13-[(6-bromo-7-fluoro-1-oxo-2-isoquinolyl)methyl]phenyl]carbamate. ES/MS m/z: 448.2 $[M+H]^+$.

Step 2. In a vial were placed tert-butyl N-[3-[(6-bromo-7-fluoro-1-oxo-2-isoquinolyl)methyl]phenyl]carbamate (500 mg, 1.12 mmol), 1,1'-Bis(diphenylphosphino)ferrocene-palladium(II)dichloride dichloromethane complex (91.0 mg, 0.112 mmol), potassium acetate (329 mg, 3.35 mmol), and bis(pinacolato)diboron (426.0 mg, 1.68 mmol) in dioxane (7.00 mL). The mixture was heated to 100° C. and stirred for 2 hrs, followed by the addition of 2 M aqueous sodium carbonate (1.68 mL, 3.36 mmol) and 2-iodo-5-(trifluoromethyl)pyrimidine (46 mg, 1.68 mmol), and 1,1'-Bis(diphenylphosphino)ferrocene-palladium(II)dichloride dichloromethane complex (91 mg, 0.112 mmol).

The reaction was then stirred for an additional hour at 100° C. Upon completion, the mixture was quenched with water and extracted with EtOAc (×3). The combined organic layers were washed with water and brine, dried ($Na_2SO_4$), and purified by flash chromatography (100% hexanes to 100% EtOAc) to give tert-butyl N-[3-[[7-fluoro-1-oxo-6-[5-(trifluoromethyl)pyrimidin-2-yl]-2-isoquinolyl]methyl]phenyl]carbamate. ES/MS m/z: 515.0 $[M+H]^+$.

Step 3. In a vial were placed tert-butyl N-[3-[[7-fluoro-1-oxo-6-[5-(trifluoromethyl)pyrimidin-2-yl]-2-isoquinolyl]methyl]phenyl]carbamate (482 mg, 0.937 mmol), and trifluoroacetic acid (1.06 mL, 18.7 mmol) in DCM (5.0 mL). After the mixture was stirred for 1 hr, it was concentrated under vacuum. The resulting material was partitioned between EtOAc and water. The organic layer was separated and washed with brine, dried ($Na_2SO_4$), and concentrated to afford 2-[(3-aminophenyl)methyl]-7-fluoro-6-[5-(trifluoromethyl)pyrimidin-2-yl]isoquinolin-1-one. ES/MS m/z: 415.0 $[M+H]^+$. In a vial were placed 2-[(3-aminophenyl)methyl]-7-fluoro-6-[5-(trifluoromethyl)pyrimidin-2-yl]isoquinolin-1-one (100 mg, 0.24 mmol), 5-chloro-4-(trifluoromethyl)-2-(2-trimethylsilylethoxymethyl)pyridazin-3-one (95 mg, 0.29 mmol), RuPhos Pd G4 (40 mg, 0.048 mmol) and Cesium carbonate (236 mg, 0.72 mmol) in toluene (2.00 mL). The mixture was heated to 80° C. and stirred for 5 mins, and then quenched with water and extracted with EtOAc (×3). The combined organic layers were washed with water and brine, dried ($MgSO_4$), and purified by flash chromatography (100% hexanes to 100% EtOAc) to give 7-fluoro-2-[[3-[[6-oxo-5-(trifluoromethyl)-1-(2-trimethylsilylethoxymethyl)pyridazin-4-yl]amino]phenyl]methyl]-6-[5-(trifluoromethyl)pyrimidin-2-yl]isoquinolin-1-one. ES/MS m/z: 707.12 $[M+H]^+$.

Step 4. In a vial were placed 7-fluoro-2-[[3-[[6-oxo-5-(trifluoromethyl)-1-(2-trimethylsilylethoxymethyl)pyridazin-4-yl]amino]phenyl]methyl]-6-[5-(trifluoromethyl)pyrimidin-2-yl]isoquinolin-1-one (120 mg, 0.17 mmol) and trifluoroacetic acid (0.79 mL) in DCM (2.00 mL) and the mixture was stirred for 1 hr at room temperature and concentrated under vacuum. The resulting product was dissolved in methanol (2.0 mL) and ethylenediamine (0.11 mL, 1.7 mmol) was added and stirred for 15 minutes, and then was concentrated under vacuum. The crude product was purified by reverse phase prep-HPLC (5-100% MeCN in water, 0.1% TFA) to afford 7-fluoro-2-[[3-[[6-oxo-5-(trifluoromethyl)-1H-pyridazin-4-yl]amino]phenyl]methyl]-6-[5-(trifluoromethyl)pyrimidin-2-yl]isoquinolin-1-one. 1H NMR (400 MHz, DMSO-d6) δ 12.66 (s, 1H), 9.48 (d, J=0.9 Hz, 2H), 9.00 (d, J=2.4 Hz, 1H), 8.46 (d, J=7.2 Hz, 1H), 8.06 (d, J=11.3 Hz, 1H), 7.68 (d, J=7.4 Hz, 1H), 7.56-7.30 (m, 2H), 7.34-7.19 (m, 3H), 6.90 (d, J=7.4 Hz, 1H), 5.23 (s, 2H). ES/MS m/z: 577.2 105 $[M+H]^+$.

Example 92: (S)-6-(5-(dimethylamino)pyrimidin-2-yl)-7-fluoro-2-(4-((6-oxo-5-(trifluoromethyl)-1,6-dihydropyridazin-4-yl)amino)pentyl)isoquinolin-1(2H)-one Example 92

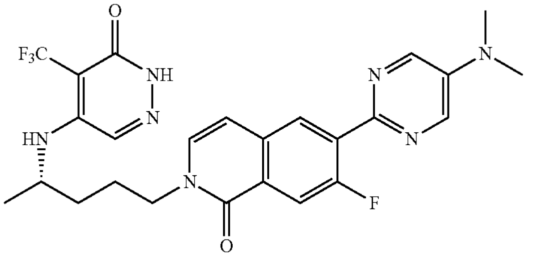

The title compound was synthesized as described in Example 17, using 6-bromo-7-fluoroisoquinolin-1(2H)-one instead of 6-bromoisoquinolin-1(2H)-one in Step 1, and using 2-chloro-N,N-dimethyl-pyrimidin-5-amine instead of 2-iodo-5-(trifluoromethyl)pyrimidine in Step 3. In Step 3, XPhos Pd G4 (0.1 equiv) was added along with the aryl halide and the resulting penultimate material was purified by flash chromatography. Final deprotection gave (S)-6-(5-(dimethylamino)pyrimidin-2-yl)-7-fluoro-2-(4-((6-oxo-5-(trifluoromethyl)-1,6-dihydropyridazin-4-yl)amino)pentyl)isoquinolin-1(2H)-one. $^1H$ NMR (400 MHz, DMSO-d6) δ 12.45 (s, 1H), 8.45 (s, 2H), 8.26 (d, J=7.4 Hz, 1H), 7.97-7.89 (m, 2H), 7.46 (d, J=7.4 Hz, 1H), 6.77 (d, J=7.4 Hz, 1H), 6.40-6.32 (m, 1H), 4.05-3.95 (m, 3H), 3.06 (s, 6H), 1.59-1.82 (m, 3H), 1.57-1.46 (m, 1H), 1.18 (d, J=6.3 Hz, 3H). ES/MS: m/z 532.2 $[M+H]^+$.

Example 93: (S)-7-fluoro-6-(5-(1-methyl-5-(trifluoromethyl)-1H-pyrazol-3-yl)pyrimidin-2-yl)-2-(4-((6-oxo-5-(trifluoromethyl)-1,6-dihydropyridazin-4-yl)amino)pentyl)isoquinolin-1(2H)-one Example 93

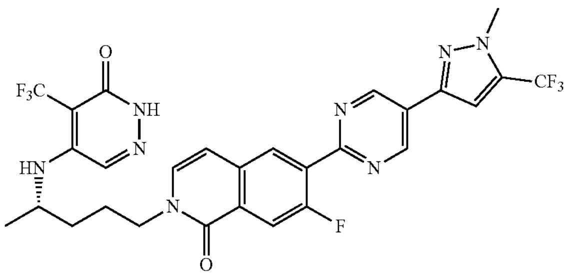

The title compound was synthesized as described in Example 17, using 6-bromo-7-fluoroisoquinolin-1(2H)-one instead of 6-bromoisoquinolin-1(2H)-one in Step 1, and using 3-chloro-1-methyl-5-(trifluoromethyl)pyrazole instead of 2-iodo-5-(trifluoromethyl)pyrimidine in Step 3. In Step 3, XPhos Pd G4 (0.1 equiv) was added along with the aryl halide and the resulting penultimate material was purified by flash chromatography. Final deprotection gave (S)-7-fluoro-6-(5-(1-methyl-5-(trifluoromethyl)-1H-pyrazol-3-yl)pyrimidin-2-yl)-2-(4-((6-oxo-5-(trifluoromethyl)-1,6-dihydropyridazin-4-yl)amino)pentyl)isoquinolin-1(2H)-one. $^1H$ NMR (400 MHz, DMSO-d6) δ 12.44 (s, 1H), 8.26 (d, J=7.2 Hz, 1H), 7.97 (d, J=11.7 Hz, 1H), 7.92 (s, 1H), 7.47 (d, J=7.4 Hz, 1H), 7.31 (d, J=3.2 Hz, 1H), 6.76 (d, J=7.4 Hz, 1H), 6.39-6.30 (m, 1H), 4.09 (s, 3H), 3.98 (t, J=6.7 Hz, 3H), 1.81-1.60 (m, 3H), 1.58-1.44 (m, 1H), 1.17 (d, J=6.3 Hz, 3H). ES/MS: m/z 559.3 $[M+H]^+$.

Example 94: (S)-6-(6,7-dihydro-5H-cyclopenta[d]pyrimidin-2-yl)-7-fluoro-2-(4-((6-oxo-5-(trifluoromethyl)-1,6-dihydropyridazin-4-yl)amino)pentyl)isoquinolin-1(2H)-one Example 94

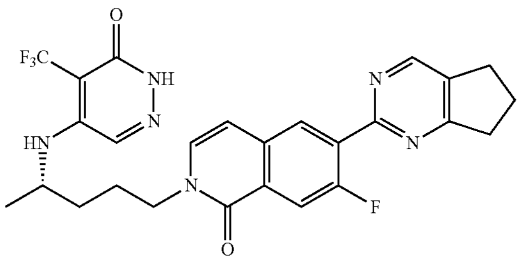

The title compound was synthesized as described in Example 17, using 6-bromo-7-fluoroisoquinolin-1(2H)-one instead of 6-bromoisoquinolin-1(2H)-one in Step 1, and using 2-chloro-6,7-dihydro-5H-cyclopenta[d]pyrimidine instead of 2-iodo-5-(trifluoromethyl)pyrimidine in Step 3. In Step 3, XPhos Pd G4 (0.1 equiv) was added along with the aryl halide and the resulting penultimate material was purified by flash chromatography. Final deprotection gave (S)-6-(6,7-dihydro-5H-cyclopenta[d]pyrimidin-2-yl)-7-fluoro-2-(4-((6-oxo-5-(trifluoromethyl)-1,6-dihydropyridazin-4-yl)amino)pentyl)isoquinolin-1(2H)-one. $^1$H NMR (400 MHz, DMSO-d6) δ 12.45 (s, 1H), 8.80-8.75 (m, 1H), 8.28 (d, J=7.2 Hz, 1H), 7.97 (d, J=11.3 Hz, 1H), 7.93 (s, 1H), 7.49 (d, J=7.4 Hz, 1H), 6.81 (d, J=7.4 Hz, 1H), 6.41-6.31 (m, 1H), 4.05-3.94 (m, 3H), 3.07-2.96 (m, 4H), 2.14 (p, J=7.7 Hz, 2H), 1.82-1.60 (m, 3H), 1.59-1.45 (m, 1H), 1.18 (d, J=6.3 Hz, 3H). ES/MS: m/z 529.3 [M+H]$^+$.

Example 95: (S)-6-fluoro-7-(5-methylpyrimidin-2-yl)-3-(4-((6-oxo-5-(trifluoromethyl)-1,6-dihydropyridazin-4-yl)amino)pentyl)quinazolin-4(3H)-one Example 95

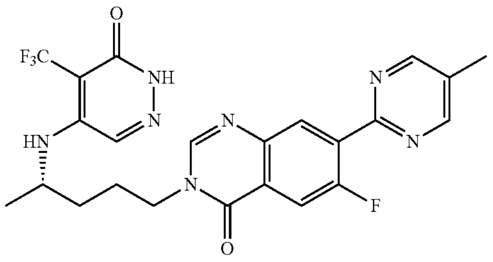

The title compound was synthesized as described in Example 17, using 7-bromo-6-fluoroquinazolin-4(3H)-one instead of 6-bromoisoquinolin-1(2H)-one in Step 1, and using 2-bromo-5-methyl-pyrimidine instead of 2-iodo-5-(trifluoromethyl)pyrimidine in Step 3. In Step 3, XPhos Pd G4 (0.1 equiv) was added along with the aryl halide and the resulting penultimate material was purified by flash chromatography. Final deprotection gave (S)-6-fluoro-7-(5-methylpyrimidin-2-yl)-3-(4-((6-oxo-5-(trifluoromethyl)-1,6-dihydropyridazin-4-yl)amino)pentyl)quinazolin-4(3H)-one. $^1$H NMR (400 MHz, DMSO-d6) δ 12.44 (s, 1H), 8.90-8.84 (m, 2H), 8.43 (s, 1H), 8.23 (d, J=6.8 Hz, 1H), 7.94 (d, J=10.5 Hz, 1H), 7.92 (s, 1H), 6.39-6.31 (m, 1H), 4.05-3.93 (m, 3H), 2.37 (s, 3H), 1.82-1.61 (m, 3H), 1.53 (t, J=11.6 Hz, 1H), 1.17 (d, J=6.3 Hz, 3H). ES/MS: m/z 504.3 [M+H]$^+$.

Example 96: (S)-6-(5-amino-4-fluoropyridin-2-yl)-7-fluoro-2-(4-((6-oxo-5-(trifluoromethyl)-1,6-dihydropyridazin-4-yl)amino)pentyl)isoquinolin-1(2H)-one Example 96

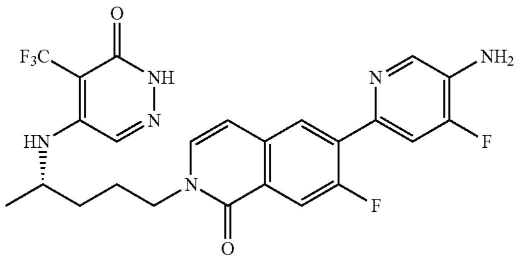

The title compound was synthesized as described in Example 17, using 6-bromo-7-fluoroisoquinolin-1(2H)-one instead of 6-bromoisoquinolin-1(2H)-one in Step 1, and using tert-butyl N-(6-chloro-4-fluoro-3-pyridyl)carbamate instead of 2-iodo-5-(trifluoromethyl)pyrimidine in Step 3. In Step 3, XPhos Pd G4 (0.1 equiv) was added along with the aryl halide and the resulting penultimate material was purified by flash chromatography. Final deprotection gave (S)-6-(5-amino-4-fluoropyridin-2-yl)-7-fluoro-2-(4-((6-oxo-5-(trifluoromethyl)-1,6-dihydropyridazin-4-yl)amino)pentyl)isoquinolin-1(2H)-one. $^1$H NMR (400 MHz, DMSO-d6) δ 12.43 (s, 1H), 8.29 (d, J=11.3 Hz, 1H), 8.21 (d, J=7.6 Hz, 1H), 7.97-7.89 (m, 2H), 7.65 (dd, J=12.7, 1.3 Hz, 1H), 7.46 (d, J=7.4 Hz, 1H), 6.74 (d, J=7.4 Hz, 1H), 6.40-6.26 (m, 1H), 4.04-3.92 (m, 3H), 1.81-1.59 (m, 3H), 1.56-1.45 (m, 1H), 1.17 (d, J=6.3 Hz, 3H). ES/MS: m/z 523.1 [M+H]$^+$.

Example 97: (S)-6-(5-amino-4-(trifluoromethyl)pyridin-2-yl)-7-fluoro-2-(4-((6-oxo-5-(trifluoromethyl)-1,6-dihydropyridazin-4-yl)amino)pentyl)isoquinolin-1(2H)-one Example 97

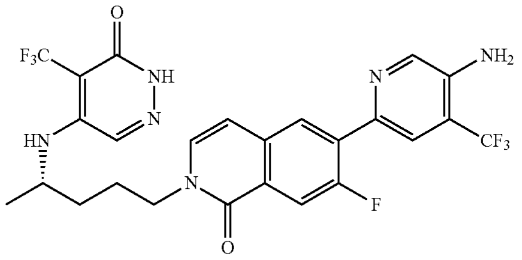

The title compound was synthesized as described in Example 17, using 6-bromo-7-fluoroisoquinolin-1(2H)-one instead of 6-bromoisoquinolin-1(2H)-one in Step 1, and using 6-chloro-4-(trifluoromethyl)pyridin-3-amine instead of 2-iodo-5-(trifluoromethyl)pyrimidine in Step 3. In Step 3, XPhos Pd G4 (0.1 equiv) was added along with the aryl halide and the resulting penultimate material was purified by flash chromatography. Final deprotection gave (S)-6-(5-amino-4-(trifluoromethyl)pyridin-2-yl)-7-fluoro-2-(4-((6-oxo-5-(trifluoromethyl)-1,6-dihydropyridazin-4-yl)amino)pentyl)isoquinolin-1(2H)-one. $^{1}$H NMR (400 MHz, DMSO-d6) δ 12.43 (s, 1H), 8.43 (s, 1H), 8.24 (d, J=7.7 Hz, 1H), 7.97-7.89 (m, 2H), 7.79 (s, 1H), 7.45 (d, J=7.4 Hz, 1H), 6.76 (d, J=7.4 Hz, 1H), 6.54-6.39 (m, 2H), 6.40-6.31 (m, 1H), 4.02-3.93 (m, 3H), 1.79-1.58 (m, 3H), 1.56-1.45 (m, 1H), 1.17 (d, J=6.3 Hz, 3H). ES/MS: m/z 571.3 [M+H]$^{+}$.

Example 98: Preparation of (S)-6-(5-chloropyrimidin-2-yl)-7-fluoro-2-(4-((6-oxo-5-(trifluoromethyl)-1,6-dihydropyridazin-4-yl)amino)pentyl)isoquinolin-1(2H)-one

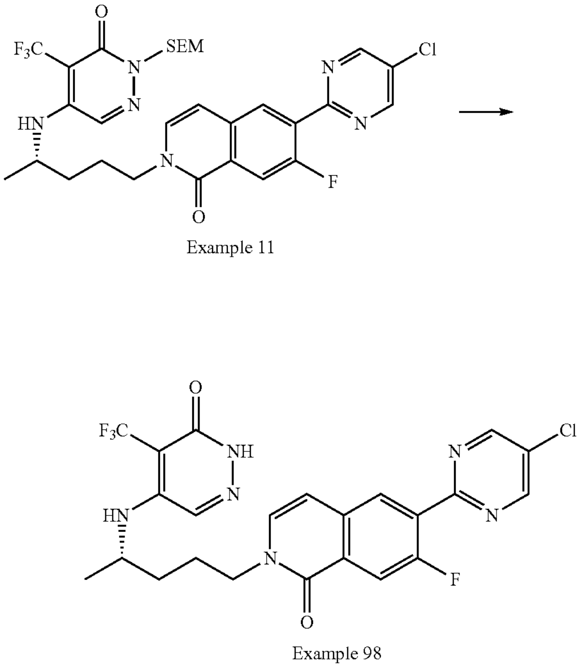

Example 11

Example 98

The title compound was synthesized as described in Example 17, using 6-bromo-7-fluoroisoquinolin-1(2H)-one instead of 6-bromoisoquinolin-1(2H)-one in Step 1, and using 5-chloro-2-iodo-pyrimidine instead of 2-iodo-5-(trifluoromethyl)pyrimidine in Step 3. In step 3, XPhos Pd G4 (0.1 equiv) was added along with the aryl halide and the resulting penultimate material Intermediate 11, which was purified by flash chromatography (100% hexanes to 100% EtOAc). Final deprotection gave (S)-6-(5-chloropyrimidin-2-yl)-7-fluoro-2-(4-((6-oxo-5-(trifluoromethyl)-1,6-dihydropyridazin-4-yl)amino)pentyl)isoquinolin-1(2H)-one. 1H NMR (400 MHz, DMSO-d6) δ 12.43 (s, 1H), 9.15 (s, 2H), 8.36 (d, J=7.2 Hz, 1H), 8.00 (d, J=11.4 Hz, 1H), 7.92 (s, 1H), 7.51 (d, J=7.4 Hz, 1H), 6.82 (d, J=7.4 Hz, 1H), 6.39-6.31 (m, 1H), 4.04-3.95 (m, 3H), 1.80-1.59 (m, 3H), 1.56-1.44 (m, 1H), 1.17 (d, J=6.3 Hz, 3H). ES/MS: m/z 523.2 [M+H]$^{+}$.

Example 99: (S)-6-(5-(2-oxa-6-azaspiro[3.3]heptan-6-yl)pyrimidin-2-yl)-7-fluoro-2-(4-((6-oxo-5-(trifluoromethyl)-1,6-dihydropyridazin-4-yl)amino)pentyl)isoquinolin-1(2H)-one

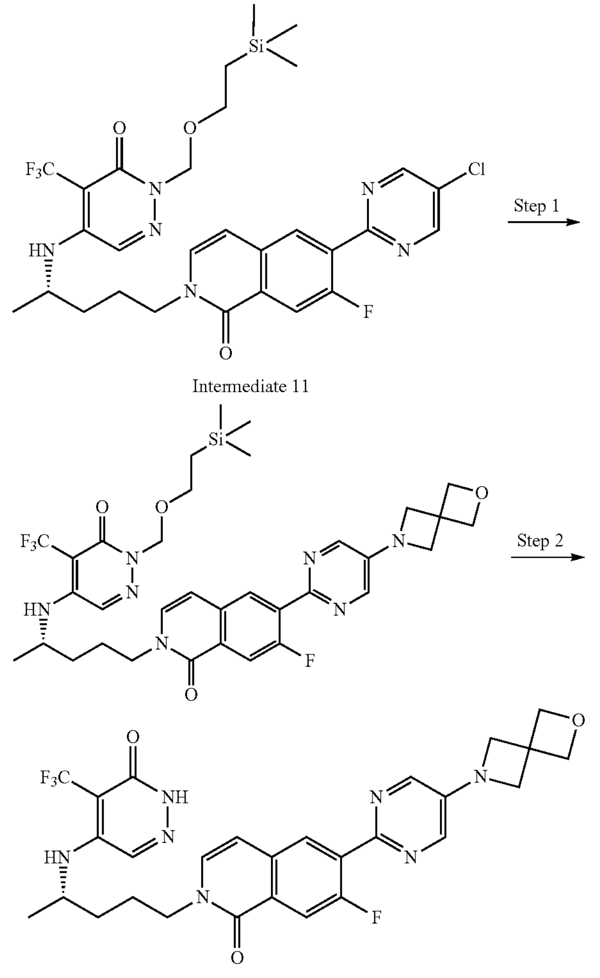

Intermediate 11

Example 99

Step 1. (S)-6-(5-chloropyrimidin-2-yl)-7-fluoro-2-(4-((6-oxo-5-(trifluoromethyl)-1-((2-(trimethylsilyl)ethoxy)methyl)-1,6-dihydropyridazin-4-yl)amino)pentyl)isoquinolin-1(2H)-one Intermediate 11 (51 mg, 0.078 mmol) was combined with 2-oxa-6-azaspiro[3.3]heptane (14 mg, 0.14 mmol), RuPhos Pd G4 (6 mg, 0.008 mmol), and cesium carbonate (52 mg, 0.16 mmol) in toluene. The mixture was sonicated, degassed with nitrogen gas, and heated to 60° C. for 12 hr. The reaction was concentrated in vacuo and the residue purified by flash chromatography (0-100% 3:1 EtOAc/EtOH in heptane) to give (S)-6-(5-(2-oxa-6-azaspiro[3.3]heptan-6-yl)pyrimidin-2-yl)-7-fluoro-2-(4-((6-oxo-5-(trifluoromethyl)-1-((2-(trimethylsilyl)ethoxy)methyl)-1,6-dihydropyridazin-4-yl)amino)pentyl)isoquinolin-1(2H)-one. ES/MS m/z: 716.3 [M+H]$^{+}$.

Step 2. (S)-6-(5-(2-oxa-6-azaspiro[3.3]heptan-6-yl)pyrimidin-2-yl)-7-fluoro-2-(4-((6-oxo-5-(trifluoromethyl)-1-((2-(trimethylsilyl)ethoxy)methyl)-1,6-dihydropyridazin-4-yl)amino)pentyl)isoquinolin-1(2H)-one was treated according to Example 5, step 8 to give (S)-6-(5-(2-oxa-6-azaspiro[3.3]heptan-6-yl)pyrimidin-2-yl)-7-fluoro-2-(4-((6-oxo-5-(trifluoromethyl)-1,6-dihydropyridazin-4-yl)amino) pentyl)isoquinolin-1(2H)-one. $^{1}$H NMR (400 MHz, DMSO-d6) δ 12.44 (s, 1H), 8.27-8.16 (m, 3H), 7.96-7.88 (m, 2H), 7.46 (d, J=7.4 Hz, 1H), 6.77 (d, J=7.4 Hz, 1H), 6.39-6.31 (m, 1H), 4.75 (s, 4H), 4.22 (s, 4H), 4.02-3.94 (m, 3H), 1.79-1.59 (m, 3H), 1.56-1.43 (m, 1H), 1.17 (d, J=6.3 Hz, 3H). ES/MS: m/z 586.3 $[M+H]^{+}$.

Example 100: 6-[4-amino-5-(trifluoromethyl)pyrimidin-2-yl]-7-fluoro-2-[(4S)-4-[[6-oxo-5-(trifluoromethyl)-1H-pyridazin-4-yl]amino]pentyl]isoquinolin-1-one Example 100

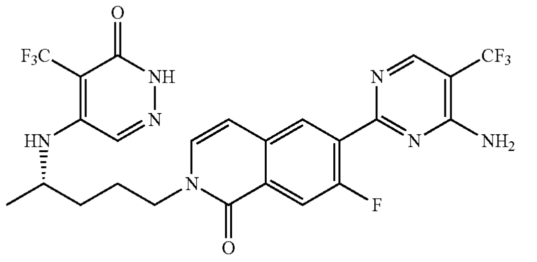

The title compound was synthesized as described in Example 9 with the following changes:

Step 5. 2-Chloro-5-(trifluoromethyl)pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-[4-amino-5-(trifluoromethyl)pyrimidin-2-yl]-7-fluoro-2-[(4S)-4-[[6-oxo-5-(trifluoromethyl)-1H-pyridazin-4-yl] amino]pentyl]isoquinolin-1-one. 1H NMR (400 MHz, DMSO-d6) δ 12.44 (s, 1H), 8.65 (d, J=1.1 Hz, 1H), 8.20 (d, J=7.1 Hz, 1H), 8.03-7.88 (m, 2H), 7.50 (d, J=7.4 Hz, 1H), 6.77 (d, J=7.3 Hz, 1H), 6.35 (dd, J=8.5, 3.9 Hz, 1H), 3.99 (t, J=6.6 Hz, 3H), 1.70 (ddt, J=20.0, 13.0, 6.3 Hz, 3H), 1.50 (dq, J=12.8, 6.4 Hz, 1H), 1.17 (d, J=6.3 Hz, 3H). ES/MS: m/z 572.3.

Example 101: 4-amino-2-[7-fluoro-1-oxo-2-[(4S)-4-[[6-oxo-5-(trifluoromethyl)-1H-pyridazin-4-yl] amino]pentyl]-6-isoquinolyl]pyrimidine-5-carbonitrile Example 101

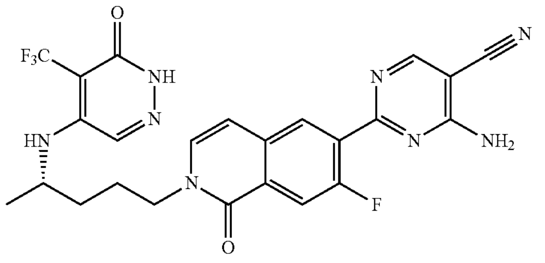

The title compound was synthesized as described in Example 9 with the following changes:

Step 5. 4-amino-2-chloro-pyrimidine-5-carbonitrile used instead of 2-iodo-5-(trifluoromethyl)pyrimidine and cataCXium Pd G4 was used instead of [1,1'-Bis(di-tert-butylphosphino)ferrocene]dichloropalladium(II) to give 4-amino-2-[7-fluoro-1-oxo-2-[(4S)-4-[[6-oxo-5-(trifluoromethyl)-1H-pyridazin-4-yl]amino]pentyl]-6-isoquinolyl] pyrimidine-5-carbonitrile. 1H NMR (400 MHz, DMSO-d6) δ 12.43 (s, 1H), 8.80 (s, 1H), 8.22 (d, J=7.1 Hz, 1H), 8.06-7.86 (m, 2H), 7.50 (d, J=7.4 Hz, 1H), 6.77 (d, J=7.4 Hz, 1H), 6.35 (dd, J=9.0, 3.6 Hz, 1H), 3.98 (t, J=6.6 Hz, 3H), 1.69 (ddt, J=21.5, 14.4, 7.3 Hz, 3H), 1.51 (dd, J=10.6, 5.8 Hz, 1H), 1.16 (d, J=6.3 Hz, 3H). ES/MS: m/z 529.3.

Example 102: 6-(4-amino-5-methoxy-pyrimidin-2-yl)-7-fluoro-2-[(4S)-4-[[6-oxo-5-(trifluoromethyl)-1H-pyridazin-4-yl]amino]pentyl]isoquinolin-1-one Example 102

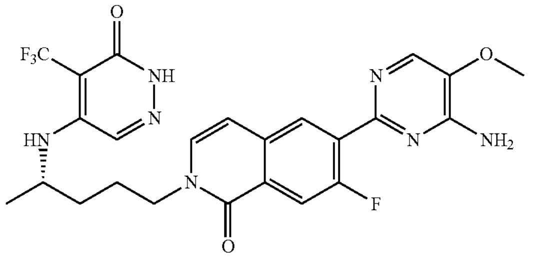

The title compound was synthesized as described in Example 9 with the following changes:

Step 5. 2-Chloro-5-methoxy-pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-(4-amino-5-methoxy-pyrimidin-2-yl)-7-fluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.44 (s, 1H), 8.21-7.83 (m, 4H), 7.52 (d, J=7.4 Hz, 1H), 6.77 (d, J=7.3 Hz, 1H), 6.35 (dd, J=8.0, 3.8 Hz, 1H), 3.98 (d, J=12.7 Hz, 6H), 1.70 (ddt, J=20.6, 13.7, 7.1 Hz, 3H), 1.51 (q, J=6.4 Hz, 1H), 1.17 (d, J=6.2 Hz, 3H). ES/MS: m/z 534.3.

Example 103: 6-(4-amino-5-fluoro-pyrimidin-2-yl)-7-fluoro-2-[(4S)-4-[[6-oxo-5-(trifluoromethyl)-1H-pyridazin-4-yl]amino]pentyl]isoquinolin-1-one Example 103

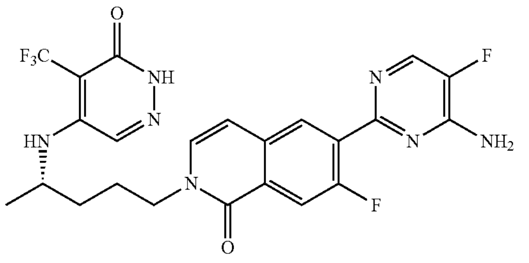

The title compound was synthesized as described in Example 9 with the following changes:

Step 5. 2-chloro-5-fluoro-pyrimidin-4-amine used instead of 2-iodo-5-(trifluoromethyl)pyrimidine and cataCXium Pd G4 was used instead of [1,1'-Bis(di-tert-butylphosphino) ferrocene]dichloropalladium(II) to give 6-(4-amino-5-fluoro-pyrimidin-2-yl)-7-fluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.44 (s, 1H), 8.36 (d, J=3.7 Hz, 1H), 8.12 (d, J=7.2 Hz, 1H), 7.99-7.83 (m, 2H), 7.60 (s, 2H), 7.48 (d, J=7.4 Hz, 1H), 6.75 (d, J=7.4 Hz, 1H), 6.36 (dt, J=8.5, 3.6 Hz, 1H), 3.98 (t, J=6.8 Hz, 3H), 1.83-1.58 (m, 3H), 1.51 (q, J=6.8, 6.4 Hz, 1H), 1.17 (d, J=6.3 Hz, 3H). ES/MS: m/z 522.3.

Example 104: 6-[4-amino-5-(difluoromethyl)pyrimidin-2-yl]-7-fluoro-2-[(4S)-4-[[6-oxo-5-(trifluoromethyl)-1H-pyridazin-4-yl]amino]pentyl]isoquinolin-1-one Example 104

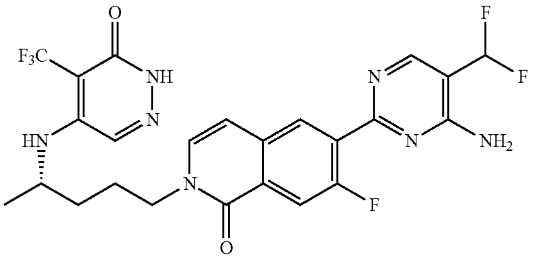

The title compound was synthesized as described in Example 9 with the following changes:

Step 5. 2-Chloro-5-(difluoromethyl)pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-[4-amino-5-(difluoromethyl)pyrimidin-2-yl]-7-fluoro-2-[(4S)-4-[[6-oxo-5-(trifluoromethyl)-1H-pyridazin-4-yl] amino]pentyl]isoquinolin-1-one. 1H NMR (400 MHz, DMSO-d6) δ 12.44 (s, 1H), 8.50 (d, J=1.6 Hz, 1H), 8.17 (d, J=7.1 Hz, 1H), 8.01-7.85 (m, 2H), 7.49 (d, J=7.4 Hz, 2H), 7.10 (t, J=54.1 Hz, 1H), 6.77 (d, J=7.4 Hz, 1H), 6.36 (dt, J=8.9, 3.5 Hz, 1H), 3.99 (t, J=6.7 Hz, 3H), 1.84-1.58 (m, 3H), 1.51 (dt, J=12.0, 6.3 Hz, 1H), 1.17 (d, J=6.3 Hz, 3H). ES/MS: m/z 554.3.

Example 105: 6-[2-amino-5-(difluoromethyl)pyrimidin-4-yl]-7-fluoro-2-[(4S)-4-[[6-oxo-5-(trifluoromethyl)-1H-pyridazin-4-yl]amino]pentyl]isoquinolin-1-one Example 105

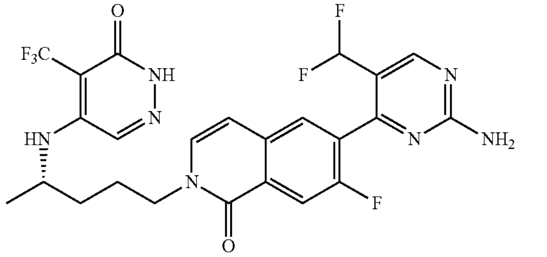

The title compound was synthesized as described in Example 9 with the following changes:

Step 5. 4-chloro-5-(difluoromethyl)pyrimidin-2-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-[2-amino-5-(difluoromethyl)pyrimidin-4-yl]-7-fluoro-2-[(4S)-4-[[6-oxo-5-(trifluoromethyl)-1H-pyridazin-4-yl] amino]pentyl]isoquinolin-1-one. 1H NMR (400 MHz, DMSO-d6) δ 12.44 (s, 1H), 8.60 (s, 1H), 8.02-7.86 (m, 2H), 7.79 (d, J=6.8 Hz, 1H), 7.59-7.28 (m, 3H), 6.92-6.53 (m, 2H), 6.36 (dq, J=6.9, 3.3 Hz, 1H), 3.99 (t, J=6.3 Hz, 4H), 1.69 (ddt, J=22.8, 9.1, 4.6 Hz, 3H), 1.51 (dt, J=9.0, 6.4 Hz, 1H), 1.17 (d, J=6.3 Hz, 3H). ES/MS: m/z 554.3.

Example 106: 7-fluoro-6-[4-(methylamino)-5-(trifluoromethyl)pyrimidin-2-yl]-2-[(4S)-4-[[6-oxo-5-(trifluoromethyl)-1H-pyridazin-4-yl]amino]pentyl] isoquinolin-1-one Example 106

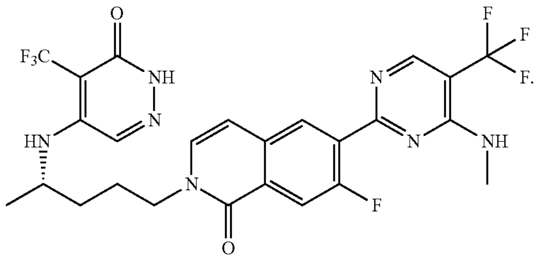

The title compound was synthesized as described in Example 9 with the following changes:

Step 5. 2-chloro-N-methyl-5-(trifluoromethyl)pyrimidin-4-amine used instead of 2-iodo-5-(trifluoromethyl)pyrimidine and cataCXium Pd G4 was used instead of [1,1'-Bis (di-tert-butylphosphino)ferrocene]dichloropalladium(II) to give 7-fluoro-6-[4-(methylamino)-5-(trifluoromethyl)pyrimidin-2-yl]-2-[(4S)-4-[[6-oxo-5-(trifluoromethyl)-1H-pyridazin-4-yl]amino]pentyl]isoquinolin-1-one. $^{1}$H NMR (400 MHz, DMSO-d6) δ 12.44 (s, 1H), 8.62 (d, J=1.1 Hz, 1H), 8.35 (d, J=7.1 Hz, 1H), 7.97 (d, J=11.3 Hz, 1H), 7.91 (d, J=5.8 Hz, 1H), 7.68 (q, J=4.5 Hz, 1H), 7.50 (d, J=7.4 Hz, 1H), 6.80 (d, J=7.4 Hz, 1H), 6.35 (dd, J=8.5, 3.9 Hz, 1H), 3.98 (q, J=8.5, 7.2 Hz, 3H), 3.01 (d, J=4.4 Hz, 3H), 1.83-1.59 (m, 2H), 1.50 (dq, J=12.9, 6.9, 6.4 Hz, 1H), 1.16 (dd, J=6.5, 3.6 Hz, 3H). ES/MS: m/z 586.3.

Example 107: 6-(4-amino-5-cyclopropyl-pyrimidin-2-yl)-7-fluoro-2-[(4S)-4-[[6-oxo-5-(trifluoromethyl)-1H-pyridazin-4-yl]amino]pentyl]isoquinolin-1-one Example 107

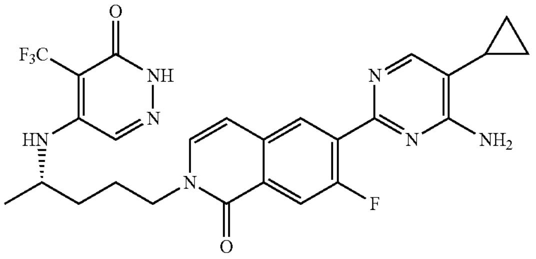

The title compound was synthesized as described in Example 9 with the following changes:

Step 5. 2-chloro-5-cyclopropyl-pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-(4-amino-5-cyclopropyl-pyrimidin-2-yl)-7-fluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.44 (s, 1H), 8.50 (s, 2H), 8.21-7.97 (m, 3H), 7.91 (s, 1H), 7.54 (d, J=7.4 Hz, 1H), 6.78 (d, J=7.4 Hz, 1H), 6.35 (dd, J=8.7, 3.8 Hz, 1H), 4.00 (t, J=6.7 Hz, 3H), 1.80-1.60 (m, 4H), 1.51 (dt, J=11.9, 6.1 Hz, 1H), 1.17 (d, J=6.3 Hz, 3H), 1.04-0.94 (m, 2H), 0.80-0.66 (m, 2H). ES/MS: m/z 544.3.

Example 108: 7-[4-amino-5-(difluoromethyl)pyrimidin-2-yl]-6-fluoro-3-[(4S)-4-[[6-oxo-5-(trifluoromethyl)-1H-pyridazin-4-yl]amino]pentyl]quinazolin-4-one Example 108

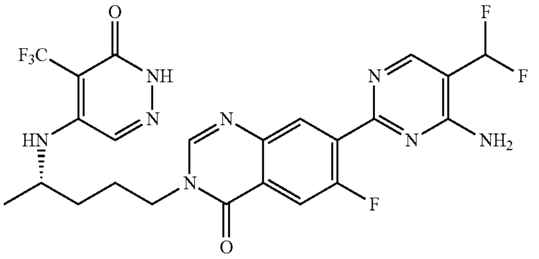

The title compound was synthesized as described in Example 9 with the following changes:

Step 5. 2-Chloro-5-(difluoromethyl)pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 7-[4-amino-5-(difluoromethyl)pyrimidin-2-yl]-6-fluoro-3-[(4S)-4-[[6-oxo-5-(trifluoromethyl)-1H-pyridazin-4-yl]amino]pentyl]quinazolin-4-one. $^1$H NMR (400 MHz, DMSO-d6) δ 12.44 (s, 1H), 8.52 (d, J=1.5 Hz, 1H), 8.43 (s, 1H), 8.15 (d, J=6.7 Hz, 1H), 7.96-7.85 (m, 2H), 7.65 (s, 1H), 7.10 (t, J=54.1 Hz, 1H), 6.39-6.30 (m, 1H), 3.99 (q, J=10.6, 8.4 Hz, 3H), 1.83-1.59 (m, 3H), 1.52 (dq, J=12.9, 6.2 Hz, 1H), 1.17 (d, J=6.3 Hz, 3H). ES/MS: m/z 555.3.

Example 109: 6-(4-amino-5-methoxy-pyrimidin-2-yl)-7,8-difluoro-2-[(4S)-4-[[6-oxo-5-(trifluoromethyl)-1H-pyridazin-4-yl]amino]pentyl]isoquinolin-1-one Example 109

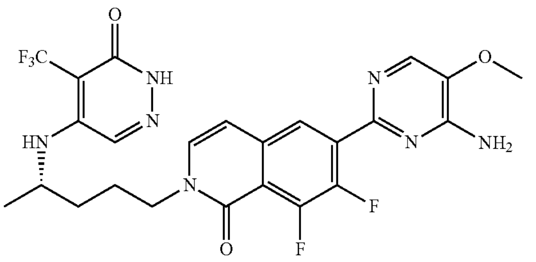

The title compound was synthesized as described in Example 9 with the following changes:

Step 5. 2-chloro-5-methoxy-pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-(4-amino-5-methoxy-pyrimidin-2-yl)-7,8-difluoro-2-[(4S)-4-[[6-oxo-5-(trifluoromethyl)-1H-pyridazin-4-yl]amino]pentyl]isoquinolin-1-one. $^1$H NMR (400 MHz, DMSO-d6) δ 12.44 (s, 1H), 8.04 (s, 1H), 7.96-7.85 (m, 2H), 7.62 (s, 1H), 7.50 (d, J=7.4 Hz, 1H), 6.70 (dd, J=7.5, 1.9 Hz, 1H), 6.39-6.29 (m, 1H), 4.04-3.85 (m, 6H), 2.77 (s, 1H), 1.78-1.40 (m, 6H), 1.18 (dd, J=6.3, 3.8 Hz, 4H). ES/MS: m/z 552.3.

Example 110: 4-amino-2-[7,8-difluoro-1-oxo-2-[(4S)-4-[[6-oxo-5-(trifluoromethyl)-1H-pyridazin-4-yl]amino]pentyl]-6-isoquinolyl]pyrimidine-5-carbonitrile Example 110

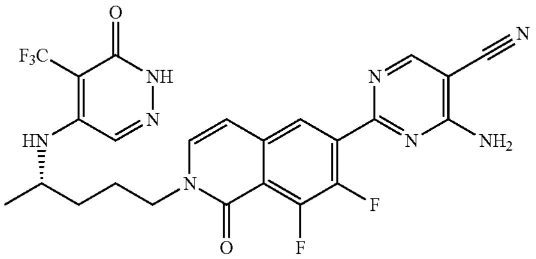

The title compound was synthesized as described in Example 9 with the following changes:

Step 5. 4-amino-2-chloro-pyrimidine-5-carbonitrile used instead of 2-iodo-5-(trifluoromethyl)pyrimidine and cataCXium Pd G4 was used instead of [1,1'-Bis(di-tert-butylphosphino)ferrocene]dichloropalladium(II) to give 4-amino-2-[7,8-difluoro-1-oxo-2-[(4S)-4-[[6-oxo-5-(trifluoromethyl)-1H-pyridazin-4-yl]amino]pentyl]-6-isoquinolyl]pyrimidine-5-carbonitrile. $^1$H NMR (400 MHz, DMSO-d6) δ 12.43 (s, 1H), 8.81 (s, 1H), 8.01 (dd, J=6.6, 1.7 Hz, 1H), 7.92 (s, 1H), 7.52 (d, J=7.4 Hz, 1H), 6.74 (dd, J=7.5, 1.9 Hz, 1H), 6.35 (dd, J=8.4, 3.8 Hz, 1H), 3.94 (t, J=6.7 Hz, 2H), 1.68 (tt, J=15.4, 6.9 Hz, 3H), 1.51 (dt, J=11.0, 6.1 Hz, 1H), 1.17 (d, J=6.2 Hz, 3H). ES/MS: m/z 547.3.

Example 111: 6-(4-amino-5-nitro-pyrimidin-2-yl)-7-fluoro-2-[(4S)-4-[[6-oxo-5-(trifluoromethyl)-1H-pyridazin-4-yl]amino]pentyl]isoquinolin-1-one Example 111

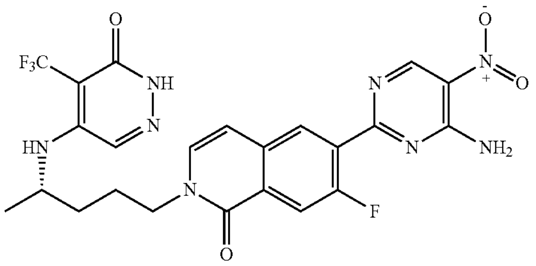

The title compound was synthesized as described in Example 9 with the following changes:

Step 5. 2-Chloro-5-nitro-pyrimidin-4-amine used instead of 2-iodo-5-(trifluoromethyl)pyrimidine and cataCXium Pd G4 was used instead of [1,1'-Bis(di-tert-butylphosphino) ferrocene]dichloropalladium(II) to give 6-(4-amino-5-nitro-pyrimidin-2-yl)-7-fluoro-2-[(4S)-4-[[6-oxo-5-(trifluoromethyl)-1H-pyridazin-4-yl]amino]pentyl]isoquinolin-1-one. $^1$H NMR (400 MHz, DMSO-d6) δ 12.44 (s, 1H), 9.26 (s, 1H), 8.96 (s, 1H), 8.44 (s, 1H), 8.28 (d, J=7.1 Hz, 1H), 7.98 (d, J=11.2 Hz, 1H), 7.92 (s, 1H), 7.51 (d, J=7.4 Hz, 1H), 6.80 (d, J=7.4 Hz, 1H), 6.35 (dd, J=8.6, 4.0 Hz, 1H), 3.99 (t, J=6.5 Hz, 3H), 1.70 (ddd, J=22.5, 13.3, 4.5 Hz, 2H), 1.51 (dt, J=8.9, 6.2 Hz, 1H), 1.17 (d, J=6.3 Hz, 3H). ES/MS: m/z 549.3.

Example 112: 6-(5,5-dimethyl-6,7-dihydropyrrolo[2,3-d]pyrimidin-2-yl)-7-fluoro-2-[(4S)-4-[[6-oxo-5-(trifluoromethyl)-1H-pyridazin-4-yl]amino]pentyl]isoquinolin-1-one Example 112

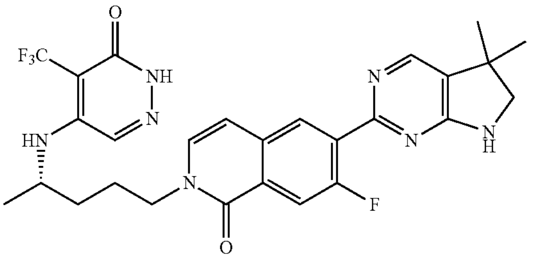

The title compound was synthesized as described in Example 9 with the following changes:

Step 5. 2-chloro-5,5-dimethyl-6,7-dihydropyrrolo[2,3-d]pyrimidine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-(5,5-dimethyl-6,7-dihydropyrrolo[2,3-d]pyrimidin-2-yl)-7-fluoro-2-[(4S)-4-[[6-oxo-5-(trifluoromethyl)-1H-pyridazin-4-yl]amino]pentyl]isoquinolin-1-one. $^1$H NMR (400 MHz, DMSO-d6) δ 12.44 (s, 1H), 9.25 (s, 1H), 8.29-8.11 (m, 2H), 8.04 (d, J=11.0 Hz, 1H), 7.93 (d, J=11.3 Hz, 1H), 7.55 (d, J=7.4 Hz, 1H), 6.78 (d, J=7.4 Hz, 1H), 6.35 (dd, J=8.6, 3.9 Hz, 1H), 3.99 (q, J=9.2, 7.8 Hz, 3H), 3.55 (s, 2H), 1.84-1.45 (m, 4H), 1.39 (s, 6H), 1.17 (d, J=6.1 Hz, 3H). ES/MS: m/z 558.4.

Example 113: 6-[4-amino-5-(difluoromethyl)pyrimidin-2-yl]-7,8-difluoro-2-[(4S)-4-[[6-oxo-5-(trifluoromethyl)-1H-pyridazin-4-yl]amino]pentyl]isoquinolin-1-one Example 113

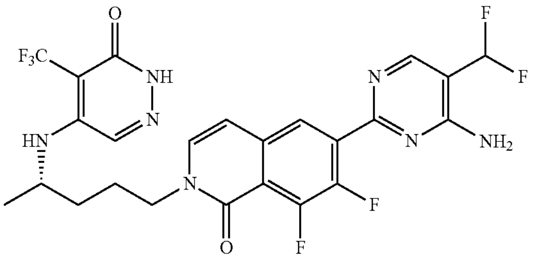

The title compound was synthesized as described in Example 9 with the following changes:

Step 5. 2-Chloro-5-(difluoromethyl)pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-[4-amino-5-(difluoromethyl)pyrimidin-2-yl]-7,8-difluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.44 (s, 1H), 8.51 (d, J=1.5 Hz, 1H), 8.03-7.79 (m, 2H), 7.51 (d, J=7.4 Hz, 1H), 7.10 (t, J=54.1 Hz, 1H), 6.73 (dd, J=7.5, 1.9 Hz, 1H), 6.35 (dd, J=8.7, 3.8 Hz, 1H), 3.96 (dt, J=13.3, 7.2 Hz, 3H), 1.68 (td, J=14.6, 14.0, 7.1 Hz, 3H), 1.50 (dq, J=12.7, 6.6 Hz, 1H), 1.17 (d, J=6.2 Hz, 3H). ES/MS: m/z 572.3.

Example 114: 6-[2-amino-5-(difluoromethyl)pyrimidin-4-yl]-7,8-difluoro-2-[(4S)-4-[[6-oxo-5-(trifluoromethyl)-1H-pyridazin-4-yl]amino]pentyl]isoquinolin-1-one Example 114

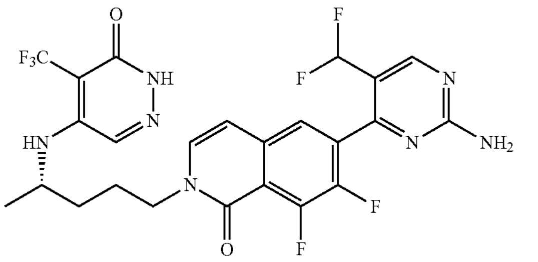

The title compound was synthesized as described in Example 9 with the following changes:

Step 5. 4-Chloro-5-(difluoromethyl)pyrimidin-2-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-[2-amino-5-(difluoromethyl)pyrimidin-4-yl]-7,8-difluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.44 (s, 1H), 8.63 (s, 1H), 7.93 (s, 1H), 7.63-7.45 (m, 4H), 6.98-6.55 (m, 2H), 6.35 (dd, J=8.7, 3.8 Hz, 1H), 3.97 (dt, J=13.4, 6.7 Hz, 3H), 1.69 (qt, J=8.7, 4.4 Hz, 3H), 1.59-1.42 (m, 1H), 1.18 (d, J=6.3 Hz, 3H). ES/MS: m/z 572.3.

Example 115: 6-fluoro-7-[4-(methylamino)-5-(trifluoromethyl)pyrimidin-2-yl]-3-[(4S)-4-[[6-oxo-5-(trifluoromethyl)-1H-pyridazin-4-yl]amino]pentyl]quinazolin-4-one Example 115

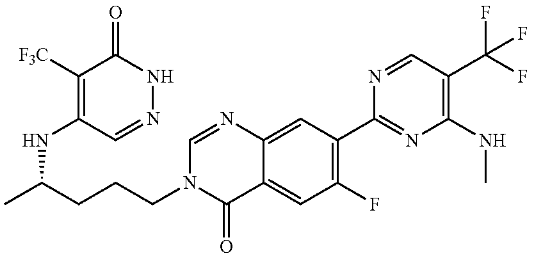

The title compound was synthesized as described in Example 9 with the following changes:

Step 5. 2-Chloro-N-methyl-5-(trifluoromethyl)pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 6-fluoro-7-[4-(methylamino)-5-(trifluoromethyl)pyrimidin-2-yl]-3-[(4S)-4-[[6-oxo-5-(trifluoromethyl)-1H-pyridazin-4-yl]amino]pentyl]quinazolin-4-one. 1H NMR (400 MHz, DMSO-d6) δ 12.44 (s, 1H), 8.71-8.60 (m, 1H), 8.44 (s, 1H), 8.30 (d, J=6.7 Hz, 1H), 8.00-7.85 (m, 2H), 7.71 (d, J=4.6 Hz, 1H), 6.35 (dq, J=7.0, 3.3 Hz, 1H), 4.01 (q, J=6.2 Hz, 3H), 3.00 (d, J=4.4 Hz, 3H), 1.85-1.44 (m, 5H), 1.17 (d, J=6.3 Hz, 3H). ES/MS: m/z 587.3.

Example 116: 7-[4-(cyclopropylamino)-5-(trifluoromethyl)pyrimidin-2-yl]-6-fluoro-3-[(4S)-4-[[6-oxo-5-(trifluoromethyl)-1H-pyridazin-4-yl]amino]pentyl]quinazolin-4-one Example 116

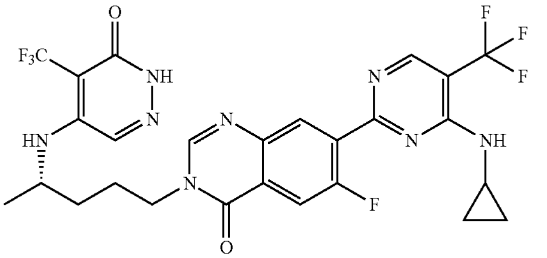

The title compound was synthesized as described in Example 9 with the following changes:

Step 5. 2-Chloro-N-cyclopropyl-5-(trifluoromethyl)pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 7-[4-(cyclopropylamino)-5-(trifluoromethyl)pyrimidin-2-yl]-6-fluoro-3-[(4S)-4-[[6-oxo-5-(trifluoromethyl)-1H-pyridazin-4-yl]amino]pentyl]quinazolin-4-one. $^1$H NMR (400 MHz, DMSO-d6) δ 12.44 (s, 1H), 8.66 (d, J=1.1 Hz, 1H), 8.43 (s, 1H), 8.33 (d, J=6.7 Hz, 1H), 7.99-7.83 (m, 2H), 7.70 (d, J=3.4 Hz, 1H), 6.35 (dd, J=8.8, 3.8 Hz, 1H), 4.01 (t, J=6.6 Hz, 2H), 3.01 (tq, J=7.3, 3.8 Hz, 1H), 1.72 (td, J=15.7, 6.6 Hz, 3H), 1.52 (dt, J=12.4, 6.4 Hz, 1H), 1.17 (d, J=6.3 Hz, 3H), 0.85-0.64 (m, 4H). ES/MS: m/z 613.3.

Example 117: 7-[4-(ethylamino)-5-(trifluoromethyl)pyrimidin-2-yl]-6-fluoro-3-[(4S)-4-[[6-oxo-5-(trifluoromethyl)-1H-pyridazin-4-yl]amino]pentyl]quinazolin-4-one Example 117

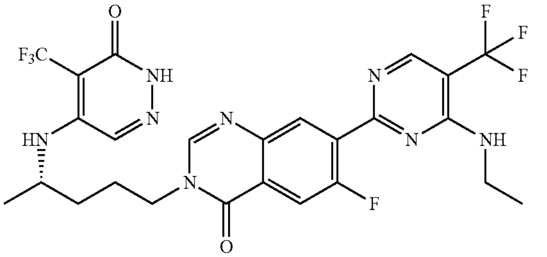

The title compound was synthesized as described in Example 9 with the following changes:

Step 5. 2-Chloro-N-ethyl-5-(trifluoromethyl)pyrimidin-4-amine used instead of 2-iodo-5-(trifluoromethyl)pyrimidine and cataCXium Pd G4 was used instead of [1,1'-Bis(di-tert-butylphosphino)ferrocene]dichloropalladium(II) to give 7-[4-(ethylamino)-5-(trifluoromethyl)pyrimidin-2-yl]-6-fluoro-3-[(4S)-4-[[6-oxo-5-(trifluoromethyl)-1H-pyridazin-4-yl]amino]pentyl]quinazolin-4-one. 1H NMR (400 MHz, DMSO-d6) δ 12.44 (s, 1H), 8.63 (d, J=1.1 Hz, 1H), 8.43 (s, 1H), 8.27 (d, J=6.7 Hz, 1H), 8.02-7.87 (m, 2H), 7.75 (t, J=5.7 Hz, 1H), 6.35 (dd, J=8.9, 3.7 Hz, 1H), 4.00 (q, J=11.3, 8.8 Hz, 3H), 3.64-3.49 (m, 2H), 1.86-1.61 (m, 3H), 1.53 (dd, J=10.7, 5.7 Hz, 1H), 1.24-1.11 (m, 6H). ES/MS: m/z 601.3.

Example 118: 6-(7,8-dihydro-6H-pyrimido[5,4-b][1,4]oxazin-2-yl)-7-fluoro-2-[(4S)-4-[[6-oxo-5-(trifluoromethyl)-1H-pyridazin-4-yl]amino]pentyl]isoquinolin-1-one Example 118

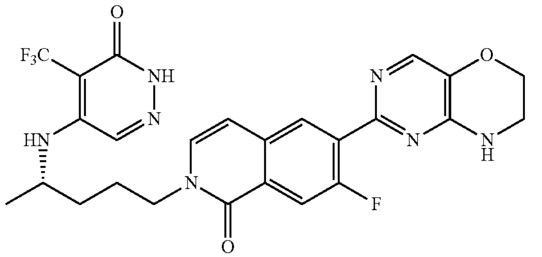

The title compound was synthesized as described in Example 9 with the following changes:

Step 5. 2-chloro-7,8-dihydro-6H-pyrimido[5,4-b][1,4]oxazine used instead of 2-iodo-5-(trifluoromethyl)pyrimidine and 20 mol % of cataCXium Pd G4 was used instead of [1,1'-Bis(di-tert-butylphosphino)ferrocene]dichloropalladium(II) to give 6-(7,8-dihydro-6H-pyrimido[5,4-b][1,4]oxazin-2-yl)-7-fluoro-2-[(4S)-4-[[6-oxo-5-(trifluoromethyl)-1H-pyridazin-4-yl]amino]pentyl]isoquinolin-1-one. 1H NMR (400 MHz, DMSO-d6) δ 12.44 (s, 1H), 8.63 (s, 1H), 8.21-7.78 (m, 4H), 7.49 (d, J=7.4 Hz, 1H), 6.75 (d, J=7.4 Hz, 1H), 6.35 (q, J=3.3 Hz, 1H), 4.23 (t, J=4.5 Hz, 2H), 3.98 (t, J=6.7 Hz, 4H), 3.56 (q, J=3.8 Hz, 2H), 1.70 (ddt, J=28.3, 15.0, 7.3 Hz, 3H), 1.51 (dd, J=10.2, 5.9 Hz, 1H), 1.17 (d, J=6.3 Hz, 3H). ES/MS: m/z 546.3.

Intermediate 12: Preparation of 1-(2-chloro-5-(trifluoromethyl)pyrimidin-4-yl)azetidine-3-carbonitrile

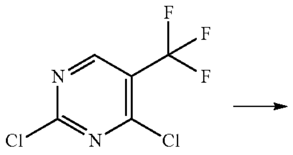

-continued

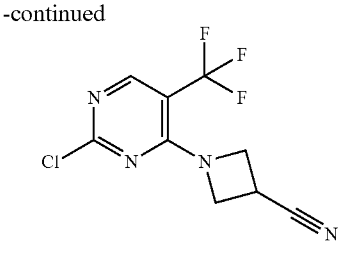

Intermediate 12

N,N-Diisopropylethylamine (0.722 mL, 4.15 mmol) was added to a solution of 2,4-dichloro-5-(trifluoromethyl)pyrimidine (300 mg, 1.38 mmol) and azetidine-3-carbonitrile hydrochloride (164 mg, 1.38 mmol) in DMF (2.5 mL). The resulting solution was stirred at room temperature for 2 h then diluted with water and extracted two times with EtOAc. The combined organic layers were washed three time with water, then washed with brine, dried over anhydrous magnesium sulfate, and concentrated under reduced pressure. The crude residue was purified via prep. HPLC and lyophilized to afford 177 mg (49%) of 1-(2-chloro-5-(trifluoromethyl)pyrimidin-4-yl)azetidine-3-carbonitrile. ES/MS: m/z 262.9 $[M+H]^+$.

Example 119: (S)-1-(2-(7-fluoro-1-oxo-2-(4-((6-oxo-5-(trifluoromethyl)-1,6-dihydropyridazin-4-yl)amino)pentyl)-1,2-dihydroisoquinolin-6-yl)-5-(trifluoromethyl)pyrimidin-4-yl)azetidine-3-carbonitrile Example 119

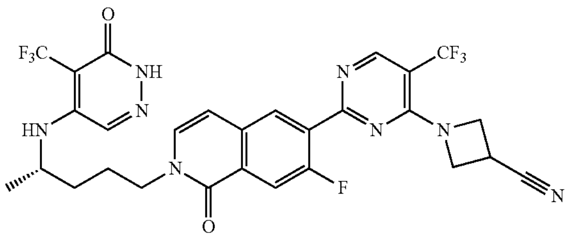

The title compound was synthesized as described in Example 17 with the following changes:

Step 1. 2-bromo-7,8-difluoroisoquinolin-1(2H)-one was used instead of 6-bromo-8-fluoro-1,2-dihydroisoquinolin-1-one Step 3. 1-(2-chloro-5-(trifluoromethyl)pyrimidin-4-yl)azetidine-3-carbonitrile was used instead of 2-bromo-5-(difluoromethoxy)pyridine and 20 mol % of cataCXium Pd G4 and 2 M aqueous sodium carbonate (1.9 equiv.) were added following the completion of the borylation step to give (S)-1-(2-(7-fluoro-1-oxo-2-(4-((6-oxo-5-(trifluoromethyl)-1,6-dihydropyridazin-4-yl)amino)pentyl)-1,2-dihydroisoquinolin-6-yl)-5-(trifluoromethyl)pyrimidin-4-yl)azetidine-3-carbonitrile. $^1$H NMR (400 MHz, DMSO-d6) δ 1H NMR (400 MHz, DMSO-d6) δ 12.43 (s, 1H), 8.78 (s, 1H), 8.35 (d, J=7.1 Hz, 1H), 7.98 (d, J=11.3 Hz, 1H), 7.92 (s, 1H), 7.51 (d, J=7.4 Hz, 1H), 6.80 (d, J=7.4 Hz, 1H), 6.42-6.27 (m, 1H), 4.63-4.53 (m, 2H), 4.50-4.43 (m, 2H), 4.01-3.97 (m, 4H), 1.80-1.59 (m, 3H), 1.57-1.43 (m, 1H), 1.17 (d, J=6.3 Hz, 3H). ES/MS: m/z 637.3 $[M+H]^+$.

Intermediate 13: Preparation of tert-butyl (S)-2-(3-(tosyloxy)propyl)pyrrolidine-1-carboxylate Intermediate 13

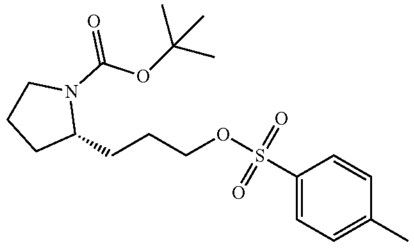

The title compound was synthesized as described in Intermediate 3, using tert-butyl (S)-2-formylpyrrolidine-1-carboxylate instead of tert-butyl (1R,2S,5S)-2-formyl-3-azabicyclo[3.1.0]hexane-3-carboxylate to give tert-butyl (S)-2-(3-(tosyloxy)propyl)pyrrolidine-1-carboxylate. ES/MS m/z: 156.28 $[M+H]^+$.

Example 120: (S)-7-fluoro-2-(3-(1-(6-oxo-5-(trifluoromethyl)-1,6-dihydropyridazin-4-yl)pyrrolidin-2-yl)propyl)-6-(5-(trifluoromethyl)pyrimidin-2-yl)isoquinolin-1(2H)-one Example 120

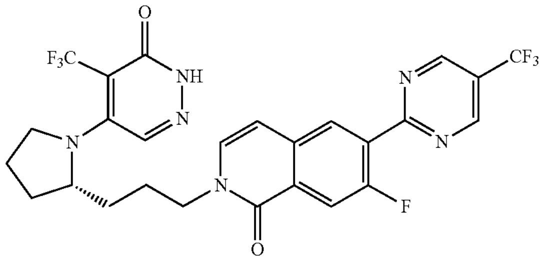

The title compound was synthesized as described in Example 17, using 2-iodo-5-(trifluoromethyl)pyrimidine instead of 2-bromo-5-(difluoromethoxy)pyridine and 7-bromo-6-fluoro-1H-quinazolin-4-one instead of 6-Bromo-8-fluoro-1,2-dihydroisoquinolin-1-one and tert-butyl (S)-2-(3-(tosyloxy)propyl)pyrrolidine-1-carboxylate instead of (S)-4-((tert-butoxycarbonyl)amino)pentyl 4-methylbenzenesulfonate. $^1$H NMR (400 MHz, DMSO-d6) δ 12.43 (s, 1H), 9.48 (s, 2H), 8.43 (d, J=7.1 Hz, 1H), 8.03 (d, J=11.4 Hz, 1H), 7.98 (s, 1H), 7.54 (d, J=7.4 Hz, 1H), 6.84 (d, J=7.3 Hz, 1H), 4.28 (q, J=8.3 Hz, 1H), 4.10-3.91 (m, 2H), 3.59-3.45 (m, 1H), 3.20 (dd, J=10.9, 6.4 Hz, 1H), 2.22-2.11 (m, 1H), 1.95-1.52 (m, 6H), 1.51-1.38 (m, 1H). ES/MS m/z: 583.30 [M+H].

Example 121: (S)-6-(4-amino-5-(trifluoromethyl)pyrimidin-2-yl)-7-fluoro-2-(3-(1-(6-oxo-5-(trifluoromethyl)-1,6-dihydropyridazin-4-yl)pyrrolidin-2-yl)propyl)isoquinolin-1(2H)-one Example 121

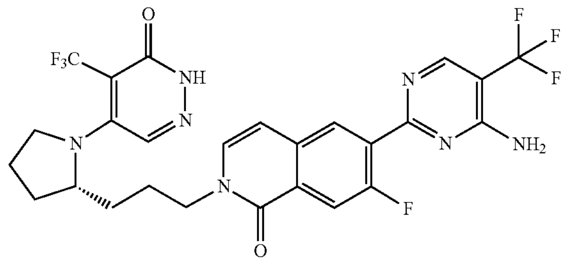

The title compound was synthesized as described in Example 17, using 2-chloro-5-(trifluoromethyl)pyrimidin-4-amine instead of 2-bromo-5-(difluoromethoxy)pyridine and 7-bromo-6-fluoro-1H-quinazolin-4-one instead of 6-Bromo-8-fluoro-1,2-dihydroisoquinolin-1-one and tert-butyl (S)-2-(3-(tosyloxy)propyl)pyrrolidine-1-carboxylate instead of (S)-4-((tert-butoxycarbonyl)amino)pentyl 4-methylbenzenesulfonate. $^1$H NMR (400 MHz, DMSO-d6) δ 12.43 (s, 1H), 8.65 (d, J=1.1 Hz, 1H), 8.20 (d, J=7.1 Hz, 1H), 8.00-7.92 (m, 2H), 7.51 (d, J=7.4 Hz, 1H), 6.76 (d, J=7.3 Hz, 1H), 4.33-4.21 (m, 1H), 4.08-3.91 (m, 2H), 3.58-3.45 (m, 1H), 3.24-3.13 (m, 1H), 2.22-2.09 (m, 1H), 1.95-1.86 (m, 1H), 1.85-1.50 (m, 5H), 1.50-1.37 (m, 1H). ES/MS m/z: 598.30 [M+H].

Example 122: (S)-6-(4-amino-5-methoxypyrimidin-2-yl)-7-fluoro-2-(3-(1-(6-oxo-5-(trifluoromethyl)-1,6-dihydropyridazin-4-yl)pyrrolidin-2-yl)propyl)isoquinolin-1(2H)-one Example 122

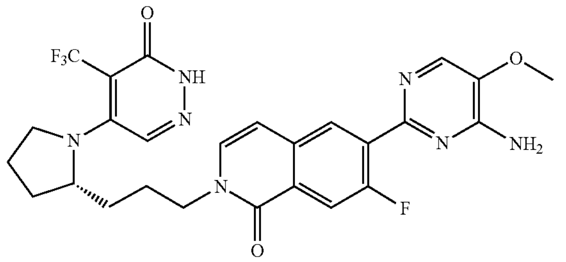

The title compound was synthesized as described in Example 17, using 2-chloro-5-methoxypyrimidin-4-amine instead of 2-bromo-5-(difluoromethoxy)pyridine and 7-bromo-6-fluoro-1H-quinazolin-4-one instead of 6-Bromo-8-fluoro-1,2-dihydroisoquinolin-1-one and tert-butyl (S)-2-(3-(tosyloxy)propyl)pyrrolidine-1-carboxylate instead of (S)-4-((tert-butoxycarbonyl)amino)pentyl 4-methylbenzenesulfonate. $^1$H NMR (400 MHz, DMSO-d6) δ 12.42 (s, 1H), 8.11 (d, J=7.0 Hz, 1H), 8.07 (s, 1H), 8.00 (d, J=11.0 Hz, 1H), 7.97 (s, 1H), 7.52 (d, J=7.4 Hz, 1H), 6.76 (d, J=7.4 Hz, 1H), 4.31-4.25 (m, 1H), 3.51 (s, 1H), 3.24-3.14 (m, 1H), 2.22-2.10 (m, 1H), 1.95-1.85 (m, 1H), 1.84-1.51 (m, 5H), 1.50-1.37 (m, 1H). One methylene peak is obstructed by water signal. ES/MS m/z: 560.30 [M+H].

Intermediate 14: Preparation of 2-((1R,2S)-2-((tert-butoxycarbonyl)amino)cyclobutyl)ethyl 4-methylbenzenesulfonate

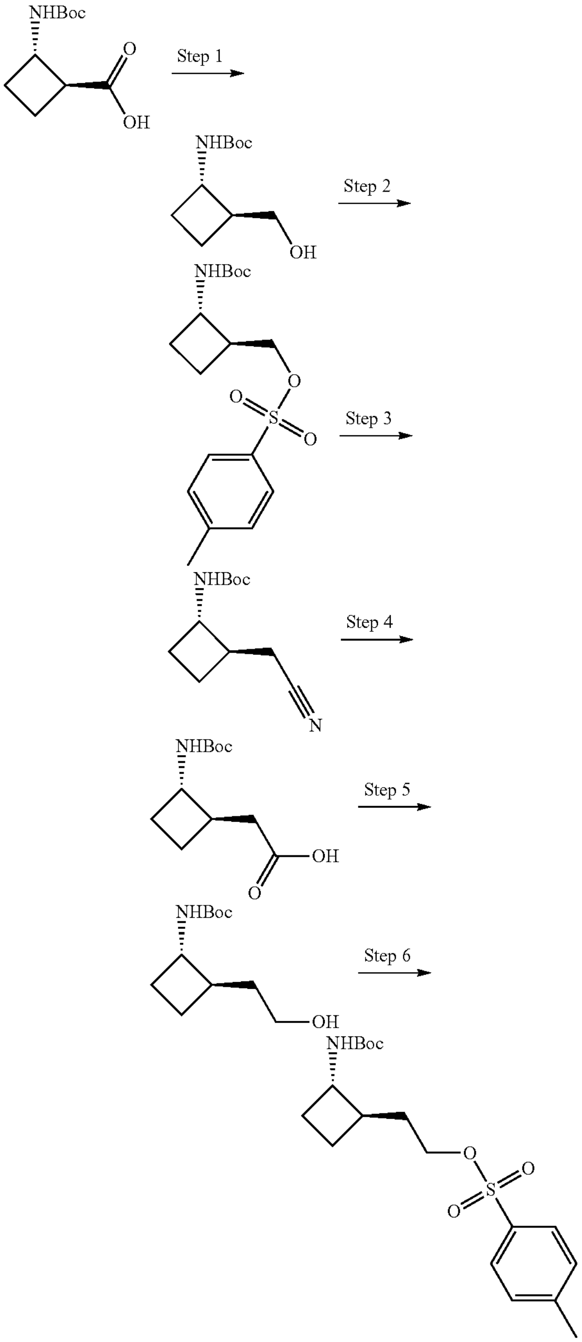

Intermediate 14

Step 1. In a vial were placed (1S,2S)-2-((tert-butoxycarbonyl)amino)cyclobutane-1-carboxylic acid (2.40 g, 11.2 mmol), and triethylamine (1.55 mL, 11.2 mmol) in THF (100 mL). The mixture was cooled to 0° C. and placed under nitrogen atmosphere. To this solution was added ethyl chloroformate (1.07 mL, 11.2 mmol) and the reaction was stirred for 30 minutes at 0° C. The mixture was then filtered to remove the precipitated triethylamine hydrochloride. The filtrate containing the mixed anhydride was slowly added to a stirred suspension of sodium borohydride (633 mg, 16.7 mmol) in 20% aqueous THF (100 mL) maintained at 0° C. The reaction mixture was then warmed to room temperature and stirred for 30 minutes, diluted with sat. aq. $NH_4Cl$, extracted with EtOAc, washed water, then brine, dried ($MgSO_4$), and concentrated. Purification via flash chromatography (elution with 0-100% v/v ethyl acetate in hexanes) afforded 1.21 g (54%) of tert-butyl ((1S,2S)-2-(hydroxymethyl)cyclobutyl) carbamate. ES/MS: m/z 223.967 [M+Na].

Step 2. In a vial were placed give tert-butyl ((1S,2S)-2-(hydroxymethyl)cyclobutyl) carbamate (1.21 g, 6.01 mmol), and N,N-diisopropylethylamine base (3.14 mL, 18.0 mmol) in DCM (45.0 mL). The mixture was cooled to 0° C. followed by the addition of p-toluenesulfonyl chloride (1.72 g, 9.02 mmol) and DMAP (147 mg, 1.20 mmol). The resulting mixture was warmed to room temperature and stirred for 64 h, then diluted with water and extracted with EtOAc, washed with brine, dried ($MgSO_4$), and concentrated. Purification via flash (elution with 0-100% v/v ethyl acetate in hexanes) afforded 756 mg (35%) of ((1S,2S)-2-((tert-butoxycarbonyl)amino)cyclobutyl)methyl 4-methylbenzenesulfonate. ES/MS m/z: 356.042 [M+H].

Step 3. To a solution of [(1S,2S)-2-(tert-butoxycarbonylamino)cyclobutyl]methyl 4-methylbenzenesulfonate (756 mg, 2.13 mmol) in DMSO (5 mL) was added NaCN (1.04 g, 21.3 mmol). The resulting mixture was then stirred at 35° C. for 72 h, then diluted with water and sat. aq. $NaHCO_3$, then extracted with EtOAc (2×) and the combined organic fractions were then washed with water (2×) and brine, dried ($MgSO_4$), and concentrated. Purification via flash chromatography (elution with 0-100% v/v ethyl acetate in hexanes) afforded 373 mg (83%) of tert-butyl-((1S,2R)-2-(cyanomethyl)cyclobutyl]carbamate. ES/MS m/z: 211.1 $[M+H]^+$.

Step 4. To a solution of tert-butyl N-[(1S,2R)-2-(cyanomethyl)cyclobutyl]carbamate (373 mg, 1.77 mmol) in EtOH (7.0 mL) was added NaOH (7.0 mL, 6.0 M, 42 mmol). The resulting mixture was then heated to 80° C. for 16 h, then cooled to room temperature and acidified to pH 4-5 with 6 M HCl. The resulting solution was extracted with EtOAc (2×), then dried ($MgSO_4$), and concentrated to afford 373.0 mg (92%) of 2-[(1R,2S)-2-(tert-butoxycarbonylamino)cyclobutyl]acetic acid. The crude material was used in the subsequent step without further purification.

Step 5. In a vial were placed 2-[(1R,2S)-2-(tert-butoxycarbonylamino)cyclobutyl]acetic acid (290 mg, 1.26 mmol), and triethylamine (0.53 mL, 3.79 mmol) in THF (15.0 mL). The mixture was cooled to 0° C. and placed under nitrogen atmosphere. To this solution was added ethyl chloroformate (0.182 mL, 1.90 mmol) and the reaction was stirred for 30 minutes at 0° C. The mixture was then filtered to remove the precipitated triethylamine hydrochloride. The filtrate containing the mixed anhydride was slowly added to a stirred suspension of sodium borohydride (144 mg, 3.79 mmol) in 20% aqueous THF (15.0 mL) maintained at 0° C. The reaction mixture was then warmed to room temperature and stirred for 30 minutes, diluted with sat. aq. $NH_4Cl$, extracted with EtOAc, washed water, then brine, dried ($MgSO_4$), and concentrated. Purification via flash chromatography (elution with 0-100% v/v ethyl acetate in hexanes) aforded 183 mg (67%) of tert-butyl N-[(1S,2R)-2-(2-hydroxyethyl)cyclobutyl]carbamate. ES/MS: m/z 216.012 [M+NH].

Step 6. In a vial were placed tert-butyl N-[(1S,2R)-2-(2-hydroxyethyl)cyclobutyl]carbamate (183 mg, 0.85 mmol), and N,N-diisopropylethylamine (0.592 mL, 3.40 mmol) in DCM (10.0 mL). The mixture was cooled to 0° C. followed by the addition of p-toluenesulfonyl chloride (324 mg, 1.70 mmol) and DMAP (20.8 mg, 0.17 mmol). The resulting mixture was warmed to room temperature and stirred for 16 h, then diluted with water and extracted with EtOAc, washed with brine, dried ($MgSO_4$), and concentrated. Purification via flash (elution with 0-100% v/v ethyl acetate in hexanes) afforded 103 mg (33%) of 2-[(1R,2S)-2-(tert-butoxycarbonylamino)cyclobutyl]ethyl 4-methylbenzenesulfonate. ES/MS m/z: 370.099 [M+H].

Example 123: 6-(4-amino-5-(trifluoromethyl)pyrimidin-2-yl)-7-fluoro-2-(2-((1R,2S)-2-((6-oxo-5-(trifluoromethyl)-1,6-dihydropyridazin-4-yl)amino)cyclobutyl)ethyl)isoquinolin-1(2H)-one Example 123

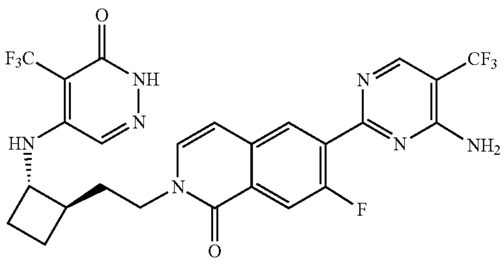

The title compound was synthesized as described in Example 17, using 2-chloro-5-(trifluoromethyl)pyrimidin-4-amine instead of 2-bromo-5-(difluoromethoxy)pyridine and 7-bromo-6-fluoro-1H-quinazolin-4-one instead of 6-Bromo-8-fluoro-1,2-dihydroisoquinolin-1-one and 2-((1R,2S)-2-((tert-butoxycarbonyl)amino)cyclobutyl)ethyl 4-methylbenzenesulfonate instead of (S)-4-((tert-butoxycarbonyl)amino)pentyl 4-methylbenzenesulfonate. $^1H$ NMR (400 MHz, DMSO-d6) δ 12.49 (s, 1H), 8.65 (d, J=1.0 Hz, 1H), 8.19 (d, J=7.1 Hz, 1H), 7.95 (d, J=11.1 Hz, 1H), 7.80 (s, 1H), 7.50 (d, J=7.4 Hz, 1H), 6.97-6.88 (m, 1H), 6.77 (d, J=7.4 Hz, 1H), 4.08-3.94 (m, 2H), 3.91-3.79 (m, 1H), 2.26 (q, J=8.8 Hz, 1H), 2.04-1.91 (m, 1H), 1.90-1.75 (m, 3H), 1.36-1.23 (m, 1H). One proton appears to overlap with the DMSO signal. ES/MS m/z: 584.30 [M+H].

Intermediate 15: Preparation of 4-(3-((tert-butyldimethylsilyl)oxy)azetidin-1-yl)-2-iodo-5-(trifluoromethyl)pyrimidine

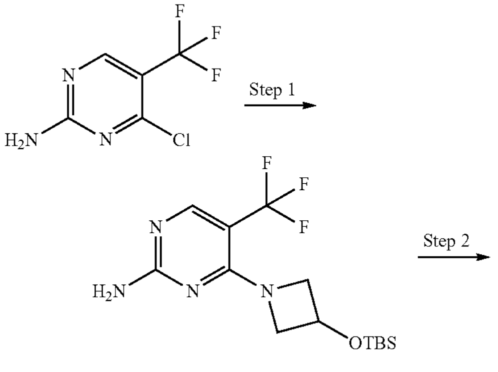

-continued

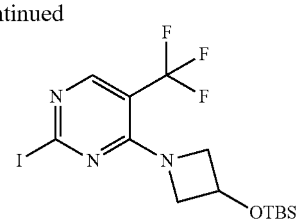

Intermediate 15

Step 1. To a solution of 4-chloro-5-(trifluoromethyl)pyrimidin-2-amine (500 mg, 2.53 mmol) and azetidin-3-ol hydrochloride (277 mg, 2.53 mmol) in DMF (16.0 mL) was added N,N-diisopropylethylamine (4.41 mL, 25.3 mmol). The resulting mixture was heated to 80° C. for 1 h, then cooled to room temperature followed by the addition of tert-butyldimethylsilyl chloride (763 mg, 5.06 mmol) and imidazole (379 mg, 5.57 mmol). The resulting solution was heated to 80° C. for 3 h, then diluted with sat. aq. $NH_4Cl$, extracted with EtOAc, washed with brine, dried ($MgSO_4$), and concentrated. Purification via flash (elution with 0-100% v/v ethyl acetate in hexanes) afforded 565 mg (64%) of 4-[3-[tert-butyl(dimethyl)silyl]oxyazetidin-1-yl]-5-(trifluoromethyl)pyrimidin-2-amine ES/MS m/z: 350.196 [M+H].

Step 2. A solution of 4-[3-[tert-butyl(dimethyl)silyl]oxyazetidin-1-yl]-5-(trifluoromethyl)pyrimidin-2-amine (465 mg, 1.33 mmol), di-iodomethane (4.30 mL, 53.4 mmol), tert-Butylnitrite (0.635 mL, 5.34 mmol), and CuI (50.8 mg, 0.267 mmol) in MeCN (5.0 mL) was heated to 80° C. for 3 h, then poured into $Na_2S2O_3$, extracted with EtOAc, washed with brine, dried ($MgSO_4$) and concentrated. Purification via flash (elution with 0-100% v/v ethyl acetate in hexanes) afforded 40 mg (7%) of tert-butyl-[1-[2-iodo-5-(trifluoromethyl)pyrimidin-4-yl]azetidin-3-yl]oxy-dimethyl-silane ES/MS m/z: 459.340 [M+H].

Example 124: (S)-6-fluoro-7-(4-(3-hydroxyazetidin-1-yl)-5-(trifluoromethyl)pyrimidin-2-yl)-3-(4-((6-oxo-5-(trifluoromethyl)-1,6-dihydropyridazin-4-yl)amino)pentyl)quinazolin-4(3H)-one Example 124

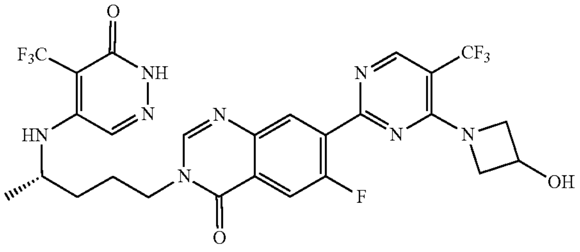

The title compound was synthesized as described in Example 17, using 4-(3-((tert-butyldimethylsilyl)oxy)azetidin-1-yl)-2-iodo-5-(trifluoromethyl)pyrimidine instead of 2-bromo-5-(difluoromethoxy)pyridine and 7-bromo-6-fluoroquinazolin-4(1H)-one instead of 6-Bromo-8-fluoro-1,2-dihydroisoquinolin-1-one. $^1$H NMR (400 MHz, DMSO-d6) δ 12.44 (s, 1H), 8.72 (s, 1H), 8.43 (s, 1H), 8.26 (d, J=6.7 Hz, 1H), 7.96-7.88 (m, 2H), 6.41-6.27 (m, 1H), 5.87 (s, 1H), 4.65-4.55 (m, 1H), 4.55-4.44 (m, 2H), 4.04-3.98 (m, 4H), 1.83-1.62 (m, 3H), 1.58-1.46 (m, 1H), 1.17 (d, J=6.3 Hz, 3H). ES/MS m/z: 629.30 [M+H].

Example 125: (S)-4-amino-2-(6-fluoro-4-oxo-3-(4-((6-oxo-5-(trifluoromethyl)-1,6-dihydropyridazin-4-yl)amino)pentyl)-3,4-dihydroquinazolin-7-yl)pyrimidine-5-carbonitrile Example 125

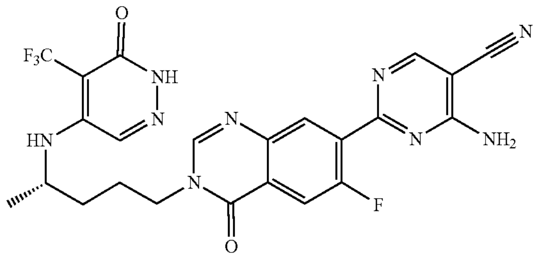

The title compound was synthesized as described in Example 17, using 4-amino-2-chloropyrimidine-5-carbonitrile instead of 2-bromo-5-(difluoromethoxy)pyridine and 7-bromo-6-fluoroquinazolin-4(1H)-one instead of 6-Bromo-8-fluoro-1,2-dihydroisoquinolin-1-one. 1H NMR (400 MHz, DMSO-d6) δ 12.44 (s, 1H), 8.81 (s, 1H), 8.43 (s, 1H), 8.19 (d, J=6.7 Hz, 1H), 7.95-7.87 (m, 2H), 6.39-6.28 (m, 1H), 4.03-3.93 (m, 3H), 1.81-1.61 (m, 3H), 1.58-1.48 (m, 1H), 1.17 (d, J=6.3 Hz, 3H). ES/MS m/z: 530.30 $[M+H]^+$.

Example 126: (S)-6-fluoro-7-(5-(methylsulfonyl)pyrimidin-2-yl)-3-(4-((6-oxo-5-(trifluoromethyl)-1,6-dihydropyridazin-4-yl)amino)pentyl)quinazolin-4(3H)-one Example 126

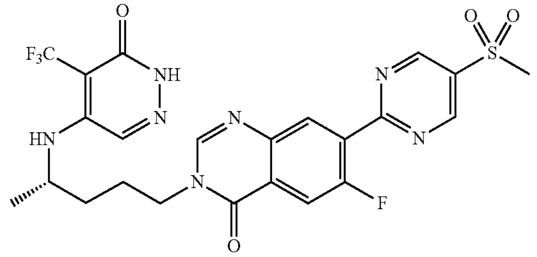

The title compound was synthesized as described in Example 17, using 2-chloro-5-(methylsulfonyl)pyrimidine instead of 2-bromo-5-(difluoromethoxy)pyridine and 7-bromo-6-fluoroquinazolin-4(1H)-one instead of 6-Bromo-8-fluoro-1,2-dihydroisoquinolin-1-one. $^1$H NMR (400 MHz, DMSO-d6) δ 12.44 (s, 1H), 9.48 (s, 2H), 8.47 (s, 1H), 8.36 (d, J=6.8 Hz, 1H), 8.01 (d, J=10.5 Hz, 1H), 7.92 (s, 1H), 6.40-6.28 (m, 1H), 4.06-3.93 (m, 3H), 3.49 (s, 3H), 1.82-1.62 (m, 3H), 1.59-1.46 (m, 1H), 1.17 (d, J=6.3 Hz, 3H). ES/MS m/z: 568.30 [M+H].

Example 127: (S)-6-fluoro-7-(5-(2-hydroxyethoxy)pyrimidin-2-yl)-3-(4-((6-oxo-5-(trifluoromethyl)-1,6-dihydropyridazin-4-yl)amino)pentyl)quinazolin-4(3H)-one Example 127

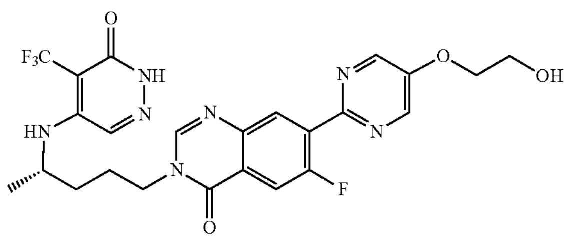

The title compound was synthesized as described in Example 17, using 5-(2-((tert-butyldimethylsilyl)oxy)ethoxy)-2-chloropyrimidine instead of 2-bromo-5-(difluoromethoxy)pyridine and 7-bromo-6-fluoroquinazolin-4(1H)-one instead of 6-Bromo-8-fluoro-1,2-dihydroisoquinolin-1-one. 1H NMR (400 MHz, DMSO-d6) δ 12.44 (s, 1H), 8.77 (s, 2H), 8.42 (s, 1H), 8.23 (d, J=7.0 Hz, 1H), 7.95-7.89 (m, 2H), 6.35 (dd, J=8.8, 3.8 Hz, 1H), 4.30-4.24 (m, 2H), 4.03-3.95 (m, 3H), 3.80-3.77 (m, 2H), 1.84-1.61 (m, 3H), 1.59-1.47 (m, 1H), 1.17 (d, J=6.3 Hz, 3H). ES/MS m/z: 550.30 [M+H].

Example 128: (S)-6-(4-amino-5-(trifluoromethyl)pyrimidin-2-yl)-7-fluoro-2-(4-((6-oxo-5-(trifluoromethyl)-1,6-dihydropyridazin-4-yl)amino)pentyl)isoquinolin-1(2H)-one Example 128

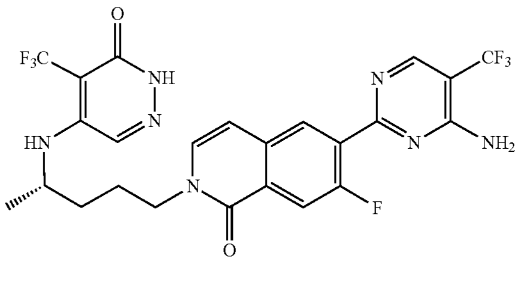

The title compound was synthesized as described in Example 17, using 2-chloro-5-(trifluoromethyl)pyrimidin-4-amine instead of 2-bromo-5-(difluoromethoxy)pyridine and 7-bromo-6-fluoroquinazolin-4(1H)-one instead of 6-Bromo-8-fluoro-1,2-dihydroisoquinolin-1-one. $^{1}H$ NMR (400 MHz, DMSO-d6) δ 12.44 (s, 1H), 8.66 (d, J=1.0 Hz, 1H), 8.43 (s, 1H), 8.18 (d, J=6.7 Hz, 1H), 7.95-7.90 (m, 2H), 6.40-6.28 (m, 1H), 4.04-3.92 (m, 3H), 1.81-1.60 (m, 3H), 1.60-1.45 (m, 1H), 1.17 (d, J=6.3 Hz, 3H). ES/MS m/z: 573.30 [M+H].

Example 129: (S)-7-fluoro-6-(5-(2-hydroxyethoxy)pyrimidin-2-yl)-2-(4-((6-oxo-5-(trifluoromethyl)-1,6-dihydropyridazin-4-yl)amino)pentyl)isoquinolin-1(2H)-one Example 129

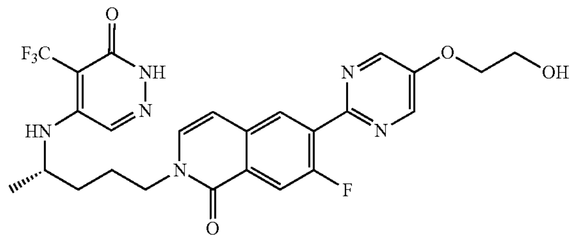

The title compound was synthesized as described in Example 17, using 5-(2-((tert-butyldimethylsilyl)oxy)ethoxy)-2-chloropyrimidine instead of 2-bromo-5-(difluoromethoxy)pyridine and 6-bromo-7-fluoroisoquinolin-1(2H)-one instead of 6-Bromo-8-fluoro-1,2-dihydroisoquinolin-1-one. 1H NMR (400 MHz, DMSO-d6) δ 12.44 (s, 1H), 8.77 (s, 2H), 8.42 (s, 1H), 8.23 (d, J=7.0 Hz, 1H), 7.95-7.89 (m, 2H), 6.35 (dd, J=8.8, 3.8 Hz, 1H), 4.30-4.24 (m, 2H), 4.03-3.95 (m, 3H), 3.80-3.77 (m, 2H), 1.84-1.61 (m, 3H), 1.59-1.47 (m, 1H), 1.17 (d, J=6.3 Hz, 3H). ES/MS m/z: 550.30 [M+H].

Example 130: 7,8-difluoro-2-(((1R,3R)-3-(((6-oxo-5-(trifluoromethyl)-1,6-dihydropyridazin-4-yl)amino)methyl)cyclobutyl)methyl)-6-(5-(trifluoromethyl)pyrimidin-2-yl)isoquinolin-1(2H)-one

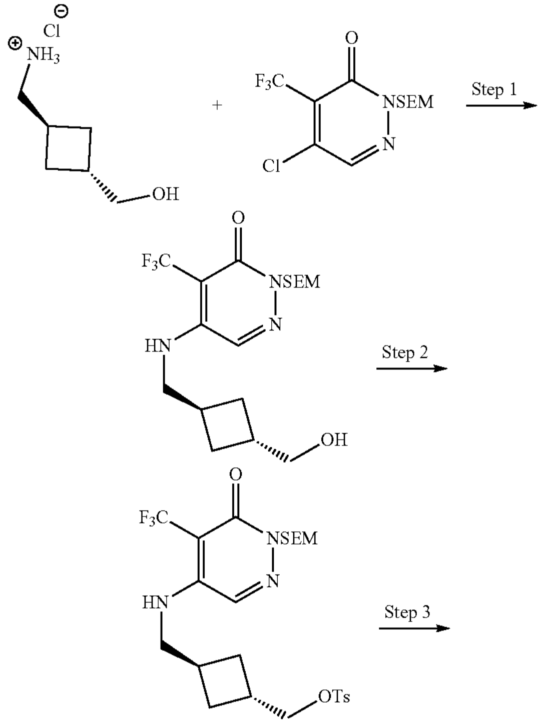

-continued

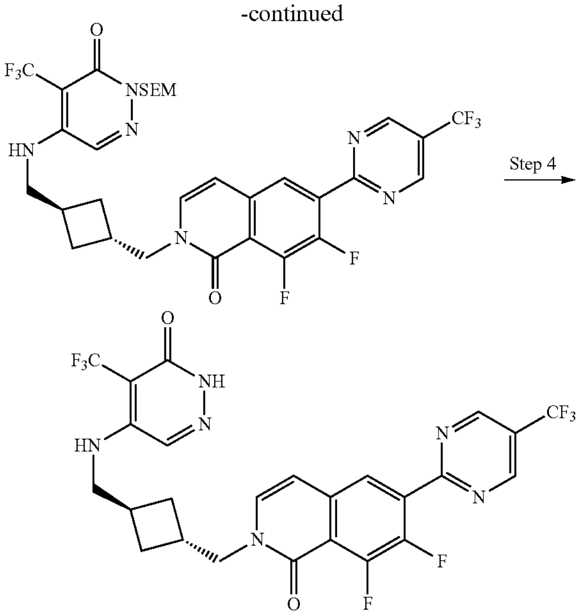

Example 130

Step 1. 5-((((1R,3R)-3-(hydroxymethyl)cyclobutyl)methyl)amino)-4-(trifluoromethyl)-2-((2-(trimethylsilyl)ethoxy)methyl)pyridazin-3(2H)-one was synthesized as described in Example 5 (step 7) using ((1R,3R)-3-(aminomethyl)cyclobutyl)methanol (HCl salt) instead of 2-[(4S)-4-aminopentyl]-6-[5-(trifluoromethyl)pyrimidin-2-yl]isoquinolin-1-one. ES/MS m/z: 408.14 $[M+H]^+$.

Step 2. ((1R,3R)-3-(((6-oxo-5-(trifluoromethyl)-1-((2-(trimethylsilyl)ethoxy)methyl)-1,6-dihydropyridazin-4-yl)amino)methyl)cyclobutyl)methyl 4-methylbenzenesulfonate was synthesized as described in Example 5 (step 2) using 5-((((1R,3R)-3-(hydroxymethyl)cyclobutyl)methyl)amino)-4-(trifluoromethyl)-2-((2-(trimethylsilyl)ethoxy)methyl)pyridazin-3(2H)-one instead of tert-butyl N-[(1S)-4-hydroxy-1-methyl-butyl]carbamate. ES/MS m/z: 562.10 $[M+H]^+$.

Step 3. 7,8-difluoro-2-(((1R,3R)-3-(((6-oxo-5-(trifluoromethyl)-1-((2-(trimethylsilyl)ethoxy)methyl)-1,6-dihydropyridazin-4-yl)amino)methyl)cyclobutyl)methyl)-6-(5-(trifluoromethyl)pyrimidin-2-yl)isoquinolin-1(2H)-one was synthesized as described in Example 5 (step 3) using ((1R,3R)-3-(((6-oxo-5-(trifluoromethyl)-1-((2-(trimethylsilyl)ethoxy)methyl)-1,6-dihydropyridazin-4-yl)amino)methyl)cyclobutyl)methyl 4-methylbenzenesulfonate instead of [(4S)-4-(tert-butoxycarbonylamino)pentyl]4-methylbenzenesulfonate and 7,8-difluoro-6-(5-(trifluoromethyl)pyrimidin-2-yl)isoquinolin-1(2H)-one instead of 6-bromo-2H-isoquinolin-1-one. ES/MS m/z: 717.12 $[M+H]^+$.

Step 4. 7,8-difluoro-2-(((1R,3R)-3-(((6-oxo-5-(trifluoromethyl)-1,6-dihydropyridazin-4-yl)amino)methyl)cyclobutyl)methyl)-6-(5-(trifluoromethyl)pyrimidin-2-yl)isoquinolin-1(2H)-one was synthesized as described in Example 5 (step 8) using 7,8-difluoro-2-(((1R,3R)-3-(((6-oxo-5-(trifluoromethyl)-1-((2-(trimethylsilyl)ethoxy)methyl)-1,6-dihydropyridazin-4-yl)amino)methyl)cyclobutyl)methyl)-6-(5-(trifluoromethyl)pyrimidin-2-yl)isoquinolin-1(2H)-one instead of 2-[(4S)-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one. $^1H$ NMR (400 MHz, DMSO-d6) δ 12.42 (s, 1H), 9.50 (d, J=1.0 Hz, 2H), 8.24 (dd, J=6.5, 1.7 Hz, 1H), 7.89 (s, 1H), 7.60 (d, J=7.4 Hz, 1H), 7.08 (d, J=5.2 Hz, 1H), 6.80 (dd, J=7.4, 1.9 Hz, 1H), 4.04 (d, J=7.6 Hz, 2H), 3.49-3.42 (m, 2H), 2.79 (p, J=7.5 Hz, 1H), 2.63-2.54 (m, 1H), 1.95-1.86 (m, 2H), 1.84-1.75 (m, 2H). ES/MS m/z: 587.30 [M+H]+.

Intermediates 16 and 17: (R)-N-((R,Z)-5-((tert-butyldiphenylsilyl)oxy)-3-fluoropent-3-en-2-yl)-2-methylpropane-2-sulfinamide (16) and (R)-N-((S,Z)-5-((tert-butyldiphenylsilyl)oxy)-3-fluoropent-3-en-2-yl)-2-methleropane-2-sulfinamide (17)

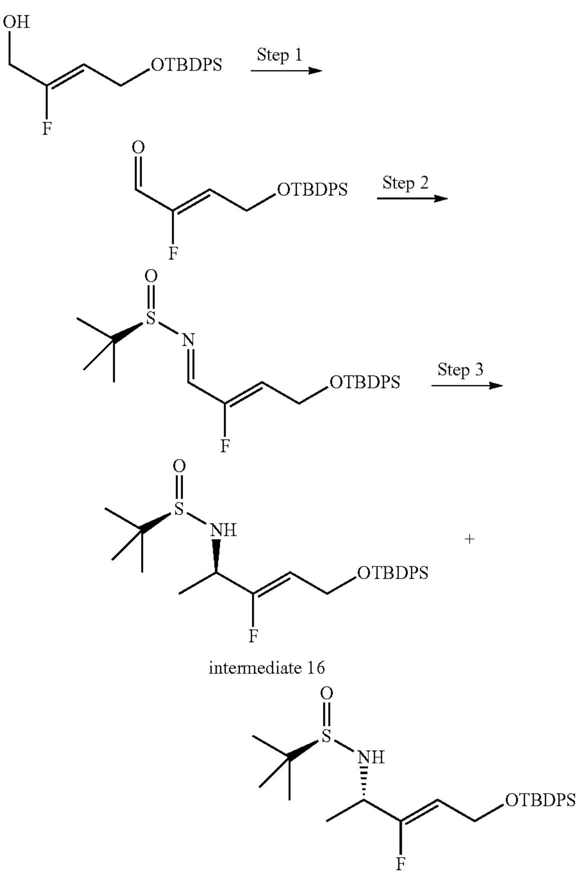

intermediate 17

(Z)-4-((tert-butyldiphenylsilyl)oxy)-2-fluorobut-2-en-1-ol was prepared as described in *Nucleosides, Nucleotides & Nucleic Acids,* 22 (5-8), 659-661; 2003.

Step 1. A suspension of (Z)-4-((tert-butyldiphenylsilyl)oxy)-2-fluorobut-2-en-1-ol (585 mg, 1.7 mmol) and IBX (45%, 3.17 g, 5.1 mmol) in ethyl acetate (15.0 mL) was heated at reflux for 3 h. Upon cooling, the solid was filtered. The filtrate was concentrated and purified using column chromatography eluting with EtOAc in hexanes 0-25% to afford (Z)-4-((tert-butyldiphenylsilyl)oxy)-2-fluorobut-2-enal. ES/MS m/z: 365.20 $[M+Na]^+$.

Step 2. To solution of (Z)-4-((tert-butyldiphenylsilyl)oxy)-2-fluorobut-2-enal (265 mg, 0.774 mmol) in THF (15.0 mL) was added $Ti(OET)_4$ (0.41 mL, 1.93 mmol) and (R)-tert-butylsulfinylamine (234 mg, 1.93 mmol). The reaction mixture was stirred at reflux for 2 h. Upon cooling, the mixture was diluted with water and extracted with EtOAc. The combined organic layers were washed with brine, dried over $MgSO_4$ and concentrated in vacuo to give the crude product. The crude residue was purified using column chromatography eluting with EtOAc in hexanes 0-50% to afford (R)—N-((1E,2Z)-4-((tert-butyldiphenylsilyl)oxy)-2-fluorobut-2-en-1-ylidene)-2-methylpropane-2-sulfinamide. ES/MS m/z: 446.12 $[M+H]^+$.

Step 3. To solution of (R)—N-((1E,2Z)-4-((tert-butyldiphenylsilyl)oxy)-2-fluorobut-2-en-1-ylidene)-2-methylpropane-2-sulfinamide (282 mg, 0.633 mmol) in PhMe (3.0 mL) at 0° C. was added a 3.0 M solution of MeMgBr in $Et_2O$ (0.548 mL, 1.65 mmol). The reaction mixture was stirred at ambient temperature for 16 h. Upon cooling, the mixture was quenched with saturated aqueous $NH_4Cl$ and extracted with EtOAc. The combined organic layers were washed with brine, dried over $MgSO_4$ and concentrated in vacuo to give the crude product. The crude residue was purified using column chromatography eluting with EtOAc in hexanes 0-80% to afford (R)—N—((R,Z)-5-((tert-butyldiphenylsilyl)oxy)-3-fluoropent-3-en-2-yl)-2-methylpropane-2-sulfinamide (X) and (R)—N—((S,Z)-5-((tert-butyldiphenylsilyl)oxy)-3-fluoropent-3-en-2-yl)-2-methylpropane-2-sulfinamide (Y). ES/MS m/z: 484.30 $[M+Na]^+$.

Example 131: Preparation of (R,Z)-7,8-difluoro-2-(3-fluoro-4-((6-oxo-5-(trifluoromethyl)-1,6-dihydropyridazin-4-yl)amino)pent-2-en-1-yl)-6-(5-(trifluoromethyl)pyrimidin-2-yl)isoquinolin-1(2H)-one

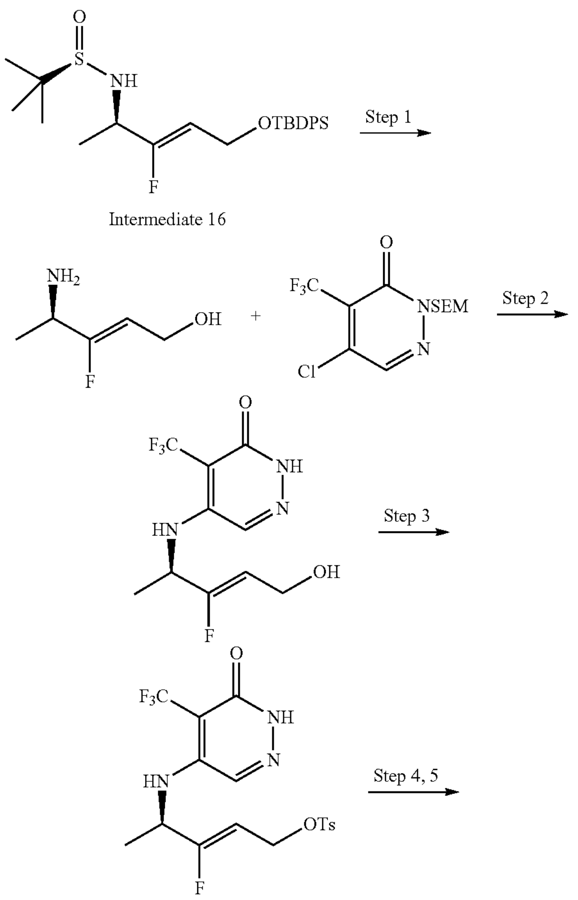

-continued

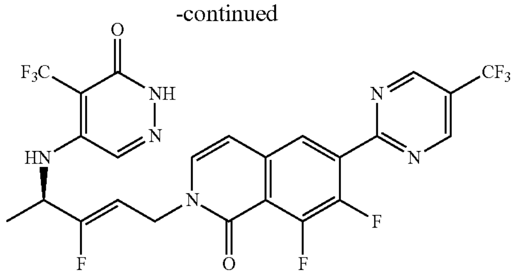

Example 131

Step 1. To a solution of (R)—N—((R,Z)-5-((tert-butyldiphenylsilyl)oxy)-3-fluoropent-3-en-2-yl)-2-methylpropane-2-sulfinamide (intermediate 16, 100 mg, 0.22 mmol) in MeOH (2.00 mL) was added 4N HCl in dioxane (0.325 mL, 1.30 mmol). The reaction mixture was stirred at ambient temperature for 1 h. Upon concentration, crude (R,Z)-4-amino-3-fluoropent-2-en-1-ol (HCl salt) was used in the next step.

Step 2. (R,Z)-5-((3-fluoro-5-hydroxypent-3-en-2-yl)amino)-4-(trifluoromethyl)pyridazin-3(2H)-one was synthesized as described in Example 5 (step 7) using (R,Z)-4-amino-3-fluoropent-2-en-1-ol (HCl salt) instead of 2-[(4S)-4-aminopentyl]-6-[5-(trifluoromethyl)pyrimidin-2-yl] isoquinolin-1-one. ES/MS m/z: 434.20 $[M+Na]^+$.

Step 3. (R,Z)-3-fluoro-4-((6-oxo-5-(trifluoromethyl)-1,6-dihydropyridazin-4-yl)amino)pent-2-en-1-yl 4-methylbenzenesulfonate was synthesized as described in Example 5 (step 2) using (R,Z)-5-((3-fluoro-5-hydroxypent-3-en-2-yl)amino)-4-(trifluoromethyl)pyridazin-3(2H)-one instead of tert-butyl N-[(1S)-4-hydroxy-1-methyl-butyl]carbamate. ES/MS m/z: 566.10 $[M+H]^+$.

Step 4. (R,Z)-7,8-difluoro-2-(3-fluoro-4-((6-oxo-5-(trifluoromethyl)-1-((2-(trimethylsilyl)ethoxy)methyl)-1,6-dihydropyridazin-4-yl)amino)pent-2-en-1-yl)-6-(5-(trifluoromethyl)pyrimidin-2-yl)isoquinolin-1(2H)-one was synthesized as described in Example 5 (step 3) using (R,Z)-3-fluoro-4-((6-oxo-5-(trifluoromethyl)-1,6-dihydropyridazin-4-yl)amino)pent-2-en-1-yl 4-methylbenzenesulfonate instead of [(4S)-4-(tert-butoxycarbonylamino)pentyl]4-methylbenzenesulfonate and 7,8-difluoro-6-(5-(trifluoromethyl)pyrimidin-2-yl)isoquinolin-1(2H)-one instead of 6-bromo-2H-isoquinolin-1-one. ES/MS m/z: 721.12 $[M+H]^+$.

Step 5. (R,Z)-7,8-difluoro-2-(3-fluoro-4-((6-oxo-5-(trifluoromethyl)-1,6-dihydropyridazin-4-yl)amino)pent-2-en-1-yl)-6-(5-(trifluoromethyl)pyrimidin-2-yl)isoquinolin-1(2H)-one was synthesized as described in Example 5 (step 8) using (R,Z)-7,8-difluoro-2-(3-fluoro-4-((6-oxo-5-(trifluoromethyl)-1-((2-(trimethylsilyl)ethoxy)methyl)-1,6-dihydropyridazin-4-yl)amino)pent-2-en-1-yl)-6-(5-(trifluoromethyl)pyrimidin-2-yl)isoquinolin-1(2H)-one instead of 2-[(4S)-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one. $^1H$ NMR (400 MHz, DMSO-d6) δ 12.60 (s, 1H), 9.51 (s, 2H), 8.25 (dd, J=6.6, 1.7 Hz, 1H), 7.92 (s, 1H), 7.52 (d, J=7.4 Hz, 1H), 6.83 (dd, J=7.5, 1.9 Hz, 1H), 6.58 (dt, J=8.1, 3.5 Hz, 1H), 5.32 (dt, J=37.3, 7.0 Hz, 1H), 4.79 (dt, J=13.0, 6.9 Hz, 1H), 4.70-4.56 (m, 2H), 1.42 (d, J=6.7 Hz, 3H). ES/MS m/z: 591.20 $[M+H]^+$.

Example 132: (S,Z)-7,8-difluoro-2-(3-fluoro-4-((6-oxo-5-(trifluoromethyl)-1,6-dihydropyridazin-4-yl)amino)pent-2-en-1-yl)-6-(5-(trifluoromethyl)pyrimidin-2-yl)isoquinolin-1(2H)-one Example 132

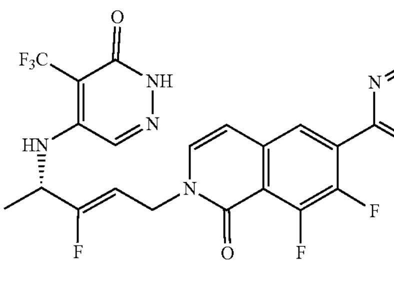

(S,Z)-7,8-difluoro-2-(3-fluoro-4-((6-oxo-5-(trifluoromethyl)-1,6-dihydropyridazin-4-yl)amino)pent-2-en-1-yl)-6-(5-(trifluoromethyl)pyrimidin-2-yl)isoquinolin-1(2H)-one was synthesized as described in Example 132 using intermediate 17 instead intermediate 16. $^1$H NMR (400 MHz, DMSO-d6) δ 12.60 (s, 1H), 9.51 (s, 2H), 8.25 (dd, J=6.6, 1.7 Hz, 1H), 7.92 (s, 1H), 7.52 (d, J=7.4 Hz, 1H), 6.83 (dd, J=7.5, 1.9 Hz, 1H), 6.58 (dt, J=8.1, 3.5 Hz, 1H), 5.32 (dt, J=37.3, 7.0 Hz, 1H), 4.79 (dt, J=13.0, 6.9 Hz, 1H), 4.70-4.56 (m, 2H), 1.42 (d, J=6.7 Hz, 3H). ES/MS m/z: 591.24 [M+H]$^+$.

Example 133: (S,E)-7,8-difluoro-2-(4-((6-oxo-5-(trifluoromethyl)-1,6-dihydropyridazin-4-yl)amino)pent-2-en-1-yl)-6-(5-(trifluoromethyl)pyrimidin-2-yl)isoquinolin-1(2H)-one Example 133

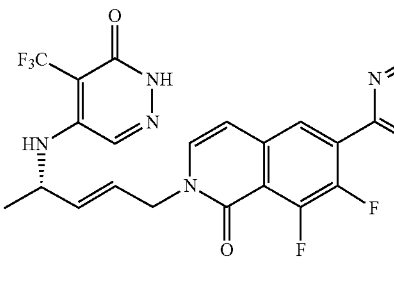

(S,E)-7,8-difluoro-2-(4-((6-oxo-5-(trifluoromethyl)-1,6-dihydropyridazin-4-yl)amino)pent-2-en-1-yl)-6-(5-(trifluoromethyl)pyrimidin-2-yl)isoquinolin-1(2H)-one was synthesized as described in Example 132 using tert-butyl (S,E)-(5-hydroxypent-3-en-2-yl)carbamate (Chem. Lett. 1986, 5, 815-18) instead of intermediate 16. $^1$H NMR (400 MHz, DMSO-d6) δ 12.60 (s, 1H), 9.51 (s, 2H), 8.25 (dd, J=6.6, 1.7 Hz, 1H), 7.92 (s, 1H), 7.52 (d, J=7.4 Hz, 1H), 6.83 (dd, J=7.5, 1.9 Hz, 1H), 6.58 (dt, J=8.1, 3.5 Hz, 1H), 5.32 (dt, J=37.3, 7.0 Hz, 1H), 4.79 (dt, J=13.0, 6.9 Hz, 1H), 4.70-4.56 (m, 2H), 1.42 (d, J=6.7 Hz, 3H). ES/MS m/z: 572.4 [M+H]$^+$.

Example 134: Preparation of (S,E)-6-(4-amino-5-methoxypyrimidin-2-yl)-7-fluoro-2-(4-((6-oxo-5-(trifluoromethyl)-1,6-dihydropyridazin-4-yl)amino)pent-2-en-1-yl)isoquinolin-1(2H)-one

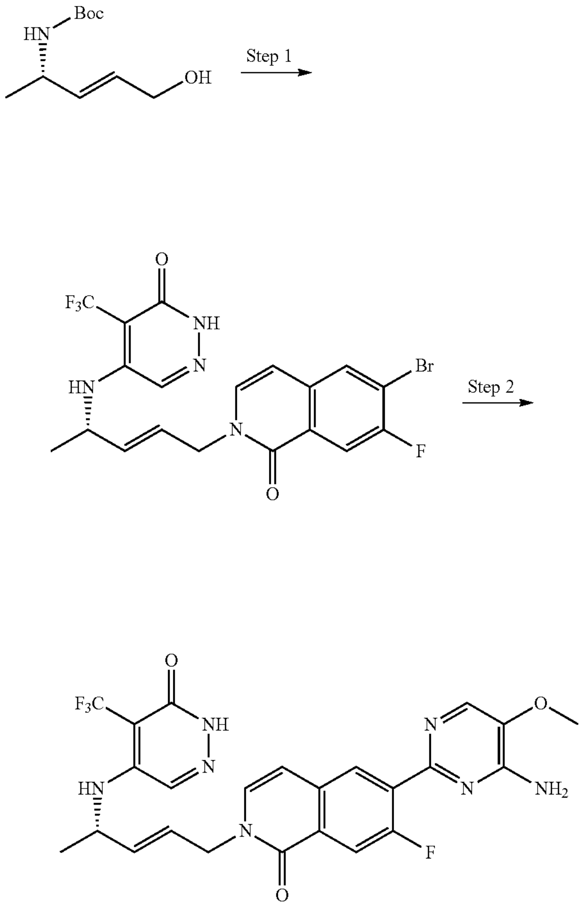

Example 134

Step 1. (S,E)-6-bromo-7-fluoro-2-(4-((6-oxo-5-(trifluoromethyl)-1,6-dihydropyridazin-4-yl)amino)pent-2-en-1-yl)isoquinolin-1(2H)-one was synthesized as described in Example 132 (Steps 1-4) using tert-butyl (S,E)-(5-hydroxypent-3-en-2-yl)carbamate (Chem. Lett. 1986, 5, 815-18) instead intermediate 16 and 6-bromo-7-fluoroisoquinolin-1(2H)-one instead of 7,8-difluoro-6-(5-(trifluoromethyl)pyrimidin-2-yl)isoquinolin-1(2H)-one. ES/MS m/z: 617.06 [M+H]$^+$.

Step 2. (S,E)-6-(4-amino-5-methoxypyrimidin-2-yl)-7-fluoro-2-(4-((6-oxo-5-(trifluoromethyl)-1,6-dihydropyridazin-4-yl)amino)pent-2-en-1-yl)isoquinolin-1(2H)-one was synthesized as described in Example 17 (step 3) using 2-chloro-5-methoxypyrimidin-4-amine instead of 2-bromo-5-(difluoromethoxy)pyridine. $^1$H NMR (400 MHz, DMSO-d6) δ 13.32 (s, 0.35H), 12.49 (s, 0.65H), 9.34 (d, J=8.1 Hz, 0.35H), 8.15 (s, 0.35H), 8.11 (d, J=7.1 Hz, 1H), 8.05 (s, 1H), 7.97 (d, J=11.0 Hz, 1H), 7.81 (s, 0.65H), 7.43 (dd, J=7.4, 1.8 Hz, 1H), 6.77 (d, J=7.4 Hz, 1H), 6.50 (dd, J=7.8, 3.8 Hz, 1H), 5.92-5.69 (m, 2H), 4.71-4.50 (m, 3H), 3.94 (s, 3H), 1.33 (d, J=6.6 Hz, 1H), 1.28 (d, J=6.6 Hz, 2H). ES/MS m/z: 532.3 [M+H]$^+$.

Example 135: Preparation of (R)-7-fluoro-2-(5-methoxy-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one

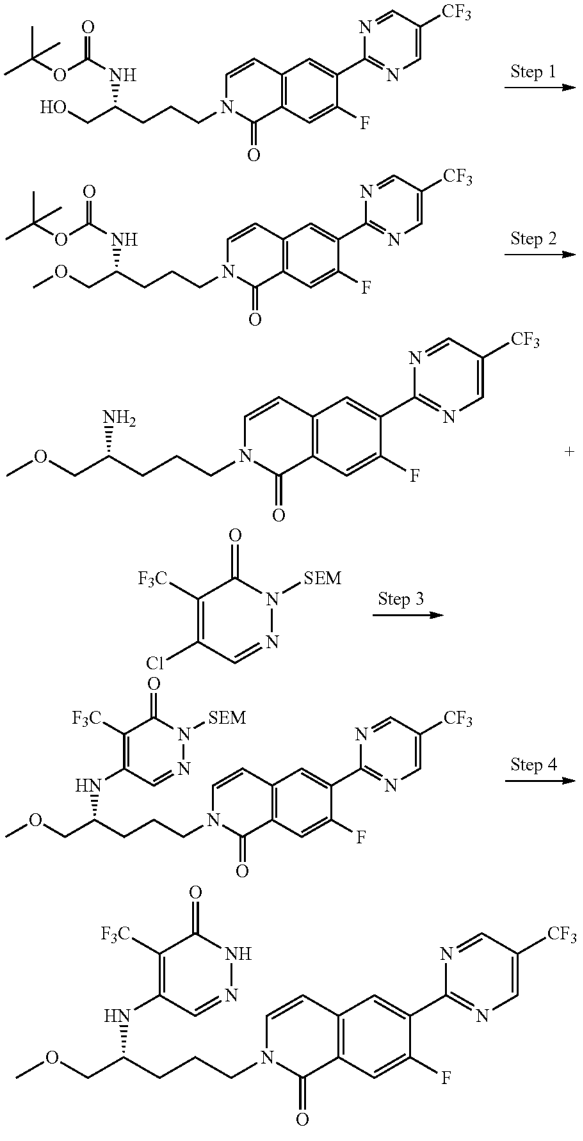

Example 135

Step 1. To a solution of (2R)-2-(tert-butoxycarbonylamino)-5-[7-fluoro-1-oxo-6-[5-(trifluoromethyl)pyrimidin-2-yl]-2-isoquinolyl]pentanoic acid (synthesized as described in Example 88, Steps 1-3) (39.3 mg, mmol) in anhydrous acetonitrile (1.00 mL) was added Silver oxide (76.3 mg, 0.329 mmol) and iodomethane (104 mg, 0.731 mmol). The heterogenous mixture was protected from light and stirred at room temperature for 12 hrs. Upon completion, the solid was filtered off and the filtrate was concentrated in vacuo. The crude product was purified using flash chromatography eluting with EtOAc in hexanes 0-100% to afford tert-butyl N-[(1R)-4-[7-fluoro-1-oxo-6-[5-(trifluoromethyl)pyrimidin-2-yl]-2-isoquinolyl]-1-(methoxymethyl)butyl]carbamate. ES/MS m/z: 525.2 $[M+H]^+$.

Step 2. 2-[(4R)-4-amino-5-methoxy-pentyl]-7-fluoro-6-[5-(trifluoromethyl)pyrimidin-2-yl]isoquinolin-1-one was synthesized as described in Example 88 (step 4) using tert-butyl N-[(1R)-4-[7-fluoro-1-oxo-6-[5-(trifluoromethyl)pyrimidin-2-yl]-2-isoquinolyl]-1-(methoxymethyl)butyl]carbamate. ES/MS m/z: 425.2 $[M+H]^+$.

Step 3. 7-fluoro-2-[(4R)-5-methoxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one was synthesized as described in Example 88 (step 5) using 2-[(4R)-4-amino-5-methoxy-pentyl]-7-fluoro-6-[5-(trifluoromethyl)pyrimidin-2-yl]isoquinolin-1-one. ES/MS m/z: 717.2 $[M+H]^+$.

Step 4. 7-fluoro-2-[(4R)-5-methoxy-4-[[6-oxo-5-(trifluoromethyl)-1H-pyridazin-4-yl]amino]pentyl]-6-[5-(trifluoromethyl)pyrimidin-2-yl]isoquinolin-1-one (was synthesized as described in Example 88 (step 6) using 7-fluoro-2-[(4R)-5-methoxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one. $^1H$ NMR (400 MHz, DMSO-d6) δ 1H NMR (400 MHz, DMSO-d6) δ 12.44 (s, 1H), 9.48 (s, 2H), 8.44 (d, J=7.1 Hz, 1H), 8.03 (d, J=11.4 Hz, 1H), 7.95 (s, 1H), 7.53 (d, J=7.3 Hz, 1H), 6.85 (d, J=7.4 Hz, 1H), 6.29 (dd, J=10.4, 2.3 Hz, 1H), 4.18-4.07 (m, 1H), 4.00 (t, J=6.8 Hz, 2H), 3.24 (s, 3H), 1.81-1.70 (m, 2H), 1.62-1.52 (m, 2H). ES/MS m/z: 587.2 $[M+H]^+$.

Example 136: Preparation of 7-fluoro-2-[4-[[6-oxo-5-(trifluoromethyl)-1H-pyridazin-4-yl]oxy]pentyl]-6-[5-(trifluoromethyl)pyrimidin-2-yl]isoquinolin-1-one

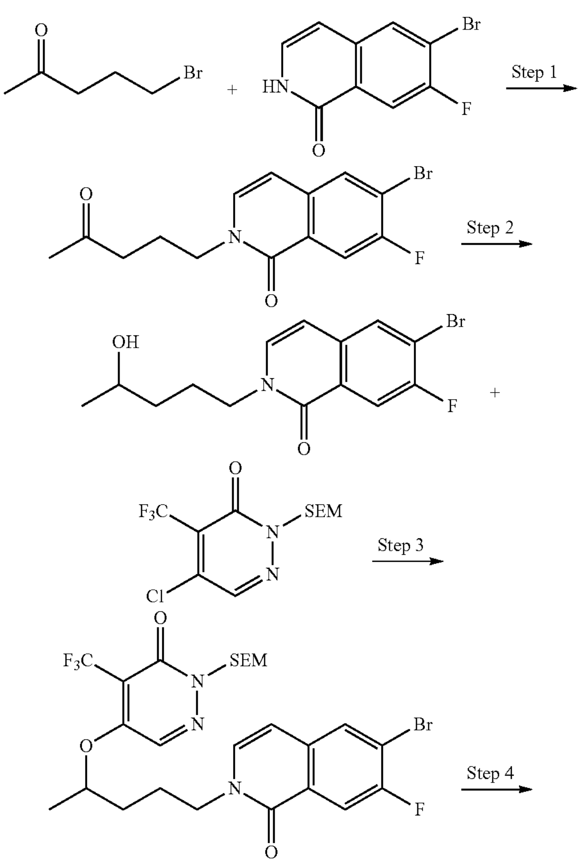

-continued

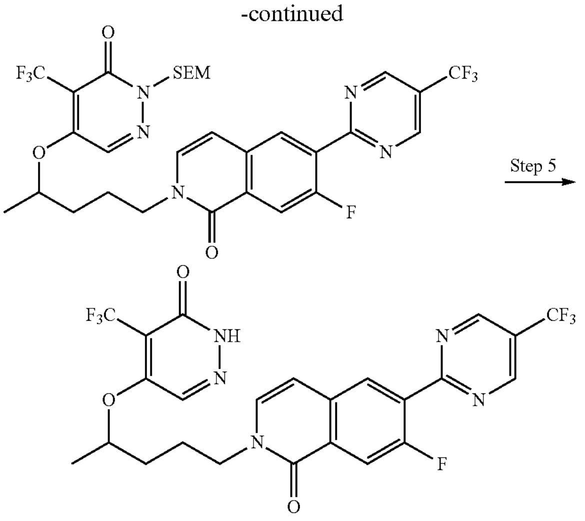

Example 136

Step 1. To a solution of 5-bromopentan-2-one (375 mg, 2.27 mmol) and 6-bromo-7-fluoro-2H-isoquinolin-1-one (250 mg, 1.03 mmol) in DMF (11.0 mL) was added $Cs_2CO_3$ (1.20 g, 3.62 mmol) and the heterogeneous mixture was stirred for 4 hrs. Upon completion, the mixture was diluted with EtOAc and the solid was filtered off and the filtrate was concentrated in vacuo. The crude product was purified using flash chromatography eluting with EtOAc in hexanes 0-100% to afford 6-bromo-7-fluoro-2-(4-oxopentyl)isoquinolin-1-one. ES/MS m/z: 327.9 $[M+H]^+$.

Step 2. To a solution of 6-bromo-7-fluoro-2-(4-oxopentyl) isoquinolin-1-one (224 mg, 0.687 mmol) in EtOH (7.0 mL) was added $NaBH_4$ (52.0 mg, 1.37 mmol) at 0° C. and the mixture was stirred at room temperature for 2 hrs. Upon completion, the mixture was acidified using 1 N $HCl_{(aq)}$ (pH~3) at 0° C. and concentrated in vacuo. The residue was diluted with EtOAc, washed with brine, dried over $Na_2SO_4$, filtered and concentrated in vacuo and used without no further purification. ES/MS m/z: 329.2 $[M+H]^+$.

Step 3. A solution of 6-bromo-7-fluoro-2-(4-hydroxypentyl)isoquinolin-1-one (124 mg, 0.378 mmol), 5-chloro-4-(trifluoromethyl)-2-(2-trimethylsilylethoxymethyl) pyridazin-3-one (248 mg, 0.756 mmol) and N,N-Diisopropylethylamine (293 mg, mmol) in DMF (3.8 mL) was heated at 80° C. for 1 hr. Upon completion, the mixture was diluted with EtOAc and water and the aqueous layer was extracted with EtOAc. Combined organic layers were dried over $Na_2SO_4$, filtered and concentrated in vacuo and the crude product was purified using flash chromatography eluting with EtOAc in hexanes 0-100% to afford 6-bromo-7-fluoro-2-[4-[6-oxo-5-(trifluoromethyl)-1-(2-trimethylsilylethoxymethyl)pyridazin-4-yl]oxypentyl]isoquinolin-1-one. ES/MS m/z: 622.2 $[M+H]^+$.

Step 4. A mixture of 6-bromo-7-fluoro-2-[4-[6-oxo-5-(trifluoromethyl)-1-(2-trimethylsilylethoxymethyl) pyridazin-4-yl]oxypentyl]isoquinolin-1-one (160.0 mg, 0.258 mmol), Bis (Pinacolato) Diboron (98.2 mg, 0.387 mmol), KOAc (75.9 mg, 0.774 mmol), dichloro 1,1'-bis (diphenylphosphino)ferrocene palladium (II) dichloromethane (21.1 mg, 0.026 mmol) in dioxane (2.0 mL) was purged with nitrogen gas and heated at 100° C. for 1 hr. Upon completion, the mixture was diluted with EtOAc, filtered through a pad of Celite© and concentrated in vacuo to afford the corresponding boronic ester. A mixture of 7-fluoro-2-[4-[6-oxo-5-(trifluoromethyl)-1-(2-trimethylsilylethoxymethyl)pyridazin-4-yl]oxypentyl]-6-(4,4,5,5-tetramethyl-1,3,2-dioxaborolan-2-yl)isoquinolin-1-one (172 mg, 0.258 mmol), 2-iodo-5-(trifluoromethyl)pyrimidine (212 mg, 0.773 mmol), cataCXium A Pd G4 (37.5 mg, 0.051 mmol), and 2M $Na_2CO_3$(aq) (0.39 mL) in dioxane (1.00 mL) was purged with nitrogen gas and heated at 95° C. for 20 minutes. Upon completion, the mixture was diluted with EtOAc and filtered through a pad of Celite© and concentrated in vacuo to afford the crude product. The crude product was purified using flash chromatography eluting with EtOAc in hexanes 0-100% to afford 7-fluoro-2-[4-[6-oxo-5-(trifluoromethyl)-1-(2-trimethylsilylethoxymethyl) pyridazin-4-yl]oxypentyl]-6-[5-(trifluoromethyl)pyrimidin-2-yl]isoquinolin-1-one. ES/MS m/z: 688.1 $[M+H]^+$.

Step 5. 7-fluoro-2-[4-[[6-oxo-5-(trifluoromethyl)-1H-pyridazin-4-yl]oxy]pentyl]-6-[5-(trifluoromethyl)pyrimidin-2-yl]isoquinolin-1-one was synthesized as described in Example 5 (step 8) using 7-fluoro-2-[4-[6-oxo-5-(trifluoromethyl)-1-(2-trimethylsilylethoxymethyl)pyridazin-4-yl] oxypentyl]-6-[5-(trifluoromethyl)pyrimidin-2-yl]isoquinolin-1-one. $^1H$ NMR (400 MHz, DMSO-d6) δ 13.26 (s, 1H), 9.48 (s, 2H), 8.44 (d, J=7.2 Hz, 1H), 8.26 (s, 1H), 8.03 (d, J=11.4 Hz, 1H), 7.54 (d, J=7.4 Hz, 1H), 6.85 (d, J=7.4 Hz, 1H), 5.08-4.96 (m, 1H), 4.02 (t, J=6.7 Hz, 2H), 1.88-1.61 (m, 4H), 1.29 (d, J=6.0 Hz, 3H). ES/MS m/z: 558.20 $[M+H]^+$.

Example 137: 6-(4-amino-5-(trifluoromethyl)pyrimidin-2-yl)-7-fluoro-2-(4-methyl-4-((6-oxo-5-(trifluoromethyl)-1,6-dihydropyridazin-4-yl)amino)pentyl)isoquinolin-1(2H)-one Example 137

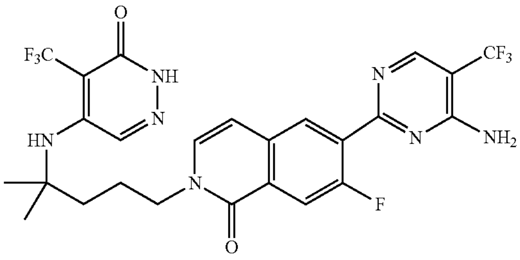

The title compound was synthesized as described in Example 5 with the following changes:

Step 1: tert-butyl (5-hydroxy-2-methylpentan-2-yl)carbamate was used instead of tert-butyl N-[(1S)-4-hydroxy-1-methyl-butyl]carbamate.

Step 4: tert-butyl (5-(6-bromo-7-fluoro-1-oxoisoquinolin-2(1H)-yl)-2-methylpentan-2-yl)carbamate was used instead of tert-butyl N-[(1S)-4-(6-bromo-1-oxo-2-isoquinolyl)-1-methyl-butyl]carbamate Step 5: tert-butyl (5-(7-fluoro-1-oxo-6-(4,4,5,5-tetramethyl-1,3,2-dioxaborolan-2-yl)isoquinolin-2(1H)-yl)-2-methylpentan-2-yl)carbamate, 2-chloro-5-(trifluoromethyl) pyrimidin-4-amine, and CataCXium Pd G4 were used instead of tert-butyl N-[(1S)-1-methyl-4-[1-oxo-6-(4,4,5,5-tetramethyl-1,3,2-dioxaborolan-2-yl)-2-isoquinolyl]butyl] carbamate, 2-iodo-5-(trifluoromethyl)pyrimidine, and [1,1'-Bis(di-tert-butylphosphino)ferrocene]dichloropalladium (II), respectively. $^1H$ NMR (400 MHz, DMSO-d6) δ 12.58 (s, 1H), 8.65 (s, 1H), 8.19 (d, J=7.1 Hz, 1H), 8.01-7.82 (m, 2H), 7.50 (d, J=7.4 Hz, 1H), 6.75 (d, J=7.4 Hz, 1H), 5.76 (m, 1H), 3.91 (m, 3H), 1.75 (m, 5H), 1.38 (s, 6H). ES/MS m/z: 586.1 [M+H]$^+$.

Intermediate 18: Preparation of tert-butyl (2R,4S)-4-((tert-butyldimethylsilyl)oxy)-2-(3-(tosyloxy)propyl)pyrrolidine-1-carboxylate Intermediate 18

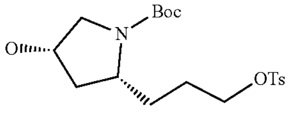

The title compound was synthesized as described in Intermediate 3, using tert-butyl (2S,4S)-4-((tert-butyldimethylsilyl)oxy)-2-(hydroxymethyl)pyrrolidine-1-carboxylate instead of tert-butyl (1R,2S,5S)-2-(hydroxymethyl)-3-azabicyclo[3.1.0]hexane-3-carboxylate. ES/MS m/z: 514.1 [M+H]$^+$.

The following intermediates were synthesized using the procedure used above or a modification of the procedure above from the corresponding starting materials.

| Intermediate No. | Structure | LCMS (ESI, m/z): [M + H]+ |
|---|---|---|
| 19 | 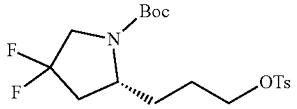 [SMILES: Cc1ccc(S(=O)(=O)OCCC[C@@H]2CC(F)(F)CN2C(=O)OC(C)(C)C)cc1] | 420.1 |
| 20 | 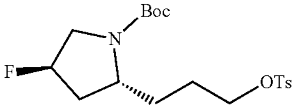 [SMILES: Cc1ccc(S(=O)(=O)OCCC[C@@H]2C[C@@H](F)CN2C(=O)OC(C)(C)C)cc1] | 402.0 |
| 21 | 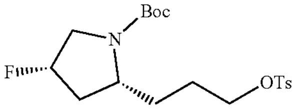 [SMILES: Cc1ccc(S(=O)(=O)OCCC[C@@H]2C[C@H](F)CN2C(=O)OC(C)(C)C)cc1] | 402.1 |
| 22 | 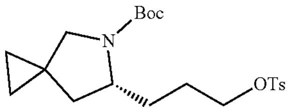 [SMILES: Cc1ccc(S(=O)(=O)OCCC[C@@H]2CC3(CC3)CN2C(=O)OC(C)(C)C)cc1] | 410.2 |

Example 138: Preparation of 7-fluoro-2-(3-((2R,4S)-4-hydroxy-1-(6-oxo-5-(trifluoromethyl)-1,6-dihydropyridazin-4-yl)pyrrolidin-2-yl)propyl)-6-(5-(trifluoromethyl)pyrimidin-2-yl)isoquinolin-1(2H)-one Example 138

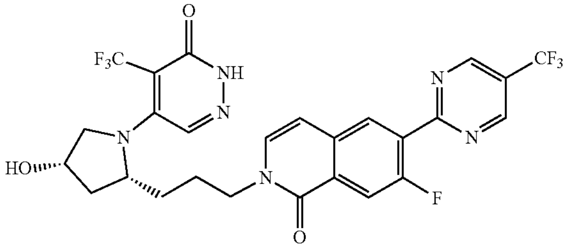

The title compound was synthesized as described in Example 5, using tert-butyl (2R,4S)-4-((tert-butyldimethylsilyl)oxy)-2-(3-(tosyloxy)propyl)pyrrolidine-1-carboxylate instead of [(4S)-4-(tert-butoxycarbonylamino)pentyl]4-methylbenzenesulfonate to afford 7-fluoro-2-(3-((2R,4S)-4-hydroxy-1l-(6-oxo-5-(trifluoromethyl)-1,6-dihydropyridazin-4-yl)pyrrolidin-2-yl)propyl)-6-(5-(trifluoromethyl)pyrimidin-2-yl)isoquinolin-1(2H)-one. (H NMR (400 MHz, DMSO-d6) δ 12.45 (s, 1H), 9.48 (s, 2H), 8.44 (d, J=7.1 Hz, 1H), 8.13-67.91 (i, 2H), 7.54 (d, J=7.4 Hz, 1H), 6.84 (d, J=7.4 Hz, 1H), 4.33 (m, 1H), 4.16-3.86 (m, 3H), 3.74-3.15 (m, 3H), 2.35-2.23 (m, 1H), 1.94-1.59 (m, 3H), 1.51 (m, 2H). ES/MS m/z: 599.1 [M+H].

The following Examples were synthesized using the procedure used above or a modification of the procedure above from the corresponding starting materials.

| Ex. No. | Structure | Int. No. | $^1$H NMR/MS [M + H]$^+$ |
|---|---|---|---|
| 139 | 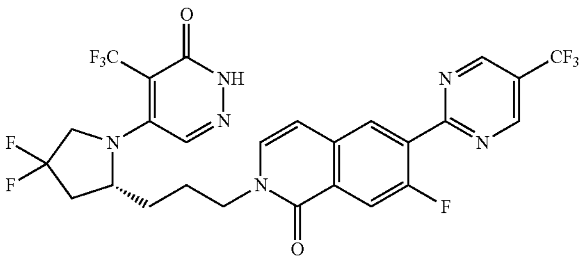 [SMILES: O=c1[nH]ncc(N2CC(F)(F)C[C@H]2CCCn2ccc3cc(-c4ncc(C(F)(F)F)cn4)c(F)cc3c2=O)c1C(F)(F)F] | 19 | $^1$H NMR (400 MHZ, DMSO-d6) δ 12.73 (s, 1H), 9.48 (d, J = 1.0 Hz, 2H), 8.44 (d, J = 7.1 Hz, 1H), 8.11 (s, 1H), 8.03 (d, J = 11.4 Hz, 1H), 7.53 (d, J = 7.4 Hz, 1H), 6.85 (d, J = 7.4 Hz, 1H), 4.63 (d, J = 9.5 Hz, 1H), 4.20-3.92 (m, 3H), 3.49 (t, J = 13.2 Hz, 1H), 2.81-2.60 (m, 1H), 2.47-2.21 (m, 1H), 1.90-1.53 (m, 4H). ES/MS m/z: 619.3 [M + H]. |

-continued

| Ex. No. | Structure | Int. No. | $^1$H NMR/MS [M + H]$^+$ |
|---|---|---|---|
| 140 | 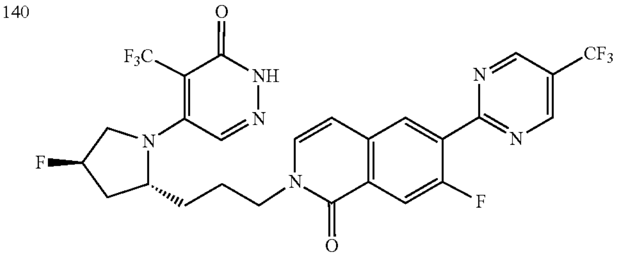 | 20 | $^1$H NMR (400 MHZ, DMSO-d6) δ 12.60 (s, 1H), 9.48 (d, J = 1.0 Hz, 2H), 8.44 (d, J = 7.2 Hz, 1H), 8.10 (s, 1H), 8.03 (d, J = 11.4 Hz, 1H), 7.53 (d, J = 7.4 Hz, 1H), 6.84 (d, J = 7.4 Hz, 1H), 5.30 (d, J = 52.6 Hz, 1H), 4.54 (d, J = 8.8 Hz, 1H), 4.01 (hept, J = 6.3 Hz, 2H), 3.84 (dd, J = 39.3, 13.1 Hz, 1H), 3.37-3.22 (m, 1H), 2.48-2.28 (m, 1H), 2.06-1.45 (m, 5H). ES/MS m/z: 601.3 [M + H]. |
| 141 | 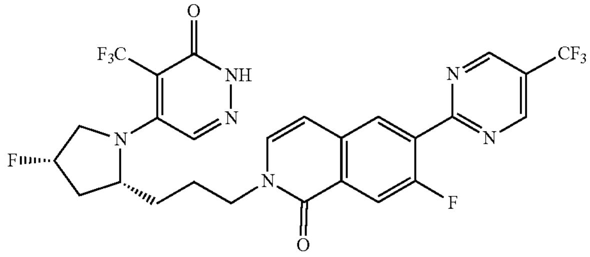 [SMILES: O=c1[nH]ncc(N2C[C@@H](F)C[C@H]2CCCn2ccc3cc(-c4ncc(C(F)(F)F)cn4)c(F)cc3c2=O)c1C(F)(F)F] | 21 | $^1$H NMR (400 MHZ, DMSO-d6) δ 12.52 (s, 1H), 9.48 (d, J = 0.9 Hz, 2H), 8.43 (d, J = 7.2 Hz, 1H), 8.09-7.99 (m, 2H), 7.53 (d, J = 7.4 Hz, 1H), 6.84 (d, J = 7.3 Hz, 1H), 5.42-5.15 (m, 1H), 4.53 (s, 1H), 4.00 (hept, J = 6.7 Hz, 2H), 3.80-3.51 (m, 2H), 2.35 (ddt, J = 26.7, 13.8, 6.9 Hz, 1H), 1.98 (ddt, J = 22.1, 13.8, 4.1 Hz, 1H), 1.87-1.46 (m, 4H). ES/MS m/z: 601.3 [M + H]. |
| 142 | 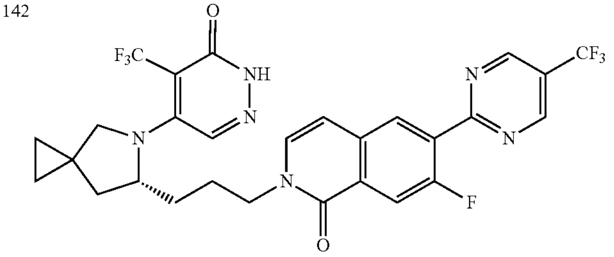 | 22 | 1H NMR (400 MHZ, DMSO-d6) δ 12.47 (s, 1H), 9.48 (s, 2H), 8.44 (d, J = 7.2 Hz, 1H), 8.05 (s, 2H), 7.54 (d, J = 7.4 Hz, 1H), 6.84 (d, J = 7.4 Hz, 1H), 4.55-4.44 (m, 1H), 4.07-3.98 (m, 4H), 3.82 (s, 1H), 2.76-2.66 (m, 1H), 1.99-1.88 (m, 1H), 1.75 (d, J = 23.5 Hz, 3H), 1.72-1.62 (m, 1H), 1.58-1.50 (m, 1H), 0.70-0.56 (m, 2H), 0.56-0.47 (m, 1H), 0.45-0.38 (m, 1H). |
| 143 | 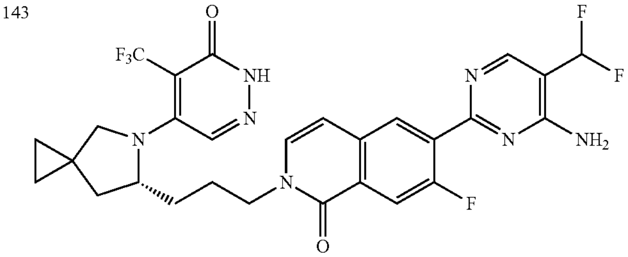 | 22 | 1H NMR (400 MHZ, DMSO-d6) δ 12.47 (s, 1H), 8.50 (s, 1H), 8.17 (d, J = 7.1 Hz, 1H), 8.05 (s, 1H), 7.95 (d, J = 11.2 Hz, 1H), 7.50 (d, J = 7.4 Hz, 1H), 7.10 (t, J = 54.1 Hz, 1H), 6.76 (d, J = 7.4 Hz, 1H), 4.55-4.42 (m, 1H), 4.07-3.93 (m, 2H), 3.83 (d, J = 11.1 Hz, 1H), 2.74 (d, J = 10.7 Hz, 1H), 1.97-1.91 (m, 1H), 1.82-1.73 (m, 3H), 1.71-1.61 (m, 1H), 1.58-1.45 (m, 1H), 0.69-0.56 (m, 2H), 0.54-0.48 (m, 1H), 0.46-0.38 (m, 1H). |

Example 144: 6-[4-amino-5-(trifluoromethyl)pyrimidin-2-yl]-2-[(4R)-4-cyclopropyl-4-[[6-oxo-5-(trifluoromethyl)-1H-pyridazin-4-yl]amino]butyl]-7-fluoro-isoquinolin-1-one (GS-1297284)

Example 144

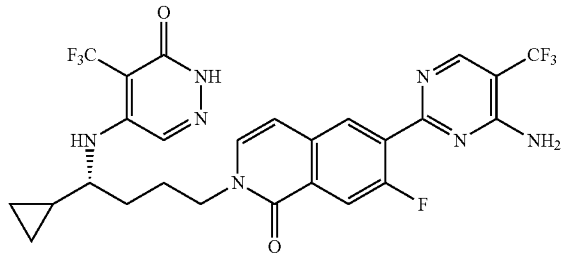

The title compound was synthesized as described in Example 17, with the following changes:

Step 1. 6-Bromo-7-fluoro-2H-isoquinolin-1-one was used instead of 6-Bromo-8-fluoro-1,2-dihydroisoquinolin-1-one and [(4R)-4-(tert-butoxycarbonylamino)-4-cyclopropyl-butyl]4-methylbenzenesulfonate was used instead of 4-(tert-butoxycarbonylamino)pentyl]4-methylbenzenesulfonate.

Step 3. 2-Chloro-5-(trifluoromethyl)pyrimidin-4-amine was used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 12.40 (s, 1H), 8.64 (d, J=1.0 Hz, 1H), 8.20 (d, J=7.1 Hz, 1H), 7.96 (d, J=11.1 Hz, 1H), 7.89 (s, 1H), 7.50 (d, J=7.4 Hz, 1H), 6.77 (d, J=7.4 Hz, 1H), 6.51 (dd, J=9.1, 3.8 Hz, 1H), 3.98 (d, J=6.7 Hz, 2H), 3.35 (s, 1H), 1.71 (d, J=38.7 Hz, 4H), 1.09 (dd, J=8.7, 4.6 Hz, 1H), 0.49 (dt, J=9.1, 4.8 Hz, 1H), 0.38 (td, J=8.8, 4.1 Hz, 1H), 0.24 (ddq, J=18.5, 9.4, 4.7 Hz, 2H). ES/MS m/z: 598.3 [M+H].

The following Examples were synthesized using the procedure used above for the synthesis of Example 144 or a modification of the procedure above from the corresponding starting materials.

| Ex. No. | Structure | $^1H$ NMR/MS [M + H]$^+$ |
|---|---|---|
| 145 | 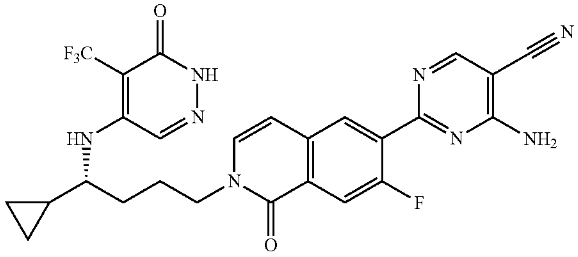 [SMILES: N#Cc1cnc(-c2cc3ccn(CCC[C@@H](Nc4cn[nH]c(=O)c4C(F)(F)F)C4CC4)c(=O)c3cc2F)nc1N] | $^1H$ NMR (400 MHZ, DMSO-d6) δ 12.40 (s, 1H), 8.80 (s, 1H), 8.22 (d, J = 7.1 Hz, 1H), 7.95 (d, J = 11.2 Hz, 1H), 7.89 (s, 1H), 7.50 (d, J = 7.4 Hz, 1H), 6.77 (d, J = 7.3 Hz, 1H), 6.51 (dd, J = 9.0, 3.8 Hz, 1H), 3.98 (d, J = 6.7 Hz, 2H), 3.35 (s, 1H), 1.70 (d, J = 38.2 Hz, 4H), 1.09 (dq, J = 8.3, 4.2, 3.5 Hz, 1H), 0.49 (dp, J = 8.5, 4.1, 3.6 Hz, 1H), 0.38 (tt, J = 9.1, 4.0 Hz, 1H), 0.24 (ddq, J = 18.4, 9.4, 4.5 Hz, 2H). ES/MS m/z: 555.3 [M + H]. |
| 146 | 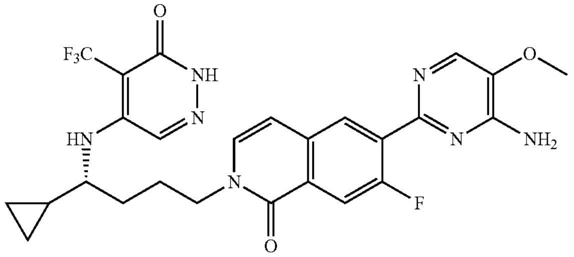 [SMILES: COc1cnc(-c2cc3ccn(CCC[C@@H](Nc4cn[nH]c(=O)c4C(F)(F)F)C4CC4)c(=O)c3cc2F)nc1N] | $^1H$ NMR (400 MHZ, DMSO-d6) δ 12.40 (s, 1H), 8.11 (d, J = 7.0 Hz, 1H), 8.05 (s, 1H), 7.98 (d, J = 10.9 Hz, 1H), 7.89 (s, 1H), 7.51 (d, J = 7.5 Hz, 1H), 6.77 (d, J = 7.4 Hz, 1H), 6.51 (d, J = 5.4 Hz, 1H), 4.02-3.93 (m, 5H), 3.35 (s, 1H), 1.70 (d, J = 39.4 Hz, 4H), 1.10 (dt, J = 8.7, 5.1 Hz, 1H), 0.49 (q, J = 4.7 Hz, 1H), 0.38 (td, J = 8.7, 4.1 Hz, 1H), 0.24 (ddq, J = 17.4, 9.4, 4.5 Hz, 2H). ES/MS m/z: 560.3 [M + H]. |
| 147 | 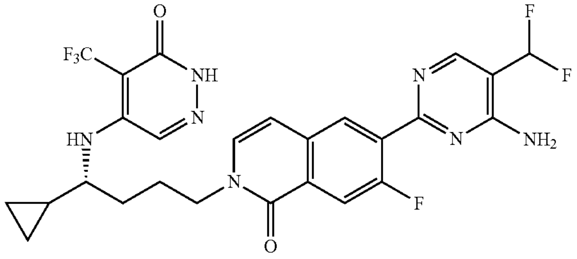 [SMILES: Nc1nc(-c2cc3ccn(CCC[C@@H](Nc4cn[nH]c(=O)c4C(F)(F)F)C4CC4)c(=O)c3cc2F)ncc1C(F)F] | $^1H$ NMR (400 MHZ, DMSO-d6) δ 12.40 (s, 1H), 8.50 (d, J = 1.5 Hz, 1H), 8.17 (d, J = 7.0 Hz, 1H), 7.95 (d, J = 11.1 Hz, 1H), 7.89 (s, 1H), 7.49 (d, J = 7.4 Hz, 1H), 7.10 (t, J = 54.2 Hz, 1H), 6.77 (d, J = 7.4 Hz, 1H), 6.51 (dd, J = 9.2, 3.7 Hz, 1H), 3.98 (d, J = 6.6 Hz, 2H), 3.35 (s, 1H), 1.71 (d, J = 38.5 Hz, 4H), 1.08 (tt, J = 8.5, 5.1 Hz, 1H), 0.49 (dp, J = 8.5, 4.2 Hz, 1H), 0.38 (tt, J = 8.9, 4.3 Hz, 1H), 0.23 (ddq, J = 18.3, 9.2, 4.6 Hz, 2H). ES/MS m/z: 580.3 [M + H]. |

Example 148 and Example 149: 7-fluoro-2-[3-[(2S)-1-[6-oxo-5-(trifluoromethyl)-1H-pyridazin-4-yl]azetidin-2-yl]propyl]-6-[5-(trifluoromethyl)pyrimidin-2-yl]isoquinolin-1-one and 7-fluoro-2-[3-[(2R)-1-[6-oxo-5-(trifluoromethyl)-1H-pyridazin-4-yl]azetidin-2-yl]propyl]-6-[5-(trifluoromethyl)pyrimidin-2-yl]isoquinolin-1-one

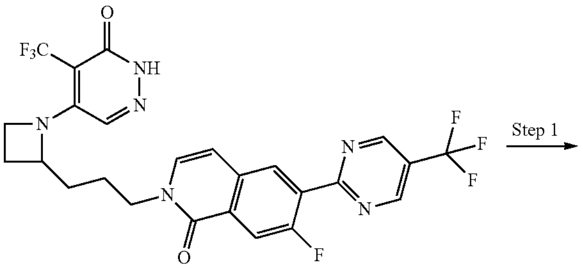

-continued

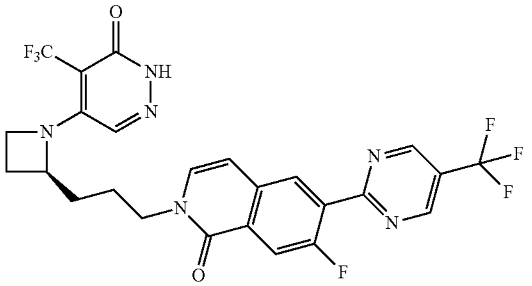

+

Example 148

-continued

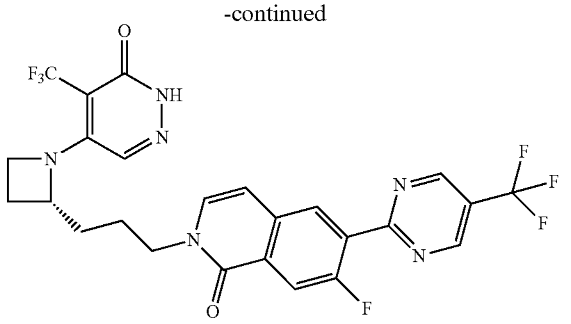

Example 149

Step 1. The racemic mixture was synthesized as described in Example 17 and separated via chiral SFC (AD-H, 5 μm, 21×250 mm column; 40% EtOH as co-solvent; 100 bar; 40° C.). The first eluting peak was assigned as the (S)-configuration (Example 149) $^1$H NMR (400 MHz, DMSO-d6) δ 12.35 (s, 1H), 9.65-9.39 (m, 2H), 8.44 (d, J=7.1 Hz, 1H), 8.04 (d, J=11.4 Hz, 1H), 7.56 (d, J=7.7 Hz, 2H), 6.86 (d, J=7.4 Hz, 1H), 4.70 (s, 1H), 4.43-4.20 (m, 1H), 4.20-3.78 (m, 3H), 2.07-1.66 (m, 6H), and the second eluting peak was assigned as the (R)-configuration (Example 150) $^1$H NMR (400 MHz, DMSO-d6) δ 12.35 (s, 1H), 9.48 (d, J=0.9 Hz, 2H), 8.44 (d, J=7.2 Hz, 1H), 8.04 (d, J=11.4 Hz, 1H), 7.56 (d, J=7.7 Hz, 2H), 6.86 (d, J=7.4 Hz, 1H), 4.70 (s, 1H), 4.32 (s, 1H), 4.17-3.79 (m, 3H), 2.09-1.66 (m, 6H). ES/MS m/z: 569.3 [M+H].

Example 150: 6-fluoro-3-[3-[1-[6-oxo-5-(trifluoromethyl)-1H-pyridazin-4-yl]azetidin-2-yl]propyl]-7-[5-(trifluoromethyl)pyrimidin-2-yl]quinazolin-4-one Example 150

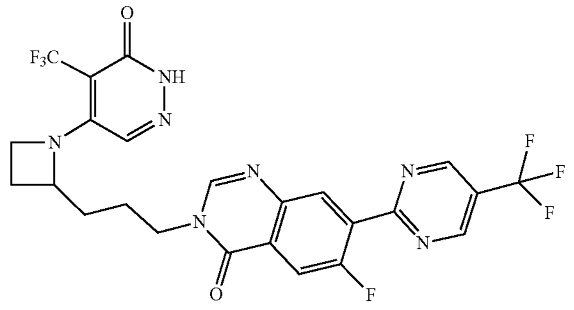

The title compound was synthesized as described in Example 73, using 7-bromo-6-fluoro-3H-quinazolin-4-one instead of 6-Bromo-7-fluoro-2H-isoquinolin-1-one to give 6-fluoro-3-[3-[1-[6-oxo-5-(trifluoromethyl)-1H-pyridazin-4-yl]azetidin-2-yl]propyl]-7-[5-(trifluoromethyl)pyrimidin-2-yl]quinazolin-4-one. $^1$H NMR (400 MHz, DMSO-d6) δ 12.35 (s, 1H), 9.50 (d, J=1.0 Hz, 2H), 8.47 (s, 1H), 8.35 (d, J=6.8 Hz, 1H), 8.01 (d, J=10.6 Hz, 1H), 7.57 (s, 1H), 4.68 (s, 1H), 4.32 (d, J=9.8 Hz, 1H), 4.13-3.99 (m, 2H), 3.91 (s, 1H), 2.12-1.61 (m, 6H). ES/MS m/z: 570.3.

Example 151 and Example 152: 6-fluoro-3-[3-[(2S)-1-[6-oxo-5-(trifluoromethyl)-1H-pyridazin-4-yl]azetidin-2-yl]propyl]-7-[5-(trifluoromethyl)pyrimidin-2-yl]quinazolin-4-one and 6-fluoro-3-[3-[(2R)-1-[6-oxo-5-(trifluoromethyl)-1H-pyridazin-4-yl]azetidin-2-yl]propyl]-7-[5-(trifluoromethyl)pyrimidin-2-yl]quinazolin-4-one

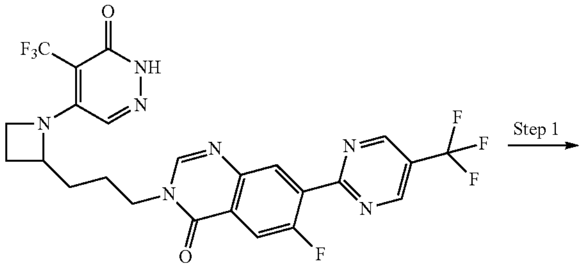

Example 150

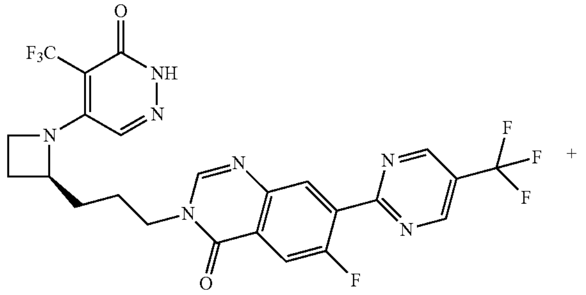

+

Example 151

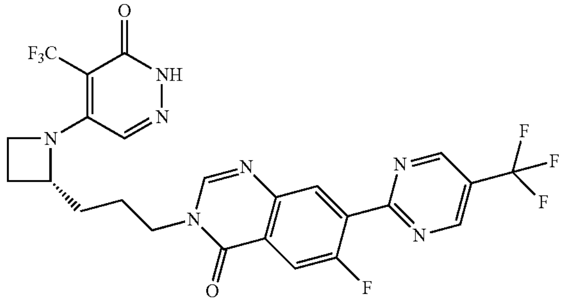

Example 152

Step 1. Examples 151 and Example 152 were separated from Example 150 via chiral SFC (AD-H, 5 μm, 21×250 mm column; 40% EtOH as co-solvent; 100 bar; 40° C.). The first eluting peak was assigned as the (S)-configuration (Example 152) $^1$H NMR (400 MHz, DMSO-d6) δ 12.35 (s, 1H), 9.50 (d, J=1.0 Hz, 2H), 8.47 (s, 1H), 8.35 (d, J=6.7 Hz, 1H), 8.01 (d, J=10.5 Hz, 1H), 7.57 (s, 1H), 4.69 (d, J=8.8 Hz, 1H), 4.32 (d, J=10.1 Hz, 1H), 4.15-3.97 (m, 2H), 3.91 (d, J=5.6 Hz, 1H), 2.04-1.65 (m, 5H), and the second eluting peak was assigned as the (R)-configuration (Example 153) $^1$H NMR (400 MHz, DMSO-d6) δ 12.35 (s, 1H), 9.50 (d, J=0.9 Hz, 2H), 8.47 (s, 1H), 8.35 (d, J=6.8 Hz, 1H), 8.01 (d, J=10.5 Hz, 1H), 7.57 (s, 1H), 4.68 (s, 1H), 4.32 (d, J=3.0 Hz, OH), 4.06 (d, J=5.4 Hz, 2H), 3.91 (s, 1H), 2.02-1.69 (m, 5H). ES/MS m/z: 570.3 [M+H].

Example 153: 6-(4-amino-5-methoxy-pyrimidin-2-yl)-7-fluoro-2-[3-[1-[6-oxo-5-(trifluoromethyl)-1H-pyridazin-4-yl]azetidin-2-yl]propyl]isoquinolin-1-one Example 153

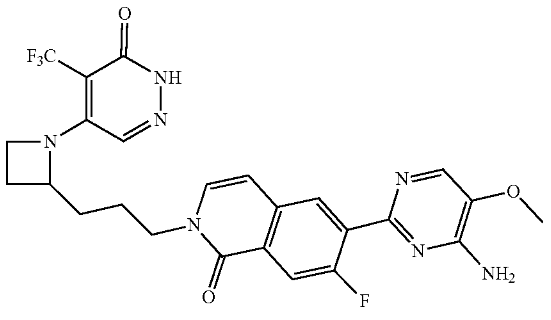

The title compound was synthesized as described in Example 17, with the following changes:

Step 1. tert-butyl 2-[3-(p-tolylsulfonyloxy)propyl]azetidine-1-carboxylate was used instead of tert-butyl 2-[3-(p-tolylsulfonyloxy)propyl]azetidine-1-carboxylate[(4S)-4-(tert-butoxycarbonylamino)pentyl]4-methylbenzenesulfonate and 6-Bromo-7-fluoro-2H-isoquinolin-1-one was used instead of 6-Bromo-8-fluoro-1,2-dihydroisoquinolin-1-one.

Step 3. 2-chloro-5-methoxy-pyrimidin-4-amine was used instead of 2-bromo-5-(difluoromethoxy)pyridine and 20 mol % of cataCXium Pd G4 and 2 M aqueous sodium carbonate (1.9 equiv.) were added following the completion of the borylation step. $^{1}$H NMR (400 MHz, DMSO-d6) δ 12.35 (s, 1H), 8.11 (d, J=7.1 Hz, 1H), 8.05 (s, 1H), 7.98 (d, J=11.0 Hz, 1H), 7.60-7.49 (m, 2H), 6.77 (d, J=7.4 Hz, 1H), 4.70 (s, 1H), 4.31 (d, J=8.5 Hz, 1H), 3.94 (s, 6H), 2.00-1.66 (m, 6H). ES/MS m/z: 546.3 [M+H].

Example 154: 7-fluoro-2-[3-[2-[6-oxo-5-(trifluoromethyl)-1H-pyridazin-4-yl]pyrazolidin-1-yl]propyl]-6-[5-(trifluoromethyl)pyrimidin-2-yl]isoquinolin-1-one

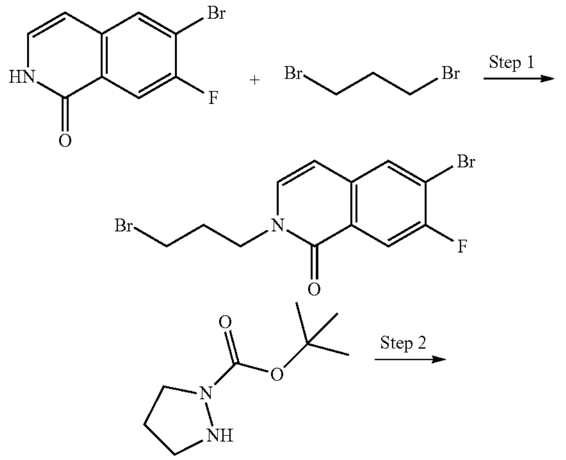

-continued

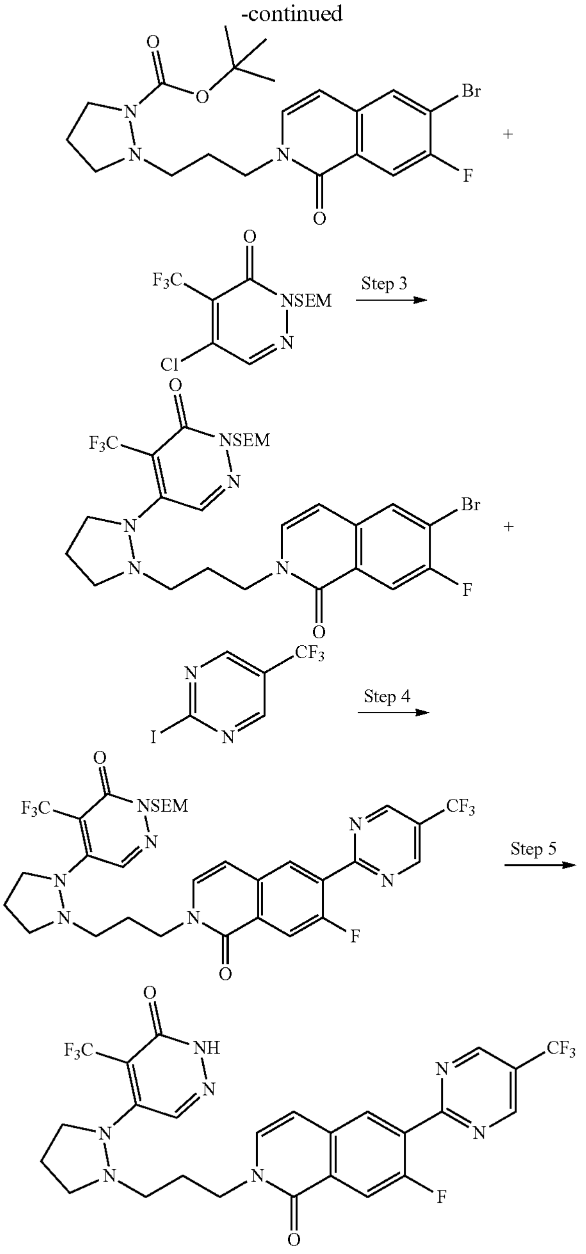

Example 154

Step 1. In a vial were placed 6-bromo-7-fluoro-2H-isoquinolin-1-one (500 mg, 2.07 mmol), 1,3-dibromopropane (4.21 mL, 41.3 mmol), and cesium carbonate (1.35 g, 4.13 mmol) in DMF (13.9 mL). After mixture was stirred at room temperature for 16 hr, it was quenched with water and extracted with EtOAc (×3). The combined organic layers were washed with water and brine, dried ($Na_2SO_4$), and purified by flash chromatography (100% hexanes to 100% EtOAc) to give 6-bromo-2-(3-bromopropyl)-7-fluoro-isoquinolin-1-one. ES/MS m/z: 363.8 [M+H].

Step 2. In a vial were placed 6-bromo-2-(3-bromopropyl)-7-fluoro-isoquinolin-1-one (226 mg, 0.62 mmol), tert-butyl pyrazolidine-1-carboxylate (129 mg, 0.75 mmol), cesium carbonate (406 mg, 1.25 mmol), and sodium iodide (93 mg, 0.62 mmol). Mixture was heated to 60° C. and allowed to stir 2 hr. After mixture was stirred at 60° C., it was quenched with saturated sodium thiosulfate solution, diluted with water, and extracted with EtOAc (3×). The combined layers were washed with water and brine, dried ($Na_2SO_4$), and purified by flash chromatography (100% hexanes to 100% EtOAc) to give tert-butyl 2-[3-(6-bromo-7-fluoro-1-oxo-2-isoquinolyl)propyl]pyrazolidine-1-carboxylate. ES/MS m/z: 455.9 [M+H].

Step 3. In a vial were placed tert-butyl 2-[3-(6-bromo-7-fluoro-1-oxo-2-isoquinolyl)propyl]pyrazolidine-1-carboxylate (169 mg, 0.37 mmol) and trifluoroacetic acid (0.29 mL, 3.7 mmol) in DCM (5.9 mL). After the mixture was stirred for 1 hr, it was concentrated under vacuum. To the same vial was then added 5-chloro-4-(trifluoromethyl)-2-(2-trimethylsilylethoxymethyl)pyridazin-3-one (135 mg, 0.41 mmol) and N,N-Diisopropylethylamine (0.33 mL, 1.86 mmol) in DMF (1.5 mL). The mixture was heated to 60° C. and stirred for 1 hr, then quenched with water and extracted with EtOAc (×3). The combined organic layers were washed with water and brine, dried ($Na_2SO_4$), and purified by flash chromatography (100% hexanes to 100% EtOAc) to give 6-bromo-7-fluoro-2-[3-[2-[6-oxo-5-(trifluoromethyl)-1-(2-trimethylsilylethoxymethyl)pyridazin-4-yl]pyrazolidin-1-yl]propyl]isoquinolin-1-one. ES/MS m/z: 648.06 [M+H].

Step 4. In a vial were placed 6-bromo-7-fluoro-2-[3-[2-[6-oxo-5-(trifluoromethyl)-1-(2-trimethylsilylethoxymethyl)pyridazin-4-yl]pyrazolidin-1-yl]propyl]isoquinolin-1-one (82 mg, 0.13 mmol), 1,1'-Bis(diphenylphosphino)ferrocene-palladium(II)dichloride dichloromethane complex (11 mg, 0.013 mmol), potassium acetate (37 mg, 0.38 mmol), and bis(pinacolato)diboron (48 mg, 0.19 mmol) in dioxane (1.5 mL). The mixture was heated to 100° C. and stirred for 1 hr, followed by the addition of 2 M aqueous sodium carbonate (0.19 mL, 0.38 mmol) and 2-iodo-5-(trifluoromethyl)pyrimidine (52 mg, 0.19 mmol). The reaction was then stirred for an addition hour at 80° C. Upon completion, the mixture was filtered through Celite©, concentrated under vacuum, and purified by flash chromatography (100% hexanes to 100% EtOAc) to give 7-fluoro-2-[3-[2-[6-oxo-5-(trifluoromethyl)-1-(2-trimethylsilylethoxymethyl)pyridazin-4-yl]pyrazolidin-1-yl]propyl]-6-[5-(trifluoromethyl)pyrimidin-2-yl]isoquinolin-1-one. ES/MS m/z: 714.3 [M+H].

Step 5. In a vial were placed 7-fluoro-2-[3-[2-[6-oxo-5-(trifluoromethyl)-1-(2-trimethylsilylethoxymethyl)pyridazin-4-yl]pyrazolidin-1-yl]propyl]-6-[5-(trifluoromethyl)pyrimidin-2-yl]isoquinolin-1-one (43 mg, 0.06 mmol), trifluoroacetic acid (0.05 mL, 0.6 mmol), and DCM (2.6 mL). Mixture stirred at room temperature and concentrated under vacuum. The resulting product was dissolved in methanol (2.6 mL) and ethylenediamine (0.04 mL, 0.6 mmol) was added and stirred for 15 minutes, and then was concentrated under vacuum. The crude product was purified by reverse phase prep-HPLC (5-100% MeCN in water, 0.1% TFA) to afford 7-fluoro-2-[3-[2-[6-oxo-5-(trifluoromethyl)-1H-pyridazin-4-yl]pyrazolidin-1-yl]propyl]-6-[5-(trifluoromethyl)pyrimidin-2-yl]isoquinolin-1-one. $^1$H NMR (400 MHz, DMSO-d6) δ 12.58 (s, 1H), 9.48 (d, J=1.0 Hz, 2H), 8.43 (d, J=7.2 Hz, 1H), 8.38 (s, 1H), 8.02 (d, J=11.4 Hz, 1H), 7.51 (d, J=7.4 Hz, 1H), 6.85 (d, J=7.4 Hz, 1H), 4.12-4.00 (m, 2H), 3.74 (s, 1H), 3.08 (d, J=53.5 Hz, 2H), 2.91-2.56 (m, 3H), 2.13 (d, J=54.4 Hz, 2H), 1.84 (t, J=7.2 Hz, 2H). ES/MS m/z: 584.3 [M+H].

Example 155: (S)-6-fluoro-3-(4-((6-oxo-5-(trifluoromethyl)-1,6-dihydropyridazin-4-yl)amino)hexyl)-7-(5-(trifluoromethyl)pyrimidin-2-yl)quinazolin-4(3H)-one Example 155

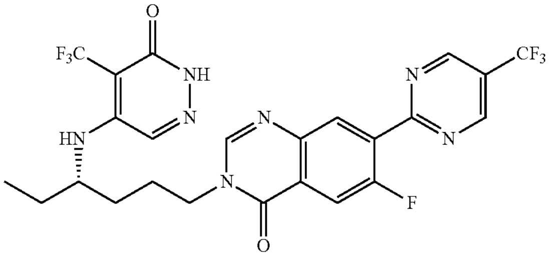

The title compound was synthesized as described in Example 37, using 7-bromo-6-fluoro-3H-quinazolin-4-one instead of 6-Bromo-7-fluoro-2H-isoquinolin-1-one to give (S)-6-fluoro-3-(4-((6-oxo-5-(trifluoromethyl)-1,6-dihydropyridazin-4-yl)amino)hexyl)-7-(5-(trifluoromethyl)pyrimidin-2-yl)quinazolin-4(3H)-one. $^1$H NMR (400 MHz, DMSO-d6) δ 12.42 (s, 1H), 9.50 (d, J=0.9 Hz, 2H), 8.46 (s, 1H), 8.35 (d, J=6.7 Hz, 1H), 8.00 (d, J=10.5 Hz, 1H), 7.96 (s, 1H), 6.39-6.17 (m, 1H), 4.01 (t, J=6.9 Hz, 2H), 3.85 (d, J=7.8 Hz, 1H), 1.90-1.41 (m, 5H), 0.82 (t, J=7.3 Hz, 3H). ES/MS m/z: 572.3 [M+H].

The following Examples were synthesized using the procedure used above or a modification of the procedure above from the corresponding starting materials.

| Ex. No. | Structure | $^1$H NMR/MS [M + H]$^+$ |
| --- | --- | --- |
| 156 | 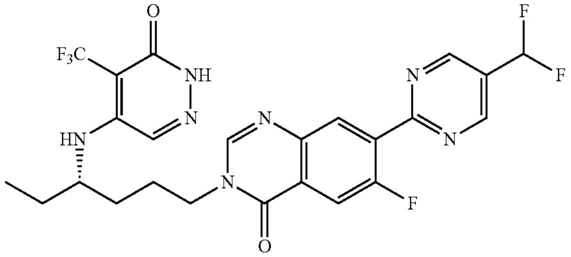 [SMILES: CC[C@@H](CCCn1cnc2cc(-c3ncc(C(F)F)cn3)c(F)cc2c1=O)Nc1cn[nH]c(=O)c1C(F)(F)F] | $^1$H NMR (400 MHZ, DMSO-d6) δ 12.42 (s, 1H), 9.26 (d, J = 1.3 Hz, 2H), 8.45 (s, 1H), 8.32 (d, J = 6.8 Hz, 1H), 8.05-7.93 (m, 2H), 7.31 (t, J = 54.7 Hz, 1H), 6.28 (dd, J = 9.1, 3.6 Hz, 1H), 4.01 (t, J = 6.8 Hz, 2H), 3.85 (d, J = 7.9 Hz, 1H), 1.87-1.46 (m, 5H), 0.82 (t, J = 7.3 Hz, 3H). ES/MS m/z: 554.3 [M + H]. |

-continued

| Ex. No. | Structure | $^1$H NMR/MS [M + H]$^+$ |
|---|---|---|
| 157 | 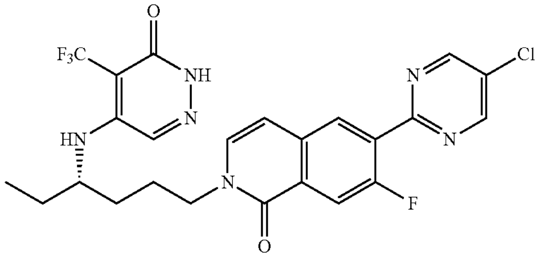 [SMILES: CC[C@@H](CCCn1ccc2cc(-c3ncc(Cl)cn3)c(F)cc2c1=O)Nc1cn[nH]c(=O)c1C(F)(F)F] | $^1$H NMR (400 MHZ, DMSO-d6) δ 12.42 (s, 1H), 9.16 (s, 2H), 8.44 (s, 1H), 8.27 (d, J = 6.8 Hz, 1H), 8.02-7.91 (m, 2H), 6.28 (d, J = 8.7 Hz, 1H), 4.00 (t, J = 6.8 Hz, 2H), 3.85 (s, 1H), 1.87-1.44 (m, 5H), 0.82 (t, J = 7.3 Hz, 3H). ES/MS m/z: 538.3 [M + H]. |

Intermediate 23: Preparation of 2-chloro-N-(2,2-difluoroethyl)-5-methoxy-pyrimidin-4-amine

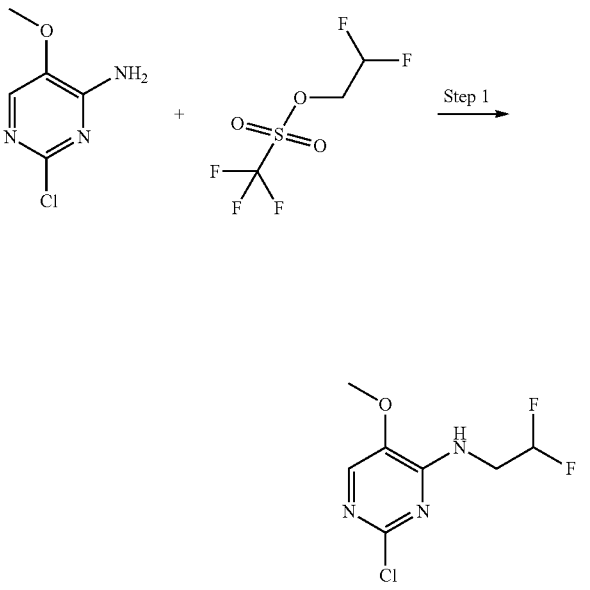

Intermediate 23

Step 1. To a vial was added 2-chloro-5-methoxy-pyrimidin-4-amine (250.0 mg, 1.57 mmol) and DMF (5.41 mL) and the reaction mixture was cooled to 0° C. and sodium hydride was added (72.0 mg, 1.88 mmol). The mixture was stirred at 0° C. and 2,2-difluoroethyl trifluoromethanesulfonate (0.229 mL, 1.72 mmol) was added and the mixture was allowed to warm to room temperature and stirred for 1 hr. Upon complete conversion, reaction was quenched with saturated aqueous ammonium chloride solution, diluted with water, and extracted with EtOAc (×3). The combined organic layers were dried ($Na_2SO_4$), concentrated, and purified by flash chromatography (100% hexanes to 100% EtOAc) to give 2-chloro-N-(2,2-difluoroethyl)-5-methoxy-pyrimidin-4-amine. ES/MS m/z: 337.9 [M+H].

Example 158: 6-[4-(2,2-difluoroethylamino)-5-methoxy-pyrimidin-2-yl]-7-fluoro-2-[(4S)-4-[[6-oxo-5-(trifluoromethyl)-1H-pyridazin-4-yl]amino]pentyl]isoquinolin-1-one Example 158

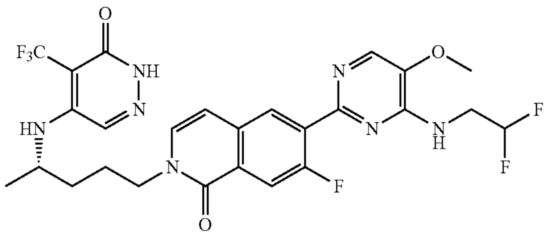

The title compound was synthesized as described in Example 17, with the following changes:

Step 1. 6-Bromo-7-fluoro-2H-isoquinolin-1-one was used instead of 6-Bromo-8-fluoro-1,2-dihydroisoquinolin-1-one.

Step 3. 2-chloro-N-(2,2-difluoroethyl)-5-methoxy-pyrimidin-4-amine was used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 12.44 (s, 1H), 8.24 (d, J=7.2 Hz, 1H), 8.11 (s, 2H), 7.98 (d, J=11.3 Hz, 1H), 7.92 (s, 1H), 7.54-7.44 (m, 1H), 6.78 (d, J=7.4 Hz, 1H), 6.42-6.08 (m, 2H), 3.88 (m, J=15.0, 6.2, 4.3 Hz, 5H), 1.79-1.43 (m, 4H), 1.17 (d, J=6.2 Hz, 3H). ES/MS m/z: 598.3 [M+H].

Example 159: 7-[4-(2,2-difluoroethylamino)-5-methoxy-pyrimidin-2-yl]-6-fluoro-3-[(4S)-4-[[6-oxo-5-(trifluoromethyl)-1-(2-trimethylsilylethoxymethyl)pyridazin-4-yl]amino]pentyl]quinazolin-4-one Example 159

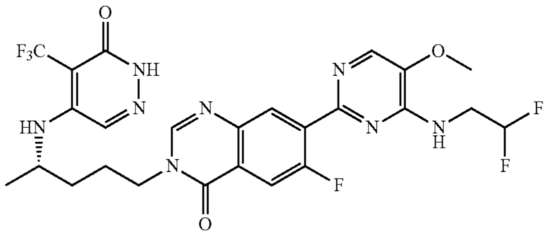

The title compound was synthesized as described in Example 29, using 2-chloro-N-(2,2-difluoroethyl)-5-methoxy-pyrimidin-4-amine instead of 2-iodo-5-(trifluoromethyl)pyrimidine to give 7-[4-(2,2-difluoroethylamino)-5-methoxy-pyrimidin-2-yl]-6-fluoro-3-[(4S)-4-[[6-oxo-5-(trifluoromethyl)-1H-pyridazin-4-yl]amino]pentyl]quinazolin-4-one. $^{1}$H NMR (400 MHz, DMSO-d6) δ 12.44 (s, 1H), 8.41 (s, 1H), 8.22 (d, J=6.9 Hz, 1H), 8.11 (s, 1H), 7.95-7.86 (m, 2H), 7.76 (d, J=11.2 Hz, 1H), 6.42-6.05 (m, 2H), 3.98 (d, J=16.4 Hz, 5H), 3.84 (dtt, J=19.3, 9.3, 4.8 Hz, 2H), 1.82-1.43 (m, 4H), 1.17 (d, J=6.3 Hz, 3H). ES/MS m/z: 599.3.

Intermediate 24: Preparation of tert-butyl N-[(1R)-1-(cyanomethyl)-4-hydroxy-butyl]carbamate

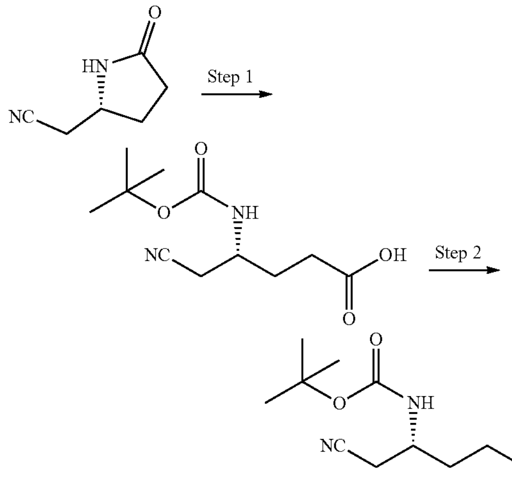

Intermediate 24

Step 1. 2-[(2R)-5-oxopyrrolidin-2-yl]acetonitrile (620 mg, 5.0 mmol) was taken up in 1N HCl (25.0 mL) and the mixture was stirred at 100° C. for 2.5 hrs. After cooling, the reaction was evaporated to dryness and the residue taken up in PhMe and evaporated twice more. The residue was then dissolved in THF (15.0 mL) and water (15.0 mL) and stirred at ambient temperature. Sodium bicarbonate (2.1 g, 25 mmol) was added followed by di-tert-butyl decarbonate (2.20 g, 10 mmol) and the reaction was stirred for 16 hrs. The pH was then adjusted to 3 with 10% $KHSO_4$ and the mixture extracted with DCM (3×). The combined organic layers were dried over $Na_2SO_4$, filtered, and evaporated to afford (4R)-4-(tert-butoxycarbonylamino)-5-cyano-pentanoic acid which was carried forward without purification assuming quantitative conversion.

Step 2. The crude (4R)-4-(tert-butoxycarbonylamino)-5-cyano-pentanoic acid was dissolved in THF (20 mL) and TEA (0.77 mL, 5.5 mmol) was added. The solution was cooled to 0° C. and stirred rapidly. Ethyl chloroformate (0.53 mL, 5.5 mmol) was then added and the reaction was stirred for an additional hour before the precipitated triethylamine hydrochloride was filtered off and washed with a small amount of THF. The filtrate was then added slowly to a 0° C. solution of sodium borohydride (570 mg, 15 mmol) in THF (20 mL) and water (6 mL). After 2 hrs, 10% $KHSO_4$ was carefully added and the mixture extracted 3× with EtOAc. The combined organics were dried over $MgSO_4$, filtered, and evaporated. The crude was purified via flash chromatography (100% hexanes→100% EtOAc) to afford tert-butyl N-[(1R)-1-(cyanomethyl)-4-hydroxy-butyl]carbamate. ES/MS m/z: 229.0 $[M+H]^+$.

Example 160: (3R)-6-[7-fluoro-1-oxo-6-[5-(trifluoromethyl)pyrimidin-2-yl]-2-isoquinolyl]-3-[[6-oxo-5-(trifluoromethyl)-1H-pyridazin-4-yl]amino]hexanenitrile Example 160

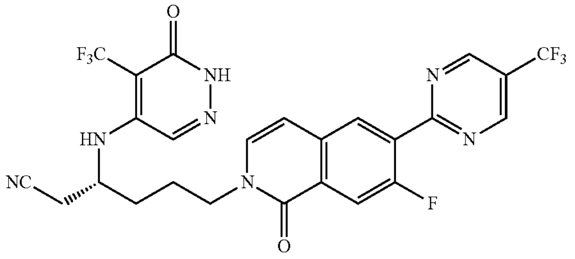

The title compound was synthesized as described in Example 5 Steps 2-8 with the following changes:

Step 2. tert-butyl N-[(1R)-1-(cyanomethyl)-4-hydroxy-butyl]carbamate was used instead of tert-butyl N-[(1S)-4-hydroxy-1-methyl-butyl]carbamate.

Step 5. 20 mol % of cataCXium Pd G4 and 2 M aqueous sodium carbonate (1.9 equiv.) were added following the completion of the borylation step give (3R)-6-[7-fluoro-1-oxo-6-[5-(trifluoromethyl)pyrimidin-2-yl]-2-isoquinolyl]-3-[[6-oxo-5-(trifluoromethyl)-1H-pyridazin-4-yl]amino]hexanenitrile. $^{1}$H NMR (400 MHz, DMSO-d6) 1H NMR (400 MHz, DMSO-d6) δ 12.56 (s, 1H), 9.48 (d, J=0.9 Hz, 2H), 8.44 (d, J=7.1 Hz, 1H), 8.08 (s, 1H), 8.03 (d, J=11.4 Hz, 1H), 7.53 (d, J=7.4 Hz, 1H), 6.85 (d, J=7.3 Hz, 1H), 6.65-6.54 (m, 1H), 4.48-4.35 (m, 1H), 4.05-3.96 (m, 2H), 2.95-2.79 (m, 2H), 1.80-1.55 (m, 4H).

ES/MS: m/z 582.2 $[M+H]^+$.

Example 161: Preparation of 7,8-difluoro-2-[(4R)-4-[[6-oxo-5-(trifluoromethyl)-1H-pyridazin-4-yl]amino]hept-5-ynyl]-6-[5-(trifluoromethyl)pyrimidin-2-yl]isoquinolin-1-one

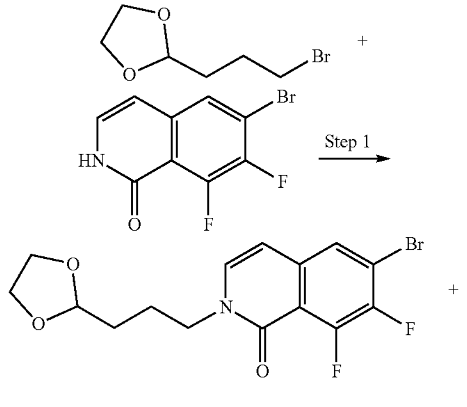

-continued

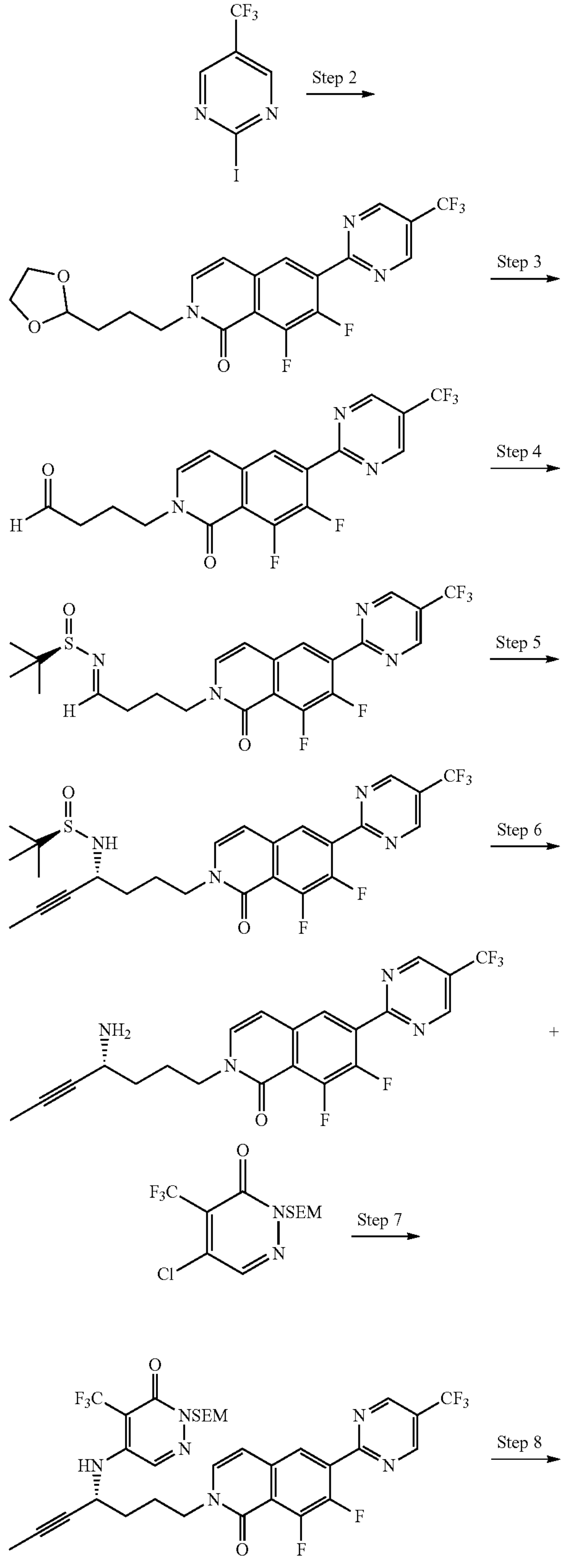

-continued

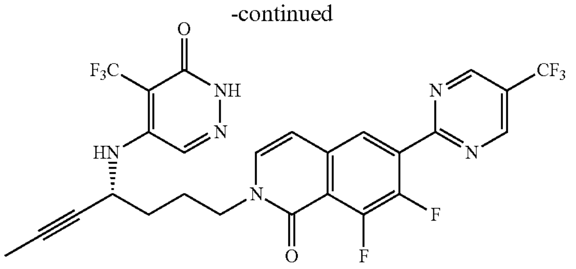

Example 161

Step 1. 6-bromo-7,8-difluoro-2H-isoquinolin-1-one (750 mg, 2.9 mmol) and 2-(3-bromopropyl)-1,3-dioxolane (0.43 mL, 3.2 mmol) were dissolved in DMF (10 mL) and stirred at ambient temperature. $Cs_2CO_3$ (1.9 g, 5.8 mmol) was then added and the reaction maintained for 3.5 hours at which point it was diluted with water and EtOAc. Solids crashed out and were filtered off to give pure product. The filtrate was then extracted 3× with EtOAc. The combined organics were dried over $MgSO_4$, filtered, and evaporated to give a yellow residue. Diethyl ether was added to this and the mixture sonicated to produce a white solid which was collected via filtration to give a second crop of 6-bromo-2-[3-(1,3-dioxolan-2-yl)propyl]-7,8-difluoro-isoquinolin-1-one. ES/MS: m/z 373.9/375.9 $[M]^+$.

Step 2. A vial was charged with 6-bromo-2-[3-(1,3-dioxolan-2-yl)propyl]-7,8-difluoro-isoquinolin-1-one (700 mg, 1.8 mmol), 1,1'-Bis(diphenylphosphino)ferrocene-palladium(II)dichloride (65 mg, 0.089 mmol), potassium acetate (530 mg, 5.4 mmol), and bis(pinacolato)diboron (1.4 g, 5.4 mmol) and flushed with dry nitrogen. Dioxane (12 mL) was added and the reaction heated to 100° C. for 4.5 hours. After cooling, 2-iodo-5-(trifluoromethyl)pyrimidine (590 mg, 2.1 mmol), CataCXium Pd G4 (66 mg, 0.089 mmol), and aqueous sodium carbonate (2.0 M, 2.7 mL) were added and the mixture bubbled with dry nitrogen briefly. The reaction was then stirred at 80° C. for 1 hour before being diluted with EtOAc and filtered through a plug of Celite. The filtrate was evaporated and the crude purified via flash chromatography to afford 2-[3-(1,3-dioxolan-2-yl)propyl]-7,8-difluoro-6-[5-(trifluoromethyl)pyrimidin-2-yl]isoquinolin-1-one as a yellow solid. ES/MS: m/z 441.7 $[M]^+$.

Step 3. 2-[3-(1,3-dioxolan-2-yl)propyl]-7,8-difluoro-6-[5-(trifluoromethyl)pyrimidin-2-yl]isoquinolin-1-one (700 mg, 1.5 mmol) was taken up in acetone (20 mL) and aqueous hydrochloric acid (1N, 14 mL). The reaction was stirred at 60° C. for 75 minutes before being cooled to ambient temperature and diluted with water. The precipitated solids were collected via filtration, washed with minimal water and heptanes, and dried to provide 4-[7,8-difluoro-1-oxo-6-[5-(trifluoromethyl)pyrimidin-2-yl]-2-isoquinolyl]butanal which was used without purification. m/z 398.0 $[M+H]^+$.

Step 4. Crude 4-[7,8-difluoro-1-oxo-6-[5-(trifluoromethyl)pyrimidin-2-yl]-2-isoquinolyl]butanal (600 mg, 1.5 mmol), (R)-2-methylpropane-2-sulfinamide (270 mg, 2.3 mmol), and Cupric sulfate (960 mg, 6.0 mmol) were suspended in DCM (14.0 mL) and stirred at ambient temperature. After 16 hours, the solids were removed via filtration, washed with additional DCM, and the filtrate evaporated. The residue was purified via flash chromatography (100% hexanes→100% EtOAc) to afford (NE,R)—N-[4-[7,8-difluoro-1-oxo-6-[5-(trifluoromethyl)pyrimidin-2-yl]-2-isoquinolyl]butylidene]-2-methyl-propane-2-sulfinamide as a yellow solid, m/z 501.0 $[M+H]^+$.

Step 5. (NE,R)—N-[4-[7,8-difluoro-1-oxo-6-[5-(trifluoromethyl)pyrimidin-2-yl]-2-isoquinolyl]butylidene]-2-methyl-propane-2-sulfinamide (350 mg, 0.66 mmol) was dissolved in DCM (14.0 mL) and the resultant solution was cooled to −78° C. 1-propynylmagnesium bromide (0.5 M in THF, 1.6 mL) was then added slowly and the reaction maintained at −78° C. for 30 minutes before warming to ambient temperature and stirring a further 1 hour. The solution was cooled to 0° C., quenched via addition of 10% $KHSO_4$, and extracted 3× with EtOAc. The combined organics were dried over $MgSO_4$, filtered, and evaporated. The residue was purified via flash chromatography (100% DCM+100% ACN) to provide (R)—N-[(1R)-1-[3-[7,8-difluoro-1-oxo-6-[5-(trifluoromethyl)pyrimidin-2-yl]-2-isoquinolyl]propyl]but-2-ynyl]-2-methyl-propane-2-sulfinamide as a yellow residue. m/z 541.1 $[M+H]^+$.

Step 6. (R)—N-[(1R)-1-[3-[7,8-difluoro-1-oxo-6-[5-(trifluoromethyl)pyrimidin-2-yl]-2-isoquinolyl]propyl]but-2-ynyl]-2-methyl-propane-2-sulfinamide (78 mg, 0.14 mmol) was dissolved in MeOH (1.0 mL) and the solution stirred at ambient temperature. Hydrochloric acid (4 M in dioxane, 0.14 mL) was then added. After 1 hour, the solvent was evaporated to afford 2-[(4R)-4-aminohept-5-ynyl]-7,8-difluoro-6-[5-(trifluoromethyl)pyrimidin-2-yl]isoquinolin-1-one. m/z 438.3 $[M+2H]^+$.

Step 7. 2-[(4R)-4-aminohept-5-ynyl]-7,8-difluoro-6-[5-(trifluoromethyl)pyrimidin-2-yl]isoquinolin-1-one (60 mg, 0.14 mmol) was dissolved in DMF (1.0 mL) before being treated with 5-chloro-4-(trifluoromethyl)-2-(2-trimethylsilylethoxymethyl)pyridazin-3-one (90 mg, 0.28 mmol) and DIPEA (0.24 mL, 1.4 mmol). The reaction was stirred at 65° C. for 1 hour before cooling to ambient temperature. 10% aq. $KHSO_4$ was added and the mixture extracted 3× with EtOAc. The combined organics were washed with brine, dried over $MgSO_4$, filtered, and evaporated. The residue was then purified via column chromatography (100% hexanes→100% EtOAc) to afford 7,8-difluoro-2-[(4R)-4-[[6-oxo-5-(trifluoromethyl)-1-(2-trimethylsilylethoxymethyl)pyridazin-4-yl]amino]hept-5-ynyl]-6-[5-(trifluoromethyl)pyrimidin-2-yl]isoquinolin-1-one. m/z 729.2 $[M+H]^+$.

Step 8. To a solution of 7,8-difluoro-2-[(4R)-4-[[6-oxo-5-(trifluoromethyl)-1-(2-trimethylsilylethoxymethyl)pyridazin-4-yl]amino]hept-5-ynyl]-6-[5-(trifluoromethyl)pyrimidin-2-yl]isoquinolin-1-one (87 mg, 0.11 mmol) in DCM (2.0 mL) stirred at ambient temperature was added TFA (0.10 mL, 1.1 mmol). The reaction was stirred for one hour then the volatiles were removed under vacuum. The resultant residue was dissolved in MeOH (1.0 mL), stirred at ambient temp, and treated with ethylenediamine (0.076 mL, 1.1 mmol). After 30 minutes, the reaction was concentrated and the residue purified by reverse phase prep-HPLC (5-100% MeCN in water, 0.1% TFA) to afford 7,8-difluoro-2-[(4R)-4-[[6-oxo-5-(trifluoromethyl)-1H-pyridazin-4-yl]amino]hept-5-ynyl]-6-[5-(trifluoromethyl)pyrimidin-2-yl]isoquinolin-1-one. $^1H$ NMR (400 MHz, DMSO-d6) 1H NMR (400 MHz, DMSO-d6) δ 12.61 (s, 1H), 9.51 (d, J=1.0 Hz, 2H), 8.25 (dd, J=6.7, 1.7 Hz, 1H), 7.95 (s, 1H), 7.56 (d, J=7.4 Hz, 1H), 6.84 (dd, J=7.5, 1.8 Hz, 1H), 6.81-6.74 (m, 1H), 4.69-4.59 (m, 1H), 4.04-3.95 (m, 2H), 1.91-1.75 (m, 7H). ES/MS: m/z 599.3 $[M+H]^+$.

Intermediate 25: 6-bromo-7-fluoro-2-[(4R)-5-hydroxy-4-[[6-oxo-5-(trifluoromethyl)-1-(2-trimethylsilylethoxymethyl)pyridazin-4-yl]amino]pentyl]isoquinolin-1-one

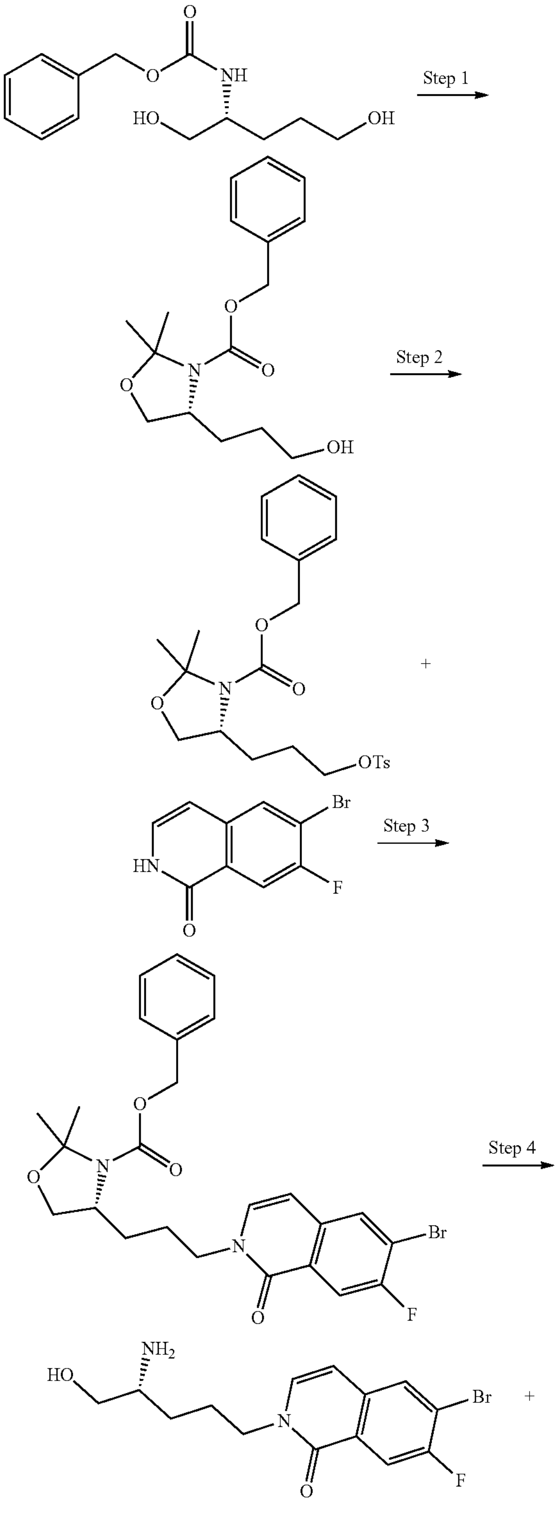

-continued

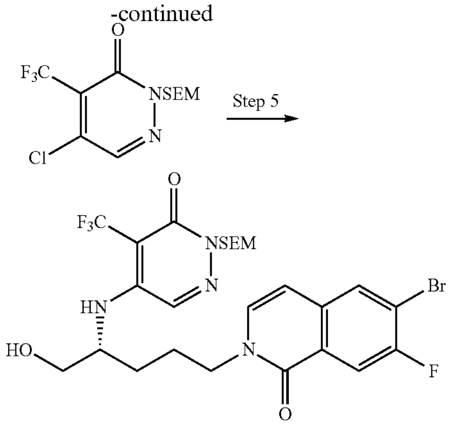

Intermediate 25

Step 1. benzyl N-[(1R)-4-hydroxy-1-(hydroxymethyl)butyl]carbamate (17 g, 67 mmol) was dissolved in DCM (147 mL) and 2,2-Dimethoxypropane (100 mL). The solution was stirred at ambient temperature and p-toluenesulfonic acid (1.3 g, 6.7 mmol) was added. After stirring for 4 hours, saturated aqueous $Na_2HCO_3$ was added. The phases were separated and the aqueous was extracted 2× with DCM. Combined organics were dried over $Na_2SO_4$, filtered, and evaporated. The residue was then purified via flash chromatography (100% hexanes→60% EtOAc) to afford benzyl (4R)-4-(3-hydroxypropyl)-2,2-dimethyl-oxazolidine-3-carboxylate. ES/MS: m/z 294.1 $[M+H]^+$.

Step 2. benzyl (4R)-4-(3-hydroxypropyl)-2,2-dimethyl-oxazolidine-3-carboxylate (15.6 g, 51 mmol) was dissolved in DCM (200 mL) and treated with TEA (14 mL, 100 mmol) before cooling to 0° C. DMAP (620 mg, 0.51 mmol) and p-toluenesulfonyl chloride (12 g, 61 mmol) were then added and the reaction was allowed to warm slowly to ambient temperature and stir for 16 hours at which point it was again cooled to 0° C. and treated with 10% $KHSO_4$ solution. This was extracted 3× with DCM and the combined organics were dried over $Na_2SO_4$, filtered, and evaporated. The crude residue was purified via column chromatography (100% hexanes→60% EtOAc/Hex) to afford benzyl (4R)-2,2-dimethyl-4-[3-(p-tolylsulfonyloxy)propyl]oxazolidine-3-carboxylate. ES/MS: m/z 448.1 $[M+H]^+$.

Step 3. Benzyl (4R)-2,2-dimethyl-4-[3-(p-tolylsulfonyloxy)propyl]oxazolidine-3-carboxylate (10.2 g, 22 mmol), 6-bromo-7-fluoro-2H-isoquinolin-1-one (6.0 g, 25 mmol), and $Cs_2CO_3$ (14 g, 43 mmol) were suspended in DMF (61 mL) and stirred at ambient temperature for 5 hours. The reaction was then diluted w/water and extracted 3× with EtOAc. The combined organics were washed with brine, dried over $MgSO_4$, filtered, and evaporated. The crude residue was purified via column chromatography (100% hexanes→60% EtOAc/Hex) to afford benzyl (4R)-4-[3-(6-bromo-7-fluoro-1-oxo-2-isoquinolyl)propyl]-2,2-dimethyl-oxazolidine-3-carboxylate. ES/MS: m/z 517.1/519.0 $[M+H]^+$.

Step 4. Benzyl (4R)-4-[3-(6-bromo-7-fluoro-1-oxo-2-isoquinolyl)propyl]-2,2-dimethyl-oxazolidine-3-carboxylate (8.4 g, 15.4 mmol) was suspended in aqueous hydrochloric acid (6 N, 51 mL) and the mixture stirred at 105° C. for 2 hours. The reaction was cooled to 0° C. and the pH adjusted to ~9-10 with 12 N aqueous NaOH. The suspension was then extracted 8× with a 3:1 mixture of DCM:MeOH while monitoring the pH of the aqueous phase and adjusting with 2N NaOH to maintain a pH~9-10. The combined organics were dried over $Na_2SO_4$, filtered, and evaporated to provide crude 2-[(4R)-4-amino-5-hydroxy-pentyl]-6-bromo-7-fluoro-isoquinolin-1-one which was used without purification. ES/MS: m/z 343.0/345.0 $[M+H]^+$.

Step 5. 2-[(4R)-4-amino-5-hydroxy-pentyl]-6-bromo-7-fluoro-isoquinolin-1-one (15.4 mmol) and 5-chloro-4-(trifluoromethyl)-2-(2-trimethylsilylethoxymethyl)pyridazin-3-one (7.3 g, 20 mmol) were dissolved in DMF (56 mL) and the solution was treated with DIPEA (8.0 mL, 46 mmol) before being warmed to 60° C. After stirring for 75 minutes, the reaction was cooled, diluted with water and aqueous 10% $KHSO_4$, and extracted 3× with EtOAc. The combined extracts were washed with brine, dried over $MgSO_4$, filtered, and evaporated. The crude residue was purified via column chromatography (100% hexanes→100% EtOAc) to afford 6-bromo-7-fluoro-2-[(4R)-5-hydroxy-4-[[6-oxo-5-(trifluoromethyl)-1-(2-trimethylsilylethoxymethyl)pyridazin-4-yl]amino]pentyl]isoquinolin-1-one. ES/MS: m/z 635.2/637.2 $[M+H]^+$.

Example 162: (2R)-5-[7-fluoro-1-oxo-6-[5-(trifluoromethyl)pyrimidin-2-yl]-2-isoquinolyl]-2-[[6-oxo-5-(trifluoromethyl)-1H-pyridazin-4-yl]amino]pentanenitrile

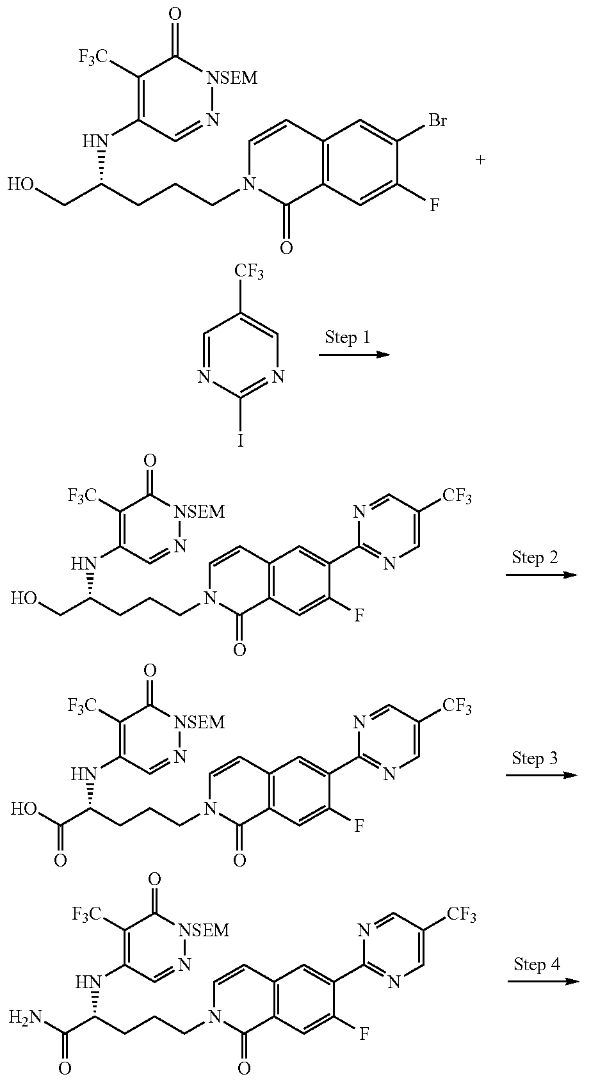

-continued

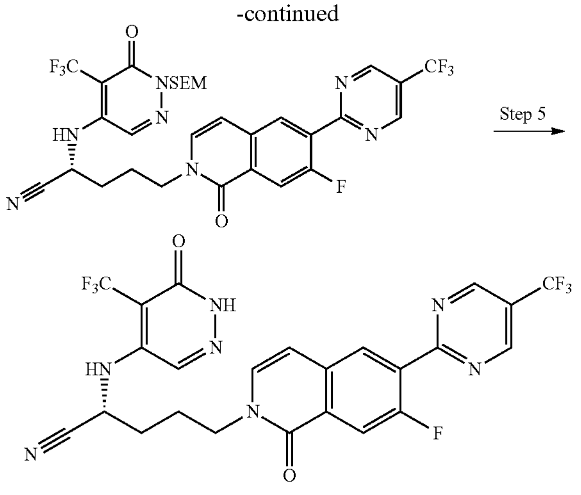

Example 162

Step 1. A vial was charged with 6-bromo-7-fluoro-2-[(4R)-5-hydroxy-4-[[6-oxo-5-(trifluoromethyl)-1-(2-trimethylsilylethoxymethyl)pyridazin-4-yl]amino]pentyl]isoquinolin-1-one (165 mg, 0.25 mmol), 1,1'-Bis (diphenylphosphino)ferrocene-palladium(II)dichloride (9.0 mg, 0.012 mmol), potassium acetate (73 mg, 0.74 mmol), and bis(pinacolato)diboron (160 mg, 0.74 mmol) and flushed with dry nitrogen. Dioxane (1.2 mL) was added and the reaction heated to 100° C. for 1.5 hours. After cooling, 2-iodo-5-(trifluoromethyl)pyrimidine (81 mg, 0.30 mmol), CataCXium Pd G4 (9.0 mg, 0.012 mmol), and aqueous sodium carbonate (2.0 M, 0.37 mL) were added and the mixture bubbled with dry nitrogen briefly. The reaction was then stirred at 80° C. for 1 hour before being diluted with EtOAc and filtered through a plug of Celite. The filtrate was evaporated and the crude purified via flash chromatography to afford 7-fluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one. ES/MS: m/z 703.3 $[M+H]^+$.

Step 2. 7-fluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one (120 mg, 0.16 mmol) was dissolved in dioxane (0.43 mL) and water (50 μL) and stirred at ambient temperature. TEMPO (1.3 mg, 8 μmol) and iodobenzene diacetate (115 mg, 0.36 mmol) were then added. After stirring for 1.5 hours, the reaction was diluted with 10% $KHSO_4$ and extracted 3× with EtOAc. The combined organics were dried over $MgSO_4$, filtered, and evaporated to provide (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanoic acid which was used immediately without purification. ES/MS: m/z 717.3 $[M+H]^+$.

Step 3. (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanoic acid (0.16 mmol) and HATU (76 mg, 0.32 mmol) were dissolved in DMF (1.6 mL) and DIPEA (85 μL, 0.49 mmol) and the solution stirred at ambient temperature. Ammonia (0.5 M in dioxane, 0.97 mL) was then added and the reaction maintained at ambient temperature. An additional portion of HATU, DIPEA, and ammonia was added after 1 hour and 1.5 hours. After a total of 2 hours, the reaction was diluted with water and extracted 3× with EtOAc. The combined organics were washed with 10% $KHSO_4$, brine, dried over $MgSO_4$, filtered, and evaporated to afford crude (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanamide which was used without purification. m/z 716.3 $[M+H]^+$.

Step 4. (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanamide (0.16 mmol) was dissolved in DMF (0.8 mL) and stirred at 0° C. Cyanuric chloride (42 mg, 0.23 mmol) was charged and the reaction stirred for 45 minutes before being diluted with EtOAc. The mixture was washed with saturated sodium bicarbonate, brine, and then dried over $MgSO_4$. This was then filtered and concentrated under vacuum. The crude purified via flash chromatography (100% hexanes→100% EtOAc) to afford (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanenitrile. m/z 698.2 $[M+H]^+$.

Step 5. (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanenitrile (75 mg, 0.096 mmol) was dissolved in DCM (2.5 mL) and stirred at ambient temperature. TFA (74 μL, 0.96 mmol) was added and the reaction maintained for 1.5 hours at which point ethylenediamine (96 μL, 0.14 mmol) was added directly. After an additional 20 minutes, the reaction was evaporated and the residue purified by reverse phase prep-HPLC (5-100% MeCN in water, 0.1% TFA) to afford (2R)-5-[7-fluoro-1-oxo-6-[5-(trifluoromethyl)pyrimidin-2-yl]-2-isoquinolyl]-2-[[6-oxo-5-(trifluoromethyl)-1H-pyridazin-4-yl]amino]pentanenitrile. $^1H$ NMR (400 MHz, DMSO-d6) δ 12.84 (s, 1H), 9.48 (d, J=1.0 Hz, 2H), 8.45 (d, J=7.1 Hz, 1H), 8.09-8.00 (m, 2H), 7.56 (d, J=7.4 Hz, 1H), 7.30-7.21 (m, 1H), 6.88 (d, J=7.4 Hz, 1H), 5.24-5.14 (m, 1H), 4.07 (t, J=6.8 Hz, 2H), 2.10-1.94 (m, 2H), 1.93-1.79 (m, 2H). ES/MS: m/z 568.3 $[M+H]^+$.

Intermediate 26: benzyl (4R)-4-[3-(6-bromo-7,8-difluoro-1-oxo-2-isoquinolyl)propyl]-2,2-dimethyl-oxazolidine-3-carboxylate Intermediate 26

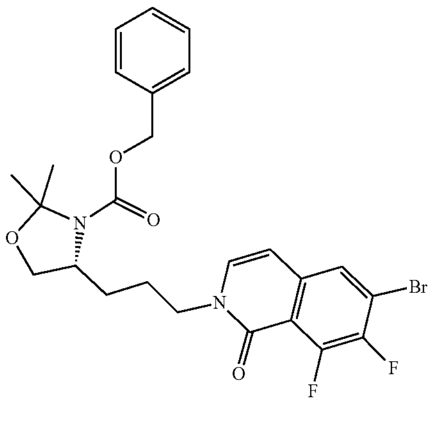

The title compound was synthesized as described in Steps 1-3 of Intermediate 25, using 6-bromo-7,8-difluoro-2H-isoquinolin-1-one in place of 6-bromo-7-fluoro-2H-isoquinolin-1-one. ES/MS: m/z 535.1/537.0 $[M+H]^+$.

Example 163: 7,8-difluoro-2-[(4R)-5-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one

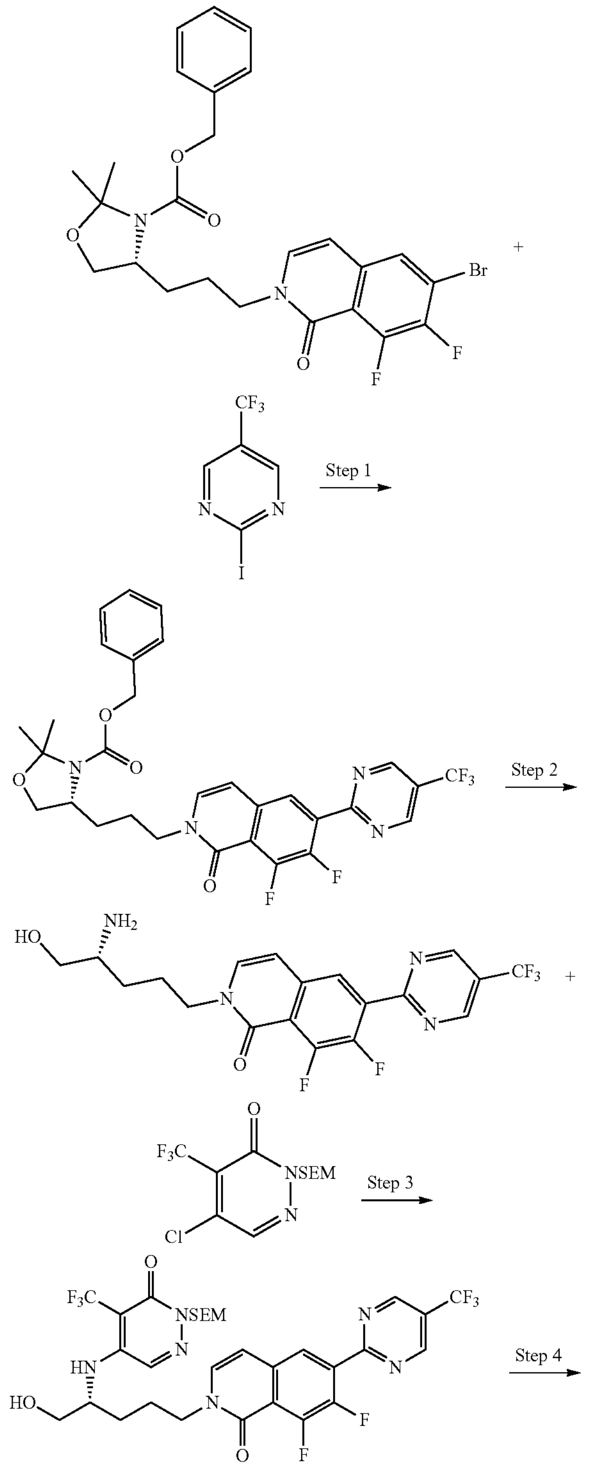

-continued

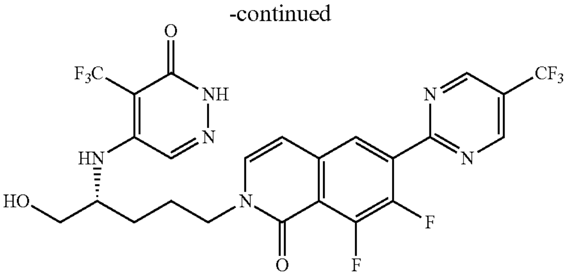

Example 163

Step 1. A vial was charged with benzyl (4R)-4-[3-(6-bromo-7,8-difluoro-1-oxo-2-isoquinolyl)propyl]-2,2-dimethyl-oxazolidine-3-carboxylate (624 mg, 0.11 mmol), 1,1'-Bis(diphenylphosphino)ferrocene-palladium(II)dichloride (41 mg, 0.055 mmol), potassium acetate (325 mg, 3.3 mmol), and bis(pinacolato)diboron (840 mg, 3.3 mmol) and flushed with dry nitrogen. Dioxane (5.6 mL) was added and the reaction was heated to 100° C. for 1.5 hours. After cooling, 2-iodo-5-(trifluoromethyl)pyrimidine (364 mg, 1.3 mmol), CataCXium Pd G4 (41 mg, 0.055 mmol), and aqueous sodium carbonate (2.0 M, 1.7 mL) were added and the mixture bubbled with dry nitrogen briefly. The reaction was then stirred at 80° C. for 45 minutes before being diluted with EtOAc and filtered through a plug of Celite. The filtrate was evaporated and the crude purified via flash chromatography (100% hexanes→80% EtOAc/Hex) to afford benzyl (4R)-4-[3-[7,8-difluoro-1-oxo-6-[5-(trifluoromethyl)pyrimidin-2-yl]-2-isoquinolyl]propyl]-2,2-dimethyl-oxazolidine-3-carboxylate. ES/MS: m/z 603.2 $[M+H]^+$.

Step 2. benzyl (4R)-4-[3-[7,8-difluoro-1-oxo-6-[5-(trifluoromethyl)pyrimidin-2-yl]-2-isoquinolyl]propyl]-2,2-dimethyl-oxazolidine-3-carboxylate (927 mg, 1.5 mmol) was suspended in aqueous hydrochloric acid (6 N, 4.9 mL) and the mixture stirred at 105° C. for 4 hours. The reaction was cooled to 0° C. and the pH adjusted to ~9-10 with 2N aqueous NaOH. The precipitate was then collected via filtration, washed with minimal water and heptanes and dried under high-vacuum to afford 2-[(4R)-4-amino-5-hydroxy-pentyl]-7,8-difluoro-6-[5-(trifluoromethyl)pyrimidin-2-yl]isoquinolin-1-one which was used without purification. ES/MS: m/z 429.0 $[M+H]^+$.

Step 3. 2-[(4R)-4-amino-5-hydroxy-pentyl]-7,8-difluoro-6-[5-(trifluoromethyl)pyrimidin-2-yl]isoquinolin-1-one (422 mg, 0.99 mmol) and 5-chloro-4-(trifluoromethyl)-2-(2-trimethylsilylethoxymethyl)pyridazin-3-one (602 mg, 1.3 mmol) were dissolved in DMF (4.5 mL) and the solution was treated with DIPEA (0.52 mL, 3.0 mmol) before being warmed to 60° C. After stirring for 75 minutes, the reaction was cooled, diluted with water and aqueous 10% $KHSO_4$, and extracted 3x with EtOAc. The combined extracts were washed with brine, dried over $MgSO_4$, filtered, and evaporated. The crude residue was purified via column chromatography (100% hexanes→100% EtOAc) to afford 7,8-difluoro-2-[(4R)-5-hydroxy-4-[[6-oxo-5-(trifluoromethyl)-1-(2-trimethylsilylethoxymethyl)pyridazin-4-yl]amino]

pentyl]-6-[5-(trifluoromethyl)pyrimidin-2-yl]isoquinolin-1-one. ES/MS: m/z 721.3 [M+H]$^+$.

Step 4. 7,8-difluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one (75 mg, 0.099 mmol) was dissolved in DCM (1.0 mL) and stirred at ambient temperature. TFA (76 μL, 0.99 mmol) was added and the reaction maintained for 30 minutes at which point it was evaporated to dryness. The residue was dissolved in MeOH (1.0 mL) and treated with ethylenediamine (66 μL, 0.99 mmol). After 30 minutes, the reaction was evaporated and the residue purified by reverse phase prep-HPLC (5-100% MeCN in water, 0.1% TFA) to afford 7,8-difluoro-2-[(4R)-5-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one. $^1$H NMR (400 MHz, DMSO-d6) δ 12.42 (s, 1H), 9.50 (d, J=1.0 Hz, 2H), 8.24 (dd, J=6.6, 1.7 Hz, 1H), 7.94 (s, 1H), 7.55 (d, J=7.4 Hz, 1H), 6.82 (dd, J=7.4, 1.8 Hz, 1H), 6.31-6.20 (m, 1H), 4.00-3.86 (m, 3H), 3.52-3.42 (m, 2H), 1.82-1.67 (m, 2H), 1.64-1.51 (m, 2H). ES/MS: m/z 591.3 [M+H]$^+$.

Intermediate 26: benzyl (4R)-4-[3-(7-bromo-6-fluoro-4-oxo-quinazolin-3-yl)propyl]-2,2-dimethyl-oxazolidine-3-carboxylate Intermediate 26

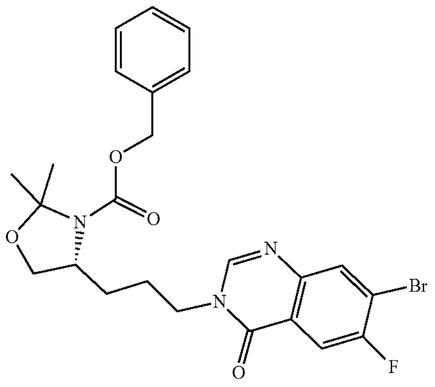

The title compound was synthesized as described in Steps 1-3 of Intermediate 25, using 7-bromo-6-fluoro-3H-quinazolin-4-one in place of 6-bromo-7-fluoro-2H-isoquinolin-1-one. ES/MS: m/z 518.1/520.0 [M+H]$^+$.

The following Examples were synthesized as described in Example 163 or a modification of the procedure above from the corresponding intermediates.

| Ex. No. | Structure | Int. No. | $^1$H NMR/MS [M + H]$^+$ |
|---|---|---|---|
| 164 | 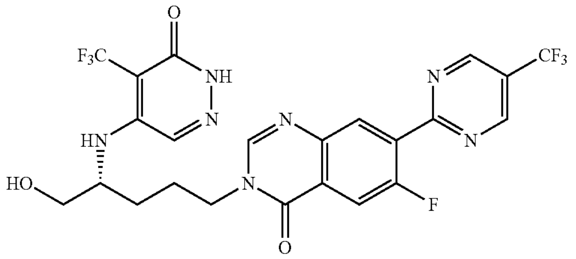 [SMILES: O=c1[nH]ncc(N[C@@H](CO)CCCn2cnc3cc(-c4ncc(C(F)(F)F)cn4)c(F)cc3c2=O)c1C(F)(F)F] | 26 | 1H NMR (400 MHZ, DMSO-d6) δ 12.42 (s, 1H), 9.50 (d, J = 1.0 Hz, 2H), 8.45 (s, 1H), 8.35 (d, J = 6.7 Hz, 1H), 8.00 (d, J = 10.6 Hz, 1H), 7.94 (s, 1H), 6.31-6.21 (m, 1H), 4.02 (t, J = 6.9 Hz, 2H), 3.96-3.86 (m, 1H), 3.52-3.41 (m, 2H), 1.86-1.69 (m, 2H), 1.65-1.52 (m, 2H). ES/MS: m/z 591.3 [M + H]$^+$. |
| 165 | 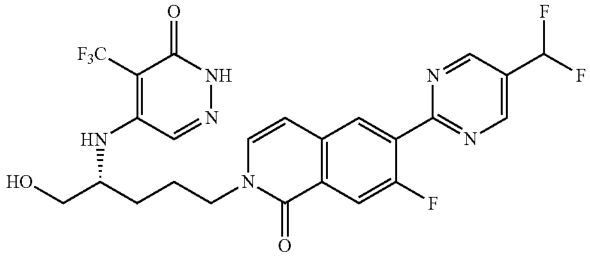 [SMILES: O=c1[nH]ncc(N[C@@H](CO)CCCn2ccc3cc(-c4ncc(C(F)F)cn4)c(F)cc3c2=O)c1C(F)(F)F] | 25 | 1H NMR (400 MHZ, DMSO-d6) δ 12.42 (s, 1H), 9.25 (d, J = 1.2 Hz, 2H), 8.40 (d, J = 7.2 Hz, 1H), 8.02 (d, J = 11.4 Hz, 1H), 7.94 (s, 1H), 7.52 (d, J = 7.4 Hz, 1H), 7.31 (t, J = 54.8 Hz, 1H), 6.83 (d, J = 7.4 Hz, 1H), 6.31-6.22 (m, 1H), 4.00 (t, J = 6.9 Hz, 2H), 3.96-3.89 (m, 1H), 3.47 (d, J = 5.0 Hz, 2H), 1.83-1.68 (m, 2H), 1.64-1.51 (m, 2H). |
| 166 | 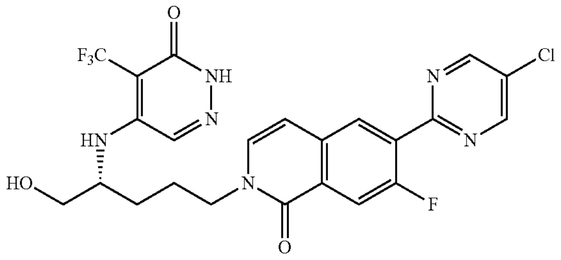 [SMILES: O=c1[nH]ncc(N[C@@H](CO)CCCn2ccc3cc(-c4ncc(Cl)cn4)c(F)cc3c2=O)c1C(F)(F)F] | 25 | 1H NMR (400 MHz, DMSO-d6) δ 12.42 (s, 1H), 8.15 (d, J = 7.3 Hz, 1H), 8.00-7.88 (m, 3H), 7.48 (d, J = 7.4 Hz, 1H), 7.12 (dd, J = 7.8, 2.1 Hz, 1H), 6.73 (d, J = 7.4 Hz, 1H), 6.68 (br s, 2H), 6.30-6.21 (m, 1H), 3.99 (t, J = 6.9 Hz, 2H), 3.95-3.87 (m, 1H), 3.51-3.41 (m, 2H), 1.84-1.65 (m, 2H), 1.65-1.49 (m, 2H). ES/MS: m/z 539.2 [M + H]$^+$ |

-continued

| Ex. No. | Structure | Int. No. | $^1$H NMR/MS [M + H]$^+$ |
|---|---|---|---|
| 167 | 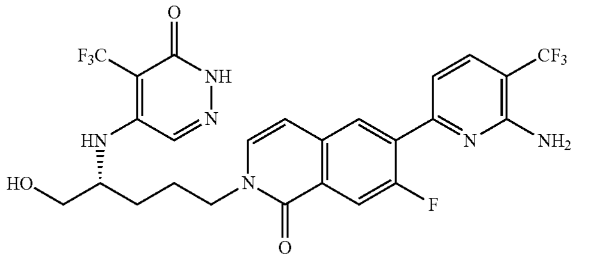 [SMILES: Nc1nc(-c2cc3ccn(CCC[C@H](CO)Nc4cn[nH]c(=O)c4C(F)(F)F)c(=O)c3cc2F)ccc1C(F)(F)F] | 25 | 1H NMR (400 MHZ, DMSO-d6) δ 12.42 (s, 1H), 8.15 (d, J = 7.3 Hz, 1H), 8.00-7.88 (m, 3H), 7.48 (d, J = 7.4 Hz, 1H), 7.12 (dd, J = 7.8, 2.1 Hz, 1H), 6.73 (d, J = 7.4 Hz, 1H), 6.68 (br s, 2H), 6.30-6.21 (m, 1H), 3.99 (t, J = 6.9 Hz, 2H), 3.95-3.87 (m, 1H), 3.51-3.41 (m, 2H), 1.84-1.65 (m, 2H), 1.65-1.49 (m, 2H). ES/MS: m/z 587.2 [M + H]$^+$ |

Example 168: 2-[(4R)-5-(difluoromethoxy)-4-[[6-oxo-5-(trifluoromethyl)-1H-pyridazin-4-yl]amino]pentyl]-7-fluoro-6-[5-(trifluoromethyl)pyrimidin-2-yl]isoquinolin-1-one

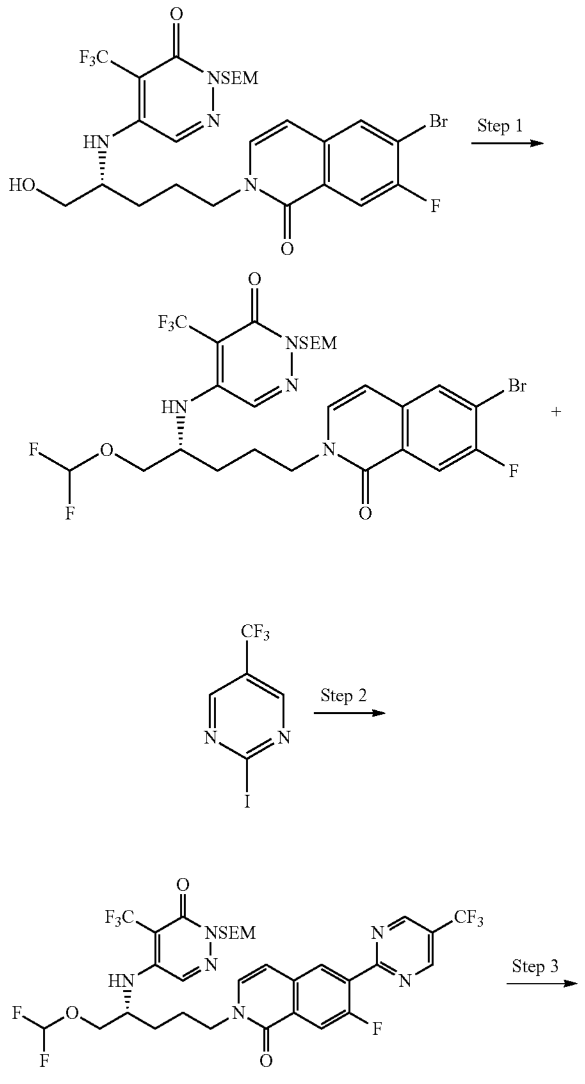

-continued

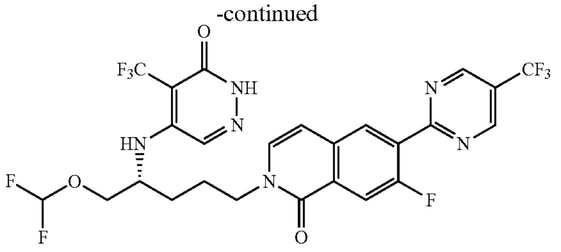

Example 168

Step 1. 6-bromo-7-fluoro-2-[(4R)-5-hydroxy-4-[[6-oxo-5-(trifluoromethyl)-1-(2-trimethylsilylethoxymethyl) pyridazin-4-yl]amino]pentyl]isoquinolin-1-one (250 mg, 0.37 mmol) and potassium acetate (293 mg, 3.0 mmol) were taken up in DCM (2.0 mL) and water (2.0 mL) and stirred very rapidly. (Bromodifluoromethyl)trimethylsilane (0.23 mL, 1.5 mmol) was then added. An additional portion of potassium acetate and (Bromodifluoromethyl)trimethylsilane was added at 7 hours and at 24 hours. After 27 hours total reaction time, water was added, and the reaction extracted 3× with DCM. The combined organics were dried over $MgSO_4$, filtered, and evaporated. The crude residue was purified via column chromatography (100% hexanes→100% EtOAc) to afford 6-bromo-2-[(4R)-5-(difluoromethoxy)-4-[[6-oxo-5-(trifluoromethyl)-1-(2-trimethylsilylethoxymethyl)pyridazin-4-yl]amino]pentyl]-7-fluoro-isoquinolin-1-one. ES/MS: m/z 685.2/687.1 [M+H]$^+$.

Step 2. A vial was charged with benzyl 6-bromo-2-[(4R)-5-(difluoromethoxy)-4-[[6-oxo-5-(trifluoromethyl)-1-(2-trimethylsilylethoxymethyl)pyridazin-4-yl]amino]pentyl]-7-fluoro-isoquinolin-1-one (235 mg, 0.33 mmol), 1,1'-Bis (diphenylphosphino)ferrocene-palladium(II)dichloride (12 mg, 0.016 mmol), potassium acetate (96 mg, 0.98 mmol), and bis(pinacolato)diboron (250 mg, 0.98 mmol) and flushed with dry nitrogen. Dioxane (3.3 mL) was added and the reaction heated to 100° C. for 16 hours. After cooling, 2-iodo-5-(trifluoromethyl)pyrimidine (107 mg, 0.39 mmol), CataCXium Pd G4 (12 mg, 0.016 mmol), and aqueous sodium carbonate (2.0 M, 0.49 mL) were added and the mixture bubbled with dry nitrogen briefly. The reaction was then stirred at 80° C. for 3 hours before being diluted with EtOAc and filtered through a plug of Celite. The filtrate was evaporated and the crude purified via flash chromatography (100% hexanes→80% EtOAc/Hex) to afford 2-[(4R)-5-(difluoromethoxy)-4-[[6-oxo-5-(trifluoromethyl)-1-(2-trimethylsilylethoxymethyl)pyridazin-4-yl]amino]pentyl]-7-fluoro-6-[5-(trifluoromethyl)pyrimidin-2-yl]isoquinolin-1-one ES/MS: m/z 753.2 [M+H]$^+$.

Step 3. 2-[(4R)-5-(difluoromethoxy)-4-[[6-oxo-5-(trifluoromethyl)-1-(2-trimethylsilylethoxymethyl)pyridazin-4-yl]amino]pentyl]-7-fluoro-6-[5-(trifluoromethyl)pyrimidin-2-yl]isoquinolin-1-one (281 mg, 0.30 mmol) was dissolved in DCM (5.0 mL) and stirred at ambient temperature. TFA (0.45 mL, 6.0 mmol) was added and the reaction maintained for 1 hour at which point it was evaporated to dryness. The residue was dissolved in MeOH (2.5 mL) and treated with ethylenediamine (0.20 mL, 3.0 mmol). After 30 minutes, the reaction was evaporated and the residue purified by reverse phase prep-HPLC (5-100% MeCN in water, 0.1% TFA) to afford 2-[(4R)-5-(difluoromethoxy)-4-[[6-oxo-5-(trifluoromethyl)-1H-pyridazin-4-yl]amino]pentyl]-7-fluoro-6-[5-(trifluoromethyl)pyrimidin-2-yl]isoquinolin-1-one. $^1H$ NMR (400 MHz, DMSO-d6) δ 12.49 (s, 1H), 9.48 (d, J=1.0 Hz, 2H), 8.44 (d, J=7.1 Hz, 1H), 8.03 (d, J=11.4 Hz, 1H), 7.98 (s, 1H), 7.52 (d, J=7.4 Hz, 1H), 6.87-6.45 (m, 2H), 6.45-6.36 (m, 1H), 4.34-4.20 (m, 1H), 4.01 (t, J=6.8 Hz, 2H), 3.96-3.87 (m, 2H), 1.86-1.70 (m, 2H), 1.69-1.51 (m, 2H). ES/MS: m/z 623.3 $[M+H]^+$.

Example 169: 7-fluoro-2-[(4R)-4-(5-methyl-1,3,4-oxadiazol-2-yl)-4-[[6-oxo-5-(trifluoromethyl)-1H-pyridazin-4-yl]amino]butyl]-6-[5-(trifluoromethyl)pyrimidin-2-yl]isoquinolin-1-one

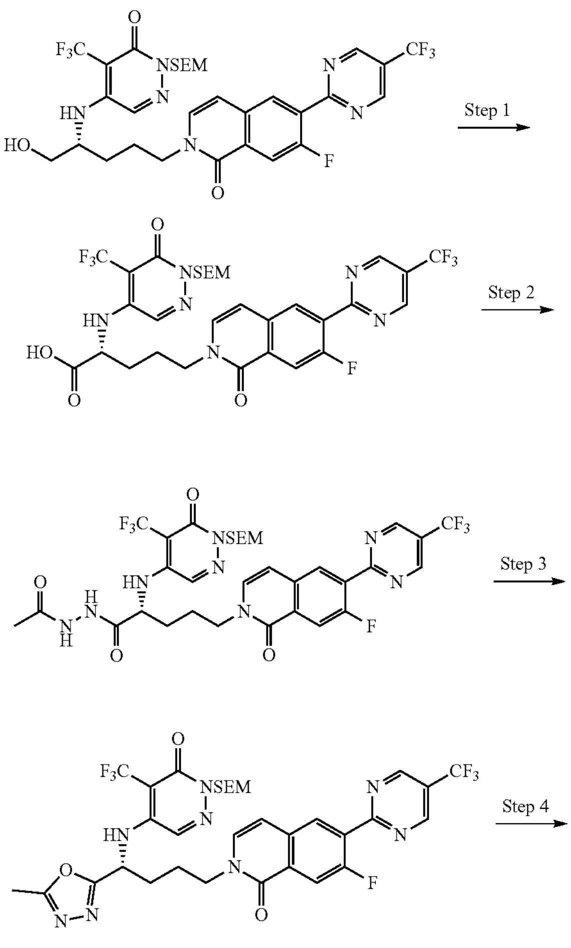

-continued

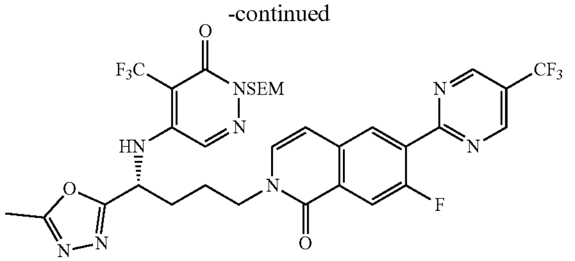

Example 169

Step 1. 7-fluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one (75 mg, 0.10 mmol) was dissolved in dioxane (0.27 mL) and water (30 μL) and stirred at ambient temperature. TEMPO (0.80 mg, 5.1 μmol) and iodobenzene diacetate (72.0 mg, 0.22 mmol) were then added. After stirring for 18 hours, the reaction was diluted with 10% $KHSO_4$ and extracted 3× with EtOAc. The combined organics were dried over $MgSO_4$, filtered, and evaporated to provide (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanoic acid which was used immediately without purification. ES/MS: m/z 717.3 $[M+H]^+$.

Step 2. (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanoic acid (0.10 mmol), acethydrazide (11 mg, 0.13 mmol), and HATU (48 mg, 0.20 mmol) were dissolved in DMF (1.0 mL) and DIPEA (53 μL, 0.30 mmol) and the solution stirred at ambient temperature. After 2 hours, the reaction was diluted with water and extracted 3× with EtOAc. The combined organics were washed with 10% $KHSO_4$, brine, dried over $MgSO_4$, filtered, and evaporated to afford crude (2R)—N'-acetyl-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanehydrazide which was used without purification. m/z 716.3 $[M+H]^+$.

Step 3. (2R)—N'-acetyl-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanehydrazide (0.10 mmol) was dissolved in DCM (1.0 mL) and stirred at ambient temperature. Burgess reagent (48 mg, 0.20 mmol) and DIPEA (35 μL, 0.20 mmol) were charged. An additional portion of Burgess reagent and DIPEA were added at 22 hours and 26 hours. After 40 hours total, the reaction was diluted with 10% $KHSO_4$ and extracted 3× with DCM. The combined organics were dried over $MgSO_4$, filtered and, concentrated under vacuum. The crude was then purified via flash chromatography (100% hexanes→100% EtOAc) to afford 7-fluoro-2-[(4R)-4-(5-methyl-1,3,4-oxadiazol-2-yl)-4-[[6-oxo-5-(trifluoromethyl)-1-(2-trimethylsilylethoxymethyl)pyridazin-4-yl]amino]butyl]-6-[5-(trifluoromethyl)pyrimidin-2-yl]isoquinolin-1-one. m/z 755.3 $[M+H]^+$.

Step 4. 7-fluoro-2-[(4R)-4-(5-methyl-1,3,4-oxadiazol-2-yl)-4-[[6-oxo-5-(trifluoromethyl)-1-(2-trimethylsilylethoxymethyl)pyridazin-4-yl]amino]butyl]-6-[5-(trifluoromethyl)pyrimidin-2-yl]isoquinolin-1-one (46 mg, 0.058 mmol) was dissolved in DCM (2.0 mL) and stirred at ambient temperature. TFA (44 μL, 0.58 mmol) was added and the reaction maintained for 40 minutes at which point it was evaporated to dryness. The residue was dissolved in MeOH (1.0 mL) and treated with ethylenediamine (39 μL, 0.58 mmol). After 25 minutes, the reaction was evaporated and the residue purified by reverse phase prep-HPLC (5-100% MeCN in water, 0.1% TFA) to afford 7-fluoro-2-[(4R)-4-(5-methyl-1,3,4-oxadiazol-2-yl)-4-[[6-oxo-5-(trifluoromethyl)-1H-pyridazin-4-yl]amino]butyl]-6-[5-(trifluoromethyl)pyrimidin-2-yl]isoquinolin-1-one. $^1$H NMR (400 MHz, DMSO-d6) δ 12.67 (s, 1H), 9.48 (d, J=1.0 Hz, 2H), 8.44 (d, J=7.1 Hz, 1H), 8.02 (s, 1H), 7.99 (s, 1H), 7.54 (d, J=7.4 Hz, 1H), 7.12-7.03 (m, 1H), 6.86 (d, J=7.4 Hz, 1H), 5.49-5.38 (m, 1H), 4.06 (t, J=6.8 Hz, 2H), 2.47 (s, 3H), 2.19-2.03 (m, 2H), 1.96-1.77 (m, 2H). ES/MS: m/z 625.3 $[M+H]^+$.

Example 170: 7-fluoro-2-[(4R)-4-[[6-oxo-5-(trifluoromethyl)-1H-pyridazin-4-yl]amino]hex-5-ynyl]-6-[5-(trifluoromethyl)pyrimidin-2-yl]isoquinolin-1-one

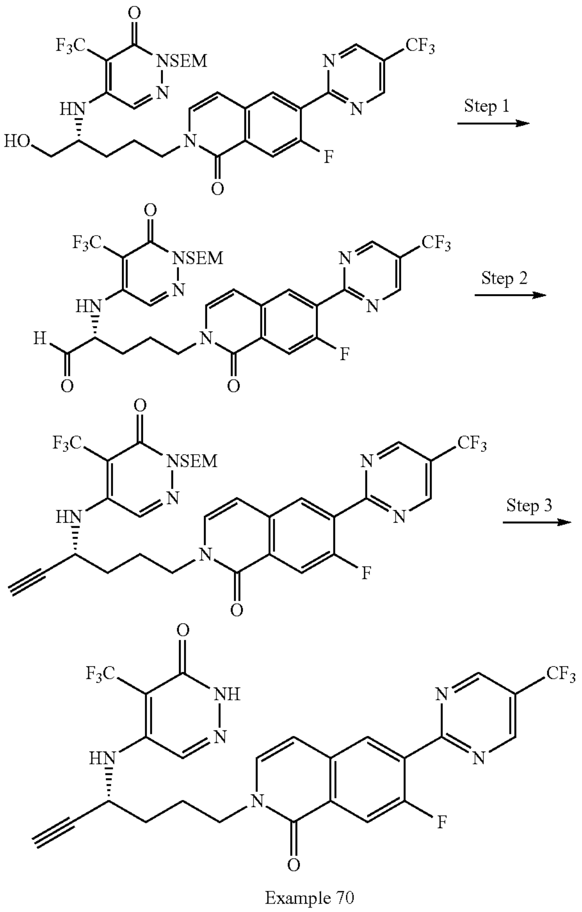

Example 70

Step 1. 7-fluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one (127 mg, 0.17 mmol) was dissolved in DCM (3.5 mL) and stirred at 0° C. DMP (80 mg, 0.19 mmol) was then added. After stirring for 16 hours, DMP (22 mg, 0.051 mmol) was added and the reaction was stirred an additional 6 hours. Saturated aqueous sodium bicarbonate was added, and the mixture extracted 3× with DCM. The combined organics were dried over $Na_2SO_4$, filtered, and evaporated to provide (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanal which was used immediately without purification. ES/MS: m/z 733.3 $[M+OMe+H]^+$.

Step 2. (2R)-5-[7-fluoro-1-oxo-6-[5-(trifluoromethyl)pyrimidin-2-yl]-2-isoquinolyl]-2-[[6-oxo-5-(trifluoromethyl)-1-(2-trimethylsilylethoxymethyl)pyridazin-4-yl]amino]pentanal (0.17 mmol) and potassium carbonate (95 mg, 0.69 mmol) were suspended in MeOH (3.0 mL) and the mixture was stirred at ambient temperature. (1-Diazo-2-oxo-propyl)-phosphonic acid dimethyl ester (40 mg, 0.21 mmol) was added in MeOH (0.75 mL) and the reaction stirred for 20 hours before being diluted with EtOAc and the solids filtered off. The filtrate was evaporated to provide crude material which was purified via flash chromatography (100% hexanes→100% EtOAc) to afford impure 7-fluoro-2-[(4R)-4-[[6-oxo-5-(trifluoromethyl)-1-(2-trimethylsilylethoxymethyl)pyridazin-4-yl]amino]hex-5-ynyl]-6-[5-(trifluoromethyl)pyrimidin-2-yl]isoquinolin-1-one which was used as is. m/z 697.3 $[M+H]^+$.

Step 3. 7-fluoro-2-[(4R)-4-[[6-oxo-5-(trifluoromethyl)-1-(2-trimethylsilylethoxymethyl)pyridazin-4-yl]amino]hex-5-ynyl]-6-[5-(trifluoromethyl)pyrimidin-2-yl]isoquinolin-1-one (38 mg, 0.054 mmol) was dissolved in DCM (2.0 mL) and stirred at ambient temperature. TFA (41 μL, 0.54 mmol) was added and the reaction maintained for 1.5 hours at which point it was evaporated to dryness. The residue was dissolved in MeOH (1.0 mL) and treated with ethylenediamine (36 μL, 0.54 mmol). After 25 minutes, the reaction was evaporated and the residue purified by reverse phase prep-HPLC (5-100% MeCN in water, 0.1% TFA) to afford 7-fluoro-2-[(4R)-4-[[6-oxo-5-(trifluoromethyl)-1H-pyridazin-4-yl]amino]hex-5-ynyl]-6-[5-(trifluoromethyl) pyrimidin-2-yl]isoquinolin-1-one. $^1$H NMR (400 MHz, DMSO-d6) δ 12.65 (s, 1H), 9.48 (d, J=1.0 Hz, 2H), 8.45 (d, J=7.1 Hz, 1H), 8.04 (d, J=11.4 Hz, 1H), 7.96 (s, 1H), 7.54 (d, J=7.4 Hz, 1H), 6.91-6.80 (m, 2H), 4.77-4.66 (m, 1H), 4.11-3.99 (m, 2H), 3.46 (d, J=2.2 Hz, 1H), 1.95-1.76 (m, 4H). ES/MS: m/z 567.3$[M+H]^+$.

Example 171: 7-fluoro-2-[(4S)-4-[[6-oxo-5-(trifluoromethyl)-1H-pyridazin-4-yl]amino]hex-5-ynyl]-6-[5-(trifluoromethyl)pyrimidin-2-yl]isoquinolin-1-one Example 171

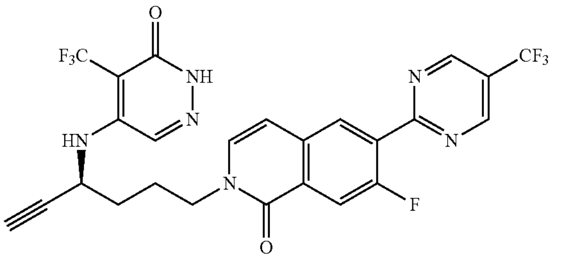

The title compound was synthesized as described in example 170, using 7-fluoro-2-[(4S)-5-hydroxy-4-[[6-oxo-5-(trifluoromethyl)-1-(2-trimethylsilylethoxymethyl) pyridazin-4-yl]amino]pentyl]-6-[5-(trifluoromethyl)pyrimidin-2-yl]isoquinolin-1-one was utilized as starting material instead of 7-fluoro-2-[(4R)-5-hydroxy-4-[[6-oxo-5-(trifluoromethyl)-1-(2-trimethylsilylethoxymethyl)pyridazin-4-yl]

amino]pentyl]-6-[5-(trifluoromethyl)pyrimidin-2-yl]isoquinolin-1-one. This material was prepared from tert-butyl N-[(1S)-4-hydroxy-1-(hydroxymethyl)butyl]carbamate instead of benzyl N-[(1R)-4-hydroxy-1-(hydroxymethyl)butyl]carbamate. $^1$H NMR (400 MHz, DMSO-d6) δ 12.65 (s, 1H), 9.51 (d, J=1.0 Hz, 2H), 8.25 (d, J=6.3 Hz, 1H), 7.96 (s, 1H), 7.57 (d, J=7.4 Hz, 1H), 6.90-6.79 (m, 2H), 4.77-4.66 (m, 1H), 4.04-3.96 (m, 2H), 3.46 (d, J=2.2 Hz, 1H), 1.95-1.77 (m, 4H). ES/MS: m/z 585.3 [M+H]$^+$.

Example 172: 7-fluoro-2-(3-(1-methyl-2-(6-oxo-5-(trifluoromethyl)-1,6-dihydropyridazin-4-yl)hydrazineyl)propyl)-6-(5-(trifluoromethyl)pyrimidin-2-yl)isoquinolin-1(2H)-one

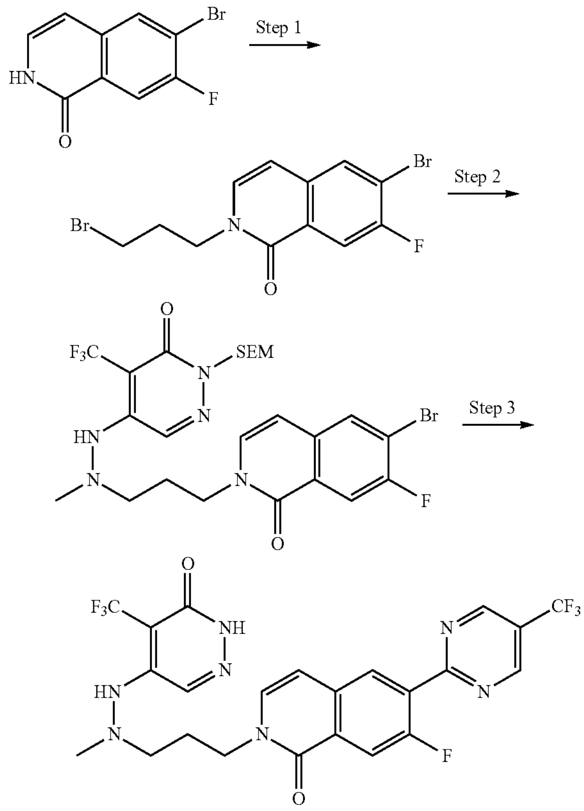

Example 172

Step 1. 1,3-dibromopropane (4.2 mL, 41 mmol) was added to a mixture of 6-bromo-7-fluoroisoquinolin-1-one (500 mg, 2.1 mmol) and cesium carbonate (1.35 g, 4.1 mmol) in DMF (8.0 mL). After stirring at ambient temperature overnight, the reaction was poured into aq. $NaHCO_3$ and extracted into EtOAc (3×). The combined extracts were washed with brine, concentrated, and purified by flash chromatography (EtOAc/hexane) to provide 6-bromo-2-(3-bromopropyl)-7-fluoro-isoquinolin-1-one. ES/MS m/z: 364.1 [M+H]$^+$.

Step 2. 6-Bromo-2-(3-bromopropyl)-7-fluoro-isoquinolin-1-one (100 mg, 0.28 mmol), methyl hydrazine (0.02 mL, 0.30 mmol), cesium carbonate (180 mg, 0.55 mmol), and sodium iodide (57 mg, 0.38 mmol) were combined in DMF (1.0 mL) and heated to 50° C. After one hour, the reaction was allowed to cool to ambient temperature. 5-Chloro-4-(trifluoromethyl)-2-(2-trimethylsilylethoxymethyl)

pyridazin-3-one (279 mg, 0.85 mmol) and DIEA (0.14 mL, 0.83 mmol) were added, and the resulting mixture was heated at 50° C. for 20 minutes, then stirred at ambient temperature for 4 days. The reaction was poured into water and extracted into EtOAc (3×). The combined extracts were washed with brine, concentrated, and purified by flash chromatography (3:1 EtOAc/EtOH in hexane) to provide 6-bromo-7-fluoro-2-[3-[methyl-[[6-oxo-5-(trifluoromethyl)-1-(2-trimethylsilylethoxymethyl)pyridazin-4-yl]amino]amino]propyl]isoquinolin-1-one. ES/MS m/z: 620.1 [M+H]$^+$.

Step 3. 6-Bromo-7-fluoro-2-[3-[methyl-[[6-oxo-5-(trifluoromethyl)-1-(2-trimethylsilylethoxymethyl)pyridazin-4-yl]amino]amino]propyl]isoquinolin-1-one was subjected to conditions in Example 17 step 3, using 2-iodo-5-(trifluoromethyl)pyrimidine instead of 2-bromo-5-(difluoromethoxy)pyridine and adding 10 mol % of XPhos Pd G4 along with the pyrimidine. 1H NMR (400 MHz, DMSO-d6) δ 12.46 (s, 1H), 9.48 (d, J=1.0 Hz, 2H), 8.44 (d, J=7.2 Hz, 1H), 8.25 (s, 1H), 8.10-8.06 (m, 1H), 8.03 (d, J=11.4 Hz, 1H), 7.52 (d, J=7.4 Hz, 1H), 6.85 (d, J=7.4 Hz, 1H), 4.12-3.94 (m, 2H), 2.95-2.83 (m, 1H), 2.80-2.69 (m, 1H), 2.57 (s, 3H), 1.82 (p, J=7.1 Hz, 2H). ES/MS m/z: 558.3 [M+H]$^+$.

Example 173: (S)-2-(4-((6-oxo-5-(trifluoromethyl)-1,6-dihydropyridazin-4-yl)amino)pentyl)-6-(4-(trifluoromethyl)-1H-pyrazol-1-yl)isoquinolin-1(2H)-one Example 173

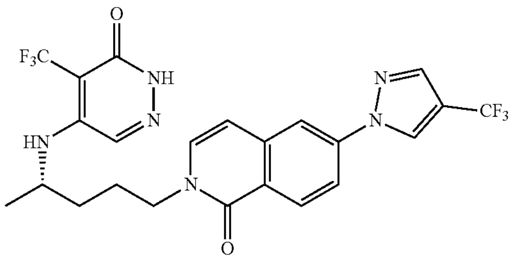

The title compound was synthesized as described in Example 5, with the following changes:

Steps 4-5 were replaced with the following conditions. tert-Butyl N-[(1S)-4-(6-bromo-1-oxo-2-isoquinolyl)-1-methyl-butyl]carbamate (90 mg, 0.22 mmol), 4-(trifluoromethyl)-1H-pyrazole (36 mg, 0.26 mmol), tBu-XPhos Pd G3 (15 mg, 0.02 mmol), cesium carbonate (143 mg, 0.44 mmol), and dioxane (0.0 mL) were combined and purged with nitrogen gas. The reaction was heated to 100° C. for 20 hours, then adsorbed onto isolute and purified by flash chromatography eluting with EtOAc in hexanes 0-100% to afford tert-butyl N-[(1S)-1-methyl-4-[1-oxo-6-[4-(trifluoromethyl)pyrazol-1-yl]-2-isoquinolyl]butyl]carbamate. ES/MS m/z: 465.2 [M+H]$^+$.

Step 6. HCl in dioxane was used instead of TFA in DCM. $^1$H NMR (400 MHz, DMSO-d6) δ 12.44 (s, 1H), 9.36 (s, 1H), 8.35 (d, J=8.8 Hz, 1H), 8.31 (s, 1H), 8.21 (d, J=2.2 Hz, 1H), 8.05 (dd, J=8.8, 2.2 Hz, 1H), 7.92 (s, 1H), 7.55 (d, J=7.4 Hz, 1H), 6.70 (d, J=7.4 Hz, 1H), 6.41-6.31 (m, 1H), 4.05-3.92 (m, 3H), 1.82-1.60 (m, 3H), 1.57-1.46 (m, 1H), 1.17 (d, J=6.3 Hz, 3H). ES/MS m/z: 527.3 [M+H]$^+$.

Intermediate 27: Preparation of tert-butyl (2R,4R)-4-methyl-2-(3-(tosyloxy)propyl)pvrrolidine-1-carboxylate

| Intermediate 27: Preparation of tert-butyl (2R,4R)-4-methyl-2-(3-(tosyloxy)propyl)pyrrolidine-1-carboxylate |
|---|

Intermediate 27

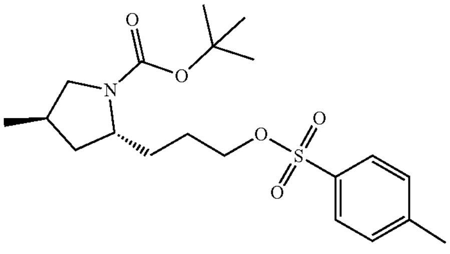

The title compound was synthesized as described in Intermediate 3, using tert-butyl (2S,4R)-2-(hydroxymethyl)-4-methylpyrrolidine-1-carboxylate instead of tert-butyl (1R, 2S,5S)-2-(hydroxymethyl)-3-azabicyclo[3.1.0]hexane-3-carboxylate. ES/MS m/z: 398.1 $[M+H]^+$.

Example 174: 7-fluoro-2-(3-((2R,4R)-4-methyl-1-(6-oxo-5-(trifluoromethyl)-1,6-dihydropyridazin-4-yl)pyrrolidin-2-yl)propyl)-6-(5-(trifluoromethyl) pyrimidin-2-yl)isoquinolin-1(2H)-one Example 174

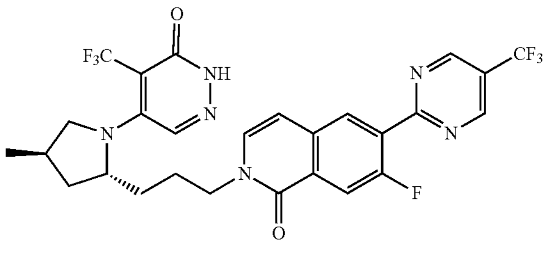

The title compound was synthesized as described in Example 17 with the following changes:

Step 1 6-bromo-7-fluoroisoquinolin-1(2H)-one was used instead of 6-bromo-8-fluoro-1,2-dihydroisoquinolin-1-one and tert-butyl (2R,4R)-4-methyl-2-(3-(tosyloxy)propyl)pyrrolidine-1-carboxylate was used instead of (S)-4-((tert-butoxycarbonyl)amino)pentyl 4-methylbenzenesulfonate Step 3. 2-iodo-5-(trifluoromethyl)pyrimidine was used instead of 2-bromo-5-(difluoromethoxy)pyridine and 10 mol % [1,1'-Bis (di-tert-butyl phosphino)ferrocene]dichloropalladium (II) was used for borylation and 20 mol % of cataCXium Pd G4 and 2 M aqueous sodium carbonate (1.9 equiv.). $^1H$ NMR (400 MHz, DMSO-$d_6$) δ 12.47 (s, 1H), 9.48 (d, J=1.0 Hz, 2H), 8.43 (d, J=7.2 Hz, 1H), 8.07-8.00 (m, 2H), 7.54 (d, J=7.4 Hz, 1H), 6.84 (d, J=7.4 Hz, 1H), 4.48-4.29 (m, 1H), 4.09-3.91 (m, 2H), 3.78-3.65 (m, 1H), 2.83 (d, J=10.9 Hz, 1H), 2.42-2.30 (m, 1H), 1.87-1.58 (m, 5H), 1.52-1.37 (m, 1H), 0.81 (d, J=6.9 Hz, 3H). ES/MS: m/z 597.3 $[M+H]^+$.

The following Examples were synthesized as described in Example 174 or a modification of the procedure above from the corresponding intermediates.

| Ex. No. | Structure | $^1H$ NMR/MS $[M + H]^+$ |
|---|---|---|
| 175 | 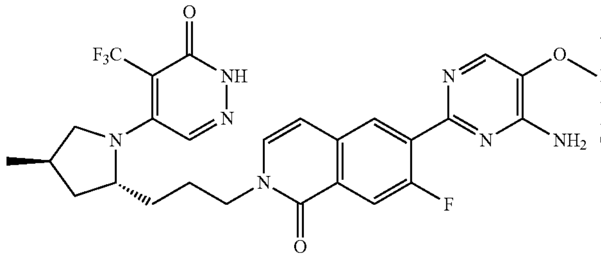 | $^1H$ NMR (400 MHz, DMSO-$d_6$) δ 12.47 (s, 1H), 8.11 (d, J = 7.0 Hz, 1H), 8.07 (s, 1H), 8.03 (s, 1H), 8.00 (d, J = 11.0 Hz, 1H), 7.52 (d, J = 7.4 Hz, 1H), 6.76 (d, J = 7.4 Hz, 1H), 4.44-4.37 (m, 1H), 4.02-3.98 (m, 2H), 3.96 (s, 3H), 3.72-3.69 (m, 1H), 2.83 (d, J = 10.9 Hz, 1H), 2.42-2.29 (m, 1H), 1.87-1.55 (m, 5H), 1.52-1.37 (m, 1H), 0.81 (d, J = 6.9 Hz, 3H). ES/MS: m/z 574.3 $[M + H]^+$. |
| 176 | 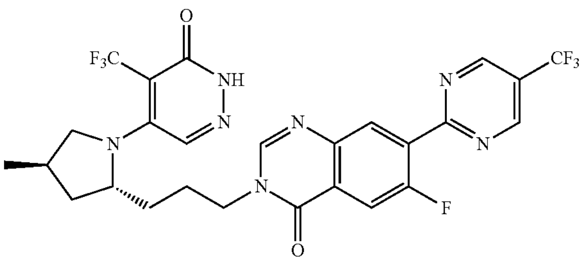 [SMILES: C[C@@H]1C[C@@H](CCCn2cnc3cc(-c4ncc(C(F)(F)F)cn4)c(F)cc3c2=O)N(c2cn[nH]c(=O)c2C(F)(F)F)C1] | $^1H$ NMR (400 MHz, DMSO-$d_6$) δ 12.47 (s, 1H), 9.50 (d, J = 0.9 Hz, 2H), 8.46 (s, 1H), 8.34 (d, J = 6.7 Hz, 1H), 8.04 (s, 1H), 7.99 (d, J = 10.5 Hz, 1H), 4.45-4.34 (m, 1H), 4.07-3.96 (m, 2H), 3.77-3.66 (m, 1H), 2.84 (d, J = 10.9 Hz, 1H), 2.41-2.31 (m, 1H), 1.84-1.63 (m, 5H), 1.53-1.41 (m, 1H), 0.82 (d, J = 6.9 Hz, 3H). ES/MS: m/z 598.3 $[M + H]^+$. |

-continued

| Ex. No. | Structure | $^1$H NMR/MS [M + H]$^+$ |
|---|---|---|
| 177 | 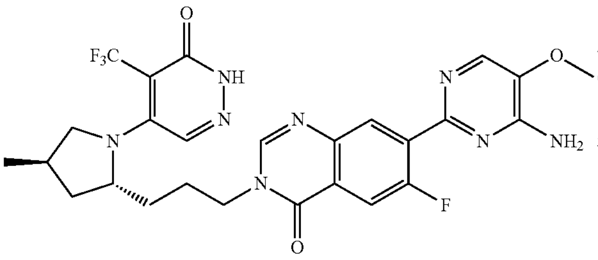 | $^1$H NMR (400 MHz, DMSO-$d_6$) δ 12.47 (s, 1H), 8.44 (s, 1H), 8.11 (d, J = 6.7 Hz, 1H), 8.08 (s, 1H), 8.03 (s, 1H), 7.97 (d, J = 10.2 Hz, 1H), 4.44-4.37 (m, 1H), 4.01 (t, J = 6.8 Hz, 2H), 3.96 (s, 3H), 3.75-3.64 (m, 1H), 2.83 (d, J = 10.9 Hz, 1H), 2.41-2.29 (m, 1H), 1.87-1.59 (m, 5H), 1.53-1.40 (m, 1H), 0.81 (d, J = 6.9 Hz, 3H). ES/MS: m/z 575.3 [M + H]$^+$. |

Intermediate 28: 2-((1R,2S)-2-((tert-butoxycarbonyl)amino)cyclopentyl)ethyl 4-methylbenzenesulfonate Intermediate 28

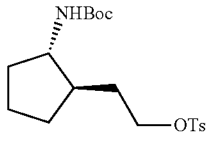

2-((1R,2S)-2-((tert-butoxycarbonyl)amino)cyclopentyl) ethyl 4-methylbenzenesulfonate was synthesized as described in Intermediate 14 (2-((1R,2S)-2-((tert-butoxycarbonyl)amino)cyclobutyl)ethyl 4-methylbenzenesulfonate) using (1S,2S)-2-((tert-butoxycarbonyl)amino)cyclopentane-1-carboxylic acid instead (1S,2S)-2-((tert-butoxycarbonyl) amino)cyclobutane-1-carboxylic acid. ES/MS m/z: 406.32 [M+Na]$^+$.

Example 178: 6-(4-amino-5-(trifluoromethyl)pyrimidin-2-yl)-7-fluoro-2-(2-((1R,2S)-2-((6-oxo-5-(trifluoromethyl)-1,6-dihydropyridazin-4-yl)amino) cyclopentyl)ethyl)isoquinolin-1(2H)-one Example 178

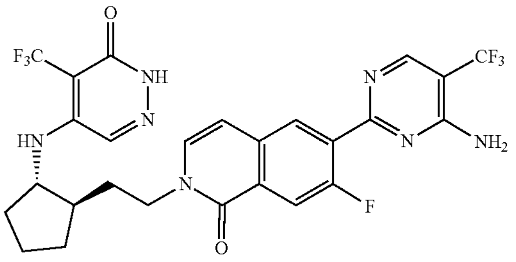

6-(4-amino-5-(trifluoromethyl)pyrimidin-2-yl)-7-fluoro-2-(2-((1R,2S)-2-((6-oxo-5-(trifluoromethyl)-1,6-dihydropyridazin-4-yl)amino)cyclopentyl)ethyl)isoquinolin-1(2H)-one was synthesized as described in Example 17 using 2-((1R,2S)-2-((tert-butoxycarbonyl)amino)cyclopentyl) ethyl 4-methylbenzenesulfonate, 6-bromo-7-fluoroisoquinolin-1(2H)-one and 2-chloro-5-(trifluoromethyl)pyrimidin-4-amine. $^1$H NMR (400 MHz, DMSO-d6) δ 12.45 (s, 1H), 8.65 (s, 1H), 8.19 (d, J=7.1 Hz, 1H), 7.95 (d, J=11.2 Hz, 1H), 7.92 (s, 1H), 7.51 (d, J=7.4 Hz, 1H), 6.76 (d, J=7.4 Hz, 1H), 6.47 (dd, J=8.3, 3.7 Hz, 1H), 3.99 (t, J=7.4 Hz, 2H), 3.85 (p, J=7.8 Hz, 1H), 2.09-1.84 (m, 3H), 1.72-1.46 (m, 4H), 1.36-1.22 (m, 1H). ES/MS m/z: 598.30 [M+H]$^+$.

Example 179: 7-fluoro-2-(2-((1R,2S)-2-((6-oxo-5-(trifluoromethyl)-1,6-dihydropyridazin-4-yl)amino) cyclopentyl)ethyl)-6-(5-(trifluoromethyl)pyrimidin-2-yl)isoquinolin-1(2H)-one Example 179

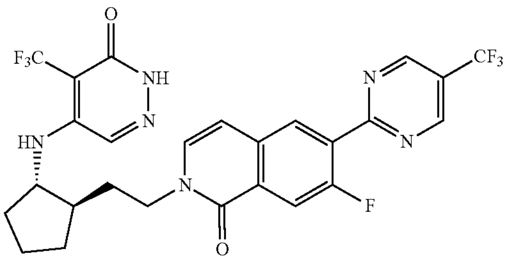

7-fluoro-2-(2-((1R,2S)-2-((6-oxo-5-(trifluoromethyl)-1,6-dihydropyridazin-4-yl)amino)cyclopentyl)ethyl)-6-(5-(trifluoromethyl)pyrimidin-2-yl)isoquinolin-1(2H)-one was synthesized as described in Example 17 using 2-((1R,2S)-2-((tert-butoxycarbonyl)amino)cyclopentyl)ethyl 4-methylbenzenesulfonate, 6-bromo-7-fluoroisoquinolin-1(2H)-one and 2-iodo-5-(trifluoromethyl)pyrimidine. $^1$H NMR (400 MHz, DMSO-d6) δ 12.45 (s, 1H), 9.48 (d, J=1.0 Hz, 2H), 8.43 (d, J=7.2 Hz, 1H), 8.02 (d, J=11.4 Hz, 1H), 7.92 (s, 1H), 7.54 (d, J=7.4 Hz, 1H), 6.84 (d, J=7.4 Hz, 1H), 6.52-6.43 (m, 1H), 4.00 (t, J=7.4 Hz, 2H), 3.85 (p, J=7.9 Hz, 1H), 2.10-1.86 (m, 4H), 1.73-1.46 (m, 4H), 1.36-1.22 (m, 1H). ES/MS m/z: 583.30 [M+H]$^+$.

Example 180: (R)-2-(5-ethoxy-4-((6-oxo-5-(trifluoromethyl)-1,6-dihydropyridazin-4-yl)amino)pentyl)-7-fluoro-6-(5-(trifluoromethyl)pyrimidin-2-yl)isoquinolin-1(2H)-one Example 180

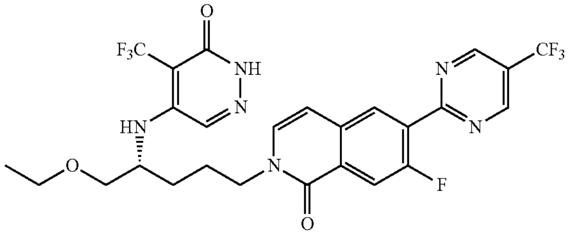

The title compound was synthesized as described in Example 135, using iodoethane instead of iodomethane in step 1 to afford (R)-2-(5-ethoxy-4-((6-oxo-5-(trifluoromethyl)-1,6-dihydropyridazin-4-yl)amino)pentyl)-7-fluoro-6-(5-(trifluoromethyl)pyrimidin-2-yl)isoquinolin-1(2H)-one. $^1$H NMR (400 MHz, DMSO-d6) δ 12.43 (s, 1H), 9.48 (s, 2H), 8.46-8.41 (m, 1H), 8.03 (d, J=11.4 Hz, 1H), 7.95 (s, 1H), 7.53 (d, J=7.4 Hz, 1H), 6.87-6.82 (m, 1H), 6.32-6.24 (m, 1H), 4.17-4.08 (m, 1H), 4.04-3.97 (m, 2H), 3.47-3.37 (m, 4H), 1.82-1.70 (m, 2H), 1.63-1.52 (m, 2H), 1.03 (t, J=7.0 Hz, 3H). ES/MS m/z: 601.3 [M+H].

Example 181: (R)-7-fluoro-2-(5-(methoxy-d3)-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one Example 181

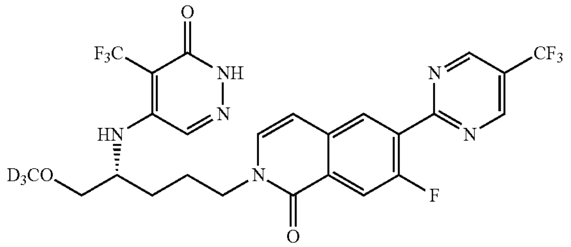

The title compound was synthesized as described in Example 135, using iodomethane-d3 instead of iodomethane in step 1 to afford (R)-7-fluoro-2-(5-(methoxy-d3)-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one. $^1$H NMR (400 MHz, Acetonitrile-d3) δ 10.44 (s, 1H), 9.25 (s, 2H), 8.36 (d, J=7.1 Hz, 1H), 8.10 (d, J=11.7 Hz, 1H), 7.74 (s, 1H), 7.28-7.24 (m, 1H), 6.71 (d, J=7.4 Hz, 1H), 5.81-5.72 (m, 1H), 4.05-4.00 (m, 2H), 3.97 (d, J=8.7 Hz, 1H), 3.48-3.41 (m, 2H), 1.82 (s, 2H), 1.72-1.58 (m, 2H). ES/MS m/z: 590.1 [M+H].

Intermediate 29

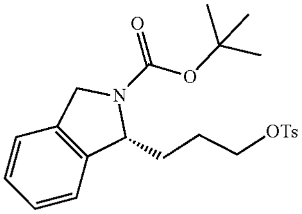

The title compound was synthesized as described in Intermediate 3, using tert-butyl (S)-1-(hydroxymethyl)isoindoline-2-carboxylate instead of tert-butyl (1R,2S,5S)-2-(hydroxymethyl)-3-azabicyclo[3.1.0]hexane-3-carboxylate. ES/MS m/z: 432.2 [M+H]$^+$.

Example 182: 7-fluoro-2-[3-[(1R)-2-[6-oxo-5-(trifluoromethyl)-1H-pyridazin-4-yl]isoindolin-1-yl]propyl]-6-[5-(trifluoromethyl)pyrimidin-2-yl]isoquinolin-1-one Example 182

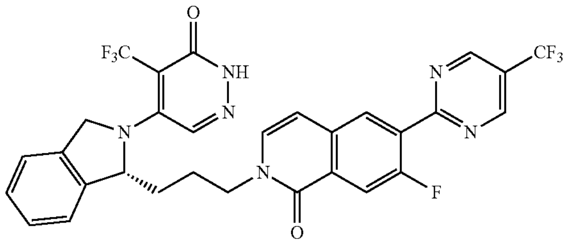

The title compound was synthesized as described in Example 5, using tert-butyl (S)-1-(hydroxymethyl)isoindoline-2-carboxylate instead of tert-butyl N-[(1S)-1-cyclopropyl-2-hydroxy-ethyl]carbamate in step 3. $^1$H NMR (400 MHz, DMSO-d6) δ 12.56 (s, 1H), 9.48 (d, J=1.0 Hz, 2H), 8.41 (d, J=7.2 Hz, 1H), 8.21 (s, 1H), 7.98 (d, J=11.4 Hz, 1H), 7.44 (d, J=7.4 Hz, 1H), 7.42-7.22 (m, 4H), 6.79 (d, J=7.4 Hz, 1H), 5.86 (s, 1H), 5.04 (d, J=14.9 Hz, 1H), 4.51 (d, J=14.9 Hz, 1H), 3.94 (dh, J=19.9, 7.0 Hz, 2H), 1.91 (dq, J=19.9, 13.6 Hz, 2H), 1.76-1.53 (m, 1H), 1.54-1.27 (m, 1H). ES/MS m/z: 631.3 [M+H]$^+$.

Intermediate 30: [(1R,3S)-3-(tert-butoxycarbonylamino)cyclohexyl]methyl 4-methylbenzenesulfonate Intermediate 30

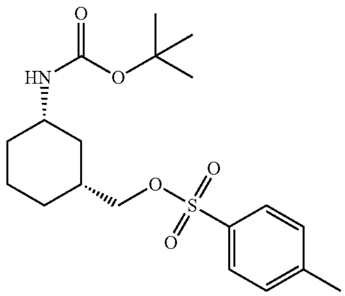

The title compound was synthesized as described in Intermediate 3, using tert-butyl N-[(1S,3R)-3-(hydroxymethyl)cyclohexyl]carbamate instead of tert-butyl (1R,2S,5S)-2-(hydroxymethyl)-3-azabicyclo[3.1.0]hexane-3-carboxylate. ES/MS m/z: 384.2 $[M+H]^+$.

Example 183: 7-fluoro-2-[[(1R,3S)-3-[[6-oxo-5-(trifluoromethyl)-1H-pyridazin-4-yl]amino]cyclohexyl]methyl]-6-[5-(trifluoromethyl)pyrimidin-2-yl]isoquinolin-1-one Example 183

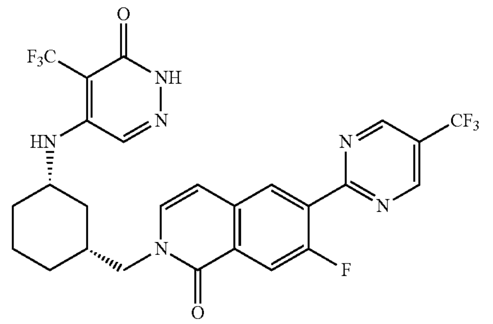

The title compound was synthesized as described in Example 63, using [(1R,3S)-3-(tert-butoxycarbonylamino)cyclohexyl]methyl 4-methylbenzenesulfonate instead of 4-(tert-butoxycarbonylamino)pentyl]4-methylbenzenesulfonate in step 1, and 2-iodo-5-(trifluoromethyl)pyrimidine instead of 2-bromo-5-(difluoromethoxy)pyridine in step 3. $^1H$ NMR (400 MHz, DMSO-d6) δ 12.42 (s, 1H), 9.48 (d, J=1.0 Hz, 2H), 8.44 (d, J=7.1 Hz, 1H), 8.03 (d, J=11.4 Hz, 1H), 7.91 (s, 1H), 7.50 (d, J=7.4 Hz, 1H), 6.84 (d, J=7.4 Hz, 1H), 6.37-6.25 (m, 1H), 3.89 (d, J=7.0 Hz, 2H), 3.89-3.79 (m, 1H), 2.04 (dd, J=24.7, 16.4 Hz, 1H), 1.76 (dd, J=30.0, 10.8 Hz, 3H), 1.57 (d, J=12.9 Hz, 1H), 1.33 (dp, J=34.1, 12.2, 11.5 Hz, 3H), 0.94 (t, J=12.0 Hz, 1H). ES/MS m/z: 583.3 $[M+H]^+$.

Example 184: 6-[4-amino-5-(trifluoromethyl)pyrimidin-2-yl]-7-fluoro-2-[[(1R,3S)-3-[[6-oxo-5-(trifluoromethyl)-1H-pyridazin-4-yl]amino]cyclohexyl]methyl]isoquinolin-1-one Example 184

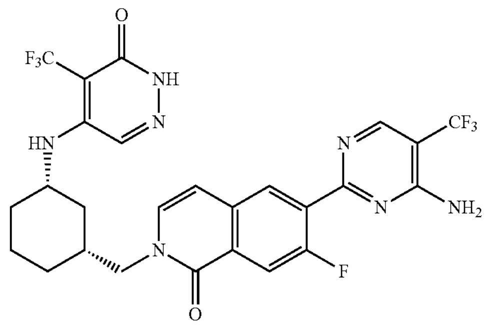

The title compound was synthesized as described in Example 63, using [(1R,3S)-3-(tert-butoxycarbonylamino)cyclohexyl]methyl 4-methylbenzenesulfonate instead of 4-(tert-butoxycarbonylamino)pentyl]4-methylbenzenesulfonate in step 1, and 2-chloro-5-(trifluoromethyl)pyrimidin-4-amine instead of 2-bromo-5-(difluoromethoxy)pyridine in step 3. $^1H$ NMR (400 MHz, DMSO-d6) δ 12.42 (s, 1H), 8.64 (s, 1H), 8.20 (d, J=7.1 Hz, 1H), 8.04-7.84 (m, 2H), 7.47 (d, J=7.4 Hz, 1H), 6.75 (d, J=7.4 Hz, 1H), 6.32 (dd, J=8.5, 3.8 Hz, 1H), 3.88 (d, J=7.0 Hz, 2H), 3.72 (d, J=10.7 Hz, 1H), 2.01 (s, 1H), 1.90-1.64 (m, 3H), 1.56 (d, J=12.7 Hz, 1H), 1.33 (dp, J=34.6, 12.2, 11.8 Hz, 3H), 0.95 (q, J=12.4, 11.9 Hz, 1H). ES/MS m/z: 593.3 $[M+H]^+$.

Intermediate 31: Preparation of 4-(azetidin-1-yl)-2-chloro-5-methoxypyrimidine

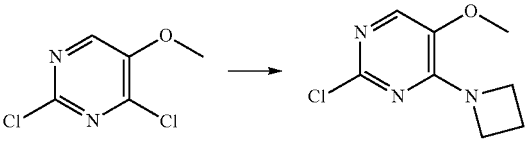

Intermediate 31

N,N-Diisopropylethylamine (1.95 mL, 11.2 mmol) was added to a solution of 2,4-dichloro-5-(trifluoromethyl)pyrimidine (200 mg, 1.12 mmol) and azetidine (64 mg, 1.12 mmol) in DMF (7.8 mL). The resulting solution was stirred at room temperature for 2 hr and then diluted with water and extracted with EtOAc (×2). The combined organic layers were washed with water (×3), then washed with brine, dried over anhydrous magnesium sulfate, and concentrated under reduced pressure afford 4-(azetidin-1-yl)-2-chloro-5-methoxypyrimidine ES/MS: m/z 200.3 $[M+H]^+$.

The following intermediates were synthesized using the procedure as described in Intermediate 12 from the corresponding starting materials.

| Intermediate No. | Structure | LCMS (ESI, m/z): $[M + H]^+$ |
|---|---|---|
| 32 | 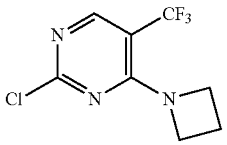 [SMILES: FC(F)(F)c1cnc(Cl)nc1N1CCC1] | 239.6 |
| 33 | 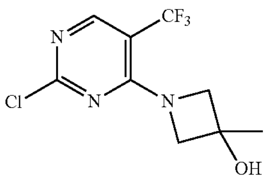 [SMILES: CC1(O)CN(c2nc(Cl)ncc2C(F)(F)F)C1] | 269.8 |
| 34 | 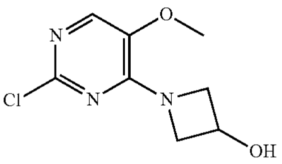 | 215.9 |

-continued

| Intermediate No. | Structure | LCMS (ESI, m/z): $[M + H]^+$ |
|---|---|---|
| 35 | 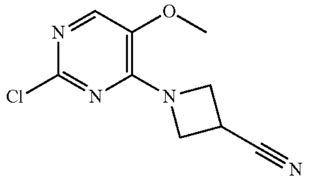 | 224.9 |
| 36 | 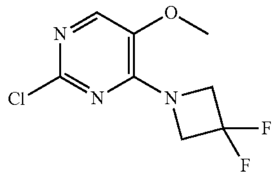 | 236.4 |

Intermediate 37: Preparation of 2-chloro-5-ethoxypyrimidin-4-amine

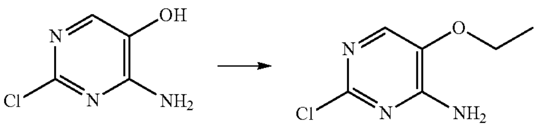

Intermediate 37

Bromoethane (0.580 mL, 0.78 mmol) was added to a solution of 4-amino-2-chloro-pyrimidin-5-ol (104 mg, 0.71 mmol) and potassium carbonate (148 mg, 1.07 mmol) in DMF (1.40 mL). The resulting solution was stirred at room temperature for 16 hr, and then diluted with water and extracted two times with EtOAc. The combined organic layers were washed three time with water, then washed with brine, dried over anhydrous magnesium sulfate, and concentrated under reduced pressure to afford 2-chloro-5-ethoxypyrimidin-4-amine. ES/MS: m/z 175.9 $[M+H]^+$.

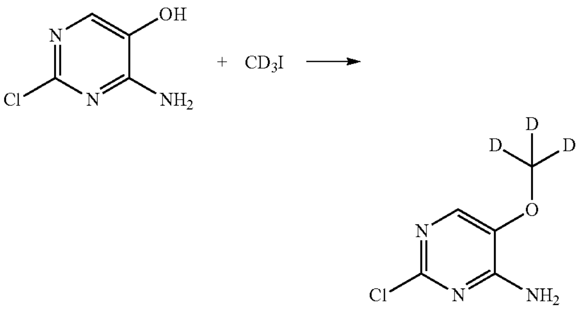

Intermediate 38

4-Amino-2-chloro-pyrimidin-5-ol (250 mg, 1.7 mmol) and potassium carbonate (240 mg, 1.7 mmol) were suspended in DMF (2.0 mL) and stirred at ambient temperature. Iodomethane-d3 (54.0 μl, 0.86 mmol) was added via syringe. After stirring for 1 hour and 45 minutes, the reaction was diluted with water and extracted with EtOAc (×3). The combined organic layers were dried over $Na_2SO_4$, filtered and evaporated. The crude residue was purified via flash chromatography (100% DCM→50% ACN/DCM) to afford 2-chloro-5-(trideuteriomethoxy)pyrimidin-4-amine. ES/MS m/z: 162.9 [M+H]+.

Intermediate 39: 4-[2-Chloro-5-(trifluoromethyl) pyrimidin-4-yl]morpholine

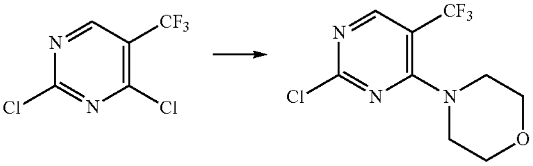

Intermediate 39

2,4-Dichloro-5-(trifluoromethyl)pyrimidine (400 mg, 1.84 mmol), morpholine (0.16 mL, 1.84 mmol), and potassium carbonate (510 mg, 3.69 mmol) were combined in EtOH (18.0 mL) and stirred at ambient temperature overnight. The reaction was poured into water and extracted into DCM (3×). The combined extracts were concentrated and purified by flash chromatography using 3:1 EtOAc/EtOH in heptane as eluent. 4-[2-chloro-5-(trifluoromethyl)pyrimidin-4-yl]morpholine was isolated as the minor regioisomer, ES/MS m/z: 268.1 $[M+H]^+$.

Intermediate 40: 3-Chloro-7,7-difluoro-5,6-dihydro-cyclopenta[c]pyridine

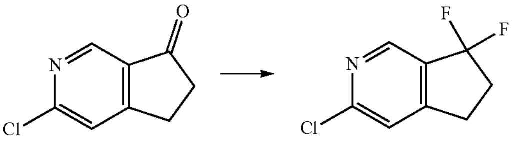

Intermediate 40

3-Chloro-5,6-dihydro-7H-cyclopenta[c]pyridin-7-one (1.0 g, 5.97 mmol) was cooled in an autoclave to −78° C. HF was added, followed by $SF_4$. The autoclave was warmed to 20° C. and the reaction stirred for 14 hours. Cold aqueous NaOH (3M, 20.0 mL) was added, followed by EtOAc (15.0 mL). The organic phase was separated and washed with brine (5.0 mL), dried over $Na_2SO_4$, filtered, and concentrated. Purification by flash chromatography using EtOAc in petroleum ether (0-100%) provided 3-chloro-7,7-difluoro-5,6-dihydrocyclopenta[c]pyridine. ES/MS m/z: 189.9 $[M+H]^+$.

Intermediate 41: Preparation of 2-chloro-N-ethyl-5-methoxy-pyrimidin-4-amine

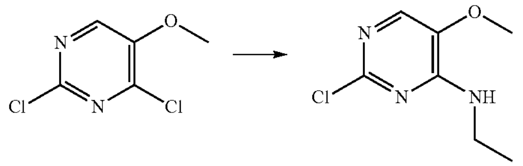

Intermediate 41

N,N-Diisopropylethylamine (0.36 mL, 2.09 mmol) was added to a solution of 2,4-dichloro-5-methoxy-pyrimidine (250 mg, 1.40 mmol) and ethylamine 2.0 M in THF (1.05 mL, 2.09 mmol) in MeOH (0.7 mL) and EtOAc (0.7 mL). The resulting solution was stirred at room temperature for 15 minutes and purified via prep. HPLC. The fractions are basified with sat. NaHCO3 and extracted with DCM. The organic layer is concentrated to afford 119 mg (45%) of 2-chloro-N-ethyl-5-methoxy-pyrimidin-4-amine ES/MS: m/z 189.5 $[M+2+H]^{++}$.

The following intermediates were synthesized using the procedure as described in Intermediate 41 from the corresponding starting materials

| Intermediate No. | Structure | LCMS (ESI, m/z): $[M + H]^+$ |
|---|---|---|
| 42 | 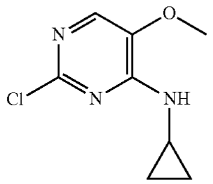 | 201.8 $[M + 2 + H]^{++}$ |
| 43 | 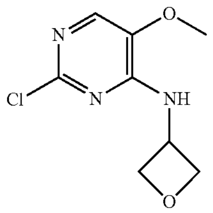 | 217.8 $[M + 2 + H]^{++}$ |

-continued

| Intermediate No. | Structure | LCMS (ESI, m/z): $[M + H]^+$ |
|---|---|---|
| 44 | 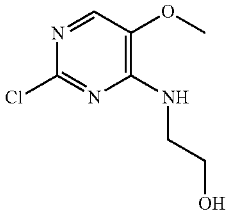 | 205.4 $[M + 2 + H]^{++}$ |
| 45 | 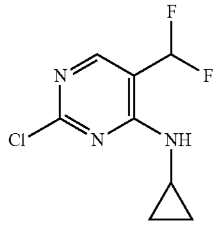 [SMILES: FC(F)c1cnc(Cl)nc1NC1CC1] | 221.7 $[M + 2 + H]^{++}$ |
| 46 | 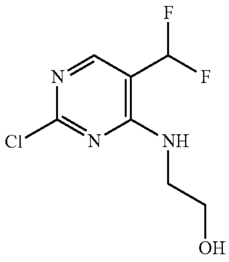 [SMILES: OCCNc1nc(Cl)ncc1C(F)F] | 225.8 $[M + 2 + H]^{++}$ |
| 47 | 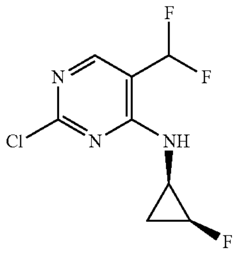 [SMILES: FC(F)c1cnc(Cl)nc1N[C@@H]1C[C@@H]1F] | 239.7 $[M + 2 + H]^{++}$ |

The Following compounds were synthesized using the procedure as described in Example 17, with the following modification: 20 mol % of cataCXium Pd G4 and 2 M aqueous sodium carbonate (1.9 equiv.) were added following the completion of the borylation step.

| Ex. No. | Structure | 1H NMR/MS $[M + H]^+$ |
|---|---|---|
| 185 | 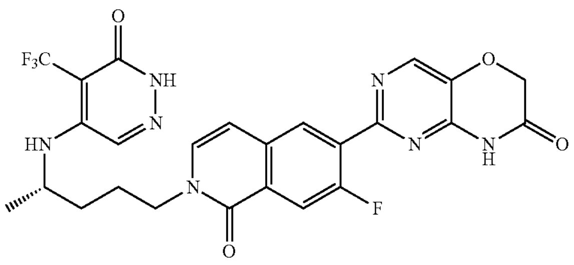 [SMILES: C[C@@H](CCCn1ccc2cc(-c3ncc4c(n3)NC(=O)CO4)c(F)cc2c1=O)Nc1cn[nH]c(=O)c1C(F)(F)F] | 1H NMR (400 MHZ, DMSO-d6) δ 12.44 (s, 1H), 11.89 (s, 1H), 8.48 (s, 1H), 8.17 (d, J = 7.2 Hz, 1H), 8.05-7.90 (m, 2H), 7.49 (d, J = 7.4 Hz, 1H), 6.77 (d, J = 7.4 Hz, 1H), 6.57-6.41 (m, 1H), 5.24-5.13 (m, 1H), 4.83 (s, 2H), 4.03-3.95 (m, 2H), 1.84-1.58 (m, 3H), 1.60-1.39 (m, 1H), 1.28-1.05 (m, 3H). ES/MS m/z: 560.2 $[M + H]^+$. |

-continued

| Ex. No. | Structure | 1H NMR/MS [M + H]+ |
|---|---|---|
| 186 | 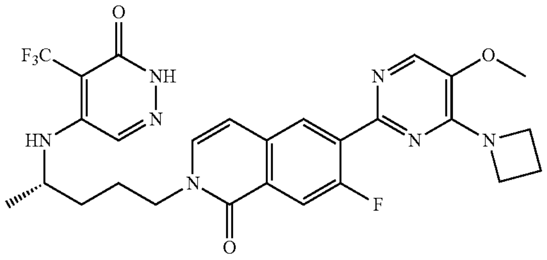 [SMILES: COc1cnc(-c2cc3ccn(CCC[C@H](C)Nc4cn[nH]c(=O)c4C(F)(F)F)c(=O)c3cc2F)nc1N1CCC1] | 1H NMR (400 MHZ, DMSO-d6) δ 12.44 (s, 1H), 8.15 (d, J = 7.0 Hz, 1H), 8.03-7.94 (m, 2H), 7.92 (s, 1H), 7.51 (d, J = 7.4 Hz, 1H), 6.77 (d, J = 7.4 Hz, 1H), 6.40-6.29 (m, 1H), 4.37 (s, 4H), 4.00-3.96 (m, 3H), 3.87 (s, 3H), 2.44-2.31 (m, 2H), 1.78-1.61 (m, 3H), 1.56-1.44 (m, 1H), 1.17 (d, J = 6.3 Hz, 3H). ES/MS m/z: 574 [M + H]+. |
| 187 | 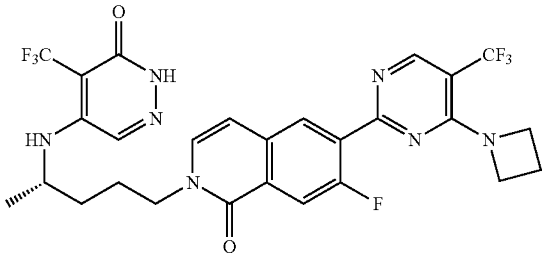 [SMILES: C[C@@H](CCCn1ccc2cc(-c3ncc(C(F)(F)F)c(N4CCC4)n3)c(F)cc2c1=O)Nc1cn[nH]c(=O)c1C(F)(F)F] | 1H NMR (400 MHZ, DMSO-d6) δ 12.44 (s, 1H), 8.68 (s, 1H), 8.30 (d, J = 7.1 Hz, 1H), 7.96 (d, J = 11.3 Hz, 1H), 7.92 (s, 1H), 7.50 (d, J = 7.4 Hz, 1H), 6.79 (d, J = 7.4 Hz, 1H), 6.41-6.25 (m, 1H), 4.36-4.24 (m, 4H), 4.05-3.89 (m, 3H), 2.45-2.29 (m, 2H), 1.80-1.59 (m, 3H), 1.56-1.41 (m, 1H), 1.21-1.12 (m, 3H). ES/MS m/z: 612.0 [M + H]+. |
| 188 | 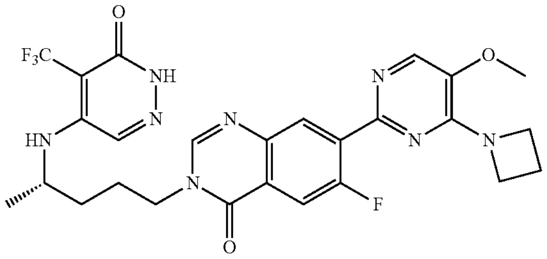 [SMILES: COc1cnc(-c2cc3ncn(CCC[C@H](C)Nc4cn[nH]c(=O)c4C(F)(F)F)c(=O)c3cc2F)nc1N1CCC1] | 1H NMR (400 MHZ, DMSO-d6) δ 12.44 (s, 1H), 8.43 (s, 1H), 8.13 (d, J = 6.7 Hz, 1H), 8.01 (s, 1H), 7.97-7.89 (m, 2H), 6.39-6.29 (m, 1H), 4.39-4.31 (m, 4H), 4.06-3.95 (m, 3H), 3.87 (s, 3H), 2.42-2.31 (m, 2H), 1.81-1.60 (m, 3H), 1.59-1.44 (m, 1H), 1.17 (d, J = 6.3 Hz, 3H). ES/MS m/z: 575.2 [M + H]+. |
| 189 | 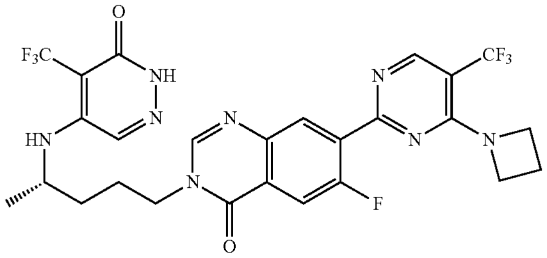 | 1H NMR (400 MHZ, DMSO-d6) δ 12.44 (s, 1H), 8.70 (s, 1H), 8.43 (s, 1H), 8.25 (d, J = 6.7 Hz, 1H), 7.96-7.88 (m, 2H), 6.39-6.27 (m, 1H), 4.36-4.24 (m, 4H), 4.06-3.93 (m, 3H), 2.45-2.32 (m, 2H), 1.81-1.60 (m, 3H), 1.59-1.46 (m, 1H), 1.17 (d, J = 6.3 Hz, 3H). ES/MS m/z: 613.2 [M + H]+. |
| 190 | 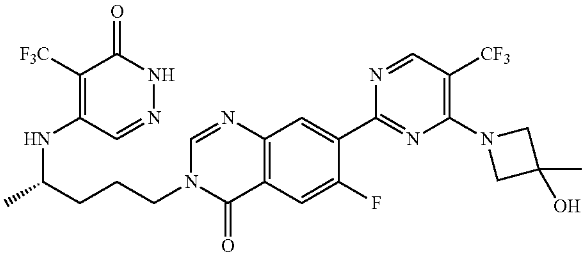 [SMILES: C[C@@H](CCCn1cnc2cc(-c3ncc(C(F)(F)F)c(N4CC(C)(O)C4)n3)c(F)cc2c1=O)Nc1cn[nH]c(=O)c1C(F)(F)F] | 1H NMR (400 MHZ, DMSO-d6) δ 12.44 (s, 1H), 8.73 (s, 1H), 8.44 (s, 1H), 8.26 (d, J = 6.7 Hz, 1H), 7.97-7.88 (m, 2H), 6.43-6.24 (m, 1H), 5.76 (s, 1H), 4.21-4.07 (m, 4H), 4.06-3.91 (m, 3H), 1.83-1.62 (m, 3H), 1.60-1.48 (m, 1H), 1.46 (s, 3H), 1.17 (d, J = 6.2 Hz, 3H). ES/MS m/z: 643.0 [M + H]+. |
| 191 | 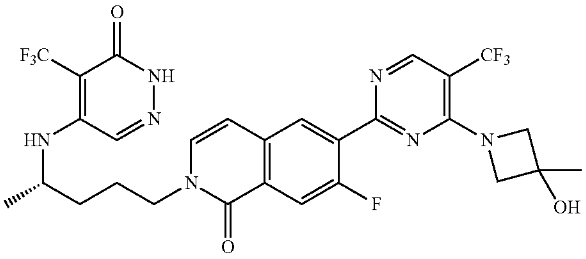 [SMILES: C[C@@H](CCCn1ccc2cc(-c3ncc(C(F)(F)F)c(N4CC(C)(O)C4)n3)c(F)cc2c1=O)Nc1cn[nH]c(=O)c1C(F)(F)F] | 1H NMR (400 MHZ, DMSO-d6) δ 12.44 (s, 1H), 8.71 (s, 1H), 8.33 (d, J = 7.1 Hz, 1H), 8.12-7.83 (m, 2H), 7.50 (d, J = 7.4 Hz, 1H), 6.80 (d, J = 7.4 Hz, 1H), 6.45-6.11 (m, 1H), 5.76 (s, 1H), 4.16-4.11 (m, 4H), 4.04-4.01 (m, 3H), 1.99 (s, 3H), 1.79-1.61 (m, 3H), 1.53-1.48 (m, 1H), 1.18 (d, 3H). ES/MS m/z: 542.2 [M + H]+. |

-continued

| Ex. No. | Structure | 1H NMR/MS [M + H]$^+$ |
|---|---|---|
| 192 | 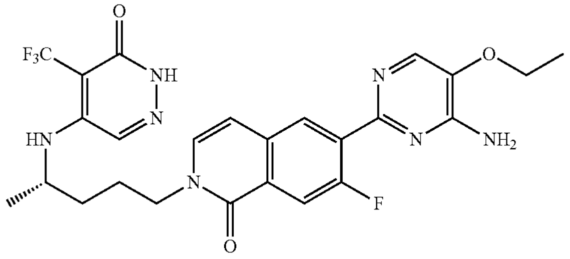 [SMILES: CCOc1cnc(-c2cc3ccn(CCC[C@H](C)Nc4cn[nH]c(=O)c4C(F)(F)F)c(=O)c3cc2F)nc1N] | 1H NMR (400 MHZ, DMSO-d6) δ 12.44 (s, 1H), 8.12 (d, J = 7.0 Hz, 1H), 8.06 (s, 1H), 8.01 (d, J = 11.0 Hz, 1H), 7.92 (s, 1H), 7.52 (d, J = 7.4 Hz, 1H), 6.77 (d, J = 7.4 Hz, 1H), 6.35 (dd, J = 8.5, 3.9 Hz, 1H), 4.22 (d, J = 7.0 Hz, 2H), 4.00 (d, J = 6.2 Hz, 3H), 1.82-1.60 (m, 3H), 1.59-1.44 (m, 1H), 1.41 (t, J = 6.9 Hz, 3H), 1.17 (d, J = 6.3 Hz, 3H). ES/MS m/z: 548.2 [M + H]$^+$. |
| 193 | 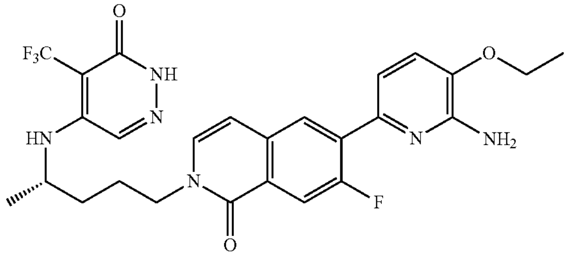 [SMILES: CCOc1ccc(-c2cc3ccn(CCC[C@H](C)Nc4cn[nH]c(=O)c4C(F)(F)F)c(=O)c3cc2F)nc1N] | 1H NMR (400 MHZ, DMSO-d6) δ 12.44 (s, 1H), 8.07 (d, J = 7.3 Hz, 1H), 7.97 (d, J = 11.5 Hz, 1H), 7.91 (s, 1H), 7.50 (d, J = 7.4 Hz, 1H), 7.37 (d, J = 8.2 Hz, 1H), 7.15-7.06 (m, 1H), 6.71 (d, J = 7.4 Hz, 1H), 6.40-6.29 (m, 1H), 4.20 (t, J = 6.9 Hz, 2H), 3.99 (t, J = 6.6 Hz, 3H), 1.81-1.59 (m, 3H), 1.58-1.45 (m, 1H), 1.41 (t, J = 6.9 Hz, 3H), 1.17 (d, J = 6.3 Hz, 3H). ES/MS m/z: 547.2 [M + H]$^+$. |
| 194 | 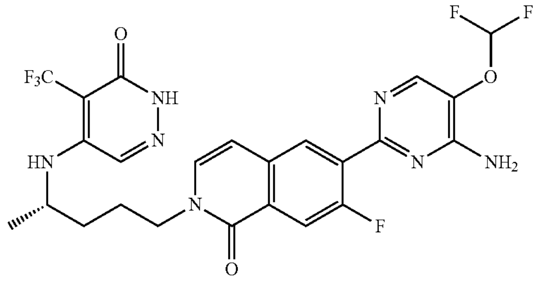 [SMILES: C[C@@H](CCCn1ccc2cc(-c3ncc(OC(F)F)c(N)n3)c(F)cc2c1=O)Nc1cn[nH]c(=O)c1C(F)(F)F] | 1H NMR (400 MHZ, DMSO-d6) δ 12.44 (s, 1H), 8.24 (s, 1H), 8.12 (d, J = 7.1 Hz, 1H), 7.96-7.91 (m, 2H), 7.55 (s, 2H), 7.49 (d, J = 7.4 Hz, 1H), 7.21 (t, J = 73.1 Hz, 1H), 6.75 (d, J = 7.4 Hz, 1H), 6.40-6.31 (m, 1H), 4.05-3.91 (m, 3H), 1.79-1.60 (m, 3H), 1.57-1.43 (m, 1H), 1.17 (d, J = 6.3 Hz, 3H). ES/MS m/z: 570.3 [M + H]$^+$. |
| 195 | 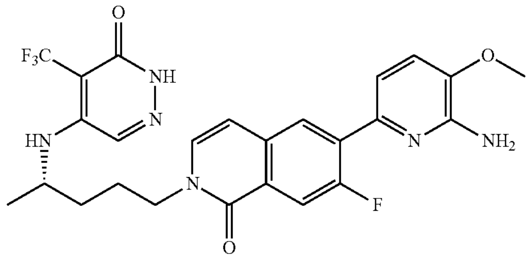 [SMILES: COc1ccc(-c2cc3ccn(CCC[C@H](C)Nc4cn[nH]c(=O)c4C(F)(F)F)c(=O)c3cc2F)nc1N] | 1H NMR (400 MHZ, DMSO-d6) δ 12.43 (s, 1H), 8.10 (d, J = 7.2 Hz, 1H), 7.93 (d, J = 16.5 Hz, 2H), 7.47 (d, J = 7.3 Hz, 1H), 7.27 (s, 1H), 7.16-7.09 (m, 1H), 6.71 (d, J = 7.4 Hz, 1H), 6.35 (d, J = 5.0 Hz, 1H), 3.98 (t, J = 6.7 Hz, 3H), 3.89 (s, 3H), 1.80-1.41 (m, 5H), 1.17 (d, J = 6.3 Hz, 3H). ES/MS m/z: 533.3 [M + H]. |
| 196 | 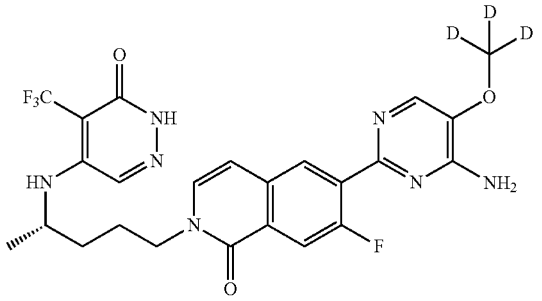 [SMILES: [2H]C([2H])([2H])Oc1cnc(-c2cc3ccn(CCC[C@H](C)Nc4cn[nH]c(=O)c4C(F)(F)F)c(=O)c3cc2F)nc1N] | 1H NMR (400 MHZ, DMSO-d6) δ 12.44 (s, 1H), 8.11 (d, J = 7.0 Hz, 1H), 8.05 (s, 1H), 7.98 (d, J = 11.0 Hz, 1H), 7.92 (s, 1H), 7.51 (d, J = 7.4 Hz, 1H), 6.77 (d, J = 7.3 Hz, 1H), 6.39-6.31 (m, 1H), 4.04-3.92 (m, 3H), 1.79-1.61 (m, 3H), 1.56-1.46 (m, 1H), 1.17 (d, J = 6.3 Hz, 3H). ES/MS m/z: 537.3 [M + H]. |

-continued

| Ex. No. | Structure | 1H NMR/MS [M + H]$^+$ |
|---|---|---|
| 197 | 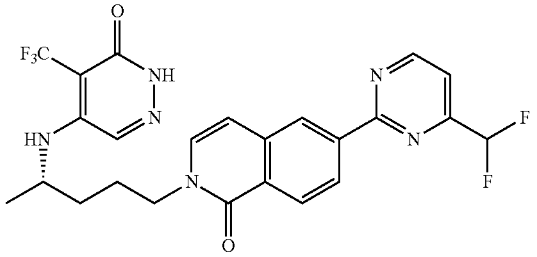 | 1H NMR (400 MHZ, DMSO-d6) δ 12.43 (s, 1H), 9.26 (d, J = 5.0 Hz, 1H), 8.36 (d, J = 7.2 Hz, 1H), 8.02 (d, J = 11.3 Hz, 1H), 8.00-7.78 (m, 2H), 7.52 (d, J = 7.4 Hz, 1H), 7.11 (t, J = 54.0 Hz, 1H), 6.84 (d, J = 7.3 Hz, 1H), 6.36 (dd, J = 8.8, 3.7 Hz, 1H), 4.00 (t, J = 6.4 Hz, 3H), 1.70 (ddt, J = 21.3, 13.9, 6.8 Hz, 3H), 1.51 (dq, J = 12.9, 6.7, 6.3 Hz, 1H), 1.17 (d, J = 6.3 Hz, 3H). ES/MS m/z: 539.3 [M + H]$^+$. |
| 198 | 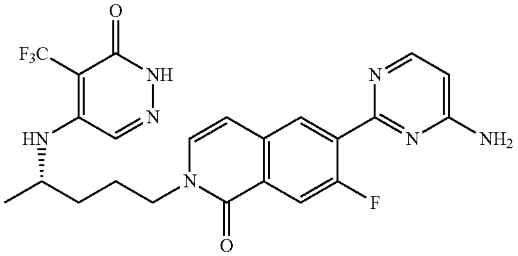 [SMILES: C[C@@H](CCCn1ccc2cc(-c3nccc(N)n3)c(F)cc2c1=O)Nc1cn[nH]c(=O)c1C(F)(F)F] | 1H NMR (400 MHz, DMSO-d6) δ 12.44 (s, 1H), 8.29 (d, J = 6.6 Hz, 1H), 8.16 (d, J = 7.0 Hz, 2H), 8.01 (d, J = 11.0 Hz, 1H), 7.91 (s, 1H), 7.53 (d, J = 7.4 Hz, 1H), 6.78 (d, J = 7.4 Hz, 1H), 6.63 (d, J = 6.5 Hz, 1H), 6.48-6.26 (m, 1H), 4.09-3.90 (m, 2H), 3.94-3.61 (m, 1H), 1.68 (ddd, J = 29.3, 14.1, 7.5 Hz, 3H), 1.51 (q, J = 7.4, 6.4 Hz, 1H), 1.17 (d, J = 6.3 Hz, 3H). ES/MS m/z: 504.3 [M + H]$^+$. |
| 199 | 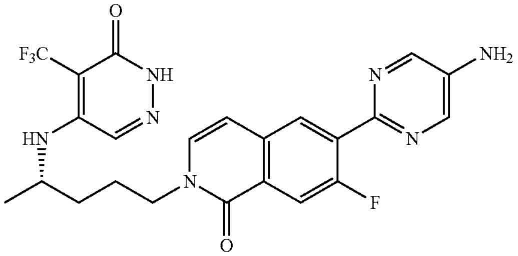 [SMILES: C[C@@H](CCCn1ccc2cc(-c3ncc(N)cn3)c(F)cc2c1=O)Nc1cn[nH]c(=O)c1C(F)(F)F] | 1H NMR (400 MHZ, DMSO-d6) δ 12.43 (s, 1H), 8.27 (s, 2H), 8.21 (d, J = 7.4 Hz, 1H), 8.01-7.77 (m, 2H), 7.45 (d, J = 7.4 Hz, 1H), 6.75 (d, J = 7.4 Hz, 1H), 6.49-6.20 (m, 1H), 3.97 (d, J = 9.0 Hz, 4H), 1.85-1.61 (m, 3H), 1.50 (q, J = 6.9, 6.2 Hz, 1H), 1.17 (d, J = 6.3 Hz, 3H). ES/MS m/z: 504.3 [M + H]$^+$. |
| 200 | 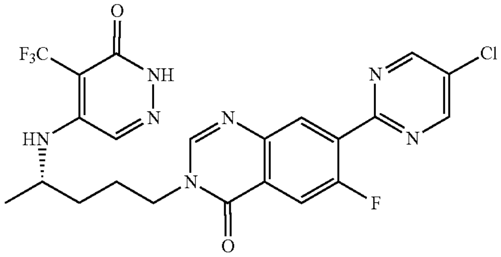 [SMILES: C[C@@H](CCCn1cnc2cc(-c3ncc(Cl)cn3)c(F)cc2c1=O)Nc1cn[nH]c(=O)c1C(F)(F)F] | 1H NMR (400 MHZ, DMSO-d6) δ 12.44 (s, 1H), 9.16 (s, 2H), 8.44 (s, 1H), 8.28 (d, J = 6.8 Hz, 1H), 7.97 (d, J = 10.5 Hz, 1H), 7.92 (s, 1H), 6.39-6.31 (m, 1H), 4.05-3.85 (m, 3H), 1.82-1.61 (m, 3H), 1.58-1.46 (m, 1H), 1.17 (d, J = 6.3 Hz, 3H). ES/MS m/z: 524.3 [M + H]$^+$. |
| 201 | 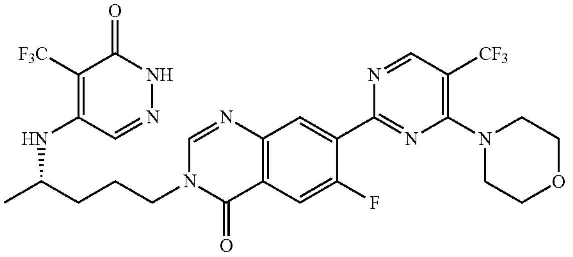 [SMILES: C[C@@H](CCCn1cnc2cc(-c3ncc(C(F)(F)F)c(N4CCOCC4)n3)c(F)cc2c1=O)Nc1cn[nH]c(=O)c1C(F)(F)F] | 1H NMR (400 MHZ, DMSO-d6) δ 12.44 (s, 1H), 8.89 (s, 1H), 8.45 (s, 1H), 8.34 (d, J = 6.8 Hz, 1H), 7.95 (d, J = 10.6 Hz, 1H), 7.92 (s, 1H), 6.39-6.30 (m, 1H), 4.06-3.94 (m, 3H), 3.74 (s, 8H), 1.84-1.61 (m, 3H), 1.58-1.48 (m, 1H), 1.17 (d, J = 6.3 Hz, 3H). ES/MS m/z: 643.4 [M + H]$^+$. |
| 202 | 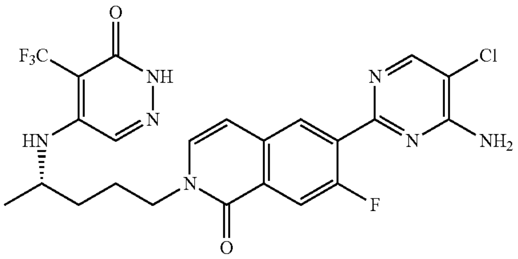 [SMILES: C[C@@H](CCCn1ccc2cc(-c3ncc(Cl)c(N)n3)c(F)cc2c1=O)Nc1cn[nH]c(=O)c1C(F)(F)F] | 1H NMR (400 MHZ, DMSO-d6) δ 12.44 (s, 1H), 8.44 (s, 1H), 8.15 (d, J = 7.1 Hz, 1H), 7.98-7.89 (m, 2H), 7.87-7.30 (m, 3H), 7.49 (d, J = 7.4 Hz, 1H), 6.76 (d, J = 7.4 Hz, 1H), 6.40-6.31 (m, 1H), 4.03-3.86 (m, 3H), 1.79-1.59 (m, 3H), 1.58-1.46 (m, 1H), 1.17 (d, J = 6.3 Hz, 3H). ES/MS m/z: 538.3 [M + H]$^+$. |

-continued

| Ex. No. | Structure | 1H NMR/MS [M + H]+ |
|---|---|---|
| 203 | 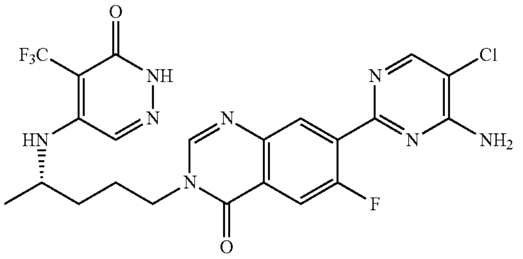 | 1H NMR (400 MHZ, DMSO-d6) δ 12.44 (s, 1H), 8.44 (s, 1H), 8.42 (s, 1H), 8.14 (d, J = 6.8 Hz, 1H), 7.95 (s, 2H), 7.92 (s, 1H), 7.90 (d, J = 10.4 Hz, 1H), 6.39-6.30 (m, 1H), 4.04-3.92 (m, 3H), 1.83-1.61 (m, 3H), 1.60-1.47 (m, 1H), 1.17 (d, J = 6.3 Hz, 3H). ES/MS m/z: 539.2 [M + H]+. |
| 204 | 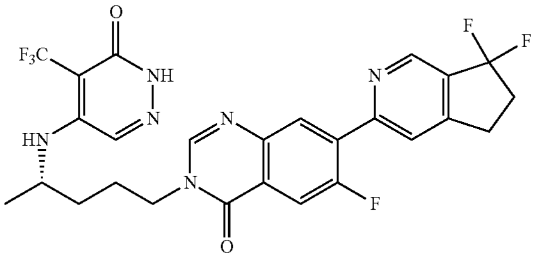 [SMILES: C[C@@H](CCCn1cnc2cc(-c3cc4c(cn3)C(F)(F)CC4)c(F)cc2c1=O)Nc1cn[nH]c(=O)c1C(F)(F)F] | 1H NMR (400 MHZ, DMSO-d6) δ 12.44 (s, 1H), 9.04-8.98 (m, 1H), 8.44 (s, 1H), 8.18 (d, J = 6.9 Hz, 1H), 7.98 (d, J = 10.8 Hz, 1H), 7.98 (s, 1H), 7.92 (s, 1H), 6.39-6.30 (m, 1H), 4.06-3.92 (m, 3H), 3.25-3.15 (m, 2H), 2.79-2.63 (m, 2H), 1.84-1.61 (m, 3H), 1.58-1.46 (m, 1H), 1.17 (d, J = 6.3 Hz, 3H). ES/MS m/z: 565.3 [M + H]+. |
| 205 | 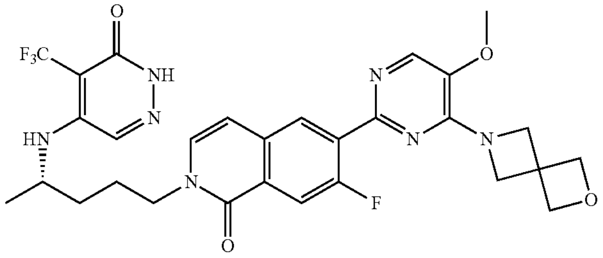 [SMILES: COc1cnc(-c2cc3ccn(CCC[C@H](C)Nc4cn[nH]c(=O)c4C(F)(F)F)c(=O)c3cc2F)nc1N1CC2(COC2)C1] | 1H NMR (400 MHZ, DMSO-d6) δ 12.44 (s, 1H), 8.15 (d, J = 7.0 Hz, 1H), 8.03 (s, 1H), 7.99 (d, J = 11.1 Hz, 1H), 7.92 (s, 1H), 7.51 (d, J = 7.4 Hz, 1H), 6.77 (d, J = 7.4 Hz, 1H), 6.40-6.31 (m, 1H), 4.73 (s, 4H), 4.53 (s, 4H), 4.03-3.95 (m, 3H), 3.88 (s, 3H), 1.78-1.59 (m, 3H), 1.56-1.45 (m, 1H), 1.17 (d, J = 6.3 Hz, 3H). ES/MS m/z: 616.4 [M + H]+. |
| 206 | 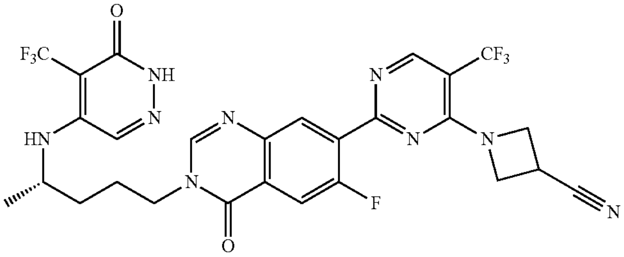 [SMILES: C[C@@H](CCCn1cnc2cc(-c3ncc(C(F)(F)F)c(N4CC(C#N)C4)n3)c(F)cc2c1=O)Nc1cn[nH]c(=O)c1C(F)(F)F] | 1H NMR (400 MHZ, DMSO-d6) δ 12.44 (s, 1H), 8.80 (s, 1H), 8.44 (s, 1H), 8.28 (d, J = 6.7 Hz, 1H), 7.95 (d, J = 10.5 Hz, 1H), 7.92 (s, 1H), 6.39-6.27 (m, 1H), 4.62-4.52 (m, 2H), 4.49-4.40 (m, 2H), 4.03-3.97 (m, 4H), 1.79-1.61 (m, 3H), 1.58-1.45 (m, 1H), 1.17 (d, J = 6.3 Hz, 3H). ES/MS: m/z 638.3 [M + H]+. |
| 207 | 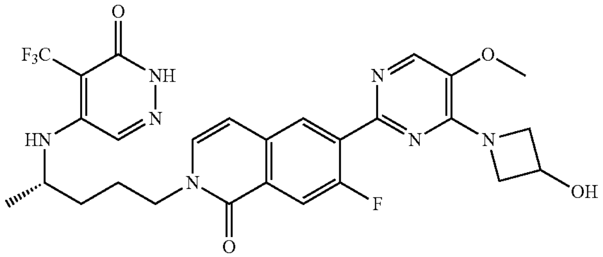 [SMILES: COc1cnc(-c2cc3ccn(CCC[C@H](C)Nc4cn[nH]c(=O)c4C(F)(F)F)c(=O)c3cc2F)nc1N1CC(O)C1] | 1H NMR (400 MHZ, DMSO-d6) δ 12.44 (s, 1H), 8.16 (d, J = 7.1 Hz, 1H), 8.02 (s, 1H), 7.99 (d, J = 11.1 Hz, 1H), 7.92 (s, 1H), 7.51 (d, J = 7.4 Hz, 1H), 6.78 (d, J = 7.4 Hz, 1H), 6.40-6.27 (m, 1H), 4.62-4.54 (m, 3H), 4.11-4.06 (m, 2H), 4.01-3.96 (m, 4H), 3.88 (s, 3H), 1.79-1.59 (m, 3H), 1.55-1.43 (m, 1H), 1.17 (d, J = 6.3 Hz, 3H). ES/MS: m/z 590.4 [M + H]+. |

-continued

| Ex. No. | Structure | 1H NMR/MS [M + H]+ |
|---|---|---|
| 208 | 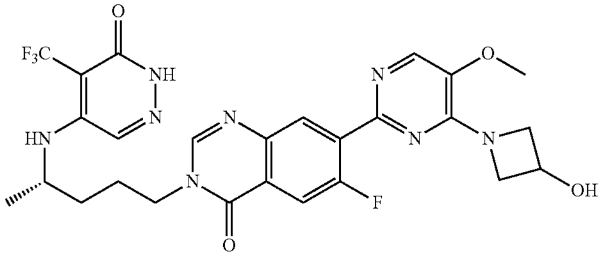 [SMILES: COc1cnc(-c2cc3ncn(CCC[C@H](C)Nc4cn[nH]c(=O)c4C(F)(F)F)c(=O)c3cc2F)nc1N1CC(O)C1] | 1H NMR (400 MHZ, DMSO-d6) δ 12.44 (s, 1H), 8.43 (s, 1H), 8.14 (d, J = 6.7 Hz, 1H), 8.03 (s, 1H), 7.96-7.89 (m, 2H), 6.39-6.29 (m, 1H), 4.61-4.51 (m, 4H), 4.10-4.04 (m, 2H), 4.03-3.96 (m, 3H), 3.88 (s, 3H), 1.82-1.59 (m, 3H), 1.59-1.46 (m, 1H), 1.17 (d, J = 6.3 Hz, 3H). ES/MS: m/z 591.3 [M + H]+. |
| 209 | 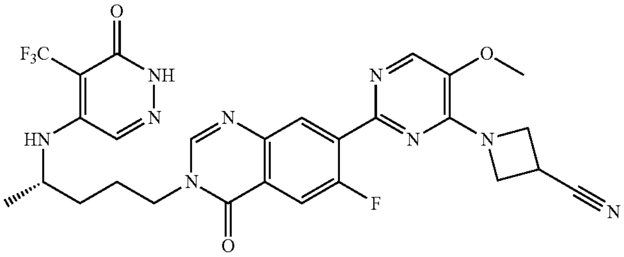 [SMILES: COc1cnc(-c2cc3ncn(CCC[C@H](C)Nc4cn[nH]c(=O)c4C(F)(F)F)c(=O)c3cc2F)nc1N1CC(C#N)C1] | 1H NMR (400 MHZ, DMSO-d6) δ 12.44 (s, 1H), 8.42 (s, 1H), 8.19-8.12 (m, 2H), 7.95-7.87 (m, 2H), 6.39-6.31 (m, 1H), 4.60-4.52 (m, 2H), 4.46-4.40 (m, 2H), 4.04-3.91 (m, 4H), 3.89 (s, 3H), 1.81-1.61 (m, 3H), 1.59-1.44 (m, 1H), 1.17 (d, J= 6.3 Hz, 3H). ES/MS: m/z 600.3 [M + H]+. |
| 210 | 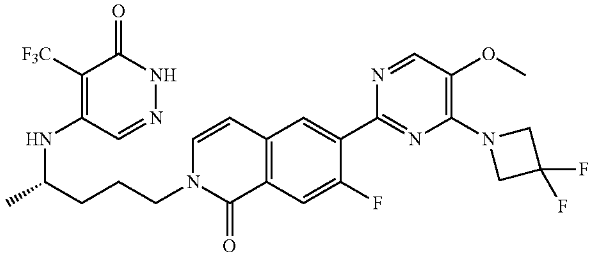 [SMILES: COc1cnc(-c2cc3ccn(CCC[C@H](C)Nc4cn[nH]c(=O)c4C(F)(F)F)c(=O)c3cc2F)nc1N1CC(F)(F)C1] | 1H NMR (400 MHZ, DMSO-d6) δ 12.44 (s, 1H), 8.26-8.16 (m, 2H), 7.98-7.88 (m, 2H), 7.49 (d, J= 7.4 Hz, 1H), 6.76 (d, J = 7.4 Hz, 1H), 6.39-6.27 (m, 1H), 4.68 (t, J = 12.5 Hz, 4H), 4.04-3.92 (m, 3H), 3.90 (s, 3H), 1.79-1.58 (m, 3H), 1.56-1.44 (m, 1H), 1.17 (d, J = 6.3 Hz, 3H). ES/MS: m/z 610.3 [M + H]+. |
| 211 | 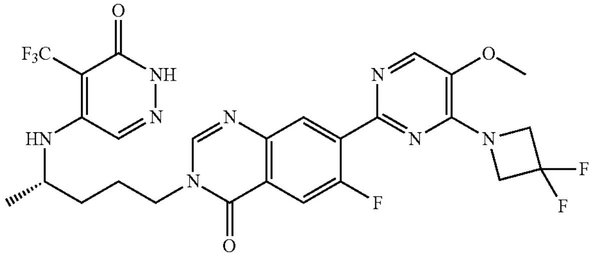 [SMILES: COc1cnc(-c2cc3ncn(CCC[C@H](C)Nc4cn[nH]c(=O)c4C(F)(F)F)c(=O)c3cc2F)nc1N1CC(F)(F)C1] | 1H NMR (400 MHZ, DMSO-d6) δ 12.44 (s, 1H), 8.42 (s, 1H), 8.22 (s, 1H), 8.19 (d, J = 6.8 Hz, 1H), 7.94-7.86 (m, 2H), 6.41-6.25 (m, 1H), 4.68 (t, J = 12.5 Hz, 4H), 4.06-3.94 (m, 3H), 3.91 (s, 3H), 1.81-1.60 (m, 3H), 1.58-1.46 (m, 1H), 1.17 (d, J = 6.3 Hz, 3H). ES/MS: m/z 611.3 [M + H]+. |
| 212 | 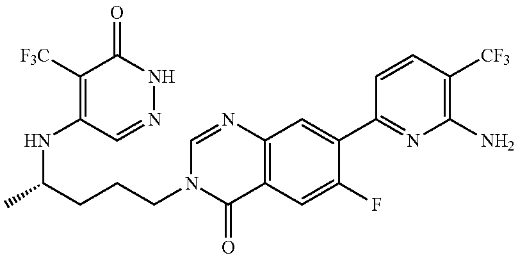 | 1H NMR (400 MHZ, DMSO-d6) δ 12.44 (s, 1H), 8.43 (s, 1H), 8.21 (d, J = 6.9 Hz, 1H), 7.94 (d, J = 5.0 Hz, 1H), 7.93-7.88 (m, 2H), 7.18 (dd, J = 7.8, 2.0 Hz, 1H), 6.71 (s, 2H), 6.39-6.30 (m, 1H), 4.03-3.94 (m, 3H), 1.81-1.60 (m, 3H), 1.58-1.45 (m, 1H), 1.17 (d, J = 6.3 Hz, 3H). ES/MS: m/z 572.3 [M + H]+. |
| 213 | 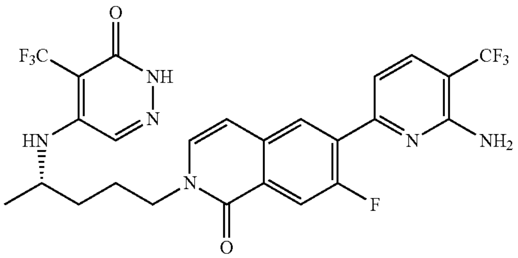 | 1H NMR (400 MHZ, DMSO-d6) δ 12.43 (s, 1H), 8.15 (dd, J = 7.3, 2.2 Hz, 1H), 8.04-7.84 (m, 3H), 7.50 (dd, J = 7.4, 4.7 Hz, 1H), 7.13 (dd, J = 7.8, 2.1 Hz, 1H), 6.83-6.56 (m, 4H), 6.35 (dt, J = 7.5, 3.8 Hz, 1H), 4.06-3.91 (m, 4H), 1.84-1.39 (m, 4H), 1.20 (dd, J = 22.0, 6.4 Hz, 4H). ES/MS: m/z 571.3. |

-continued

| Ex. No. | Structure | 1H NMR/MS [M + H]$^+$ |
|---|---|---|
| 214 | 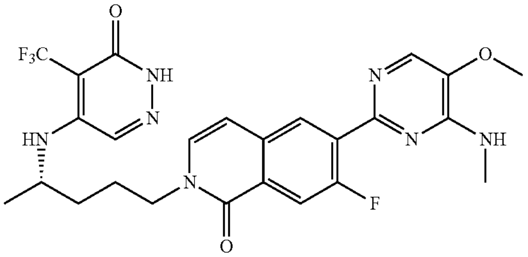 [SMILES: CNc1nc(-c2cc3ccn(CCC[C@H](C)Nc4cn[nH]c(=O)c4C(F)(F)F)c(=O)c3cc2F)ncc1OC] | 1H NMR (400 MHZ, DMSO-d6) δ 12.44 (s, 1H), 8.32 (s, 1H), 8.23 (d, J = 7.0 Hz, 1H), 8.05-7.97 (m, 2H), 7.92 (s, 1H), 7.53 (d, J = 7.4 Hz, 1H), 6.79 (d, J = 7.4 Hz, 1H), 6.35 (dd, J = 8.6, 3.9 Hz, 1H), 3.97 (s, 5H), 3.01 (d, J = 4.5 Hz, 3H), 1.70 (dp, J = 23.9, 9.1, 7.7 Hz, 3H), 1.50 (td, J = 12.7, 11.9, 6.1 Hz, 1H), 1.17 (d, J = 6.3 Hz, 3H). ES/MS: m/z 548.3. |
| 215 | 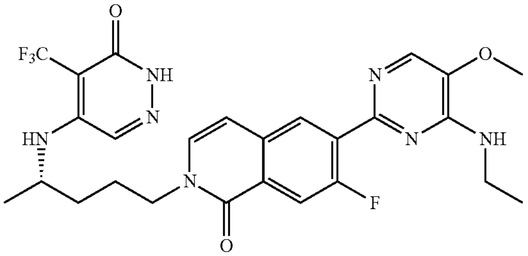 [SMILES: CCNc1nc(-c2cc3ccn(CCC[C@H](C)Nc4cn[nH]c(=O)c4C(F)(F)F)c(=O)c3cc2F)ncc1OC] | 1H NMR (400 MHZ, DMSO-d6) δ 12.44 (s, 1H), 8.52 (s, 1H), 8.20 (d, J = 7.0 Hz, 1H), 8.11-7.98 (m, 2H), 7.92 (s, 1H), 7.53 (d, J = 7.4 Hz, 1H), 6.80 (d, J = 7.4 Hz, 1H), 6.35 (dd, J = 8.9, 3.6 Hz, 1H), 4.01 (d, J = 6.5 Hz, 2H), 3.63-3.43 (m, 2H), 1.83-1.57 (m, 3H), 1.51 (dt, J = 11.9, 6.1 Hz, 1H), 1.24-1.11 (m, 6H). ES/MS: m/z 562.3. |
| 216 | 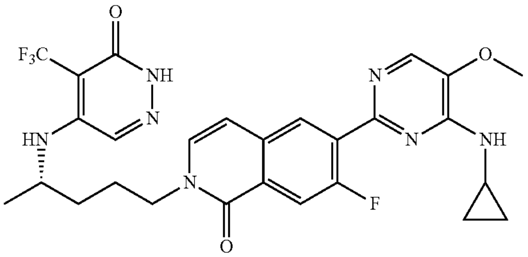 [SMILES: COc1cnc(-c2cc3ccn(CCC[C@H](C)Nc4cn[nH]c(=O)c4C(F)(F)F)c(=O)c3cc2F)nc1NC1CC1] | 1H NMR (400 MHZ, DMSO-d6) δ 12.44 (s, 1H), 8.23 (d, J = 7.1 Hz, 1H), 8.08-7.97 (m, 2H), 7.92 (s, 1H), 7.52 (d, J = 7.4 Hz, 1H), 6.79 (d, J = 7.4 Hz, 1H), 6.35 (dd, J = 8.5, 3.7 Hz, 1H), 3.99 (t, J = 6.5 Hz, 2H), 3.24-3.04 (m, 1H), 1.69 (ddp, J = 22.5, 15.5, 8.0, 7.3 Hz, 3H), 1.50 (dq, J = 13.0, 6.0 Hz, 1H), 1.17 (d, J = 6.3 Hz, 3H), 0.75 (ddt, J = 25.0, 7.9, 3.8 Hz, 4H). ES/MS: m/z 574.3. |
| 217 | 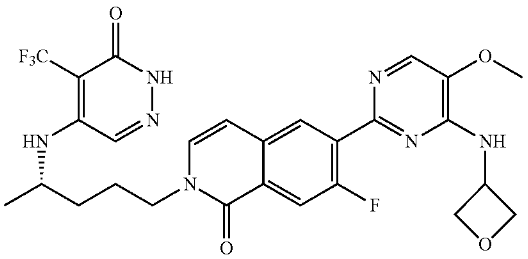 [SMILES: COc1cnc(-c2cc3ccn(CCC[C@H](C)Nc4cn[nH]c(=O)c4C(F)(F)F)c(=O)c3cc2F)nc1NC1COC1] | 1H NMR (400 MHZ, DMSO-d6) δ 12.44 (s, 1H), 8.45 (s, 1H), 8.20 (d, J = 7.2 Hz, 1H), 8.08 (s, 1H), 8.00-7.86 (m, 2H), 7.50 (d, J = 7.3 Hz, 1H), 6.79 (d, J = 7.4 Hz, 1H), 6.35 (dd, J = 8.8, 3.8 Hz, 1H), 5.12 (p, J = 6.7 Hz, 1H), 4.80 (t, J = 6.8 Hz, 2H), 4.68 (t, J = 6.5 Hz, 2H), 4.00 (s, 2H), 1.68 (ddt, J = 30.3, 15.7, 7.9 Hz, 3H), 1.50 (dt, J = 11.3, 6.1 Hz, 1H), 1.17 (d, J = 6.3 Hz, 3H). ES/MS: m/z 590.3. |
| 218 | 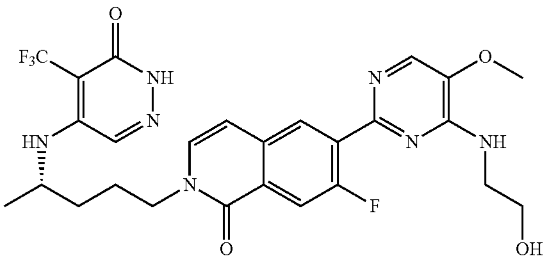 [SMILES: COc1cnc(-c2cc3ccn(CCC[C@H](C)Nc4cn[nH]c(=O)c4C(F)(F)F)c(=O)c3cc2F)nc1NCCO] | 1H NMR (400 MHZ, DMSO-d6) δ 12.43 (s, 1H), 8.19 (d, J = 7.0 Hz, 1H), 8.00 (d, J = 12.0 Hz, 2H), 7.92 (s, 1H), 7.52 (d, J = 7.3 Hz, 1H), 6.78 (d, J = 7.4 Hz, 1H), 6.35 (dd, J = 8.7, 3.8 Hz, 1H), 3.98 (d, J= 8.6 Hz, 7H), 3.59 (q, J = 4.8, 4.1 Hz, 4H), 1.81-1.40 (m, 5H), 1.17 (d, J = 6.3 Hz, 3H). ES/MS: m/z 578.3. |
| 219 | 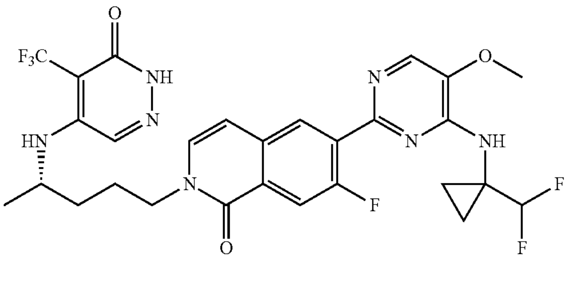 [SMILES: COc1cnc(-c2cc3ccn(CCC[C@H](C)Nc4cn[nH]c(=O)c4C(F)(F)F)c(=O)c3cc2F)nc1NC1(C(F)F)CC1] | 1H NMR (400 MHZ, DMSO-d6) δ 12.43 (s, 1H), 8.22 (d, J = 7.2 Hz, 1H), 8.10 (s, 2H), 8.01-7.84 (m, 2H), 7.49 (d, J = 7.4 Hz, 1H), 6.76 (d, J = 7.4 Hz, 1H), 6.54-6.04 (m, 2H), 3.96 (d, J = 20.9 Hz, 5H), 1.84-1.57 (m, 3H), 1.50 (dt, J = 12.3, 6.3 Hz, 1H), 1.20-1.10 (m, 5H), 1.03-0.96 (m, 2H). ES/MS: m/z 624.4. |

-continued

| Ex. No. | Structure | 1H NMR/MS [M + H]+ |
| --- | --- | --- |
| 220 | 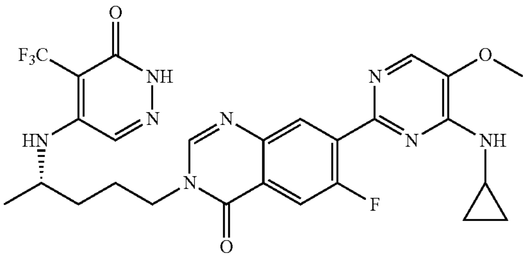 [SMILES: COc1cnc(-c2cc3ncn(CCC[C@H](C)Nc4cn[nH]c(=O)c4C(F)(F)F)c(=O)c3cc2F)nc1NC1CC1] | 1H NMR (400 MHZ, DMSO-d6) δ 12.44 (s, 1H), 8.43 (d, J = 3.0 Hz, 1H), 8.30-8.16 (m, 2H), 8.06-7.80 (m, 4H), 6.35 (dd, J = 8.1, 3.8 Hz, 1H), 3.97 (d, J = 29.9 Hz, 7H), 3.01 (s, 1H), 1.84-1.45 (m, 2H), 1.23 (d, J = 6.3 Hz, 1H), 1.17 (d, J = 6.3 Hz, 3H), 0.86-0.56 (m, 5H). ES/MS: m/z 575.3. |
| 221 | 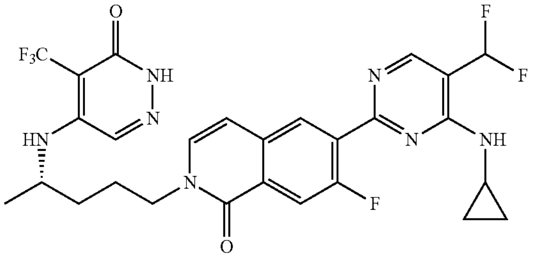 [SMILES: C[C@@H](CCCn1ccc2cc(-c3ncc(C(F)F)c(NC4CC4)n3)c(F)cc2c1=O)Nc1cn[nH]c(=O)c1C(F)(F)F] | 1H NMR (400 MHZ, DMSO-d6) δ 12.44 (s, 1H), 8.49 (d, J = 1.5 Hz, 1H), 8.31 (d, J = 7.1 Hz, 1H), 8.03-7.88 (m, 2H), 7.75 (d, J = 4.8 Hz, 1H), 7.50 (d, J = 7.4 Hz, 1H), 7.12 (t, J = 54.1 Hz, 1H), 6.79 (d, J = 7.4 Hz, 1H), 6.46-6.20 (m, 1H), 4.00 (t, J = 6.6 Hz, 3H), 3.03 (tq, J = 7.4, 3.8 Hz, 1H), 1.86-1.37 (m, 5H), 1.17 (d, J = 6.3 Hz, 3H), 0.79 (td, J = 7.1, 4.8 Hz, 2H), 0.70-0.59 (m, 2H). ES/MS: m/z 594.3. |
| 222 | 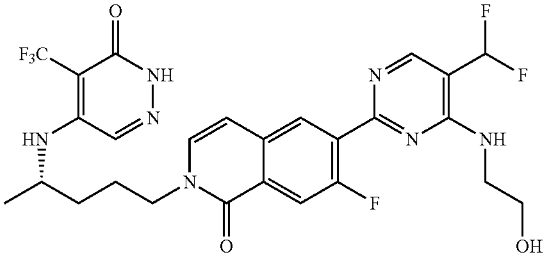 [SMILES: C[C@@H](CCCn1ccc2cc(-c3ncc(C(F)F)c(NCCO)n3)c(F)cc2c1=O)Nc1cn[nH]c(=O)c1C(F)(F)F] | 1H NMR (400 MHZ, DMSO-d6) δ 12.43 (s, 1H), 8.47 (d, J = 1.6 Hz, 1H), 8.28 (d, J = 7.1 Hz, 1H), 8.06-7.82 (m, 2H), 7.51 (t, J = 7.5 Hz, 2H), 7.13 (t, J = 54.0 Hz, 1H), 6.79 (d, J = 7.4 Hz, 1H), 6.48-6.23 (m, 1H), 3.99 (t, J = 6.5 Hz, 3H), 3.59 (h, J = 5.2 Hz, 4H), 1.88-1.36 (m, 4H), 1.17 (d, J = 6.3 Hz, 3H). ES/MS: m/z 598.3. |
| 223 | 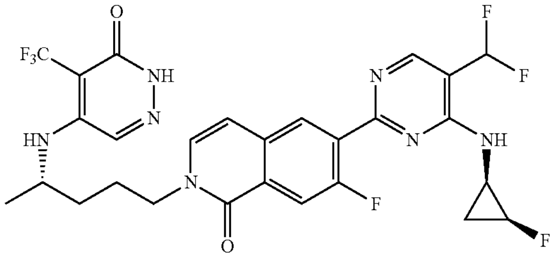 [SMILES: C[C@@H](CCCn1ccc2cc(-c3ncc(C(F)F)c(N[C@@H]4C[C@@H]4F)n3)c(F)cc2c1=O)Nc1cn[nH]c(=O)c1C(F)(F)F] | 1H NMR (400 MHZ, DMSO-d6) δ 12.43 (s, 1H), 8.53 (d, J = 3.0 Hz, 1H), 8.34 (dd, J = 13.2, 7.1 Hz, 1H), 8.03-7.84 (m, 2H), 7.80-7.40 (m, 3H), 7.37-7.01 (m, 1H), 6.78 (dd, J = 13.6, 7.4 Hz, 1H), 6.34 (s, 1H), 5.00-4.66 (m, 1H), 3.98 (d, J = 8.5 Hz, 3H), 3.07-2.69 (m, 1H), 1.91-1.34 (m, 4H), 1.33-0.96 (m, 6H). ES/MS: m/z 612.3. |
| 224 | 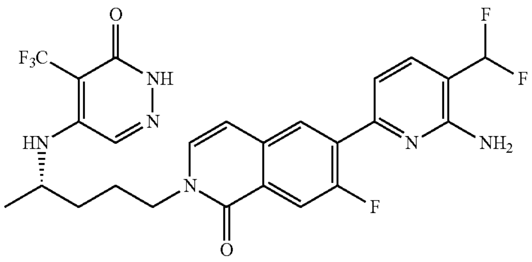 [SMILES: C[C@@H](CCCn1ccc2cc(-c3ccc(C(F)F)c(N)n3)c(F)cc2c1=O)Nc1cn[nH]c(=O)c1C(F)(F)F] | 1H NMR (400 MHZ, DMSO-d6) δ 12.43 (s, 1H), 8.14 (d, J = 7.3 Hz, 1H), 8.01-7.87 (m, 2H), 7.79 (d, J = 7.9 Hz, 1H), 7.48 (d, J = 7.3 Hz, 1H), 7.27-6.87 (m, 2H), 6.73 (d, J = 7.4 Hz, 1H), 6.49 (s, 1H), 6.34 (s, 1H), 3.98 (t, J = 6.6 Hz, 3H), 1.87-1.34 (m, 5H), 1.17 (d, J = 6.4 Hz, 3H). ES/MS: m/z 553.3. |
| 225 | 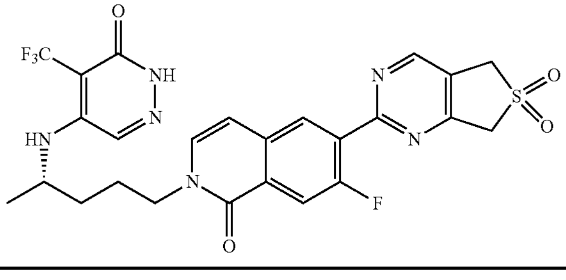 | 1H NMR (400 MHZ, DMSO-d6) δ 12.43 (s, 1H), 9.01 (s, 1H), 8.34 (d, J = 7.1 Hz, 1H), 8.00 (d, J = 11.3 Hz, 1H), 7.92 (s, 1H), 7.51 (d, J = 7.4 Hz, 1H), 6.82 (d, J = 7.4 Hz, 1H), 6.35 (dt, J = 7.1, 3.6 Hz, 1H), 4.82 (s, 2H), 4.76 (s, 2H), 4.00 (t, J = 6.5 Hz, 3H), 1.83-1.38 (m, 4H), 1.17 (d, J = 6.3 Hz, 3H). ES/MS: m/z 579.3. |

Example 226: 7-fluoro-2-(3-(1-methyl-2-(6-oxo-5-(trifluoromethyl)-1,6-dihydropyridazin-4-yl)hydrazineyl)propyl)-6-(5-(trifluoromethyl)pyrimidin-2-yl) isoquinolin-1(2H)-one

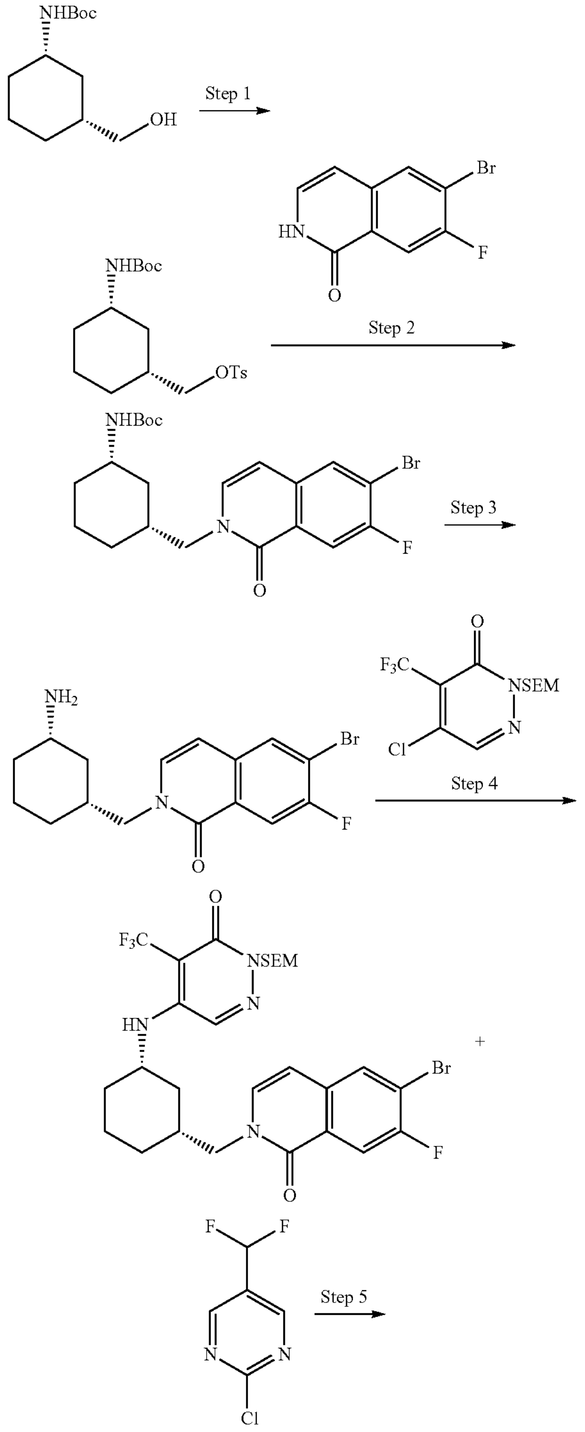

-continued

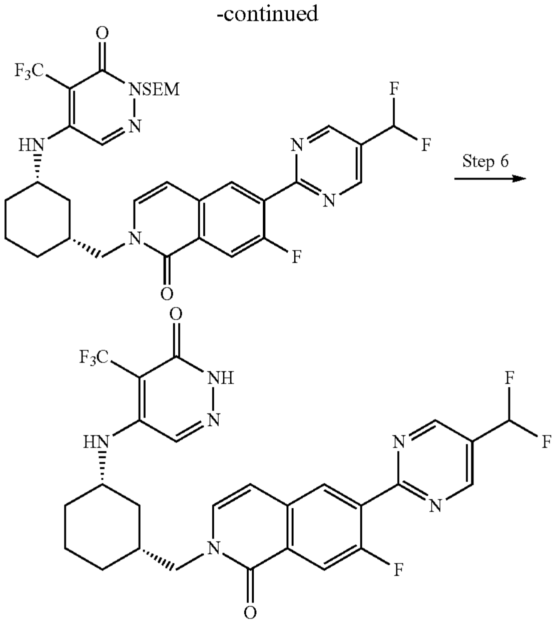

Example 226

Step 1. To a stirred solution of tert-butyl N-[(1S,3R)-3-(hydroxymethyl)cyclohexyl]carbamate (1500 mg, 6.54 mmol) and triethylamine (1.82 mL, 13.1 mmol), in dichloromethane (10 mL) was added p-Toluenesulfonyl chloride (1434 mg, 7.52 mmol) dropwise, followed by DMAP (20 mg). The mixture was stirred at room temperature and stirred for 16 h. Upon completion, the mixture was diluted with water and extracted with dicholoromethane. The combined organic layers were washed with brine, dried over $Na_2SO_4$ and concentrated in vacuo to give the crude product. The crude residue was purified using column chromatography eluting with EtOAc in hexanes 0-100% to afford [(1R, 3S)-3-(tert-butoxycarbonylamino)cyclohexyl]methyl 4-methylbenzenesulfonate ES/MS: m/z 384.1 $[M+H]^+$.

Step 2. To a mixture of 6-bromo-2H-isoquinolin-1-one (694 mg, 2.87 mmol) and [(1R,3S)-3-(tert-butoxycarbonylamino)cyclohexyl]methyl 4-methylbenzenesulfonate (1000 mg, 2.61 mmol) in DMF (12 mL) was added $Cs_2CO_3$ (2550 mg, 7.82 mmol) and the reaction was stirred at room temperature for 18 h. Upon completion, the mixture was diluted with EtOAc, washed with water, washed with brine, dried over $Na_2SO_4$ and concentrated in vacuo to give the crude product. The crude residue was purified using column chromatography eluting with EA in hexanes 0-100% to afford tert-butyl N-[(1S,3R)-3-[(6-bromo-7-fluoro-1-oxo-2-isoquinolyl)methyl]cyclohexyl]carbamate. ES/MS: m/z 455.1 $[M+H]^+$.

Step 3. In a vial were placed tert-butyl N-[(1S,3R)-3-[(6-bromo-7-fluoro-1-oxo-2-isoquinolyl)methyl]cyclohexyl] carbamate (230 mg, 0.57 mmol), trifluoroacetic acid (0.51 mL) and DCM (4 mL). The mixture was stirred at room temperature for 1 hour. Upon completion, the mixture was concentrated in vacuo, the resultant was partitioned between EtOAc and sat. aq. Sodium bicarbonate solution. The organic layer was washed with brine, dried over $Na_2SO_4$ and concentrated in vacuo to give 2-[[(1R,3S)-3-aminocyclohexyl]methyl]-6-bromo-7-fluoro-isoquinolin-1-one ES/MS m/z: 355.5$[M+H]^+$.

Step 4. A mixture of 2-[[(1R,3S)-3-aminocyclohexyl] methyl]-6-bromo-7-fluoro-isoquinolin-1-one (170 mg, 0.48 mmol), 5-chloro-4-(trifluoromethyl)-2-(2-trimethylsilylethoxymethyl)pyridazin-3-one (237 mg, 0.722 mmol), and N,N-diisopropylethylamine (0.5 mL, 2.9 mmol) in DMF (5.0 mL) was heated at 80° C. for 1 hour. Upon completion, the reaction was diluted with EtOAc, washed with water, washed with brine, dried over $Na_2SO_4$ and concentrated in vacuo to give the crude product. The crude residue was purified using column chromatography eluting with EtOAc in hexanes 0-100% to provide 6-bromo-7-fluoro-2-[[(1R,3S)-3-[[6-oxo-5-(trifluoromethyl)-1-(2-trimethylsilylethoxymethyl)pyridazin-4-yl]amino]cyclohexyl]methyl]isoquinolin-1-one. ES/MS: m/z 647.1 $[M+H]^+$.

Step 5. A vial was charged with 6-bromo-7-fluoro-2-[[(1R,3S)-3-[[6-oxo-5-(trifluoromethyl)-1-(2-trimethylsilylethoxymethyl)pyridazin-4-yl]amino]cyclohexyl]methyl]isoquinolin-1-one (118 mg, 0.18 mmol), 1,1'-Bis(diphenylphosphino)ferrocene-palladium(II)dichloride (15 mg, 0.018 mmol), potassium acetate (54 mg, 0.54 mmol), and bis(pinacolato)diboron (70 mg, 0.27 mmol) and flushed with dry nitrogen. Dioxane (5 mL) was added and the reaction heated to 100° C. for 2 hours. After cooling, 2-chloro-5-(difluoromethyl)pyrimidine (45 mg, 0.28 mmol), CataCXium Pd G4 (14 mg, 0.018 mmol), and aqueous sodium carbonate (2.0 M, 0.28 mL) were added and the mixture bubbled with dry nitrogen briefly. The reaction was then stirred at 100° C. for 1 hour before being diluted with EtOAc and filtered through a plug of Celite. The filtrate was evaporated and the crude purified via chromatography eluting with EtOAc in hexanes 0-100% to provide 6-[5-(difluoromethyl)pyrimidin-2-yl]-7-fluoro-2-[[(1R,3S)-3-[[6-oxo-5-(trifluoromethyl)-1-(2-trimethylsilylethoxymethyl)pyridazin-4-yl]amino]cyclohexyl]methyl]isoquinolin-1-one ES/MS: m/z 695.3 $[M+H]^+$.

Step 6. To a solution of 6-[5-(difluoromethyl)pyrimidin-2-yl]-7-fluoro-2-[[(1R,3S)-3-[[6-oxo-5-(trifluoromethyl)-1-(2-trimethylsilylethoxymethyl)pyridazin-4-yl]amino]cyclohexyl]methyl]isoquinolin-1-one (73 mg, 0.11 mmol) in dichloromethane (2.0 mL) was added trifluoroacetic acid (0.5 mL, 6.41 mmol) at room temperature and the mixture was stirred for 1 hour. The excess trifluoroacetic acid and solvent was removed under reduced pressure and the residue was dissolved in MeOH (1.0 mL). To this was added ethylenediamine (0.072 mL, 1.05 mmol) and the resulting mixture was stirred at room temperature for 10 minutes. Upon completion, the mixture was concentrated in vacuo and purified via reverse phase prep-HPLC (5-100% MeCN in water, 0.1% TFA) to afford 6-[5-(difluoromethyl)pyrimidin-2-yl]-7-fluoro-2-[[(1R,3S)-3-[[6-oxo-5-(trifluoromethyl)-1H-pyridazin-4-yl]amino]cyclohexyl]methyl]isoquinolin-1-one 1H NMR (400 MHz, DMSO-d6) δ 12.42 (s, 1H), 9.25 (s, 1H), 8.41 (d, J=7.2 Hz, 1H), 8.02 (d, J=11.4 Hz, 1H), 7.91 (s, 1H), 7.49 (d, J=7.4 Hz, 1H), 7.31 (t, J=54.8 Hz, 1H), 6.82 (d, J=7.4 Hz, 1H), 6.32 (dd, J=8.6, 3.9 Hz, 1H), 3.89 (d, J=7.0 Hz, 2H), 3.73 (s, 1H), 2.03 (s, 1H), 1.80 (d, J=10.2 Hz, 2H), 1.75-1.67 (m, 1H), 2.11-1.92 (m, 1H), 1.57 (d, J=12.5 Hz, 1H), 1.44-1.33 (m, 2H), 1.27 (q, J=11.1 Hz, 2H), 0.96 (q, J=12.8, 12.0 Hz, 1H). ES/MS m/z=565.3 $[M+H]^+$.

Intermediate 48: 2,5-dichloro-6-methylpyrimidin-4-amine

Intermediate 48

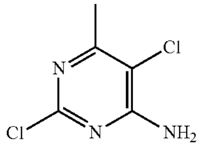

2,4,5-Trichloro-6-methyl-pyrimidine (300 mg, 1.52 mmol) was dissolved in THF (5 mL) and treated with ammonia (7M in MeOH, 0.65 mL, 4.56 mmol). The reaction was allowed to stir at ambient temperature overnight, then was poured into water. The resulting precipitate was collected and dried to afford the title compound as a white crystalline solid. ES/MS m/z: 177.9 $[M+H]^+$.

Intermediate 49: 2-chloro-6-methyl-5-(trifluoromethyl)pyrimidin-4-amine

Intermediate 49

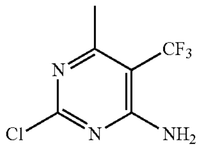

2,4-Dichloro-6-methyl-5-(trifluoromethyl)pyrimidine (250 mg, 1.08 mmol) was dissolved in THF (3 mL) and treated with ammonia (7M in MeOH, 0.46 mL, 3.25 mmol). The reaction was allowed to stir at ambient temperature overnight, then was poured into water and extracted 3× into EtOAc. The combined extracts were washed with brine, concentrated and purified by flash chromatography using 3:1 EtOAc/EtOH in heptane as eluent to give a mixture of isomers. The first-eluting minor isomer was isolated to give the title compound as a white solid. ES/MS m/z: 211.9 $[M+H]^+$.

Intermediate 50: tert-butyl (tert-butoxycarbonyl)(2,5-dichloro-6-cyclopropylpyrimidin-4-yl)carbamate

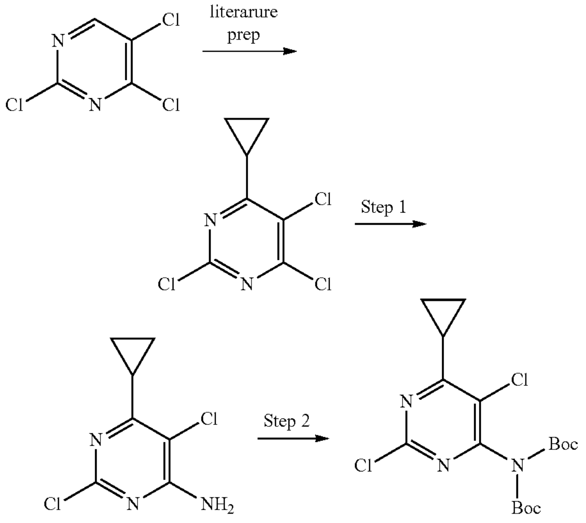

Intermediate 50

Step 1. 2,4,5-trichloro-6-cyclopropyl-pyrimidine (115 mg, 0.52 mmol) and DIEA (0.18 mL, 1.0 mmol) were dissolved in DMF (1 mL) and treated with ammonia (7M in MeOH, 0.10 mL, 0.67 mmol). After stirring at ambient temperature 18 hours, the reaction was poured into water and extracted 3× into EtOAc. The combined extracts were washed with brine, concentrated and purified by flash chromatography using 3:1 EtOAc/EtOH in heptane as eluent to give 2,5-dichloro-6-cyclopropylpyrimidin-4-amine as a white solid. ES/MS z: 203.9 [M+H].

Step 2. DIEA (0.11 mL, 0.65 mmol), di-tert-butyldicarbonate (490 mg, 2.25 mmol), and DMAP (2.5 mg, 0.021 mmol) were added to a suspension of 2,5-dichloro-6-cyclopropylpyrimidin-4-amine (126 mg, 0.62 mmol) in DCM (3 mL). The resulting solution was allowed to stir at ambient temperature. Upon completion, the reaction was poured into aq. $NaHCO_3$ and extracted 3× into DCM. The combined extracts were concentrated and purified by flash chromatography using EtOAc in hexane as eluent to give the title compound as a colorless oil. ES/MS m/z: 426.0 [M+Na]m.

The Following compounds were synthesized using the procedure as described in Example 226 from the corresponding starting materials.

| Ex. No. | Structure | 1H NMR/MS [M + H]$^+$ |
|---|---|---|
| 227 | 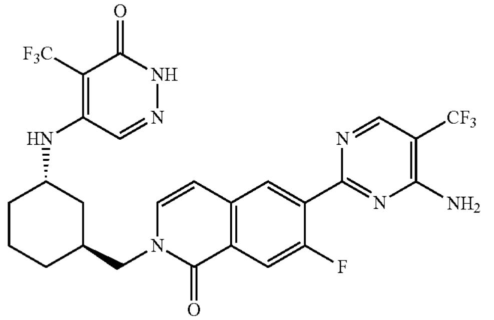 [SMILES: Nc1nc(-c2cc3ccn(C[C@H]4CCC[C@H](Nc5cn[nH]c(=O)c5C(F)(F)F)C4)c(=O)c3cc2F)ncc1C(F)(F)F] | 1H NMR (400 MHZ, DMSO-d6) δ 12.48 (s, 1H), 8.65 (s, 1H), 8.20 (d, J = 7.0 Hz, 1H), 8.16-7.88 (m, 2H), 7.50 (d, J = 7.4 Hz, 1H), 6.78 (d, J = 7.4 Hz, 1H), 6.08 (dd, J = 7.9, 4.1 Hz, 1H), 4.33-3.99 (m, 4H), 3.91 (dd, J = 13.2, 7.2 Hz, 1H), 2.24 (s, 1H), 1.84-1.21 (m, 6H). ES/MS m/z: 598.3 [M + H]$^+$. |
| 228 | 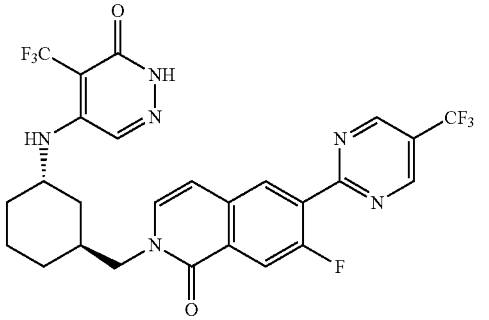 [SMILES: O=c1[nH]ncc(N[C@H]2CCC[C@H](Cn3ccc4cc(-c5ncc(C(F)(F)F)cn5)c(F)cc4c3=O)C2)c1C(F)(F)F] | 1H NMR (400 MHZ, DMSO-d6) δ 12.48 (s, 1H), 9.48 (s, 2H), 8.44 (d, J = 7.1 Hz, 1H), 8.11-7.95 (m, 2H), 7.54 (d, J = 7.4 Hz, 1H), 6.87 (d, J = 7.4 Hz, 1H), 6.08 (dd, J = 8.2, 4.1 Hz, 1H), 4.17 (ddd, J= 21.3, 13.3, 9.0 Hz, 2H), 3.94 (dd, J = 13.1, 7.2 Hz, 1H), 2.25 (s, 1H), 1.81-1.27 (m, 8H). ES/MS m/z: 583.3 [M + H]$^+$. |
| 229 | 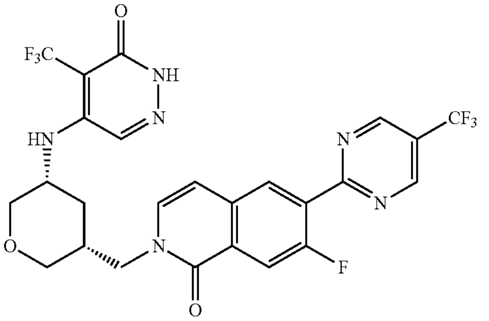 [SMILES: O=c1[nH]ncc(N[C@H]2COC[C@@H](Cn3ccc4cc(-c5ncc(C(F)(F)F)cn5)c(F)cc4c3=O)C2)c1C(F)(F)F] | 1H NMR (400 MHZ, DMSO-d6) δ 12.48 (s, 1H), 9.48 (s, 2H), 8.45 (d, J = 7.2 Hz, 1H), 8.05 (d, J = 11.3 Hz, 1H), 7.96 (s, 1H), 7.51 (d, J = 7.4 Hz, 1H), 6.86 (d, J = 7.4 Hz, 1H), 6.35 (d, J = 5.5 Hz, 1H), 3.91 (dt, J = 12.7, 6.5 Hz, 2H), 3.86-3.70 (m, 3H), 3.24 (t, J = 10.5 Hz, 1H), 3.08 (t, J = 11.2 Hz, 1H), 2.48-2.14 (m, 1H), 1.97 (d, J = 12.2 Hz, 1H), 1.52 (q, J = 11.9 Hz, 1H). ES/MS m/z: 585.3 [M + H]$^+$. |
| 230 | 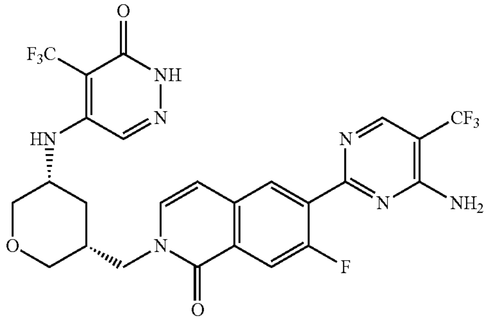 [SMILES: Nc1nc(-c2cc3ccn(C[C@@H]4COC[C@H](Nc5cn[nH]c(=O)c5C(F)(F)F)C4)c(=O)c3cc2F)ncc1C(F)(F)F] | 1H NMR (400 MHZ, DMSO-d6) δ 12.49 (s, 1H), 8.65 (s, 1H), 8.21 (d, J = 7.0 Hz, 1H), 8.05-7.81 (m, 2H), 7.47 (d, J = 7.4 Hz, 1H), 6.78 (d, J = 7.4 Hz, 1H), 6.34 (dd, J = 8.5, 3.9 Hz, 1H), 4.00-3.61 (m, 5H), 3.24 (t, J = 10.5 Hz, 1H), 3.07 (t, J = 11.2 Hz, 1H), 2.39-2.15 (m, 1H), 1.96 (d, J = 12.1 Hz, 1H), 1.52 (q, J = 11.8 Hz, 1H). ES/MS m/z: 600.3 [M + H]$^+$. |

-continued

| Ex. No. | Structure | 1H NMR/MS $[M + H]^+$ |
|---|---|---|
| 231 | 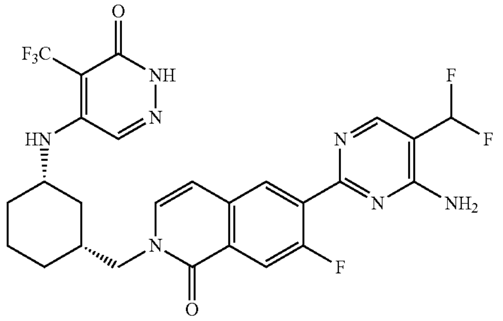 [SMILES: Nc1nc(-c2cc3ccn(C[C@@H]4CCC[C@H](Nc5cn[nH]c(=O)c5C(F)(F)F)C4)c(=O)c3cc2F)ncc1C(F)F] | 1H NMR (400 MHZ, DMSO-d6) δ 12.42 (s, 1H), 8.50 (s, 1H), 8.17 (d, J = 7.0 Hz, 1H), 7.99-7.75 (m, 2H), 7.69-7.34 (m, 2H), 7.09 (t, J = 54.2 Hz, 1H), 6.75 (d, J = 7.4 Hz, 1H), 6.32 (dd, J = 8.5, 4.1 Hz, 1H), 3.87 (d, J = 7.0 Hz, 2H), 3.80-3.65 (m, 1H), 2.02 (s, 1H), 1.92-1.66 (m, 4H), 1.56 (d, J = 12.7 Hz, 1H), 1.31 (dq, J = 34.6, 11.9 Hz, 2H), 0.95 (d, J = 12.9 Hz, 1H). ES/MS m/z: 580.3 $[M + H]^+$. |
| 232 | 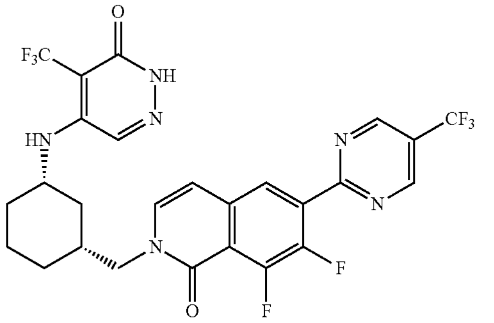 [SMILES: O=c1[nH]ncc(N[C@H]2CCC[C@@H](Cn3ccc4cc(-c5ncc(C(F)(F)F)cn5)c(F)c(F)c4c3=O)C2)c1C(F)(F)F] | 1H NMR (400 MHZ, DMSO-d6) δ 12.42 (s, 1H), 9.50 (s, 2H), 8.35-8.16 (m, 1H), 7.92 (s, 1H), 7.52 (d, J = 7.4 Hz, 1H), 6.81 (dd, J = 7.4, 1.8 Hz, 1H), 6.44-6.03 (m, 1H), 3.91-3.73 (m, 2H), 3.77-3.65 (m, 2H), 1.93-1.66 (m, 3H), 1.58 (d, J = 12.6 Hz, 1H), 1.31 (dq, J = 36.5, 11.7 Hz, 3H), 0.95 (q, J= 12.0 Hz, 1H). ES/MS m/z: 601.3 $[M + H]^+$. |
| 233 | 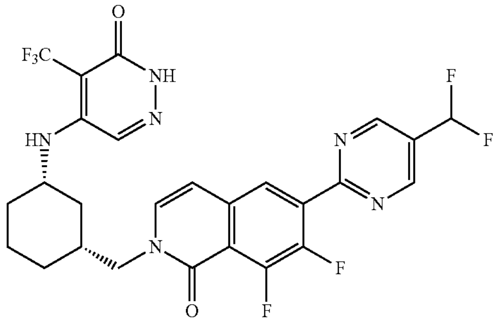 [SMILES: O=c1[nH]ncc(N[C@H]2CCC[C@@H](Cn3ccc4cc(-c5ncc(C(F)F)cn5)c(F)c(F)c4c3=O)C2)c1C(F)(F)F] | 1H NMR (400 MHZ, DMSO-d6) δ 12.42 (s, 1H), 9.26 (d, J = 1.2 Hz, 2H), 8.21 (dd, J = 6.4, 1.6 Hz, 1H), 7.92 (s, 1H), 7.51 (d, J = 7.4 Hz, 1H), 7.31 (t, J= 54.7 Hz, 1H), 6.79 (dd, J = 7.5, 1.8 Hz, 1H), 6.33 (dd, J = 8.3, 4.0 Hz, 1H), 3.85 (dt, J = 7.1, 4.3 Hz, 2H), 2.11-1.94 (m, 1H), 1.87-1.64 (m, 4H), 1.58 (d, J = 12.7 Hz, 1H), 1.31 (dq, J = 36.1, 11.7 Hz, 3H), 0.95 (q, J = 12.1 Hz, 1H). ES/MS m/z: 583.3 $[M + H]^+$. |
| 234 | 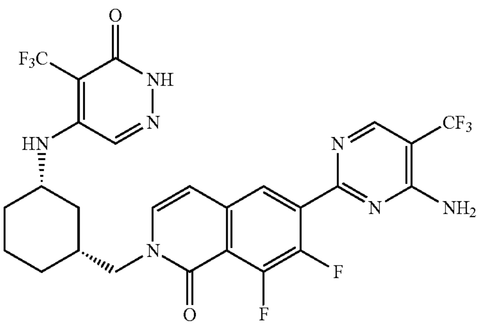 | 1H NMR (400 MHZ, DMSO-d6) δ 12.42 (s, 1H), 8.66 (s, 1H), 8.13-7.96 (m, 1H), 7.91 (s, 1H), 7.49 (d, J = 7.4 Hz, 1H), 6.72 (dd, J = 7.4, 1.8 Hz, 1H), 6.32 (dd, J = 8.4, 4.0 Hz, 1H), 3.83 (dd, J = 7.0, 2.9 Hz, 2H), 3.76-3.58 (m, 1H), 2.01 (s, 1H), 1.92-1.64 (m, 3H), 1.57 (d, J = 12.6 Hz, 1H), 1.31 (dq, J = 36.6, 11.8 Hz, 3H), 0.94 (q, J = 12.0, 10.6 Hz, 1H). ES/MS m/z: 616.3 $[M + H]^+$. |

-continued

| Ex. No. | Structure | 1H NMR/MS $[M + H]^+$ |
|---|---|---|
| 235 | 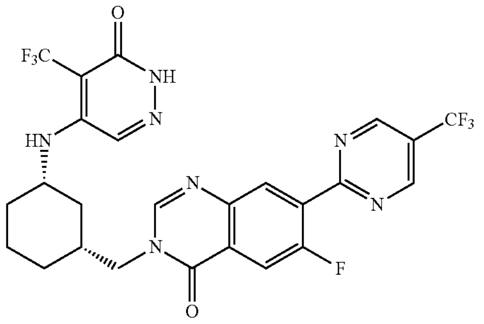 [SMILES: O=c1[nH]ncc(N[C@H]2CCC[C@@H](Cn3cnc4cc(-c5ncc(C(F)(F)F)cn5)c(F)cc4c3=O)C2)c1C(F)(F)F] | 1H NMR (400 MHZ, DMSO-d6) δ 12.42 (s, 1H), 9.50 (s, 2H), 8.43 (s, 1H), 8.35 (d, J = 6.7 Hz, 1H), 8.01 (d, J = 10.5 Hz, 1H), 7.92 (s, 1H), 7.80 (s, 1H), 6.49-6.15 (m, 1H), 3.91 (d, J = 7.0 Hz, 2H), 3.01 (d, J = 5.1 Hz, 1H), 2.02 (s, 1H), 1.87-1.77 (m, 1H), 1.73 (d, J = 10.6 Hz, 1H), 1.61 (d, J = 12.7 Hz, 1H), 1.36 (q, J = 11.7, 11.3 Hz, 2H), 1.26 (q, J = 11.8 Hz, 1H), 0.93 (t, J = 12.1 Hz, 1H). ES/MS m/z: 584.3 $[M + H]^+$. |
| 236 | 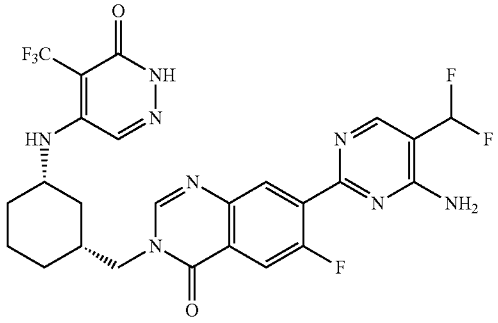 [SMILES: Nc1nc(-c2cc3ncn(C[C@@H]4CCC[C@H](Nc5cn[nH]c(=O)c5C(F)(F)F)C4)c(=O)c3cc2F)ncc1C(F)F] | 1H NMR (400 MHZ, DMSO-d6) δ 12.42 (s, 1H), 8.51 (d, J = 1.6 Hz, 1H), 8.39 (s, 1H), 8.15 (d, J = 6.7 Hz, 1H), 7.92 (t, J = 5.2 Hz, 2H), 7.58 (s, 1H), 7.09 (t, J = 54.1 Hz, 1H), 6.32 (dd, J = 8.5, 3.9 Hz, 1H), 3.89 (d, J = 6.9 Hz, 2H), 3.71 (d, J = 9.5 Hz, 1H), 2.10-1.87 (m, 1H), 1.89-1.68 (m, 3H), 1.60 (d, J= 12.6 Hz, 1H), 1.30 (dq, J = 43.7, 11.8, 11.4 Hz, 3H), 0.94 (q, J = 12.6, 12.0 Hz, 1H). ES/MS m/z: 581.3 $[M + H]^+$. |
| 237 | 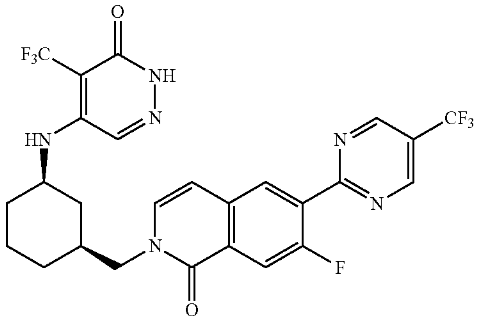 [SMILES: O=c1[nH]ncc(N[C@@H]2CCC[C@H](Cn3ccc4cc(-c5ncc(C(F)(F)F)cn5)c(F)cc4c3=O)C2)c1C(F)(F)F] | 1H NMR (400 MHZ, DMSO-d6) δ 12.42 (s, 1H), 9.48 (d, J = 1.0 Hz, 2H), 8.44 (d, J = 7.2 Hz, 1H), 8.03 (d, J = 11.4 Hz, 1H), 7.91 (s, 1H), 7.50 (d, J = 7.4 Hz, 1H), 6.84 (d, J = 7.4 Hz, 1H), 6.32 (dd, J = 8.5, 4.0 Hz, 1H), 3.94-3.78 (m, 3H), 2.03 (s, 1H), 1.76 (dd, J = 30.5, 10.8 Hz, 3H), 1.57 (d, J = 12.7 Hz, 1H), 1.33 (dp, J = 33.6, 12.2, 11.7 Hz, 3H), 0.95 (q, J = 12.2 Hz, 1H). ES/MS m/z: 583.3 $[M + H]^+$. |
| 238 | 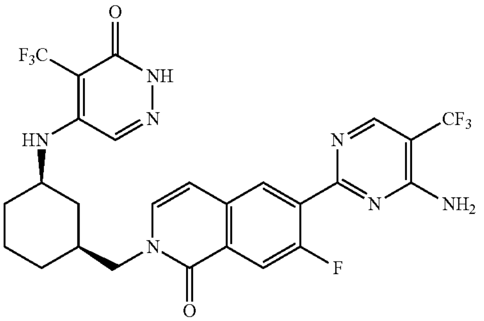 [SMILES: Nc1nc(-c2cc3ccn(C[C@H]4CCC[C@@H](Nc5cn[nH]c(=O)c5C(F)(F)F)C4)c(=O)c3cc2F)ncc1C(F)(F)F] | 1H NMR (400 MHZ, DMSO-d6) δ 12.42 (s, 1H), 8.83-8.52 (m, 1H), 8.20 (d, J = 7.1 Hz, 1H), 7.96 (d, J = 11.1 Hz, 1H), 7.90 (s, 1H), 7.47 (d, J = 7.4 Hz, 1H), 6.75 (d, J = 7.4 Hz, 1H), 6.32 (dd, J = 8.5, 3.8 Hz, 1H), 3.88 (d, J = 7.0 Hz, 2H), 3.73 (d, J = 10.4 Hz, 1H), 2.05 (d, J = 23.3 Hz, 1H), 1.92-1.65 (m, 3H), 1.57 (d, J = 12.6 Hz, 1H), 1.31 (dq, J = 35.1, 12.2 Hz, 3H), 0.95 (q, J = 12.0 Hz, 1H). ES/MS m/z: 598.3 $[M + H]^+$. |

-continued

| Ex. No. | Structure | 1H NMR/MS [M + H]+ |
|---|---|---|
| 239 | 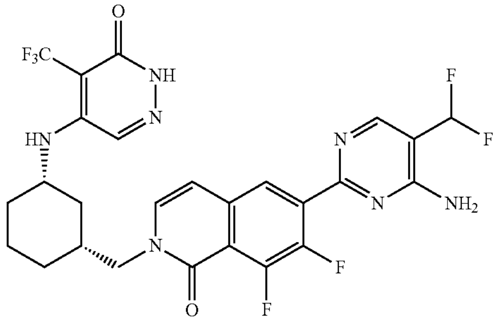 [SMILES: Nc1nc(-c2cc3ccn(C[C@@H]4CCC[C@H](Nc5cn[nH]c(=O)c5C(F)(F)F)C4)c(=O)c3c(F)c2F)ncc1C(F)F] | 1H NMR (400 MHZ, DMSO-d6) δ 12.42 (s, 1H), 8.50 (d, J = 1.7 Hz, 1H), 8.08-7.96 (m, 1H), 7.91 (s, 1H), 7.48 (d, J = 7.4 Hz, 1H), 7.09 (t, J = 54.1 Hz, 1H), 6.71 (dd, J = 7.5, 1.8 Hz, 1H), 6.32 (dd, J = 8.5, 3.9 Hz, 1H), 3.94-3.57 (m, 3H), 2.01 (s, 1H), 1.87-1.66 (m, 3H), 1.57 (d, J = 12.7 Hz, 1H), 1.32 (dp, J= 36.4, 12.2 Hz, 3H), 0.94 (q, J = 12.8, 12.2 Hz, 1H). ES/MS m/z: 598.3 [M + H]+. |
| 240 | 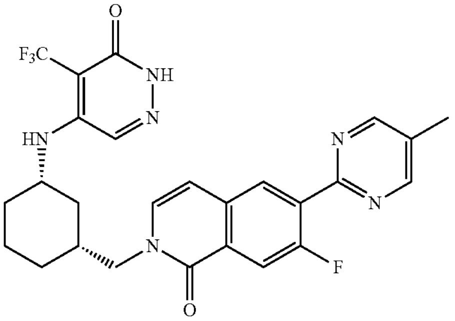 [SMILES: Cc1cnc(-c2cc3ccn(C[C@@H]4CCC[C@H](Nc5cn[nH]c(=O)c5C(F)(F)F)C4)c(=O)c3cc2F)nc1] | 1H NMR (400 MHz, DMSO-d6) δ 12.42 (s, 1H), 8.85 (s, 2H), 8.31 (d, J = 7.2 Hz, 1H), 7.97 (d, J = 11.3 Hz, 1H), 7.91 (s, 1H), 7.46 (d, J = 7.4 Hz, 1H), 6.79 (d, J = 7.4 Hz, 1H), 6.32 (d, J = 3.7 Hz, 1H), 3.88 (d, J = 7.0 Hz, 2H), 3.73 (m, 3H), 2.37 (s, 3H), 2.02 (s, 1H), 1.89-1.66 (m, 3H), 1.57 (d, J = 12.7 Hz, 1H), 1.45-1.18 (m, 3H), 1.10-0.82 (m, 1H). ES/MS m/z: 529.1 [M + H]+. |
| 241 | 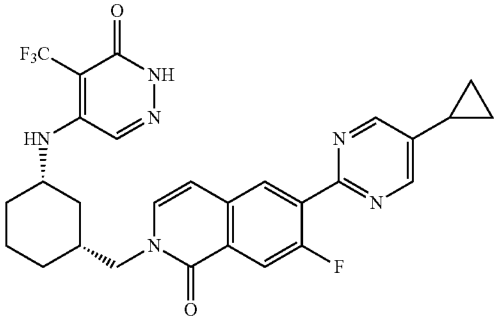 [SMILES: O=c1[nH]ncc(N[C@H]2CCC[C@@H](Cn3ccc4cc(-c5ncc(C6CC6)cn5)c(F)cc4c3=O)C2)c1C(F)(F)F] | 1H NMR (400 MHZ, DMSO-d6) δ 12.42 (s, 1H), 8.76 (s, 2H), 8.30 (d, J = 7.2 Hz, 1H), 8.08-7.79 (m, 2H), 7.46 (d, J = 7.4 Hz, 1H), 6.78 (d, J = 7.4 Hz, 1H), 6.31 (dd, J = 7.5, 4.0 Hz, 1H), 3.88 (d, J = 7.0 Hz, 2H), 3.73 (s, 1H), 2.04 (ddd, J = 13.4, 8.5, 5.0 Hz, 2H), 1.92-1.60 (m, 3H), 1.57 (d, J = 12.9 Hz, 1H), 1.33 (dp, J = 35.2, 12.2 Hz, 3H), 1.11 (dt, J= 8.5, 3.2 Hz, 2H), 0.95 (dt, J = 7.0, 4.5 Hz, 3H). ES/MS m/z: 555.2 [M + H]+. |
| 242 | 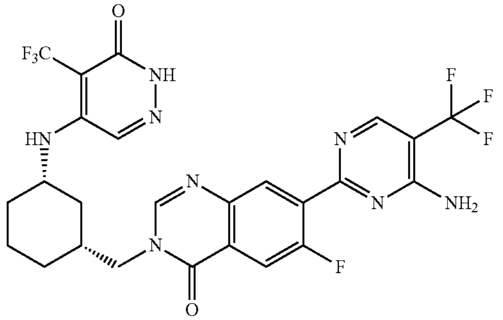 [SMILES: Nc1nc(-c2cc3ncn(C[C@@H]4CCC[C@H](Nc5cn[nH]c(=O)c5C(F)(F)F)C4)c(=O)c3cc2F)ncc1C(F)(F)F] | 1H NMR (400 MHZ, DMSO-d6) δ 12.42 (s, 1H), 8.66 (s, 1H), 8.40 (s, 1H), 8.18 (d, J = 6.7 Hz, 1H), 7.93 (d, J = 8.7 Hz, 2H), 6.37-6.28 (m, 1H), 3.93-3.86 (m, 2H), 3.77-3.66 (m, 1H), 2.06-1.94 (m, 1H), 1.85-1.70 (m, 3H), 1.59 (d, J = 10.6 Hz, 1H), 1.42-1.19 (m, 3H), 0.99-0.86 (m, 1H). ES/MS m/z: 529.1 [M + H]+. |

-continued

| Ex. No. | Structure | 1H NMR/MS [M + H]$^+$ |
|---|---|---|
| 243 | 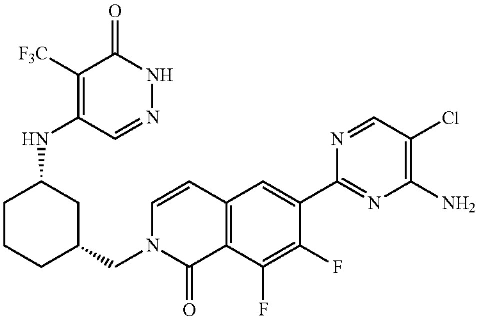 [SMILES: Nc1nc(-c2cc3ccn(C[C@@H]4CCC[C@H](Nc5cn[nH]c(=O)c5C(F)(F)F)C4)c(=O)c3c(F)c2F)ncc1Cl] | 1H NMR (400 MHZ, DMSO-d6) δ 12.42 (s, 1H), 9.25 (t, J = 1.8 Hz, 1H), 9.17 (s, 1H), 8.33 (d, J = 7.2 Hz, 1H), 8.07 (d, J = 11.5 Hz, 1H), 7.90 (s, 1H), 7.50 (d, J = 7.4 Hz, 1H), 7.23 (t, J = 54.1 Hz, 1H), 6.81 (d, J = 7.4 Hz, 1H), 6.32 (dd, J = 8.5, 3.9 Hz, 1H), 3.90 (d, J = 7.0 Hz, 2H), 3.73 (d, J = 10.1 Hz, 1H), 2.03 (s, 1H), 1.86-1.67 (m, 3H), 1.57 (d, J = 12.7 Hz, 1H), 1.31 (dq, J = 35.2, 12.0 Hz, 3H), 0.95 (d, J= 12.3 Hz, 1H). ES/MS m/z: 582.3 [M + H]$^+$. |
| 244 | 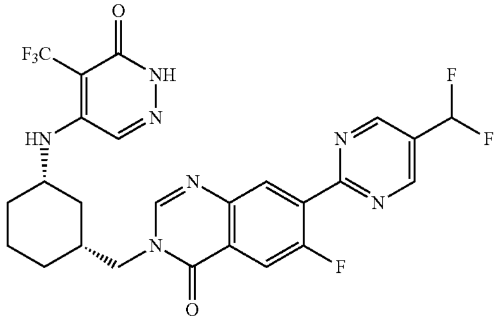 [SMILES: O=c1[nH]ncc(N[C@H]2CCC[C@@H](Cn3cnc4cc(-c5ncc(C(F)F)cn5)c(F)cc4c3=O)C2)c1C(F)(F)F] | 1H NMR (400 MHZ, DMSO-d6) δ 12.42 (s, 1H), 9.26 (s, 2H), 8.42 (s, 1H), 8.32 (d, J = 6.7 Hz, 1H), 7.99 (d, J = 10.4 Hz, 1H), 7.92 (s, 1H), 7.31 (t, J = 54.8 Hz, 1H), 6.33 (dt, J = 8.5, 3.9 Hz, 1H), 3.91 (d, J = 6.9 Hz, 2H), 3.72 (d, J = 9.7 Hz, 1H), 2.05-1.98 (m, 1H), 1.87-1.69 (m, 3H), 1.61 (d, J = 12.5 Hz, 1H), 1.44-1.21 (m, 3H), 0.95 (td, J = 12.5, 8.8 Hz, 1H). ES/MS m/z: 566.3 [M + H]$^+$. |
| 245 | 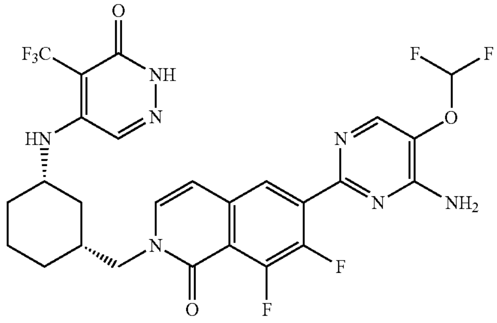 [SMILES: Nc1nc(-c2cc3ccn(C[C@@H]4CCC[C@H](Nc5cn[nH]c(=O)c5C(F)(F)F)C4)c(=O)c3c(F)c2F)ncc1OC(F)F] | 1H NMR (400 MHZ, DMSO-d6) δ 12.42 (s, 1H), 8.23 (s, 1H), 7.92 (d, J = 8.5 Hz, 2H), 7.47 (d, J = 7.4 Hz, 2H), 7.11 (d, J = 73.1 Hz, 1H), 6.72-6.66 (m, 1H), 6.33 (dd, J = 7.6, 3.6 Hz, 1H), 3.88-3.79 (m, 2H), 3.79-3.69 (m, 2H), 2.07-1.95 (m, 1H), 1.75 (d, J = 17.0 Hz, 2H), 1.56 (d, J = 16.4 Hz, 1H), 1.43-1.21 (m, 3H), 0.98-0.86 (m, 1H). ES/MS m/z: 614.2 [M + H]$^+$. |
| 246 | 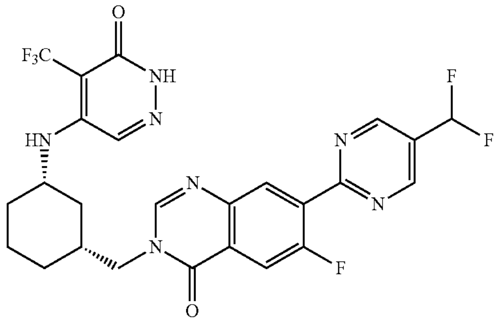 [SMILES: O=c1[nH]ncc(N[C@H]2CCC[C@@H](Cn3cnc4cc(-c5ncc(C(F)F)cn5)c(F)cc4c3=O)C2)c1C(F)(F)F] | 1H NMR (400 MHZ, DMSO-d6) δ 12.42 (s, 1H), 9.17 (s, 2H), 8.17 (d, J = 6.1 Hz, 1H), 7.91 (s, 1H), 7.50 (d, J = 7.4 Hz, 1H), 6.78 (d, J = 6.3 Hz, 1H), 6.35-6.27 (m, 1H), 3.90-3.77 (m, 3H), 2.05-1.97 (m, 1H), 1.84-1.70 (m, 3H), 1.58 (d, J = 14.4 Hz, 1H), 1.46-1.22 (m, 4H), 0.99-0.87 (m, 1H). ES/MS m/z: 567.2 [M + H]$^+$. |

-continued

| Ex. No. | Structure | 1H NMR/MS [M + H]$^+$ |
| --- | --- | --- |
| 247 | 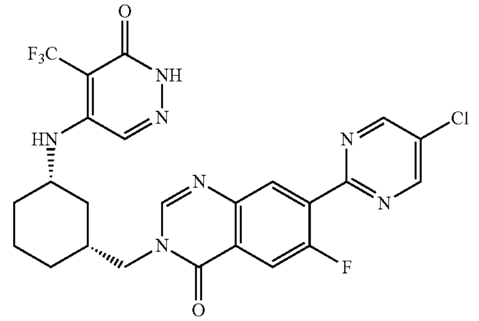 [SMILES: O=c1[nH]ncc(N[C@H]2CCC[C@@H](Cn3cnc4cc(-c5ncc(Cl)cn5)c(F)cc4c3=O)C2)c1C(F)(F)F] | 1H NMR (400 MHZ, DMSO-d6) δ 12.42 (s, 1H), 9.16 (s, 2H), 8.41 (s, 1H), 8.28 (d, J = 6.8 Hz, 1H), 7.92 (s, 1H), 6.35-6.29 (m, 1H), 3.90 (d, J = 6.9 Hz, 3H), 2.08-1.96 (m, 1H), 1.87-1.70 (m, 3H), 1.60 (d, J = 10.9 Hz, 1H), 1.43-1.21 (m, 3H), 1.01-0.87 (m, 1H). ES/MS m/z: 550.2 [M + H]$^+$. |
| 248 | 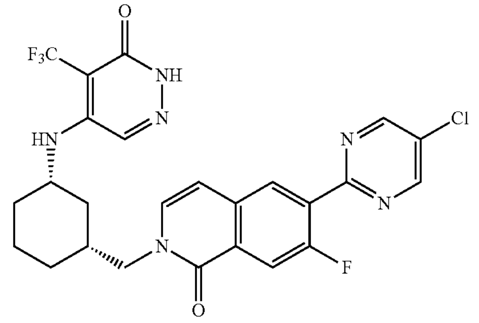 [SMILES: O=c1[nH]ncc(N[C@H]2CCC[C@@H](Cn3ccc4cc(-c5ncc(Cl)cn5)c(F)cc4c3=O)C2)c1C(F)(F)F] | 1H NMR (400 MHZ, DMSO-d6) δ 12.42 (s, 1H), 9.15 (s, 2H), 8.36 (d, J = 7.2 Hz, 1H), 8.00 (d, J = 11.3 Hz, 1H), 7.91 (s, 1H), 7.48 (d, J = 7.4 Hz, 1H), 6.81 (d, J = 7.3 Hz, 1H), 6.35-6.28 (m, 1H), 3.88 (d, J = 6.7 Hz, 2H), 3.73 (s, 1H), 2.06-1.97 (m, 1H), 1.85-1.69 (m, 3H), 1.57 (d, J = 20.3 Hz, 1H), 1.41-1.23 (m, 3H), 1.00-0.87 (m, 1H). ES/MS m/z: 549.1 [M + H]$^+$. |
| 249 | 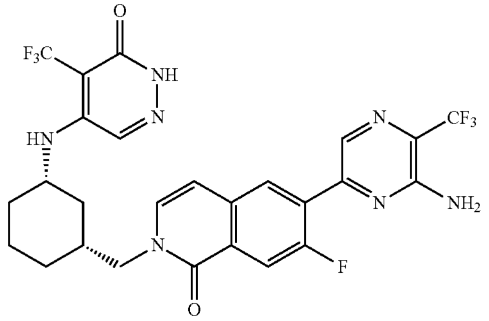 [SMILES: Nc1nc(-c2cc3ccn(C[C@@H]4CCC[C@H](Nc5cn[nH]c(=O)c5C(F)(F)F)C4)c(=O)c3cc2F)cnc1C(F)(F)F] | 1H NMR (400 MHZ, DMSO-d6) δ 12.43 (s, 1H), 8.31 (d, J = 2.6 Hz, 1H), 8.18 (d, J = 7.1 Hz, 1H), 8.02 (d, J = 11.4 Hz, 1H), 7.90 (s, 1H), 7.48 (d, J = 7.4 Hz, 1H), 7.14 (s, 2H), 6.74 (d, J = 7.4 Hz, 1H), 6.39-6.24 (m, 1H), 3.96-3.81 (m, 2H), 3.80-3.65 (m, 1H), 2.10-1.94 (m, 1H), 1.88-1.64 (m, 3H), 1.57 (d, J = 12.6 Hz, 1H), 1.41-1.22 (m, 3H), 1.04-0.87 (m, 1H). ES/MS m/z: 598.3 [M + H]$^+$. |
| 250 | 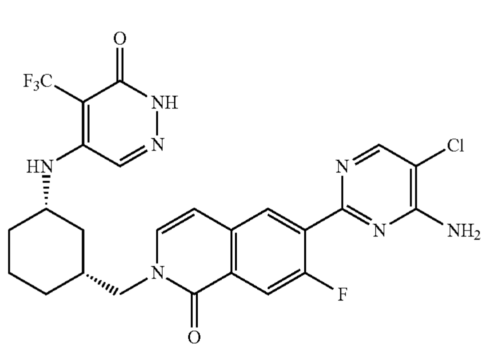 [SMILES: Nc1nc(-c2cc3ccn(C[C@@H]4CCC[C@H](Nc5cn[nH]c(=O)c5C(F)(F)F)C4)c(=O)c3cc2F)ncc1Cl] | 1H NMR (400 MHZ, DMSO-d6) δ 12.43 (s, 1H), 8.44 (s, 1H), 8.15 (d, J = 7.1 Hz, 1H), 7.94 (d, J = 11.2 Hz, 1H), 7.91 (s, 1H), 7.85-7.03 (m, 3H), 6.74 (d, J = 7.4 Hz, 1H), 6.32 (dd, J = 8.3, 3.9 Hz, 1H), 2.08-1.93 (m, 1H), 1.88-1.64 (m, 3H), 1.62-1.49 (m, 1H), 1.44-1.19 (m, 3H), 1.03-0.86 (m, 1H). ES/MS m/z: 564.3 [M + H]$^+$. |

-continued

| Ex. No. | Structure | 1H NMR/MS [M + H]+ |
|---|---|---|
| 251 | 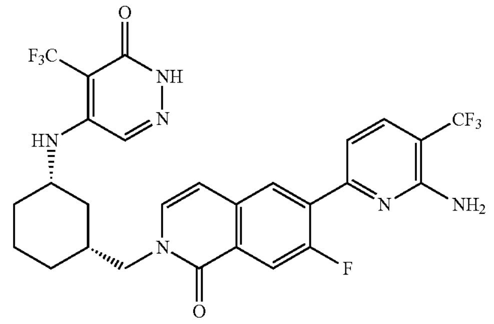 [SMILES: Nc1nc(-c2cc3ccn(C[C@@H]4CCC[C@H](Nc5cn[nH]c(=O)c5C(F)(F)F)C4)c(=O)c3cc2F)ccc1C(F)(F)F] | 1H NMR (400 MHZ, DMSO-d6) δ 12.42 (s, 1H), 8.15 (d, J = 7.2 Hz, 1H), 8.01-7.85 (m, 3H), 7.46 (d, J = 7.4 Hz, 1H), 7.12 (dd, J = 7.9, 2.1 Hz, 1H), 6.70 (t, J = 11.9 Hz, 3H), 6.32 (dd, J = 8.6, 4.0 Hz, 1H), 3.88 (d, J = 7.0 Hz, 2H), 3.73 (d, J = 10.6 Hz, 1H), 2.01 (s, 1H), 1.85-1.67 (m, 3H), 1.56 (d, J = 12.7 Hz, 1H), 1.31 (dq, J = 35.0, 12.0 Hz, 3H), 0.95 (q, J = 12.6, 11.5 Hz, 1H). ES/MS m/z: $[M + H]^+$. |
| 252 | 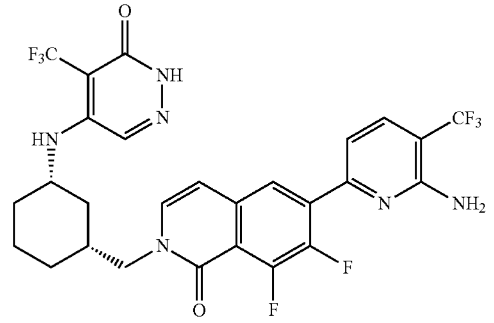 [SMILES: Nc1nc(-c2cc3ccn(C[C@@H]4CCC[C@H](Nc5cn[nH]c(=O)c5C(F)(F)F)C4)c(=O)c3c(F)c2F)ccc1C(F)(F)F] | 1H NMR (400 MHZ, DMSO-d6) δ 12.43 (s, 1H), 7.98-7.87 (m, 3H), 7.48 (d, J = 7.4 Hz, 1H), 7.13 (d, J = 7.9 Hz, 1H), 6.80-6.62 (m, 3H), 6.37-6.27 (m, 1H), 3.89-3.64 (m, 3H), 2.01 (s, 1H), 1.86-1.68 (m, 3H), 1.57 (d, J = 12.8 Hz, 1H), 1.32 (dp, J = 36.8, 12.3 Hz, 3H), 0.94 (q, J = 12.1 Hz, 1H). ES/MS m/z: 615.3 $[M + H]^+$. |
| 253 | 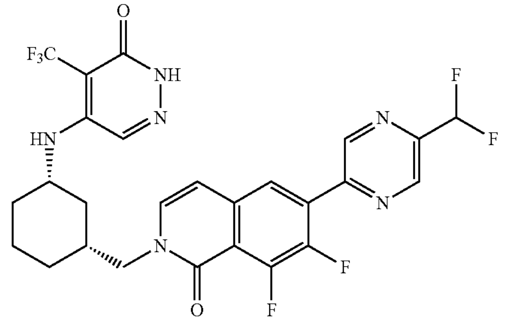 [SMILES: O=c1[nH]ncc(N[C@H]2CCC[C@@H](Cn3ccc4cc(-c5cnc(C(F)F)cn5)c(F)c(F)c4c3=O)C2)c1C(F)(F)F] | 1H NMR (400 MHZ, DMSO-d6) δ 12.42 (s, 1H), 9.27 (d, J = 1.8 Hz, 1H), 9.18 (s, 1H), 8.15-8.06 (m, 1H), 7.91 (s, 1H), 7.53 (d, J = 7.4 Hz, 1H), 7.24 (t, J = 54.1 Hz, 1H), 6.77 (dd, J = 7.4, 1.8 Hz, 1H), 6.38-6.28 (m, 1H), 3.85 (dd, J = 7.1, 2.4 Hz, 2H), 3.73 (s, 1H), 2.02 (s, 1H), 1.77 (dt, J = 20.8, 10.2 Hz, 3H), 1.58 (d, J = 12.7 Hz, 1H), 1.31 (dq, J = 37.3, 11.9 Hz, 3H), 0.95 (q, J = 11.8 Hz, 1H). ES/MS m/z: 583.3 $[M + H]^+$. |
| 254 | 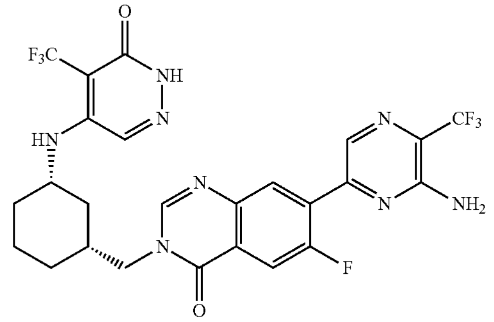 [SMILES: Nc1nc(-c2cc3ncn(C[C@@H]4CCC[C@H](Nc5cn[nH]c(=O)c5C(F)(F)F)C4)c(=O)c3cc2F)cnc1C(F)(F)F] | 1H NMR (400 MHz, DMSO-d6) δ 12.43 (s, 1H), 8.41 (s, 1H), 8.35 (d, J = 2.5 Hz, 1H), 8.22 (d, J = 6.7 Hz, 1H), 7.99 (d, J = 10.7 Hz, 1H), 7.92 (s, 1H), 7.17 (m, 2H), 6.32 (m, 1H), 4.33-3.45 (m, 2H), 2.14-1.94 (m, 1H), 1.88-1.50 (m, 5H), 1.31 (m, 3H), 0.97-0.77 (m, 1H). ES/MS m/z: 599.2 $[M + H]^+$. |

-continued

| Ex. No. | Structure | 1H NMR/MS $[M + H]^+$ |
|---|---|---|
| 255 | 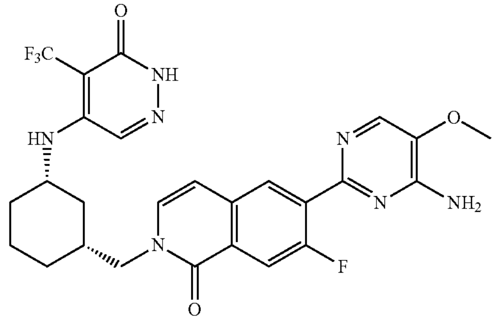 [SMILES: COc1cnc(-c2cc3ccn(C[C@@H]4CCC[C@H](Nc5cn[nH]c(=O)c5C(F)(F)F)C4)c(=O)c3cc2F)nc1N] | 1H NMR (400 MHZ, DMSO-d6) δ 12.43 (s, 1H), 8.41 (s, 1H), 8.35 (d, J = 2.5 Hz, 1H), 8.22 (d, J = 6.7 Hz, 1H), 7.99 (d, J = 10.7 Hz, 1H), 7.92 (s, 1H), 7.17 (m, 2H), 6.32 (m, 1H), 4.33-3.45 (m, 2H), 2.14-1.94 (m, 1H), 1.88-1.50 (m, 5H), 1.31 (m, 3H), 0.97-0.77 (m, 1H). ES/MS m/z: 560.1 $[M + H]^+$. |
| 256 | 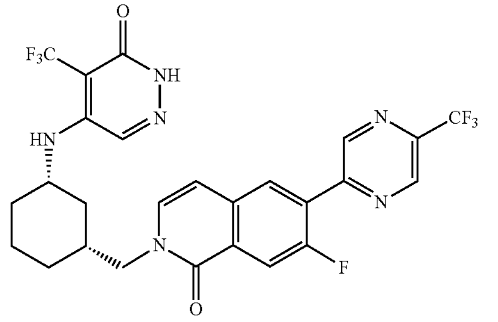 [SMILES: O=c1[nH]ncc(N[C@H]2CCC[C@@H](Cn3ccc4cc(-c5cnc(C(F)(F)F)cn5)c(F)cc4c3=O)C2)c1C(F)(F)F] | 1H NMR (400 MHZ, DMSO-d6) δ 12.43 (s, 1H), 9.40 (d, J = 1.3 Hz, 1H), 9.34 (d, J = 1.8 Hz, 1H), 8.35 (d, J = 7.1 Hz, 1H), 8.08 (d, J = 11.5 Hz, 1H), 7.91 (s, 1H), 7.51 (d, J = 7.4 Hz, 1H), 6.82 (d, J = 7.4 Hz, 1H), 6.33 (m, 1H), 3.90 (m, 2H), 3.74 (m, 1H), 2.13-1.96 (m, 1H), 1.87-1.65 (m, 3H), 1.63-1.50 (m, 1H), 1.47-1.19 (m, 3H), 1.06-0.87 (m, 1H). ES/MS m/z: 583.2 $[M + H]^+$. |
| 257 | 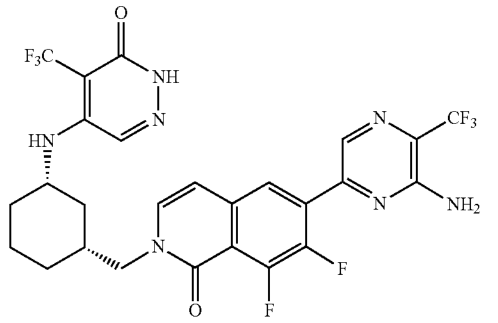 [SMILES: Nc1nc(-c2cc3ccn(C[C@@H]4CCC[C@H](Nc5cn[nH]c(=O)c5C(F)(F)F)C4)c(=O)c3c(F)c2F)cnc1C(F)(F)F] | 1H NMR (400 MHZ, DMSO-d6) δ 12.43 (s, 1H), 8.32 (d, J = 2.5 Hz, 1H), 8.07-7.86 (m, 2H), 7.50 (d, J = 7.4 Hz, 1H), 7.18 (s, 2H), 6.69 (m, 1H), 6.33 (m, 1H), 3.97-3.35 (m, 3H), 2.11-1.94 (m, 1H), 1.88-1.65 (m, 3H), 1.57 (m, 1H), 1.31 (m, 3H), 1.02-0.77 (m, 1H). ES/MS m/z: 616.2 $[M + H]^+$. |
| 258 | 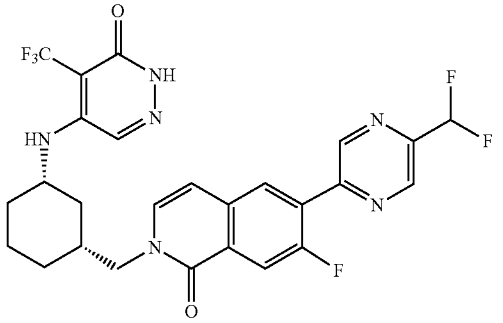 [SMILES: O=c1[nH]ncc(N[C@H]2CCC[C@@H](Cn3ccc4cc(-c5cnc(C(F)F)cn5)c(F)cc4c3=O)C2)c1C(F)(F)F] | 1H NMR (400 MHz, DMSO-d6) δ 12.42 (s, 1H), 9.25 (t, J = 1.8 Hz, 1H), 9.17 (s, 1H), 8.33 (d, J = 7.2 Hz, 1H), 8.07 (d, J = 11.5 Hz, 1H), 7.90 (s, 1H), 7.50 (d, J = 7.4 Hz, 1H), 7.23 (t, J = 54.1 Hz, 1H), 6.81 (d, J = 7.4 Hz, 1H), 6.32 (dd, J = 8.5, 3.9 Hz, 1H), 3.90 (d, J = 7.0 Hz, 2H), 3.73 (d, J = 10.1 Hz, 1H), 2.03 (s, 1H), 1.86-1.67 (m, 3H), 1.57 (d, J = 12.7 Hz, 1H), 1.31 (dq, J = 35.2, 12.0 Hz, 3H), 0.95 (d, J= 12.3 Hz, 1H). ES/MS m/z: 565.1 $[M + H]^+$. |

-continued

| Ex. No. | Structure | 1H NMR/MS [M + H]+ |
|---|---|---|
| 259 | 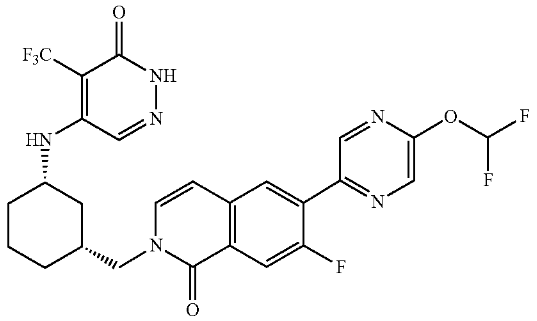 [SMILES: O=c1[nH]ncc(N[C@H]2CCC[C@@H](Cn3ccc4cc(-c5cnc(OC(F)F)cn5)c(F)cc4c3=O)C2)c1C(F)(F)F] | 1H NMR (400 MHZ, DMSO-d6) δ 12.42 (s, 1H), 8.90-8.71 (m, 2H), 8.25 (d, J = 7.3 Hz, 1H), 8.03 (d, J = 11.5 Hz, 1H), 7.90 (s, 1H), 7.79 (t, J = 71.7 Hz, 1H), 7.48 (d, J = 7.4 Hz, 1H), 6.79 (d, J = 7.4 Hz, 1H), 6.37-6.28 (m, 1H), 3.93-3.84 (m, 2H), 3.79-3.67 (m, 1H), 1.87-1.66 (m, 3H), 1.63-1.51 (m, 1H), 1.46-1.19 (m, 3H), 1.04-0.87 (m, 1H). ES/MS m/z: 581.1 [M + H]+. |
| 260 | 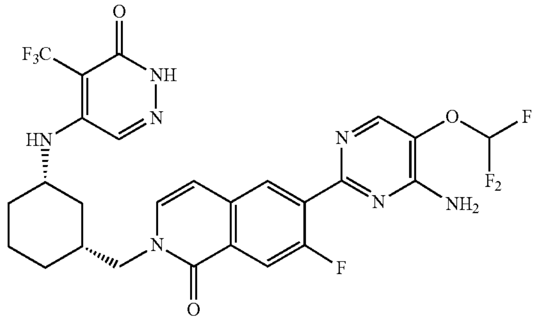 | 1H NMR (400 MHZ, DMSO-d6) δ 12.42 (s, 1H), 8.22 (s, 1H), 8.12 (d, J = 7.2 Hz, 1H), 8.00-7.88 (m, 2H), 7.47 (d, J = 7.4 Hz, 1H), 7.20 (t, J = 73.1 Hz, 1H), 6.75 (d, J = 7.4 Hz, 1H), 6.34-6.22 (m, 1H), 3.98 (t, J = 6.8 Hz, 2H), 3.85 (d, J = 7.6 Hz, 1H), 1.81-1.46 (m, 5H), 0.81 (t, J = 7.3 Hz, 3H). ES/MS m/z: 596.1 [M + H]+. |
| 261 | 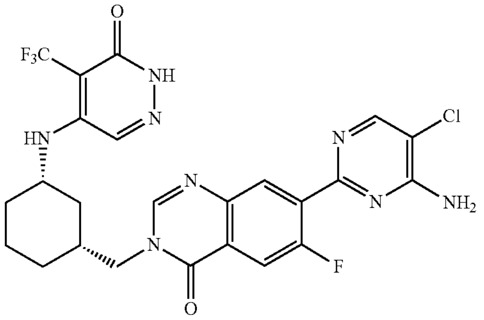 [SMILES: Nc1nc(-c2cc3ncn(C[C@@H]4CCC[C@H](Nc5cn[nH]c(=O)c5C(F)(F)F)C4)c(=O)c3cc2F)ncc1Cl] | 1H NMR (400 MHZ, DMSO-d6) δ 12.42 (s, 1H), 8.47-8.33 (m, 2H), 8.14 (d, J = 6.8 Hz, 1H), 7.98-7.82 (m, 2H), 7.80-7.07 (m, 2H), 6.39-6.23 (m, 1H), 3.89 (d, J = 6.9 Hz, 2H), 3.77-3.65 (m, 1H), 2.08-1.91 (m, 1H), 1.89-1.67 (m, 3H), 1.65-1.53 (m, 1H), 1.41-1.19 (m, 3H), 1.03-0.84 (m, 1H). ES/MS m/z: 565.3 [M + H]+. |
| 262 | 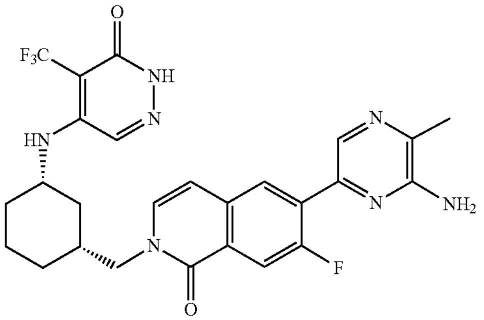 [SMILES: Cc1ncc(-c2cc3ccn(C[C@@H]4CCC[C@H](Nc5cn[nH]c(=O)c5C(F)(F)F)C4)c(=O)c3cc2F)nc1N] | 1H NMR (400 MHZ, DMSO-d6) δ 12.42 (s, 1H), 8.25-7.72 (m, 3H), 7.46 (dd, J = 13.7, 7.3 Hz, 1H), 7.28-6.87 (m, 1H), 6.87-6.60 (m, 1H), 6.48 (s, 1H), 6.32 (s, 1H), 4.00-3.62 (m, 4H), 2.36 (s, 1H), 2.01 (s, 1H), 1.90-1.63 (m, 3H), 1.62-1.44 (m, 1H), 1.32 (dt, J = 35.1, 11.8 Hz, 1H), 1.03-0.85 (m, 1H). ES/MS m/z: 543.8 [M + H]+. |

-continued

| Ex. No. | Structure | 1H NMR/MS [M + H]$^+$ |
| --- | --- | --- |
| 263 | 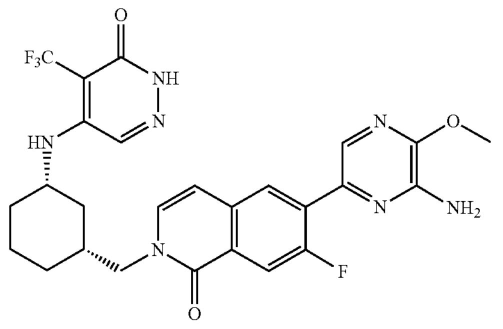 [SMILES: COc1ncc(-c2cc3ccn(C[C@@H]4CCC[C@H](Nc5cn[nH]c(=O)c5C(F)(F)F)C4)c(=O)c3cc2F)nc1N] | 1H NMR (400 MHZ, DMSO-d6) δ 12.42 (s, 1H), 8.13 (d, J = 7.3 Hz, 1H), 8.02-7.69 (m, 3H), 7.42 (d, J = 7.4 Hz, 1H), 7.28-6.87 (m, 1H), 6.77-6.50 (m, 2H), 6.31 (s, OH), 4.02-3.66 (m, 7H), 2.01 (s, 1H), 1.76 (d, J = 23.4 Hz, 4H), 1.56 (d, J = 12.5 Hz, 1H), 1.31 (dq, J = 34.4, 11.7 Hz, 3H), 1.04-0.76 (m, 1H). ES/MS m/z: 560.2 [M + H]$^+$. |
| 264 | 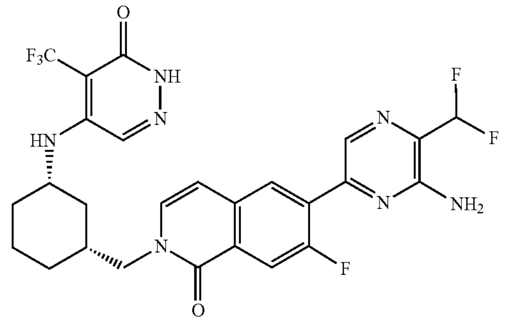 [SMILES: Nc1nc(-c2cc3ccn(C[C@@H]4CCC[C@H](Nc5cn[nH]c(=O)c5C(F)(F)F)C4)c(=O)c3cc2F)cnc1C(F)F] | 1H NMR (400 MHZ, DMSO-d6) δ 12.42 (s, 1H), 8.27 (d, J = 2.7 Hz, 1H), 8.19-8.12 (m, 1H), 8.00 (d, J = 11.5 Hz, 1H), 7.89 (d, J = 5.7 Hz, 1H), 7.51-7.43 (m, 1H), 7.21 (d, J = 4.3 Hz, 1H), 7.07 (d, J = 6.8 Hz, 1H), 6.94 (d, J = 8.6 Hz, 1H), 6.74 (d, J = 7.4 Hz, 1H), 6.32 (s, 1H), 3.94-3.84 (m, 2H), 3.72 (s, 1H), 2.01 (s, 2H), 1.82-1.71 (m, 2H), 1.59-1.52 (m, 1H), 1.36-1.24 (m, 2H), 0.94 (d, J = 12.0 Hz, 2H). ES/MS m/z: 580.1 [M + H]$^+$. |
| 265 | 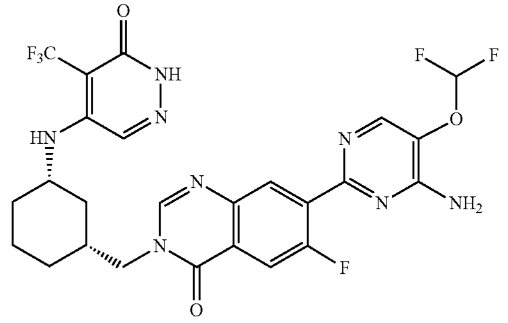 [SMILES: Nc1nc(-c2cc3ncn(C[C@@H]4CCC[C@H](Nc5cn[nH]c(=O)c5C(F)(F)F)C4)c(=O)c3cc2F)ncc1OC(F)F] | 1H NMR (400 MHZ, DMSO-d6) δ 12.42 (s, 1H), 8.38 (s, 1H), 8.23 (s, 1H), 8.11 (d, J = 6.8 Hz, 1H), 7.95-7.86 (m, 2H), 7.47 (d, J = 13.4 Hz, 2H), 7.20 (t, J = 73.1 Hz, 1H), 6.37-6.27 (m, 1H), 3.89 (d, J = 6.9 Hz, 2H), 3.71 (s, 1H), 2.00 (s, 1H), 1.80 (s, 2H), 1.74 (s, 1H), 1.59 (d, J = 12.7 Hz, 1H), 1.30 (dq, J = 43.8, 11.9, 11.3 Hz, 3H), 0.94 (q, J = 12.6 Hz, 1H). ES/MS m/z: 597.1 [M + H]$^+$. |
| 266 | 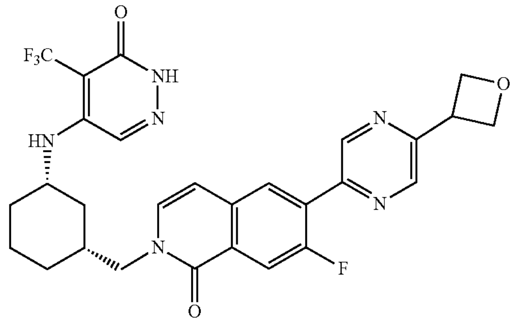 [SMILES: O=c1[nH]ncc(N[C@H]2CCC[C@@H](Cn3ccc4cc(-c5cnc(C6COC6)cn5)c(F)cc4c3=O)C2)c1C(F)(F)F] | 1H NMR (400 MHZ, DMSO-d6) δ 12.42 (s, 1H), 9.16 (t, J = 1.9 Hz, 1H), 8.79 (d, J = 1.4 Hz, 1H), 8.29 (d, J = 7.2 Hz, 1H), 8.04 (d, J = 11.5 Hz, 1H), 7.91 (s, 1H), 7.48 (d, J = 7.4 Hz, 1H), 6.80 (d, J = 7.4 Hz, 1H), 6.32 (dd, J = 8.4, 4.0 Hz, 1H), 4.96 (dd, J = 8.5, 5.7 Hz, 2H), 4.85 (t, J = 6.2 Hz, 2H), 4.60 (ddd, J = 15.1, 8.4, 6.7 Hz, 1H), 3.89 (d, J = 7.0 Hz, 2H), 3.85-3.50 (m, 2H), 2.02 (s, OH), 1.91-1.64 (m, 4H), 1.57 (d, J = 12.8 Hz, 1H), 1.31 (dq, J = 34.8, 11.8 Hz, 3H), 0.94 (dd, J = 13.8, 10.4 Hz, 1H). ES/MS m/z: 571.2 [M + H]$^+$. |

-continued

| Ex. No. | Structure | 1H NMR/MS [M + H]$^+$ |
|---|---|---|
| 267 | 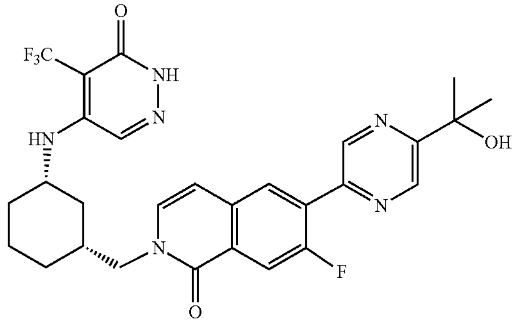 [SMILES: CC(C)(O)c1cnc(-c2cc3ccn(C[C@@H]4CCC[C@H](Nc5cn[nH]c(=O)c5C(F)(F)F)C4)c(=O)c3cc2F)cn1] | 1H NMR (400 MHZ, DMSO-d6) δ 12.42 (s, 1H), 9.17-8.87 (m, 2H), 8.28 (d, J = 7.2 Hz, 1H), 8.03 (d, J = 11.4 Hz, 1H), 7.91 (s, 1H), 7.48 (d, J = 7.3 Hz, 1H), 6.79 (d, J = 7.4 Hz, 1H), 6.42-6.23 (m, 1H), 4.02-3.58 (m, 7H), 2.02 (s, 1H), 1.86-1.67 (m, 3H), 1.53 (s, 8H), 1.31 (dq, J = 35.2, 12.0 Hz, 3H), 0.95 (q, J = 12.2 Hz, 1H). ES/MS m/z: 573.2 [M + H]$^+$. |
| 268 | 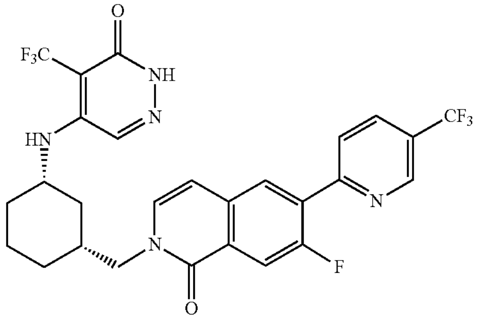 [SMILES: O=c1[nH]ncc(N[C@H]2CCC[C@@H](Cn3ccc4cc(-c5ccc(C(F)(F)F)cn5)c(F)cc4c3=O)C2)c1C(F)(F)F] | 1H NMR (400 MHZ, DMSO-d6) δ 12.42 (s, 1H), 9.22-9.14 (m, 1H), 8.41 (dd, J = 8.4, 2.4 Hz, 1H), 8.30 (d, J = 7.3 Hz, 1H), 8.12 (d, J = 8.3 Hz, 1H), 8.03 (d, J = 11.7 Hz, 1H), 7.91 (s, 1H), 7.49 (d, J = 7.4 Hz, 1H), 6.80 (d, J = 7.4 Hz, 1H), 6.32 (dd, J = 8.5, 4.0 Hz, 1H), 3.89 (d, J = 7.0 Hz, 2H), 3.73 (d, J= 9.7 Hz, 1H), 2.02 (s, 1H), 1.86-1.69 (m, 3H), 1.57 (d, J = 12.8 Hz, 1H), 1.31 (dq, J = 34.3, 12.2, 11.6 Hz, 3H), 0.95 (q, J = 13.1, 12.5 Hz, 1H). ES/MS m/z: 582.1 [M + H]$^+$. |
| 269 | 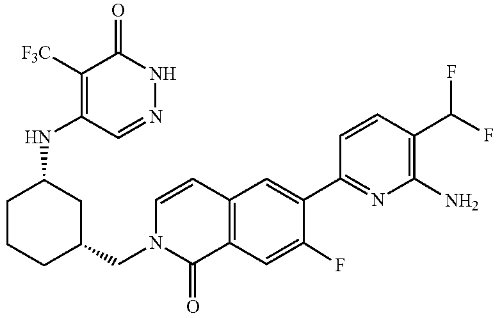 [SMILES: Nc1nc(-c2cc3ccn(C[C@@H]4CCC[C@H](Nc5cn[nH]c(=O)c5C(F)(F)F)C4)c(=O)c3cc2F)ccc1C(F)F] | 1H NMR (400 MHZ, DMSO-d6) δ 12.42 (s, 1H), 8.14 (d, J = 7.3 Hz, 1H), 7.96 (d, J = 11.6 Hz, 1H), 7.90 (s, 1H), 7.79 (d, J = 7.8 Hz, 1H), 7.45 (d, J = 7.4 Hz, 1H), 7.26-6.93 (m, 2H), 6.72 (d, J = 7.4 Hz, 1H), 6.32 (dd, J = 8.4, 4.0 Hz, 1H), 3.87 (d, J = 7.0 Hz, 2H), 3.73 (d, J = 10.4 Hz, 1H), 2.01 (s, 1H), 1.86-1.66 (m, 3H), 1.56 (d, J = 12.7 Hz, 1H), 1.31 (dq, J= 35.0, 11.9 Hz, 3H), 0.95 (q, J = 12.0 Hz, 1H). ES/MS m/z: 579.2 [M + H]$^+$. |
| 270 | 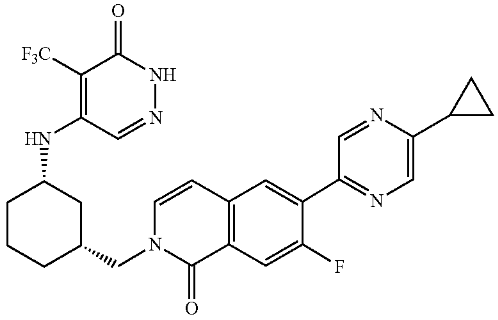 [SMILES: O=c1[nH]ncc(N[C@H]2CCC[C@@H](Cn3ccc4cc(-c5cnc(C6CC6)cn5)c(F)cc4c3=O)C2)c1C(F)(F)F] | 1H NMR (400 MHZ, DMSO-d6) δ 12.42 (s, 1H), 8.92 (t, J = 2.0 Hz, 1H), 8.82 (d, J = 1.5 Hz, 1H), 8.26 (d, J = 7.3 Hz, 1H), 8.00 (d, J = 11.6 Hz, 1H), 7.90 (s, 1H), 7.47 (d, J = 7.4 Hz, 1H), 6.78 (d, J = 7.3 Hz, 1H), 6.37-6.27 (m, 1H), 3.88 (d, J = 7.0 Hz, 2H), 3.79-3.66 (m, 1H), 2.37-2.26 (m, 1H), 2.10-1.95 (m, 1H), 1.84-1.68 (m, 3H), 1.56 (br. d, J = 11.8 Hz, 1H), 1.45-1.20 (m, 3H), 1.18-1.08 (m, 2H), 1.08-1.02 (m, 2H), 1.01-0.88 (m, 1H). ES/MS m/z: 555.2 [M + H]$^+$. |

-continued

| Ex. No. | Structure | 1H NMR/MS [M + H]+ |
|---|---|---|
| 271 | 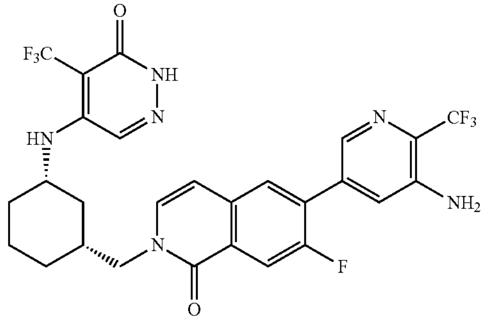 [SMILES: Nc1cc(-c2cc3ccn(C[C@@H]4CCC[C@H](Nc5cn[nH]c(=O)c5C(F)(F)F)C4)c(=O)c3cc2F)cnc1C(F)(F)F] | 1H NMR (400 MHZ, DMSO-d6) δ 12.43 (s, 1H), 8.08 (d, J = 1.6 Hz, 1H), 8.00 (d, J = 11.1 Hz, 1H), 7.94 (d, J = 7.3 Hz, 1H), 7.91 (s, 1H), 7.52 (d, J = 1.8 Hz, 1H), 7.48 (d, J = 7.4 Hz, 1H), 6.72 (d, J = 7.4 Hz, 1H), 6.38-6.28 (m, 1H), 3.89 (d, J = 7.0 Hz, 2H), 3.81-3.66 (m, 1H), 2.09-1.94 (m, 1H), 1.87-1.65 (m, 3H), 1.63-1.50 (m, 1H), 1.47-1.19 (m, 3H), 1.03-0.87 (m, 1H). ES/MS m/z: 597.1 $[M + H]^+$. |
| 272 | 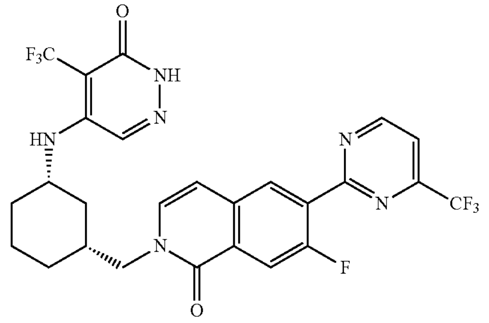 [SMILES: O=c1[nH]ncc(N[C@H]2CCC[C@@H](Cn3ccc4cc(-c5nccc(C(F)(F)F)n5)c(F)cc4c3=O)C2)c1C(F)(F)F] | 1H NMR (400 MHZ, DMSO-d6) δ 12.43 (s, 1H), 9.40 (d, J = 5.1 Hz, 1H), 8.40 (d, J = 7.1 Hz, 1H), 8.12 (d, J = 5.0 Hz, 1H), 8.03 (d, J = 11.3 Hz, 1H), 7.91 (s, 1H), 7.50 (d, J = 7.4 Hz, 1H), 6.85 (d, J = 7.4 Hz, 1H), 6.38-6.25 (m, 1H), 3.89 (d, J = 7.0 Hz, 2H), 3.81-3.65 (m, 1H), 2.12-1.95 (m, 1H), 1.87-1.66 (m, 3H), 1.63-1.48 (m, 1H), 1.47-1.21 (m, 3H), 1.05-0.87 (m, 1H). ES/MS m/z: 583.2 $[M + H]^+$. |
| 273 | 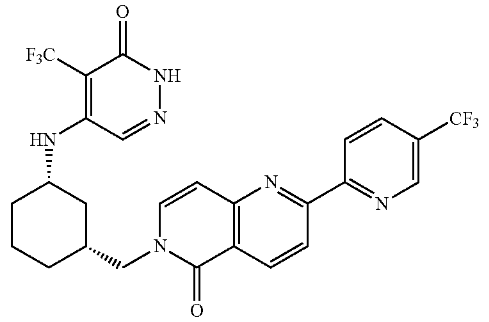 [SMILES: O=c1[nH]ncc(N[C@H]2CCC[C@@H](Cn3ccc4nc(-c5ccc(C(F)(F)F)cn5)ccc4c3=O)C2)c1C(F)(F)F] | 1H NMR (400 MHZ, DMSO-d6) δ 12.42 (s, 1H), 9.16 (s, 1H), 8.80-8.68 (m, 2H), 8.54 (d, J = 8.4 Hz, 1H), 8.45 (dd, J = 8.6, 2.3 Hz, 1H), 7.91 (s, 1H), 7.79 (d, J = 7.6 Hz, 1H), 6.83 (d, J = 7.6 Hz, 1H), 6.38-6.26 (m, 1H), 3.91 (d, J = 6.9 Hz, 2H), 3.80-3.65 (m, 1H), 2.13-1.97 (m, 1H), 1.86-1.76 (m, 2H), 1.77-1.69 (m, 1H), 1.64-1.54 (m, 1H), 1.46-1.20 (m, 3H), 1.03-0.87 (m, 1H). ES/MS m/z: 565.1 $[M + H]^+$. |
| 274 | 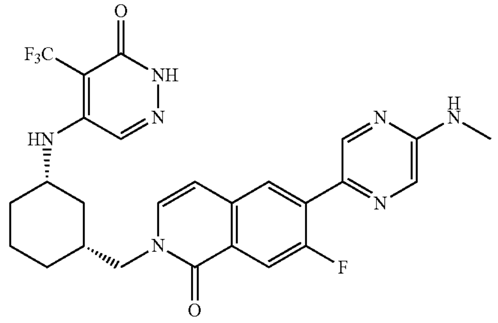 [SMILES: CNc1cnc(-c2cc3ccn(C[C@@H]4CCC[C@H](Nc5cn[nH]c(=O)c5C(F)(F)F)C4)c(=O)c3cc2F)cn1] | 1H NMR (400 MHZ, DMSO-d6) δ 12.42 (s, 1H), 8.52 (d, J = 1.9 Hz, 1H), 8.18 (d, J = 7.4 Hz, 1H), 8.10 (d, J = 1.5 Hz, 1H), 8.00-7.82 (m, 2H), 7.59-7.34 (m, 2H), 6.73 (d, J = 7.4 Hz, 1H), 6.32 (q, J = 4.6, 4.1 Hz, 1H), 3.86 (d, J = 7.0 Hz, 2H), 3.73 (s, 1H), 2.88 (s, 3H), 2.01 (s, 1H), 1.89-1.67 (m, 3H), 1.56 (d, J = 12.7 Hz, 1H), 1.32 (dp, J = 35.1, 12.2, 11.7 Hz, 3H), 0.94 (q, J = 12.1 Hz, 1H). ES/MS m/z: 544.5 $[M + H]^+$. |

-continued

| Ex. No. | Structure | 1H NMR/MS [M + H]$^+$ |
|---|---|---|
| 275 | 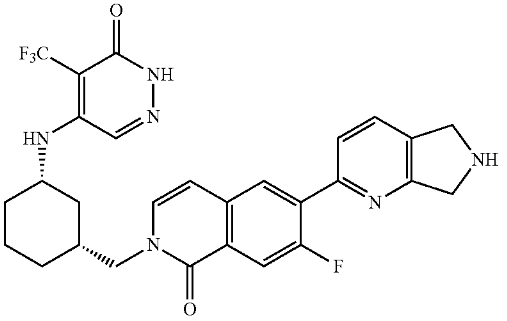 [SMILES: O=c1[nH]ncc(N[C@H]2CCC[C@@H](Cn3ccc4cc(-c5ccc6c(n5)CNC6)c(F)cc4c3=O)C2)c1C(F)(F)F] | 1H NMR (400 MHZ, DMSO-d6) δ 12.43 (s, 1H), 9.35 (d, J = 1.5 Hz, 1H), 9.26-9.10 (m, 4H), 8.32 (d, J = 7.2 Hz, 1H), 8.08 (d, J = 11.4 Hz, 1H), 7.90 (s, 1H), 7.51 (d, J = 7.4 Hz, 1H), 6.83 (d, J = 7.4 Hz, 1H), 6.33 (dt, J = 8.6, 3.9 Hz, 1H), 5.08 (d, J = 7.7 Hz, 2H), 4.97 (d, J = 7.7 Hz, 2H), 3.90 (d, J = 7.0 Hz, 2H), 3.72 (s, 1H), 2.03 (s, 1H), 1.89-1.65 (m, 3H), 1.57 (d, J = 12.7 Hz, 1H), 1.32 (dq, J = 34.7, 11.8 Hz, 3H), 1.10-0.78 (m, 1H). ES/MS m/z: 586.2 [M + H]$^+$. |
| 276 | 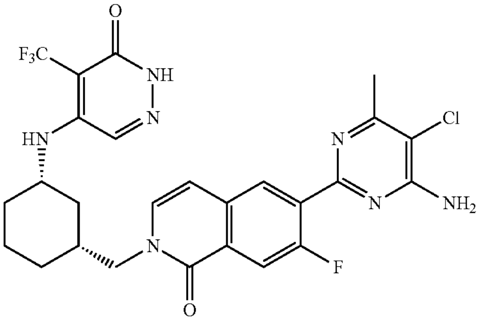 [SMILES: Cc1nc(-c2cc3ccn(C[C@@H]4CCC[C@H](Nc5cn[nH]c(=O)c5C(F)(F)F)C4)c(=O)c3cc2F)nc(N)c1Cl] | 1H NMR (400 MHZ, DMSO-d6) δ 12.42 (s, 1H), 8.11 (d, J = 7.0 Hz, 1H), 7.93 (d, J = 11.0 Hz, 1H), 7.90 (s, 1H), 7.45 (d, J = 7.4 Hz, 1H), 7.85-7.08 (br. m, 2H), 6.75 (d, J = 7.4 Hz, 1H), 6.37-6.28 (m, 1H), 3.87 (d, J = 7.0 Hz, 2H), 3.80-3.66 (m, 1H), 2.45 (s, 3H), 2.08-1.95 (m, 1H), 1.86-1.68 (m, 3H), 1.56 (d, J = 12.3 Hz, 1H), 1.44-1.20 (m, 3H), 1.02-0.88 (m, 1H). ES/MS m/z: 578.2 [M + H]$^+$. |
| 277 | 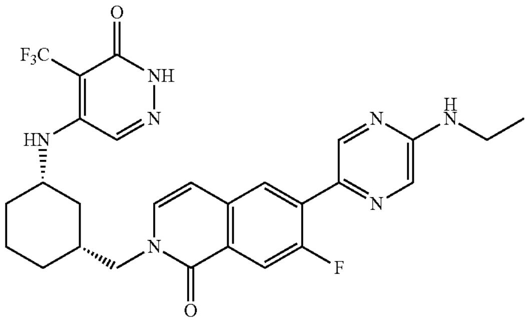 [SMILES: CCNc1cnc(-c2cc3ccn(C[C@@H]4CCC[C@H](Nc5cn[nH]c(=O)c5C(F)(F)F)C4)c(=O)c3cc2F)cn1] | 1H NMR (400 MHZ, DMSO-d6) δ 12.42 (s, 1H), 8.50 (t, J = 1.8 Hz, 1H), 8.18 (d, J = 7.4 Hz, 1H), 8.09 (d, J = 1.4 Hz, 1H), 7.98-7.82 (m, 2H), 7.53 (s, 1H), 7.41 (d, J = 7.4 Hz, 1H), 6.72 (d, J = 7.3 Hz, 1H), 6.32 (dd, J = 8.5, 3.9 Hz, 1H), 3.86 (d, J = 7.0 Hz, 2H), 3.73 (d, J = 10.2 Hz, 1H), 3.36 (q, J = 7.2 Hz, 2H), 2.01 (s, 1H), 1.88-1.63 (m, 3H), 1.56 (d, J= 12.8 Hz, 1H), 1.48-1.11 (m, 6H), 0.94 (q, J = 11.9 Hz, 1H). ES/MS m/z: 558.2 [M + H]$^+$. |
| 278 | 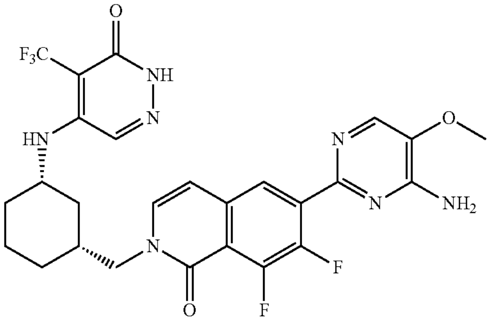 [SMILES: COc1cnc(-c2cc3ccn(C[C@@H]4CCC[C@H](Nc5cn[nH]c(=O)c5C(F)(F)F)C4)c(=O)c3c(F)c2F)nc1N] | 1H NMR (400 MHZ, DMSO-d6) δ 12.43 (s, 1H), 8.06 (s, 1H), 7.94-7.86 (m, 2H), 7.85-7.52 (m, 2H), 7.49 (d, J = 7.3 Hz, 1H), 6.70 (d, J = 7.3 Hz, 1H), 6.37-6.28 (m, 1H), 3.94 (s, 3H), 3.88-3.78 (m, 2H), 3.78-3.65 (m, 1H), 2.07-1.94 (m, 1H), 1.86-1.68 (m, 3H), 1.57 (d, J = 12.5 Hz, 1H), 1.46-1.19 (m, 3H), 1.01-0.87 (m, 1H). ES/MS m/z: 578.1 [M + H]$^+$. |

-continued

| Ex. No. | Structure | 1H NMR/MS $[M + H]^+$ |
|---|---|---|
| 279 | 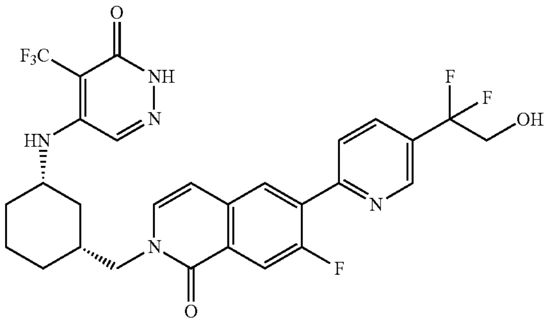 [SMILES: O=c1[nH]ncc(N[C@H]2CCC[C@@H](Cn3ccc4cc(-c5ccc(C(F)(F)CO)cn5)c(F)cc4c3=O)C2)c1C(F)(F)F] | 1H NMR (400 MHZ, DMSO-d6) δ 12.42 (s, 1H), 8.92 (d, J = 2.2 Hz, 1H), 8.28 (d, J = 7.4 Hz, 1H), 8.13 (dd, J = 8.4, 2.3 Hz, 1H), 8.06-7.98 (m, 2H), 7.91 (s, 1H), 7.48 (d, J = 7.4 Hz, 1H), 6.79 (d, J = 7.4 Hz, 1H), 6.38-6.29 (m, 1H), 3.97 (t, J = 13.7 Hz, 2H), 3.89 (d, J = 7.0 Hz, 2H), 3.73 (d, J = 10.7 Hz, 1H), 2.05 (d, J = 21.2 Hz, 1H), 1.85-1.66 (m, 3H), 1.57 (d, J = 12.8 Hz, 1H), 1.31 (dq, J = 35.0, 11.8 Hz, 3H), 0.95 (q, J = 12.5, 12.0 Hz, 1H). ES/MS m/z: 594.2 $[M + H]^+$. |
| 280 | 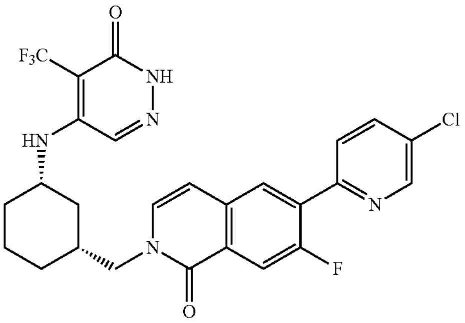 [SMILES: O=c1[nH]ncc(N[C@H]2CCC[C@@H](Cn3ccc4cc(-c5ccc(Cl)cn5)c(F)cc4c3=O)C2)c1C(F)(F)F] | 1H NMR (400 MHZ, DMSO-d6) δ 12.42 (s, 1H), 8.83 (d, J = 2.5 Hz, 1H), 8.25 (d, J = 7.4 Hz, 1H), 8.12 (dd, J = 8.5, 2.6 Hz, 1H), 8.00 (d, J = 11.7 Hz, 1H), 7.97-7.87 (m, 2H), 7.47 (d, J = 7.4 Hz, 1H), 6.78 (d, J = 7.4 Hz, 1H), 6.32 (dd, J = 8.5, 3.8 Hz, 1H), 3.88 (d, J = 7.0 Hz, 2H), 3.73 (s, 1H), 2.02 (s, 1H), 1.86-1.67 (m, 3H), 1.56 (d, J = 12.7 Hz, 1H), 1.31 (dq, J = 35.0, 12.2 Hz, 3H), 0.95 (q, J = 12.2 Hz, 1H). ES/MS m/z: 548.1 $[M + H]^+$. |
| 281 | 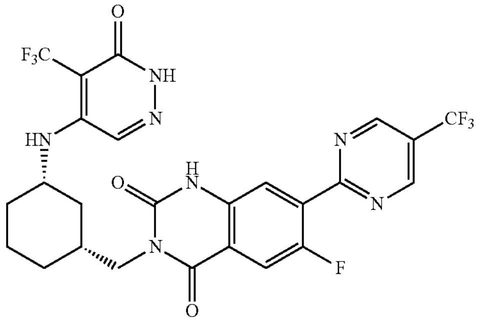 [SMILES: O=c1[nH]ncc(N[C@H]2CCC[C@@H](Cn3c(=O)[nH]c4cc(-c5ncc(C(F)(F)F)cn5)c(F)cc4c3=O)C2)c1C(F)(F)F] | 1H NMR (400 MHZ, DMSO-d6) δ 12.40 (s, 1H), 11.67 (s, 1H), 9.48 (s, 2H), 7.98-7.86 (m, 2H), 7.81 (d, J = 10.4 Hz, 1H), 6.31 (dd, J = 8.5, 3.9 Hz, 1H), 3.84-3.79 (m, 2H), 3.74-3.67 (m, 1H), 2.06-1.89 (m, 1H), 1.87-1.75 (m, 2H), 1.75-1.67 (m, 1H), 1.66-1.54 (m, 1H), 1.46-1.20 (m, 3H), 1.02-0.82 (m, 1H). ES/MS m/z: 600.1 $[M + H]^+$. |
| 282 | 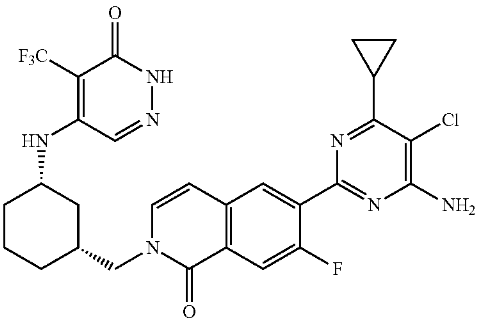 [SMILES: Nc1nc(-c2cc3ccn(C[C@@H]4CCC[C@H](Nc5cn[nH]c(=O)c5C(F)(F)F)C4)c(=O)c3cc2F)nc(C2CC2)c1Cl] | 1H NMR (400 MHZ, DMSO-d6) δ 12.43 (s, 1H), 8.09 (d, J = 7.1 Hz, 1H), 7.95-7.87 (m, 2H), 7.44 (d, J = 7.4 Hz, 1H), 7.56-7.01 (m, 2H), 6.73 (d, J = 7.4 Hz, 1H), 6.37-6.27 (m, 1H), 3.90-3.83 (m, 2H), 3.79-3.66 (m, 1H), 2.46-2.35 (m, 1H), 2.06-1.96 (m, 1H), 1.87-1.65 (m, 3H), 1.56 (d, J = 12.7 Hz, 1H), 1.45-1.19 (m, 3H), 1.13-1.01 (m, 4H), 1.01-0.87 (m, 1H). ES/MS m/z: 605.2 $[M + H]^+$. |

-continued

| Ex. No. | Structure | 1H NMR/MS [M + H]$^+$ |
|---|---|---|
| 283 | 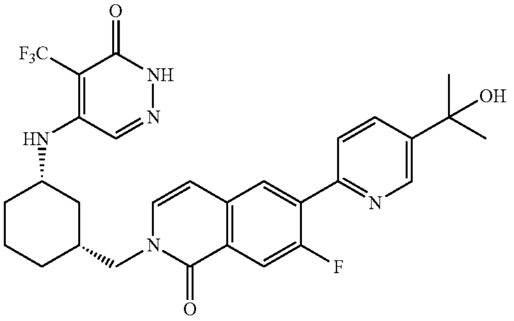 [SMILES: CC(C)(O)c1ccc(-c2cc3ccn(C[C@@H]4CCC[C@H](Nc5cn[nH]c(=O)c5C(F)(F)F)C4)c(=O)c3cc2F)nc1] | 1H NMR (400 MHZ, DMSO-d6) δ 8.87 (d, J = 2.3 Hz, 1H), 8.24 (d, J = 7.4 Hz, 1H), 8.06-7.95 (m, 2H), 7.91 (s, 1H), 7.83 (dd, J = 8.5, 2.2 Hz, 1H), 7.45 (d, J = 7.4 Hz, 1H), 6.77 (d, J = 7.4 Hz, 1H), 6.32 (dd, J = 8.4, 4.0 Hz, 1H), 3.88 (d, J = 7.0 Hz, 2H), 3.73 (s, 1H), 2.02 (s, 1H), 1.86-1.65 (m, 3H), 1.51 (s, 7H), 1.33 (dp, J = 34.8, 12.3, 11.8 Hz, 3H), 0.95 (q, J = 11.8, 11.3 Hz, 1H). ES/MS m/z: 572.2 [M + H]$^+$. |
| 284 | 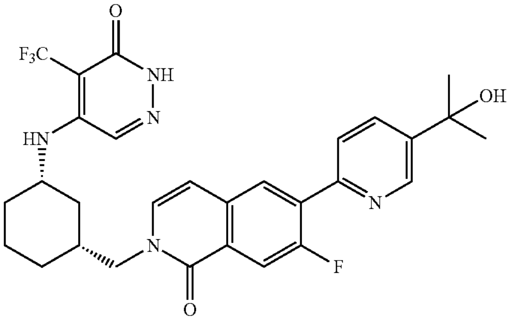 [SMILES: CC(C)(O)c1ccc(-c2cc3ccn(C[C@@H]4CCC[C@H](Nc5cn[nH]c(=O)c5C(F)(F)F)C4)c(=O)c3cc2F)nc1] | 1H NMR (400 MHZ, DMSO-d6) δ 12.42 (s, 1H), 9.06 (s, 2H), 8.32 (d, J = 7.2 Hz, 1H), 7.98 (d, J = 11.3 Hz, 1H), 7.91 (s, 1H), 7.47 (d, J = 7.3 Hz, 1H), 6.79 (d, J = 7.4 Hz, 1H), 6.38-6.28 (m, 1H), 3.88 (d, J = 7.0 Hz, 2H), 3.73 (s, 1H), 2.02 (s, 1H), 1.76 (dd, J = 30.7, 10.4 Hz, 3H), 1.55 (s, 7H), 1.33 (dp, J= 34.2, 12.4, 11.7 Hz, 3H), 0.97 (dd, J = 13.8, 10.3 Hz, 1H). ES/MS m/z: 573.2 [M + H]$^+$. |
| 285 | 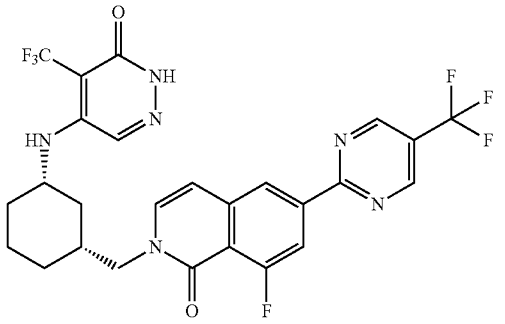 [SMILES: O=c1[nH]ncc(N[C@H]2CCC[C@@H](Cn3ccc4cc(-c5ncc(C(F)(F)F)cn5)cc(F)c4c3=O)C2)c1C(F)(F)F] | 1H NMR (400 MHz, DMSO-d6) δ 12.42 (s, 1H), 9.45 (s, 2H), 8.56 (s, 1H), 8.14-7.99 (m, 1H), 7.91 (s, 1H), 7.57 (d, J = 7.3 Hz, 1H), 6.92-6.80 (m, 1H), 6.40-6.23 (m, 1H), 3.91-3.78 (m, 2H), 3.78-3.66 (m, 1H), 2.09-1.93 (m, 1H), 1.86-1.67 (m, 3H), 1.65-1.51 (m, 1H), 1.47-1.16 (m, 3H), 1.02-0.85 (m, 1H). ES/MS m/z: 583.1 [M + H]$^+$. |

The following intermediates were synthesized using the procedure as described in Intermediate 41 from the corresponding starting materials.

| Intermediate No. | Structure | LCMS (ESI, m/z): [M + H]$^+$ |
|---|---|---|
| 51 | 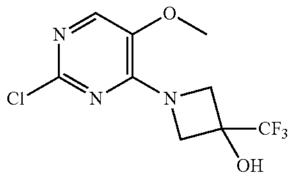 [SMILES: COc1cnc(Cl)nc1N1CC(O)(C(F)(F)F)C1] | 284.2 |
| 52 | 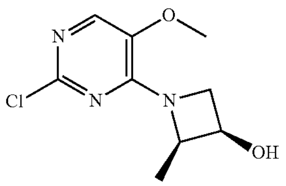 | 268.2 |

-continued

| Intermediate No. | Structure | LCMS (ESI, m/z): [M + H]$^+$ |
|---|---|---|
| 53 | 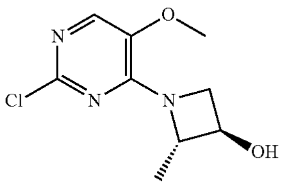 | 268.2 |
| 54 | 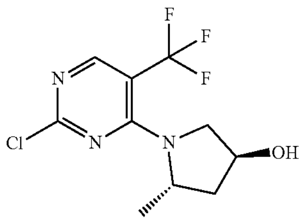 [SMILES: C[C@H]1C[C@H](O)CN1c1nc(Cl)ncc1C(F)(F)F] | 264.2 |

-continued

| Intermediate No. | Structure | LCMS (ESI, m/z): [M + H]$^+$ |
|---|---|---|
| 55 | 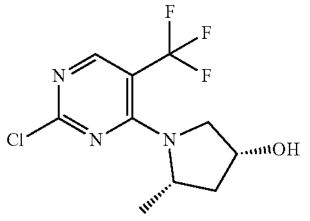 [SMILES: C[C@H]1C[C@@H](O)CN1c1nc(Cl)ncc1C(F)(F)F] | 264.2 |
| 56 | 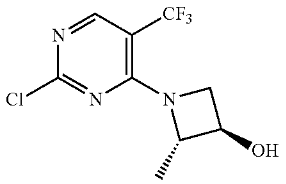 [SMILES: C[C@H]1[C@H](O)CN1c1nc(Cl)ncc1C(F)(F)F] | 267.2 |
| 57 | 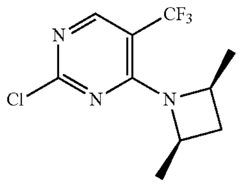 [SMILES: C[C@@H]1C[C@H](C)N1c1nc(Cl)ncc1C(F)(F)F] | 266.2 |

Intermediate 58: 3-[2-chloro-5-(trifluoromethyl) pyrimidin-4-yl]-1,3-thiazolidine 1,1-dioxide

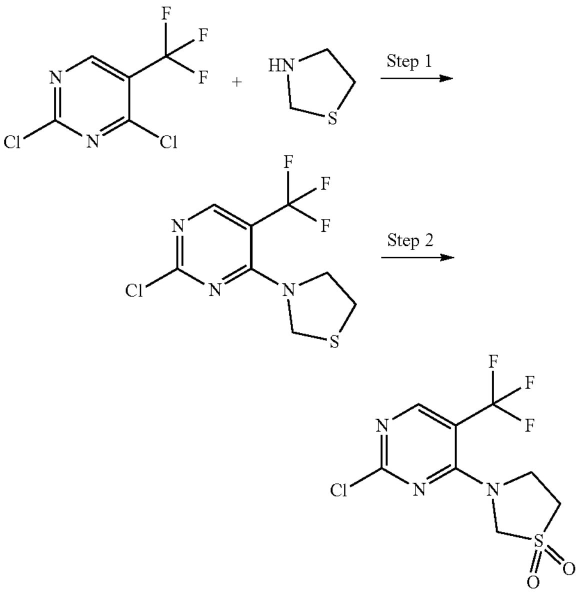

Intermediate 58

Step 1. 2,4-dichloro-5-(trifluoromethyl)pyrimidine (656 mg, 3.02 mmol), thiazolidine (0.239 ml, 3.02 mmol), and triethylamine (1.26 ml, 9.0 mmol) were stirred in DMF at room temperature for 18 hr. Reaction was then poured into water and extracted with $Et_2O$. The organic layer was washed with brine and dried over $MgSO_4$. The crude product was purified via prep-HPLC (5-100% MeCN in water, 0.1% TFA) to provide 3-[2-chloro-5-(trifluoromethyl)pyrimidin-4-yl]thiazolidine. ES/MS: m/z 270.50 [M+H]$^+$.

Step 2. 3-[2-chloro-5-(trifluoromethyl)pyrimidin-4-yl] thiazolidine (125 mg, 0.464 mmol), $NaHCO_3$ (195 mg, 2.32 mmol), and 3-Chloroperoxybenzoic acid (260 mg, 1.16 mmol) was stirred in DCM (5.0 ml) at room temperature for 18 hr. Reaction was then poured into sat. aq. $NaHCO_3$ and extracted with DCM, washed with brine and dried over $MgSO_4$. The crude product was purified with column chromatography eluting with EtOAc in hexanes 0-100% to provide 3-[2-chloro-5-(trifluoromethyl)pyrimidin-4-yl]-1,3-thiazolidine 1,1-dioxide. ES/MS: m/z 301.9 [M+H]$^+$.

Intermediate 59: Preparation of 2-chloro-5-(3-fluorooxetan-3-yl)pyrimidin-4-amine

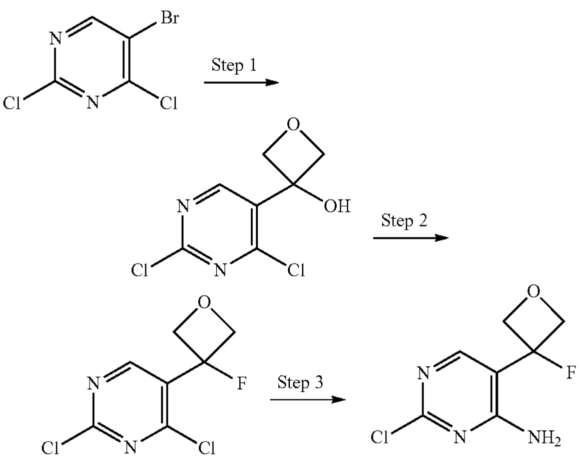

Intermediate 59

Step 1. In a flask were placed 5-bromo-2,4-dichloropyrimidine (800 mg, 3.51 mmol) and THF (18 mL). The solution was sparged with nitrogen gas and cooled to −78° C. 2.0 M Isopropylmagnesium chloride in THF (1.93 mL, 3.86 mmol) was added dropwise. After 15 minutes, 3-oxetanone (0.25 mL, 3.86 mmol) was added dropwise and the reaction was warmed to 0° C. After 1 hour the reaction is quenched with saturated $NH_4Cl$, diluted with water and extracted with EtOAc. The organic layer is concentrated and purified by flash chromatography to give 3-(2,4-dichloropyrimidin-5-yl)oxetan-3-ol. 1H NMR (400 MHz, Chloroform-d) δ 8.54 (s, 1H), 5.19 (dd, J=7.7, 1.0 Hz, 2H), 4.90 (dd, J=7.7, 1.0 Hz, 2H), 3.50 (s, 1H).

Step 2. In a vial were placed 3-(2,4-dichloropyrimidin-5-yl)oxetan-3-ol (114 mg, 0.52 mmol) and XtalFluor-M (251 mg, 1.03 mmol) in DCE (5.0 mL). The mixture was heated at 75° C. and stirred overnight. The mixture was then cooled to room temperature and purified by column chromatography (Hex/EtOAc) to give 2,4-dichloro-5-(3-fluorooxetan-3-yl)pyrimidine. 1H NMR (400 MHz, Chloroform-d) δ 8.59 (d, J=1.9 Hz, 1H), 5.29-5.04 (m, 4H). 19F NMR (376 MHz, Chloroform-d) 6-141.21 (m, 1F).

Step 3. In a vial were placed 2,4-dichloro-5-(3-fluorooxetan-3-yl)pyrimidine (32 mg, 0.14 mmol) and 0.4 M ammonia in dioxane (1.08 mL, 0.43 mmol). The mixture was stirred at room temperature for 4 hours and concentrated to give 2-chloro-5-(3-fluorooxetan-3-yl)pyrimidin-4-amine. ES/MS m/z=203.9 [M+H].

The Following compounds were synthesized using the procedure as described in Example 17, with the following modification: 20 mol % of cataCXium Pd G4 and 2 M aqueous sodium carbonate (1.9 equiv.) were added following the completion of the borylation step.

| Ex. No. | Structure | 1H NMR/MS [M + H]+ |
|---|---|---|
| 286 | 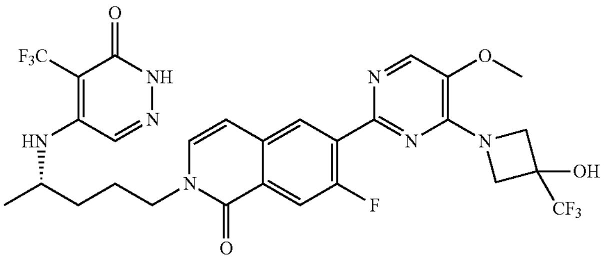 [SMILES: COc1cnc(-c2cc3ccn(CCC[C@H](C)Nc4cn[nH]c(=O)c4C(F)(F)F)c(=O)c3cc2F)nc1N1CC(O)(C(F)(F)F)C1] | 1H NMR (400 MHz, DMSO-d6) δ 12.44 (s, 1H), 8.22 (d, J = 7.2 Hz, 1H), 8.14 (s, 1H), 7.99-7.88 (m, 2H), 7.49 (d, J = 7.4 Hz, 1H), 6.77 (d, J = 7.4 Hz, 1H), 6.43-6.27 (m, 1H), 4.55-4.50 (m, 2H), 4.35-4.23 (m, 3H), 4.06-3.92 (m, 3H), 3.90 (s, 3H), 1.82-1.57 (m, 3H), 1.58-1.41 (m, 1H), 1.17 (d, J = 6.3 Hz, 3H). ES/MS m/z: 658.2 [M + H]+. |
| 287 | 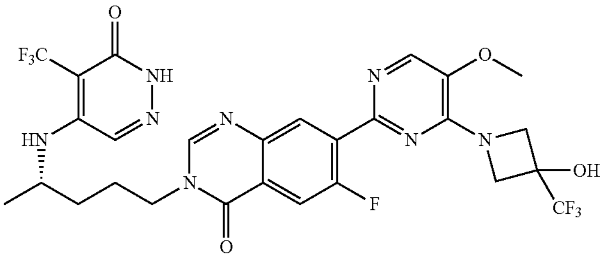 [SMILES: COc1cnc(-c2cc3ncn(CCC[C@H](C)Nc4cn[nH]c(=O)c4C(F)(F)F)c(=O)c3cc2F)nc1N1CC(O)(C(F)(F)F)C1] | 1H NMR (400 MHz, DMSO-d6) δ 12.44 (s, 1H), 8.42 (s, 1H), 8.24-8.07 (m, 2H), 7.91 (d, J = 10.9 Hz, 2H), 6.41-6.26 (m, 1H), 4.51 (d, J = 10.8 Hz, 2H), 4.30-4.21 (m, 3H), 4.05-3.96 (m, 3H), 3.90 (s, 3H), 1.84-1.58 (m, 3H), 1.60-1.43 (m, 1H), 1.17 (d, J = 6.3 Hz, 3H). ES/MS m/z: 659.2 [M + H]+. |
| 288 | 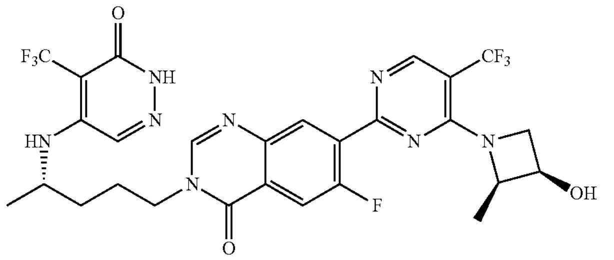 [SMILES: C[C@@H]1[C@H](O)CN1c1nc(-c2cc3ncn(CCC[C@H](C)Nc4cn[nH]c(=O)c4C(F)(F)F)c(=O)c3cc2F)ncc1C(F)(F)F] | 1H NMR (400 MHz, DMSO-d6) δ 12.44 (s, 1H), 8.71 (s, 1H), 8.43 (s, 1H), 8.26 (d, J = 6.7 Hz, 1H), 7.99-7.85 (m, 2H), 6.40-6.29 (m, 1H), 4.88-4.78 (m, 2H), 4.64-4.56 (m, 1H), 4.49-4.39 (m, 1H), 4.09-3.92 (m, 4H), 1.84-1.60 (m, 3H), 1.60-1.48 (m, 1H), 1.44 (d, J = 6.5 Hz, 3H), 1.17 (d, J = 6.3 Hz, 3H). ES/MS m/z: 643.2 [M + H]+. |
| 289 | 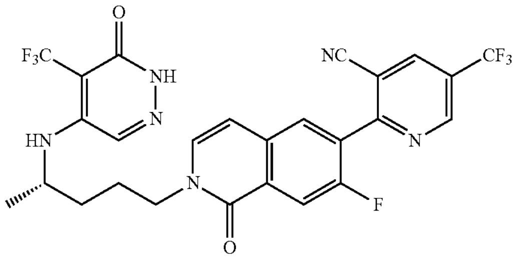 [SMILES: C[C@@H](CCCn1ccc2cc(-c3ncc(C(F)(F)F)cc3C#N)c(F)cc2c1=O)Nc1cn[nH]c(=O)c1C(F)(F)F] | 1H NMR (400 MHz, DMSO-d6) δ 12.44 (s, 1H), 9.45 (dd, J = 2.3, 1.0 Hz, 1H), 9.18-9.11 (m, 1H), 8.14-8.03 (m, 2H), 7.93 (s, 1H), 7.57 (d, J = 7.4 Hz, 1H), 6.79 (d, J = 7.4 Hz, 1H), 6.42-6.30 (m, 1H), 4.06-3.93 (m, 3H), 1.82-1.61 (m, 3H), 1.58-1.46 (m, 1H), 1.17 (d, J = 6.3 Hz, 3H). ES/MS m/z: 581.1 [M + H]+. |
| 290 | 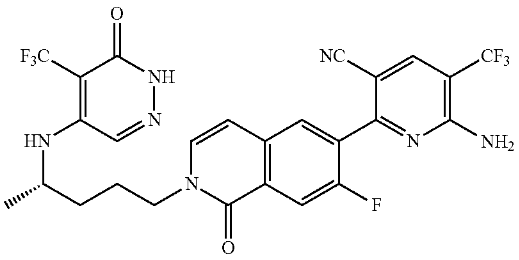 [SMILES: C[C@@H](CCCn1ccc2cc(-c3nc(N)c(C(F)(F)F)cc3C#N)c(F)cc2c1=O)Nc1cn[nH]c(=O)c1C(F)(F)F] | 1H NMR (400 MHz, DMSO-d6) δ 12.44 (s, 1H), 8.43 (s, 1H), 8.04 (d, J = 10.4 Hz, 1H), 7.95 (d, J = 6.8 Hz, 1H), 7.93 (s, 1H), 7.80 (br s, 2H), 7.54 (d, J = 7.4 Hz, 1H), 6.76 (d, J = 7.4 Hz, 1H), 6.41-6.30 (m, 1H), 4.07-3.92 (m, 3H), 1.81-1.60 (m, 3H), 1.57-1.44 (m, 1H), 1.17 (d, J = 6.3 Hz, 3H). ES/MS m/z: 596.3 [M + H]+. |
| 291 | 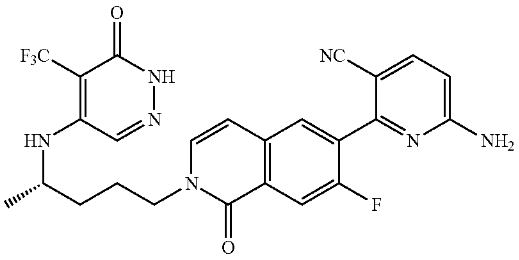 [SMILES: C[C@@H](CCCn1ccc2cc(-c3nc(N)ccc3C#N)c(F)cc2c1=O)Nc1cn[nH]c(=O)c1C(F)(F)F] | 1H NMR (400 MHz, DMSO-d6) δ 12.43 (s, 1H), 7.99 (d, J = 10.4 Hz, 1H), 7.93 (s, 1H), 7.88 (d, J = 6.9 Hz, 1H), 7.85 (d, J = 8.8 Hz, 1H), 7.52 (d, J = 7.4 Hz, 1H), 7.28 (br s, 2H), 6.75 (d, J = 7.4 Hz, 1H), 6.59 (d, J = 8.8 Hz, 1H), 6.40-6.32 (m, 1H), 4.07-3.93 (m, 3H), 1.81-1.60 (m, 3H), 1.57-1.44 (m, 1H), 1.17 (d, J = 6.3 Hz, 3H). ES/MS m/z: 528.3 [M + H]+. |

-continued

| Ex. No. | Structure | 1H NMR/MS [M + H]+ |
| --- | --- | --- |
| 292 | 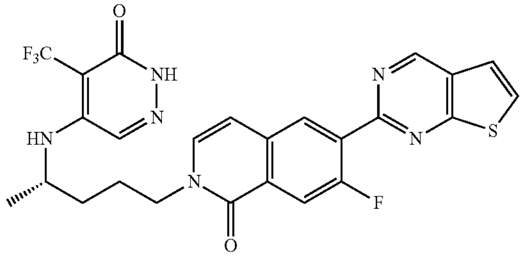 [SMILES: C[C@@H](CCCn1ccc2cc(-c3ncc4ccsc4n3)c(F)cc2c1=O)Nc1cn[nH]c(=O)c1C(F)(F)F] | 1H NMR (400 MHz, DMSO-d6) δ 12.44 (s, 1H), 9.51 (s, 1H), 8.44 (d, J = 7.1 Hz, 1H), 8.09 (d, J = 5.9 Hz, 1H), 8.00 (d, J = 11.4 Hz, 1H), 7.92 (s, 1H), 7.67 (d, J = 5.9 Hz, 1H), 7.50 (d, J = 7.3 Hz, 1H), 6.84 (d, J = 7.3 Hz, 1H), 6.39-6.31 (m, 1H), 4.06-3.93 (m, 3H), 1.86-1.45 (m, 4H), 1.17 (d, J = 6.2 Hz, 3H). ES/MS m/z: 545.3 $[M + H]^+$. |
| 293 | 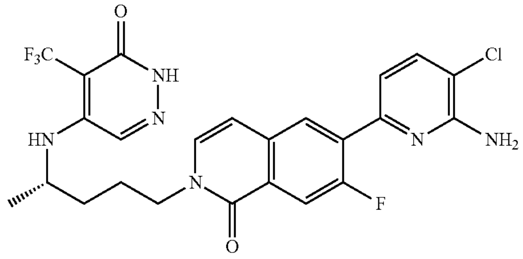 [SMILES: C[C@@H](CCCn1ccc2cc(-c3ccc(Cl)c(N)n3)c(F)cc2c1=O)Nc1cn[nH]c(=O)c1C(F)(F)F] | 1H NMR (400 MHz, DMSO-d6) δ 12.43 (s, 1H), 8.13 (d, J = 7.4 Hz, 1H), 7.94 (d, J = 11.7 Hz, 1H), 7.91 (s, 1H), 7.74 (d, J = 7.9 Hz, 1H), 7.47 (d, J = 7.4 Hz, 1H), 7.04 (dd, J = 8.0, 2.2 Hz, 1H), 6.72 (d, J = 7.4 Hz, 1H), 6.50 (br. s, 2H), 6.35 (dq, J = 7.0, 3.4 Hz, 1H), 4.02-3.94 (m, 3H), 1.79-1.59 (m, 3H), 1.56-1.45 (m, 1H), 1.17 (d, J = 6.3 Hz, 3H). ES/MS m/z: 537.2 $[M + H]^+$. |
| 294 | 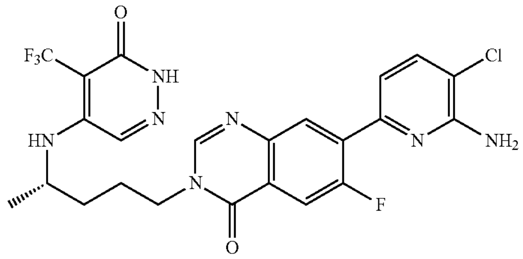 [SMILES: C[C@@H](CCCn1cnc2cc(-c3ccc(Cl)c(N)n3)c(F)cc2c1=O)Nc1cn[nH]c(=O)c1C(F)(F)F] | 1H NMR (400 MHz, DMSO-d6) δ 12.44 (s, 1H), 8.42 (s, 1H), 8.19 (d, J = 7.0 Hz, 1H), 7.94-7.87 (m, 2H), 7.75 (d, J = 8.0 Hz, 1H), 7.10 (dd, J = 8.0, 2.1 Hz, 1H), 6.35 (dd, J = 8.7, 3.8 Hz, 1H), 7.03-5.89 (m, 2H), 4.04-3.93 (m, 3H), 1.80-1.60 (m, 3H), 1.57-1.45 (m, 1H), 1.17 (d, J = 6.3 Hz, 3H). ES/MS m/z: 538.2 $[M + H]^+$. |
| 295 | 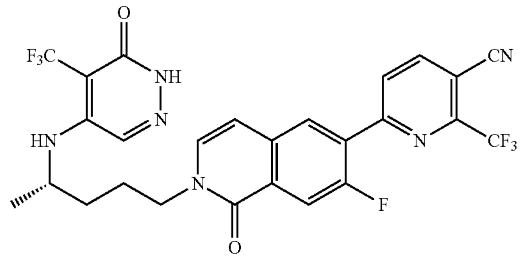 [SMILES: C[C@@H](CCCn1ccc2cc(-c3ccc(C#N)c(C(F)(F)F)n3)c(F)cc2c1=O)Nc1cn[nH]c(=O)c1C(F)(F)F] | 1H NMR (400 MHz, DMSO-d6) δ 12.42 (s, 1H), 8.83 (d, J = 8.3 Hz, 1H), 8.41 (d, J = 8.1 Hz, 1H), 8.29 (d, J = 7.2 Hz, 1H), 8.06 (d, J = 11.7 Hz, 1H), 7.90 (s, 1H), 7.54 (d, J = 7.4 Hz, 1H), 6.86 (d, J = 7.4 Hz, 1H), 6.39-6.30 (m, 1H), 4.03-3.98 (m, 3H), 1.80-1.60 (m, 3H), 1.59-1.42 (m, 1H), 1.16 (d, J = 6.6 Hz, 3H). ES/MS m/z: 581.3 $[M + H]^+$. |
| 296 | 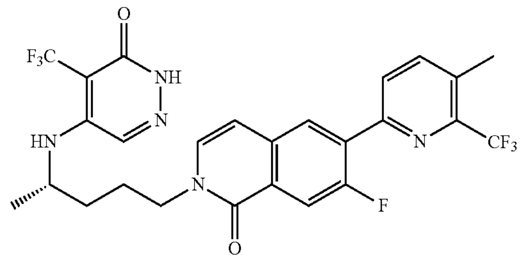 [SMILES: Cc1ccc(-c2cc3ccn(CCC[C@H](C)Nc4cn[nH]c(=O)c4C(F)(F)F)c(=O)c3cc2F)nc1C(F)(F)F] | 1H NMR (400 MHz, DMSO-d6) δ 12.43 (s, 1H), 8.19 (d, J = 7.3 Hz, 1H), 8.15-8.05 (m, 2H), 8.01 (d, J = 11.6 Hz, 1H), 7.91 (s, 1H), 7.50 (d, J = 7.4 Hz, 1H), 6.82 (d, J = 7.4 Hz, 1H), 6.40-6.30 (m, 1H), 4.04-3.93 (m, 3H), 2.54 (s, 3H), 1.82-1.59 (m, 3H), 1.55-1.45 (m, 1H), 1.16 (d, J = 6.4 Hz, 3H). ES/MS m/z: $[M + H]^+$. ES/MS m/z: 570.3 $[M + H]^+$. |
| 297 | 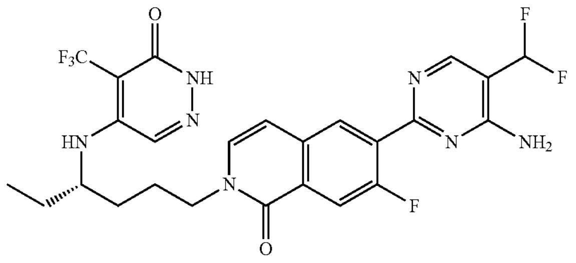 [SMILES: CC[C@@H](CCCn1ccc2cc(-c3ncc(C(F)F)c(N)n3)c(F)cc2c1=O)Nc1cn[nH]c(=O)c1C(F)(F)F] | 1H NMR (400 MHz, DMSO-d6) δ 12.42 (s, 1H), 8.50 (d, J = 1.4 Hz, 1H), 8.17 (d, J = 7.1 Hz, 1H), 7.95 (d, J = 11.4 Hz, 2H), 7.55 (s, 2H), 7.49 (d, J = 7.4 Hz, 1H), 7.10 (t, J = 54.1 Hz, 1H), 6.76 (d, J = 7.4 Hz, 1H), 6.28 (dd, J = 8.8, 3.9 Hz, 1H), 3.98 (t, J = 6.8 Hz, 2H), 3.93-3.73 (m, 1H), 1.87-1.44 (m, 5H), 0.82 (t, J = 7.3 Hz, 3H). ES/MS m/z: 568.3 $[M + H]^+$. |

-continued

| Ex. No. | Structure | 1H NMR/MS [M + H]$^+$ |
|---|---|---|
| 298 | 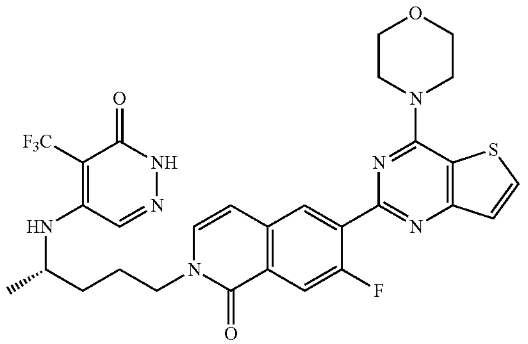 [SMILES: C[C@@H](CCCn1ccc2cc(-c3nc(N4CCOCC4)c4sccc4n3)c(F)cc2c1=O)Nc1cn[nH]c(=O)c1C(F)(F)F] | 1H NMR (400 MHz, DMSO-d6) δ 12.44 (s, 1H), 8.35 (d, J = 6.2 Hz, 2H), 7.97 (d, J = 11.4 Hz, 1H), 7.92 (s, 1H), 7.58 (d, J = 5.5 Hz, 1H), 7.49 (d, J = 7.4 Hz, 1H), 6.81 (d, J = 7.4 Hz, 1H), 6.41-6.31 (m, 1H), 4.06-3.96 (m, 7H), 3.83-3.78 (m, 4H), 1.82-1.59 (m, 3H), 1.59-1.44 (m, 1H), 1.17 (d, J = 6.2 Hz, 3H). ES/MS m/z: 630.2 [M + H]$^+$. |
| 299 | 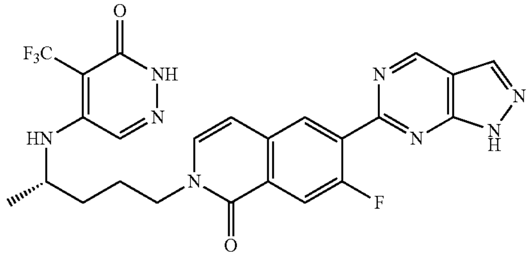 [SMILES: C[C@@H](CCCn1ccc2cc(-c3ncc4cn[nH]c4n3)c(F)cc2c1=O)Nc1cn[nH]c(=O)c1C(F)(F)F] | 1H NMR (400 MHz, DMSO-d6) δ 12.43 (s, 1H), 9.52 (s, 1H), 8.47-8.39 (m, 2H), 8.00 (d, J = 11.4 Hz, 1H), 7.92 (s, 1H), 7.51 (d, J = 7.4 Hz, 1H), 6.83 (d, J = 7.3 Hz, 1H), 6.40-6.29 (m, 1H), 4.02-3.96 (m, 4H), 1.80-1.59 (m, 3H), 1.58-1.46 (m, 1H), 1.17 (d, J = 2.8 Hz, 3H). ES/MS m/z: 529.3 [M + H]$^+$. |
| 300 | 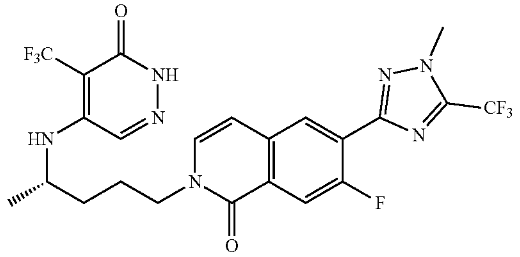 [SMILES: C[C@@H](CCCn1ccc2cc(-c3nc(C(F)(F)F)n(C)n3)c(F)cc2c1=O)Nc1cn[nH]c(=O)c1C(F)(F)F] | 1H NMR (400 MHz, DMSO-d6) δ 12.43 (s, 1H), 8.38 (d, J = 6.9 Hz, 1H), 8.07-7.80 (m, 2H), 7.51 (d, J = 7.4 Hz, 1H), 6.85 (d, J = 7.4 Hz, 1H), 6.35 (m, 1H), 4.16 (s, 3H), 3.99 (m, 3H), 1.83-1.41 (m, 4H), 1.27-1.09 (m, 3H). ES/MS m/z: 560.2 [M + H]$^+$. |
| 301 | 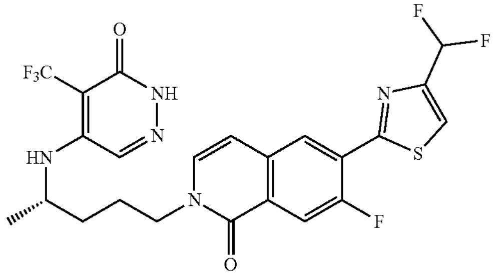 [SMILES: C[C@@H](CCCn1ccc2cc(-c3nc(C(F)F)cs3)c(F)cc2c1=O)Nc1cn[nH]c(=O)c1C(F)(F)F] | 1H NMR (400 MHz, DMSO-d6) δ 12.43 (s, 1H), 8.57 (d, J = 7.1 Hz, 1H), 8.45-8.41 (m, 1H), 8.09 (d, J = 11.9 Hz, 1H), 7.91 (s, 1H), 7.52 (d, J = 7.4 Hz, 1H), 7.24 (t, J = 54.4 Hz, 1H), 6.90 (d, J = 7.4 Hz, 1H), 6.39-6.30 (m, 1H), 4.01-3.96 (m, 3H), 1.74-1.61 (m, 3H), 1.55-1.44 (m, 1H), 1.16 (d, J = 6.3 Hz, 3H). ES/MS m/z: 545.2 [M + H]$^+$. |
| 302 | 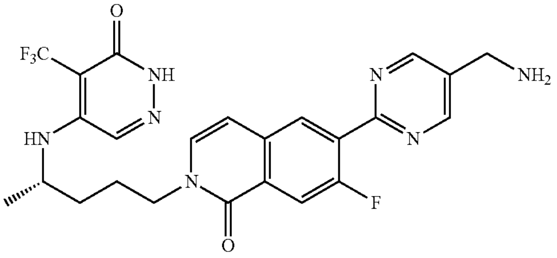 [SMILES: C[C@@H](CCCn1ccc2cc(-c3ncc(CN)cn3)c(F)cc2c1=O)Nc1cn[nH]c(=O)c1C(F)(F)F] | 1H NMR (400 MHz, DMSO-d6) δ 12.44 (s, 1H), 9.07 (s, 2H), 8.40-8.24 (m, 4H), 8.01 (d, J = 11.3 Hz, 1H), 7.92 (s, 1H), 7.52 (d, J = 7.3 Hz, 1H), 6.83 (d, J = 7.4 Hz, 1H), 6.43-6.26 (m, 1H), 4.21 (s, 2H), 3.99 (q, J = 5.7, 5.1 Hz, 3H), 1.84-1.60 (m, 3H), 1.58-1.44 (m, 1H), 1.17 (d, J = 6.3 Hz, 3H). ES/MS m/z: 518.2 [M + H]$^+$. |

-continued

| Ex. No. | Structure | 1H NMR/MS [M + H]+ |
|---|---|---|
| 303 | 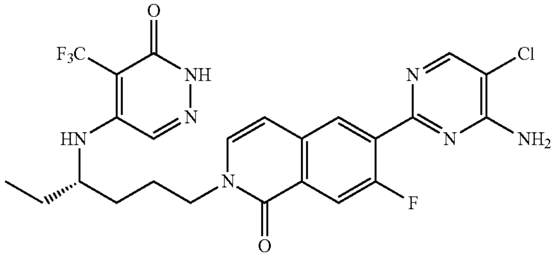 [SMILES: CC[C@@H](CCCn1ccc2cc(-c3ncc(Cl)c(N)n3)c(F)cc2c1=O)Nc1cn[nH]c(=O)c1C(F)(F)F] | 1H NMR (400 MHz, DMSO-d6) δ 12.42 (s, 1H), 8.43 (s, 1H), 8.15 (d, J = 7.1 Hz, 1H), 7.96 (s, 1H), 7.93 (d, J = 11.2 Hz, 1H), 7.87-7.19 (br. m, 2H), 7.48 (d, J = 7.4 Hz, 1H), 6.75 (d, J = 7.4 Hz, 1H), 6.32-6.24 (m, 1H), 4.02-3.77 (m, 4H), 1.78-1.48 (m, 5H), 0.82 (t, J = 7.3 Hz, 3H). ES/MS m/z: 552.2 [M + H]+. |
| 304 | 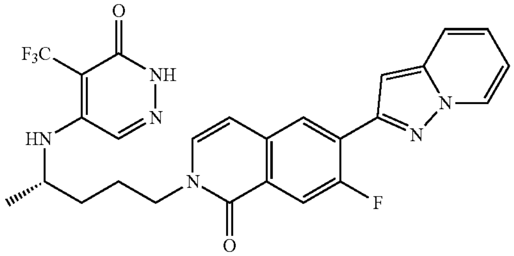 [SMILES: C[C@@H](CCCn1ccc2cc(-c3cc4ccccn4n3)c(F)cc2c1=O)Nc1cn[nH]c(=O)c1C(F)(F)F] | 1H NMR (400 MHz, DMSO-d6) δ 12.43 (s, 1H), 8.78 (d, J = 7.0 Hz, 1H), 8.45 (d, J = 7.1 Hz, 1H), 8.01 (d, J = 11.8 Hz, 1H), 7.92 (s, 1H), 7.80 (d, J = 8.8 Hz, 1H), 7.48 (d, J = 7.4 Hz, 1H), 7.30 (dd, J = 8.9, 6.7 Hz, 1H), 7.14 (d, J = 4.0 Hz, 1H), 7.07-6.98 (m, 1H), 6.81 (d, J = 7.4 Hz, 1H), 6.35 (dt, J = 6.6, 3.6 Hz, 1H), 3.99 (t, J = 6.6 Hz, 3H), 1.80-1.41 (m, 4H), 1.17 (d, J = 6.3 Hz, 3H). ES/MS m/z: 527.2 [M + H]+. |
| 305 | 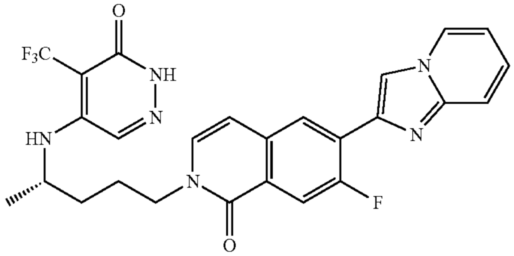 [SMILES: C[C@@H](CCCn1ccc2cc(-c3nc4ccccn4n3)c(F)cc2c1=O)Nc1cn[nH]c(=O)c1C(F)(F)F] | 1H NMR (400 MHz, DMSO-d6) δ 12.43 (s, 1H), 8.67 (d, J = 6.8 Hz, 1H), 8.55 (m, 2H), 7.99 (d, J = 12.0 Hz, 1H), 7.92 (s, 1H), 7.67 (d, J = 9.0 Hz, 1H), 7.48 (d, J = 7.3 Hz, 1H), 7.39 (m, 1H), 7.01 (m, 1H), 6.82 (d, J = 7.4 Hz, 1H), 6.36 (s, 1H), 3.99 (m, 3H), 1.72 (m, 4H), 1.17 (m, 3H). ES/MS m/z: 527.3 [M + H]+. |
| 306 | 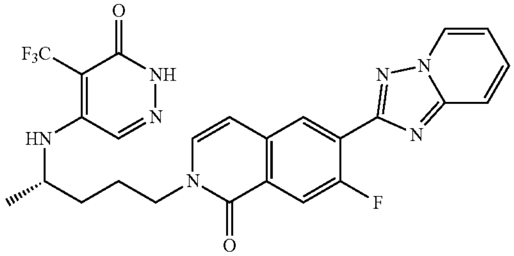 | 1H NMR (400 MHz, DMSO-d6) δ 12.43 (s, 1H), 9.08 (d, J = 6.8 Hz, 1H), 8.57 (d, J = 6.9 Hz, 1H), 8.18-7.88 (m, 3H), 7.82-7.60 (m, 1H), 7.52 (d, J = 7.4 Hz, 1H), 7.29 (m, 1H), 6.85 (m, 1H), 6.36 (m, 1H), 4.00 (m, 3H), 1.88-1.39 (m, 4H), 1.17 (m, 3H). ES/MS m/z: 528.2 [M + H]+. |
| 307 | 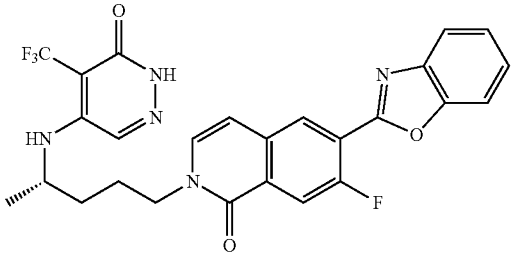 | 1H NMR (400 MHz, DMSO-d6) δ 12.43 (s, 1H), 8.63 (d, J = 6.8 Hz, 1H), 8.10 (s, 1H), 8.00-7.80 (m, 3H), 7.66-7.36 (m, 3H), 6.89 (d, J = 7.4 Hz, 1H), 6.35 (m, 1H), 3.99 (m, 3H), 1.83-1.39 (m, 4H), 1.17 (m, 3H). ES/MS m/z: 528.2 [M + H]+. |
| 308 | 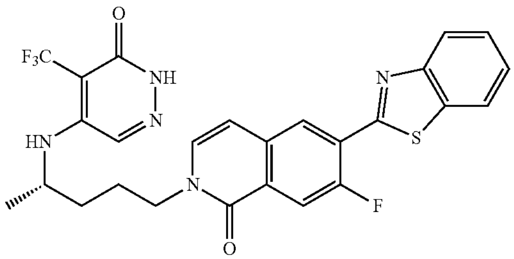 [SMILES: C[C@@H](CCCn1ccc2cc(-c3nc4ccccc4s3)c(F)cc2c1=O)Nc1cn[nH]c(=O)c1C(F)(F)F] | 1H NMR (400 MHz, DMSO-d6) δ 12.43 (s, 1H), 8.74 (d, J = 7.0 Hz, 1H), 8.26 (d, J = 7.9 Hz, 1H), 8.19 (d, J = 8.1 Hz, 1H), 8.12 (d, J = 11.9 Hz, 1H), 7.92 (s, 1H), 7.70-7.60 (m, 1H), 7.56 (m, 2H), 6.92 (d, J = 7.4 Hz, 1H), 6.36 (m, 1H), 3.99 (m, 3H), 1.85-1.42 (m, 4H), 1.17 (m, 3H). ES/MS m/z: 544.2 [M + H]+. |

-continued

| Ex. No. | Structure | 1H NMR/MS [M + H]+ |
|---|---|---|
| 309 | 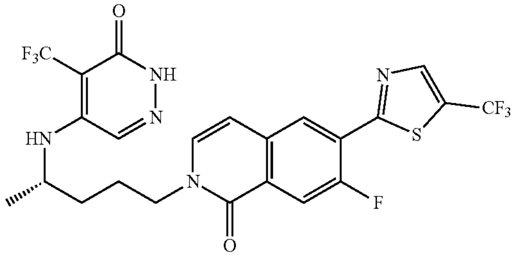 [SMILES: C[C@@H](CCCn1ccc2cc(-c3ncc(C(F)(F)F)s3)c(F)cc2c1=O)Nc1cn[nH]c(=O)c1C(F)(F)F] | 1H NMR (400 MHz, DMSO-d6) δ 12.42 (s, 1H), 8.76 (s, 1H), 8.65 (d, J = 6.9 Hz, 1H), 8.12 (d, J = 11.8 Hz, 1H), 7.90 (s, 1H), 7.55 (d, J = 7.4 Hz, 1H), 6.87 (d, J = 7.4 Hz, 1H), 6.35 (m, 1H), 3.99 (m, 3H), 1.82-1.41 (m, 4H), 1.23-1.06 (m, 3H). ES/MS m/z: 562.1 [M + H]+. |
| 310 | 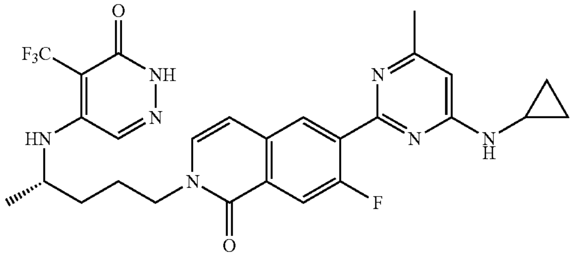 [SMILES: Cc1cc(NC2CC2)nc(-c2cc3ccn(CCC[C@H](C)Nc4cn[nH]c(=O)c4C(F)(F)F)c(=O)c3cc2F)n1] | 1H NMR (400 MHz, DMSO-d6) δ 12.44 (s, 1H), 9.14 (br. s, 1H), 8.15 (s, 1H), 8.05 (d, J = 10.8 Hz, 1H), 7.92 (s, 1H), 7.55 (d, J = 7.4 Hz, 1H), 6.78 (d, J = 7.3 Hz, 1H), 6.98-6.39 (m, 1H), 6.39-6.30 (m, 1H), 4.04-3.93 (m, 3H), 3.22-2.58 (m, 1H), 2.51-2.45 (m, 3H), 1.80-1.59 (m, 3H), 1.58-1.46 (m, 1H), 1.17 (d, J = 6.2 Hz, 3H), 0.90-0.83 (m, 2H), 0.66-0.58 (m, 2H). ES/MS m/z: 558.5 [M + H]+. |
| 311 | 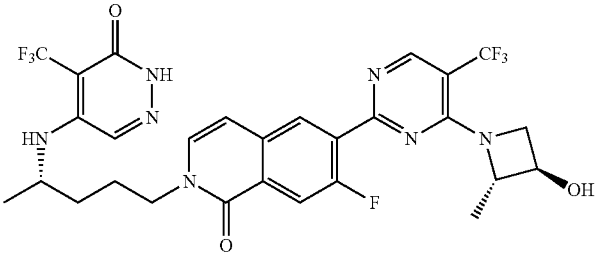 [SMILES: C[C@@H](CCCn1ccc2cc(-c3ncc(C(F)(F)F)c(N4C[C@@H](O)[C@@H]4C)n3)c(F)cc2c1=O)Nc1cn[nH]c(=O)c1C(F)(F)F] | 1H NMR (400 MHz, DMSO-d6) & 12.44 (s, 1H), 8.73 (s, 1H), 8.33 (d, J = 7.1 Hz, 1H), 7.98 (d, J = 11.4 Hz, 1H), 7.92 (s, 1H), 7.50 (d, J = 7.4 Hz, 1H), 6.81 (d, J = 7.4 Hz, 1H), 6.40-6.26 (m, 1H), 4.55-4.49 (m, 1H), 4.45-4.39 (m, 1H), 4.17-4.14 (m, 1H), 4.02-3.96 (m, 3H), 3.90-3.85 (m, 1H), 1.79-1.58 (m, 3H), 1.58-1.44 (m, 4H), 1.17 (d, J = 6.3 Hz, 3H). ES/MS m/z: 642.2 [M + H]+. |
| 312 | 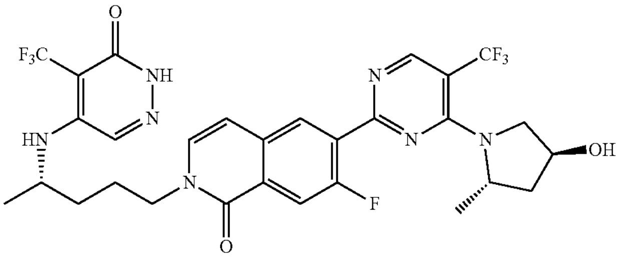 | 1H NMR (400 MHz, DMSO-d6) δ 12.44 (s, 1H), 8.80 (s, 1H), 8.38 (d, J = 7.1 Hz, 1H), 7.99 (d, J = 11.4 Hz, 1H), 7.92 (s, 1H), 7.51 (d, J = 7.4 Hz, 1H), 6.81 (d, J = 7.4 Hz, 1H), 6.35 (dd, J = 8.7, 3.7 Hz, 1H), 4.72-4.66 (m, 1H), 4.39-4.36 (m, 1H), 4.04-3.95 (m, 3H), 3.79-3.70 (m, 1H), 3.39 (d, J = 11.3 Hz, 1H), 2.15-2.04 (m, 1H), 1.81-1.59 (m, 4H), 1.57-1.44 (m, 1H), 1.34 (d, J = 6.1 Hz, 3H), 1.17 (d, J = 6.3 Hz, 3H). ES/MS m/z: 565.2 [M + H]+. |
| 313 | 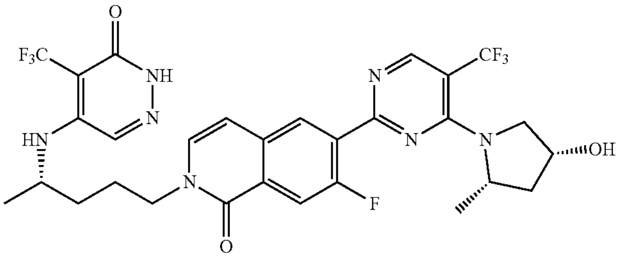 [SMILES: C[C@@H](CCCn1ccc2cc(-c3ncc(C(F)(F)F)c(N4C[C@H](O)C[C@@H]4C)n3)c(F)cc2c1=O)Nc1cn[nH]c(=O)c1C(F)(F)F] | 1H NMR (400 MHz, DMSO-d6) δ 12.44 (s, 1H), 8.78 (s, 1H), 8.36 (d, J = 7.1 Hz, 1H), 7.98 (d, J = 11.4 Hz, 1H), 7.92 (s, 1H), 7.50 (d, J = 7.4 Hz, 1H), 6.80 (d, J = 7.4 Hz, 1H), 6.40-6.28 (m, 1H), 4.67-4.60 (m, 1H), 4.36-4.28 (m, 1H), 4.04-3.92 (m, 3H), 3.70 (dd, J = 11.0, 6.0 Hz, 1H), 3.46 (dd, J = 11.1, 5.5 Hz, 1H), 2.29 (ddd, J = 13.1, 7.7, 6.0 Hz, 1H), 1.79-1.57 (m, 4H), 1.55-1.44 (m, 1H), 1.40 (d, J = 6.2 Hz, 3H), 1.17 (d, J = 6.3 Hz, 3H). ES/MS m/z: 656.4 [M + H]+. |
| 314 | 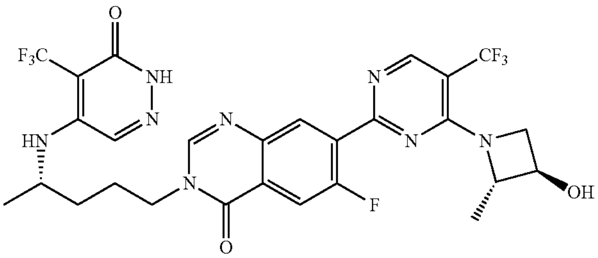 [SMILES: C[C@@H](CCCn1cnc2cc(-c3ncc(C(F)(F)F)c(N4C[C@@H](O)[C@@H]4C)n3)c(F)cc2c1=O)Nc1cn[nH]c(=O)c1C(F)(F)F] | 1H NMR (400 MHz, DMSO-d6) δ 12.44 (s, 1H), 8.75 (s, 1H), 8.44 (s, 1H), 8.27 (d, J = 6.7 Hz, 1H), 7.99-7.87 (m, 2H), 6.40-6.27 (m, 1H), 4.52 (t, J = 8.4 Hz, 1H), 4.45-4.37 (m, 1H), 4.16 (dt, J = 6.8, 4.3 Hz, 1H), 4.00 (q, J = 7.5, 6.9 Hz, 3H), 3.88 (ddd, J = 10.2, 4.6, 2.3 Hz, 1H), 1.82-1.60 (m, 3H), 1.52 (d, J = 6.4 Hz, 4H), 1.17 (d, J = 6.3 Hz, 3H). ES/MS m/z: 643.4 [M + H]+. |

-continued

| Ex. No. | Structure | 1H NMR/MS [M + H]$^+$ |
|---|---|---|
| 315 | 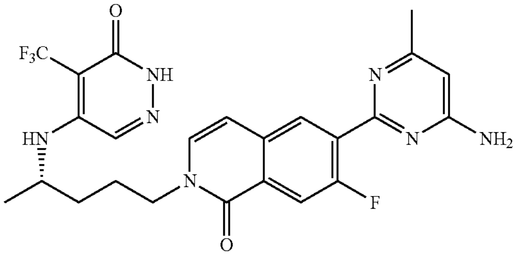 [SMILES: Cc1cc(N)nc(-c2cc3ccn(CCC[C@H](C)Nc4cn[nH]c(=O)c4C(F)(F)F)c(=O)c3cc2F)n1] | 1H NMR (400 MHz, DMSO-d6) δ 12.44 (s, 1H), 8.61 (br. s, 2H), 8.14 (d, J = 6.7 Hz, 1H), 8.06 (d, J = 10.8 Hz, 1H), 7.92 (s, 1H), 7.56 (d, J = 7.4 Hz, 1H), 6.79 (d, J = 7.4 Hz, 1H), 6.56 (s, 1H), 6.39-6.30 (m, 1H), 4.04-3.96 (m, 3H), 2.44 (s, 3H), 1.80-1.59 (m, 3H), 1.57-1.46 (m, 1H), 1.17 (d, J = 6.3 Hz, 3H). ES/MS m/z: 518.3 [M + H]$^+$. |
| 316 | 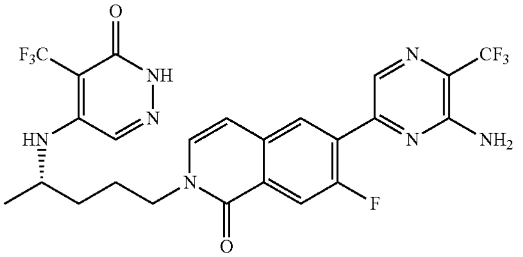 [SMILES: C[C@@H](CCCn1ccc2cc(-c3cnc(C(F)(F)F)c(N)n3)c(F)cc2c1=O)Nc1cn[nH]c(=O)c1C(F)(F)F] | 1H NMR (400 MHz, DMSO-d6) δ 12.43 (s, 1H), 8.31 (d, J = 2.6 Hz, 1H), 8.18 (d, J = 7.1 Hz, 1H), 8.02 (d, J = 11.4 Hz, 1H), 7.91 (s, 1H), 7.51 (d, J = 7.4 Hz, 1H), 7.14 (s, 2H), 6.75 (d, J = 7.4 Hz, 1H), 6.38-6.29 (m, 1H), 4.03-3.92 (m, 3H), 1.80-1.59 (m, 3H), 1.56-1.44 (m, 1H), 1.17 (d, J = 6.3 Hz, 3H). ES/MS m/z: 572.3 [M + H]$^+$. |
| 317 | 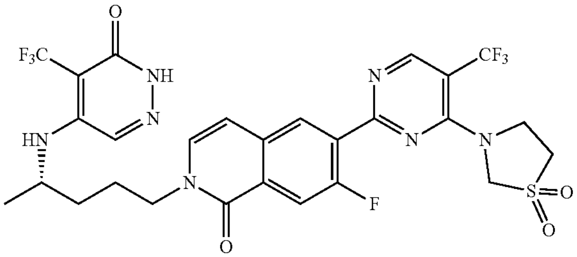 [SMILES: C[C@@H](CCCn1ccc2cc(-c3ncc(C(F)(F)F)c(N4CCS(=O)(=O)C4)n3)c(F)cc2c1=O)Nc1cn[nH]c(=O)c1C(F)(F)F] | 1H NMR (400 MHz, DMSO-d6) δ 12.44 (s, 1H), 9.01 (s, 1H), 8.50 (d, J = 7.2 Hz, 1H), 8.00 (d, J = 11.5 Hz, 1H), 7.92 (s, 1H), 7.52 (d, J = 7.4 Hz, 1H), 6.83 (d, J = 7.4 Hz, 1H), 6.40-6.27 (m, 1H), 4.84 (s, 2H), 4.27 (t, J = 7.0 Hz, 2H), 4.07-3.90 (m, 3H), 3.65 (t, J = 7.0 Hz, 2H), 1.83-1.59 (m, 3H), 1.58-1.42 (m, 1H), 1.17 (d, J = 6.3 Hz, 3H). ES/MS m/z: 676.3 [M + H]$^+$. |
| 318 | 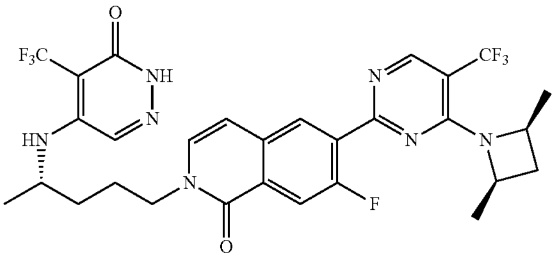 [SMILES: C[C@@H]1C[C@H](C)N1c1nc(-c2cc3ccn(CCC[C@H](C)Nc4cn[nH]c(=O)c4C(F)(F)F)c(=O)c3cc2F)ncc1C(F)(F)F] | 1H NMR (400 MHz, DMSO-d6) δ 12.44 (s, 1H), 8.70 (s, 1H), 8.32 (d, J = 7.1 Hz, 1H), 7.97 (d, J = 11.4 Hz, 1H), 7.92 (s, 1H), 7.50 (d, J = 7.4 Hz, 1H), 6.79 (d, J = 7.4 Hz, 1H), 6.40-6.30 (m, 1H), 4.72-4.59 (m, 2H), 4.02-3.97 (m, 4H), 2.95-2.79 (m, 1H), 1.81-1.64 (m, 3H), 1.60 (d, J = 6.3 Hz, 6H), 1.56-1.47 (m, 1H), 1.16 (d, J = 6.2 Hz, 3H). ES/MS m/z: 640.3 [M + H]$^+$. |
| 319 | 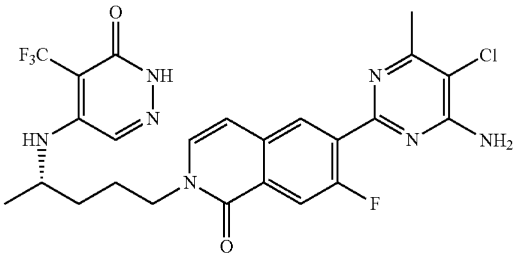 [SMILES: Cc1nc(-c2cc3ccn(CCC[C@H](C)Nc4cn[nH]c(=O)c4C(F)(F)F)c(=O)c3cc2F)nc(N)c1Cl] | 1H NMR (400 MHz, DMSO-d6) δ 12.44 (s, 1H), 8.10 (d, J = 7.0 Hz, 1H), 7.97-7.90 (m, 2H), 7.73-7.22 (m, 2H), 7.49 (d, J = 7.4 Hz, 1H), 6.76 (d, J = 7.4 Hz, 1H), 6.40-6.31 (m, 1H), 4.04-3.92 (m, 3H), 2.46 (s, 3H), 1.79-1.59 (m, 3H), 1.56-1.44 (m, 1H), 1.17 (d, J = 6.3 Hz, 3H). ES/MS m/z: 552.3 [M + H]$^+$. |
| 320 | 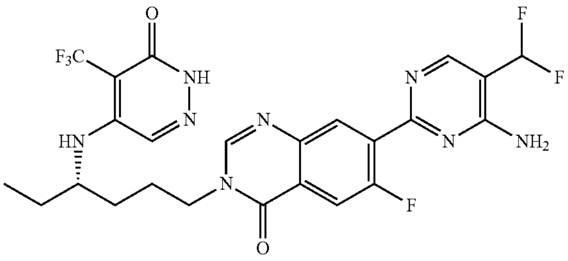 [SMILES: CC[C@@H](CCCn1cnc2cc(-c3ncc(C(F)F)c(N)n3)c(F)cc2c1=O)Nc1cn[nH]c(=O)c1C(F)(F)F] | 1H NMR (400 MHz, DMSO-d6) δ 12.42 (s, 1H), 8.51 (s, 1H), 8.42 (s, 1H), 8.15 (d, J = 6.7 Hz, 1H), 8.04-7.88 (m, 2H), 7.09 (t, J = 54.2 Hz, 1H), 6.28 (dd, J = 9.0, 3.9 Hz, 1H), 4.00 (t, J = 6.9 Hz, 2H), 3.85 (d, J = 8.1 Hz, 1H), 1.85-1.46 (m, 5H), 0.82 (t, J = 7.3 Hz, 3H). ES/MS m/z: 569.3 [M + H]$^+$. |

-continued

| Ex. No. | Structure | 1H NMR/MS [M + H]+ |
|---|---|---|
| 321 | 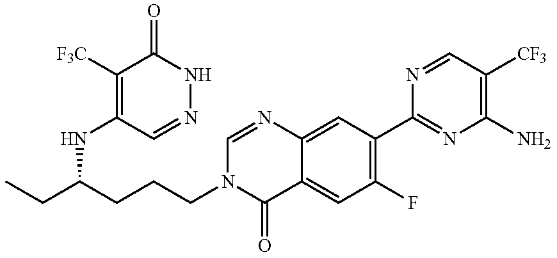 [SMILES: CC[C@@H](CCCn1cnc2cc(-c3ncc(C(F)(F)F)c(N)n3)c(F)cc2c1=O)Nc1cn[nH]c(=O)c1C(F)(F)F] | 1H NMR (400 MHz, DMSO-d6) δ 12.42 (s, 1H), 8.66 (s, 1H), 8.42 (s, 1H), 8.18 (d, J = 6.7 Hz, 1H), 8.02-7.80 (m, 2H), 6.27 (d, J = 8.8 Hz, 1H), 4.00 (t, J = 6.8 Hz, 2H), 3.84 (s, 1H), 1.79-1.51 (m, 5H), 0.82 (t, J = 7.3 Hz, 3H). ES/MS m/z: 587.3 [M + H]+. |
| 322 | 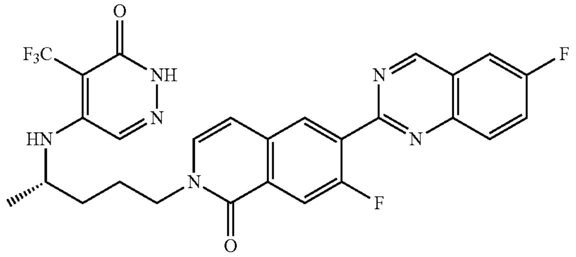 [SMILES: C[C@@H](CCCn1ccc2cc(-c3ncc4cc(F)ccc4n3)c(F)cc2c1=O)Nc1cn[nH]c(=O)c1C(F)(F)F] | 1H NMR (400 MHz, DMSO-d6) δ 12.44 (s, 1H), 9.79 (s, 1H), 8.45 (d, J = 7.2 Hz, 1H), 8.25-8.19 (m, 1H), 8.12-7.99 (m, 3H), 7.92 (s, 1H), 7.52 (d, J = 7.3 Hz, 1H), 6.85 (d, J = 7.4 Hz, 1H), 6.42-6.32 (m, 1H), 4.05-3.95 (m, 3H), 1.83-1.58 (m, 3H), 1.58-1.42 (m, 1H), 1.17 (d, J = 6.3 Hz, 3H). ES/MS m/z: 557.1 [M + H]+. |
| 323 | 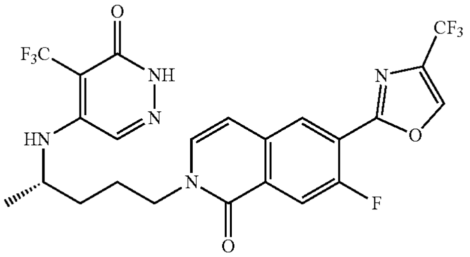 [SMILES: C[C@@H](CCCn1ccc2cc(-c3nc(C(F)(F)F)co3)c(F)cc2c1=O)Nc1cn[nH]c(=O)c1C(F)(F)F] | 1H NMR (400 MHz, DMSO-d6) δ 12.42 (s, 1H), 9.20 (d, J = 1.7 Hz, 1H), 8.48 (d, J = 6.9 Hz, 1H), 8.05 (d, J = 11.4 Hz, 1H), 7.90 (s, 1H), 7.54 (d, J = 7.4 Hz, 1H), 6.86 (d, J = 7.4 Hz, 1H), 6.39-6.28 (m, 1H), 4.06-3.92 (m, 3H), 1.79-1.58 (m, 3H), 1.56-1.44 (m, 1H), 1.16 (d, J = 6.3 Hz, 3H). ES/MS m/z: 546.3 [M + H]+. |
| 324 | 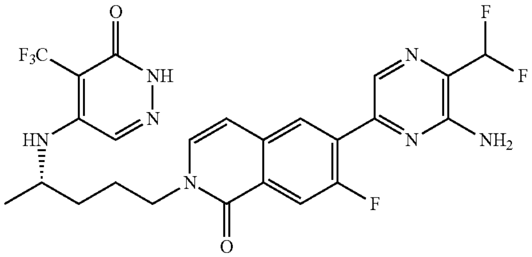 [SMILES: C[C@@H](CCCn1ccc2cc(-c3cnc(C(F)F)c(N)n3)c(F)cc2c1=O)Nc1cn[nH]c(=O)c1C(F)(F)F] | 1H NMR (400 MHz, DMSO-d6) δ 12.43 (s, 1H), 8.28 (d, J = 2.7 Hz, 1H), 8.16 (d, J = 7.1 Hz, 1H), 8.00 (d, J = 11.5 Hz, 1H), 7.91 (s, 1H), 7.50 (d, J = 7.4 Hz, 1H), 7.07 (t, J = 53.5 Hz, 1H), 6.75 (d, J = 7.4 Hz, 1H), 6.35 (dd, J = 8.9, 3.7 Hz, 1H), 3.99 (t, J = 6.7 Hz, 3H), 1.82-1.43 (m, 4H), 1.17 (d, J = 6.3 Hz, 3H). ES/MS m/z: 554.3 [M + H]+. |
| 325 | 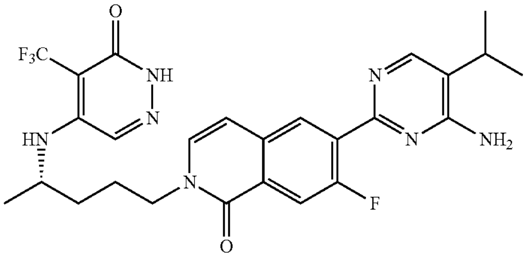 [SMILES: CC(C)c1cnc(-c2cc3ccn(CCC[C@H](C)Nc4cn[nH]c(=O)c4C(F)(F)F)c(=O)c3cc2F)nc1N] | 1H NMR (400 MHz, DMSO-d6) δ 12.44 (s, 1H), 8.60-8.26 (m, 2H), 8.23-8.11 (m, 2H), 8.05 (d, J = 10.9 Hz, 1H), 7.91 (s, 1H), 7.55 (d, J = 7.4 Hz, 1H), 6.77 (d, J = 7.4 Hz, 1H), 6.35 (dd, J = 8.7, 4.0 Hz, 1H), 4.00 (t, J = 6.6 Hz, 3H), 2.98 (p, J = 6.8 Hz, 1H), 1.83-1.44 (m, 4H), 1.21 (dd, J = 29.4, 6.5 Hz, 9H). ES/MS m/z: 545.3 [M + H]+. |
| 326 | 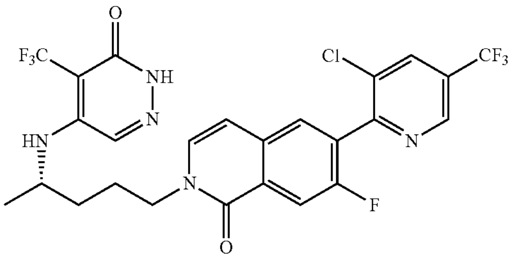 [SMILES: C[C@@H](CCCn1ccc2cc(-c3ncc(C(F)(F)F)cc3Cl)c(F)cc2c1=O)Nc1cn[nH]c(=O)c1C(F)(F)F] | 1H NMR (400 MHz, DMSO-d6) δ 12.44 (s, 1H), 9.13 (d, J = 1.9 Hz, 1H), 8.73 (d, J = 1.9 Hz, 1H), 8.04 (d, J = 10.3 Hz, 1H), 7.93 (t, J = 3.4 Hz, 2H), 7.54 (d, J = 7.4 Hz, 1H), 6.75 (d, J = 7.3 Hz, 1H), 6.36 (dd, J = 8.4, 3.8 Hz, 1H), 4.01 (t, J = 6.7 Hz, 3H), 1.87-1.38 (m, 4H), 1.17 (d, J = 6.3 Hz, 3H). ES/MS m/z: 590.2 [M + H]+. |

-continued

| Ex. No. | Structure | 1H NMR/MS [M + H]$^+$ |
| --- | --- | --- |
| 327 | 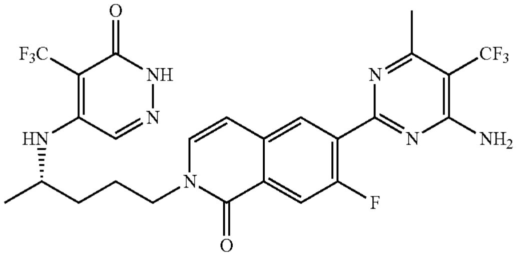 | 1H NMR (400 MHz, DMSO-d6) δ 12.44 (s, 1H), 8.16 (d, J = 7.0 Hz, 1H), 7.95 (d, J = 11.1 Hz, 1H), 7.92 (s, 1H), 8.02-7.22 (br. m, 2H), 7.50 (d, J = 7.4 Hz, 1H), 6.77 (d, J = 7.4 Hz, 1H), 6.40-6.31 (m, 1H), 4.05-3.95 (m, 3H), 2.56-2.51 (m, 3H), 1.81-1.59 (m, 3H), 1.57-1.46 (m, 1H), 1.17 (d, J = 6.3 Hz, 3H). ES/MS m/z: 586.3 [M + H]$^+$. |
| 328 | 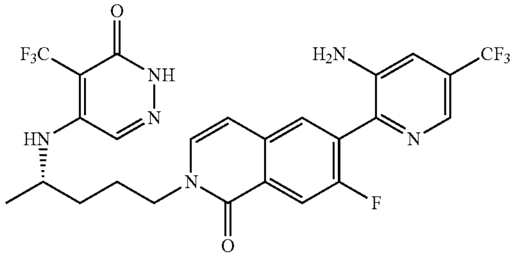 [SMILES: C[C@@H](CCCn1ccc2cc(-c3ncc(C(F)(F)F)cc3N)c(F)cc2c1=O)Nc1cn[nH]c(=O)c1C(F)(F)F] | 1H NMR (400 MHz, DMSO-d6) δ 12.44 (s, 1H), 8.19 (d, J = 1.9 Hz, 1H), 8.01-7.89 (m, 2H), 7.81 (d, J = 6.8 Hz, 1H), 7.49 (d, J = 7.4 Hz, 1H), 7.43 (d, J = 2.0 Hz, 1H), 6.73 (d, J = 7.4 Hz, 1H), 6.36 (dd, J = 8.9, 3.6 Hz, 1H), 4.00 (t, J = 6.7 Hz, 3H), 1.82-1.43 (m, 4H), 1.17 (d, J = 6.3 Hz, 3H). ES/MS m/z: 571.3 [M + H]$^+$. |
| 329 | 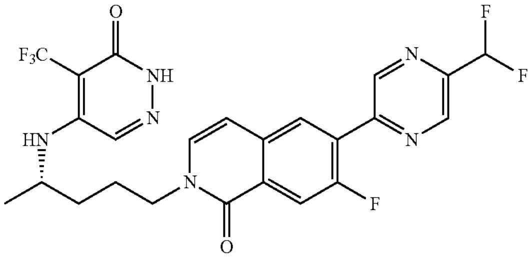 [SMILES: C[C@@H](CCCn1ccc2cc(-c3cnc(C(F)F)cn3)c(F)cc2c1=O)Nc1cn[nH]c(=O)c1C(F)(F)F] | 1H NMR (400 MHz, DMSO-d6) δ 12.43 (s, 1H), 9.26 (t, J = 1.9 Hz, 1H), 9.17 (s, 1H), 8.33 (d, J = 7.2 Hz, 1H), 8.06 (d, J = 11.5 Hz, 1H), 7.91 (s, 1H), 7.53 (d, J = 7.4 Hz, 1H), 7.44-6.89 (m, 2H), 6.82 (d, J = 7.4 Hz, 1H), 6.41-6.28 (m, 1H), 4.01 (t, J = 6.8 Hz, 3H), 1.87-1.37 (m, 5H), 1.17 (d, J = 6.3 Hz, 3H). ES/MS m/z: 539.2 [M + H]$^+$. |
| 330 | 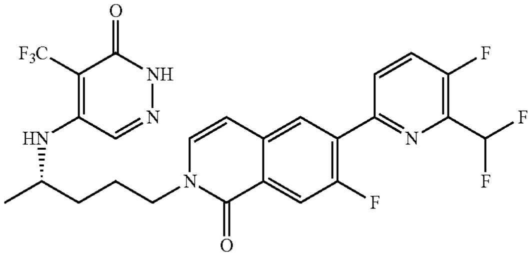 [SMILES: C[C@@H](CCCn1ccc2cc(-c3ccc(F)c(C(F)F)n3)c(F)cc2c1=O)Nc1cn[nH]c(=O)c1C(F)(F)F] | 1H NMR (400 MHz, DMSO-d6) δ 12.43 (s, 1H), 8.24-8.08 (m, 3H), 8.01 (d, J = 11.5 Hz, 1H), 7.91 (s, 1H), 7.51 (d, J = 7.3 Hz, 1H), 7.25 (t, J = 53.0 Hz, 1H), 6.80 (d, J = 7.4 Hz, 1H), 6.40-6.26 (m, 1H), 4.10-3.90 (m, 3H), 1.83-1.58 (m, 3H), 1.57-1.42 (m, 1H), 1.16 (d, J = 6.3 Hz, 3H). ES/MS m/z: 556.3 [M + H]$^+$. |
| 331 | 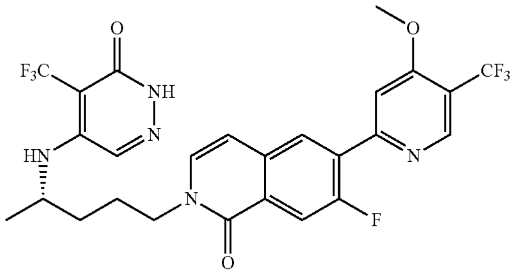 [SMILES: COc1cc(-c2cc3ccn(CCC[C@H](C)Nc4cn[nH]c(=O)c4C(F)(F)F)c(=O)c3cc2F)ncc1C(F)(F)F] | 1H NMR (400 MHz, DMSO-d6) δ 12.43 (s, 1H), 8.85 (s, 1H), 8.25 (d, J = 7.2 Hz, 1H), 8.03 (d, J = 11.5 Hz, 1H), 7.91 (s, 1H), 7.74 (s, 1H), 7.52 (d, J = 7.4 Hz, 1H), 6.79 (d, J = 7.4 Hz, 1H), 6.35 (dd, J = 8.7, 3.8 Hz, 1H), 4.08 (s, 3H), 4.00 (t, J = 6.7 Hz, 3H), 1.85-1.43 (m, 4H), 1.17 (d, J = 6.3 Hz, 3H). ES/MS m/z: 586.3 [M + H]$^+$. |
| 332 | 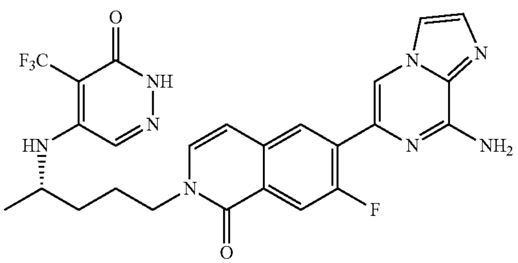 [SMILES: C[C@@H](CCCn1ccc2cc(-c3cn4ccnc4c(N)n3)c(F)cc2c1=O)Nc1cn[nH]c(=O)c1C(F)(F)F] | 1H NMR (400 MHz, DMSO-d6) δ 12.43 (s, 1H), 8.48 (s, 1H), 8.30 (d, J = 7.3 Hz, 1H), 8.10 (s, 1H), 8.02-7.86 (m, 2H), 7.68 (s, 1H), 7.48 (d, J = 7.4 Hz, 1H), 6.72 (d, J = 7.4 Hz, 1H), 6.35 (dd, J = 9.0, 3.7 Hz, 1H), 3.99 (t, J = 6.1 Hz, 3H), 1.87-1.33 (m, 5H), 1.17 (d, J = 6.3 Hz, 3H). ES/MS m/z: 543.2 [M + H]$^+$. |

-continued

| Ex. No. | Structure | 1H NMR/MS [M + H]$^+$ |
|---|---|---|
| 333 | 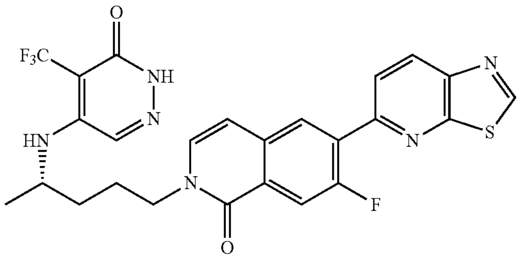 [SMILES: C[C@@H](CCCn1ccc2cc(-c3ccc4ncsc4n3)c(F)cc2c1=O)Nc1cn[nH]c(=O)c1C(F)(F)F] | 1H NMR (400 MHz, DMSO-d6) δ 12.43 (s, 1H), 9.66 (s, 1H), 8.65 (d, J = 8.6 Hz, 1H), 8.32 (d, J = 7.3 Hz, 1H), 8.15-7.87 (m, 3H), 7.51 (d, J = 7.4 Hz, 1H), 6.83 (d, J = 7.4 Hz, 1H), 6.41-6.27 (m, 1H), 4.05-3.94 (m, 3H), 1.81-1.60 (m, 3H), 1.58-1.45 (m, 1H), 1.17 (d, J = 6.0 Hz, 3H). ES/MS m/z: 545.3 [M + H]$^+$. |
| 334 | 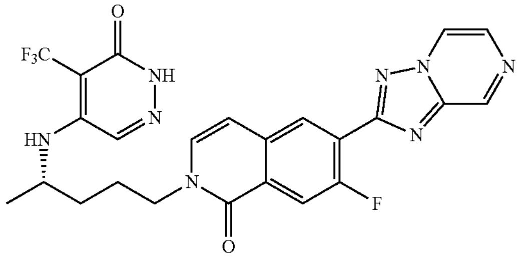 [SMILES: C[C@@H](CCCn1ccc2cc(-c3nc4cnccn4n3)c(F)cc2c1=O)Nc1cn[nH]c(=O)c1C(F)(F)F] | 1H NMR (400 MHz, DMSO-d6) δ 12.43 (s, 1H), 9.53 (m, 1H), 9.42-9.13 (m, 1H), 8.62 (m, 1H), 8.36 (m, 1H), 8.07 (m, 1H), 7.92 (m, 1H), 7.54 (m, 1H), 6.88 (m, 1H), 6.52 (m, 1H), 6.36 (m, 1H), 4.00 (m, 3H), 1.62 (m, 3H), 1.17 (m, 3H). ES/MS m/z: 529.2 [M + H]$^+$. |
| 335 | 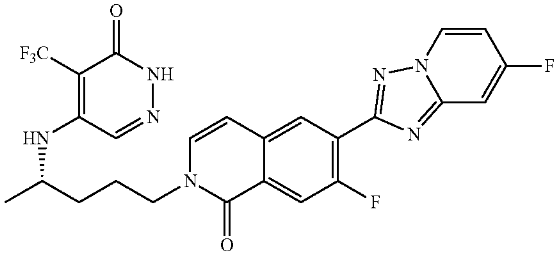 [SMILES: C[C@@H](CCCn1ccc2cc(-c3nc4cc(F)ccn4n3)c(F)cc2c1=O)Nc1cn[nH]c(=O)c1C(F)(F)F] | 1H NMR (400 MHz, DMSO-d6) δ 12.43 (s, 1H), 9.46 (m, 1H), 8.55 (d, J = 6.9 Hz, 1H), 8.10-8.00 (m, 2H), 7.95-7.81 (m, 2H), 7.52 (d, J = 7.4 Hz, 1H), 6.85 (d, J = 7.4 Hz, 1H), 6.36 (m, 1H), 4.00 (m, 3H), 1.80-1.33 (m, 4H), 1.26-1.10 (m, 3H). ES/MS m/z: 546.2 [M + H]$^+$. |
| 336 | 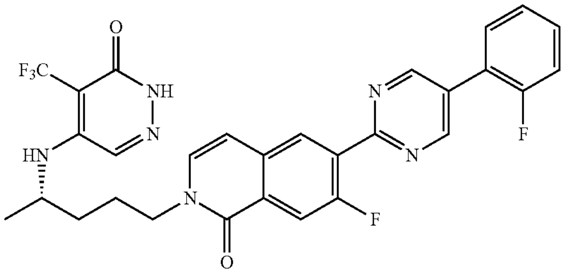 [SMILES: C[C@@H](CCCn1ccc2cc(-c3ncc(-c4ccccc4F)cn3)c(F)cc2c1=O)Nc1cn[nH]c(=O)c1C(F)(F)F] | 1H NMR (400 MHz, DMSO-d6) δ 12.43 (s, 1H), 9.24 (d, J = 1.4 Hz, 2H), 8.43 (d, J = 7.2 Hz, 1H), 8.02 (d, J = 11.3 Hz, 1H), 7.92 (s, 1H), 7.85-7.75 (m, 1H), 7.65-7.36 (m, 4H), 6.84 (d, J = 7.4 Hz, 1H), 6.39-6.29 (m, 1H), 4.07-3.91 (m, 3H), 1.86-1.60 (m, 3H), 1.60-1.44 (m, 1H), 1.17 (d, J = 6.3 Hz, 3H). ES/MS m/z: 583.3 [M + H]$^+$. |
| 337 | 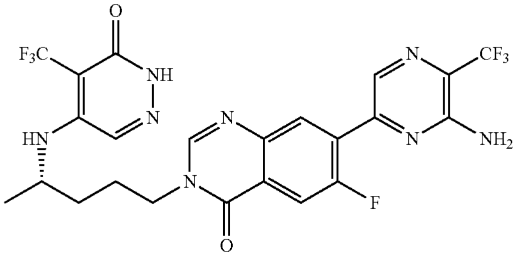 [SMILES: C[C@@H](CCCn1cnc2cc(-c3cnc(C(F)(F)F)c(N)n3)c(F)cc2c1=O)Nc1cn[nH]c(=O)c1C(F)(F)F] | 1H NMR (400 MHz, DMSO-d6) δ 12.43 (s, 1H), 8.44 (s, 1H), 8.35 (d, J = 2.5 Hz, 1H), 8.22 (d, J = 6.7 Hz, 1H), 7.99 (d, J = 10.7 Hz, 1H), 7.91 (s, 1H), 7.17 (s, 2H), 6.39-6.27 (m, 1H), 4.04-3.96 (m, 3H), 1.81-1.60 (m, 3H), 1.58-1.45 (m, 1H), 1.17 (d, J = 6.3 Hz, 3H). ES/MS m/z: 573.3 [M + H]$^+$. |

-continued

| Ex. No. | Structure | 1H NMR/MS [M + H]+ |
|---|---|---|
| 338 | 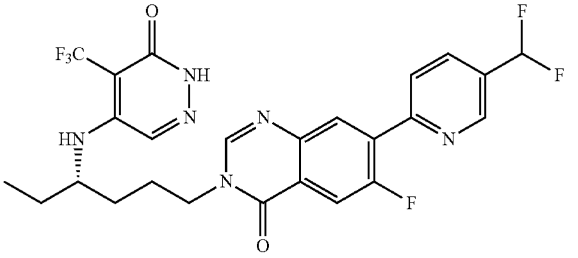 [SMILES: CC[C@@H](CCCn1cnc2cc(-c3ccc(C(F)F)cn3)c(F)cc2c1=O)Nc1cn[nH]c(=O)c1C(F)(F)F] | 1H NMR (400 MHz, DMSO-d6) δ 12.42 (s, 1H), 8.99 (s, 1H), 8.44 (s, 1H), 8.25-8.17 (m, 2H), 8.09-8.04 (m, 1H), 8.02-7.93 (m, 2H), 7.25 (t, J = 55.2 Hz, 1H), 6.36-6.20 (m, 1H), 4.01 (t, J = 6.8 Hz, 2H), 1.83-1.68 (m, 2H), 1.68-1.48 (m, 3H), 0.82 (t, J = 7.3 Hz, 3H). ES/MS m/z: 553.3 $[M + H]^+$. |
| 339 | 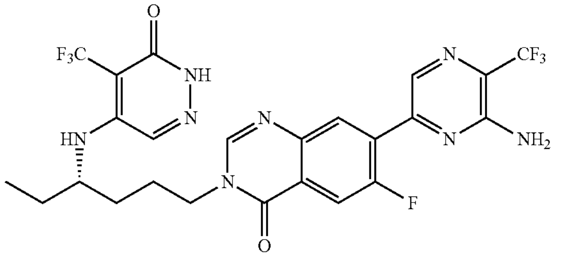 [SMILES: CC[C@@H](CCCn1cnc2cc(-c3cnc(C(F)(F)F)c(N)n3)c(F)cc2c1=O)Nc1cn[nH]c(=O)c1C(F)(F)F] | 1H NMR (400 MHz, DMSO-d6) δ 12.41 (s, 1H), 8.31 (d, J = 2.6 Hz, 1H), 8.18 (d, J = 7.1 Hz, 1H), 8.01 (d, J = 11.4 Hz, 1H), 7.95 (s, 1H), 7.51 (d, J = 7.4 Hz, 1H), 7.14 (s, 2H), 6.75 (d, J = 7.4 Hz, 1H), 6.32-6.23 (m, 1H), 3.99 (t, J = 6.8 Hz, 2H), 3.85 (d, J = 7.9 Hz, 1H), 1.82-1.46 (m, 5H), 0.82 (t, J = 7.3 Hz, 3H). ES/MS m/z: 586.2 $[M + H]^+$. |
| 340 | 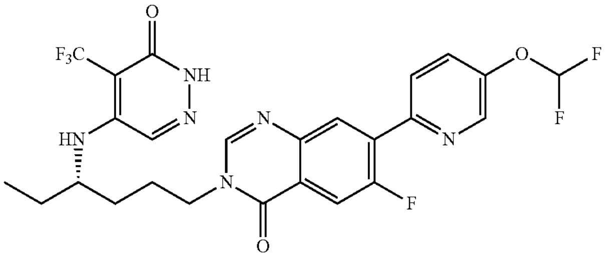 [SMILES: CC[C@@H](CCCn1cnc2cc(-c3ccc(OC(F)F)cn3)c(F)cc2c1=O)Nc1cn[nH]c(=O)c1C(F)(F)F] | 1H NMR (400 MHz, DMSO-d6) δ 12.42 (s, 1H), 8.70 (d, J = 2.9 Hz, 1H), 8.43 (s, 1H), 8.17 (d, J = 7.0 Hz, 1H), 8.04-7.92 (m, 2H), 7.89-7.82 (m, 1H), 7.44 (t, J = 73.1 Hz, 1H), 6.34-6.20 (m, 1H), 1.82-1.66 (m, 2H), 1.66-1.48 (m, 3H), 0.82 (t, J = 7.3 Hz, 3H). ES/MS m/z: 569.3 $[M + H]^+$. |
| 341 | 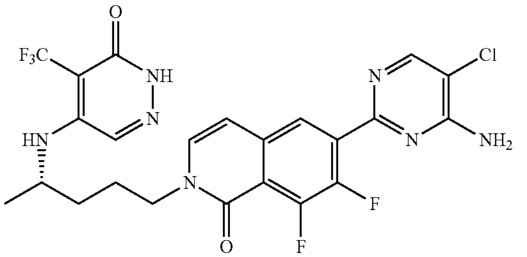 [SMILES: C[C@@H](CCCn1ccc2cc(-c3ncc(Cl)c(N)n3)c(F)c(F)c2c1=O)Nc1cn[nH]c(=O)c1C(F)(F)F] | 1H NMR (400 MHz, DMSO-d6) δ 12.44 (s, 1H), 8.44 (s, 1H), 7.95 (dd, J = 6.7, 1.6 Hz, 1H), 7.92 (s, 1H), 7.88-7.20 (m, 2H), 7.50 (d, J = 7.4 Hz, 1H), 6.72 (dd, J = 7.4, 1.8 Hz, 1H), 6.35 (dq, J = 7.1, 3.4 Hz, 1H), 4.02-3.90 (m, 3H), 1.79-1.59 (m, 3H), 1.56-1.44 (m, 1H), 1.17 (d, J = 6.3 Hz, 3H). ES/MS m/z: 556.3 $[M + H]^+$. |
| 342 | 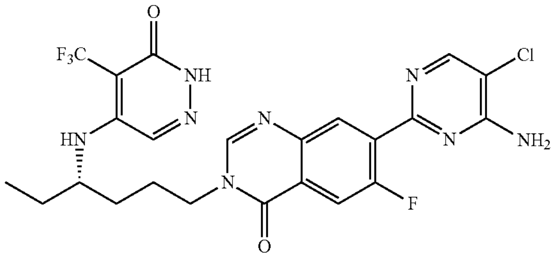 [SMILES: CC[C@@H](CCCn1cnc2cc(-c3ncc(Cl)c(N)n3)c(F)cc2c1=O)Nc1cn[nH]c(=O)c1C(F)(F)F] | 1H NMR (400 MHz, DMSO-d6) δ 12.42 (s, 1H), 8.45 (s, 1H), 8.42 (s, 1H), 8.13 (d, J = 6.8 Hz, 1H), 7.96 (s, 1H), 7.90 (d, J = 10.4 Hz, 1H), 7.84-7.20 (m, 2H), 6.33-6.24 (m, 1H), 4.00 (t, J = 6.9 Hz, 2H), 3.92-3.78 (m, 1H), 1.84-1.49 (m, 6H), 0.82 (t, J = 7.3 Hz, 3H). ES/MS m/z: 553.3 $[M + H]^+$. |
| 343 | 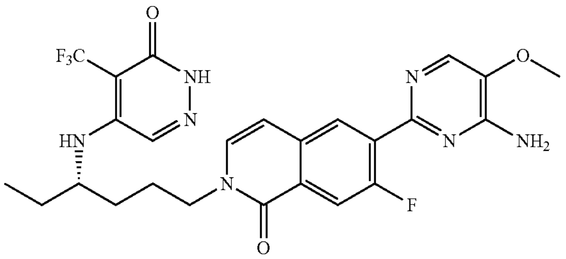 [SMILES: CC[C@@H](CCCn1ccc2cc(-c3ncc(OC)c(N)n3)c(F)cc2c1=O)Nc1cn[nH]c(=O)c1C(F)(F)F] | 1H NMR (400 MHz, DMSO-d6) δ 12.42 (s, 1H), 8.11 (d, J = 7.0 Hz, 1H), 8.05 (s, 1H), 7.98 (d, J = 13.7 Hz, 2H), 7.50 (d, J = 7.3 Hz, 1H), 6.76 (d, J = 7.4 Hz, 1H), 6.28 (dd, J = 9.5, 4.0 Hz, 1H), 3.98 (t, J = 6.9 Hz, 5H), 3.85 (d, J = 7.8 Hz, 1H), 1.87-1.42 (m, 5H), 0.82 (t, J = 7.3 Hz, 3H). ES/MS m/z: 548.3 $[M + H]^+$. |

-continued

| Ex. No. | Structure | 1H NMR/MS [M + H]$^+$ |
|---|---|---|
| 344 | 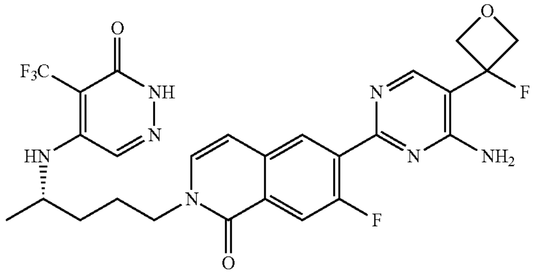 [SMILES: C[C@@H](CCCn1ccc2cc(-c3ncc(C4(F)COC4)c(N)n3)c(F)cc2c1=O)Nc1cn[nH]c(=O)c1C(F)(F)F] | 1H NMR (400 MHz, DMSO-d6) δ 12.43 (s, 1H), 8.50 (d, J = 2.7 Hz, 1H), 8.16 (d, J = 7.1 Hz, 1H), 8.00-7.84 (m, 2H), 7.49 (d, J = 7.4 Hz, 1H), 6.76 (d, J = 7.4 Hz, 1H), 6.35 (d, J = 5.0 Hz, OH), 5.22-4.97 (m, 4H), 3.99 (t, J = 6.7 Hz, 3H), 1.86-1.39 (m, 5H), 1.17 (d, J = 6.3 Hz, 3H). ES/MS m/z: 578.3 [M + H]$^+$. |
| 345 | 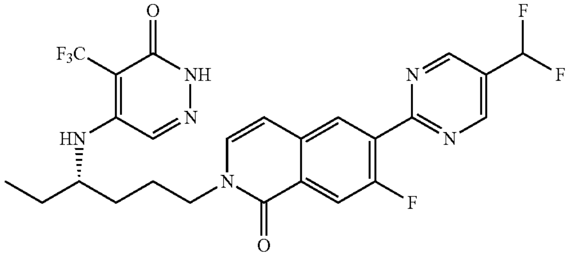 [SMILES: CC[C@@H](CCCn1ccc2cc(-c3ncc(C(F)F)cn3)c(F)cc2c1=O)Nc1cn[nH]c(=O)c1C(F)(F)F] | 1H NMR (400 MHz, DMSO-d6) δ 12.42 (s, 1H), 9.25 (d, J = 1.5 Hz, 2H), 8.40 (d, J = 7.1 Hz, 1H), 8.06-7.93 (m, 2H), 7.52 (d, J = 7.4 Hz, 1H), 7.31 (t, J = 54.8 Hz, 1H), 6.83 (d, J = 7.3 Hz, 1H), 6.29 (dq, J = 10.1, 3.5 Hz, 1H), 4.00 (t, J = 6.8 Hz, 2H), 3.86 (q, J = 7.3 Hz, 1H), 1.84-1.48 (m, 5H), 0.82 (t, J = 7.3 Hz, 3H). ES/MS m/z: 553.3 [M + H]$^+$. |
| 346 | 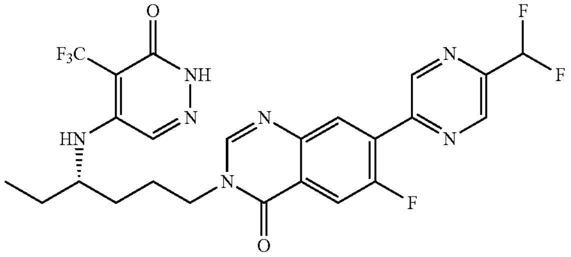 [SMILES: CC[C@@H](CCCn1cnc2cc(-c3cnc(C(F)F)cn3)c(F)cc2c1=O)Nc1cn[nH]c(=O)c1C(F)(F)F] | 1H NMR (400 MHz, DMSO-d6) δ 12.41 (s, 1H), 9.29-9.15 (m, 2H), 8.46 (s, 1H), 8.26 (d, J = 6.8 Hz, 1H), 8.04 (d, J = 10.6 Hz, 1H), 7.96 (s, 1H), 7.24 (t, J = 54.1 Hz, 1H), 6.37-6.15 (m, 1H), 4.02 (t, J = 6.8 Hz, 2H), 3.92-3.76 (m, 1H), 1.83-1.67 (m, 2H), 1.67-1.48 (m, 3H), 0.82 (t, J = 7.3 Hz, 3H). ES/MS m/z: 554.3 [M + H]$^+$. |
| 347 | 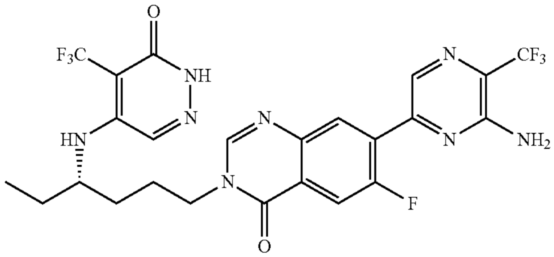 [SMILES: CC[C@@H](CCCn1cnc2cc(-c3cnc(C(F)(F)F)c(N)n3)c(F)cc2c1=O)Nc1cn[nH]c(=O)c1C(F)(F)F] | 1H NMR (400 MHz, DMSO-d6) δ 12.42 (s, 1H), 8.44 (s, 1H), 8.35 (d, J = 2.5 Hz, 1H), 8.22 (d, J = 6.7 Hz, 1H), 8.03-7.90 (m, 2H), 7.17 (s, 2H), 6.33-6.22 (m, 1H), 4.01 (t, J = 6.8 Hz, 2H), 3.88-3.79 (m, 1H), 1.83-1.66 (m, 2H), 1.66-1.42 (m, 3H), 0.82 (t, J = 7.3 Hz, 3H). ES/MS m/z: 587.3 [M + H]$^+$. |
| 348 | 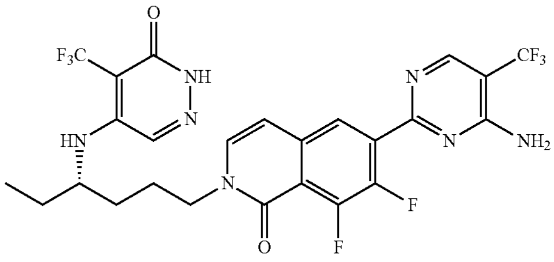 | 1H NMR (400 MHz, DMSO-d6) δ 12.42 (s, 1H), 8.66 (s, 1H), 8.05-7.92 (m, 2H), 7.52 (d, J = 7.4 Hz, 1H), 6.73 (dd, J = 7.4, 1.8 Hz, 1H), 6.33-6.22 (m, 1H), 4.02-3.75 (m, 3H), 1.83-1.45 (m, 5H), 0.82 (t, J = 7.3 Hz, 3H). ES/MS m/z: 604.3 [M + H]$^+$. |
| 349 | 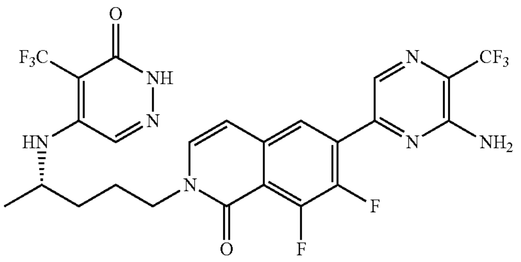 [SMILES: C[C@@H](CCCn1ccc2cc(-c3cnc(C(F)(F)F)c(N)n3)c(F)c(F)c2c1=O)Nc1cn[nH]c(=O)c1C(F)(F)F] | 1H NMR (400 MHz, DMSO-d6) δ 12.43 (s, 1H), 8.32 (d, J = 2.4 Hz, 1H), 7.97-7.87 (m, 2H), 7.54 (d, J = 7.4 Hz, 1H), 7.18 (s, 2H), 6.73-6.65 (m, 1H), 6.40-6.28 (m, 1H), 1.78-1.59 (m, 3H), 1.59-1.44 (m, 1H), 1.17 (d, J = 6.3 Hz, 3H). *methylene/methyne peaks hidden under water. ES/MS m/z: 590.3 [M + H]$^+$. |

-continued

| Ex. No. | Structure | 1H NMR/MS [M + H]+ |
|---|---|---|
| 350 | 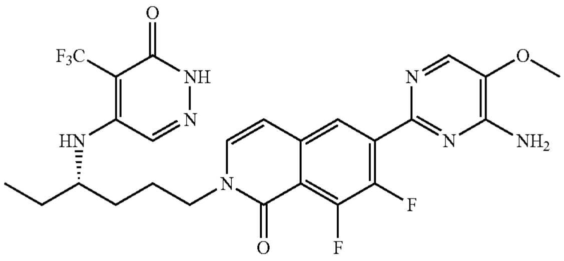 [SMILES: CC[C@@H](CCCn1ccc2cc(-c3ncc(OC)c(N)n3)c(F)c(F)c2c1=O)Nc1cn[nH]c(=O)c1C(F)(F)F] | 1H NMR (400 MHz, DMSO-d6) δ 12.42 (s, 1H), 8.06 (s, 1H), 7.96 (s, 1H), 7.89 (d, J = 6.2 Hz, 1H), 7.69 (s, 2H), 7.51 (d, J = 7.4 Hz, 1H), 6.75-6.68 (m, 1H), 6.32-6.24 (m, 1H), 3.98-3.91 (m, 4H), 1.77-1.62 (m, 2H), 1.62-1.48 (m, 3H), 0.82 (t, J = 7.3 Hz, 3H). *methylene/methyne protons hidden under water. ES/MS m/z: 566.3 [M + H]+. |
| 351 | 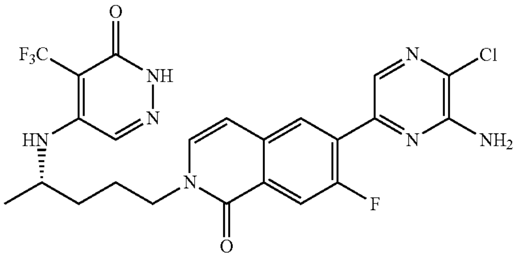 | 1H NMR (400 MHz, DMSO-d6) δ 12.43 (s, 1H), 8.15 (d, J = 7.2 Hz, 1H), 8.03 (d, J = 2.5 Hz, 1H), 7.98 (d, J = 11.6 Hz, 1H), 7.91 (s, 1H), 7.49 (d, J = 7.4 Hz, 1H), 7.10 (s, 2H), 6.74 (d, J = 7.4 Hz, 1H), 6.35 (dd, J = 8.7, 3.7 Hz, 1H), 4.04-3.93 (m, 3H), 1.81-1.58 (m, 3H), 1.56-1.45 (m, 1H), 1.16 (d, J = 6.2 Hz, 3H). ES/MS m/z: 583.3 [M + H]+. |
| 352 | 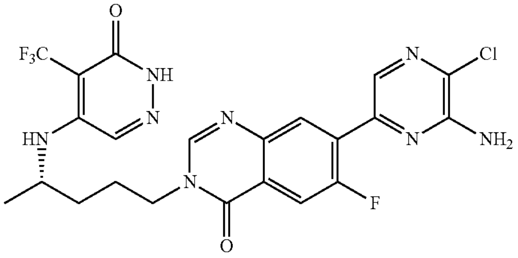 | 1H NMR (400 MHz, DMSO-d6) δ 12.43 (s, 1H), 8.42 (s, 1H), 8.19 (d, J = 6.8 Hz, 1H), 8.08 (d, J = 2.4 Hz, 1H), 7.95 (d, J = 10.9 Hz, 1H), 7.91 (s, 1H), 7.13 (s, 2H), 6.35 (dd, J = 8.7, 3.8 Hz, 1H), 4.04-3.93 (m, 3H), 1.80-1.61 (m, 3H), 1.59-1.45 (m, 1H), 1.17 (d, J = 6.3 Hz, 3H). ES/MS m/z: 583.3 [M + H]+. |
| 353 | 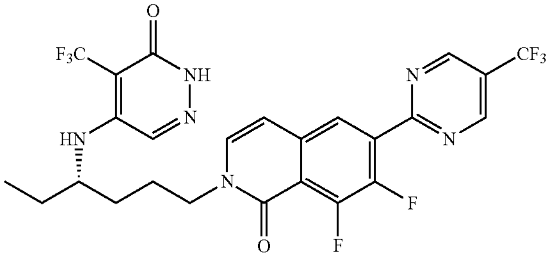 [SMILES: CC[C@@H](CCCn1ccc2cc(-c3ncc(C(F)(F)F)cn3)c(F)c(F)c2c1=O)Nc1cn[nH]c(=O)c1C(F)(F)F] | 1H NMR (400 MHz, DMSO-d6) δ 12.42 (s, 1H), 9.50 (s, 2H), 8.33-8.13 (m, 1H), 7.96 (s, 1H), 7.55 (d, J = 7.4 Hz, 1H), 6.92-6.71 (m, 1H), 6.39-6.08 (m, 1H), 3.99-3.89 (m, 2H), 3.91-3.68 (m, 2H), 1.78-1.51 (m, 5H), 0.83 (t, J = 7.3 Hz, 3H). ES/MS m/z: 589.2 [M + H]+. |
| 354 | 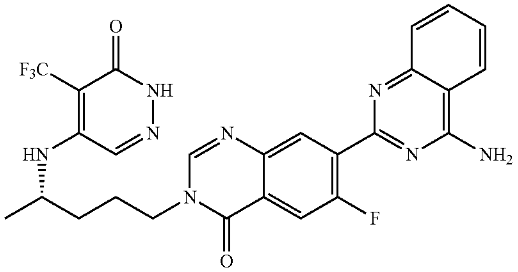 [SMILES: C[C@@H](CCCn1cnc2cc(-c3nc(N)c4ccccc4n3)c(F)cc2c1=O)Nc1cn[nH]c(=O)c1C(F)(F)F] | 1H NMR (400 MHz, DMSO-d6) δ 12.45 (s, 1H), 8.47 (s, 1H), 8.40 (d, J = 8.3 Hz, 1H), 8.25 (d, J = 6.5 Hz, 1H), 8.07-7.95 (m, 2H), 7.93 (s, 1H), 7.86 (d, J = 8.3 Hz, 1H), 7.79-7.61 (m, 2H), 7.38-7.23 (m, 1H), 6.43-6.32 (m, 1H), 4.07-3.97 (m, 3H), 1.83-1.64 (m, 3H), 1.60-1.49 (m, 1H), 1.23-1.10 (m, 3H). ES/MS m/z: 555.3 [M + H]+. |

-continued

| Ex. No. | Structure | 1H NMR/MS [M + H]$^+$ |
|---|---|---|
| 355 | 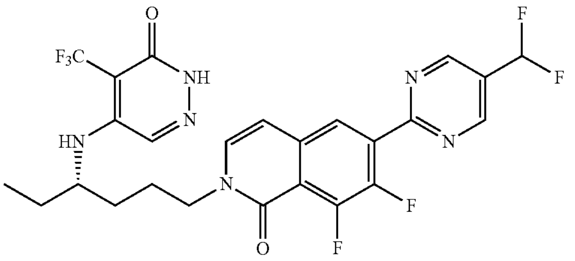 [SMILES: CC[C@@H](CCCn1ccc2cc(-c3ncc(C(F)F)cn3)c(F)c(F)c2c1=O)Nc1cn[nH]c(=O)c1C(F)(F)F] | 1H NMR (400 MHz, DMSO-d6) δ 12.42 (s, 1H), 9.27 (d, J = 1.5 Hz, 2H), 8.26-8.15 (m, 1H), 7.97 (s, 1H), 7.54 (d, J = 7.4 Hz, 1H), 7.48-7.15 (m, 1H), 6.84-6.72 (m, 1H), 6.34-6.18 (m, 1H), 4.01-3.91 (m, 2H), 3.90-3.76 (m, 1H), 1.83-1.45 (m, 6H), 0.83 (t, J = 7.3 Hz, 3H). ES/MS m/z: 571.3 [M + H]$^+$. |
| 356 | 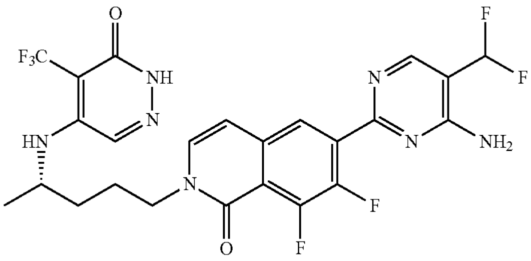 | 1H NMR (400 MHz, DMSO-d6) δ 12.43 (s, 1H), 8.52 (d, J = 1.6 Hz, 1H), 7.97 (d, J = 5.3 Hz, 2H), 7.86-7.32 (m, 3H), 7.11 (t, J = 54.1 Hz, 1H), 6.73 (dd, J = 7.4, 1.8 Hz, 1H), 6.32-6.24 (m, 1H), 3.95 (t, J = 6.7 Hz, 2H), 3.89-3.78 (m, 1H), 1.83-1.41 (m, 6H), 0.83 (t, J = 7.3 Hz, 3H). ES/MS m/z: 586.1 [M + H]$^+$. |
| 357 | 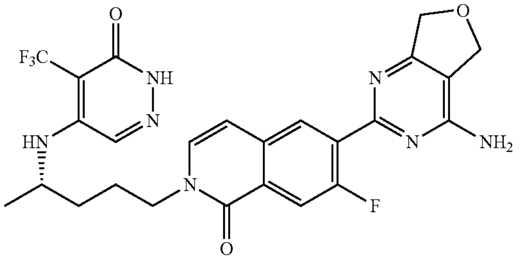 [SMILES: C[C@@H](CCCn1ccc2cc(-c3nc(N)c4c(n3)COC4)c(F)cc2c1=O)Nc1cn[nH]c(=O)c1C(F)(F)F] | 1H NMR (400 MHz, DMSO-d6) δ 12.44 (s, 1H), 8.13 (d, J = 7.1 Hz, 1H), 7.97-7.89 (m, 2H), 7.48 (d, J = 7.4 Hz, 1H), 7.32 (br. s, 2H), 6.76 (d, J = 7.4 Hz, 1H), 6.40-6.31 (m, 1H), 4.95 (t, J = 2.7 Hz, 2H), 4.88 (t, J = 2.6 Hz, 2H), 4.02-3.94 (m, 3H), 1.79-1.60 (m, 3H), 1.57-1.44 (m, 1H), 1.17 (d, J = 6.2 Hz, 3H). ES/MS m/z: 546.1 [M + H]$^+$. |
| 358 | 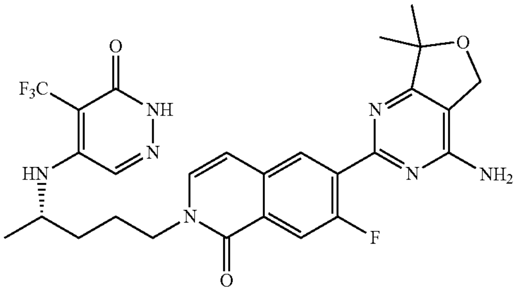 [SMILES: C[C@@H](CCCn1ccc2cc(-c3nc(N)c4c(n3)C(C)(C)OC4)c(F)cc2c1=O)Nc1cn[nH]c(=O)c1C(F)(F)F] | 1H NMR (400 MHz, DMSO-d6) δ 12.44 (s, 1H), 8.10 (d, J = 7.0 Hz, 1H), 7.98-7.88 (m, 2H), 7.49 (d, J = 7.4 Hz, 1H), 7.34 (br. s, 2H), 6.77 (d, J = 7.4 Hz, 1H), 6.40-6.31 (m, 1H), 4.86 (s, 2H), 4.03-3.94 (m, 3H), 1.80-1.59 (m, 3H), 1.58-1.46 (m, 1H), 1.41 (s, 6H), 1.17 (d, J = 6.3 Hz, 3H). ES/MS m/z: 574.2 [M + H]$^+$. |
| 359 | 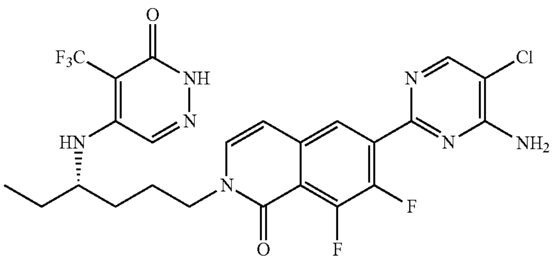 [SMILES: CC[C@@H](CCCn1ccc2cc(-c3ncc(Cl)c(N)n3)c(F)c(F)c2c1=O)Nc1cn[nH]c(=O)c1C(F)(F)F] | 1H NMR (400 MHz, DMSO-d6) δ 12.42 (s, 1H), 8.45 (s, 1H), 7.99-7.92 (m, 2H), 7.64 (br. s, 2H), 7.50 (d, J = 7.4 Hz, 1H), 6.71 (dd, J = 7.5, 1.9 Hz, 1H), 6.33-6.23 (m, 1H), 3.94 (t, J = 6.7 Hz, 2H), 3.90-3.78 (m, 1H), 1.81-1.47 (m, 4H), 1.56 (t, J = 6.9 Hz, 2H), 0.83 (t, J = 7.3 Hz, 3H). ES/MS m/z: 570.1 [M + H]$^+$. |

-continued

| Ex. No. | Structure | 1H NMR/MS [M + H]$^+$ |
|---|---|---|
| 360 | 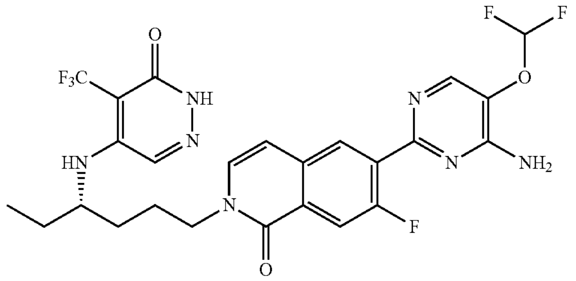 [SMILES: CC[C@@H](CCCn1ccc2cc(-c3ncc(OC(F)F)c(N)n3)c(F)cc2c1=O)Nc1cn[nH]c(=O)c1C(F)(F)F] | 1H NMR (400 MHz, DMSO-d6) δ 12.42 (s, 1H), 8.22 (s, 1H), 8.12 (d, J = 7.2 Hz, 1H), 8.00-7.88 (m, 2H), 7.47 (d, J = 7.4 Hz, 1H), 7.20 (t, J = 73.1 Hz, 1H), 6.75 (d, J = 7.4 Hz, 1H), 6.34-6.22 (m, 1H), 3.98 (t, J = 6.8 Hz, 2H), 3.85 (d, J = 7.6 Hz, 1H), 1.81-1.46 (m, 5H), 0.81 (t, J = 7.3 Hz, 3H). ES/MS m/z: 584.1 [M + H]$^+$. |
| 361 | 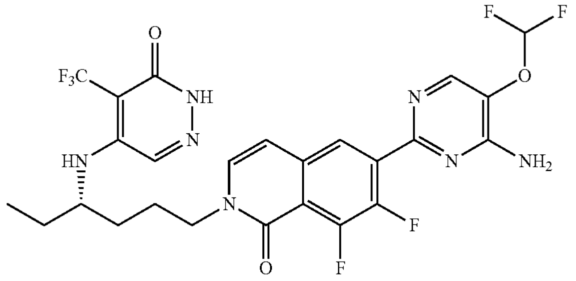 [SMILES: CC[C@@H](CCCn1ccc2cc(-c3ncc(OC(F)F)c(N)n3)c(F)c(F)c2c1=O)Nc1cn[nH]c(=O)c1C(F)(F)F] | 1H NMR (400 MHz, DMSO-d6) δ 12.42 (s, 1H), 8.23 (s, 1H), 7.96 (s, 1H), 7.94-7.88 (m, 1H), 7.49 (d, J = 7.4 Hz, 1H), 7.21 (t, J = 73.1 Hz, 1H), 6.71 (dd, J = 7.5, 1.8 Hz, 1H), 6.27 (d, J = 8.8 Hz, 1H), 4.02-3.74 (m, 3H), 1.82-1.38 (m, 5H), 0.82 (t, J = 7.3 Hz, 3H). ES/MS m/z: 602.2 [M + H]$^+$. |
| 362 | 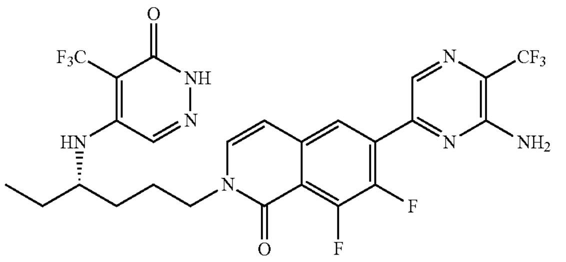 [SMILES: CC[C@@H](CCCn1ccc2cc(-c3cnc(C(F)(F)F)c(N)n3)c(F)c(F)c2c1=O)Nc1cn[nH]c(=O)c1C(F)(F)F] | 1H NMR (400 MHz, DMSO-d6) δ 12.41 (s, 1H), 8.32 (d, J = 2.4 Hz, 1H), 7.98-7.89 (m, 2H), 7.53 (d, J = 7.4 Hz, 1H), 7.18 (s, 2H), 6.70 (dd, J = 7.5, 1.8 Hz, 1H), 6.33-6.20 (m, 1H), 3.95 (t, J = 6.7 Hz, 2H), 3.89-3.76 (m, 1H), 1.79-1.64 (m, 2H), 1.64-1.45 (m, 4H), 0.83 (t, J = 7.3 Hz, 3H). ES/MS m/z: 604.1 [M + H]$^+$. |
| 363 | 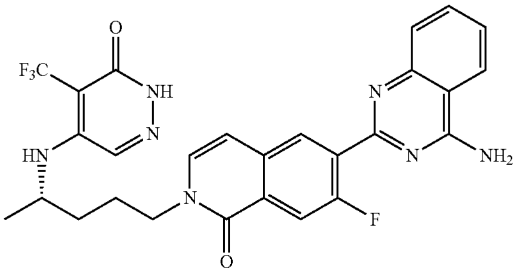 [SMILES: C[C@@H](CCCn1ccc2cc(-c3nc(N)c4ccccc4n3)c(F)cc2c1=O)Nc1cn[nH]c(=O)c1C(F)(F)F] | 1H NMR (400 MHz, DMSO-d6) δ 12.44 (s, 1H), 8.40 (d, J = 8.3 Hz, 1H), 8.24 (d, J = 6.9 Hz, 1H), 8.06 (d, J = 10.9 Hz, 1H), 8.03-7.95 (m, 1H), 7.92 (s, 1H), 7.85 (d, J = 8.4 Hz, 1H), 7.77-7.68 (m, 1H), 7.55 (d, J = 7.4 Hz, 1H), 6.82 (d, J = 7.4 Hz, 1H), 6.40-6.31 (m, 1H), 4.03-3.99 (m, 2H), 1.83-1.60 (m, 4H), 1.60-1.41 (m, 2H), 1.18 (d, J = 6.3 Hz, 3H), 1.14-1.10 (m, 1H). ES/MS m/z: 554.3 [M + H]$^+$. |
| 364 | 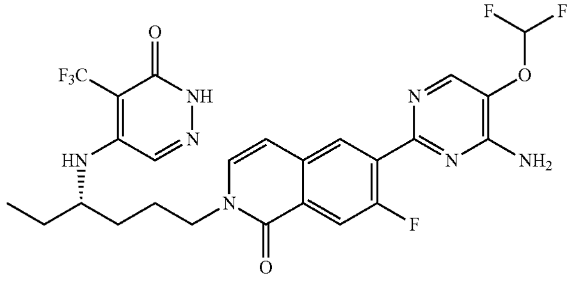 [SMILES: CC[C@@H](CCCn1ccc2cc(-c3ncc(OC(F)F)c(N)n3)c(F)cc2c1=O)Nc1cn[nH]c(=O)c1C(F)(F)F] | 1H NMR (400 MHz, DMSO-d6) & 12.42 (s, 1H), 8.41 (s, 1H), 8.23 (s, 1H), 8.10 (d, J = 6.8 Hz, 1H), 7.96 (s, 1H), 7.89 (d, J = 10.3 Hz, 1H), 7.47 (s, 2H), 7.21 (t, J = 73.1 Hz, 1H), 6.28 (dd, J = 9.4, 3.6 Hz, 1H), 3.99 (t, J = 6.9 Hz, 2H), 3.85 (d, J = 7.6 Hz, 1H), 1.84-1.47 (m, 5H), 0.82 (t, J = 7.3 Hz, 3H). ES/MS m/z: 585.2 [M + H]$^+$. |

-continued

| Ex. No. | Structure | 1H NMR/MS [M + H]$^+$ |
|---|---|---|
| 365 | 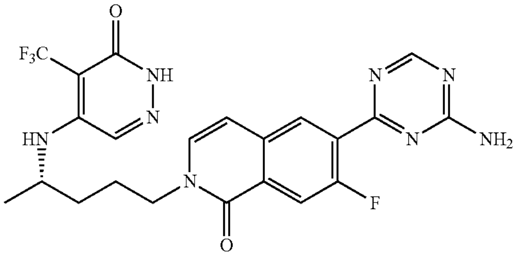 [SMILES: C[C@@H](CCCn1ccc2cc(-c3ncnc(N)n3)c(F)cc2c1=O)Nc1cn[nH]c(=O)c1C(F)(F)F] | 1H NMR (400 MHz, DMSO-d6) δ 12.43 (s, 1H), 8.65 (s, 1H), 8.26 (d, J = 7.0 Hz, 1H), 7.98-7.90 (m, 2H), 7.86-7.78 (m, 2H), 7.50 (d, J = 7.4 Hz, 1H), 6.78 (d, J = 7.4 Hz, 1H), 6.39-6.32 (m, 1H), 4.03-3.93 (m, 3H), 1.75-1.64 (m, 3H), 1.53-1.47 (m, 1H), 1.16 (d, J = 6.3 Hz, 3H). ES/MS m/z: 504.8 [M + H]$^+$. |
| 366 | 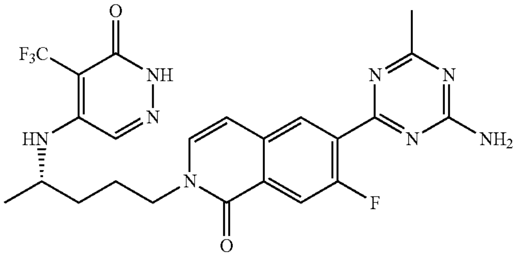 | 1H NMR (400 MHz, DMSO-d6) & 12.43 (s, 1H), 8.21 (d, J = 7.0 Hz, 1H), 8.01-7.85 (m, 2H), 7.70 (s, 2H), 7.50 (d, J = 7.4 Hz, 1H), 6.79 (d, J = 7.4 Hz, 1H), 6.39-6.27 (m, 1H), 4.05-3.92 (m, 3H), 2.39 (s, 3H), 1.78-1.45 (m, 4H), 1.17 (d, J = 6.3 Hz, 3H). ES/MS m/z: 519.2 [M + H]$^+$. |
| 367 | 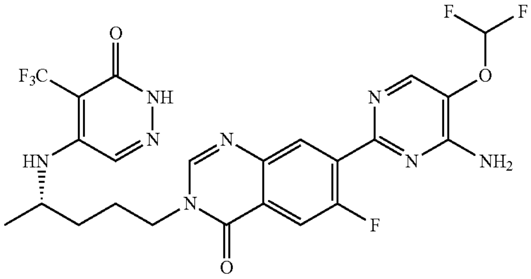 [SMILES: C[C@@H](CCCn1cnc2cc(-c3ncc(OC(F)F)c(N)n3)c(F)cc2c1=O)Nc1cn[nH]c(=O)c1C(F)(F)F] | 1H NMR (400 MHz, DMSO-d6) δ 12.44 (s, 1H), 8.42 (s, 1H), 8.25 (s, 1H), 8.11 (d, J = 6.7 Hz, 1H), 7.96-7.85 (m, 2H), 7.21 (t, J = 73.0 Hz, 1H), 6.44-6.25 (m, 1H), 4.04-3.90 (m, 2H), 1.83-1.61 (m, 3H), 1.61-1.41 (m, 1H), 1.17 (d, J = 6.2 Hz, 3H). ES/MS m/z: 571.2 [M + H]$^+$. |

The Following compounds were synthesized using the procedure as described in Example 168 from the corresponding starting materials.

| Ex. No. | Structure | $^1$H NMR/MS [M + H]$^+$ |
|---|---|---|
| 368 | 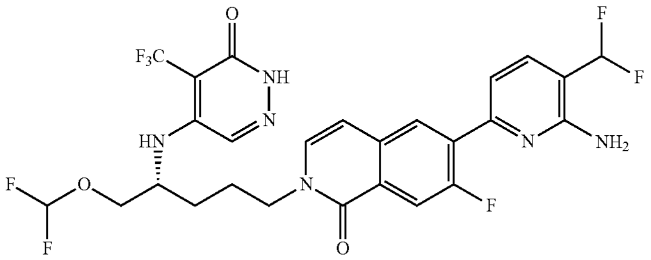 [SMILES: Nc1nc(-c2cc3ccn(CCC[C@H](COC(F)F)Nc4cn[nH]c(=O)c4C(F)(F)F)c(=O)c3cc2F)ccc1C(F)F] | 1H NMR (400 MHz, DMSO-d6) δ 12.48 (s, 1H), 8.14 (d, J = 7.3 Hz, 1H), 8.00-7.92 (m, 2H), 7.79 (d, J = 7.8 Hz, 1H), 7.47 (d, J = 7.4 Hz, 1H), 7.25-6.94 (m, 2H), 6.87-6.46 (m, 2H), 6.44-6.37 (m, 1H), 4.26 (s, 1H), 3.99 (t, J = 6.9 Hz, 2H), 3.92 (d, J = 5.9 Hz, 2H), 1.86-1.46 (m, 4H). ES/MS m/z: 619.1 [M + H]$^+$. |
| 369 | 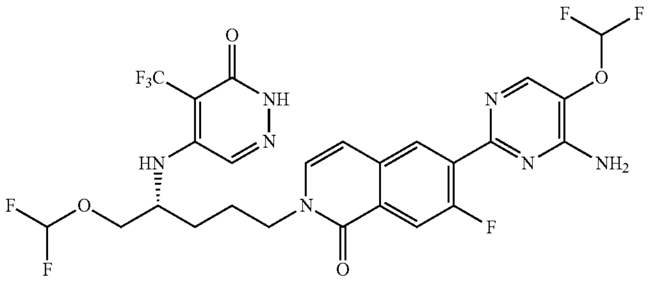 [SMILES: Nc1nc(-c2cc3ccn(CCC[C@H](COC(F)F)Nc4cn[nH]c(=O)c4C(F)(F)F)c(=O)c3cc2F)ncc1OC(F)F] | 1H NMR (400 MHz, DMSO-d6) δ 12.49 (s, 1H), 8.23 (s, 1H), 8.12 (d, J = 7.1 Hz, 1H), 7.98 (s, 1H), 7.92 (d, J = 11.1 Hz, 1H), 7.50-7.45 (m, 2H), 7.20 (t, J = 73.1 Hz, 1H), 6.75 (d, J = 7.4 Hz, 1H), 6.65 (t, J = 75.5 Hz, 1H), 6.41 (dt, J = 9.6, 3.8 Hz, 1H), 4.32-4.18 (m, 1H), 3.99 (t, J = 6.8 Hz, 2H), 3.92 (d, J = 5.9 Hz, 2H), 1.84-1.68 (m, 2H), 1.68-1.51 (m, 2H). ES/MS m/z: 636.2 [M + H]$^+$. |

-continued

| Ex. No. | Structure | $^1$H NMR/MS [M + H]$^+$ |
|---|---|---|
| 370 | 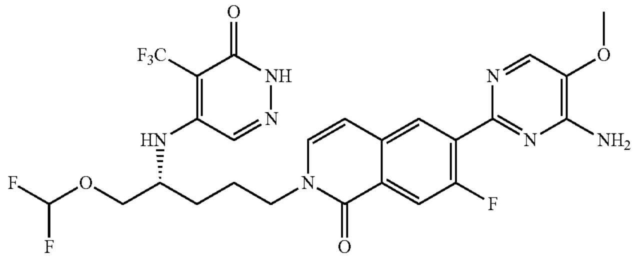 [SMILES: COc1cnc(-c2cc3ccn(CCC[C@H](COC(F)F)Nc4cn[nH]c(=O)c4C(F)(F)F)c(=O)c3cc2F)nc1N] | 1H NMR (400 MHz, DMSO-d6) δ 12.49 (s, 1H), 8.11 (d, J = 7.1 Hz, 1H), 8.04 (s, 1H), 7.96 (d, J = 10.4 Hz, 2H), 7.49 (d, J = 7.4 Hz, 1H), 6.76 (d, J = 7.4 Hz, 1H), 6.65 (t, J = 75.5 Hz, 1H), 6.45-6.33 (m, 1H), 4.31-4.20 (m, 1H), 4.03-3.96 (m, 2H), 3.96-3.87 (m, 5H), 1.84-1.68 (m, 2H), 1.69-1.47 (m, 2H). ES/MS m/z: 600.3 [M + H]$^+$. |
| 371 | 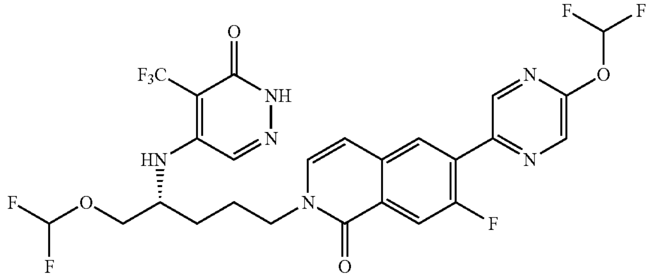 [SMILES: O=c1[nH]ncc(N[C@H](CCCn2ccc3cc(-c4cnc(OC(F)F)cn4)c(F)cc3c2=O)COC(F)F)c1C(F)(F)F] | 1H NMR (400 MHz, DMSO-d6) δ 12.48 (s, 1H), 8.90-8.74 (m, 2H), 8.25 (d, J = 7.3 Hz, 1H), 8.03 (d, J = 11.6 Hz, 1H), 8.00-7.58 (m, 4H), 7.50 (d, J = 7.4 Hz, 1H), 6.81 (d, J = 7.4 Hz, 1H), 6.65 (t, J = 75.5 Hz, 1H), 6.44-6.36 (m, 1H), 4.32-4.20 (m, 1H), 4.00 (t, J = 6.8 Hz, 2H), 3.92 (d, J = 5.9 Hz, 2H), 1.84-1.69 (m, 2H), 1.69-1.50 (m, 2H). ES/MS m/z: 621.3 [M + H]$^+$. |
| 372 | 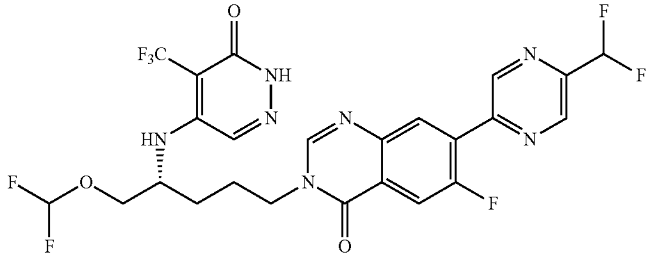 [SMILES: O=c1[nH]ncc(N[C@H](CCCn2cnc3cc(-c4cnc(C(F)F)cn4)c(F)cc3c2=O)COC(F)F)c1C(F)(F)F] | 1H NMR (400 MHz, DMSO-d6) δ 12.49 (s, 1H), 9.23 (d, J = 36.2 Hz, 2H), 8.46 (s, 1H), 8.26 (d, J = 6.8 Hz, 1H), 8.04 (d, J = 10.6 Hz, 1H), 7.97 (s, 1H), 7.24 (t, J = 54.1 Hz, 1H), 6.66 (t, J = 75.5 Hz, 1H), 6.45-6.37 (m, 1H), 4.32-4.20 (m, 1H), 4.03 (t, J = 6.8 Hz, 2H), 3.93 (d, J = 5.9 Hz, 2H), 1.90-1.71 (m, 2H), 1.71-1.51 (m, 2H). ES/MS m/z: 606.1 [M + H]$^+$. |
| 373 | 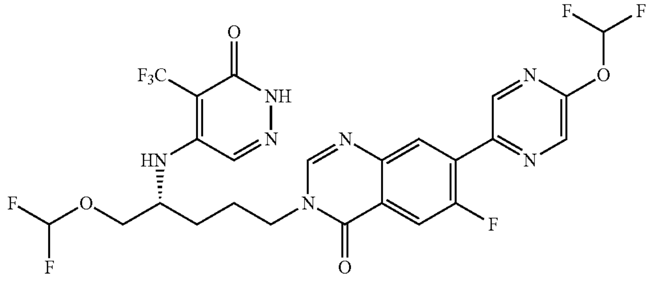 [SMILES: O=c1[nH]ncc(N[C@H](CCCn2cnc3cc(-c4cnc(OC(F)F)cn4)c(F)cc3c2=O)COC(F)F)c1C(F)(F)F] | 1H NMR (400 MHz, DMSO-d6) δ 12.49 (s, 1H), 8.90-8.73 (m, 2H), 8.44 (s, 1H), 8.19 (d, J = 6.9 Hz, 1H), 8.04-7.60 (m, 3H), 6.66 (t, J = 75.5 Hz, 1H), 6.44-6.36 (m, 1H), 4.31-4.21 (m, 1H), 4.02 (t, J = 6.8 Hz, 2H), 3.92 (d, J = 5.9 Hz, 2H), 1.88-1.71 (m, 2H), 1.71-1.56 (m, 2H). ES/MS m/z: 621.9 [M + H]$^+$. |
| 374 | 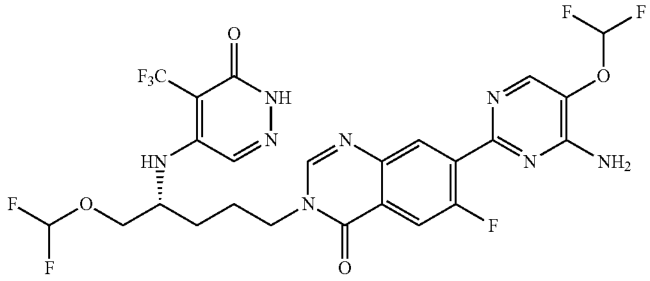 [SMILES: Nc1nc(-c2cc3ncn(CCC[C@H](COC(F)F)Nc4cn[nH]c(=O)c4C(F)(F)F)c(=O)c3cc2F)ncc1OC(F)F] | 1H NMR (400 MHz, DMSO-d6) δ 12.49 (s, 1H), 8.41 (s, 1H), 8.25 (s, 1H), 8.11 (d, J = 6.8 Hz, 1H), 7.97 (s, 1H), 7.89 (d, J = 10.3 Hz, 1H), 7.21 (t, J = 73.1 Hz, 1H), 6.65 (t, J = 75.5 Hz, 1H), 6.44-6.34 (m, 1H), 3.94-3.89 (m, 2H), 1.87-1.70 (m, 2H), 1.70-1.54 (m, 2H). ES/MS m/z: 368.1 [M + H]$^+$. |

-continued

| Ex. No. | Structure | $^1$H NMR/MS [M + H]$^+$ |
|---|---|---|
| 375 | 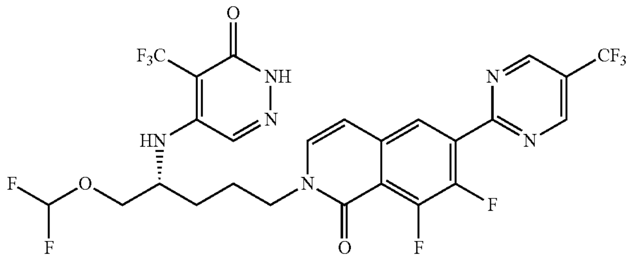 [SMILES: O=c1[nH]ncc(N[C@H](CCCn2ccc3cc(-c4ncc(C(F)(F)F)cn4)c(F)c(F)c3c2=O)COC(F)F)c1C(F)(F)F] | 1H NMR (400 MHz, DMSO-d6) δ 12.48 (s, 1H), 9.50 (d, J = 1.0 Hz, 2H), 8.24 (dd, J = 6.6, 1.7 Hz, 1H), 7.98 (s, 1H), 7.55 (d, J = 7.4 Hz, 1H), 6.88-6.45 (m, 2H), 6.45-6.36 (m, 1H), 4.31-4.22 (m, 1H), 4.00-3.90 (m, 4H), 1.82-1.69 (m, 2H), 1.68-1.54 (m, 2H). ES/MS m/z: 641.1 [M + H]$^+$. |
| 376 | 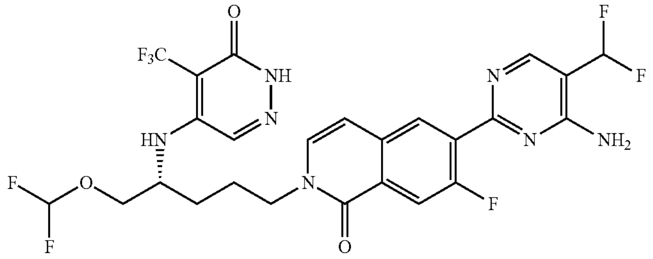 [SMILES: Nc1nc(-c2cc3ccn(CCC[C@H](COC(F)F)Nc4cn[nH]c(=O)c4C(F)(F)F)c(=O)c3cc2F)ncc1C(F)F] | 1H NMR (400 MHz, DMSO-d6) δ 12.49 (s, 1H), 8.50 (d, J = 1.3 Hz, 1H), 8.17 (d, J = 7.0 Hz, 1H), 8.00-7.91 (m, 2H), 7.58 (br s, 2H), 7.48 (d, J = 7.4 Hz, 1H), 7.10 (t, J = 54.1 Hz, 1H), 6.77 (d, J = 7.4 Hz, 1H), 6.65 (t, J = 75.5 Hz, 1H), 6.45-6.36 (m, 1H), 4.33-4.20 (m, 1H), 3.99 (t, J = 6.9 Hz, 2H), 3.92 (d, J = 6.0 Hz, 2H), 1.84-1.68 (m, 2H), 1.68-1.52 (m, 2H). ES/MS m/z: 620.3 [M + H]$^+$. |
| 377 | 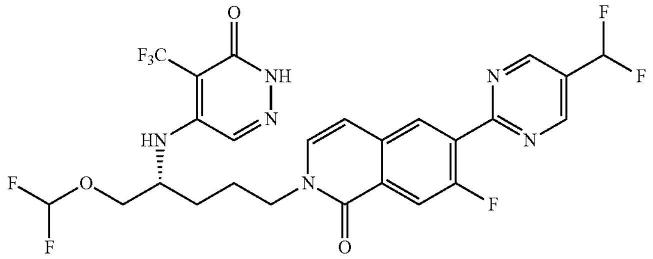 [SMILES: O=c1[nH]ncc(N[C@H](CCCn2ccc3cc(-c4ncc(C(F)F)cn4)c(F)cc3c2=O)COC(F)F)c1C(F)(F)F] | 1H NMR (400 MHz, DMSO-d6) δ 12.48 (s, 1H), 9.25 (d, J = 1.2 Hz, 2H), 8.40 (d, J = 7.2 Hz, 1H), 8.02 (d, J = 11.4 Hz, 1H), 7.98 (s, 1H), 7.51 (d, J = 7.4 Hz, 1H), 7.31 (t, J = 54.8 Hz, 1H), 6.87-6.45 (m, 2H), 6.45-6.36 (m, 1H), 4.27 (s, 1H), 4.01 (t, J = 6.8 Hz, 2H), 3.92 (d, J = 6.0 Hz, 2H), 1.84-1.70 (m, 2H), 1.70-1.53 (m, 2H). ES/MS m/z: 605.3 [M + H]$^+$. |
| 378 | 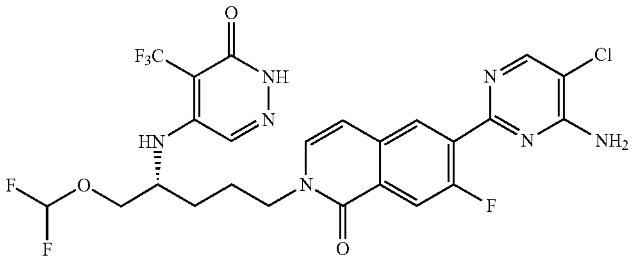 [SMILES: Nc1nc(-c2cc3ccn(CCC[C@H](COC(F)F)Nc4cn[nH]c(=O)c4C(F)(F)F)c(=O)c3cc2F)ncc1Cl] | 1H NMR (400 MHz, DMSO-d6) δ 12.48 (s, 1H), 8.43 (s, 1H), 8.15 (d, J = 7.1 Hz, 1H), 7.98 (s, 1H), 7.93 (d, J = 11.2 Hz, 1H), 7.64 (br s, 2H), 7.47 (d, J = 7.4 Hz, 1H), 6.76 (d, J = 7.4 Hz, 1H), 6.65 (t, J = 75.5 Hz, 1H), 6.45-6.35 (m, 1H), 4.31-4.22 (m, 1H), 3.99 (t, J = 6.8 Hz, 2H), 3.92 (d, J = 6.0 Hz, 2H), 1.83-1.69 (m, 2H), 1.69-1.52 (m, 2H). ES/MS m/z: 604.3 [M + H]$^+$. |
| 379 | 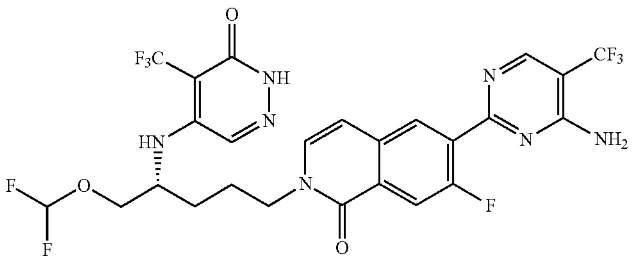 [SMILES: Nc1nc(-c2cc3ccn(CCC[C@H](COC(F)F)Nc4cn[nH]c(=O)c4C(F)(F)F)c(=O)c3cc2F)ncc1C(F)(F)F] | 1H NMR (400 MHz, DMSO-d6) δ 12.49 (s, 1H), 8.65 (d, J = 1.1 Hz, 1H), 8.20 (d, J = 7.0 Hz, 1H), 8.03-7.90 (m, 2H), 7.49 (d, J = 7.4 Hz, 1H), 6.77 (d, J = 7.4 Hz, 1H), 6.65 (t, J = 75.5 Hz, 1H), 6.44-6.35 (m, 1H), 4.33-4.20 (m, 1H), 3.99 (t, J = 6.8 Hz, 2H), 3.92 (d, J = 6.0 Hz, 2H), 1.84-1.69 (m, 2H), 1.69-1.52 (m, 2H). ES/MS m/z: 638.3 [M + H]$^+$. |
| 380 | 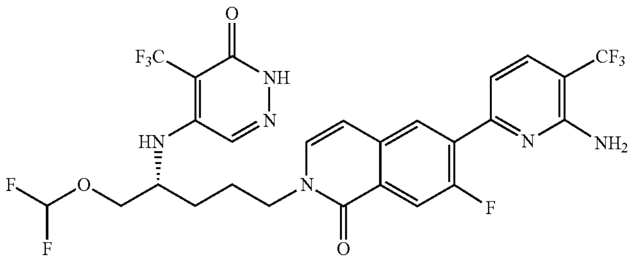 [SMILES: Nc1nc(-c2cc3ccn(CCC[C@H](COC(F)F)Nc4cn[nH]c(=O)c4C(F)(F)F)c(=O)c3cc2F)ccc1C(F)(F)F] | 1H NMR (400 MHz, DMSO-d6) δ 12.49 (s, 1H), 8.15 (d, J = 7.2 Hz, 1H), 8.02-7.94 (m, 2H), 7.92 (d, J = 8.1 Hz, 1H), 7.48 (d, J = 7.4 Hz, 1H), 7.12 (dd, J = 7.9, 2.1 Hz, 1H), 6.73 (d, J = 7.4 Hz, 1H), 6.65 (t, J = 75.5 Hz, 1H), 6.45-6.36 (m, 1H), 4.33-4.19 (m, 1H), 3.99 (t, J = 6.8 Hz, 2H), 3.92 (d, J = 5.9 Hz, 2H), 1.85-1.68 (m, 2H), 1.68-1.50 (m, 2H). ES/MS m/z: 637.3 [M + H]+. |

-continued

| Ex. No. | Structure | $^1$H NMR/MS [M + H]$^+$ |
|---|---|---|
| 381 | 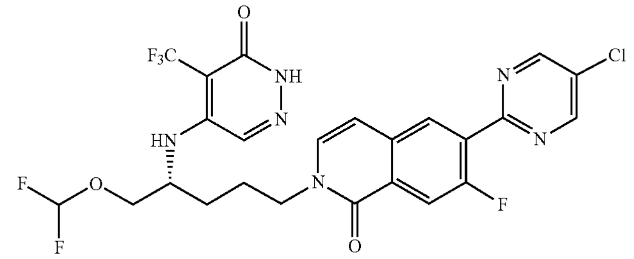 [SMILES: O=c1[nH]ncc(N[C@H](CCCn2ccc3cc(-c4ncc(Cl)cn4)c(F)cc3c2=O)COC(F)F)c1C(F)(F)F] | 1H NMR (400 MHz, DMSO-d6) δ 12.48 (s, 1H), 9.15 (s, 2H), 8.36 (d, J = 7.2 Hz, 1H), 8.03-7.94 (m, 2H), 7.50 (d, J = 7.3 Hz, 1H), 6.85-6.46 (m, 2H), 6.44-6.35 (m, 1H), 4.32-4.21 (m, 1H), 4.00 (t, J = 6.8 Hz, 2H), 3.92 (d, J = 5.9 Hz, 2H), 1.86-1.70 (m, 2H), 1.70-1.51 (m, 2H). ES/MS m/z: 589.2 [M + H]$^+$. |
| 382 | 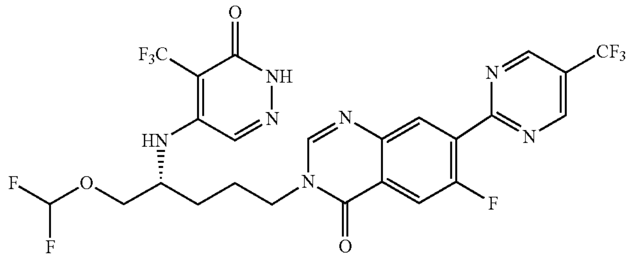 [SMILES: O=c1[nH]ncc(N[C@H](CCCn2cnc3cc(-c4ncc(C(F)(F)F)cn4)c(F)cc3c2=O)COC(F)F)c1C(F)(F)F] | 1H NMR (400 MHz, DMSO-d6) δ 12.49 (s, 1H), 9.50 (s, 2H), 8.45 (s, 1H), 8.35 (d, J = 6.7 Hz, 1H), 8.00 (d, J = 10.5 Hz, 1H), 7.97 (s, 1H), 6.66 (t, J = 75.5 Hz, 1H), 6.43-6.36 (m, 1H), 4.31-4.21 (m, 1H), 4.02 (t, J = 6.8 Hz, 2H), 3.92 (d, J = 5.9 Hz, 2H), 1.88-1.71 (m, 2H), 1.71-1.55 (m, 2H). ES/MS m/z: 624.3 [M + H]$^+$. |
| 383 | 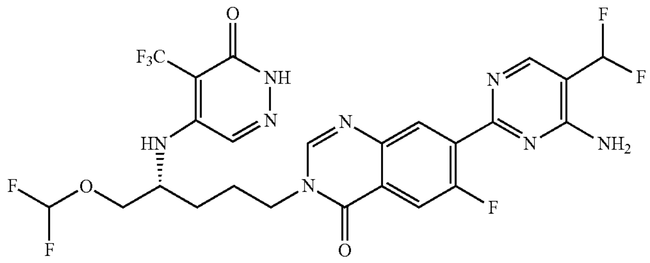 [SMILES: Nc1nc(-c2cc3ncn(CCC[C@H](COC(F)F)Nc4cn[nH]c(=O)c4C(F)(F)F)c(=O)c3cc2F)ncc1C(F)F] | 1H NMR (400 MHz, DMSO-d6) δ 12.49 (s, 1H), 8.51 (d, J = 1.7 Hz, 1H), 8.42 (s, 1H), 8.15 (d, J = 6.7 Hz, 1H), 7.97 (s, 1H), 7.91 (d, J = 10.3 Hz, 1H), 7.59 (br s, 2H), 7.09 (t, J = 54.1 Hz, 1H), 6.66 (t, J = 75.5 Hz, 1H), 6.44-6.36 (m, 1H), 4.32-4.19 (m, 1H), 4.01 (t, J = 6.8 Hz, 2H), 3.92 (d, J = 5.9 Hz, 2H), 1.86-1.70 (m, 2H), 1.70-1.53 (m, 2H). ES/MS m/z: 621.3 [M + H]$^+$. |
| 384 | 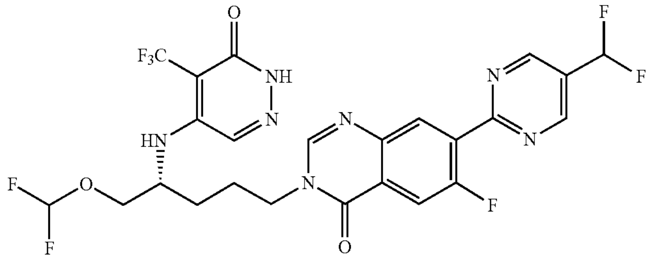 [SMILES: O=c1[nH]ncc(N[C@H](CCCn2cnc3cc(-c4ncc(C(F)F)cn4)c(F)cc3c2=O)COC(F)F)c1C(F)(F)F] | 1H NMR (400 MHz, DMSO-d6) δ 12.49 (s, 1H), 9.26 (d, J = 1.2 Hz, 2H), 8.45 (s, 1H), 8.32 (d, J = 6.7 Hz, 1H), 8.02-7.94 (m, 2H), 7.31 (t, J = 54.8 Hz, 1H), 6.66 (t, J = 75.5 Hz, 1H), 6.45-6.36 (m, 1H), 4.32-4.21 (m, 1H), 4.02 (t, J = 6.8 Hz, 2H), 3.92 (d, J = 5.9 Hz, 2H), 1.87-1.72 (m, 2H), 1.72-1.55 (m, 2H). ES/MS m/z: 606.3 [M + H]$^+$. |
| 385 | 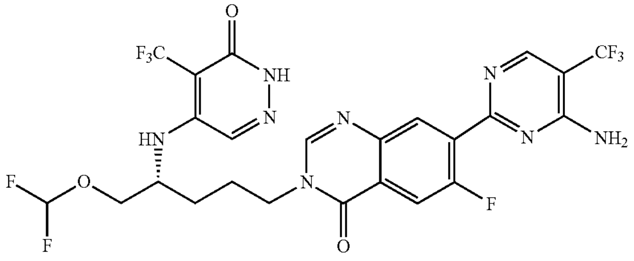 [SMILES: Nc1nc(-c2cc3ncn(CCC[C@H](COC(F)F)Nc4cn[nH]c(=O)c4C(F)(F)F)c(=O)c3cc2F)ncc1C(F)(F)F] | 1H NMR (400 MHz, DMSO-d6) δ 12.49 (s, 1H), 8.66 (s, 1H), 8.42 (s, 1H), 8.18 (d, J = 6.7 Hz, 1H), 7.97 (s, 1H), 7.92 (d, J = 10.4 Hz, 1H), 6.66 (t, J = 75.5 Hz, 1H), 6.45-6.35 (m, 1H), 4.33-4.18 (m, 1H), 4.01 (t, J = 6.8 Hz, 2H), 3.92 (d, J = 5.9 Hz, 2H), 1.86-1.70 (m, 2H), 1.70-1.54 (m, 2H). ES/MS m/z: 639.3 [M + H]$^+$. |

-continued

| Ex. No. | Structure | $^1$H NMR/MS [M + H]$^+$ |
|---|---|---|
| 386 | 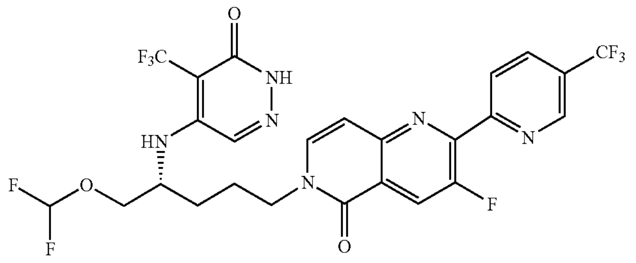 [SMILES: O=c1[nH]ncc(N[C@H](CCCn2ccc3nc(-c4ccc(C(F)(F)F)cn4)c(F)cc3c2=O)COC(F)F)c1C(F)(F)F] | 1H NMR (400 MHz, DMSO-d6) δ 12.48 (s, 1H), 9.21-9.12 (m, 1H), 8.78-8.67 (m, 2H), 8.53 (d, J = 8.4 Hz, 1H), 8.45 (dd, J = 8.5, 2.3 Hz, 1H), 7.98 (s, 1H), 7.82 (d, J = 7.6 Hz, 1H), 6.87-6.44 (m, 2H), 6.45-6.35 (m, 1H), 4.34-4.20 (m, 1H), 4.03 (t, J = 6.8 Hz, 2H), 3.92 (d, J = 5.9 Hz, 2H), 1.86-1.71 (m, 2H), 1.71-1.53 (m, 2H). ES/MS m/z: 605.3 [M + H]$^+$. |
| 387 | 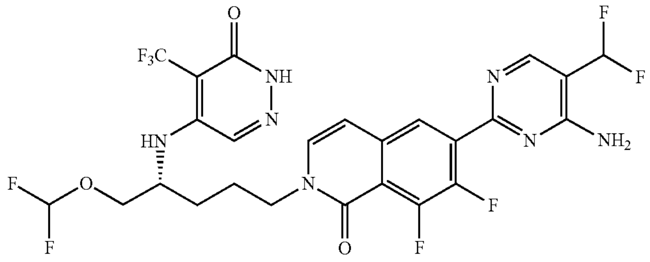 [SMILES: Nc1nc(-c2cc3ccn(CCC[C@H](COC(F)F)Nc4cn[nH]c(=O)c4C(F)(F)F)c(=O)c3c(F)c2F)ncc1C(F)F] | 1H NMR (400 MHz, DMSO-d6) δ 12.49 (s, 1H), 8.51 (d, J = 1.7 Hz, 1H), 8.04-7.90 (m, 2H), 7.57 (br s, 2H), 7.51 (d, J = 7.4 Hz, 1H), 7.10 (t, J = 54.1 Hz, 2H), 6.73 (dd, J = 7.4, 1.8 Hz, 1H), 6.66 (t, J = 75.5 Hz, 1H), 6.44-6.35 (m, 1H), 4.33-4.20 (m, 1H), 4.00-3.88 (m, 4H), 1.82-1.67 (m, 2H), 1.67-1.52 (m, 2H). ES/MS m/z: 638.3 [M + H]$^+$. |
| 388 | 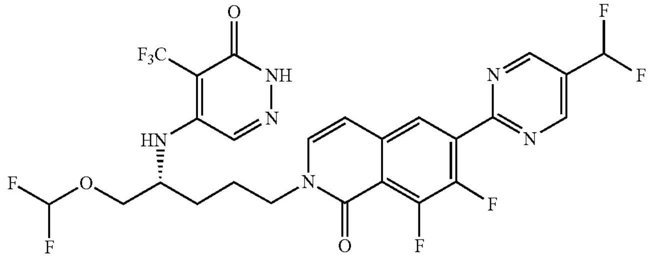 [SMILES: O=c1[nH]ncc(N[C@H](CCCn2ccc3cc(-c4ncc(C(F)F)cn4)c(F)c(F)c3c2=O)COC(F)F)c1C(F)(F)F] | 1H NMR (400 MHz, DMSO-d6) δ 12.49 (s, 1H), 9.27 (d, J = 1.6 Hz, 2H), 8.21 (dd, J = 6.6, 1.7 Hz, 1H), 7.98 (s, 1H), 7.54 (d, J = 7.4 Hz, 1H), 7.31 (t, J = 54.8 Hz, 1H), 6.81 (dd, J = 7.4, 1.8 Hz, 1H), 6.66 (t, J = 75.5 Hz, 1H), 6.45-6.36 (m, 1H), 4.34-4.20 (m, 1H), 4.02-3.88 (m, 4H), 1.84-1.69 (m, 2H), 1.69-1.53 (m, 2H). ES/MS m/z: 623.3 [M + H]$^+$. |
| 389 | 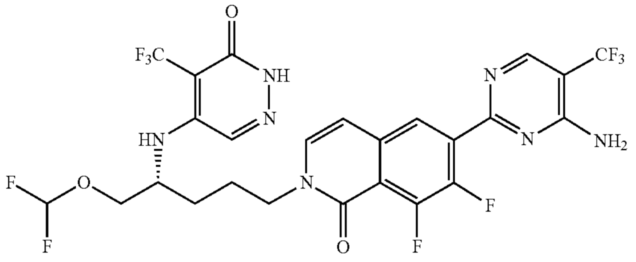 [SMILES: Nc1nc(-c2cc3ccn(CCC[C@H](COC(F)F)Nc4cn[nH]c(=O)c4C(F)(F)F)c(=O)c3c(F)c2F)ncc1C(F)(F)F] | 1H NMR (400 MHz, DMSO-d6) δ 12.49 (s, 1H), 8.66 (s, 1H), 8.04-7.94 (m, 2H), 7.51 (d, J = 7.4 Hz, 1H), 6.73 (dd, J = 7.5, 1.8 Hz, 1H), 6.66 (t, J = 75.5 Hz, 1H), 6.45-6.35 (m, 1H), 4.32-4.20 (m, 1H), 4.02-3.86 (m, 4H), 1.83-1.68 (m, 2H), 1.68-1.51 (m, 2H). ES/MS m/z: 656.3 [M + H]$^+$. |
| 390 | 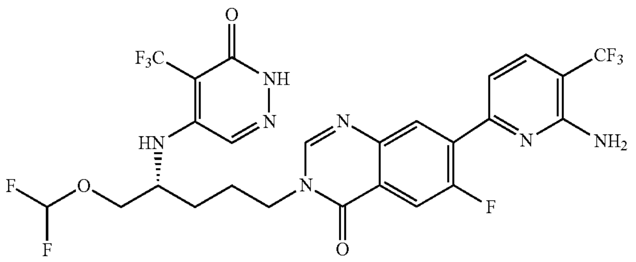 [SMILES: Nc1nc(-c2cc3ncn(CCC[C@H](COC(F)F)Nc4cn[nH]c(=O)c4C(F)(F)F)c(=O)c3cc2F)ccc1C(F)(F)F] | 1H NMR (400 MHz, DMSO-d6) δ 12.49 (s, 1H), 8.42 (s, 1H), 8.21 (d, J = 6.9 Hz, 1H), 8.01-7.88 (m, 3H), 7.18 (dd, J = 7.9, 2.0 Hz, 1H), 6.68 (br s, 2H), 6.66 (t, J = 75.5 Hz, 1H), 6.40 (dd, J = 9.2, 4.0 Hz, 1H), 4.31-4.20 (m, 1H), 4.01 (t, J = 6.8 Hz, 2H), 3.92 (d, J = 5.9 Hz, 2H), 1.88-1.71 (m, 2H), 1.71-1.52 (m, 2H). ES/MS m/z: 638.3 [M + H]$^+$. |

-continued

| Ex. No. | Structure | $^1$H NMR/MS [M + H]$^+$ |
|---|---|---|
| 391 | 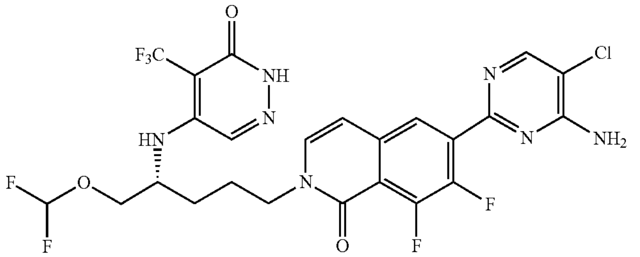 [SMILES: Nc1nc(-c2cc3ccn(CCC[C@H](COC(F)F)Nc4cn[nH]c(=O)c4C(F)(F)F)c(=O)c3c(F)c2F)ncc1Cl] | 1H NMR (400 MHz, DMSO-d6) δ 12.49 (s, 1H), 8.44 (s, 1H), 8.01-7.91 (m, 2H), 7.65 (br s, 3H), 7.49 (d, J = 7.4 Hz, 1H), 6.72 (dd, J = 7.4, 1.8 Hz, 1H), 6.66 (t, J = 75.5 Hz, 1H), 6.45-6.35 (m, 1H), 4.31-4.21 (m, 1H), 4.01-3.87 (m, 4H), 1.83-1.66 (m, 2H), 1.66-1.53 (m, 2H). ES/MS m/z: 622.3 [M + H]$^+$. |
| 392 | 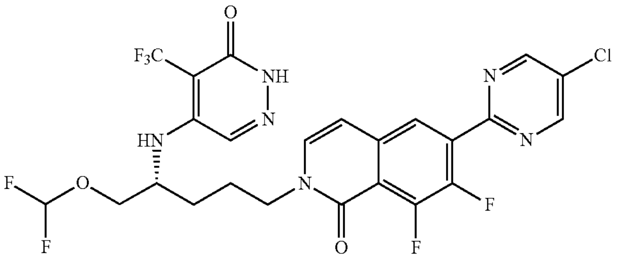 [SMILES: O=c1[nH]ncc(N[C@H](CCCn2ccc3cc(-c4ncc(Cl)cn4)c(F)c(F)c3c2=O)COC(F)F)c1C(F)(F)F] | 1H NMR (400 MHz, DMSO-d6) δ 12.48 (s, 1H), 9.17 (s, 2H), 8.16 (dd, J = 6.7, 1.7 Hz, 1H), 7.98 (s, 1H), 7.53 (d, J = 7.4 Hz, 1H), 6.79 (dd, J = 7.4, 1.8 Hz, 1H), 6.66 (t, J = 75.5 Hz, 1H), 6.44-6.36 (m, 1H), 4.32-4.20 (m, 1H), 4.00-3.89 (m, 4H), 1.83-1.67 (m, 2H), 1.67-1.53 (m, 2H). ES/MS m/z: 607.0 [M + H]$^+$. |
| 393 | 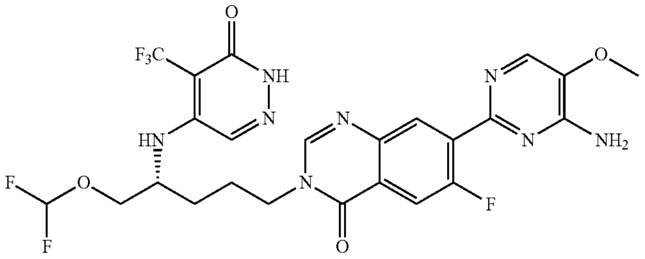 [SMILES: COc1cnc(-c2cc3ncn(CCC[C@H](COC(F)F)Nc4cn[nH]c(=O)c4C(F)(F)F)c(=O)c3cc2F)nc1N] | 1H NMR (400 MHz, DMSO-d6) δ 12.49 (s, 1H), 8.43 (s, 1H), 8.11 (d, J = 6.6 Hz, 1H), 8.08 (s, 1H), 8.00-7.94 (m, 2H), 6.66 (t, J = 75.5 Hz, 1H), 6.44-6.35 (m, 1H), 4.32-4.20 (m, 1H), 4.01 (t, J = 6.9 Hz, 2H), 3.96 (s, 3H), 3.92 (d, J = 5.9 Hz, 2H), 1.86-1.71 (m, 2H), 1.71-1.54 (m, 2H). ES/MS m/z: 601.1 [M + H]$^+$. |
| 394 | 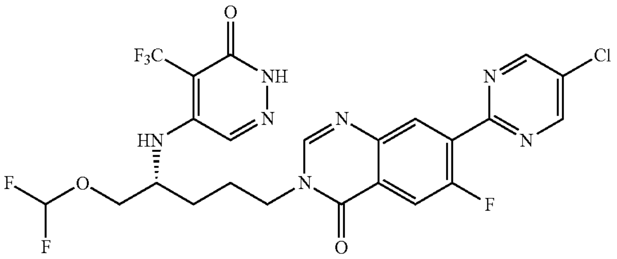 | 1H NMR (400 MHz, DMSO-d6) δ 12.49 (s, 1H), 9.16 (s, 2H), 8.44 (s, 1H), 8.28 (d, J = 6.8 Hz, 1H), 8.01-7.92 (m, 2H), 6.66 (t, J = 75.5 Hz, 1H), 6.45-6.35 (m, 1H), 4.33-4.19 (m, 1H), 4.02 (t, J = 6.8 Hz, 2H), 3.92 (d, J = 5.9 Hz, 2H), 1.87-1.71 (m, 2H), 1.71-1.54 (m, 2H). ES/MS m/z: 590.1 [M + H]$^+$. |
| 395 | 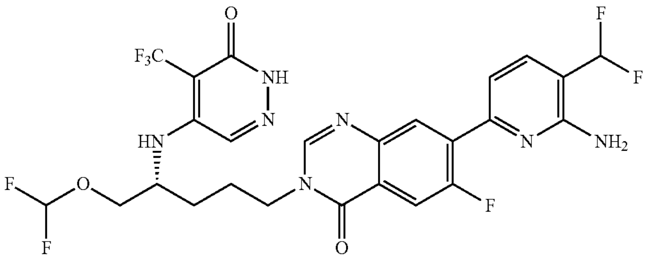 [SMILES: Nc1nc(-c2cc3ncn(CCC[C@H](COC(F)F)Nc4cn[nH]c(=O)c4C(F)(F)F)c(=O)c3cc2F)ccc1C(F)F] | 1H NMR (400 MHz, DMSO-d6) δ 12.49 (s, 1H), 8.41 (s, 1H), 8.19 (d, J = 6.9 Hz, 1H), 7.97 (s, 1H), 7.92 (d, J = 10.9 Hz, 1H), 7.81 (d, J = 7.8 Hz, 1H), 7.17 (dd, J = 7.8, 2.1 Hz, 1H), 7.10 (t, J = 54.7 Hz, 1H), 6.66 (t, J = 75.5 Hz, 1H), 6.44-6.35 (m, 1H), 4.32-4.19 (m, 1H), 4.01 (t, J = 6.7 Hz, 2H), 3.92 (d, J = 5.9 Hz, 2H), 1.86-1.70 (m, 2H), 1.70-1.53 (m, 2H). ES/MS m/z: 620.1 [M + H]$^+$. |
| 396 | 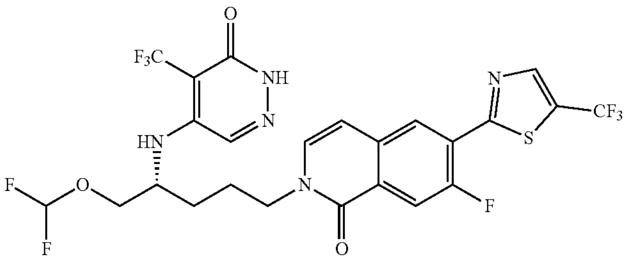 [SMILES: O=c1[nH]ncc(N[C@H](CCCn2ccc3cc(-c4ncc(C(F)(F)F)s4)c(F)cc3c2=O)COC(F)F)c1C(F)(F)F] | 1H NMR (400 MHz, DMSO-d6) δ 12.48 (s, 1H), 8.79-8.72 (m, 1H), 8.66 (d, J = 6.9 Hz, 1H), 8.12 (d, J = 11.9 Hz, 1H), 7.96 (s, 1H), 7.54 (d, J = 7.4 Hz, 1H), 6.88 (d, J = 7.4 Hz, 1H), 6.65 (t, J = 75.5 Hz, 1H), 6.45-6.36 (m, 1H), 4.31-4.21 (m, 1H), 4.00 (t, J = 6.8 Hz, 2H), 3.92 (d, J = 6.0 Hz, 2H), 1.85-1.68 (m, 2H), 1.68-1.52 (m, 2H). ES/MS m/z: 628.0 [M + H]$^+$. |

-continued

| Ex. No. | Structure | $^1$H NMR/MS [M + H]$^+$ |
| --- | --- | --- |
| 397 | 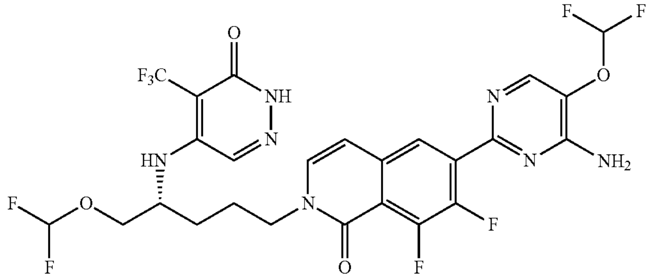 [SMILES: Nc1nc(-c2cc3ccn(CCC[C@H](COC(F)F)Nc4cn[nH]c(=O)c4C(F)(F)F)c(=O)c3c(F)c2F)ncc1OC(F)F] | 1H NMR (400 MHz, DMSO-d6) δ 12.49 (s, 1H), 8.24 (s, 1H), 7.98 (s, 1H), 7.92 (dd, J = 6.6, 1.6 Hz, 1H), 7.59-7.42 (m, 3H), 7.21 (t, J = 73.1 Hz, 1H), 6.71 (dd, J = 7.5, 1.8 Hz, 1H), 6.66 (t, J = 75.5 Hz, 1H), 6.44-6.36 (m, 1H), 4.32-4.20 (m, 1H), 4.00-3.87 (m, 4H), 1.82-1.67 (m, 2H), 1.67-1.52 (m, 2H). ES/MS m/z: 654.1 [M + H]$^+$. |
| 398 | 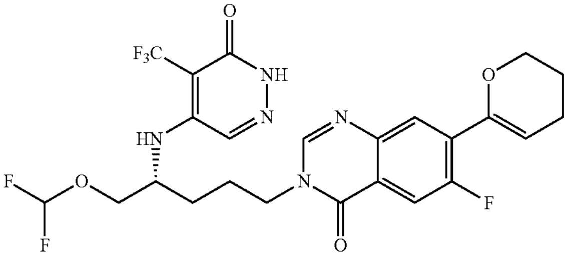 [SMILES: O=c1[nH]ncc(N[C@H](CCCn2cnc3cc(C4=CCCCO4)c(F)cc3c2=O)COC(F)F)c1C(F)(F)F] | 1H NMR (400 MHz, DMSO-d6) δ 12.48 (s, 1H), 8.36 (s, 1H), 7.96 (s, 1H), 7.83-7.75 (m, 2H), 6.65 (t, J = 75.5 Hz, 1H), 6.43-6.35 (m, 1H), 5.67 (t, J = 4.1 Hz, 1H), 4.31-4.20 (m, 1H), 4.21-4.15 (m, 2H), 3.98 (t, J = 6.8 Hz, 2H), 3.91 (d, J = 5.9 Hz, 2H), 2.24 (q, J = 6.3 Hz, 2H), 1.88 (p, J = 6.1 Hz, 2H), 1.82-1.69 (m, 2H), 1.68-1.52 (m, 2H). ES/MS m/z: 560.1 [M + H]$^+$. |
| 399 | 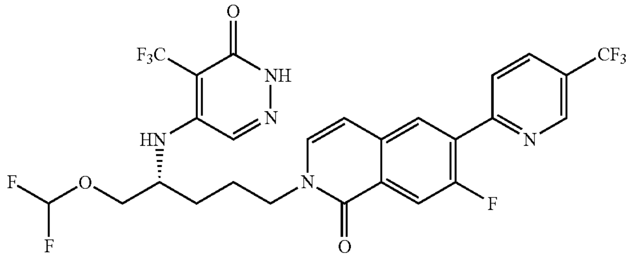 [SMILES: O=c1[nH]ncc(N[C@H](CCCn2ccc3cc(-c4ccc(C(F)(F)F)cn4)c(F)cc3c2=O)COC(F)F)c1C(F)(F)F] | 1H NMR (400 MHz, DMSO-d6) δ 12.48 (s, 1H), 9.21-9.14 (m, 1H), 8.41 (dd, J = 8.4, 2.4 Hz, 1H), 8.30 (d, J = 7.3 Hz, 1H), 8.12 (d, J = 8.3 Hz, 1H), 8.03 (d, J = 11.7 Hz, 1H), 7.98 (s, 1H), 7.51 (d, J = 7.4 Hz, 1H), 6.82 (d, J = 7.4 Hz, 1H), 6.66 (t, J = 75.5 Hz, 1H), 6.45-6.36 (m, 1H), 4.32-4.21 (m, 1H), 4.01 (t, J = 6.8 Hz, 2H), 3.92 (d, J = 6.0 Hz, 2H), 1.86-1.69 (m, 2H), 1.69-1.52 (m, 2H). ES/MS m/z: 622.1 [M + H]$^+$. |
| 400 | 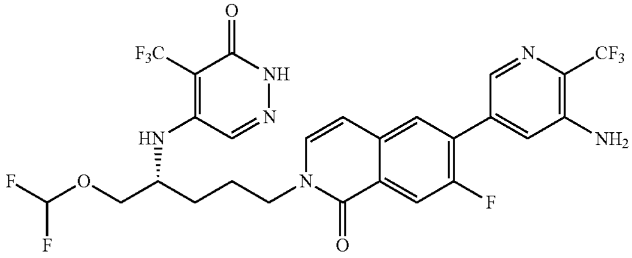 [SMILES: Nc1cc(-c2cc3ccn(CCC[C@H](COC(F)F)Nc4cn[nH]c(=O)c4C(F)(F)F)c(=O)c3cc2F)cnc1C(F)(F)F] | 1H NMR (400 MHz, DMSO-d6) δ 12.48 (s, 1H), 8.08 (d, J = 1.6 Hz, 1H), 8.04-7.90 (m, 3H), 7.55-7.45 (m, 2H), 6.73 (d, J = 7.4 Hz, 1H), 6.65 (t, J = 75.5 Hz, 1H), 6.44-6.35 (m, 1H), 5.99 (br s, 2H), 4.33-4.19 (m, 1H), 4.00 (t, J = 6.8 Hz, 2H), 3.92 (d, J = 6.0 Hz, 2H), 1.85-1.68 (m, 2H), 1.68-1.49 (m, 2H). ES/MS m/z: 637.1 [M + H]$^+$. |
| 401 | 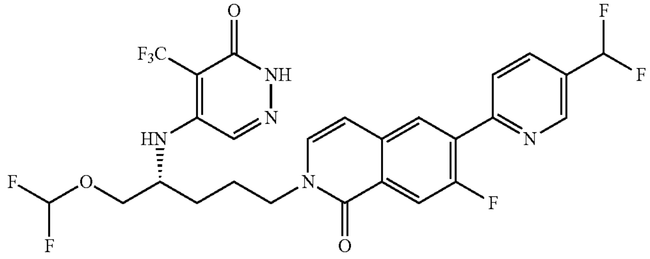 [SMILES: O=c1[nH]ncc(N[C@H](CCCn2ccc3cc(-c4ccc(C(F)F)cn4)c(F)cc3c2=O)COC(F)F)c1C(F)(F)F] | 1H NMR (400 MHz, DMSO-d6) δ 12.48 (s, 1H), 8.98 (d, J = 2.2 Hz, 1H), 8.29 (d, J = 7.3 Hz, 1H), 8.23-8.17 (m, 1H), 8.08-7.94 (m, 3H), 7.50 (d, J = 7.3 Hz, 1H), 7.25 (t, J = 55.3 Hz, 1H), 6.81 (d, J = 7.4 Hz, 1H), 6.66 (t, J = 75.5 Hz, 1H), 6.45-6.36 (m, 1H), 4.32-4.22 (m, 1H), 4.00 (t, J = 6.8 Hz, 2H), 3.92 (d, J = 5.9 Hz, 2H), 1.84-1.69 (m, 2H), 1.69-1.51 (m, 2H). ES/MS m/z: 604.1 [M + H]$^+$. |

-continued

| Ex. No. | Structure | $^1$H NMR/MS [M + H]$^+$ |
| --- | --- | --- |
| 402 | 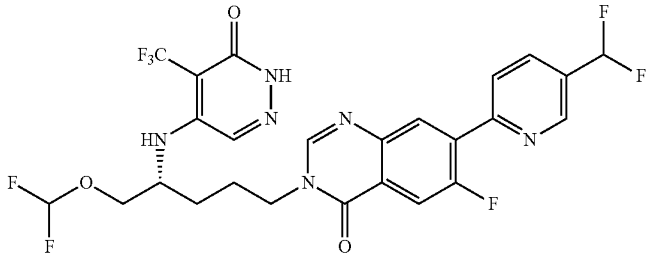 [SMILES: O=c1[nH]ncc(N[C@H](CCCn2cnc3cc(-c4ccc(C(F)F)cn4)c(F)cc3c2=O)COC(F)F)c1C(F)(F)F] | 1H NMR (400 MHz, DMSO-d6) δ 12.49 (s, 1H), 8.99 (d, J = 2.1 Hz, 1H), 8.44 (s, 1H), 8.25-8.17 (m, 2H), 8.06 (d, J = 8.1 Hz, 1H), 8.03-7.95 (m, 2H), 7.26 (t, J = 55.2 Hz, 1H), 6.66 (t, J = 75.5 Hz, 1H), 6.44-6.35 (m, 1H), 4.32-4.20 (m, 1H), 4.02 (t, J = 6.8 Hz, 2H), 3.92 (d, J = 5.9 Hz, 2H), 1.87-1.71 (m, 2H), 1.71-1.54 (m, 2H). ES/MS m/z: 605.0 [M + H]$^+$. |
| 403 | 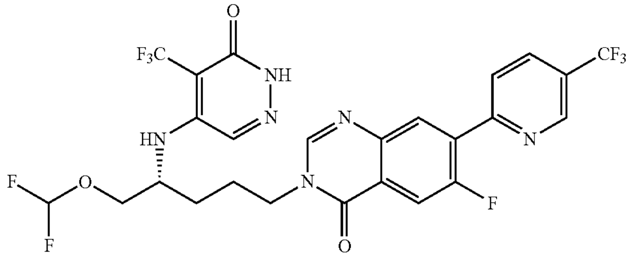 [SMILES: O=c1[nH]ncc(N[C@H](CCCn2cnc3cc(-c4ccc(C(F)(F)F)cn4)c(F)cc3c2=O)COC(F)F)c1C(F)(F)F] | 1H NMR (400 MHz, DMSO-d6) δ 12.49 (s, 1H), 9.19 (d, J = 2.2 Hz, 1H), 8.44 (s, 1H), 8.46-8.38 (m, 2H), 8.24 (d, J = 6.7 Hz, 1H), 8.14 (d, J = 8.2 Hz, 1H), 8.01 (d, J = 10.7 Hz, 1H), 7.97 (s, 1H), 6.66 (t, J = 75.5 Hz, 1H), 6.44-6.35 (m, 1H), 4.32-4.19 (m, 1H), 4.02 (t, J = 6.8 Hz, 2H), 3.92 (d, J = 5.9 Hz, 2H), 1.87-1.71 (m, 2H), 1.71-1.54 (m, 2H). ES/MS m/z: 623.1 [M + H]$^+$. |
| 404 | 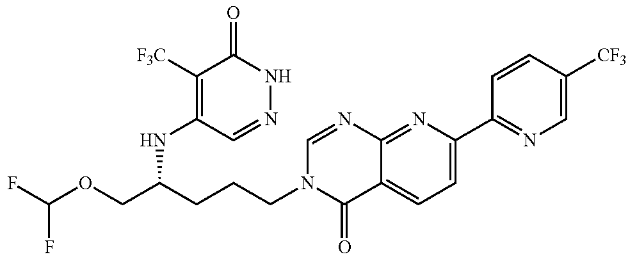 [SMILES: O=c1[nH]ncc(N[C@H](CCCn2cnc3nc(-c4ccc(C(F)(F)F)cn4)ccc3c2=O)COC(F)F)c1C(F)(F)F] | 1H NMR (400 MHz, DMSO-d6) δ 12.49 (s, 1H), 9.18 (d, J = 2.2 Hz, 1H), 8.78-8.65 (m, 3H), 8.59 (dd, J = 8.2, 1.6 Hz, 1H), 8.47 (dd, J = 8.5, 2.4 Hz, 1H), 7.98 (s, 1H), 6.66 (t, J = 75.5 Hz, 1H), 6.45-6.35 (m, 1H), 4.33-4.21 (m, 1H), 4.04 (t, J = 6.9 Hz, 2H), 3.92 (d, J = 5.9 Hz, 2H), 1.89-1.71 (m, 2H), 1.71-1.56 (m, 2H). ES/MS m/z: 606.1 [M + H]$^+$. |
| 405 | 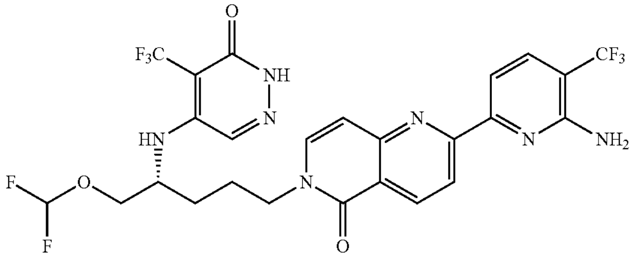 [SMILES: Nc1nc(-c2ccc3c(=O)n(CCC[C@H](COC(F)F)Nc4cn[nH]c(=O)c4C(F)(F)F)ccc3n2)ccc1C(F)(F)F] | 1H NMR (400 MHz, DMSO-d6) δ 12.48 (s, 1H), 8.69 (d, J = 8.4 Hz, 1H), 8.40 (d, J = 8.4 Hz, 1H), 8.02-7.95 (m, 2H), 7.82-7.74 (m, 2H), 6.85-6.45 (m, 4H), 6.44-6.36 (m, 1H), 4.33-4.22 (m, 1H), 4.02 (t, J = 6.8 Hz, 2H), 3.92 (d, J = 6.0 Hz, 2H), 1.84-1.69 (m, 3H), 1.69-1.54 (m, 3H). ES/MS m/z: 620.1 [M + H]$^+$. |
| 406 | 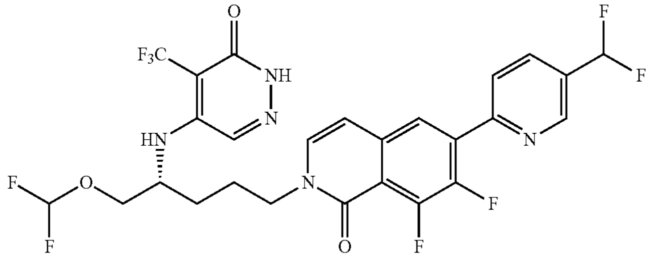 [SMILES: O=c1[nH]ncc(N[C@H](CCCn2ccc3cc(-c4ccc(C(F)F)cn4)c(F)c(F)c3c2=O)COC(F)F)c1C(F)(F)F] | 1H NMR (400 MHz, DMSO-d6) δ 12.49 (s, 1H), 8.99 (s, 1H), 8.22 (dt, J = 8.5, 1.4 Hz, 1H), 8.10-8.01 (m, 2H), 7.98 (s, 1H), 7.52 (d, J = 7.4 Hz, 1H), 7.26 (t, J = 55.2 Hz, 1H), 6.77 (dd, J = 7.4, 1.8 Hz, 1H), 6.66 (t, J = 75.5 Hz, 1H), 6.45-6.35 (m, 1H), 4.32-4.20 (m, 1H), 4.01-3.89 (m, 4H), 1.82-1.68 (m, 2H), 1.68-1.52 (m, 2H). ES/MS m/z: 622.1 [M + H]$^+$. |
| 407 | 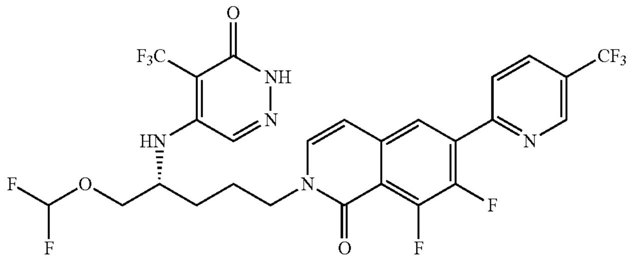 [SMILES: O=c1[nH]ncc(N[C@H](CCCn2ccc3cc(-c4ccc(C(F)(F)F)cn4)c(F)c(F)c3c2=O)COC(F)F)c1C(F)(F)F] | 1H NMR (400 MHz, DMSO-d6) δ 12.48 (s, 1H), 9.19 (d, J = 2.2 Hz, 1H), 8.44 (dd, J = 8.4, 2.3 Hz, 1H), 8.14 (d, J = 8.2 Hz, 1H), 8.06 (d, J = 6.5 Hz, 1H), 7.97 (s, 1H), 7.53 (d, J = 7.4 Hz, 1H), 6.77 (dd, J = 7.5, 1.8 Hz, 1H), 6.66 (t, J = 75.5 Hz, 1H), 6.44-6.36 (m, 1H), 4.32-4.20 (m, 1H), 4.02-3.86 (m, 4H), 1.84-1.69 (m, 2H), 1.68-1.53 (m, 2H). ES/MS m/z: 640.1 [M + H]$^+$. |

-continued

| Ex. No. | Structure | $^1$H NMR/MS [M + H]$^+$ |
| --- | --- | --- |
| 408 | 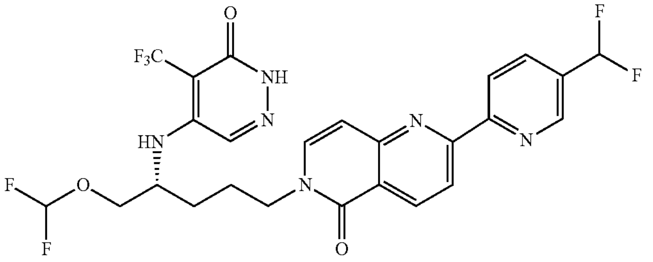 [SMILES: O=c1[nH]ncc(N[C@H](CCCn2ccc3nc(-c4ccc(C(F)F)cn4)ccc3c2=O)COC(F)F)c1C(F)(F)F] | 1H NMR (400 MHz, DMSO-d6) δ 12.48 (s, 1H), 8.99-8.94 (m, 1H), 8.71 (d, J = 8.4 Hz, 1H), 8.65 (d, J = 8.2 Hz, 1H), 8.52 (d, J = 8.4 Hz, 1H), 8.25 (dt, J = 8.3, 1.5 Hz, 1H), 7.98 (s, 1H), 7.81 (d, J = 7.6 Hz, 1H), 7.27 (t, J = 55.2 Hz, 1H), 6.82 (d, J = 7.6 Hz, 1H), 6.65 (t, J = 75.5 Hz, 1H), 6.41 (dd, J = 9.2, 4.0 Hz, 1H), 4.34-4.20 (m, 1H), 4.03 (t, J = 6.8 Hz, 2H), 3.92 (d, J = 5.9 Hz, 2H), 1.86-1.71 (m, 2H), 1.71-1.53 (m, 2H). ES/MS m/z: 587.1 [M + H]$^+$. |
| 409 | 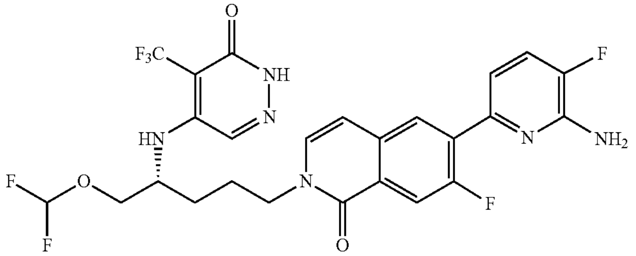 [SMILES: Nc1nc(-c2cc3ccn(CCC[C@H](COC(F)F)Nc4cn[nH]c(=O)c4C(F)(F)F)c(=O)c3cc2F)ccc1F] | 1H NMR (400 MHz, DMSO-d6) δ 12.48 (s, 1H), 8.09 (d, J = 7.4 Hz, 1H), 7.97 (s, 1H), 7.92 (d, J = 11.7 Hz, 1H), 7.50 (dd, J = 11.0, 8.1 Hz, 1H), 7.45 (d, J = 7.4 Hz, 1H), 7.07-6.97 (m, 1H), 6.72 (d, J = 7.4 Hz, 1H), 6.65 (t, J = 75.5 Hz, 1H), 6.44-6.35 (m, 1H), 4.33-4.19 (m, 1H), 3.98 (t, J = 6.8 Hz, 2H), 3.92 (d, J = 5.7 Hz, 2H), 1.83-1.68 (m, 2H), 1.68-1.50 (m, 2H). ES/MS m/z: 587.1 [M + H]$^+$. |
| 410 | 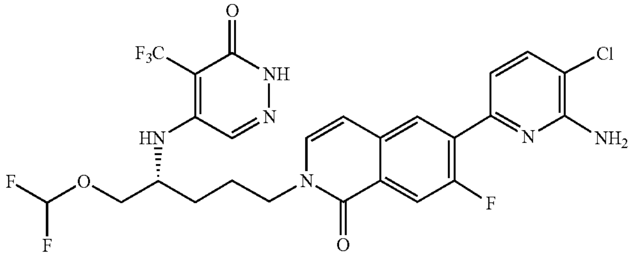 [SMILES: Nc1nc(-c2cc3ccn(CCC[C@H](COC(F)F)Nc4cn[nH]c(=O)c4C(F)(F)F)c(=O)c3cc2F)ccc1Cl] | 1H NMR (400 MHz, DMSO-d6) δ 12.48 (s, 1H), 8.13 (d, J = 7.3 Hz, 1H), 7.97 (s, 1H), 7.94 (d, J = 11.8 Hz, 1H), 7.73 (d, J = 8.0 Hz, 1H), 7.46 (d, J = 7.4 Hz, 1H), 7.06-7.01 (m, 1H), 6.72 (d, J = 7.4 Hz, 1H), 6.65 (t, J = 75.5 Hz, 1H), 6.44-6.36 (m, 1H), 4.32-4.20 (m, 1H), 3.99 (t, J = 6.8 Hz, 2H), 3.92 (d, J = 5.9 Hz, 2H), 1.83-1.69 (m, 2H), 1.70-1.50 (m, 2H). ES/MS m/z: 603.0 [M + H]$^+$. |
| 411 | 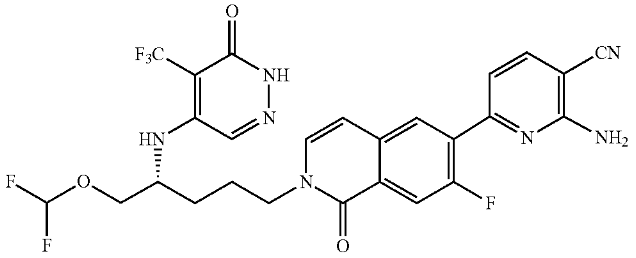 [SMILES: N#Cc1ccc(-c2cc3ccn(CCC[C@H](COC(F)F)Nc4cn[nH]c(=O)c4C(F)(F)F)c(=O)c3cc2F)nc1N] | 1H NMR (400 MHz, DMSO-d6) δ 12.48 (s, 1H), 8.13 (d, J = 7.2 Hz, 1H), 8.04 (d, J = 7.9 Hz, 1H), 7.99-7.92 (m, 2H), 7.48 (d, J = 7.3 Hz, 1H), 7.25-6.99 (m, 3H), 6.74 (d, J = 7.4 Hz, 1H), 6.65 (t, J = 75.5 Hz, 1H), 6.44-6.35 (m, 1H), 4.33-4.19 (m, 1H), 3.99 (t, J = 6.8 Hz, 2H), 3.92 (d, J = 6.0 Hz, 2H), 1.84-1.68 (m, 2H), 1.68-1.50 (m, 2H). ES/MS m/z: 594.1 [M + H]$^+$. |
| 412 | 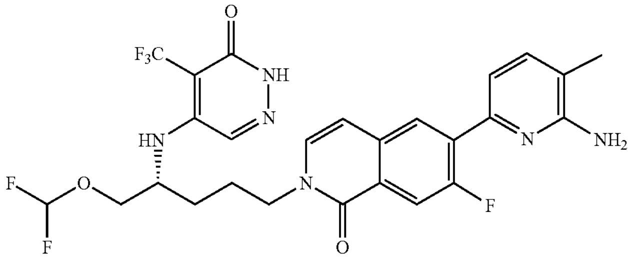 [SMILES: Cc1ccc(-c2cc3ccn(CCC[C@H](COC(F)F)Nc4cn[nH]c(=O)c4C(F)(F)F)c(=O)c3cc2F)nc1N] | 1H NMR (400 MHz, DMSO-d6) δ 12.49 (s, 1H), 8.08 (d, J = 7.1 Hz, 1H), 8.01 (d, J = 11.2 Hz, 1H), 7.97 (s, 1H), 7.78 (d, J = 7.5 Hz, 1H), 7.52 (d, J = 7.4 Hz, 1H), 7.10 (d, J = 7.4 Hz, 1H), 6.73 (d, J = 7.4 Hz, 1H), 6.66 (t, J = 75.5 Hz, 1H), 6.44-6.34 (m, 1H), 4.34-4.20 (m, 1H), 4.00 (t, J = 6.9 Hz, 2H), 3.92 (d, J = 5.6 Hz, 2H), 2.22 (s, 3H), 1.85-1.67 (m, 2H), 1.69-1.50 (m, 2H). ES/MS m/z: 583.1 [M + H]$^+$. |

-continued

| Ex. No. | Structure | $^1$H NMR/MS $[M + H]^+$ |
| --- | --- | --- |
| 413 | 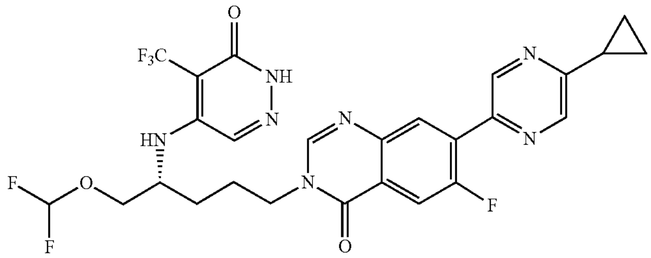 [SMILES: O=c1[nH]ncc(N[C@H](CCCn2cnc3cc(-c4cnc(C5CC5)cn4)c(F)cc3c2=O)COC(F)F)c1C(F)(F)F] | 1H NMR (400 MHz, DMSO-d6) δ 12.48 (s, 1H), 8.95 (t, J = 2.0 Hz, 1H), 8.84 (d, J = 1.5 Hz, 1H), 8.43 (s, 1H), 8.19 (d, J = 6.9 Hz, 1H), 8.01-7.94 (m, 2H), 6.65 (t, J = 75.5 Hz, 1H), 6.45-6.35 (m, 1H), 4.31-4.21 (m, 1H), 4.02 (t, J = 6.8 Hz, 2H), 3.92 (d, J = 5.9 Hz, 2H), 2.37-2.26 (m, 1H), 1.87-1.71 (m, 2H), 1.70-1.53 (m, 2H), 1.19-1.09 (m, 2H), 1.09-1.01 (m, 2H). ES/MS m/z: 596.2 $[M + H]^+$. |
| 414 | 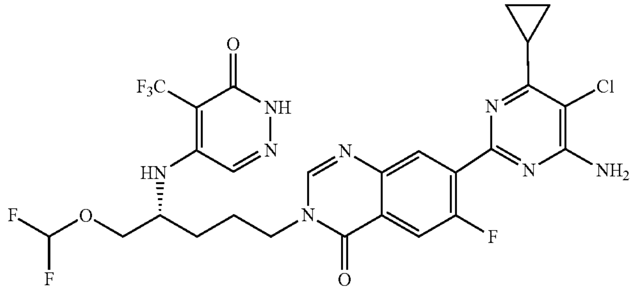 [SMILES: Nc1nc(-c2cc3ncn(CCC[C@H](COC(F)F)Nc4cn[nH]c(=O)c4C(F)(F)F)c(=O)c3cc2F)nc(C2CC2)c1Cl] | 1H NMR (400 MHz, DMSO-d6) δ 12.49 (s, 1H), 8.41 (s, 1H), 8.11 (d, J = 6.7 Hz, 1H), 7.98 (s, 1H), 7.87 (d, J = 10.3 Hz, 1H), 7.39 (br. s, 2H), 6.66 (t, J = 75.5 Hz, 1H), 6.45-6.35 (m, 1H), 4.32-4.21 (m, 1H), 4.01 (t, J = 6.9 Hz, 2H), 3.92 (d, J = 5.9 Hz, 2H), 2.46-2.35 (m, 1H), 1.87-1.70 (m, 2H), 1.70-1.53 (m, 2H), 1.13-1.01 (m, 4H). ES/MS m/z: 645.1 $[M + H]^+$. |
| 415 | 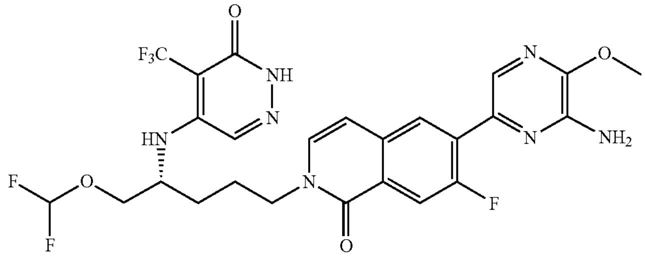 [SMILES: COc1ncc(-c2cc3ccn(CCC[C@H](COC(F)F)Nc4cn[nH]c(=O)c4C(F)(F)F)c(=O)c3cc2F)nc1N] | 1H NMR (400 MHz, DMSO-d6) δ 12.48 (s, 1H), 8.13 (d, J = 7.3 Hz, 1H), 8.01-7.87 (m, 2H), 7.82 (d, J = 2.5 Hz, 1H), 7.45 (d, J = 7.3 Hz, 1H), 6.76-6.57 (m, 2H), 6.40 (dd, J = 9.6, 3.8 Hz, 1H), 4.33-4.17 (m, 2H), 4.04-3.80 (m, 7H), 1.90-1.46 (m, 5H). ES/MS m/z: 600.2 $[M + H]^+$. |
| 416 | 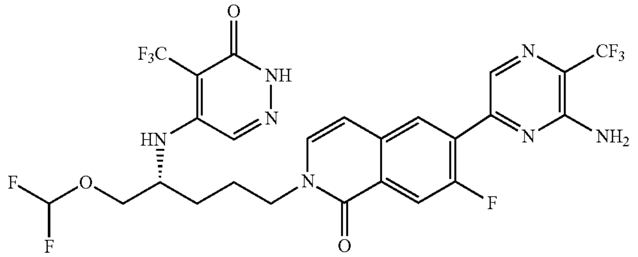 [SMILES: Nc1nc(-c2cc3ccn(CCC[C@H](COC(F)F)Nc4cn[nH]c(=O)c4C(F)(F)F)c(=O)c3cc2F)cnc1C(F)(F)F] | 1H NMR (400 MHz, DMSO-d6) δ 12.48 (s, 1H), 8.31 (d, J = 2.6 Hz, 1H), 8.18 (d, J = 7.1 Hz, 1H), 8.02 (d, J = 11.4 Hz, 1H), 7.97 (s, 1H), 7.51 (d, J = 7.4 Hz, 1H), 7.14 (s, 2H), 6.75 (d, J = 7.4 Hz, 1H), 6.66 (t, J = 75.5 Hz, 1H), 6.44-6.36 (m, 1H), 1.83-1.69 (m, 2H), 1.60 (hd, J = 13.9, 6.9 Hz, 2H). ES/MS m/z: 638.2 $[M + H]^+$. |
| 417 | 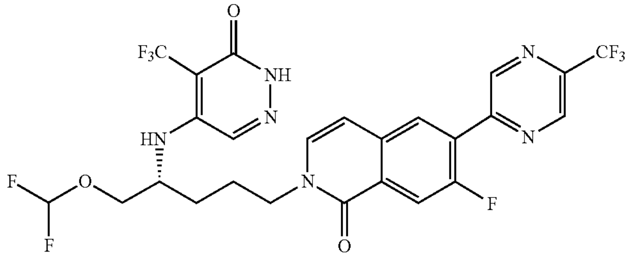 [SMILES: O=c1[nH]ncc(N[C@H](CCCn2ccc3cc(-c4cnc(C(F)(F)F)cn4)c(F)cc3c2=O)COC(F)F)c1C(F)(F)F] | 1H NMR (400 MHz, DMSO-d6) δ 12.49 (s, 1H), 9.40 (d, J = 1.3 Hz, 1H), 9.34 (d, J = 1.8 Hz, 1H), 8.35 (d, J = 7.2 Hz, 1H), 8.07 (d, J = 11.5 Hz, 1H), 7.97 (s, 1H), 7.54 (d, J = 7.4 Hz, 1H), 6.66 (m, 2H), 6.55-6.30 (m, 1H), 4.90-3.59 (m, 6H), 1.88-1.44 (m, 4H). ES/MS m/z: 623.3 $[M + H]^+$. |

-continued

| Ex. No. | Structure | $^1$H NMR/MS [M + H]$^+$ |
|---|---|---|
| 418 | 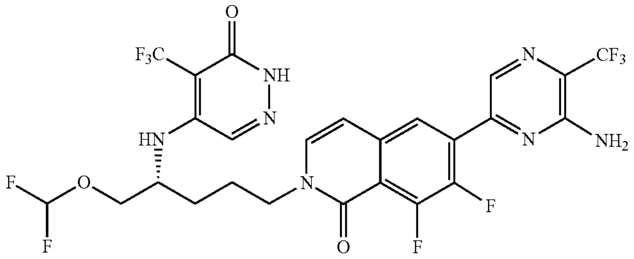 [SMILES: Nc1nc(-c2cc3ccn(CCC[C@H](COC(F)F)Nc4cn[nH]c(=O)c4C(F)(F)F)c(=O)c3c(F)c2F)cnc1C(F)(F)F] | 1H NMR (400 MHz, DMSO-d6) δ 12.48 (s, 1H), 8.32 (d, J = 2.5 Hz, 1H), 7.95 (d, J = 16.0 Hz, 2H), 7.53 (d, J = 7.4 Hz, 1H), 7.18 (bs, 2H), 6.90-6.30 (m, 3H), 4.24 (m, 1H), 4.09-3.80 (m, 4H), 1.85-1.50 (m, 4H). ES/MS m/z: 656.2 [M + H]$^+$. |
| 419 | 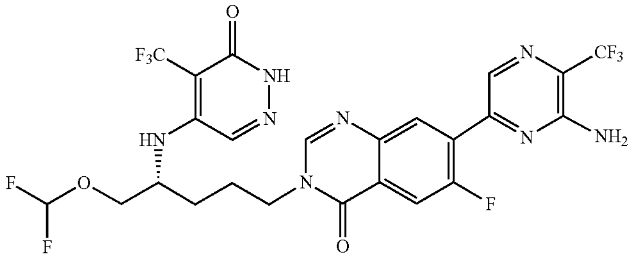 [SMILES: Nc1nc(-c2cc3ncn(CCC[C@H](COC(F)F)Nc4cn[nH]c(=O)c4C(F)(F)F)c(=O)c3cc2F)cnc1C(F)(F)F] | 1H NMR (400 MHz, DMSO-d6) δ 12.49 (s, 1H), 8.44 (s, 1H), 8.35 (d, J = 2.5 Hz, 1H), 8.22 (d, J = 6.7 Hz, 1H), 8.03-7.92 (m, 2H), 7.17 (bs, 2H), 6.89-6.34 (m, 2H), 4.42-4.15 (m, 1H), 4.19-3.80 (m, 4H), 1.94-1.32 (m, 4H). ES/MS m/z: 639.2 [M + H]$^+$. |
| 420 | 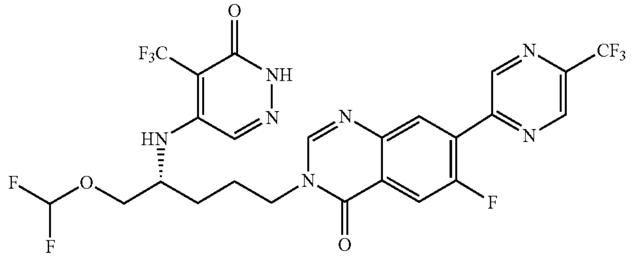 [SMILES: O=c1[nH]ncc(N[C@H](CCCn2cnc3cc(-c4cnc(C(F)(F)F)cn4)c(F)cc3c2=O)COC(F)F)c1C(F)(F)F] | 1H NMR (400 MHz, DMSO-d6) δ 12.49 (s, 1H), 9.39 (m, 2H), 8.46 (s, 1H), 8.28 (d, J = 6.7 Hz, 1H), 8.22-7.80 (m, 2H), 6.98-6.27 (m, 2H), 4.60-3.56 (m, 5H), 1.72 (m, 4H). ES/MS m/z: 624.1 [M + H]$^+$. |
| 421 | 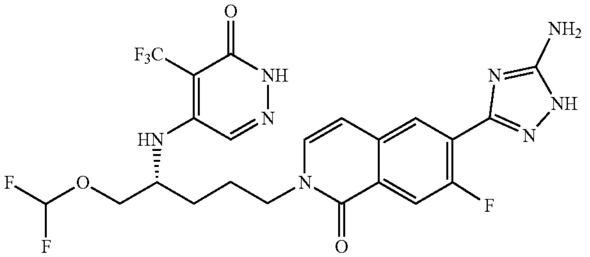 [SMILES: Nc1nc(-c2cc3ccn(CCC[C@H](COC(F)F)Nc4cn[nH]c(=O)c4C(F)(F)F)c(=O)c3cc2F)n[nH]1] | 1H NMR (400 MHz, DMSO-d6) δ 12.48 (s, 1H), 8.21 (d, J = 6.9 Hz, 1H), 8.04-7.79 (m, 2H), 7.46 (d, J = 7.4 Hz, 1H), 6.86-6.45 (m, 2H), 6.40 (m, 1H), 4.26 (m, 1H), 4.10-2.94 (m, 6H), 1.88-1.48 (m, 5H). ES/MS m/z: 559.1 [M + H]$^+$. |
| 422 | 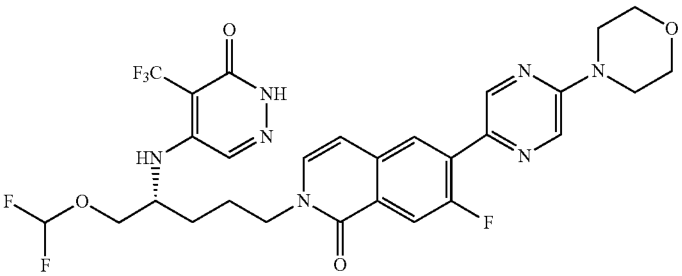 [SMILES: O=c1[nH]ncc(N[C@H](CCCn2ccc3cc(-c4cnc(N5CCOCC5)cn4)c(F)cc3c2=O)COC(F)F)c1C(F)(F)F] | 1H NMR (400 MHz, DMSO-d6) δ 12.48 (s, 1H), 8.62 (d, J = 2.1 Hz, 1H), 8.51 (s, 1H), 8.21 (d, J = 7.4 Hz, 1H), 8.06-7.89 (m, 2H), 7.45 (d, J = 7.4 Hz, 1H), 6.87-6.30 (m, 3H), 4.51-3.29 (m, 13H), 1.94-1.36 (m, 4H). ES/MS m/z: 640.2 [M + H]$^+$. |

-continued

| Ex. No. | Structure | $^1H$ NMR/MS $[M + H]^+$ |
| --- | --- | --- |
| 423 | 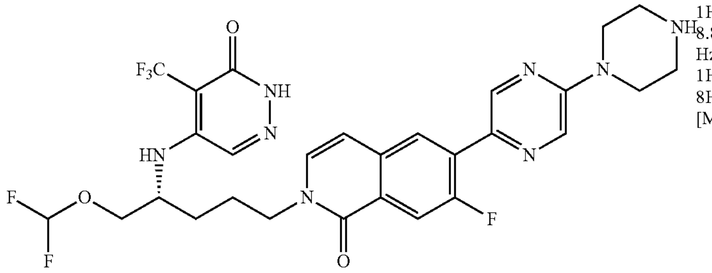 | 1H NMR (400 MHz, DMSO-d6) δ 12.49 (s, 1H), 8.86 (bs, 2H), 8.75-8.48 (m, 2H), 8.21 (d, J = 7.4 Hz, 1H), 8.04-7.83 (m, 2H), 7.47 (d, J = 7.4 Hz, 1H), 7.01-6.21 (m, 3H), 4.26 (m, 1H), 3.95 (m, 8H), 3.42 (m, 3H), 1.68 (m, 4H). ES/MS m/z: 639.2 $[M + H]^+$. |
| 424 | 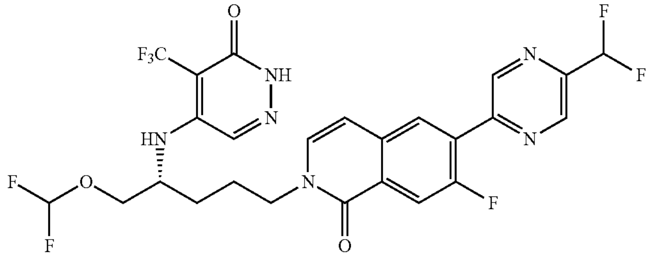 [SMILES: O=c1[nH]ncc(N[C@H](CCCn2ccc3cc(-c4cnc(C(F)F)cn4)c(F)cc3c2=O)COC(F)F)c1C(F)(F)F] | 1H NMR (400 MHz, DMSO-d6) δ 12.49 (s, 1H), 9.36-8.98 (m, 2H), 8.33 (d, J = 7.2 Hz, 1H), 8.13-7.85 (m, 2H), 7.53 (d, J = 7.4 Hz, 1H), 7.23 (t, J = 54.1 Hz, 1H), 6.92-6.27 (m, 3H), 4.67-3.21 (m, 6H), 1.70 (m, 4H). ES/MS m/z: 605.2 $[M + H]^+$. |
| 425 | 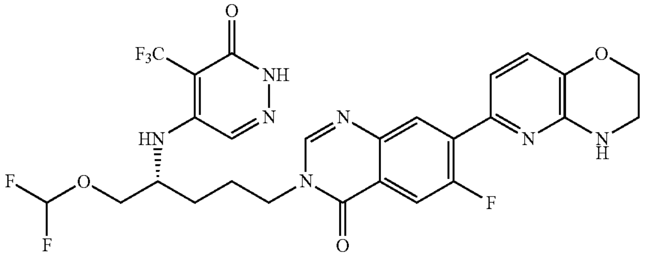 [SMILES: O=c1[nH]ncc(N[C@H](CCCn2cnc3cc(-c4ccc5c(n4)NCCO5)c(F)cc3c2=O)COC(F)F)c1C(F)(F)F] | 1H NMR (400 MHz, DMSO-d6) δ 12.48 (s, 1H), 8.38 (s, 1H), 8.16 (d, J = 7.1 Hz, 1H), 7.97 (s, 1H), 7.86 (d, J = 11.2 Hz, 1H), 7.09 (m, 2H), 6.87-6.27 (m, 2H), 4.37-4.15 (m, 3H), 4.06-3.18 (m, 6H), 1.88-1.50 (m, 5H). ES/MS m/z: 612.7 $[M + H]^+$. |
| 426 | 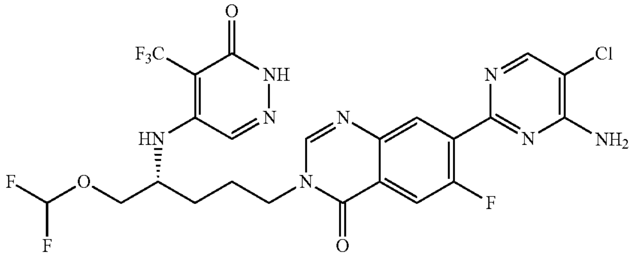 [SMILES: Nc1nc(-c2cc3ncn(CCC[C@H](COC(F)F)Nc4cn[nH]c(=O)c4C(F)(F)F)c(=O)c3cc2F)ncc1Cl] | 1H NMR (400 MHz, DMSO-d6) δ 12.49 (s, 1H), 8.42 (d, J = 12.6 Hz, 2H), 8.13 (d, J = 6.8 Hz, 1H), 7.97 (s, 1H), 7.89 (d, J = 10.4 Hz, 1H), 6.65 (t, J = 75.4 Hz, 1H), 6.42-6.36 (m, 1H), 4.29-4.22 (m, 1H), 4.00 (t, J = 6.7 Hz, 3H), 3.92 (d, J = 5.9 Hz, 2H), 1.84-1.72 (m, 2H), 1.68-1.55 (m, 2H). ES/MS m/z: 605.3 $[M + H]^+$. |

The Following compounds were synthesized using the procedure as described in Example 181 from the corresponding starting materials.

| Ex. No. | Structure | $^1H$ NMR/MS $[M + H]^+$ |
| --- | --- | --- |
| 427 | 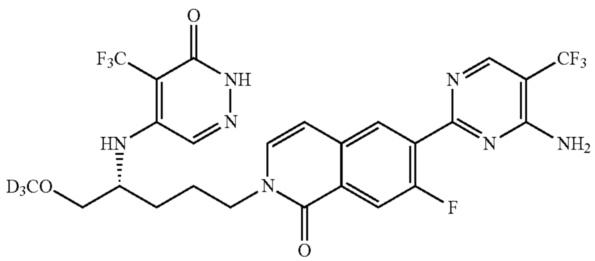 | 1H NMR (400 MHz, DMSO-d6) δ 12.44 (s, 1H), 8.64 (s, 1H), 8.20 (d, J = 7.1 Hz, 1H), 7.97-7.94 (m, 1H), 7.49 (d, J = 7.4 Hz, 1H), 6.77 (d, J = 7.4 Hz, 1H), 6.29 (dd, J = 12.0, 3.0 Hz, 1H), 4.14 (s, 1H), 3.99 (t, J = 6.9 Hz, 2H), 3.44-3.33 (m, 2H), 1.74 (t, J = 16.5 Hz, 2H), 1.64-1.49 (m, 2H). ES/MS m/z: 605.2 $[M + H]^+$. |

-continued

| Ex. No. | Structure | $^1$H NMR/MS [M + H]$^+$ |
|---|---|---|
| 428 | 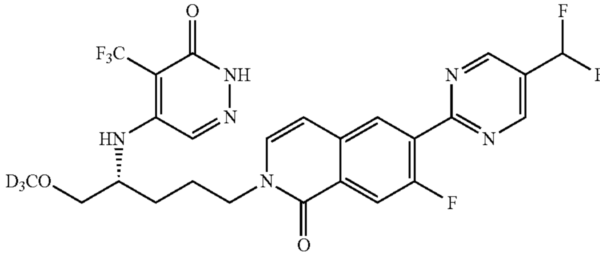 | 1H NMR (400 MHz, DMSO-d6) δ 12.43 (s, 1H), 9.25 (s, 2H), 8.40 (d, J = 7.2 Hz, 1H), 8.01 (d, J = 11.4 Hz, 1H), 7.96 (s, 1H), 7.52 (d, J = 7.4 Hz, 1H), 7.31 (t, J = 54.8 Hz, 1H), 6.83 (d, J = 7.3 Hz, 1H), 6.34-6.25 (m, 1H), 4.18-4.08 (m, 1H), 4.02-3.94 (m, 2H), 3.45-3.35 (m, 3H), 1.82-1.69 (m, 2H), 1.62-1.50 (m, 2H). ES/MS m/z: 572.3 [M + H]$^+$. |
| 429 | 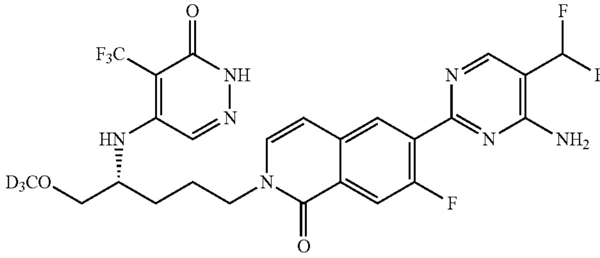 | 1H NMR (400 MHz, DMSO-d6) δ 12.44 (s, 1H), 8.50 (s, 1H), 8.17 (d, J = 7.1 Hz, 1H), 7.94 (d, J = 10.6 Hz, 2H), 7.48 (d, J = 7.4 Hz, 1H), 7.09 (t, J = 54.2 Hz, 1H), 6.76 (d, J = 7.4 Hz, 1H), 6.29 (dq, J = 8.3, 4.2 Hz, 1H), 4.17-4.10 (m, 2H), 3.98 (t, J = 6.9 Hz, 2H), 3.43-3.33 (m, 2H), 1.83-1.66 (m, 2H), 1.62-1.49 (m, 2H). ES/MS m/z: 587.2 [M + H]$^+$. |
| 430 | 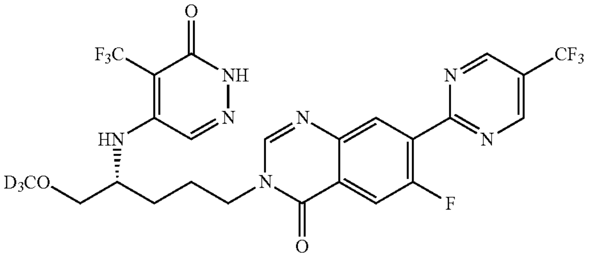 | 1H NMR (400 MHz, DMSO-d6) δ 12.44 (s, 1H), 9.50 (s, 2H), 8.46 (s, 1H), 8.35 (d, J = 6.7 Hz, 1H), 8.01 (d, J = 10.5 Hz, 1H), 7.96 (s, 1H), 6.29 (dt, J = 6.9, 3.5 Hz, 1H), 4.14 (d, J = 15.1 Hz, 1H), 4.02 (t, J = 6.8 Hz, 2H), 3.40 (d, J = 5.0 Hz, 2H), 1.85-1.70 (m, 2H), 1.59 (dt, J = 15.7, 7.0 Hz, 2H). ES/MS m/z: 591.2 [M + H]$^+$. |
| 431 | 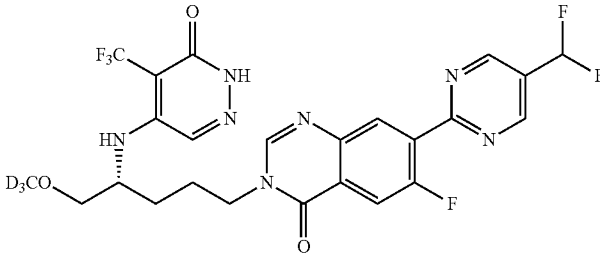 | 1H NMR (400 MHz, DMSO-d6) δ 12.44 (s, 1H), 9.26 (s, 2H), 8.45 (s, 1H), 8.32 (d, J = 6.8 Hz, 1H), 8.02-7.93 (m, 2H), 7.31 (t, J = 54.7 Hz, 1H), 6.32-6.24 (m, 1H), 4.13 (d, J = 6.9 Hz, 1H), 4.02 (t, J = 6.8 Hz, 2H), 3.40 (d, J = 4.9 Hz, 2H), 1.77 (dt, J = 12.4, 6.8 Hz, 2H), 1.59 (dt, J = 16.9, 7.9 Hz, 2H). ES/MS m/z: 5731 [M + H]$^+$. |
| 432 | 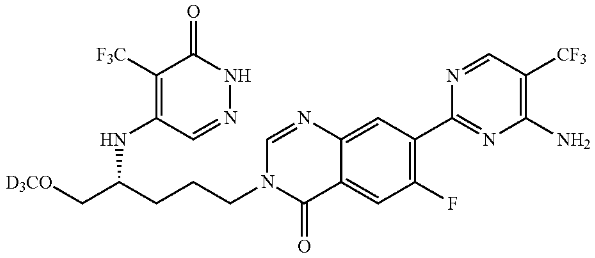 | 1H NMR (400 MHz, DMSO-d6) δ 12.44 (s, 1H), 8.66 (s, 1H), 8.42 (s, 1H), 8.18 (d, J = 6.7 Hz, 1H), 7.98-7.88 (m, 2H), 6.29 (dd, J = 9.3, 4.1 Hz, 1H), 4.12 (d, J = 7.7 Hz, 1H), 4.00 (t, J = 6.9 Hz, 2H), 3.43-3.35 (m, 2H), 1.75 (dd, J = 15.3, 7.6 Hz, 2H), 1.65-1.54 (m, 2H). ES/MS m/z: 606.1 [M + H]$^+$. |
| 433 | 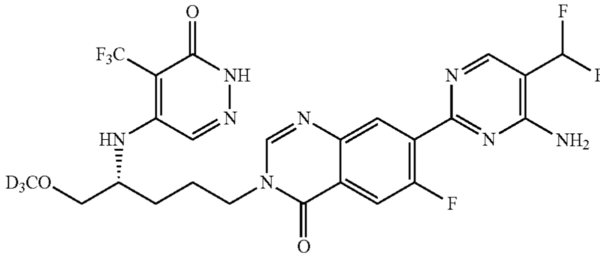 | 1H NMR (400 MHz, DMSO-d6) δ 12.44 (s, 1H), 8.51 (s, 1H), 8.42 (s, 1H), 8.15 (d, J = 6.7 Hz, 1H), 7.95 (s, 1H), 7.91 (d, J = 10.3 Hz, 1H), 7.09 (t, J = 54.1 Hz, 1H), 6.29 (dt, J = 8.8, 3.6 Hz, 1H), 4.13 (q, J = 7.3 Hz, 1H), 4.00 (t, J = 6.8 Hz, 2H), 3.40 (d, J = 6.0 Hz, 2H), 1.84-1.70 (m, 2H), 1.65-1.52 (m, 2H). ES/MS m/z: 588.1 [M + H]$^+$. |

-continued

| Ex. No. | Structure | $^1$H NMR/MS [M + H]$^+$ |
|---|---|---|
| 434 | 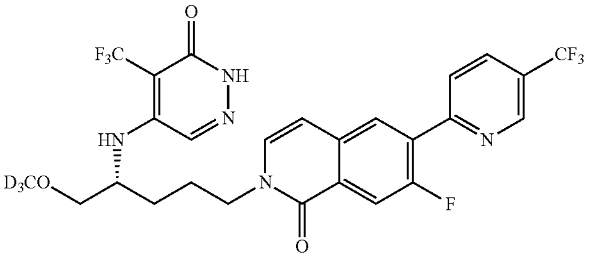 | 1H NMR (400 MHz, DMSO-d6) δ 12.43 (s, 1H), 9.17 (s, 1H), 8.41 (dd, J = 8.4, 2.4 Hz, 1H), 8.30 (d, J = 7.3 Hz, 1H), 8.12 (d, J = 8.4 Hz, 1H), 8.03 (d, J = 11.7 Hz, 1H), 7.95 (s, 1H), 7.51 (d, J = 7.4 Hz, 1H), 6.81 (d, J = 7.4 Hz, 1H), 6.29 (dd, J = 9.1, 4.4 Hz, 1H), 4.17-4.08 (m, 1H), 4.00 (t, J = 6.9 Hz, 2H), 3.45-3.35 (m, 2H), 1.83-1.69 (m, 2H), 1.63-1.50 (m, 2H). ES/MS m/z: 589.1 [M + H]$^+$. |

Example 435: (R)-7-fluoro-2-(4-((6-oxo-5-(trifluoromethyl)-1,6-dihydropyridazin-4-yl)amino)-5-(trifluoromethoxy)pentyl)-6-(5-(trifluoromethyl)pyrimidin-2-yl)isoquinolin-1(2H)-one Example 435

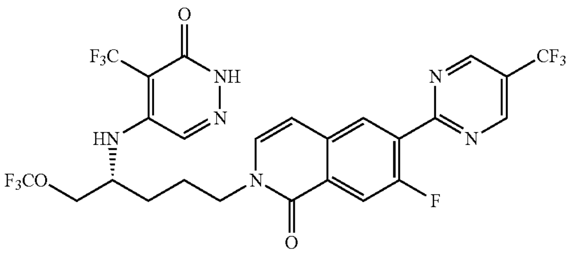

The title compound was synthesized as described in Example 135 with the following modification in step 1. $^1$H NMR (400 MHz, Acetonitrile-d3) δ 10.44 (s, 1H), 9.15 (s, 2H), 8.27 (d, J=7.1 Hz, 1H), 8.00 (d, J=11.6 Hz, 1H), 7.66 (s, 1H), 7.16 (d, J=7.4 Hz, 1H), 6.62 (d, J=7.4 Hz, 1H), 5.60-5.52 (m, 1H), 4.16-4.07 (m, 1H), 4.06-4.02 (m, 1H), 3.99-3.90 (m, 3H), 1.78-1.72 (m, 2H), 1.60 (d, J=4.9 Hz, 2H). ES/MS m/z: 641.2 [M+H]$^+$.

Step 1. To a mixture of (2R)-2-(tert-butoxycarbonylamino)-5-[7-fluoro-1-oxo-6-[5-(trifluoromethyl)pyrimidin-2-yl]-2-isoquinolyl]pentanoic acid (synthesized as described in Example 89, Steps 1-3) (40.0 mg, 0.09 mmol), Silver trifluoromethanesulfonate (70.0 mg, 0.27 mmol), Selectfluor (48.0 mg, 0.14 mmol), potassium fluoride (21.0 mg, 0.36 mmol) in anhydrous EtOAc (1.0 mL) under an atmosphere of nitrogen was added Trifluoromethyltrimethylsilane (38.0 mg, 0.27 mmol) and 2-fluoropyridine (26.0 mg, 0.27 mmol) and the mixture was stirred at room temperature for 12 hr. The mixture was then filtered through a pad of Celite® and the filtrate was concentrated under reduced pressure. The crude product was purified using flash chromatography eluting with EtOAc in hexanes 0-100% to afford tert-butyl N-[(1R)-4-(6-bromo-7-fluoro-1-oxo-2-isoquinolyl)-1-(trifluoromethoxymethyl)butyl]carbamate. ES/MS m/z: 512.9 [M+H]$^+$+.

Example 436: (rac)-7-fluoro-2-(2-((1S,2S)-2-((6-oxo-5-(trifluoromethyl)-1,6-dihydropyridazin-4-yl)amino)cyclohexyl)ethyl)-6-(5-(trifluoromethyl)pyrimidin-2-yl)isoquinolin-1(2H)-one

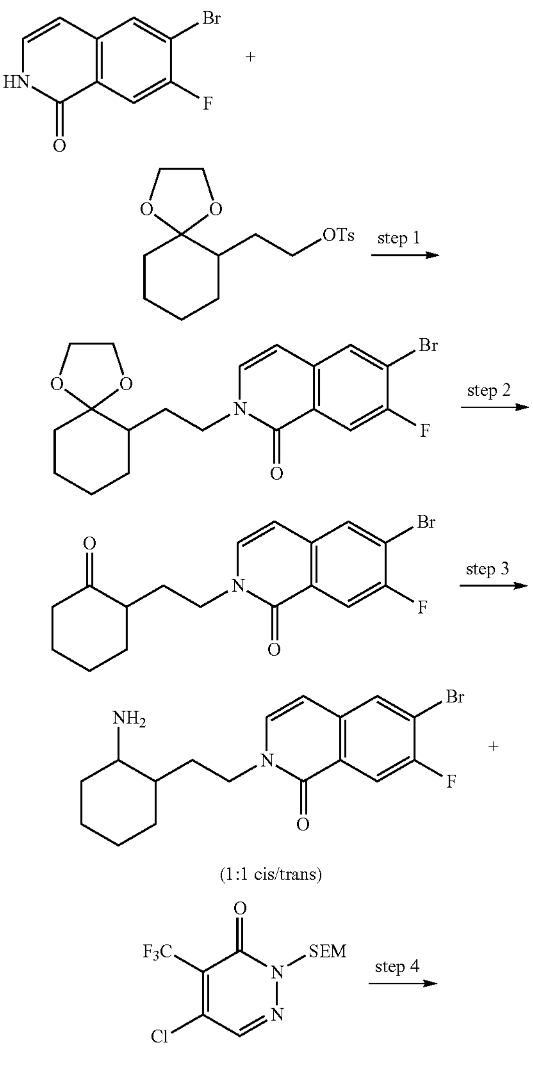

-continued

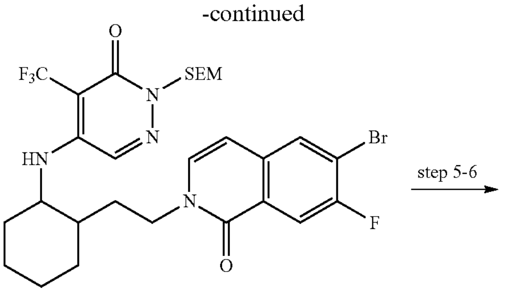

(1:1 cis/trans)

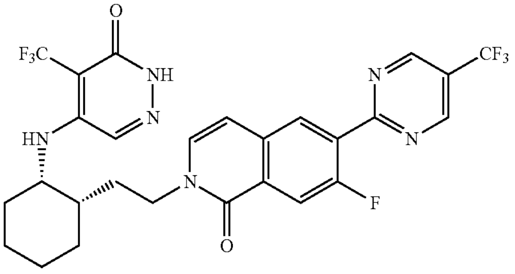

Example 436 (racemic)

Step 1: 2-(2-(1,4-dioxaspiro[4.5]decan-6-yl)ethyl)-6-bromo-7-fluoroisoquinolin-1(2H)-one was synthesized as described in step 2 of Example 1 using 6-bromo-7-fluoroisoquinolin-1(2H)-one and 2-(1,4-dioxaspiro[4.5]decan-6-yl)ethyl 4-methylbenzenesulfonate. ES/MS m/z: 410.2 $[M+H]^+$.

Step 2: A solution of 2-(2-(1,4-dioxaspiro[4.5]decan-6-yl)ethyl)-6-bromo-7-fluoroisoquinolin-1(2H)-one (644 mg, 1.57 mmol) and pyridinium p-toluenesulfonate (237 mg, 0.942 mmol) in toluene (15.0 mL) was stirred under reflux for 2 hr. Upon cooling, saturated $NaHCO_3$ and ethyl acetate were added. The layers were separated, and the aqueous layer was extracted with ethyl acetate. The combined organic layers were dried ($MgSO_4$) and concentrated under reduced pressure. The solid was triturated with a small amount of ethyl acetate and filtered to afford 6-bromo-7-fluoro-2-(2-(2-oxocyclohexyl)ethyl)isoquinolin-1(2H)-one. ES/MS m/z: 366.2 $[M+H]^+$.

Step 3: A solution of 6-bromo-7-fluoro-2-(2-(2-oxocyclohexyl)ethyl)isoquinolin-1(2H)-one (550 mg, 1.50 mmol) and ammonium formate (947 mg, 15 mmol) in EtOH (15 mL) was stirred at 60° C. for 1 hr. Upon cooling, sodium cyanoborohydride (472 mg, 7.5 mmol) was added and the reaction mixture was stirred at room temperature for 24 hr. The mixture was concentrated under reduced pressure. Ethyl acetate and saturated $NaHCO_3$ were added. The layers were separated, and the aqueous layer was extracted with ethyl acetate. The combined organic layers were dried ($MgSO_4$) and concentrated under reduced pressure. Crude 2-(2-(2-aminocyclohexyl)ethyl)-6-bromo-7-fluoroisoquinolin-1(2H)-one was used without further purification in the next step. ES/MS m/z: 367.2 $[M+H]^+$.

Step 4: 6-Bromo-7-fluoro-2-(2-(2-((6-oxo-5-(trifluoromethyl)-1-((2-(trimethylsilyl)ethoxy)methyl)-1,6-dihydropyridazin-4-yl)amino)cyclohexyl)ethyl)isoquinolin-1(2H)-one was synthesized as described in step 7 of Example 5 using 2-(2-(2-aminocyclohexyl)ethyl)-6-bromo-7-fluoroisoquinolin-1(2H)-one. ES/MS m/z: 659.2 $[M+H]^+$.

Step 5: 7-fluoro-2-(2-(2-((6-oxo-5-(trifluoromethyl)-1-((2-(trimethylsilyl)ethoxy)methyl)-1,6-dihydropyridazin-4-yl)amino)cyclohexyl)ethyl)-6-(5-(trifluoromethyl)pyrimidin-2-yl)isoquinolin-1(2H)-one was synthesized as described in step 2 of Example 168 using 6-bromo-7-fluoro-2-(2-(2-((6-oxo-5-(trifluoromethyl)-1-((2-(trimethylsilyl)ethoxy)methyl)-1,6-dihydropyridazin-4-yl)amino)cyclohexyl)ethyl)isoquinolin-1(2H)-one. ES/MS m/z: 727.3 $[M+H]^+$.

Step 6: (rac)-7-fluoro-2-(2-((1S,2S)-2-((6-oxo-5-(trifluoromethyl)-1,6-dihydropyridazin-4-yl)amino)cyclohexyl)ethyl)-6-(5-(trifluoromethyl)pyrimidin-2-yl)isoquinolin-1(2H)-one was synthesized as described in step 3 of Example 168 using 7-fluoro-2-(2-(2-((6-oxo-5-(trifluoromethyl)-1-((2-(trimethylsilyl)ethoxy)methyl)-1,6-dihydropyridazin-4-yl)amino)cyclohexyl)ethyl)-6-(5-(trifluoromethyl)pyrimidin-2-yl)isoquinolin-1(2H)-one. The cis diastereoisomer was isolated after purification by reverse phase prep-HPLC (5-100% MeCN in water, 0.1% TFA). ES/MS m/z: 597.3; $^1H$ NMR (400 MHz, DMSO-d6) δ 12.45 (s, 1H), 9.48 (s, 2H), 8.42 (d, J=7.1 Hz, 1H), 8.00 (d, J=11.4 Hz, 1H), 7.90 (s, 1H), 7.50 (d, J=7.4 Hz, 1H), 6.80 (d, J=7.4 Hz, 1H), 5.83-5.75 (m, 1H), 4.09-3.91 (m, 3H), 1.88-1.25 (m, 11H).

Example 437: (rac)-7-fluoro-2-(2-((1S,2S)-2-((6-oxo-5-(trifluoromethyl)-1,6-dihydropyridazin-4-yl)amino)cyclopentyl)ethyl)-6-(5-(trifluoromethyl)pyrimidin-2-yl)isoquinolin-1(2H)-one Example 437 (racemic)

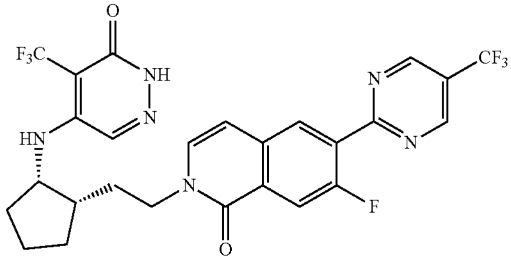

(rac)-7-fluoro-2-(2-((1S,2S)-2-((6-oxo-5-(trifluoromethyl)-1,6-dihydropyridazin-4-yl)amino)cyclopentyl)ethyl)-6-(5-(trifluoromethyl)pyrimidin-2-yl)isoquinolin-1(2H)-one was synthesized as described in Example 436 using 2-(1,4-dioxaspiro[4.4]nonan-6-yl)ethyl 4-methylbenzenesulfonate instead of 2-(1,4-dioxaspiro[4.5]decan-6-yl)ethyl 4-methylbenzenesulfonate. ES/MS m/z: 583.3; $^1H$ NMR (400 MHz, DMSO-d6) δ 12.47 (s, 1H), 9.48 (s, 2H), 8.42 (d, J=7.1 Hz, 1H), 8.00 (d, J=11.4 Hz, 1H), 7.88 (s, 1H), 7.51 (d, J=7.4 Hz, 1H), 6.82 (d, J=7.4 Hz, 1H), 6.08-5.98 (m, 1H), 4.28-4.18 (m, 1H), 4.11-3.89 (m, 2H), 2.16-1.43 (m, 9H).

Example 438: 6-(4-amino-5-(trifluoromethyl)pyrimidin-2-yl)-7-fluoro-2-(3-((6-oxo-5-(trifluoromethyl)-1,6-dihydropyridazin-4-yl)amino)benzyl)isoquinolin-1(2H)-one Example 438

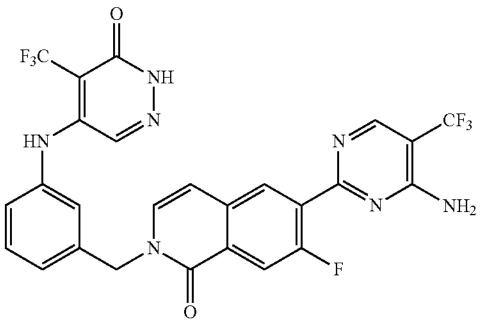

The title compound was synthesized as described in Example 91, using 2-chloro-5-(trifluoromethyl)pyrimidin-4-amine instead of 2-iodo-5-(trifluoromethyl)pyrimidine in step 2. $^1$H NMR (400 MHz, DMSO-d6) δ 12.67 (s, 1H), 9.00 (s, 1H), 8.65 (s, 1H), 8.22 (d, J=7.0 Hz, 1H), 7.98 (d, J=11.1 Hz, 1H), 7.64 (d, J=7.4 Hz, 1H), 7.47 (s, 1H), 7.41 (m, 1H), 7.33-7.19 (m, 3H), 6.82 (d, J=7.4 Hz, 1H), 5.22 (s, 2H). ES/MS m/z: 591.7 [M+H].

Example 439: (R)-2-(5-(difluoromethoxy)-4-((6-oxo-5-(trifluoromethyl)-1,6-dihydropyridazin-4-yl)amino)pentyl)-7-fluoro-6-(5,6,7,8-tetrahydro-[1,2,4]triazolo[1,5-a]pyrazin-2-yl)isoquinolin-1(2H)-one Example 439

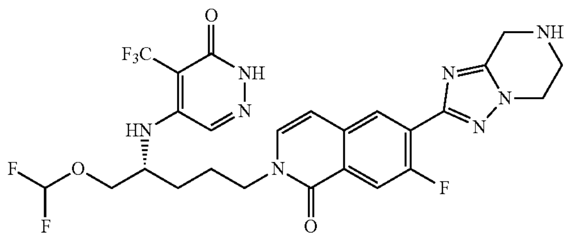

The title compound was synthesized as described in Example 168, using tert-butyl 2-bromo-5,6-dihydro-[1,2,4]triazolo[1,5-a]pyrazine-7(8H)-carboxylate instead of 2-iodo-5-(trifluoromethyl)pyrimidine in step 2. $^1$H NMR (400 MHz, DMSO-d6) δ 12.49 (s, 1H), 9.64 (s, 2H), 8.34 (d, J=7.0 Hz, 1H), 7.99 (m, 2H), 7.49 (d, J=7.4 Hz, 1H), 6.89-6.45 (m, 2H), 6.44-6.34 (m, 1H), 4.65 (s, 2H), 4.49 (m, 2H), 4.26 (m, 1H), 4.05-3.90 (m, 4H), 3.79 (m, 2H), 1.87-1.45 (m, 4H). ES/MS m/z: 598.5 [M+H].

Example 440: Preparation of (S)-6-(5-(difluoromethoxy)pyridin-2-yl)-8-fluoro-2-(4-((6-oxo-5-(trifluoromethyl)-1,6-dihydropyridazin-4-yl)amino)pentyl)isoquinolin-1(2H)-one

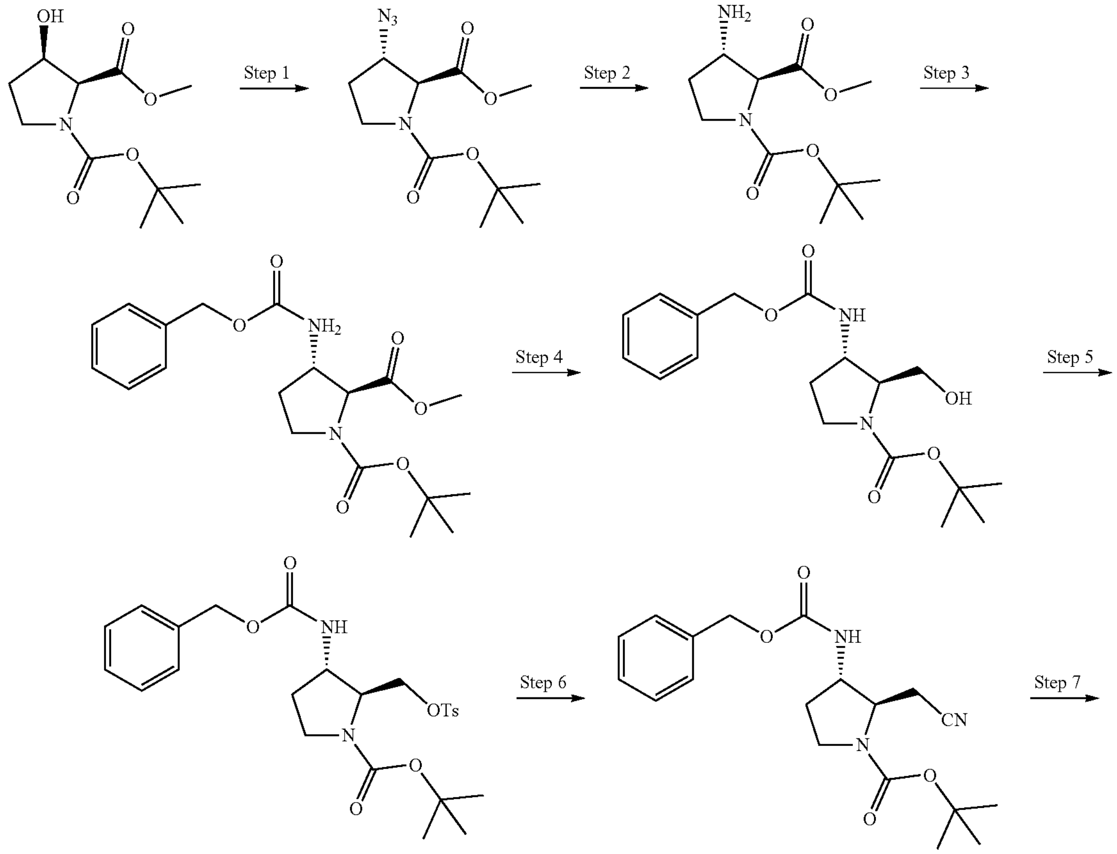

-continued

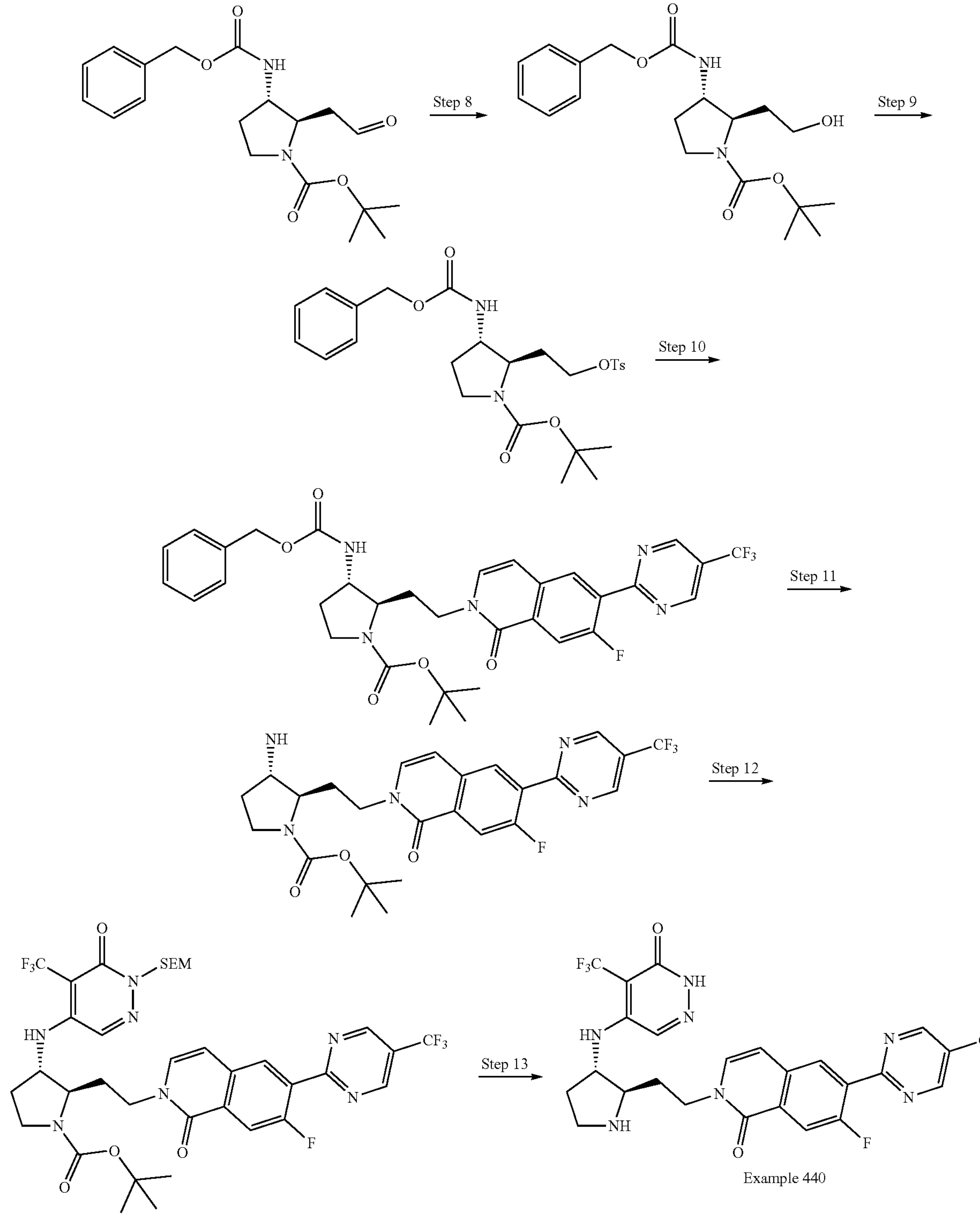

Example 440

Step 1. In a 100 mL round bottomed single necked flask were placed 1-(tert-butyl) 2-methyl (2S,3R)-3-hydroxypyrrolidine-1,2-dicarboxylate (3.0 g, 12.0 mmol) and $PPh_3$ (4.8 g, 18.0 mmol) in THF (20.0 mL). The mixture was cooled to 0° C. and to this mixture were added a solution of diisopropyl azodicarboxylate (3.6 mL, 18.0 mmol) in THF (3.0 mL) followed by the solution of diphenylphosphoryl azide (3.9 mL, 18.0 mmol) in THF (3.0 mL). The resulting mixture was warmed to room temperature and stirred for 16 hr. The reaction was then concentrated and purified by flash chromatography (100% Hexane to 100% EtOAc then 100% DCM to 100% MeOH) to give 1-(tert-butyl) 2-methyl (2S,3S)-3-azidopyrrolidine-1,2-dicarboxylate.

Step 2. In a 100 mL round bottomed single necked flask was placed 1-(tert-butyl) 2-methyl (2S,3S)-3-azidopyrrolidine-1,2-dicarboxylate (2.9 g, 11.0 mmol) in MeOH (15.0 mL). The solution was purged with $N_2$ followed by the addition of Pd/C (10%, 340 mg, 0.320 mmol). The mixture was stirred at room temperature under $H_2$ at 1 ATM for 16 hr, and filtered through a pad of Celite©. The filtrate was concentrated and carried onto the next step without further purification. ES/MS m/z: 245.1 [M+H].

Step 3. To a mixture of 1-(tert-butyl) 2-methyl (2S,3S)-3-aminopyrrolidine-1,2-dicarboxylate (660 mg, 2.7 mmol) and DIPEA (0.94 mL, 5.4 mmol) was added THF (3.0 mL). The mixture was cooled to 0° C. followed by the addition of benzyl chloroformate (50% in xylene (v/v), 1.2 mL, 4.1 mmol). The mixture was slowly warmed to room temperature and stirred at this temperature for 16 h. Upon completion, the mixture was loaded onto the Silica pre-packed cartridge and purified by flash chromatography (100% Hexane to 100% EtOAc then 100% DCM to 100% MeOH) to give 1-(tert-butyl) 2-methyl (2S,3S)-3-(((benzyloxy)carbonyl)amino)pyrrolidine-1,2-dicarboxylate. ES/MS m/z: 379.1 [M+H].

Step 4. In a 100 mL round bottomed single necked flask was placed 1-(tert-butyl) 2-methyl (2S,3S)-3-(((benzyloxy)carbonyl)amino)pyrrolidine-1,2-dicarboxylate (2.7 g, 7.1 mmol) in THF (30 mL), and the solution was cooled to 0° C. To this was added lithium borohydride (2.0 M in THF, 8.9 mL, 18 mmol). The mixture was warmed to room temperature and stirred for 3 h. Then, it was quenched with sat. $NaHCO_3$ and extracted with EtOAc. The combined organic layers were washed with water and brine, dried ($Na_2SO_4$), and purified by flash chromatography (100% Hexane to 100% EtOAc then 100% DCM to 100% MeOH) to give tert-butyl (2S,3S)-3-(((benzyloxy)carbonyl)amino)-2-(hydroxymethyl)pyrrolidine-1-carboxylate. ES/MS m/z: 351.1 [M+H].

Step 5. In a 100 mL round bottomed single necked flask were placed tert-butyl (2S,3S)-3-(((benzyloxy)carbonyl)amino)-2-(hydroxymethyl)pyrrolidine-1-carboxylate (2.2 g, 6.3 mmol), triethylamine (8.8 mL, 62 mmol), p-toluenesulfonyl chloride (2.4 g, 13 mmol), and 4-dimethylaminopyridine (77 mg, 0.63 mmol)) in DCM (30 mL). The mixture was stirred at room temperature for 2 hr. The mixture was concentrated and purified by flash chromatography (100% Hexane to 100% EtOAc then 100% DCM to 100% MeOH) to give tert-butyl (2S,3S)-3-(((benzyloxy)carbonyl)amino)-2-((tosyloxy)methyl)pyrrolidine-1-carboxylate. ES/MS m/z: 505.2 [M+H].

Step 6. In a 100 mL round bottomed single necked flask was placed tert-butyl (2S,3S)-3-(benzyloxycarbonylamino)-2-(p-tolylsulfonyloxymethyl)pyrrolidine-1-carboxylate (2.7 g, 5.4 mmol) in DMSO (35 mL). To this was added sodium cyanide (1.0 g, 21 mmol). The mixture was stirred at room temperature for 7 days. Then, it was quenched with sat. $NaHCO_3$ and extracted with EtOAc. The combined organic layers were washed with water and brine, dried ($Na_2SO_4$), and purified by flash chromatography (100% Hexane to 100% EtOAc then 100% DCM to 100% MeOH) to give tert-butyl (2R,3S)-3-(((benzyloxy)carbonyl)amino)-2-(cyanomethyl)pyrrolidine-1-carboxylate. ES/MS m/z: 360.1 [M+H].

Step 7. In a 100 mL round bottomed single necked flask was placed tert-butyl (2R,3S)-3-(benzyloxycarbonylamino)-2-(cyanomethyl)pyrrolidine-1-carboxylate (1.5 g, 4.2 mmol) in DCM (30 mL), and the mixture was cooled to 0° C. To this was added diisobutylaluminum hydride (1.0 M in DCM, 17 mL, 17 mmol), and the resulting mixture was stirred at 0° C. for 2 hr. The mixture was quenched with potassium sodium tartrate salt solution and filtered through a pad of Celite©. The filtrate was extracted with DCM, and the combined organic layers were washed with water, dried ($Na_2SO_4$), concentrated, and carried onto the next step without further purification. ES/MS m/z: 363.1 [M+H].

Step 8. In a 100 mL, round bottomed, single necked flask was placed tert-butyl (2R,3S)-3-(((benzyloxy)carbonyl)amino)-2-(2-oxoethyl)pyrrolidine-1-carboxylate (1.3 g, 3.6 mmol) in MeOH (15 mL), and the solution was cooled to 0° C. To this was added sodium borohydride (0.27 g, 7.2 mmol). The mixture was warmed to room temperature and stirred for 2 hr. Then, it was cooled to 0° C. and quenched with sat. $NaHCO_3$ and extracted with DCM. The combined organic layers were washed with water and brine, dried ($Na_2SO_4$), and purified by flash chromatography (100% Hexane to 100% EtOAc then 100% DCM to 100% MeOH) to give tert-butyl (2R,3S)-3-(((benzyloxy)carbonyl)amino)-2-(2-hydroxyethyl)pyrrolidine-1-carboxylate. ES/MS m/z: 365.1 [M+H].

Step 9. In a vial were placed tert-butyl (2R,3S)-3-(((benzyloxy)carbonyl)amino)-2-(2-hydroxyethyl)pyrrolidine-1-carboxylate (30 mg, 0.082 mmol), triethylamine (83 mg, 0.82 mmol), 4-dimethylaminopyridine (0.50 mg, 0.0041 mmol), and p-toluenesulfonyl chloride (19 mg, 0.099 mmol) in DCM (2.0 mL). After the mixture was stirred at room temperature for 24 hr, it was loaded onto the Silica pre-packed cartridge and purified by flash chromatography (100% Hexane to 100% EtOAc then 100% DCM to 100% MeOH) to give tert-butyl (2R,3S)-3-(((benzyloxy)carbonyl)amino)-2-(2-(tosyloxy)ethyl)pyrrolidine-1-carboxylate. ES/MS m/z: 519.2 [M+H].

Step 10. In a vial were placed tert-butyl (2R,3S)-3-(benzyloxycarbonylamino)-2-[2-(p-tolylsulfonyloxy)ethyl]pyrrolidine-1-carboxylate (15 mg, 0.029 mmol), 7-fluoro-6-(5-(trifluoromethyl)pyrimidin-2-yl)isoquinolin-1(2H)-one (18 mg, 0.058 mmol), and cesium carbonate (28 mg, 0.087 mmol) in DMF (2.0 mL). The mixture was stirred at room temperature for 72 hr and was loaded onto the Silica pre-packed cartridge and purified by flash chromatography (100% DCM to 100% MeOH) to give tert-butyl (2R,3S)-3-(((benzyloxy)carbonyl)amino)-2-(2-(7-fluoro-1-oxo-6-(5-(trifluoromethyl)pyrimidin-2-yl)isoquinolin-2(1H)-yl)ethyl)pyrrolidine-1-carboxylate. ES/MS m/z: 656.4 [M+H].

Step 11. In a vial was placed tert-butyl (2R,3S)-3-(((benzyloxy)carbonyl)amino)-2-(2-(7-fluoro-1-oxo-6-(5-(trifluoromethyl)pyrimidin-2-yl)isoquinolin-2(1H)-yl)ethyl)pyrrolidine-1-carboxylate (9.0 mg, 0.014 mmol) in MeOH (2.0 mL). The solution purged with $N_2$ followed by the addition of Pd/C (10%, 2.5 mg, 0.0023 mmol). Then, the mixture was stirred at room temperature under $H_2$ at 1 ATM for 16 h and filtered through a pad of Celite. The filtrate was concentrated and carried onto the next step without further purification. ES/MS m/z: 656.4 [M+H].

Step 12. In a vial were placed tert-butyl (2R,3S)-3-amino-2-(2-(7-fluoro-1-oxo-6-(5-(trifluoromethyl)pyrimidin-2-yl)isoquinolin-2(1H)-yl)ethyl)pyrrolidine-1-carboxylate (8.0 mg, 0.015 mmol), 5-chloro-4-(trifluoromethyl)-2-(2-trimethylsilylethoxymethyl)pyridazin-3-one (6.1 mg, 0.018 mmol), and N,N-diisopropylethylamine (0.027 mL, 0.15 mmol) in DMF (1.0 mL). After the mixture was stirred at 80° C. for 2 hr, it was loaded onto the Silica pre-packed cartridge and purified by flash chromatography (100% Hexane to 100% EtOAc then 100% DCM to 100% MeOH) to give tert-butyl (2R,3S)-2-(2-(7-fluoro-1-oxo-6-(5-(trifluoromethyl)pyrimidin-2-yl)isoquinolin-2(1H)-yl)ethyl)-3-((6-oxo-5-(trifluoromethyl)-1-((2-(trimethylsilyl)ethoxy)methyl)-1,6-dihydropyridazin-4-yl)amino)pyrrolidine-1-carboxylate. ES/MS m/z: 814.3 [M+H].

Step 13. In a vial was placed tert-butyl (2R,3S)-2-(2-(7-fluoro-1-oxo-6-(5-(trifluoromethyl)pyrimidin-2-yl)isoquinolin-2(1H)-yl)ethyl)-3-((6-oxo-5-(trifluoromethyl)-1-((2-(trimethylsilyl)ethoxy)methyl)-1,6-dihydropyridazin-4-yl)amino)pyrrolidine-1-carboxylate (5.0 mg, 0.0061 mmol) in DCM (1 mL). To this was added TFA (0.0093 mL, 0.12 mmol) and the mixture was stirred at room temperature for 1 hr. The reaction was concentrated and re-dissolved in MeOH (1.0 mL) followed by the addition of ethylenediamine (0.0087 mL, 0.13 mmol). After the mixture was stirred at room temperature for 1 hr, it was concentrated and purified by reverse phase chromatography to give 7-fluoro-2-(2-((2R,3S)-3-((6-oxo-5-(trifluoromethyl)-1,6-dihydropyridazin-4-yl)amino)pyrrolidin-2-yl)ethyl)-6-(5-(trifluoromethyl)pyrimidin-2-yl)isoquinolin-1(2H)-one. $^1$H NMR (400 MHz, Methanol-d4) δ 9.30 (s, 2H), 8.46 (d, J=7.0 Hz, 1H), 8.16 (d, J=11.3 Hz, 1H), 7.92 (s, 1H), 7.44 (d, J=7.4 Hz, 1H), 6.88 (d, J=7.4 Hz, 1H), 4.41 (m, 2H), 4.09 (m, 1H), 3.77-3.63 (m, 1H), 3.60-3.39 (m, 2H), 2.59-2.50 (m, 1H), 2.42-2.28 (m, 1H), 2.24-2.13 (m, 1H), 2.01 (m, 1H). ES/MS m/z: 584.1 [M+H].

Intermediate 60: (rac) 2-((3R,4R)-4-((tert-butoxycarbonyl)amino)tetrahydrofuran-3-yl)ethyl 4-methylbenzenesulfonate

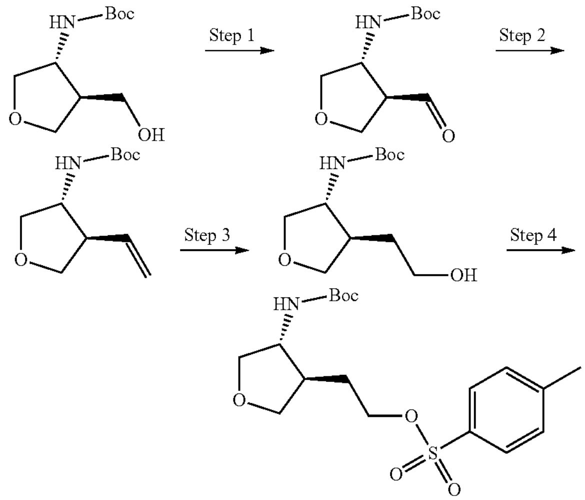

Intermediate 60

Step 1. (rac)tert-Butyl ((3R,4S)-4-(hydroxymethyl)tetrahydrofuran-3-yl)carbamate (2.0 g, 9.2 mmol) was dissolved in DCM (30 mL) in a flask and cooled to 0° C. under $N_2$. DMSO was added (1.96 mL, 27.6 mmol), followed by triethylamine (3.85 mL, 27.6 mmol), then sulfur trioxide pyridine complex (2.93 g, 18.4 mmol). The $N_2$ line was removed and the reaction was allowed to gradually reach to ambient temperature and stirred overnight. Upon completion, water was added and the reaction was poured into aq. $NH_4Cl$ and extracted 3× into DCM. The combined extracts were concentrated and purified by flash chromatography using EtOAc in hexane as eluent and ELS detection to give (rac) tert-butyl ((3R,4R)-4-formyltetrahydrofuran-3-yl)carbamate as a colorless oil. ES/MS m/z: 238.1 [M+Na]$^+$.

Step 2. Methyl(triphenyl)phosphonium bromide (1.08 g, 3.02 mmol) was suspended in THF (6.0 mL) and cooled in an ice bath under $N_2$. NaHMDS (1M solution in THF; 3.48 mL, 3.48 mmol) was added gradually. The resulting yellow suspension was stirred at ambient temperature for one hour, then was cooled again to 0° C. A solution of (rac) tert-butyl ((3R,4R)-4-formyltetrahydrofuran-3-yl)carbamate (500 mg, 2.32 mmol) in THF (3 mL) was added portionwise. Following addition, the $N_2$ line was removed and the reaction was allowed to reach ambient temperature and stirred overnight. Upon completion, water was added and the reaction was poured into aq. $NH_4Cl$ and extracted 3× into EtOAc. The combined extracts were washed with brine, concentrated and purified by flash chromatography using EtOAc in hexane as eluent and ELS detection to give (rac) tert-butyl ((3R,4R)-4-vinyltetrahydrofuran-3-yl)carbamate as a colorless oil. ES/MS m/z: 236.2 [M+Na]$^+$.

Step 3. (rac) tert-butyl ((3R,4R)-4-vinyltetrahydrofuran-3-yl)carbamate (370 mg, 1.73 mmol) was combined with chlorotris(triphenylphosphine)rhodium(I) (80 mg, 0.089 mmol) in THF (6 mL) in a vial and cooled to 0° C. under $N_2$. Catecholborane (1M solution in THF; 3.47 mL, 3.47 mmol) was added dropwise. Following addition, the $N_2$ line was removed and the reaction was allowed to attain ambient temperature and stir overnight. The reaction was cooled again to 0° C., then treated with aq. $NaHCO_3$ (3 mL), $H_2O_2$(30% aqueous; 1.0 mL), and water (3 mL). The reaction was allowed to attain ambient temperature. Upon completion, the reaction was poured into aq. $NaHCO_3$ and extracted 3× into EtOAc. The combined extracts were washed with brine, concentrated and purified by flash chromatography using EtOAc in hexane as eluent and ELS detection to give (rac) tert-butyl ((3R,4R)-4-(2-hydroxyethyl)tetrahydrofuran-3-yl)carbamate as an amber oil. ES/MS m/z: 254.2 [M+Na]$^+$.

Step 4. (rac) tert-butyl ((3R,4R)-4-(2-hydroxyethyl)tetrahydrofuran-3-yl)carbamate was treated following Example 1, Step 1 to provide (rac) 2-((3R,4R)-4-((tert-butoxycarbonyl)amino)tetrahydrofuran-3-yl)ethyl 4-methylbenzenesulfonate, ES/MS m/z: 408.3 [M+Na]$^+$.

Example 441: (rac) 6-(4-amino-5-(trifluoromethyl)pyrimidin-2-yl)-7-fluoro-2-(2-((3R,4R)-4-((6-oxo-5-(trifluoromethyl)-1,6-dihydropyridazin-4-yl)amino)tetrahydrofuran-3-yl)ethyl)isoquinolin-1(2H)-one Example 441

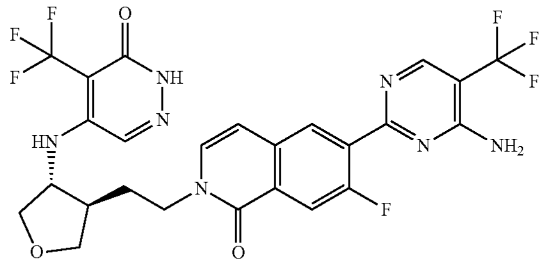

The title compound was synthesized as described in Example 17, using (rac) 2-((3R,4R)-4-((tert-butoxycarbonyl)amino)tetrahydrofuran-3-yl)ethyl 4-methylbenzenesulfonate and 6-bromo-7-fluoro-2H-isoquinolin-1-one in Step 1, and 2-chloro-5-(trifluoromethyl)pyrimidin-4-amine instead of 2-bromo-5-(difluoromethoxy)pyridine in Step 3. $^1$H NMR (400 MHz, DMSO-d6) δ 12.55 (s, 1H), 8.65 (s, 1H), 8.19 (d, J=7.0 Hz, 1H), 7.95 (d, J=11.1 Hz, 1H), 7.91 (s, 1H), 8.09-6.83 (m, 2H), 7.53 (d, J=7.4 Hz, 1H), 6.77 (d, J=7.4 Hz, 1H), 6.65-6.58 (m, 1H), 4.24 (p, J=6.2 Hz, 1H), 4.09-3.91 (m, 4H), 3.55 (dd, J=8.9, 5.4 Hz, 1H), 3.46 (dd, J=8.7, 6.9 Hz, 1H), 2.38 (td, J=13.2, 6.4 Hz, 1H), 1.96 (dq, J=13.3, 7.0 Hz, 1H), 1.85-1.71 (m, 1H). ES/MS m/z: 600.1 [M+H]$^+$.
Example 442: 7-fluoro-2-((3S,4S)-3-hydroxy-4-((6-oxo-5-(trifluoromethyl)-1,6-dihydropyridazin-4-yl)amino)pentyl)-6-(5-(trifluoromethyl)pyrimidin-2-yl)isoquinolin
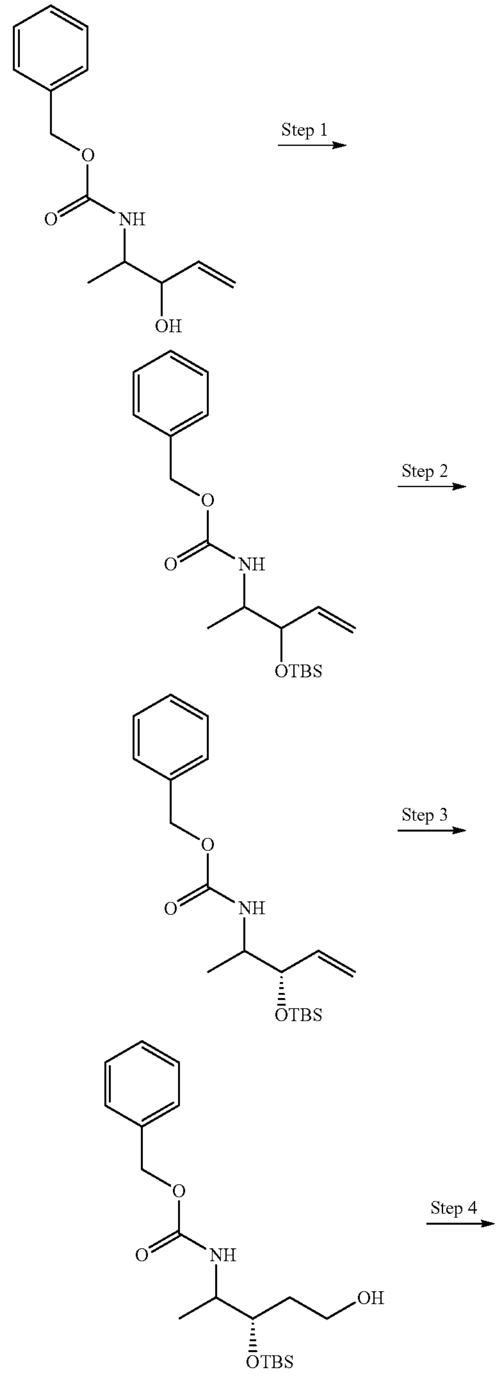
-continued
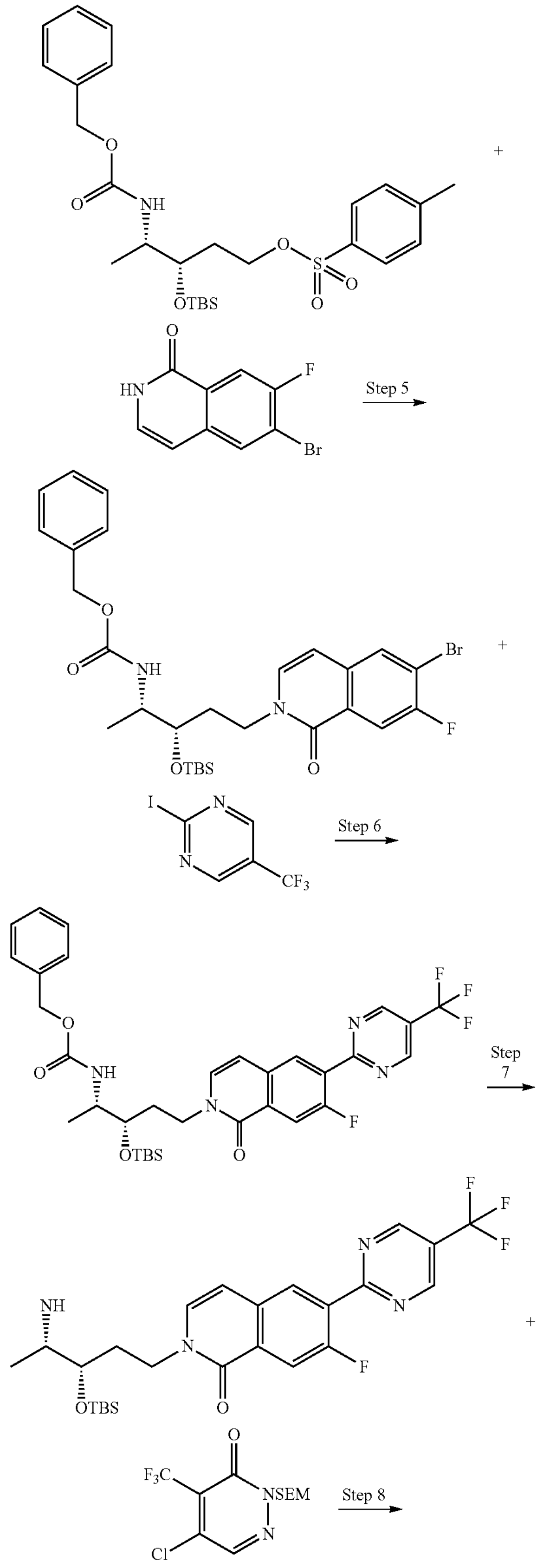

-continued

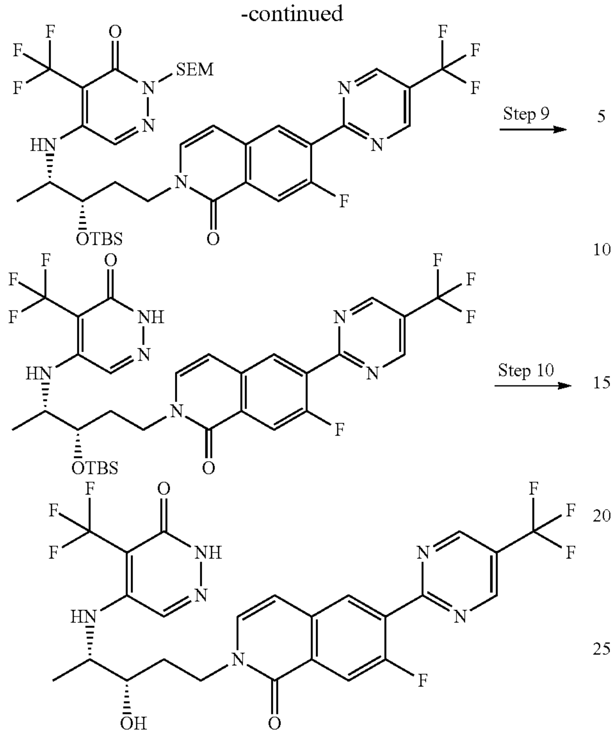

Example 442

Step 1. Benzyl (3-hydroxypent-4-en-2-yl)carbamate, isolated as a mixture of isomers from a literature preparation (17 g, 72.2 mmol), was dissolved in THF (119 mL). Imidazole (9.84 g, 144 mmol) was added, followed by TBSCl (13.0 g, 86.7 mmol). After stirring for 2 hours, the reaction was poured into water (100 mL) and extracted with DCM (2×100 mL). The combined extracts were washed with brine (100 mL), dried over $Na_2SO_4$, filtered, and concentrated. Purification by flash chromatography using EtOAc in petroleum ether as eluent and ELS detection provided benzyl (3-((tert-butyldimethylsilyl)oxy)pent-4-en-2-yl)carbamate as a mixture of isomers. ES/MS m/z: 350.2 $[M+H]^+$.

Step 2. Benzyl (3-((tert-butyldimethylsilyl)oxy)pent-4-en-2-yl)carbamate was separated by reverse phase chiral prep-SFC (Chiralpak AD, 0.1% $NH_3H_2O$ in MeOH) to give benzyl ((2S,3S)-3-((tert-butyldimethylsilyl)oxy)pent-4-en-2-yl)carbamate, ES/MS m/z: 350.2 $[M+H]^+$.

Step 3. Benzyl ((2S,3S)-3-((tert-butyldimethylsilyl)oxy)pent-4-en-2-yl)carbamate was treated following the method used in Intermediate 60, Step 3 to provide benzyl ((2S,3S)-3-((tert-butyldimethylsilyl)oxy)-5-hydroxypentan-2-yl)carbamate, ES/MS m/z: 368.3 $[M+H]^+$.

Step 4. Benzyl ((2S,3S)-3-((tert-butyldimethylsilyl)oxy)-5-hydroxypentan-2-yl)carbamate was treated following the method used in Example 1, Step 1 to provide (3S,4S)-4-(((benzyloxy)carbonyl)amino)-3-((tert-butyldimethylsilyl)oxy)pentyl 4-methylbenzenesulfonate, ES/MS m/z: 522.2 $[M+H]^+$.

Step 5. (3S,4S)-4-(((Benzyloxy)carbonyl)amino)-3-((tert-butyldimethylsilyl)oxy)pentyl 4-methylbenzenesulfonate was treated following the method used in Example 1, Step 2 using 6-bromo-7-fluoro-2H-isoquinolin-1-one instead of 6-bromo-2H-isoquinolin-1-one to provide benzyl ((2S,3S)-5-(6-bromo-7-fluoro-1-oxoisoquinolin-2(1H)-yl)-3-((tert-butyldimethylsilyl)oxy)pentan-2-yl)carbamate, ES/MS m/z: 591.2 $[M+H]^+$.

Step 6. Benzyl ((2S,3S)-5-(6-bromo-7-fluoro-1-oxoisoquinolin-2(1H)-yl)-3-((tert-butyldimethylsilyl)oxy)pentan-2-yl)carbamate was treated following the method used in Example 17, Step 3, using 2-Iodo-5-(trifluoromethyl)pyrimidine instead of 2-bromo-5-(difluoromethoxy)pyridine. XPhos Pd G4 (0.1 equiv) was added along with the aryl halide and the reaction was purified by flash chromatography to give benzyl ((2S,3S)-3-((tert-butyldimethylsilyl)oxy)-5-(7-fluoro-1-oxo-6-(5-(trifluoromethyl)pyrimidin-2-yl)isoquinolin-2(1H)-yl)pentan-2-yl)carbamate. ES/MS m/z: 659.3 $[M+H]^+$.

Step 7. A solution of benzyl ((2S,3S)-3-((tert-butyldimethylsilyl)oxy)-5-(7-fluoro-1-oxo-6-(5-(trifluoromethyl)pyrimidin-2-yl)isoquinolin-2(1H)-yl)pentan-2-yl)carbamate (80 mg, 0.121 mmol) in EtOH (2 mL) and EtOAc (2 mL) was added to 10% Pd/C in a flask purged with $N_2$. The flask was evacuated and purged with $N_2$, then fitted with a balloon filled with $H_2$ and stirred under an $H_2$ atmosphere. Upon completion, the reaction was evacuated and purged with $N_2$, then filtered through a celite plug. The filtrate was concentrated to give 2-((3S,4S)-4-amino-3-((tert-butyldimethylsilyl)oxy)pentyl)-7-fluoro-6-(5-(trifluoromethyl)pyrimidin-2-yl)isoquinolin-1(2H)-one, which was used in the next step without purification. ES/MS m/z: 525.3 $[M+H]^+$.

Step 8. 2-((3S,4S)-4-amino-3-((tert-butyldimethylsilyl)oxy)pentyl)-7-fluoro-6-(5-(trifluoromethyl)pyrimidin-2-yl)isoquinolin-1(2H)-one was treated following the method used in Example 1, Step 5 to give 2-((3S,4S)-3-((tert-butyldimethylsilyl)oxy)-4-((6-oxo-5-(trifluoromethyl)-1-((2-(trimethylsilyl)ethoxy)methyl)-1,6-dihydropyridazin-4-yl)amino)pentyl)-7-fluoro-6-(5-(trifluoromethyl)pyrimidin-2-yl)isoquinolin-1(2H)-one, ES/MS m/z: 817.3 $[M+H]^+$.

Step 9. 2-((3S,4S)-3-((tert-Butyldimethylsilyl)oxy)-4-((6-oxo-5-(trifluoromethyl)-1-((2-(trimethylsilyl)ethoxy)methyl)-1,6-dihydropyridazin-4-yl)amino)pentyl)-7-fluoro-6-(5-(trifluoromethyl)pyrimidin-2-yl)isoquinolin-1(2H)-one was subjected to the conditions in Example 1, Step 6. After concentration, the residue was subjected to aqueous workup to give crude 2-((3S,4S)-3-((tert-butyldimethylsilyl)oxy)-4-((6-oxo-5-(trifluoromethyl)-1,6-dihydropyridazin-4-yl)amino)pentyl)-7-fluoro-6-(5-(trifluoromethyl)pyrimidin-2-yl)isoquinolin-1(2H)-one, which was used directly in the subsequent step. ES/MS m/z: 687.3 $[M+H]^+$.

Step 10. 2-((3S,4S)-3-((tert-Butyldimethylsilyl)oxy)-4-((6-oxo-5-(trifluoromethyl)-1,6-dihydropyridazin-4-yl)amino)pentyl)-7-fluoro-6-(5-(trifluoromethyl)pyrimidin-2-yl)isoquinolin-1(2H)-one (43 mg, 0.062 mmol) was dissolved in THF (0.6 mL) and treated with TBAF (1M solution in THF; 0.081 mL, 0.081 mmol). After 1 hour, the reaction was poured into aq. $NaHCO_3$ and extracted 3× into EtOAc. The combined extracts were washed with brine, concentrated, and purified via reverse phase prep-HPLC (5-100% MeCN in water, 0.1% TFA) to afford the title compound, 7-fluoro-2-((3S,4S)-3-hydroxy-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one. 1H NMR (400 MHz, DMSO-d6) δ 12.47 (s, 1H), 9.48 (s, 2H), 8.44 (d, J=7.1 Hz, 1H), 8.03 (d, J=11.4 Hz, 1H), 7.91 (s, 1H), 7.53 (d, J=7.3 Hz, 1H), 6.85 (d, J=7.4 Hz, 1H), 6.27-6.17 (m, 1H), 4.22-4.10 (m, 2H), 4.08-3.90 (m, 2H), 3.57 (dt, J=9.5, 3.4 Hz, 1H), 1.95-1.82 (m, 1H), 1.81-1.67 (m, 1H), 1.17 (d, J=6.4 Hz, 3H). ES/MS m/z: 573.3 $[M+H]^+$.

Example 443: 7-fluoro-2-(((1R,3S)-3-((6-oxo-5-(trifluoromethyl)-1,6-dihydropyridazin-4-yl)amino)cyclopentyl)methyl)-6-(5-(trifluoromethyl)pyrimidin-2-yl)isoquinolin-1(2H)-one Example 443

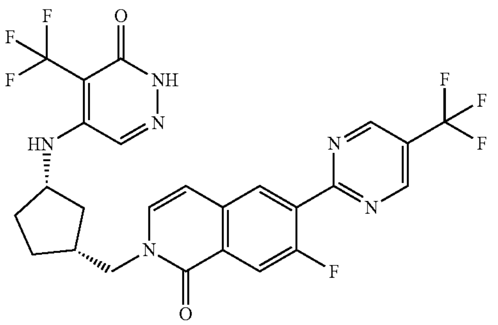

The title compound was prepared following the method used for Example 17, starting with ((1R,3S)-3-((tert-butoxycarbonyl)amino)cyclopentyl)methyl 4-methylbenzenesulfonate and 6-bromo-7-fluoro-2H-isoquinolin-1-one in Step 1 and using 2-iodo-5-(trifluoromethyl)pyrimidine instead of 2-bromo-5-(difluoromethoxy)pyridine in Step 3. 1H NMR (400 MHz, DMSO-d6) δ 12.47 (s, 1H), 9.48 (s, 2H), 8.45 (d, J=7.2 Hz, 1H), 8.04 (d, J=11.4 Hz, 1H), 7.89 (s, 1H), 7.55 (d, J=7.3 Hz, 1H), 6.85 (d, J=7.4 Hz, 1H), 6.58-6.50 (m, 1H), 4.18 (dt, J=15.5, 7.2 Hz, 1H), 4.06 (dd, J=13.0, 7.2 Hz, 1H), 3.97 (dd, J=13.0, 7.6 Hz, 1H), 2.50-2.37 (m, 1H), 2.16-1.95 (m, 2H), 1.78-1.61 (m, 2H), 1.60-1.41 (m, 2H). ES/MS m/z: 569.3 $[M+H]^+$.

Intermediate 61: ((1R,3S)-3-((tert-butoxycarbonyl)amino)cyclopentyl)methyl 4-methylbenzenesulfonate Intermediate 61

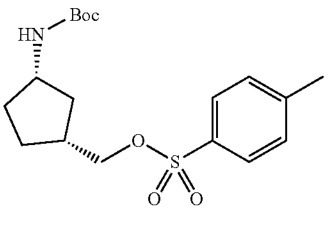

The title compound was prepared following Example 1, Step 1, starting with tert-butyl N-[(1S,3R)-3-(hydroxymethyl)cyclopentyl]carbamate to provide ((1R,3S)-3-((tert-butoxycarbonyl)amino)cyclopentyl)methyl 4-methylbenzenesulfonate. ES/MS m/z: 392.2 $[M+Na]^+$.

Example 444: 6-(4-amino-5-(trifluoromethyl)pyrimidin-2-yl)-7-fluoro-2-(((1R,3S)-3-((6-oxo-5-(trifluoromethyl)-1,6-dihydropyridazin-4-yl)amino)cyclopentyl)methyl)isoquinolin-1(2H)-one Example 444

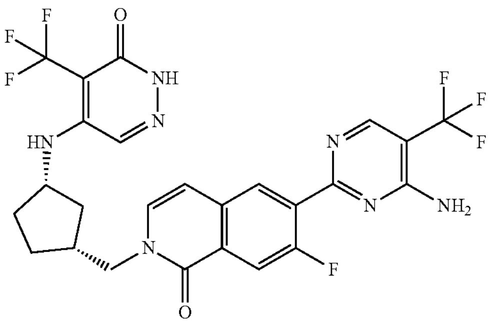

The title compound was prepared following the method used for Example 17, starting with ((1R,3S)-3-((tert-butoxycarbonyl)amino)cyclopentyl)methyl 4-methylbenzenesulfonate and 6-bromo-7-fluoro-2H-isoquinolin-1-one in Step 1 and using 2-chloro-5-(trifluoromethyl)pyrimidin-4-amine instead of 2-bromo-5-(difluoromethoxy)pyridine in Step 3. 1H NMR (400 MHz, DMSO-d6) δ 12.48 (s, 1H), 8.65 (s, 1H), 8.21 (d, J=7.0 Hz, 1H), 7.97 (d, J=11.1 Hz, 1H), 7.89 (s, 1H), 8.37-7.21 (br. m, 2H), 7.52 (d, J=7.4 Hz, 1H), 6.77 (d, J=7.4 Hz, 1H), 6.59-6.50 (m, 1H), 4.17 (h, J=7.7 Hz, 1H), 4.05 (dd, J=13.0, 7.2 Hz, 1H), 3.96 (dd, J=13.0, 7.6 Hz, 1H), 2.42 (dt, J=14.7, 7.3 Hz, 1H), 2.16-1.95 (m, 2H), 1.78-1.60 (m, 2H), 1.60-1.40 (m, 2H). ES/MS m/z: 584.3 $[M+H]^+$.

Example 445: 7-fluoro-2-((3R,4S)-3-hydroxy-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one Example 445

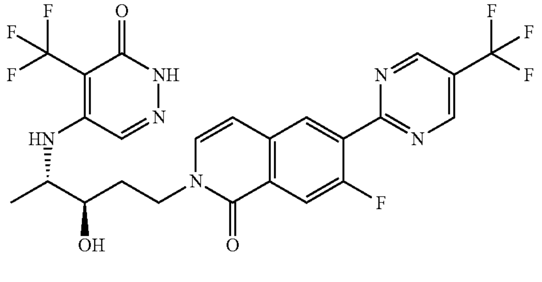

The title compound was prepared according to the procedure of Example 442, using benzyl ((2S,3R)-3-((tert-butyldimethylsilyl)oxy)pent-4-en-2-yl)carbamate isolated from Step 2. 1H NMR (400 MHz, DMSO-d6) δ 12.48 (s, 1H), 9.48 (s, 2H), 8.44 (d, J=7.1 Hz, 1H), 8.04 (d, J=11.4 Hz, 1H), 7.92 (s, 1H), 7.53 (d, J=7.4 Hz, 1H), 6.86 (d, J=7.4 Hz, 1H), 6.32-6.21 (m, 1H), 4.17 (ddd, J=13.3, 8.2, 5.2 Hz, 1H), 4.08-3.93 (m, 2H), 3.68-3.59 (m, 2H), 1.96-1.83 (m, 1H), 1.80-1.66 (m, 1H), 1.11 (d, J=6.4 Hz, 3H). ES/MS m/z: 573.3 $[M+H]^+$.

Example 446: 7-fluoro-2-(((1S,3R)-3-((6-oxo-5-(trifluoromethyl)-1,6-dihydropyridazin-4-yl)amino)cyclopentyl)methyl)-6-(5-(trifluoromethyl)pyrimidin-2-yl)isoquinolin-1(2H)-one Example 446

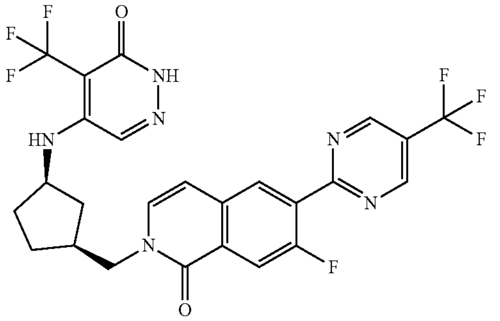

The title compound was prepared following the method used for Example 17, starting with ((1S,3R)-3-((tert-butoxycarbonyl)amino)cyclopentyl)methyl 4-methylbenzenesulfonate and 6-bromo-7-fluoro-2H-isoquinolin-1-one in Step 1 and using 2-iodo-5-(trifluoromethyl)pyrimidine instead of 2-bromo-5-(difluoromethoxy)pyridine in Step 3. 1H NMR (400 MHz, DMSO-d6) δ 12.47 (s, 1H), 9.48 (s, 2H), 8.45 (d, J=7.1 Hz, 1H), 8.04 (d, J=11.4 Hz, 1H), 7.89 (s, 1H), 0.55 (d, J=7.4 Hz, 1H), 6.85 (d, J=7.4 Hz, 1H), 6.59-6.51 (m, 1H), 4.18 (h, J=7.7 Hz, 1H), 4.06 (dd, J=13.0, 7.2 Hz, 1H), 3.97 (dd, J=12.8, 7.6 Hz, 1H), 2.50-2.37 (m, 1H), 2.16-1.95 (m, 2H), 1.89-1.61 (m, 2H), 1.60-1.38 (m, 2H). ES/MS m/z: 569.3 $[M+H]^+$.

Intermediate 62: ((1S,3R)-3-((tert-butoxycarbonyl)amino)cyclopentyl)methyl 4-methylbenzenesulfonate Intermediate 62

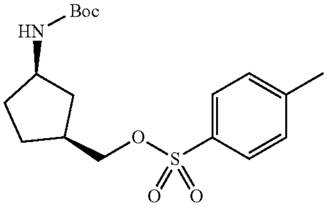

The title compound was prepared following Example 1, Step 1, starting with tert-butyl N-[(1R,3S)-3-(hydroxymethyl)cyclopentyl]carbamate to provide ((1S,3R)-3-((tert-butoxycarbonyl)amino)cyclopentyl)methyl 4-methylbenzenesulfonate. ES/MS m/z: 392.1 $[M+Na]^+$.

Example 447: 6-(4-amino-5-(trifluoromethyl)pyrimidin-2-yl)-7-fluoro-2-(((1S,3R)-3-((6-oxo-5-(trifluoromethyl)-1,6-dihydropyridazin-4-yl)amino)cyclopentyl)methyl)isoquinolin-1(2H)-one Example 447

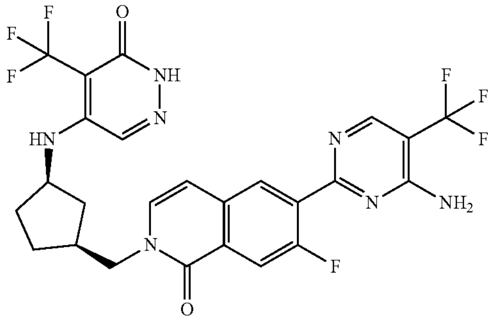

The title compound was prepared following the method used for Example 17, starting with ((1S,3R)-3-((tert-butoxycarbonyl)amino)cyclopentyl)methyl 4-methylbenzenesulfonate and 6-bromo-7-fluoro-2H-isoquinolin-1-one in Step 1 and using 2-chloro-5-(trifluoromethyl)pyrimidin-4-amine instead of 2-bromo-5-(difluoromethoxy)pyridine in Step 3. 1H NMR (400 MHz, DMSO-d6) δ 12.48 (s, 1H), 8.65 (s, 1H), 8.21 (d, J=7.0 Hz, 1H), 7.97 (d, J=11.1 Hz, 1H), 7.89 (s, 1H), 8.10-7.37 (m, 3H), 7.52 (d, J=7.4 Hz, 1H), 6.77 (d, J=7.4 Hz, 1H), 6.59-6.51 (m, 1H), 4.21-4.14 (m, 1H), 4.05 (dd, J=13.0, 7.2 Hz, 1H), 3.96 (dd, J=13.0, 7.6 Hz, 1H), 2.48-2.36 (m, 1H), 2.16-1.95 (m, 2H), 1.88-1.60 (m, 2H), 1.60-1.38 (m, 2H). ES/MS m/z: 584.3 $[M+H]^+$.

Example 448: 7-(5-chloropyrimidin-2-yl)-6-fluoro-3-(2-((1R,2S)-2-((6-oxo-5-(trifluoromethyl)-1,6-dihydropyridazin-4-yl)amino)cyclopentyl)ethyl)quinazolin-4(3H)-one Example 448

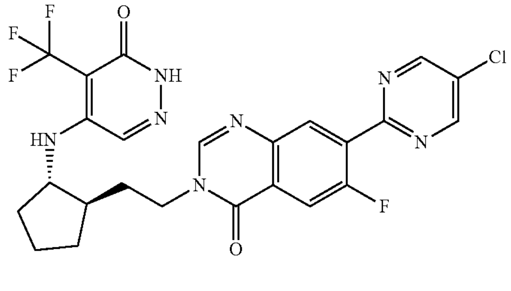

The title compound was synthesized as described in Example 17, using 2-((1R,2S)-2-((tert-butoxycarbonyl)amino)cyclopentyl)ethyl 4-methylbenzenesulfonate and 7-bromo-6-fluoro-1H-quinazolin-4-one in Step 1, and 2,5-dichloropyrimidine instead of 2-bromo-5-(difluoromethoxy)pyridine in Step 3. 1H NMR (400 MHz, DMSO-d6) δ 12.45 (s, 1H), 9.16 (s, 2H), 8.46 (s, 1H), 8.27 (d, J=6.8 Hz, 1H), 7.96 (d, J=10.5 Hz, 1H), 7.94-7.88 (m, 1H), 6.52-6.43 (m, 1H), 4.09-3.93 (m, 2H), 3.85 (p, J=7.9 Hz, 1H), 2.10-1.85 (m, 4H), 1.73-1.58 (m, 3H), 1.57-1.44 (m, 1H), 1.29 (dq, J=12.0, 8.6, 8.2 Hz, 1H). ES/MS m/z: 550.1 $[M+H]^+$.

Example 449: 7-(4-amino-5-chloropyrimidin-2-yl)-6-fluoro-3-(2-((1R,2S)-2-((6-oxo-5-(trifluoromethyl)-1,6-dihydropyridazin-4-yl)amino)cyclopentyl)ethyl)quinazolin-4(3H)-one Example 449

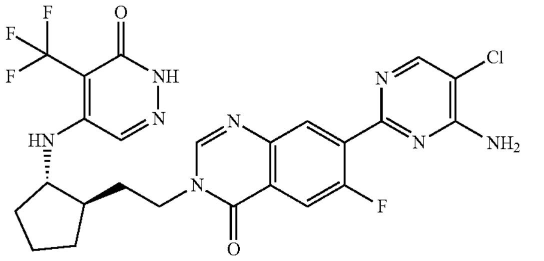

The title compound was synthesized as described in Example 17, using 2-((1R,2S)-2-((tert-butoxycarbonyl)amino)cyclopentyl)ethyl 4-methylbenzenesulfonate and 7-bromo-6-fluoro-1H-quinazolin-4-one in Step 1, and tert-butyl N-tert-butoxycarbonyl-N-(2,5-dichloropyrimidin-4-yl)carbamate instead of 2-bromo-5-(difluoromethoxy)pyridine in Step 3. 1H NMR (400 MHz, DMSO-d6) δ 12.45 (s, 1H), 8.44 (s, 1H), 8.43 (s, 1H), 8.13 (d, J=6.7 Hz, 1H), 7.92 (s, 1H), 7.89 (d, J=10.4 Hz, 1H), 7.84-7.19 (m, 2H), 6.56-6.41 (m, 1H), 4.09-3.94 (m, 3H), 2.06-1.86 (m, 4H), 1.74-1.58 (m, 3H), 1.57-1.45 (m, 1H), 1.35-1.21 (m, 1H). ES/MS m/z: 565.1 $[M+H]^+$.

Example 450: Preparation of 7-fluoro-2-[2-[(1R,2S)-2-[[6-oxo-5-(trifluoromethyl)-1H-pyridazin-4-yl]amino]cyclohexyl]ethyl]-6-[5-(trifluoromethyl)pyrimidin-2-yl]isoquinolin-1-one

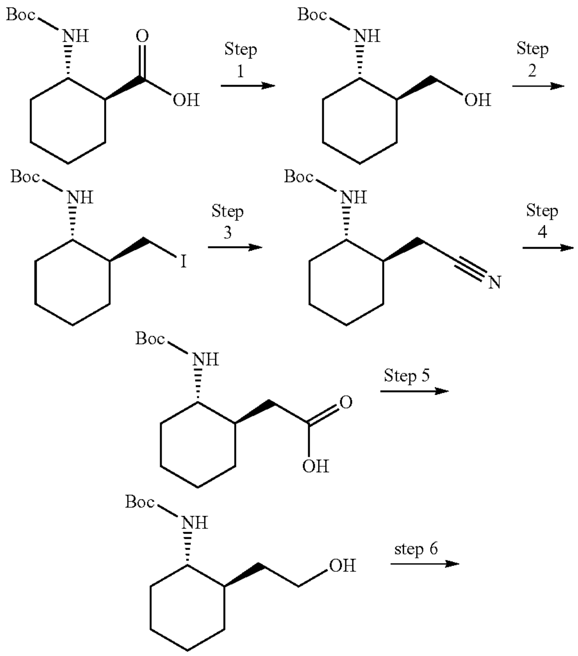

-continued

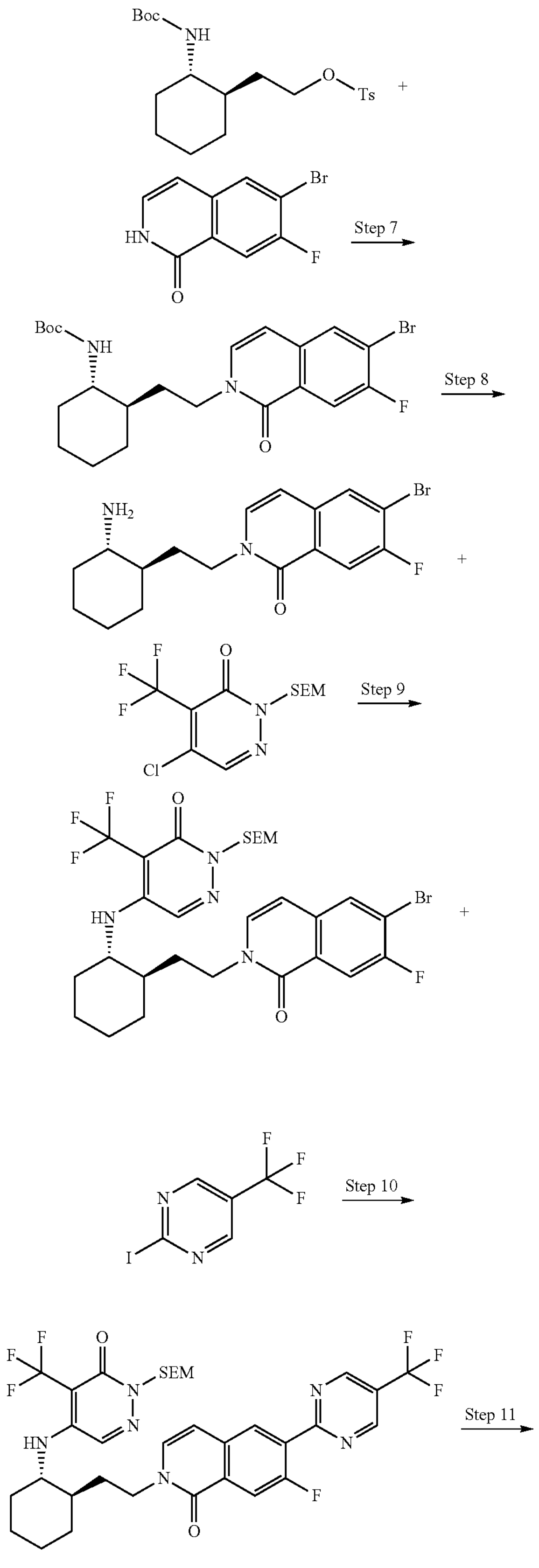

-continued

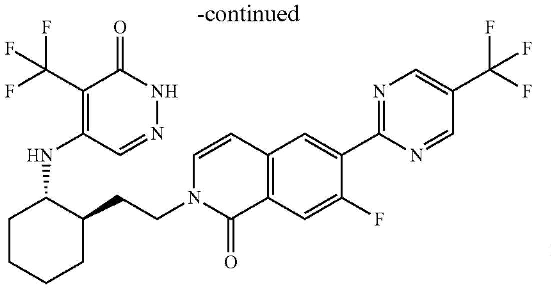

Example 450

Step 1. In a flask was placed (1S,2S)-2-(tert-butoxycarbonylamino)cyclohexanecarboxylic acid (2000 mg, 8.2 mmol), and triethylamine (3.4 mL, 24.7 mmol) in THF (40 mL). The mixture was cool to 0° C. and placed under nitrogen atmosphere. To this solution was added ethyl chloroformate (1.2 mL, 12.3 mmol) and the reaction was stirred for 30 minutes at 0° C. The mixture was then filtered to remove the precipitated triethylamine hydrochloride. The filtrate containing the mixed anhydride was slowly added to a stirred suspension of sodium borohydride (933 mg, 24.7 mmol) in 20% aqueous THF (10.0 mL) maintained at 10° C. After the mixture was stirred for 30 minutes, it was quenched by the slow addition of sat. aq. $NH_4Cl$. The mixture was then extracted with EtOAc, washed with 2M NaOH solution, washed with brine, dried ($MgSO_4$), and purified by flash chromatography (100% hexanes to 100% EtOAc) to give tert-butyl N-[(1S,2S)-2-(hydroxymethyl)cyclohexyl]carbamate. ES/MS: m/z 230.08 $[M+H]^+$.

Step 2. Iodine (2.02 g, 7.96 mmol) was added to a solution of triphenylphosphine (2.09 g, 7.96 mmol) and imidazole (0.542 g, 7.96 mmol) in DCM (27 ml). The mixture is stirred at room temperature until a solution forms (30 minutes) then tert-butyl N-[(1S,2S)-2-(hydroxymethyl)cyclohexyl]carbamate (1.522 g, 6.64 mmol) is added. After stirring the mixture at room temperature for 18 h the mixture is filtered, and the filtrate evaporated. The residue is dissolved in EtOAc and washed with sat. aq. sodium bisulfite and then brine. The organic phase is dried over $MgSO_4$ and the solvent is removed under reduced pressure. The residue is purified by flash chromatography using a gradient of EtOAc/hexane (0 to 100%) as eluent to give tert-butyl N-[(1S,2S)-2-(iodomethyl)cyclohexyl]carbamate. ES/MS: m/z 340.02 $[M+H]^+$.

Step 3. To a suspension of tert-butyl N-[(1S,2S)-2-(iodomethyl)cyclohexyl]carbamate (1841 mg, 5.43 mmol) in acetonitrile (53.0 ml) was added $n-Bu_4NCN$ at RT and was stirred for 2 hr. The reaction was then diluted with water and the mixture was extracted with EtOAc. Organic phases were washed with water and brine then dried ($MgSO_4$) and concentrated to afford tert-butyl N-[(1S,2R)-2-(cyanomethyl)cyclohexyl]carbamate which was used without further purification ES/MS: m/z 239.09 $[M+H]^+$.

Step 4. Aqueous NaOH (5.12 g, 128 mmol, 6 M) was added to a solution of tert-butyl N-[(1S,2R)-2-(cyanomethyl)cyclohexyl]carbamate (1290 mg, 5.41 mmol) in EtOH (21 ml). The suspension was heated at 80° C. ON. Upon completion the reaction was diluted with EtOAc and extracted. Aqueous phase was then acidified with 6 M HCl to pH 4-5 and extracted with EtOAc (2×100 mL), dried ($MgSO_4$), and concentrated to afford 2-[(1R,2S)-2-(tert-butoxycarbonylamino)cyclohexyl]acetic acid which was used without further purification. ES/MS: m/z 258.09 $[M+H]^+$.

Step 5. In a flask was placed 2-[(1R,2S)-2-(tert-butoxycarbonylamino)cyclohexyl]acetic acid (833 mg, 3.24 mmol), and triethylamine (1.35 mL, 9.71 mmol) in THF (16.0 mL). The mixture was cool to 0° C. and placed under nitrogen atmosphere. To this solution was added ethyl chloroformate (0.47 mL, 4.86 mmol) and the reaction was stirred for 30 minutes at 0° C. The mixture was then filtered to remove the precipitated triethylamine hydrochloride. The filtrate containing the mixed anhydride was slowly added to a stirred suspension of sodium borohydride (367 mg, 9.71 mmol) in 20% aqueous THF (10.0 mL) maintained at 10° C. After the mixture was stirred for 30 minutes, it was acidified with 1N HCl to pH ~4. The mixture was then extracted with EtOAc, washed with 2M NaOH solution, washed with brine, dried ($MgSO_4$), and purified by flash chromatography (100% hexanes to 100% EtOAc) to give tert-butyl N-[(1S,2R)-2-(2-hydroxyethyl)cyclohexyl]carbamate. ES/MS: m/z 244.14 $[M+H]^+$.

Step 6. To a stirred solution of tert-butyl N-[(1S,2R)-2-(2-hydroxyethyl)cyclohexyl]carbamate (445 mg, 1.83 mmol) and triethylamine (0.7 ml, 5.49 mmol) in dichloromethane (18 mL) at 0° C. was added p-toluenesulfonyl chloride (558 mg, 2.93 mmol), DMAP (13.2 mg, 0.1 mmol) and the mixture was warmed to room temperature and stirred overnight. Upon completion, the mixture was diluted with water and extracted with dicholoromethane. The combined organic layers were washed with brine, dried over $MgSO_4$ and concentrated in vacuo to give the crude product. The residue was purified using column chromatography eluting with EtOAc in hexanes 0-100% to afford 2-[(1R,2S)-2-(tert-butoxycarbonylamino)cyclohexyl]ethyl 4-methylbenzenesulfonate. ES/MS: m/z 398.18 $[M+H]^+$.

Step 7. To a mixture of 6-bromo-2H-isoquinolin-1-one (360.0 mg, 1.49 mmol) and 2-[(1R,2S)-2-(tert-butoxycarbonylamino)cyclohexyl]ethyl 4-methylbenzenesulfonate (537 mg, 1.35 mmol) in DMF (12 mL) was added $Cs_2CO_3$ (880 mg, 2.70 mmol) and the reaction was stirred at room temperature for 18 hr. Upon completion, the mixture was diluted with EtOAc, washed with water, washed with brine, dried over $MgSO_4$ and concentrated in vacuo to give the crude product. The crude residue was purified using column chromatography eluting with EA in hexanes 0-100% to afford tert-butyl N-[(1S,2R)-2-[2-(6-bromo-7-fluoro-1-oxo-2-isoquinolyl)ethyl]cyclohexyl]carbamate. ES/MS: m/z 469.10 $[M+H]^+$.

Step 8. To a solution of tert-butyl N-[(1S,2R)-2-[2-(6-bromo-7-fluoro-1-oxo-2-isoquinolyl)ethyl]cyclohexyl]carbamate (207 mg, 0.443 mmol) in dichloromethane (4 mL) was added trifluoroacetic acid (0.67 mL, 8.86 mmol) at room temperature and the mixture was stirred for 1 hr. Upon completion, the solvent was removed under reduced pressure to afford 2-(2-((1R,2S)-2-aminocyclohexyl)ethyl)-6-bromo-7-fluoroisoquinolin-1(2H)-one which was used without further purification. ES/MS: m/z 369.67 $[M+H]^+$.

Step 9. A mixture of 2-(2-((1R,2S)-2-aminocyclohexyl)ethyl)-6-bromo-7-fluoroisoquinolin-1(2H)-one (213 mg, 0.443 mmol), 5-chloro-4-(trifluoromethyl)-2-(2-trimethylsilylethoxymethyl)pyridazin-3-one (432 mg, 1.18 mmol), and N,N-diisopropylethylamine (0.90 mL, 5.22 mmol) in DMF (4.0 mL) was stirred at RT for 2 h. Upon completion, the reaction was diluted with EtOAc, washed with water, washed with brine, dried over $MgSO_4$ and concentrated in vacuo to give the crude product. The crude residue was purified using column chromatography eluting with EtOAc in hexanes 0-100% to provide 6-bromo-7-fluoro-2-[2-[(1R,2S)-2-[[6-oxo-5-(trifluoromethyl)-1-(2-trimethylsilylethoxymethyl)pyridazin-4-yl]amino]cyclohexyl]ethyl]isoquinolin-1-one ES/MS: m/z 660.33 $[M+H]^+$.

Step 10. In a vial were placed methyl 6-bromo-7-fluoro-2-[2-[(1R,2S)-2-[[6-oxo-5-(trifluoromethyl)-1-(2-trimethylsilylethoxymethyl)pyridazin-4-yl]amino]cyclohexyl]ethyl] isoquinolin-1-one (75 mg, 0.114 mmol), 1,1'-Bis (diphenylphosphino)ferrocene-palladium(II)dichloride dichloromethane complex (10 mg, 0.014 mmol), potassium acetate (33.5 mg, 0.341 mmol), and bis(pinacolato)diboron (43.3 mg, 0.171 mmol) in dioxane (2 mL). The mixture was bubbled with dry Nitrogen and stirred at 80° C. for 18 hr. The reaction was cooled to ambient temperature and 2 M aqueous sodium carbonate (0.125 mL, 0.249 mmol), 2-iodo-5-(trifluoromethyl)pyrimidine (46.7 mg, 0.171 mmol), and CataCXIum Pd G4 (8 mg, 0.011 mmol) were added. The mixture was bubbled with dry nitrogen gas and stirred at 80° C. for 3 hr. The reaction was then cooled, diluted with EtOAc and filtered through a plug of Celite®. The volatiles were evaporated in vacuo and the residue purified via flash chromatography (100% hexanes to 100% EtOAc) to give 7-fluoro-2-[2-[(1R,2S)-2-[[6-oxo-5-(trifluoromethyl)-1-(2-trimethylsilylethoxymethyl)pyridazin-4-yl]amino]cyclohexyl]ethyl]-6-[5-(trifluoromethyl)pyrimidin-2-yl]isoquinolin-1-one. ES/MS m/z: 727.21 $[M+H]^+$.

Step 11. In a vial were placed 7-fluoro-2-[2-[(1R,2S)-2-[[6-oxo-5-(trifluoromethyl)-1-(2-trimethylsilylethoxymethyl)pyridazin-4-yl]amino]cyclohexyl]ethyl]-6-[5-(trifluoromethyl)pyrimidin-2-yl]isoquinolin-1-one (82.6 mg, 0.114 mmol), and trifluoroacetic acid (0.3 mL, 3.98 mmol) in DCM (5 mL). The mixture was stirred for 1 hr, and then was concentrated under vacuum. The resulting crude product was dissolved in methanol (5 mL) and ethylenediamine (0.266 mL, 3.98 mmol) was added and the mixture was stirred for 15 minutes and then concentrated under vacuum. The resulting crude product was purified by reverse phase prep-HPLC (5-100% MeCN in water, 0.1% TFA) to afford 7-fluoro-2-[2-[(1R,2S)-2-[[6-oxo-5-(trifluoromethyl)-1H-pyridazin-4-yl]amino]cyclohexyl]ethyl]-6-[5-(trifluoromethyl)pyrimidin-2-yl]isoquinolin-1-one. $^1H$ NMR (400 MHz, DMSO-d6) δ 12.38 (s, 1H), 9.48 (s, 2H), 8.42 (d, J=7.1 Hz, 1H), 8.01 (d, J=11.4 Hz, 1H), 7.93 (s, 1H), 7.44 (d, J=7.4 Hz, 1H), 6.83 (d, J=7.4 Hz, 1H), 6.41-6.26 (m, 1H), 4.02-3.99 (m, 2H), 3.63-3.45 (m, 1H), 2.03 (d, J=10.0 Hz, 1H), 1.98-1.84 (m, 1H), 1.78 (d, J=8.7 Hz, 1H), 1.72-1.56 (m, 3H), 1.55-1.44 (m, 1H), 1.44-1.30 (m, 2H), 1.25-1.01 (m, 2H). ES/MS m/z: 597.3 $[M+H]^+$.

Example 451: 6-[4-amino-5-(trifluoromethyl)pyrimidin-2-yl]-7-fluoro-2-[2-[(1R,2S)-2-[[6-oxo-5-(trifluoromethyl)-1H-pyridazin-4-yl]amino]cyclohexyl]ethyl]isoquinolin-1-one Example 451

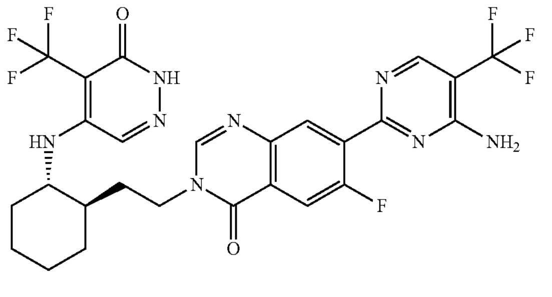

The title compound was synthesized as described in Example 450, using 2-chloro-5-(trifluoromethyl)pyrimidin-4-amine instead of 2-iodo-5-(trifluoromethyl)pyrimidine. $^1H$ NMR (400 MHz, DMSO-d6) δ 12.39 (s, 1H), 8.65 (s, 1H), 8.18 (d, J=7.0 Hz, 1H), 8.00-7.90 (m, 2H), 7.41 (d, J=7.4 Hz, 1H), 6.75 (d, J=7.4 Hz, 1H), 6.48-6.23 (m, 1H), 4.12-3.89 (m, 2H), 3.63-3.45 (m, 1H), 2.03 (d, J=10.1 Hz, 1H), 1.98-1.84 (m, 1H), 1.78 (d, J=8.7 Hz, 1H), 1.73-1.56 (m, 3H), 1.53-1.30 (m, 3H), 1.23-1.04 (m, 2H). ES/MS m/z: 612.3 $[M+H]^+$.

Example 452: 6-fluoro-3-[2-[(1R,2S)-2-[[6-oxo-5-(trifluoromethyl)-1H-pyridazin-4-yl]amino]cyclobutyl]ethyl]-7-[5-(trifluoromethyl)pyrimidin-2-yl]quinazolin-4-one Example 452

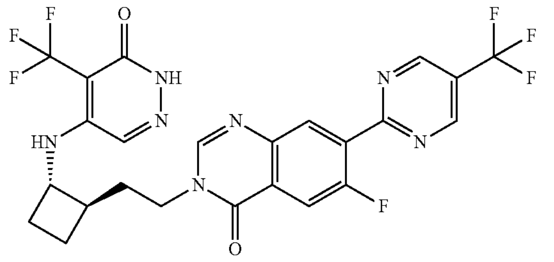

The title compound was synthesized as described in Example 450, using (1S,2S)-2-(tert-butoxycarbonylamino) cyclobutanecarboxylic acid instead of (1S,2S)-2-(tert-butoxycarbonylamino)cyclohexanecarboxylic acid and 7-bromo-6-fluoro-3H-quinazolin-4-one instead of 6-bromo-7-fluoro-2H-isoquinolin-1-one. $^1H$ NMR (400 MHz, DMSO-d6) δ 12.49 (s, 1H), 9.49 (s, 2H), 8.45 (s, 1H), 8.34 (d, J=6.7 Hz, 1H), 7.99 (d, J=10.5 Hz, 1H), 7.80 (s, 1H), 6.92-6.77 (m, 1H), 4.08-3.86 (m, 3H), 2.66-2.52 (m, 1H), 2.34-2.19 (m, 1H), 2.08-1.97 (m, 1H), 1.94-1.77 (m, 3H), 1.40-1.21 (m, 1H). ES/MS m/z: 570.3 $[M+H]^+$.

Intermediate 63: Preparation of (R)-4-((tert-butoxycarbonyl)amino)-6,6,6-trifluorohexyl 4-methylbenzenesulfonate

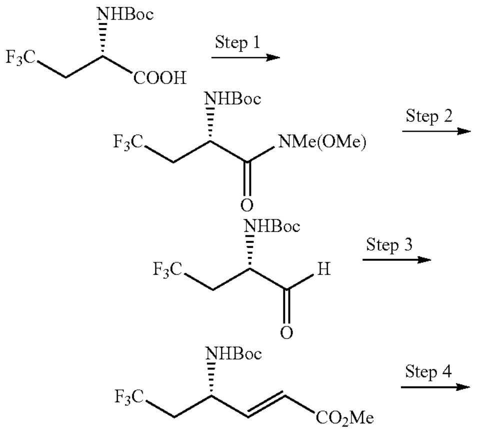

-continued

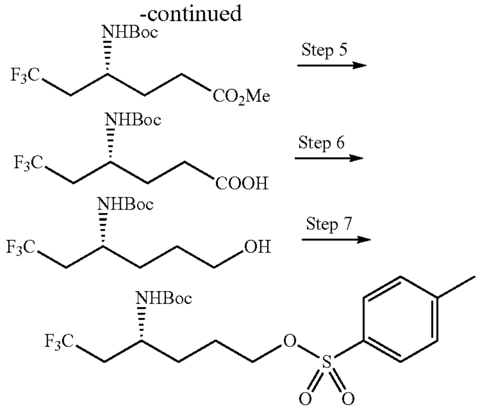

Intermediate 63

Step 1. In a vial were placed (S)-2-((tert-butoxycarbonyl)amino)-4,4,4-trifluorobutanoic acid (2.73 g, 10.6 mmol) and THF (16.0 mL). 1,1'-carbonyldiimidazole (1.70 g, 10.5 mmol) was added portion-wise over 10 minutes. After stirring for 1 hr at room temperature, a solution of N,O-dimethylhydroxylamine hydrochloride (0.932 g, 9.55 mmol) and DIPEA (1.66 mL, 9.55 mmol) in DMF (4.0 mL) was added. The reaction mixture was stirred at room temperature for 15 hr, followed by concentration in vacuo. The residue was diluted with EtOAc (100 mL) and washed with 1 M aq. HCl (2×50 mL), saturated aq. $NaHCO_3$ (2×50 mL), and brine (50.0 mL). The organic layer was dried over $MgSO_4$, filtered, and concentrated in vacuo to give tert-butyl (S)-(4,4,4-trifluoro-1-(methoxy(methyl)amino)-1-oxobutan-2-yl)carbamate.

Step 2. In a 200 mL round bottom flask was added $LiAlH_4$ (0.444 g, 11.7 mmol) in $Et_2O$ (30 mL) at 0° C. was added dropwise a solution of tert-butyl (S)-(4,4,4-trifluoro-1-(methoxy(methyl)amino)-1-oxobutan-2-yl)carbamate (2.56 g, 10.6 mmol) in $Et_2O$ (20 mL) so that the internal temperature did not exceed 5° C. The reaction mixture was stirred for 30 min at 0° C. and quenched by the dropwise addition of EtOAc (20.0 mL) followed by 5% aq. potassium bisulfate (20 mL), maintaining the internal temperature<5° C. The reaction mixture was then washed with 1 M aq. HCl (2×40 mL), saturated aq. $NaHCO_3$ (2×40 mL), and brine (40 mL). The organic layer was dried over $MgSO_4$, filtered, and concentrated in vacuo to afford tert-butyl (S)-(4,4,4-trifluoro-1-oxobutan-2-yl)carbamate.

Step 3. In a vial was placed methyl (triphenylphosphoranylidene)acetate (4.26 g, 12.7 mmol) and tert-butyl (S)-(4,4,4-trifluoro-1-oxobutan-2-yl)carbamate (2.56 g, 10.6 mmol) in $Et_2O$ (45 mL) The reaction mixture was stirred at room temperature for 15 hrs. The solid was removed by filtration and the solution was concentrated in vacuo. Purification via flash column chromatography (0-100% EtOAc/hexanes) afforded methyl (S,E)-4-((tert-butoxycarbonyl)amino)-6,6,6-trifluorohex-2-enoate.

Step 4. In a 200 mL round bottom flask was placed methyl (S,E)-4-((tert-butoxycarbonyl)amino)-6,6,6-trifluorohex-2-enoate (8.11 mg, 2.73 mmol) and 10% Pd on C (290 mg) in EtOH (25 mL). The reaction was placed under a hydrogen balloon and stirred for 6 hrs. The reaction was filtered over Celite© and rinsed with ethyl acetate (2×30 mL) and concentrated give methyl (R)-4-((tert butoxycarbonyl)amino)-6,6,6-trifluorohexanoate.

Step 5. In a vial was placed methyl (R)-4-((tert-butoxycarbonyl)amino)-6,6,6-trifluorohexanoate. (816 mg, 2.73 mmol) and sodium hydroxide (545 mg, 13.6 mmol) in 5:2 methanol/water (20 mL). The solution was stirred for 1 hr and then diluted with water (100 mL), and washed with DCM (2×50 mL). The aqueous solution was acidified to pH=4 with 1M HCl, and then extracted with DCM (3×50 mL). The combined DCM extracts were dried over $MgSO_4$, filtered, and concentrated to give (R)-4-((tert-butoxycarbonyl)amino)-6,6,6-trifluorohexanoic acid.

Step 6. In a vial were placed (R)-4-((tert-butoxycarbonyl)amino)-6,6,6-trifluorohexanoic acid (861 mg, 3.02 mmol), triethylamine (0.421 mL, 3.02 mmol), and THF (30.0 mL). The mixture was cooled to 0° C. and placed under nitrogen atmosphere. To this solution was added ethyl chloroformate (0.289 mL, 3.02 mmol) and stirred for 30 min at 0° C. The reaction was then filtered to remove the precipitated triethylamine hydrochloride. The filtrate containing the mixed anhydride was slowly added to a stirred suspension of sodium borohydride (343 mg, 9.05 mmol) in 20% aqueous THF (10.0 mL) maintained at 10° C. After mixture stirred for 30 minutes, it was acidified with 1N HCl to pH~4. The mixture was then extracted with EtOAc (×3), washed with 2M NaOH solution, washed with brine, dried ($MgSO_4$), and purified by flash chromatography (100% hexanes to 100% EtOAc) to give tert-butyl (R)-(1,1,1-trifluoro-6-hydroxyhexan-3-yl)carbamate. ES/MS m/z: 215.9 [M−tBu+1]

Step 7. In a vial were placed tert-butyl (R)-(1,1,1-trifluoro-6-hydroxyhexan-3-yl)carbamate (436 mg, 1.61 mmol), and triethylamine (0.448 mL, 3.21 mmol) in DCM (8.0 mL). The mixture was cooled to 0° C. and p-toluenesulfonyl chloride (337 mg, 1.77 mmol) and a few crystals of DMAP was added. The mixture was warmed to room temperature and stirred for 2 h and was then quenched with water and extracted with EtOAc (50 mL×3). The combined organic layers were washed with brine, dried ($MgSO_4$), and purified by flash chromatography (100% hexanes to 100% EtOAc) to give (R)-(1,1,1-trifluoro-6-(tosyloxy)hexan-3-yl)carbamic acid. ES/MS m/z: 370.1 [M+H]

Example 453: (R)-7-fluoro-2-(6,6,6-trifluoro-4-((6-oxo-5-(trifluoromethyl)-1,6-dihydropyridazin-4-yl)amino)hexyl)-6-(5-(trifluoromethyl)pyrimidin-2-yl)isoquinolin-1(2H)-one Example 453

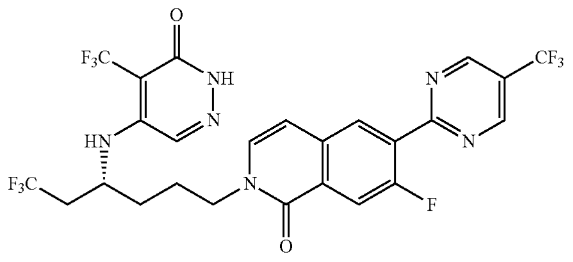

The title compound was synthesized as described in Example 17, with the following changes:

Step 1. 6-Bromo-7-fluoro-2H-isoquinolin-1-one was used instead of 6-Bromo-8-fluoro-1,2-dihydroisoquinolin-1-one and (R)-4-((tert-butoxycarbonyl)amino)-6,6,6-trifluorohexyl 4-methylbenzenesulfonate instead of [(4S)-4-(tert-butoxycarbonylamino)pentyl]4-methylbenzenesulfonate Step 3. 2-iodo-5-(trifluoromethyl)pyrimidine was used instead of 2-bromo-5-(difluoromethoxy)pyridine and 20 mol % of cataCXium Pd G4 and 2 M aqueous sodium carbonate (1.9 equiv.) were added following the completion of the borylation step. $^1$H NMR (400 MHz, DMSO-d6) δ 12.51 (s, 1H), 9.48 (d, J=1.0 Hz, 2H), 8.44 (d, J=7.1 Hz, 1H), 8.03 (s, 1H), 7.52 (d, J=7.4 Hz, 1H), 6.86 (d, J=7.4 Hz, 1H), 6.62-6.52 (m, 1H), 4.42-4.31 (m, 1H), 4.07-3.89 (m, 1H), 2.90-2.67 (m, 1H), 2.68-2.46 (m, 1H), 1.85-1.46 (m, 3H). ES/MS m/z: 625.3 [M+H].

Example 454: Synthesis of 7-fluoro-2-(((1R,3S)-3-((6-oxo-5-(trifluoromethyl)-1,6-dihydropyridazin-4-yl)oxy)cyclohexyl)methyl)-6-(5-(trifluoromethyl)pyrimidin-2-yl)isoquinolin-1(2H)-one

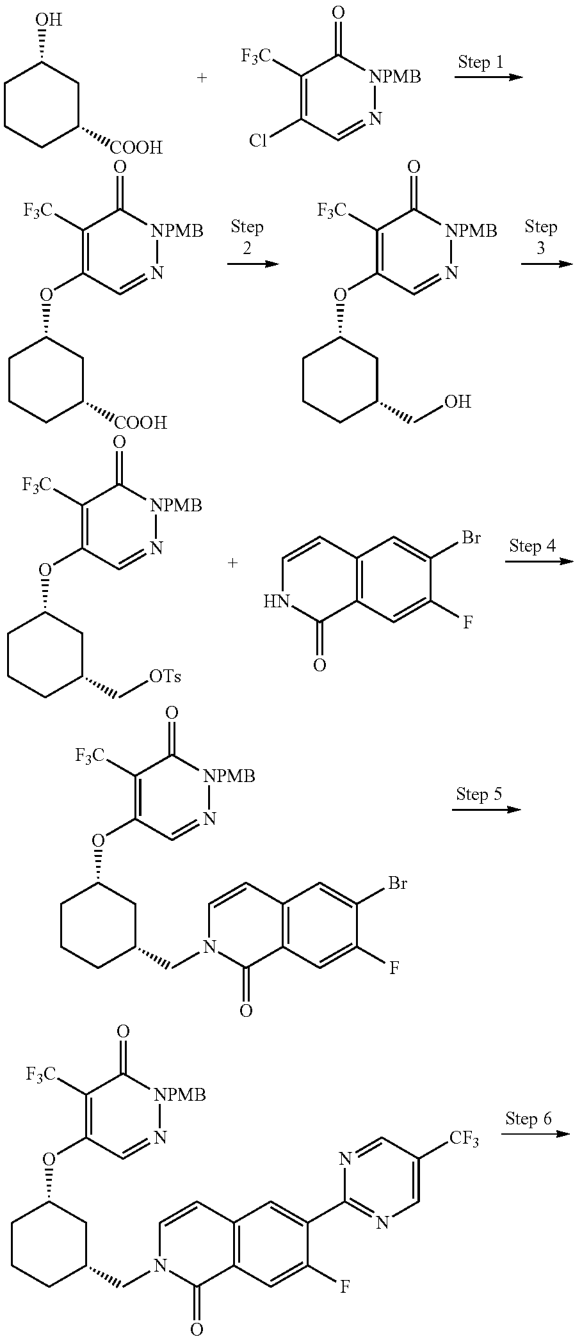

-continued

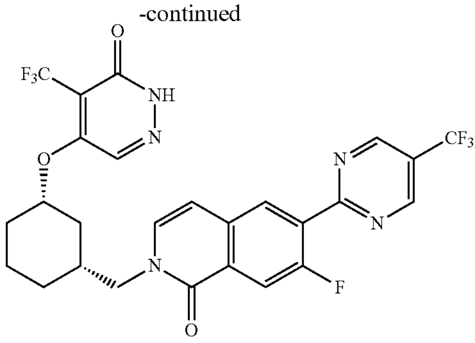

Example 454

Step 1. In a vial MTBE (1.50 mL) and KOtBu (374 mg, 3.33 mmol) were added at room temperature. A solution of (1R,3S)-3-hydroxycyclohexanecarboxylic acid (200 mg, 1.39 mmol) in DMF (1.50 mL) was added dropwise and stirred for 30 minutes at which point 5-chloro-2-[(4-methoxyphenyl)methyl]-4-(trifluoromethyl)pyridazin-3-one (442 mg, 1.39 mmol) was added in a single portion and stirred for 16 hrs. Upon completion, the reaction is diluted with water (50 mL), and acidified to pH~5 using 1M HCl. The mixture is extracted with EtOAc (3×50 mL), and the combined organic extracts are dried over $MgSO_4$, filtered, and concentrated by rotary evaporation. Purification by flash chromatography (0-100% EtOAc in Hexane) gave (1R,3S)-3-[1-[(4-methoxyphenyl)methyl]-6-oxo-5-(trifluoromethyl)pyridazin-4 yl]oxycyclohexanecarboxylic acid. ES/MS m/z: 427.1 [M+1]

Step 2. In a vial were placed (1R,3S)-3-[1-[(4-methoxyphenyl)methyl]-6-oxo-5-(trifluoromethyl)pyridazin-4 yl]oxycyclohexanecarboxylic acid (515 mg, 1.21 mmol), triethylamine (0.185 mL, 1.33 mmol), and THF (12.0 mL). The mixture was cooled to 0° C. and placed under nitrogen atmosphere. To this solution was added ethyl chloroformate (0.116 mL, 1.21 mmol) and stirred for 30 min at 0° C. The reaction was then filtered to remove the precipitated triethylamine hydrochloride. The filtrate containing the mixed anhydride was slowly added to a stirred suspension of sodium borohydride (137 mg, 3.62 mmol) in 20% aqueous THF (10.0 mL) maintained at 10° C. After mixture stirred for 30 minutes, it was acidified with 1N HCl to pH~4. The mixture was then extracted with EtOAc (×3), washed with brine, dried ($MgSO_4$), and purified by flash chromatography (100% hexanes to 100% EtOAc) to give 5-[(1S,3R)-3-(hydroxymethyl)cyclohexoxy]-2-[(4-methoxyphenyl)methyl]-4-(trifluoromethyl)pyridazin-3-one. ES/MS m/z: 413.1 [M+1]

Step 3. In a vial were placed tert-butyl 5-[(1S,3R)-3-(hydroxymethyl)cyclohexoxy]-2-[(4-methoxyphenyl)methyl]-4-(trifluoromethyl)pyridazin-3-one (260 mg, 0.63 mmol), and triethylamine (0.176 mL, 1.26 mmol) in DCM (5 mL). The mixture was cooled to 0° C. and p-toluenesulfonyl chloride (144 mg, 0.76 mmol) and a few crystals of DMAP was added. The mixture was warmed to room temperature and stirred for 2 h and was then quenched with water and extracted with EtOAc (50 mL×3). The combined organic layers were washed with brine, dried ($MgSO_4$), and purified by flash chromatography (100% hexanes to 100% EtOAc) to give [(1R,3S)-3-[1-[(4-methoxyphenyl)methyl]-6-oxo-5-(trifluoromethyl)pyridazin-4-yl]oxycyclohexyl] methyl 4-methylbenzenesulfonate. ES/MS m/z: 567.1 [M+H]

Step 4. In a vial were placed 6-bromo-7-fluoro-1,2-dihydroisoquinolin-1-one (133 mg, 0.55 mmol), [(1R,3S)-3-[1-[(4-methoxyphenyl)methyl]-6-oxo-5-(trifluoromethyl) pyridazin-4-yl]oxycyclohexyl]methyl 4-methylbenzenesulfonate (312 mg, 0.55 mmol), and cesium carbonate (358 mg, 1.01 mmol) in DMF (2 mL). After mixture was stirred at room temperature for 16 hr, it was quenched with water and extracted with EtOAc (×3). The combined organic layers were washed with water and brine, dried ($MgSO_4$), and purified by flash chromatography (100% hexanes to 100% EtOAc) to give 6-bromo-7-fluoro-2-[[(1R,3S)-3-[1-[(4-methoxyphenyl)methyl]-6-oxo-5-(trifluoromethyl)pyridazin-4-yl]oxycyclohexyl]methyl]isoquinolin-1-one. ES/MS m/z: 638.0 $[M+2+H]^+$.

Step 5. In a vial were placed 6-bromo-7-fluoro-2-[[(1R, 3S)-3-[1-[(4-methoxyphenyl)methyl]-6-oxo-5-(trifluoromethyl)pyridazin-4-yl]oxycyclohexyl]methyl]isoquinolin-1-one (100 mg, 0.157 mmol), 1,1'-Bis(diphenylphosphino) ferrocene-palladium(II)dichloride dichloromethane complex (25.7 mg, 0.031 mmol), potassium acetate (46.3 mg, 0.471 mmol), and bis(pinacolato)diboron (60 mg, 0.236 mmol) in dioxane (2 mL). The mixture was degassed for 15 minutes and heated to 80° C. and stirred for 2 hr, cooled to room temperature, and cataCXium Pd G4 (23.3 mg, 0.031 mmol) was added followed by the addition of 2 M aqueous sodium carbonate (0.24 mL, 0.471 mmol) and 2-iodo-5-(trifluoromethyl)pyrimidine (65 mg, 0.236 mmol). The reaction was then stirred for an additional hour at 80° C. Upon completion, the mixture was filtered through Celite© and concentrated under vacuum to afford the crude product that was purified by flash chromatography (0-100% EtOAc in Hexane) to give [2-[7-fluoro-2-[[(1R,3S)-3-[1-[(4-methoxyphenyl)methyl]-6-oxo-5-(trifluoromethyl)pyridazin-4-yl] oxycyclohexyl]methyl]-1-oxo-6-isoquinolyl]pyrimidin-5-yl]. ES/MS m/z: 704.3 [M+H]

Step 6. In a vial was added [2-[7-fluoro-2-[[(1R,3S)-3-[1-[(4-methoxyphenyl)methyl]-6-oxo-5-(trifluoromethyl) pyridazin-4-yl]oxycyclohexyl]methyl]-1-oxo-6-isoquinolyl]pyrimidin-5-yl](111 mg, 0.18 mmol), trifluoroacetic acid (6 mL), and trifluoromethanesulfonic acid (a few drops). Upon completion reaction is carefully poured into saturated $NaHCO_3$ solution (50 mL). The mixture is extracted with EtOAc (3×25 mL), and the combined organic extracts are dried over $MgSO_4$, filtered, and concentrated by rotary evaporation. The crude product was purified by reverse phase prep-HPLC (5-100% MeCN in water, 0.1% TFA) to afford 7-fluoro-2-(((1R,3S)-3-((6-oxo-5-(trifluoromethyl)-1,6-dihydropyridazin-4-yl)oxy)cyclohexyl) methyl)-6-(5-(trifluoromethyl)pyrimidin-2-yl)isoquinolin-1 (2H)-one. $^1$H NMR (400 MHz, DMSO-d6) δ 13.24 (s, 1H), 9.48 (s, 2H), 8.44 (d, J=7.1 Hz, 1H), 8.30 (s, 1H), 8.04 (d, J=11.4 Hz, 1H), 7.51 (d, J=7.4 Hz, 1H), 6.84 (d, J=7.4 Hz, 1H), 4.88-4.72 (m, 1H), 2.15-1.97 (m, 4H), 1.83-1.74 (m, 1H), 1.63-1.52 (m, 1H), 1.42-1.20 (m, 3H), 1.10-0.97 (m, 1H). ES/MS: m/z 584.1 $[M+H]^+$.

Example 455: 6-(4-amino-5-(trifluoromethyl)pyrimidin-2-yl)-7-fluoro-2-(((1R,3S)-3-((6-oxo-5-(trifluoromethyl)-1,6-dihydropyridazin-4-yl)oxy)cyclohexyl)methyl)isoquinolin-1(2H)-one Example 455

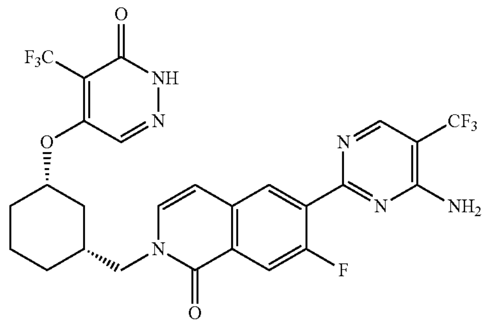

The title compound was synthesized as described in Example 454, with the following changes:

Step 5. 2-chloro-5-(trifluoromethyl)pyrimidin-4-amine was used instead of 2-iodo-5-(trifluoromethyl)pyrimidine. $^1$H NMR (400 MHz, DMSO-d6) δ 13.24 (s, 1H), 8.65 (s, 1H), 8.29 (s, 1H), 8.20 (d, J=7.0 Hz, 1H), 7.96 (d, J=11.1 Hz, 1H), 7.47 (d, J=7.4 Hz, 1H), 6.75 (d, J=7.4 Hz, 1H), 4.89-4.72 (m, 1H), 4.01-3.78 (m, 2H), 2.15-1.96 (m, 4H), 1.83-1.70 (m, 1H), 1.62-1.48 (m, 1H), 1.43-1.18 (m, 3H), 1.11-0.94 (m, 1H). ES/MS m/z: 599.1 [M+H].

Example 456: 6-(5-(difluoromethyl)pyrimidin-2-yl)-7-fluoro-2-(((1R,3S)-3-((6-oxo-5-(trifluoromethyl)-1,6-dihydropyridazin-4-yl)oxy)cyclohexyl)methyl) isoquinolin-1(2H)-one Example 456

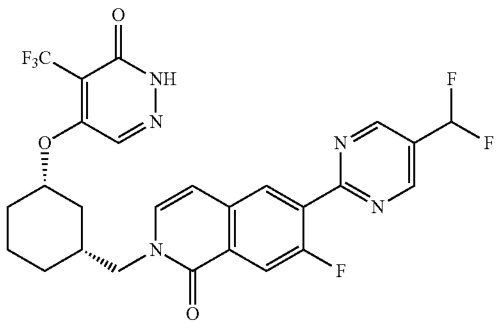

The title compound was synthesized as described in Example 454, with the following changes:

Step 5. 2-chloro-5-(difluoromethyl)pyrimidine was used instead of 2-iodo-5-(trifluoromethyl)pyrimidine. H NMR (400 MHz, DMSO-d6) δ 13.24 (s, 1H), 9.25 (d, J=1.6 Hz, 2H), 8.40 (d, J=7.2 Hz, 1H), 8.29 (s, 1H), 8.02 (d, J=11.3 Hz, 1H), 7.50 (d, J=7.4 Hz, 1H), 7.31 (t, J=54.8 Hz, 1H), 6.82 (d, J=7.4 Hz, 1H), 4.86-4.71 (m, 1H), 4.00-3.83 (m, 2H), 2.13-1.97 (m, 4H), 1.85-1.71 (m, 1H), 1.63-1.48 (m, 1H), 1.43-1.17 (m, 3H), 1.11-0.93 (m, 1H). ES/MS m/z: 566.1 [M+H].

Example 457: 7-(5-(difluoromethyl)pyrimidin-2-yl)-6-fluoro-3-(((1R,3S)-3-((6-oxo-5-(trifluoromethyl)-1,6-dihydropyridazin-4-yl)oxy)cyclohexyl)methyl)quinazolin-4(3H)-one Example 457

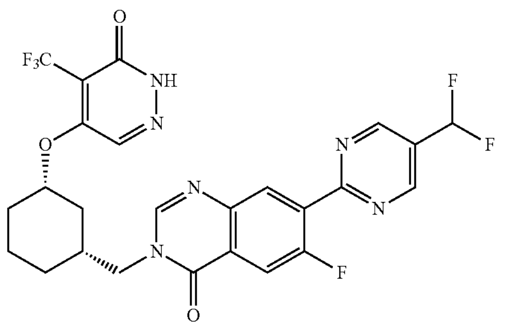

The title compound was synthesized as described in Example 454, with the following changes:

Step 4. 7-bromo-6-fluoroquinazolin-4(3H)-one was used instead of 6-Bromo-7-fluoro-2H-isoquinolin-1-one Step 5. 2-chloro-5-(difluoromethyl)pyrimidine was used instead of 2-iodo-5-(trifluoromethyl)pyrimidine. $^1$H NMR (400 MHz, DMSO-d6) δ 13.24 (s, 1H), 9.26 (d, J=1.6 Hz, 2H), 8.42 (s, 1H), 8.35-8.26 (m, 2H), 7.99 (d, J=10.5 Hz, 1H), 7.31 (t, J=54.8 Hz, 1H), 4.06-3.81 (m, 2H), 2.08-2.01 (m, 3H), 1.87-1.72 (m, 1H), 1.66-1.54 (m, 1H), 1.45-1.18 (m, 3H), 1.12-0.95 (m, 1H). ES/MS m/z: 567.1 [M+H].

Example 458: 7-(4-bromo-5-(trifluoromethyl)pyrimidin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one Example 458

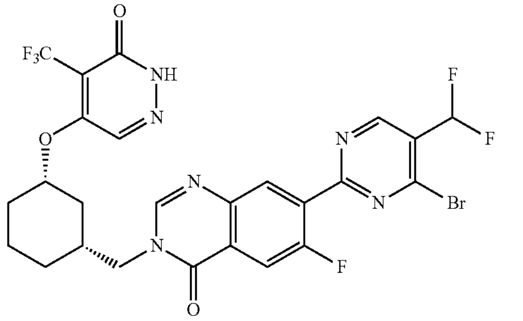

To a suspension of Example 242 (179 mg, 0.30 mmol) in MeCN (3.9 mL) was added $CuBr_2$ (80 mg, 0.36 mmol) and t-butyl nitrite (60 µL, 0.51 mmol). The reaction mixture was then heated to 60° C. for 1 hr, and diluted with EtOAc, washed with sat. aq. $Na_2SO_3$, then brine, dried with anhydrous magnesium sulfate, and concentrated. Purification via flash chromatography (elution with 0-100% v/v ethyl acetate in hexanes) afforded 7-(4-bromo-5-(trifluoromethyl)pyrimidin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one. 1H NMR (400 MHz, DMSO-d6) δ 12.42 (s, 1H), 9.36 (s, 1H), 8.44 (s, 1H), 8.36 (d, J=6.7 Hz, 1H), 8.01 (d, J=10.5 Hz, 1H), 7.92 (s, 1H), 6.37-6.26 (m, 1H), 3.91 (d, J=6.9 Hz, 2H), 3.79-3.63 (m, 1H), 2.07-1.94 (m, 1H), 1.90-1.78 (m, 2H), 1.73 (d, J=10.9 Hz, 1H), 1.61 (d, J=12.7 Hz, 1H), 1.46-1.19 (m, 3H), 1.03-0.87 (m, 1H). ES/MS m/z: 662.0 [M+H].

Example 459: 4-bromo-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one Example 459

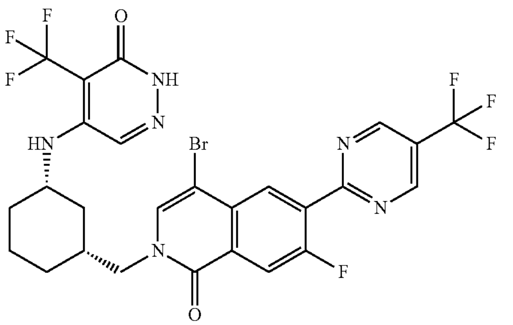

To a solution of Example 183 (60.0 mg, 0.103 mmol) in DMSO (3.0 mL) was added NBS (27.5 mg, 0.155 mmol). The reaction mixture was stirred at room temperature for 10 minutes and then purified by reverse phase prep-HPLC (5-100% MeCN in water, 0.1% TFA) to afford 4-bromo-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one. $^1$H NMR (400 MHz, DMSO-d6) δ 12.43 (s, 1H), 9.51 (s, 2H), 8.54 (d, J=6.8 Hz, 1H), 8.12 (d, J=11.1 Hz, 1H), 8.01 (s, 1H), 7.92 (s, 1H), 6.44-6.20 (m, 1H), 3.96-3.85 (m, 2H), 3.73 (d, J=9.8 Hz, 1H), 2.09-1.94 (m, 1H), 1.88-1.76 (m, 2H), 1.77-1.68 (m, 1H), 1.64-1.52 (m, 1H), 1.45-1.19 (m, 3H), 1.05-0.86 (m, 1H). ES/MS m/z: 661.0 [M+H].

Example 460: (R)-7-(6-amino-5-(trifluoromethyl)pyrazin-2-yl)-3-(4-cyclopropyl-4-((6-oxo-5-(trifluoromethyl)-1,6-dihydropyridazin-4-yl)amino)butyl)-6-fluoroquinazolin-4(3H)-one Example 460

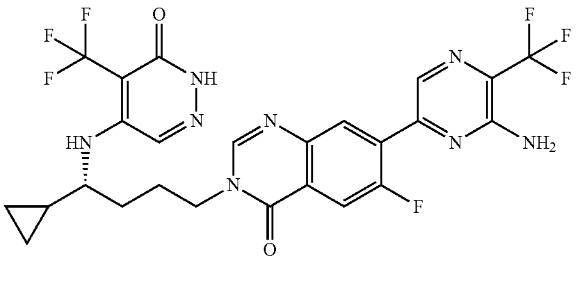

The title compound was synthesized as described in Example 144, with the following changes:

Step 1: 7-bromo-6-fluoroquinazolin-4(3H)-one was used instead of 6-Bromo-8-fluoro-1,2-dihydroisoquinolin-1-one.

Step 3: tert-butyl (tert-butoxycarbonyl)(6-chloro-3-(trifluoromethyl)pyrazin-2-yl)carbamate was used instead of 2-Chloro-5-(trifluoromethyl)pyrimidin-4-amine and 10 mol % of cataCXium Pd G4 and 2 M aqueous sodium carbonate (1.9 equiv.) were added following the completion of the borylation step. $^1$H NMR (400 MHz, DMSO-d6) δ 12.40 (s, 1H), 8.45 (s, 1H), 8.35 (d, J=2.5 Hz, 1H), 8.22 (d, J=6.7 Hz, 1H), 7.99 (d, J=10.7 Hz, 1H), 7.88 (s, 1H), 7.17 (s, 2H), 6.55-6.44 (m, 1H), 3.41-3.30 (m, 1H), 1.88-1.62 (m, 4H), 1.18-1.01 (m, 1H), 0.56-0.45 (m, 1H), 0.45-0.33 (m, 1H), 0.32-0.16 (m, 2H). One methylene peak is obstructed by the water signal. ES/MS m/z: 599.3 [M+H].

Example 461: (R)-7-(4-amino-5-chloropyrimidin-2-yl)-3-(4-cyclopropyl-4-((6-oxo-5-(trifluoromethyl)-1,6-dihydropyridazin-4-yl)amino)butyl)-6-fluoroquinazolin-4(3H)-one Example 461

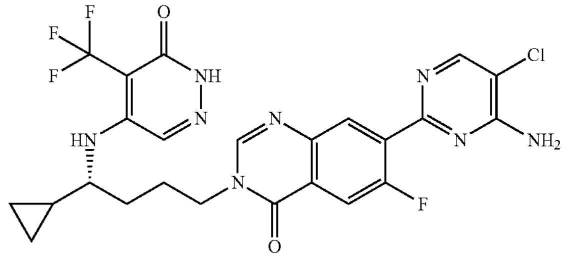

The title compound was synthesized as described in Example 144, with the following changes:

Step 1: 7-bromo-6-fluoroquinazolin-4(3H)-one was used instead of 6-Bromo-8-fluoro-1,2-dihydroisoquinolin-1-one.

Step 3: tert-butyl N-tert-butoxycarbonyl-N-(2,5-dichloropyrimidin-4-yl)carbamate was used instead of 2-Chloro-5-(trifluoromethyl)pyrimidin-4-amine and 10 mol % of cataCXium Pd G4 and 2 M aqueous sodium carbonate (1.9 equiv.) were added following the completion of the borylation step. 1H NMR (400 MHz, DMSO-d6) δ 12.40 (s, 1H), 8.43 (d, J=8.4 Hz, 2H), 8.14 (d, J=6.7 Hz, 1H), 7.90 (d, J=9.8 Hz, 4H), 6.58-6.42 (m, 1H), 4.00 (t, J=6.4 Hz, 2H), 3.35 (s, 1H), 1.87-1.62 (m, 4H), 1.16-1.02 (m, 1H), 0.55-0.45 (m, 1H), 0.45-0.33 (m, 1H), 0.33-0.15 (m, 2H). ES/MS m/z: 565.3 [M+H].

Example 462: (R)-7-(4-amino-5-(difluoromethyl)pyrimidin-2-yl)-3-(4-cyclopropyl-4-((6-oxo-5-(trifluoromethyl)-1,6-dihydropyridazin-4-yl)amino)butyl)-6-fluoroquinazolin-4(3H)-one Example 462

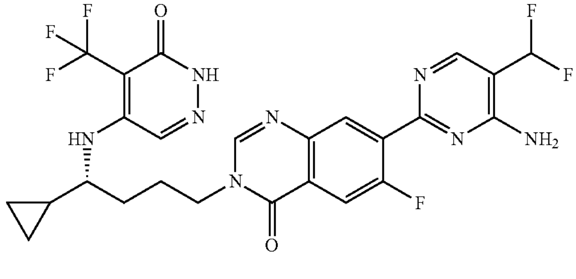

The title compound was synthesized as described in Example 144, with the following changes:

Step 1: 7-bromo-6-fluoroquinazolin-4(3H)-one was used instead of 6-Bromo-8-fluoro-1,2-dihydroisoquinolin-1-one.

Step 3: 2-chloro-5-(difluoromethyl)pyrimidin-4-amine was used instead of 2-Chloro-5-(trifluoromethyl)pyrimidin-4-amine and 10 mol % of cataCXium Pd G4 and 2 M aqueous sodium carbonate (1.9 equiv.) were added following the completion of the borylation step. 1H NMR (400 MHz, DMSO-d6) δ 12.41 (s, 1H), 8.52 (s, 1H), 8.44 (s, 1H), 8.16 (d, J=6.7 Hz, 1H), 7.93 (d, J=10.3 Hz, 1H), 7.89 (s, 1H), 7.66 (s, 2H), 7.10 (t, J=54.1 Hz, 1H), 6.56-6.42 (m, 1H), 4.05-3.95 (m, 2H), 3.40-3.26 (m, 1H), 1.88-1.57 (m, 4H), 1.17-1.00 (m, 1H), 0.57-0.44 (m, 1H), 0.44-0.33 (m, 1H), 0.33-0.15 (m, 2H). ES/MS m/z: 581.4 [M+H].

Example 463: 6-fluoro-3-(2-((1R,2S)-2-((6-oxo-5-(trifluoromethyl)-1,6-dihydropyridazin-4-yl)amino)cyclopentyl)ethyl)-7-(5-(trifluoromethyl)pyrimidin-2-yl)quinazolin-4(3H)-one Example 463

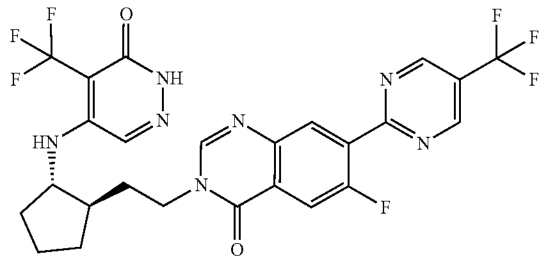

The title compound was synthesized as described in Example 17, with the following changes:

Step 1: 2-((1R,2S)-2-((tert-butoxycarbonyl)amino)cyclopentyl)ethyl 4-methylbenzenesulfonate (intermediate 28) was used instead of [(4S)-4-(tert-butoxycarbonylamino)pentyl]4-methylbenzenesulfonate and 7-bromo-6-fluoroquinazolin-4(3H)-one was used instead of 6-Bromo-8-fluoro-1,2-dihydroisoquinolin-1-one.

Step 3: 2-iodo-5-(trifluoromethyl)pyrimidine was used instead of 2-bromo-5-(difluoromethoxy)pyridine and 10 mol % of cataCXium Pd G4 and 2 M aqueous sodium carbonate (1.9 equiv.) were added following the completion of the borylation step. $^1$H NMR (400 MHz, DMSO-d6) δ 12.45 (s, 1H), 9.50 (s, 2H), 8.47 (s, 1H), 8.34 (d, J=6.7 Hz, 1H), 7.99 (d, J=10.5 Hz, 1H), 7.92 (s, 1H), 6.56-6.39 (m, 1H), 4.05-3.96 (m, 2H), 3.91-3.78 (m, 1H), 2.11-1.87 (m, 4H), 1.74-1.58 (m, 3H), 1.57-1.44 (m, 1H), 1.36-1.21 (m, 1H). ES/MS m/z: 584.1 [M+H].

Example 464: 7-(4-amino-5-(trifluoromethyl)pyrimidin-2-yl)-6-fluoro-3-(2-((1R,2S)-2-((6-oxo-5-(trifluoromethyl)-1,6-dihydropyridazin-4-yl)amino)cvclopentyl)ethyl)quinazolin-4(3H)-one Example 464

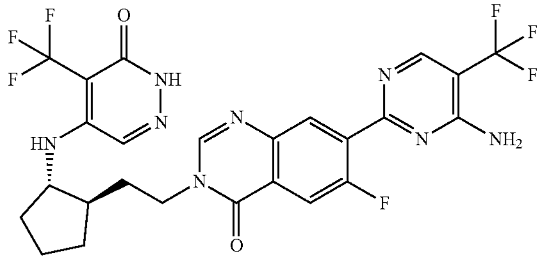

The title compound was synthesized as described in Example 17, with the following changes:

Step 1: 2-((1R,2S)-2-((tert-butoxycarbonyl)amino)cyclopentyl)ethyl 4-methylbenzenesulfonate (intermediate 28) was used instead of [(4S)-4-(tert-butoxycarbonylamino)pentyl]4-methylbenzenesulfonate and 7-bromo-6-fluoroquinazolin-4(3H)-one was used instead of 6-Bromo-8-fluoro-1,2-dihydroisoquinolin-1-one.

Step 3: 2-chloro-5-(trifluoromethyl)pyrimidin-4-amine was used instead of 2-bromo-5-(difluoromethoxy)pyridine and 10 mol % of cataCXium Pd G4 and 2 M aqueous sodium carbonate (1.9 equiv.) were added following the completion of the borylation step. 1H NMR (400 MHz, DMSO-d6) δ 12.45 (s, 1H), 8.66 (s, 1H), 8.44 (s, 1H), 8.17 (d, J=6.7 Hz, 1H), 7.94-7.87 (m, 2H), 6.52-6.41 (m, 1H), 4.02-3.98 (m, 2H), 3.89-3.81 (m, 1H), 2.10-1.84 (m, 4H), 1.74-1.57 (m, 3H), 1.56-1.44 (m, 1H), 1.29 (dq, J=12.2, 8.8, 8.3 Hz, 1H). ES/MS m/z: 599.1 [M+H].

Example 465: 7-(6-amino-5-(trifluoromethyl)pyrazin-2-yl)-6-fluoro-3-(2-((1R,2S)-2-((6-oxo-5-(trifluoromethyl)-1,6-dihydropyridazin-4-yl)amino)cyclopentyl)ethyl)quinazolin-4(3H)-one Example 465

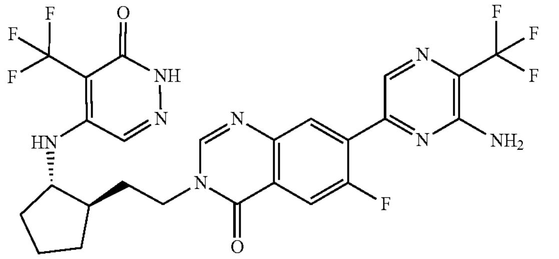

The title compound was synthesized as described in Example 17, with the following changes:

Step 1: 2-((1R,2S)-2-((tert-butoxycarbonyl)amino)cyclopentyl)ethyl 4-methylbenzenesulfonate (intermediate 28) was used instead of [(4S)-4-(tert-butoxycarbonylamino)pentyl]4-methylbenzenesulfonate and 7-bromo-6-fluoroquinazolin-4(3H)-one was used instead of 6-Bromo-8-fluoro-1,2-dihydroisoquinolin-1-one.

Step 3: tert-butyl (tert-butoxycarbonyl)(6-chloro-3-(trifluoromethyl)pyrazin-2-yl)carbamate was used instead of 2-bromo-5-(difluoromethoxy)pyridine and 10 mol % of cataCXium Pd G4 and 2 M aqueous sodium carbonate (1.9 equiv.) were added following the completion of the borylation step. 1H NMR (400 MHz, DMSO-d6) δ 12.44 (s, 1H), 8.46 (s, 1H), 8.35 (d, J=2.5 Hz, 1H), 8.21 (d, J=6.7 Hz, 1H), 7.97 (d, J=10.7 Hz, 1H), 7.91 (s, 1H), 7.16 (s, 2H), 6.52-6.40 (m, 1H), 2.11-1.86 (m, 4H), 1.74-1.57 (m, 3H), 1.57-1.42 (m, 1H), 1.39-1.20 (m, 1H). One methylene and one methine peak are obstructed by the water signal." ES/MS m/z: 599.1 [M+H].

Example 466: 2-[(4R)-6-(difluoromethoxy)-4-[[6-oxo-5-(trifluoromethyl)-1H-pyridazin-4-yl]amino]hexyl]-7-fluoro-6-[5-(trifluoromethyl)pyrimidin-2-yl]isoquinolin-1-one

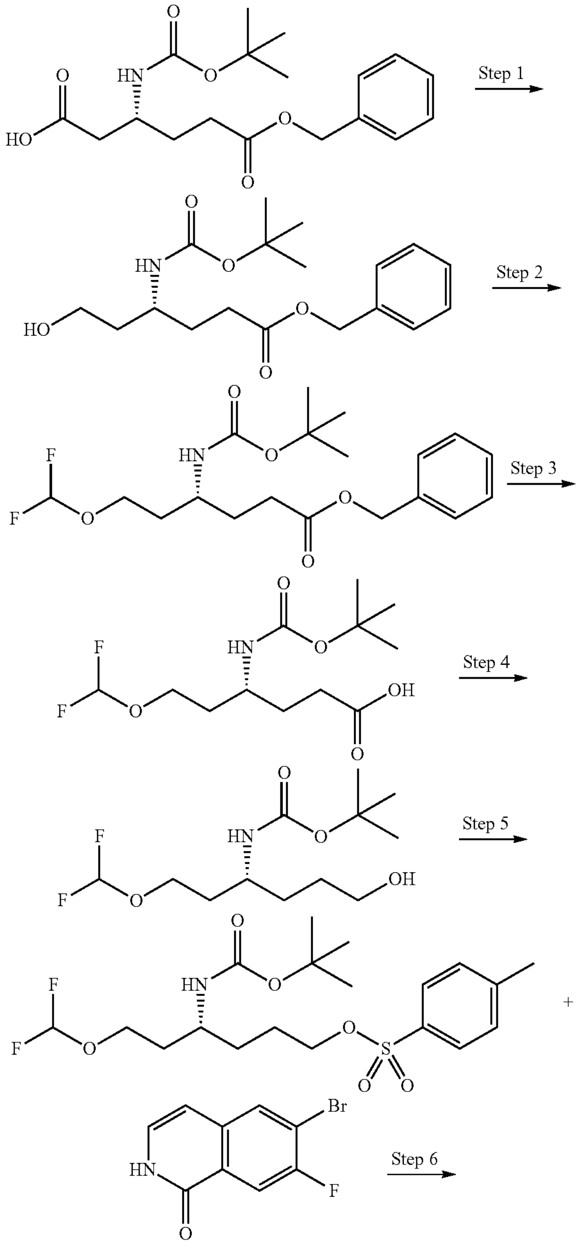

-continued

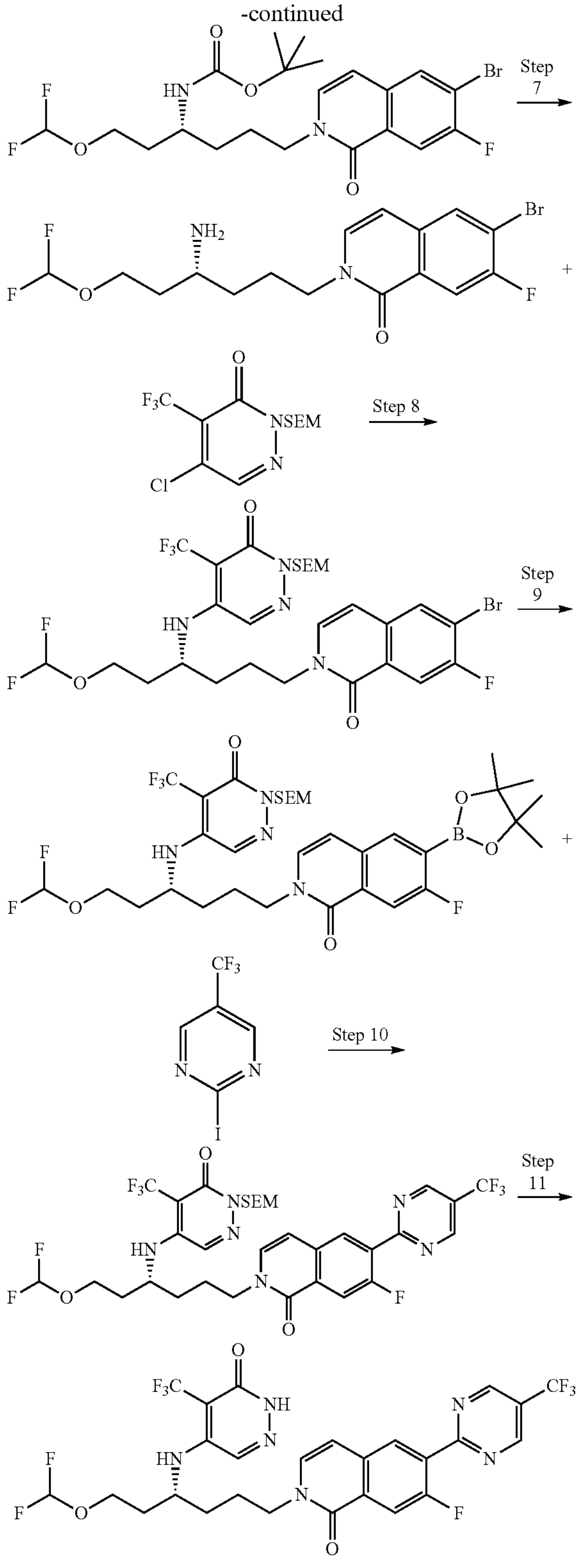

Example 466

Step 1. (3R)-6-benzyloxy-3-(tert-butoxycarbonylamino)-6-oxo-hexanoic acid (1500 mg, 4.27 mmol) and triethylamine (0.60 mL, 4.27 mmol) were taken up in THF (17.5 mL) and cooled to 0° C. under $N_2$ atmosphere. While stirring at 0° C., ethyl chloroformate (0.41 mL, 4.27 mmol) was added and solution allowed to stir for 30 minutes. Solution filtered to remove triethylamine hydrochloride. The filtrate containing the mixed anhydride was slowly added to a stirred suspension of $NaBH_4$ (484 mg, 12.8 mmol) in 20% aqueous THF (10 mL) maintained at 10° C. and allowed to stir for 30 minutes. Solution was then acidified with 1N HCl to pH 4. Mixture extracted 3× with EtOAc, washed with 2M NaOH solution, washed with brine, dried over $Na_2SO_4$ and concentrated. The crude residue was purified via column chromatography (100% hexanes→100% EtOAc) to afford benzyl (4R)-4-(tert-butoxycarbonylamino)-6-hydroxy-hexanoate. ES/MS: m/z 338.088 $[M+H]^+$.

Step 2. A plastic centrifuge tube was charged with benzyl (4R)-4-(tert-butoxycarbonylamino)-6-hydroxy-hexanoate (500 mg, 1.41 mmol), potassium acetate (1105 mg, 11.3 mmol), and stir bar. DCM (1.5 mL) and water (1.5 mL) added to centrifuge tube and allowed to stir rapidly to thoroughly mix. [bromo(difluoro)methyl]-trimethyl-silane (0.88 mL, 5.63 mmol) was added and solution was allowed to stir overnight. The Solution was then diluted with saturated aqueous sodium bicarbonate solution, extracted (3×) with DCM, dried over $Na_2SO_4$, filtered, concentrated, and purified via column chromatography to (100% hexanes→100% EtOAc) to afford benzyl (4R)-4-(tert-butoxycarbonylamino)-6-(difluoromethoxy)hexanoate. ES/MS: m/z 388.173 $[M+H]^+$.

Step 3. A vial was charged with benzyl (4R)-4-(tert-butoxycarbonylamino)-6-(difluoromethoxy)hexanoate (338 mg, 0.87 mmol), stir bar, and MeOH (11.2 mL). To this solution was added 10% palladium on carbon (92.8 mg, 0.087 mmol). Vial evacuated and fitted with a gas bag filled with $H_2$ and solution allowed to stir for 4 h. Upon complete conversion, reaction filtered through celite, and concentrated to afford (4R)-4-(tert-butoxycarbonylamino)-6-(difluoromethoxy)hexanoic acid. ES/MS: m/z 298.003 $[M+H]^+$.

Step 4. (4R)-4-(tert-butoxycarbonylamino)-6-(difluoromethoxy)hexanoic acid (326 mg, 1.1 mmol) and triethylamine (0.15 mL, 1.1 mmol) were taken up in THF (4.51 mL) and cooled to 0° C. under $N_2$ atmosphere. While stirring at 0° C., ethyl chloroformate (0.11 mL, 1.1 mmol) was added and solution allowed to stir for 30 min. Solution filtered to remove triethylamine hydrochloride. The filtrate containing the mixed anhydride was slowly added to a stirred suspension of $NaBH_4$ (124 mg, 3.29 mmol) in 20% aqueous THF (5 mL) maintained at 10° C. and allowed to stir for 30 min. Solution then acidified with 1N HCl to pH 4. Mixture extracted 3× with EtOAc, washed with 2M NaOH solution, washed with brine, dried over $Na_2SO_4$ and concentrated. The crude residue was purified via column chromatography (100% hexanes→100% EtOAc) to afford tert-butyl N-[(1R)-1-[2-(difluoromethoxy)ethyl]-4-hydroxy-butyl]carbamate. ES/MS: m/z 284.037 $[M+H]^+$.

Step 5. tert-butyl N-[(1R)-1-[2-(difluoromethoxy)ethyl]-4-hydroxy-butyl]carbamate (227 mg, 0.80 mmol), triethylamine (0.22 mL, 1.6 mmol), 4-(dimethylamino)pyridine (1 mg, 0.008 mmol) added to a vial with stir bar and dissolved in DCM. Solution was cooled to 0° C. and p-toluenesulfonyl chloride (183 mg, 0.96 mmol) added. Reaction was warmed to room temperature and allowed to stir for 2 hr. Reaction was diluted with water, extracted (3×) with EtOAc, washed with brine, dried over $Na_2SO_4$ and concentrated. The crude residue was purified via column chromatography (100% hexanes→100% EtOAc) to afford [(4R)-4-(tert-butoxycarbonylamino)-6-(difluoromethoxy)hexyl]4-methylbenzenesulfonate. ES/MS: m/z 438.167 $[M+H]^+$.

Step 6. A vial was charged with [(4R)-4-(tert-butoxycarbonylamino)-6-(difluoromethoxy)hexyl]4-methylbenzenesulfonate (243 mg, 0.56 mmol), 6-bromo-7-fluoro-2H-isoquinolin-1-one (148 mg, 0.61 mmol), cesium carbonate (362 mg, 1.11 mmol), and DMF (4.12 mL). Reaction allowed to stir overnight at room temperature. Reaction was diluted with water, extracted 3× with EtOAc, washed with brine, dried over $Na_2SO_4$ and concentrated. The crude residue was purified via column chromatography (100% hexanes→100% EtOAc) to afford tert-butyl N-[(1R)-4-(6-bromo-7-fluoro-1-oxo-2-isoquinolyl)-1-[2-(difluoromethoxy)ethyl]butyl]carbamate. ES/MS: m/z 509.006 $[M+H]^+$.

Step 7. A vial was charged with tert-butyl N-[(1R)-4-(6-bromo-7-fluoro-1-oxo-2-isoquinolyl)-1-[2-(difluoromethoxy)ethyl]butyl]carbamate (172 mg, 0.34 mmol) and DCM (5.35 mL). Trifluoroacetic acid (0.26 mL, 3.4 mmol) was then added and the reaction was allowed to stir at room temperature for 1 hr. Reaction was concentrated to afford 2-[(4R)-4-amino-6-(difluoromethoxy)hexyl]-6-bromo-7-fluoro-isoquinolin-1-one. ES/MS: m/z 409.652 $[M+H]^+$.

Step 8. A vial was charged with 5-chloro-4-(trifluoromethyl)-2-(2-trimethylsilylethoxymethyl)pyridazin-3-one (191 mg, 0.41 mmol), 2-[(4R)-4-amino-6-(difluoromethoxy)hexyl]-6-bromo-7-fluoro-isoquinolin-1-one (138 mg, 0.34 mmol), N,N-diisopropylethylamine (0.30 mL, 1.69 mmol), and DMF (1.32 mL). Reaction was heated to 60° C. and allowed to stir overnight. Reaction was diluted with water, extracted 3× with EtOAc, washed with brine, dried over $Na_2SO_4$ and concentrated. The crude residue was purified via column chromatography (100% hexanes→100% EtOAc) to afford 6-bromo-2-[(4R)-6-(difluoromethoxy)-4-[[6-oxo-5-(trifluoromethyl)-1-(2-trimethylsilylethoxymethyl)pyridazin-4-yl]amino]hexyl]-7-fluoro-isoquinolin-1-one. ES/MS: m/z 701.133 $[M+H]^+$.

Step 9. A vial was charged with 6-bromo-2-[(4R)-6-(difluoromethoxy)-4-[[6-oxo-5-(trifluoromethyl)-1-(2-trimethylsilylethoxymethyl)pyridazin-4-yl]amino]hexyl]-7-fluoro-isoquinolin-1-one (114 mg, 0.16 mmol), 1,1'-Bis(diphenylphosphino)ferrocene-palladium(II)dichloride dichloromethane complex (13.5 mg, 0.016 mmol), potassium acetate (48 mg, 0.49 mmol), bis(pinacolato)diboron (62.1 mg, 0.24 mmol), and dioxane (1.9 mL). The reaction was sparged with $N_2$, heated to 100° C., and allowed to stir for 1 hr to afford 2-[(4R)-6-(difluoromethoxy)-4-[[6-oxo-5-(trifluoromethyl)-1-(2-trimethylsilylethoxymethyl)pyridazin-4-yl]amino]hexyl]-7-fluoro-6-(4,4,5,5-tetramethyl-1,3,2-dioxaborolan-2-yl)isoquinolin-1-one in a dioxane solution to be used in the next step. ES/MS: m/z 747.334 $[M+H]^+$.

Step 10. To the reaction mixture from the previous step was added 2-iodo-5-(trifluoromethyl)pyrimidine (62.1 mg, 0.23 mmol), cataCXium Pd G4 (11.2 mg, 0.015 mmol), and 2M aqueous sodium carbonate solution (0.23 mL, 0.45 mmol). The reaction was sparged with $N_2$, heated to 80° C., and allowed to stir for 1 hr. Reaction filtered through Celite©, concentrated, and purified via column (100% hexanes→100% EtOAc) to afford 2-[(4R)-6-(difluoromethoxy)-4-[[6-oxo-5-(trifluoromethyl)-1-(2-trimethylsilylethoxymethyl)pyridazin-4-yl]amino]hexyl]-7-fluoro-6-[5-(trifluoromethyl)pyrimidin-2-yl]isoquinolin-1-one. ES/MS: m/z 767.349 $[M+H]^+$.

Step 11. A vial was charged with 2-[(4R)-6-(difluoromethoxy)-4-[[6-oxo-5-(trifluoromethyl)-1-(2-trimethylsilylethoxymethyl)pyridazin-4-yl]amino]hexyl]-7-fluoro-6-[5-(trifluoromethyl)pyrimidin-2-yl]isoquinolin-1-one (68 mg, 0.089 mmol) and DCM (3.89 mL). Trifluoroacetic acid (0.068 mL, 0.89 mmol) and reaction allowed to stir at room temperature for 1 hr. Upon complete conversion, the reaction was concentrated and taken up in MeOH (3.89 mL), and ethylenediamine (0.059 mL, 0.89 mmol) was added. Reaction was allowed to stir for 10 minutes, concentrated, and purified by reverse phase prep-HPLC (5-100% MeCN in water, 0.1% TFA) to afford 2-[(4R)-6-(difluoromethoxy)-4-[[6-oxo-5-(trifluoromethyl)-1H-pyridazin-4-yl]amino]hexyl]-7-fluoro-6-[5-(trifluoromethyl)pyrimidin-2-yl]isoquinolin-1-one. $^1H$ NMR (400 MHz, DMSO-d6) δ 12.45 (s, 1H), 9.48 (s, 2H), 8.44 (d, J=7.1 Hz, 1H), 8.03 (d, J=11.4 Hz, 1H), 7.92 (s, 1H), 7.52 (d, J=7.4 Hz, 1H), 6.85 (d, J=7.3 Hz, 1H), 6.82-6.38 (m, 2H), 4.11-3.94 (m, 3H), 3.83 (dtt, J=15.4, 9.9, 5.6 Hz, 2H), 2.03-1.48 (m, 4H). ES/MS: m/z 637.33 $[M+H]^+$.

Example 467: 6-[4-amino-5-(trifluoromethyl)pyrimidin-2-yl]-2-[(4R)-6-(difluoromethoxy)-4-[[6-oxo-5-(trifluoromethyl)-1H-pyridazin-4-yl]amino]hexyl]-7-fluoro-isoquinolin-1-one Example 467

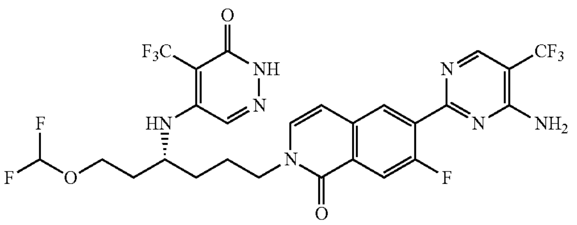

The title compound was synthesized as described in Example 466 with the following changes:

Step 10 2-chloro-5-(trifluoromethyl)pyrimidin-4-amine was used instead of 2-iodo-5-(trifluoromethyl)pyrimidine. $^1H$ NMR (400 MHz, DMSO-d6) δ 12.44 (s, 1H), 8.64 (s, 1H), 8.19 (d, J=7.1 Hz, 1H), 8.08-7.84 (m, 2H), 7.49 (d, J=7.4 Hz, 1H), 6.88-6.32 (m, 3H), 4.12-3.93 (m, 3H), 3.82 (dtd, J=18.6, 10.2, 5.5 Hz, 2H), 2.01-1.46 (m, 4H). ES/MS: m/z 652.3 $[M+H]^+$.

Example 468: 3-[(4R)-4-cyclopropyl-4-[[6-oxo-5-(trifluoromethyl)-1H-pyridazin-4-yl]amino]butyl]-7-[5-(difluoromethyl)pyrimidin-2-yl]-6-fluoro-quinazolin-4-one Example 468

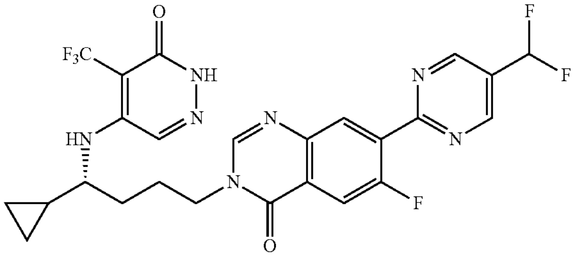

The title compound was synthesized as described in Example 144, with the following changes:

Step 1 7-bromo-6-fluoro-3H-quinazolin-4-one used instead of 6-bromo-7-fluoro-2H-isoquinolin-1-one and reaction heated to 80 C.

Step 3 2-chloro-5-(difluoromethyl)pyrimidine used instead of 2-Chloro-5-(trifluoromethyl)pyrimidin-4-amine. $^1$H NMR (400 MHz, DMSO-d6) δ 12.40 (s, 1H), 9.26 (d, J=1.2 Hz, 2H), 8.46 (s, 1H), 8.32 (d, J=6.8 Hz, 1H), 7.99 (d, J=10.5 Hz, 1H), 7.89 (s, 1H), 7.31 (t, J=54.8 Hz, 1H), 6.50 (dd, J=9.0, 4.1 Hz, 1H), 4.02 (t, J=6.3 Hz, 2H), 3.35 (s, 1H), 1.73 (d, J=39.3 Hz, 4H), 1.09 (dt, J=8.0, 4.9 Hz, 1H), 0.57-0.19 (m, 4H). ES/MS: m/z 566.3 [M+H]$^+$.

Example 469: 7-[4-amino-5-(trifluoromethyl)pyrimidin-2-yl]-3-[(4R)-4-cyclopropyl-4-[[6-oxo-5-(trifluoromethyl)-1H-pyridazin-4-yl]amino]butyl]-6-fluoro-quinazolin-4-one Example 469

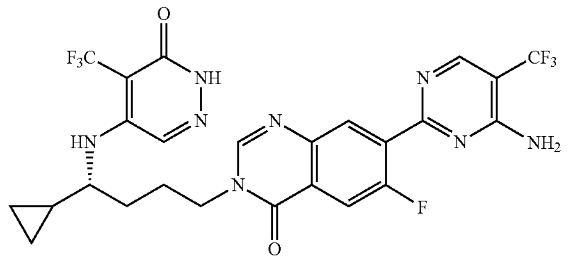

The title compound was synthesized as described in example 144, with the following changes:

Step 3 2-chloro-5-(trifluoromethyl)pyrimidin-4-amine was used instead of 2-chloro-5-(difluoromethyl)pyrimidine. $^1$H NMR (400 MHz, DMSO-d6) δ 12.40 (s, 1H), 8.66 (s, 1H), 8.43 (s, 1H), 8.18 (d, J=6.7 Hz, 1H), 7.96-7.86 (m, 2H), 6.50 (d, J=8.4 Hz, 1H), 4.01 (s, 2H), 3.40 (s, 1H), 1.73 (d, J=35.8 Hz, 4H), 1.20-0.98 (m, 1H), 0.59-0.17 (m, 4H). ES/MS: m/z 599.3 [M+H]$^+$.

Example 470: 7-(5-chloropyrimidin-2-yl)-3-[(4R)-4-cyclopropyl-4-[[6-oxo-5-(trifluoromethyl)-1H-pyridazin-4-yl]amino]butyl]-6-fluoro-quinazolin-4-one Example 470

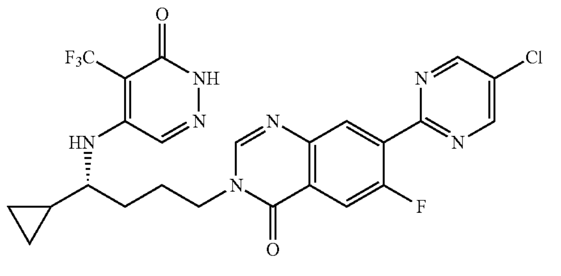

The title compound was synthesized as described in example 144, with the following changes:

Step 3 2,5-dichloropyrimidine was used instead of 2-chloro-5-(difluoromethyl)pyrimidine. $^1$H NMR (400 MHz, DMSO-d6) δ 12.40 (s, 1H), 9.16 (s, 2H), 8.45 (s, 1H), 8.28 (d, J=6.8 Hz, 1H), 7.97 (d, J=10.5 Hz, 1H), 7.89 (s, 1H), 6.50 (s, 1H), 4.01 (d, J=6.7 Hz, 1H), 3.35 (s, 1H), 1.73 (d, J=35.2 Hz, 4H), 1.17-1.02 (m, 1H), 0.65-0.15 (m, 4H). ES/MS: m/z 550.24 [M+H]$^+$.

Example 471: 3-[(4R)-4-cyclopropyl-4-[[6-oxo-5-(trifluoromethyl)-1H-pyridazin-4-yl]amino]butyl]-6-fluoro-7-[5-(trifluoromethyl)pyrimidin-2-yl]quinazolin-4-one Example 471

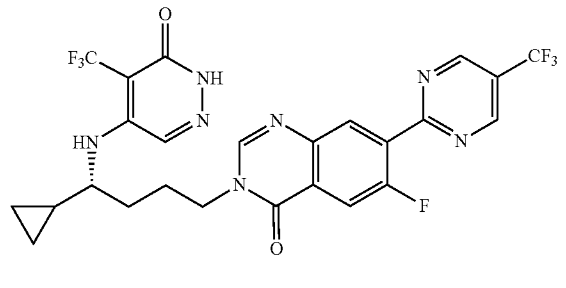

The title compound was synthesized as described in Example 144, with the following changes:

Step 3 2-iodo-5-(trifluoromethyl)pyrimidine used instead of 2-chloro-5-(difluoromethyl)pyrimidine. $^1$H NMR (400 MHz, DMSO-d6) δ 12.40 (s, 1H), 9.50 (s, 2H), 8.47 (s, 1H), 8.35 (d, J=6.7 Hz, 1H), 8.01 (d, J=10.5 Hz, 1H), 7.89 (s, 1H), 6.50 (dd, J=9.1, 3.9 Hz, 1H), 4.02 (t, J=6.3 Hz, 2H), 3.35 (s, 1H), 1.73 (d, J=39.5 Hz, 4H), 1.10 (ddd, J=13.5, 8.8, 5.1 Hz, 1H), 0.59-0.19 (m, 4H). ES/MS: m/z 584.3 [M+H]$^+$.

Example 472: 7-[4-amino-5-(difluoromethoxy)pyrimidin-2-yl]-3-[(4R)-4-cyclopropyl-4-[[6-oxo-5-(trifluoromethyl)-1H-pyridazin-4-yl]amino]butyl]-6-fluoro-quinazolin-4-one Example 472

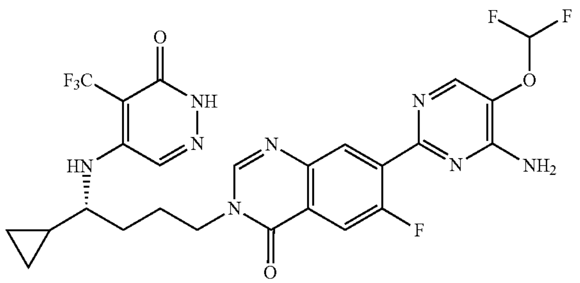

The title compound was synthesized as described in example 144, with the following changes:

Step 3 tert-butyl N-tert-butoxycarbonyl-N-[2-chloro-5-(difluoromethoxy)pyrimidin-4-yl]carbamate was used instead of 2-chloro-5-(difluoromethyl)pyrimidine. $^1$H NMR (400 MHz, DMSO-d6) δ 12.40 (s, 1H), 8.42 (s, 1H), 8.24 (s, 1H), 8.11 (d, J=6.7 Hz, 1H), 7.94-7.85 (m, 2H), 7.48 (s, 2H), 7.21 (t, J=73.1 Hz, 1H), 6.50 (dd, J=9.1, 3.7 Hz, 1H), 4.10-3.89 (m, 2H), 3.35 (s, 1H), 1.72 (d, J=38.8 Hz, 5H), 1.08 (dq, J=13.3, 8.3, 6.7 Hz, 1H), 0.50 (tt, J=8.5, 4.2 Hz, 1H), 0.38 (tt, J=8.9, 4.1 Hz, 1H), 0.25 (ddq, J=19.0, 9.4, 4.7 Hz, 2H). ES/MS: m/z 597.099 [M+H]$^+$.

Example 473: 2-[(4R)-5-(dimethylamino)-4-[[6-oxo-5-(trifluoromethyl)-1H-pyridazin-4-yl]amino] pentyl]-7-fluoro-6-[5-(trifluoromethyl)pyrimidin-2-yl]isoquinolin-1-one

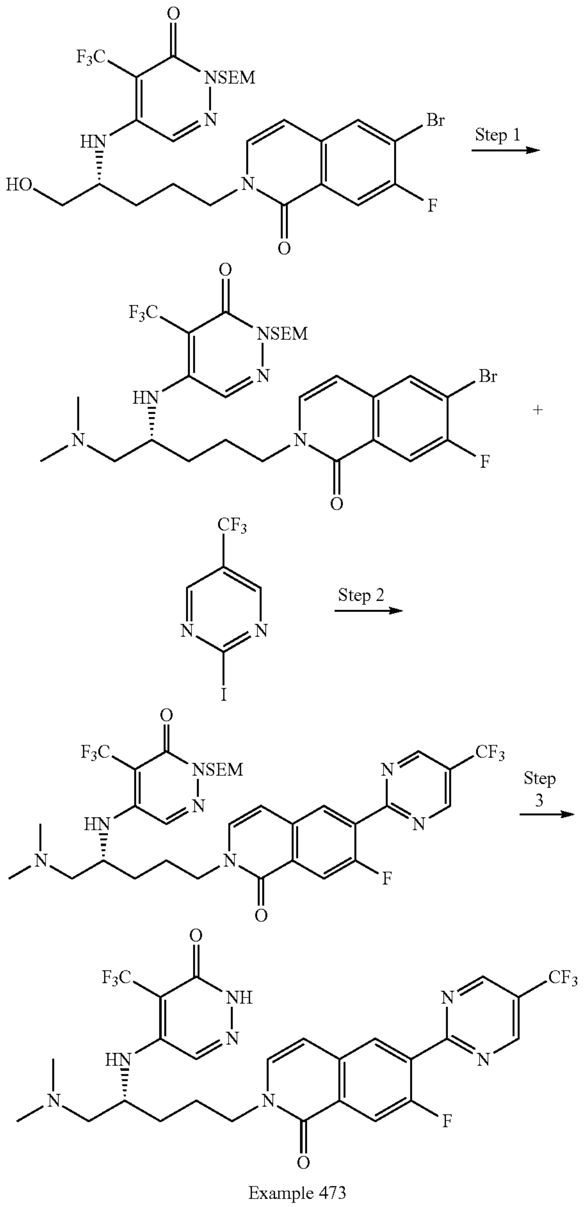

Example 473

Step 1. 6-bromo-7-fluoro-2-[(4R)-5-hydroxy-4-[[6-oxo-5-(trifluoromethyl)-1-(2-trimethylsilylethoxymethyl) pyridazin-4-yl]amino]pentyl]isoquinolin-1-one (100 mg, 0.15 mmol) and iodobenzene diacetate (48 mg, 0.15 mmol) were dissolved in DCM (1.5 mL) and stirred at ambient temperature. TEMPO (4.7 mg, 0.03 mmol) was then added. After stirring for 20 hours, 2.0 M dimethylamine solution (0.75 ml, 1.5 mmol) and sodium triacetoxyborohydride (63 mg, 0.3 mmol) were added. The reaction was stirred a further 4 hours and quenched with saturated bicarb. Extracted (3×) with DCM and the organics were dried over $Na_2SO_4$, filtered, evaporated and the crude residue was purified via column chromatography (100% heptanes→100% 3:1 EtOAc:EtOH) to afford 6-bromo-2-[(4R)-5-(dimethylamino)-4-[[6-oxo-5-(trifluoromethyl)-1-(2-trimethylsilylethoxymethyl)pyridazin-4-yl]amino]pentyl]-7-fluoro-isoquinolin-1-one. ES/MS: m/z 662.3/664.2 $[M+H]^+$.

Step 2. A vial was charged with 6-bromo-2-[(4R)-5-(dimethylamino)-4-[[6-oxo-5-(trifluoromethyl)-1-(2-trimethylsilylethoxymethyl)pyridazin-4-yl]amino]pentyl]-7-fluoro-isoquinolin-1-one (33 mg, 0.05 mmol), 1,1'-Bis (diphenylphosphino)ferrocene-palladium(II)dichloride (1.7 mg, 2 μmol), potassium acetate (14 mg, 0.14 mmol), and bis(pinacolato)diboron (30 mg, 0.12 mmol) and flushed with dry nitrogen. Dioxane (0.75 mL) was added and the reaction heated to 100° C. for 8 hours. After cooling, 2-iodo-5-(trifluoromethyl)pyrimidine (15 mg, 0.06 mmol), CataCXium Pd G4 (1.7 mg, 2 μmol), and aqueous sodium carbonate (2.0 M, 0.07 mL) were added and the mixture bubbled with dry nitrogen briefly. The reaction was then stirred at 80° C. for 1 hour before being diluted with EtOAc and filtered through a plug of Celite©. The filtrate was evaporated and the crude purified via flash chromatography (100% hexanes→100% EtOAc→35% MeOH/EtOAc) to afford 2-[(4R)-5-(dimethylamino)-4-[[6-oxo-5-(trifluoromethyl)-1-(2-trimethylsilylethoxymethyl)pyridazin-4-yl] amino]pentyl]-7-fluoro-6-[5-(trifluoromethyl)pyrimidin-2-yl]isoquinolin-1-one ES/MS: m/z 730.0 $[M+H]^+$.

Step 3. 2-[(4R)-5-(dimethylamino)-4-[[6-oxo-5-(trifluoromethyl)-1-(2-trimethylsilylethoxymethyl)pyridazin-4-yl] amino]pentyl]-7-fluoro-6-[5-(trifluoromethyl)pyrimidin-2-yl]isoquinolin-1-one (32 mg, 0.04 mmol) was dissolved in DCM (2.0 mL) and stirred at ambient temperature. TFA (0.03 mL, 0.42 mmol) was added and the reaction maintained for 1.5 hours at which point it was evaporated to dryness. The residue was dissolved in MeOH (1.0 mL) and treated with ethylenediamine (0.03 mL, 0.42 mmol). After 10 minutes, the reaction was evaporated and the residue purified by reverse phase prep-HPLC (5-100% MeCN in water, 0.1% TFA) to afford 2-[(4R)-5-(dimethylamino)-4-[[6-oxo-5-(trifluoromethyl)-1H-pyridazin-4-yl]amino]pentyl]-7-fluoro-6-[5-(trifluoromethyl)pyrimidin-2-yl]isoquinolin-1-one. $^1H$ NMR (400 MHz, DMSO-d6) δ 12.64 (s, 1H), 9.49 (s, 2H), 9.12 (br s, 1H), 8.45 (d, J=7.1 Hz, 1H), 8.10 (s, 1H), 8.03 (d, J=11.4 Hz, 1H), 7.52 (d, J=7.4 Hz, 1H), 6.86 (d, J=7.4 Hz, 1H), 6.57-6.46 (m, 1H), 4.53-4.40 (m, 1H), 4.07-3.95 (m, 2H), 3.57-3.48 (m, 1H), 3.28-3.18 (m, 1H), 2.79 (s, 3H), 2.78 (s, 3H), 1.80-1.67 (m, 2H), 1.61-1.51 (m, 2H). ES/MS: m/z 600.3 $[M+H]^+$.

Example 474: 7,8-difluoro-2-[(4R)-4-(5-methyl-1,3,4-oxadiazol-2-yl)-4-[[6-oxo-5-(trifluoromethyl)-1H-pyridazin-4-yl]amino]butyl]-6-[5-(trifluoromethyl) pyrimidin-2-yl]isoquinolin-1-one Example 474

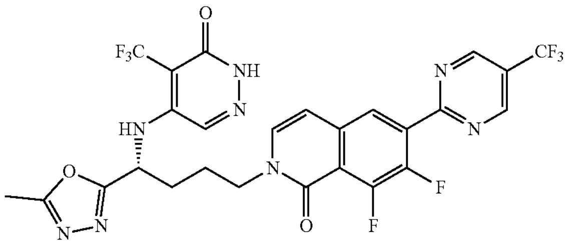

The title compound was synthesized as described in example 169, using 7,8-difluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one was utilized as starting material instead of 7-fluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one. $^{1}$H NMR (400 MHz, DMSO-d6) δ 12.67 (s, 1H), 9.50 (d, J=1.0 Hz, 2H), 8.25 (dd, J=6.7, 1.7 Hz, 1H), 7.99 (s, 1H), 7.57 (d, J=7.4 Hz, 1H), 7.11-7.03 (m, 1H), 6.83 (dd, J=7.5, 1.8 Hz, 1H), 5.43 (q, J=7.5 Hz, 1H), 4.02 (t, J=6.8 Hz, 2H), 2.48 (s, 3H), 2.19-2.05 (m, 2H), 1.92-1.76 (m, 2H). ES/MS: m/z 643.3 [M+H]$^{+}$.

Example 475: 2-[(4R)-4-(5-cyclopropyl-1,3,4-oxadiazol-2-yl)-4-[[6-oxo-5-(trifluoromethyl)-1H-pyridazin-4-yl]amino]butyl]-7,8-difluoro-6-[5-(trifluoromethyl)pyrimidin-2-yl]isoquinolin-1-one Example 475

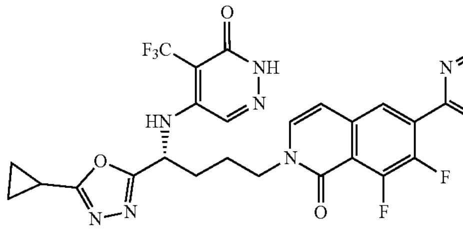

The title compound was synthesized as described in example 169 with the following modifications:

Step 1: 7,8-difluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one was utilized instead of 7-fluoro-2-[(4R)-5-hydroxy-4-[[6-oxo-5-(trifluoromethyl)-1-(2-trimethylsilylethoxymethyl)pyridazin-4-yl]amino]pentyl]-6-[5-(trifluoromethyl)pyrimidin-2-yl]isoquinolin-1-one.

Step 2: Cyclopropanecarbohydrazide was utilized instead of acethydrazide.

$^{1}$H NMR (400 MHz, DMSO-d6) δ 12.66 (s, 1H), 9.50 (d, J=1.0 Hz, 2H), 8.24 (dd, J=6.6, 1.7 Hz, 1H), 8.00 (s, 1H), 7.57 (d, J=7.4 Hz, 1H), 7.08-7.00 (m, 1H), 6.83 (dd, J=7.5, 1.8 Hz, 1H), 5.39 (q, J=7.5 Hz, 1H), 4.02 (t, J=6.8 Hz, 2H), 2.21 (tt, J=8.4, 4.9 Hz, 1H), 2.16-2.04 (m, 2H), 1.93-1.74 (m, 2H), 1.15-1.08 (m, 2H), 0.96-0.90 (m, 2H). ES/MS: m/z 669.3 [M+H]$^{+}$.

Example 476: 2-[(4R)-4-(5-cyclopropyl-1,3,4-oxadiazol-2-yl)-4-[[6-oxo-5-(trifluoromethyl)-1H-pyridazin-4-yl]amino]butyl]-7-fluoro-6-[5-(trifluoromethyl)pyrimidin-2-yl]isoquinolin-1-one Example 476

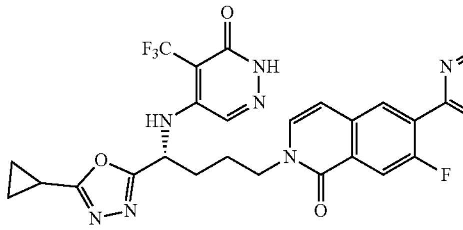

The title compound was synthesized as described in example 169, using cyclopropanecarbohydrazide instead of acethydrazide. $^{1}$H NMR (400 MHz, DMSO-d6) δ 12.66 (s, 1H), 9.48 (s, 2H), 8.44 (d, J=7.1 Hz, 1H), 8.07-7.97 (m, 2H), 7.54 (d, J=7.4 Hz, 1H), 7.09-7.00 (m, 1H), 6.86 (d, J=7.4 Hz, 1H), 5.39 (q, J=7.5 Hz, 1H), 4.06 (t, J=6.8 Hz, 2H), 2.20 (tt, J=8.4, 4.9 Hz, 1H), 2.16-2.03 (m, 2H), 1.94-1.76 (m, J=6.8 Hz, 2H), 1.15-1.07 (m, 2H), 0.96-0.88 (m, 2H). ES/MS: m/z 651.3 [M+H]$^{+}$.

Example 477: 2-[(4R)-4-[5-(difluoromethyl)-1,3,4-oxadiazol-2-yl]-4-[[6-oxo-5-(trifluoromethyl)-1H-pyridazin-4-yl]amino]butyl]-7-fluoro-6-[5-(trifluoromethyl)pyrimidin-2-yl]isoquinolin-1-one Example 477

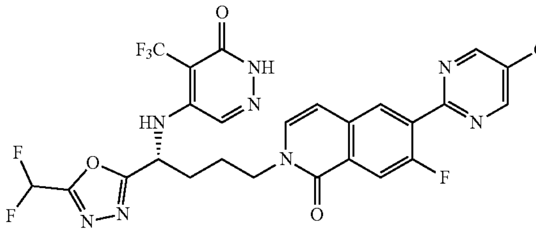

The title compound was synthesized as described in example 169, using 2,2-difluoroacetohydrazide instead of acethydrazide. $^{1}$H NMR (400 MHz, DMSO-d6) δ 12.71 (s, 1H), 9.48 (s, 2H), 8.44 (d, J=7.1 Hz, 1H), 8.08-7.99 (m, 2H), 7.55 (d, J=7.4 Hz, 1H), 7.49 (t, J=51.3 Hz, 1H), 7.20-7.13 (m, 1H), 6.86 (d, J=7.4 Hz, 1H), 5.63-5.52 (m, 1H), 4.08 (t, J=6.8 Hz, 2H), 2.23-2.13 (m, 2H), 1.96-1.84 (m, 2H). ES/MS: m/z 661.3 [M+H]$^{+}$.

Example 478: Preparation of 7-fluoro-2-[(4S)-2-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one

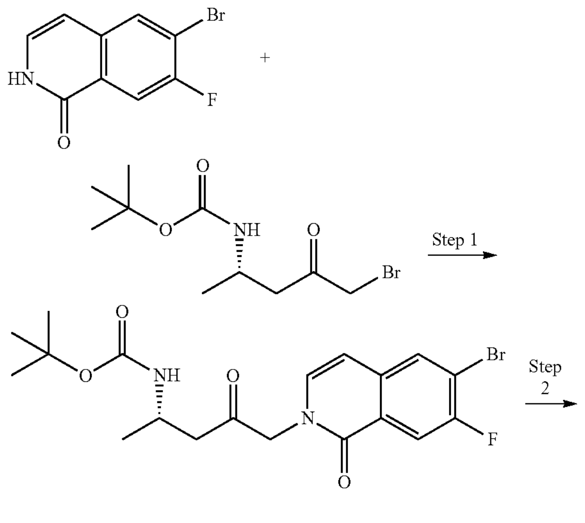

-continued

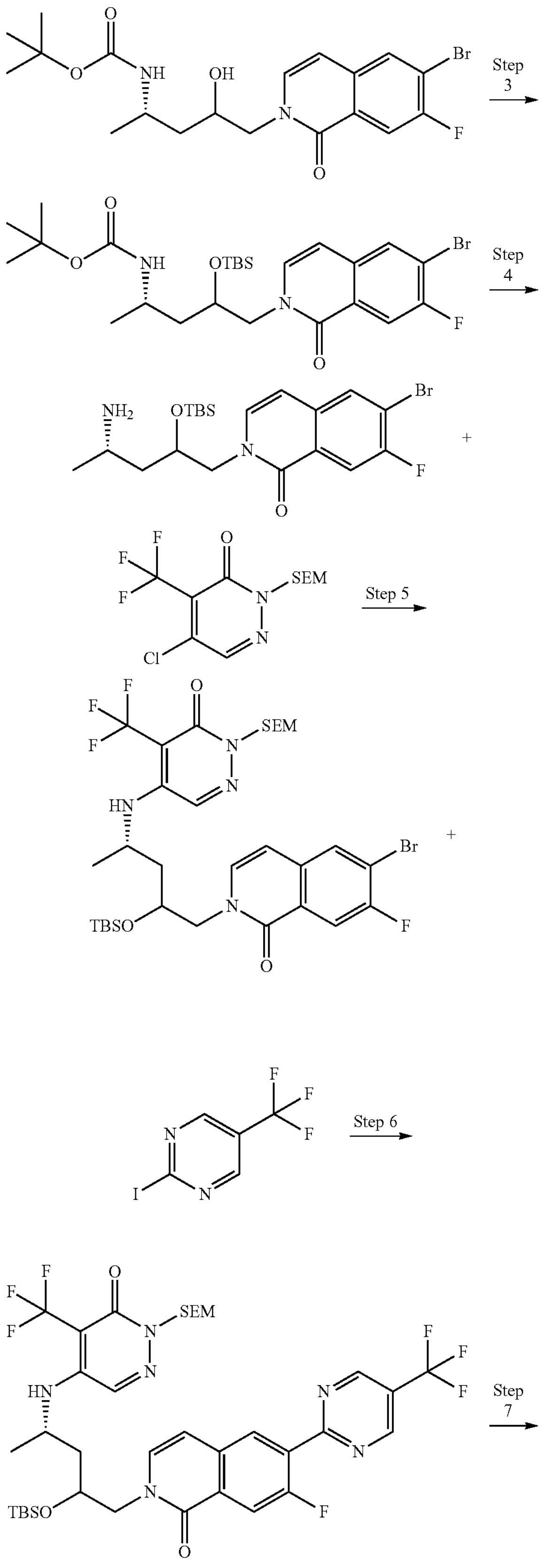

-continued

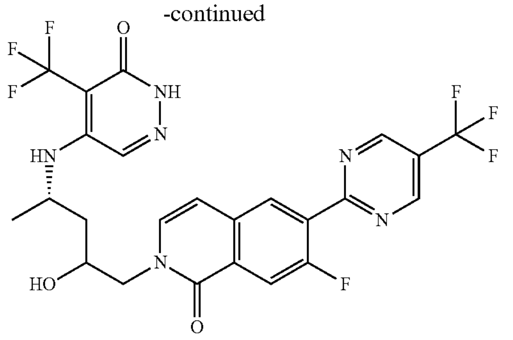

Example 478

Step 1. In a flask were placed 6-bromo-7-fluoro-2H-isoquinolin-1-one (2.10 g, 8.68 mmol), tert-butyl N-[(1S)-4-bromo-1-methyl-3-oxo-butyl]carbamate (2.55 g, 9.11 mmol), cesium carbonate (5.65 g, 17.4 mmol) in DMF (43.0 mL). The solution was stirred at room temperature overnight, filtered through a pad of Celite©, concentrated, and purified by flash chromatography (Hex/EtOAc) to give tert-butyl N-[(1S)-4-(6-bromo-7-fluoro-1-oxo-2-isoquinolyl)-1-methyl-3-oxo-butyl]carbamate. ES/MS m/z=442.9 [M+H].

Step 2. In a flask were placed tert-butyl N-[(1S)-4-(6-bromo-7-fluoro-1-oxo-2-isoquinolyl)-1-methyl-3-oxo-butyl]carbamate (1.04 g, 2.36 mmol) in THF (23.0 mL) and $NaBH_4$ (134 mg, 3.54 mmol) is added. After stirring for 90 minutes, the reaction is carefully quenched with water (5.0 mL) and the pH is adjusted to ~4 with 1N HCl. Diluted with water, extracted with EtOAc, and concentrated to give tert-butyl N-[(1S)-4-(6-bromo-7-fluoro-1-oxo-2-isoquinolyl)-3-hydroxy-1-methyl-butyl]carbamate. ES/MS m/z=444.9 [M+H].

Step 3. In a flask were placed tert-butyl N-[(1S)-4-(6-bromo-7-fluoro-1-oxo-2-isoquinolyl)-3-hydroxy-1-methyl-butyl]carbamate (1.0 g, 2.30 mmol), imidazole (798 mg, 12 mmol), DMAP (86 mg, 0.7 mmol), and TBSCl (1.06 g, 7.0 mmol) in DMF (12 mL). The mixture was stirred at room temperature overnight. Quenched with sat. NH4Cl and extracted with EtOAc. The organic layer is concentrated and purified by flash chromatography (Hex/EtOAc) to give tert-butyl N-[(1S)-4-(6-bromo-7-fluoro-1-oxo-2-isoquinolyl)-3-[tert-butyl(dimethyl)silyl]oxy-1-methyl-butyl]carbamate. ES/MS m/z=559.1 [M+H].

Step 4. In a flask were placed tert-butyl N-[(1S)-4-(6-bromo-7-fluoro-1-oxo-2-isoquinolyl)-3-[tert-butyl(dimethyl)silyl]oxy-1-methyl-butyl]carbamate (224 mg, 0.40 mmol) and TFA (4 mL) in DCM (4.0 mL). The mixture was stirred at room temperature for 15 minutes and concentrated to give 2-[(4S)-4-amino-2-[tert-butyl(dimethyl)silyl]oxy-pentyl]-6-bromo-7-fluoro-isoquinolin-1-one. ES/MS m/z=460.3 [M+2H].

Step 5. In a vial were placed 2-[(4S)-4-amino-2-[tert-butyl(dimethyl)silyl]oxy-pentyl]-6-bromo-7-fluoro-isoquinolin-1-one (184 mg, 0.40 mmol), 5-chloro-4-(trifluoromethyl)-2-(2-trimethylsilylethoxymethyl)pyridazin-3-one (198 mg, 0.60 mmol), triethylamine (0.28 mL, 2.01 mmol), and DMF (2 mL). The mixture was heated to 85° C. for 3 hours, concentrated, and purified by flash chromatography (Hex/EtOAc) to give 6-bromo-2-[(4S)-2-[tert-butyl(dimethyl)silyl]oxy-4-[[6-oxo-5-(trifluoromethyl)-1-(2-trimethylsilylethoxymethyl)pyridazin-4-yl]amino]pentyl]-7-fluoro-isoquinolin-1-one. ES/MS m/z=751.2 [M+H].

Step 6. A vial was charged with 2-[(4S)-2-[tert-butyl(dimethyl)silyl]oxy-4-[[6-oxo-5-(trifluoromethyl)-1-(2-trimethylsilylethoxymethyl)pyridazin-4-yl]amino]pentyl]-7-fluoro-6-(4,4,5,5-tetramethyl-1,3,2-dioxaborolan-2-yl)isoquinolin-1-one (166 mg, 0.22 mmol), 1,1'-Bis(diphenylphosphino)ferrocene-palladium(II)dichloride (36 mg, 0.04 mmol), potassium acetate (87 mg, 0.89 mmol), and bis(pinacolato)diboron (169 mg, 0.66 mmol) and flushed with dry nitrogen. Dioxane (2.2 mL) was added and the reaction heated to 100° C. for 4 hours. After cooling, 2-iodo-5-(trifluoromethyl)pyrimidine (91 mg, 0.33 mmol), CataCXium Pd G4 (8.2 mg, 0.011 mmol), cesium carbonate (216 mg, 0.66 mmol), and water (0.5 mL) were added. The reaction was then stirred at 80° C. for 2 hours before being purified by column chromatography (Hex/EtOAc) to give 2-[(4S)-2-[tert-butyl(dimethyl)silyl]oxy-4-[[6-oxo-5-(trifluoromethyl)-1-(2-trimethylsilylethoxymethyl)pyridazin-4-yl]amino]pentyl]-7-fluoro-6-[5-(trifluoromethyl)pyrimidin-2-yl]isoquinolin-1-one. ES/MS: m/z 817.3 $[M+H]^+$.

Step 7. A vial was charged with 2-[(4S)-2-[tert-butyl(dimethyl)silyl]oxy-4-[[6-oxo-5-(trifluoromethyl)-1-(2-trimethylsilylethoxymethyl)pyridazin-4-yl]amino]pentyl]-7-fluoro-6-[5-(trifluoromethyl)pyrimidin-2-yl]isoquinolin-1-one (180 mg, 0.22 mmol), TFA (2 mL), and DCM (2 mL). The reaction was stirred for 1 hour and concentrated. MeOH (2 mL) and ethylenediamine (0.5 mL) was added. The reaction was stirred for 15 minutes before being purified by prep HPLC to give 7-fluoro-2-[(4S)-2-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one. ES/MS: m/z 573.0 $[M+H]^+$. 1H NMR (400 MHz, DMSO-d6) δ 12.48 (s, 1H), 12.39 (s, 1H), 9.48 (s, 3H), 8.43 (dd, J=7.1, 1.4 Hz, 2H), 8.04 (dd, J=11.4, 3.6 Hz, 2H), 7.88 (d, J=8.6 Hz, 2H), 7.45 (dd, J=8.8, 7.4 Hz, 2H), 7.04-6.88 (m, 1H), 6.81 (d, J=7.4 Hz, 2H), 6.57 (dd, J=7.7, 3.8 Hz, 1H), 4.31-3.88 (m, 4H), 1.94-1.47 (m, 3H), 1.21 (dd, J=6.4, 3.2 Hz, 6H).

Example 479 and Example 480: 7-fluoro-2-[(2S,4S)-2-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one and 7-fluoro-2-[(2R,4S)-2-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one

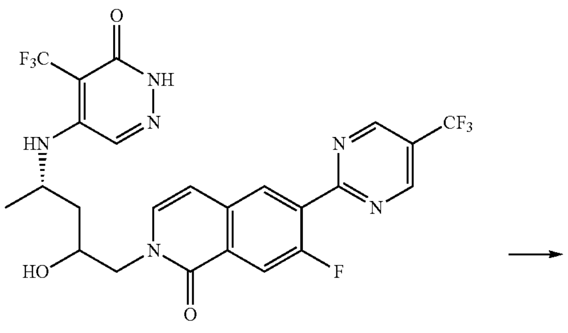

Example 478

-continued

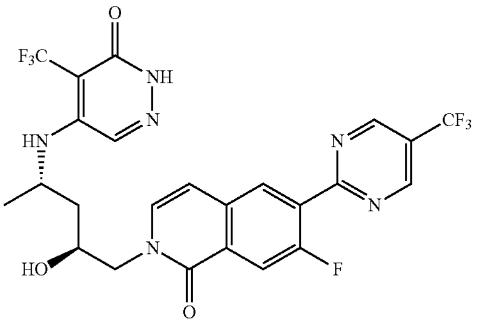

Example 479

+

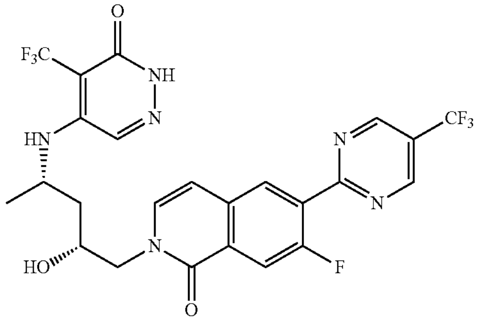

Example 480

Examples 479 and Example 480 were separated via chiral SFC (AD-H, 5 □m, 21×250 mm column; 35% EtOH as co-solvent; 100 bar; 40° C.). The first eluting peak was assigned as the (S)-configuration (Example 479), and the second eluting peak was assigned as the (R)-configuration (Example 480). The final compounds were free of TFA.

Example 479: $^1$H NMR (400 MHz, DMSO-d6) δ 12.48 (s, 1H), 9.48 (s, 2H), 8.44 (d, J=7.1 Hz, 1H), 8.03 (d, J=11.4 Hz, 1H), 7.87 (s, 1H), 7.46 (d, J=7.4 Hz, 1H), 6.81 (d, J=7.4 Hz, 1H), 6.57 (dd, J=8.0, 4.0 Hz, 1H), 5.23 (s, 1H), 4.25-3.87 (m, 3H), 3.76 (dd, J=13.0, 8.0 Hz, 1H), 1.69 (t, J=6.7 Hz, 2H), 1.21 (d, J=6.2 Hz, 3H). ES/MS: m/z 573.0 $[M+H]^+$.

Example 480: $^1$H NMR (400 MHz, DMSO-d6) δ 12.39 (s, 1H), 9.48 (s, 2H), 8.43 (d, J=7.1 Hz, 1H), 8.04 (d, J=11.3 Hz, 1H), 7.89 (s, 1H), 7.44 (d, J=7.4 Hz, 1H), 6.96 (dt, J=7.3, 3.7 Hz, 1H), 6.81 (d, J=7.4 Hz, 1H), 4.32-3.95 (m, 3H), 3.79 (dd, J=12.8, 7.5 Hz, 1H), 1.83 (dd, J=13.5, 8.3 Hz, 1H), 1.60 (ddd, J=14.0, 10.4, 3.3 Hz, 1H), 1.21 (d, J=6.4 Hz, 3H). ES/MS: m/z 573.0 $[M+H]^+$.

Example 481: 4,7-difluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one Example 481

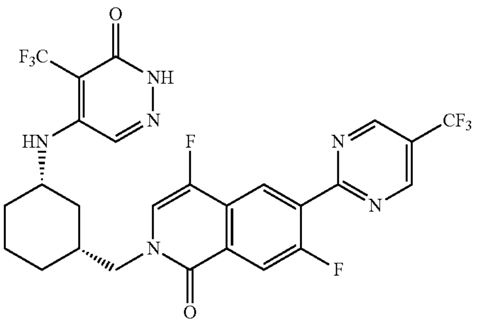

The title compound was synthesized as described in Example 459, with the following changes:

Step 1: N-Fluorobenzenesulfonimide was used instead of NBS and DMF was used instead of DMSO. $^1$H NMR (400 MHz, DMSO-d6) δ 12.42 (s, 1H), 9.50 (s, 2H), 8.47 (d, J=6.8 Hz, 1H), 8.11 (dd, J=11.1, 1.9 Hz, 1H), 7.92 (s, 1H), 7.85 (d, J=6.8 Hz, 1H), 6.37-6.28 (m, 1H), 3.88-3.83 (m, 2H), 2.10-1.97 (m, 1H), 1.81 (d, J=11.4 Hz, 2H), 1.73 (d, J=11.0 Hz, 1H), 1.59 (d, J=12.2 Hz, 1H), 1.43-1.22 (m, 3H), 1.02-0.88 (m, 1H). One methine in obstructed by the water signal. ES/MS m/z: 601.10 [M+H].

Example 482: 6-(5-(difluoromethyl)pyrimidin-2-yl)-4,7-difluoro-2-(((1R,3S)-3-((6-oxo-5-(trifluoromethyl)-1,6-dihydropyridazin-4-yl)amino)cyclohexyl)methyl)isoquinolin-1(2H)-one Example 482

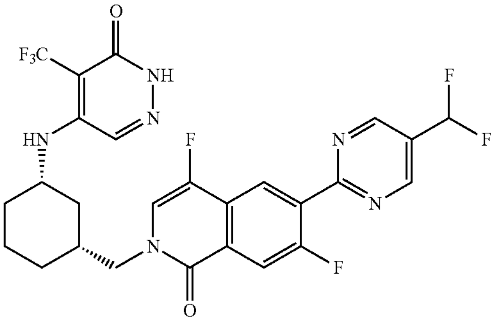

The title compound was synthesized as described in Example 459, with the following changes:

Step 1: N-Fluorobenzenesulfonimide was used instead of NBS and 6-(5-(difluoromethyl)pyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one was used instead of 7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one and DMF was used instead of DMSO. $^1$H NMR (400 MHz, DMSO-d6) δ 12.42 (s, 1H), 9.27 (s, 2H), 8.43 (d, J=6.8 Hz, 1H), 8.09 (dd, J=11.1, 1.9 Hz, 1H), 7.92 (s, 1H), 7.84 (d, J=6.8 Hz, 1H), 7.32 (t, J=54.8 Hz, 1H), 6.40-6.25 (m, 1H), 3.89-3.83 (m, 2H), 3.76-3.68 (m, 1H), 2.05 (d, J=17.9 Hz, 1H), 1.86-1.76 (m, 2H), 1.76-1.68 (m, 1H), 1.63-1.53 (m, 1H), 1.46-1.20 (m, 3H), 1.03-0.88 (m, 1H). ES/MS m/z: 583.10 [M+H].

Example 483: 7-fluoro-1-oxo-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)-1,2-dihydroisoquinoline-4-carbonitrile

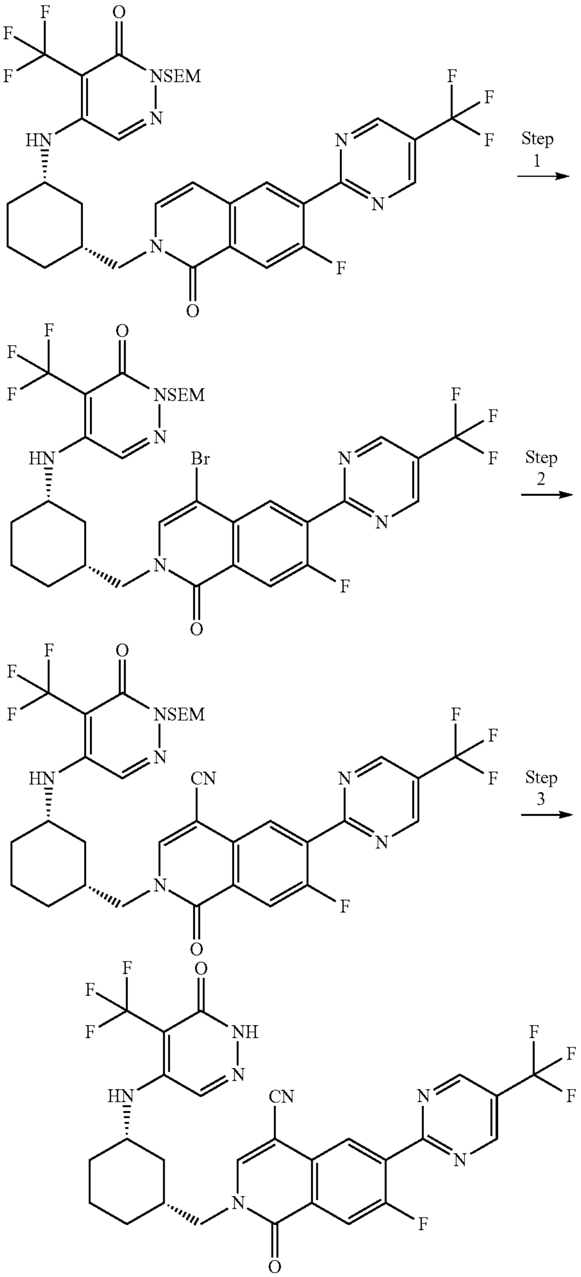

Example 483

Step 1. NBS (65.4 mg, 0.368 mmol) was added to a solution of 7-fluoro-2-(((1R,3S)-3-((6-oxo-5-(trifluoromethyl)-1-((2-(trimethylsilyl)ethoxy)methyl)-1,6-dihydro-pyridazin-4-yl)amino)cyclohexyl)methyl)-6-(5-(trifluoromethyl)pyrimidin-2-yl)isoquinolin-1(2H)-one (262 mg, 0.368 mmol) in MeCN (4.0 mL). The resulting solution was stirred at room temperature for 2 hr, then diluted with water, extracted with EtOAc, washed with brine, dried with anhydrous magnesium sulfate, and concentrated. Purification via flash chromatography (gradient solution with 0-100% EtOAc/Hexanes) afforded 4-bromo-7-fluoro-2-[[(1R,3S)-3-[[6-oxo-5-(trifluoromethyl)-1-(2-trimethylsilylethoxymethyl)pyridazin-4-yl]amino]cyclohexyl]methyl]-6-[5-(trifluoromethyl)pyrimidin-2-yl]isoquinolin-1-one.

Step 2. To a solution of 4-bromo-7-fluoro-2-[[(1R,3S)-3-[[6-oxo-5-(trifluoromethyl)-1-(2-trimethylsilylethoxymethyl)pyridazin-4-yl]amino]cyclohexyl]methyl]-6-[5-(trifluoromethyl)pyrimidin-2-yl]isoquinolin-1-one (118 mg, 0.149 mmol) in DMF (3 mL) was added zinc cyanide (23.0 mg, 0.194 mmol) and Tetrakis(triphenylphosphine)palladium(0) (17.2 mg, 0.015 mmol). The reaction mixture was then sparged with $N_2$ for 10 minutes, and heated to 120° C. for 3 hr. No reaction was observed at this time, so cataCXium Pd G4 (11 mg, 0.015 mmol) was added and the reaction mixture was heated to 100° C. for 10 minutes, then cooled to room temperature and diluted with EtOAc, washed with water (3×) then brine, dried with anhydrous magnesium sulfate, and concentrated. Purification via flash chromatography (gradient solution with 0-100% EtOAc/Hexanes) afforded 7-fluoro-1-oxo-2-(((1R,3S)-3-((6-oxo-5-(trifluoromethyl)-1-((2-(trimethylsilyl)ethoxy)methyl)-1,6-dihydropyridazin-4-yl)amino)cyclohexyl)methyl)-6-(5-(trifluoromethyl)pyrimidin-2-yl)-1,2-dihydroisoquinoline-4-carbonitrile.

Step 3. TFA (1.17 mL, 15.2 mmol) was added to a solution of 7-fluoro-1-oxo-2-(((1R,3S)-3-((6-oxo-5-(trifluoromethyl)-1-((2-(trimethylsilyl)ethoxy)methyl)-1,6-dihydropyridazin-4-yl)amino)cyclohexyl)methyl)-6-(5-(trifluoromethyl)pyrimidin-2-yl)-1,2-dihydroisoquinoline-4-carbonitrile (75 mg, 0.102 mmol) in DCM (10.0 mL). The resulting solution was stirred at room temperature for 2 hr, then concentrated under reduced pressure. The resulting crude oil was taken up in MeOH (5.0 mL) followed by the addition of ethylenediamine (0.17 mL, 2.54 mmol). After stirring at room temperature for 5 minutes the reaction mixture was concentrated in vacuo and purified via reverse phase prep-HPLC (5-100% MeCN in water, 0.1% TFA) to afford 7-fluoro-1-oxo-2-[[(1R,3S)-3-[[6-oxo-5-(trifluoromethyl)-1H-pyridazin-4-yl]amino]cyclohexyl]methyl]-6-[5-(trifluoromethyl)pyrimidin-2-yl]isoquinoline-4-carbonitrile. $^1$H NMR (400 MHz, DMSO-d6) δ 12.43 (s, 1H), 9.53 (s, 2H), 8.60 (s, 1H), 8.47 (d, J=6.7 Hz, 1H), 8.15 (d, J=10.9 Hz, 1H), 7.92 (s, 1H), 6.42-6.26 (m, 1H), 3.75-3.67 (m, 1H), 2.10-1.93 (m, 1H), 1.89-1.77 (m, 2H), 1.74 (d, J=11.6 Hz, 1H), 1.59 (d, J=12.0 Hz, 1H), 1.47-1.19 (m, 3H), 1.02-0.86 (m, 1H). one methylene peak in obstructed by the water signal. ES/MS m/z: 608.10 [M+H].

Example 484: 4-chloro-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one

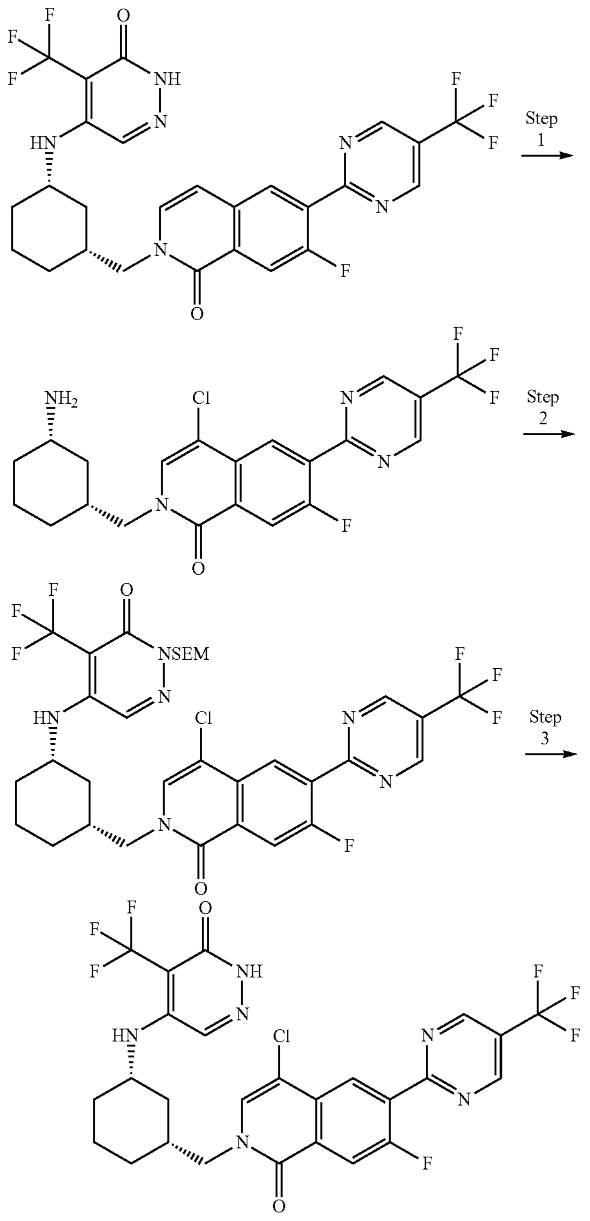

Example 484

Step 1. NCS (28.0 mg, 0.206 mmol) was added to a solution of 7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one (60 mg, 0.103 mmol) in DMF (1.5 mL). The resulting solution was stirred at room temperature for 16 hr, at which point bis-chlorination was observed as the sole product (second chlorination site suspected to be the 4-position on the pyridazinone). The reaction mixture was loaded directly onto prep HPLC (5-100% MeCN in water, 0.1% TFA; aqueous condition resulted in hydrolysis of the pyridazinone) to afford 2-(((1R,3S)-3-aminocyclohexyl)methyl)-4-chloro-7-fluoro-6-(5-(trifluoromethyl)pyrimidin-2-yl)isoquinolin-1(2H)-one.

Step 2. A solution of 5-chloro-4-(trifluoromethyl)-2-(2-trimethylsilylethoxymethyl)pyridazin-3-one (170 mg, 0.515 mmol) in DMF (2.0 mL) was added to a solution of 2-[[(1R,3S)-3-aminocyclohexyl]methyl]-4-chloro-7-fluoro-6-[5-(trifluoromethyl)pyrimidin-2-yl]isoquinolin-1-one (ca. 0.13 mmol) in DMF (3.0 mL). The reaction mixture was stirred at room temperature for 2 hr, then diluted with EtOAc, washed with water (3×) then brine, dried with anhydrous magnesium sulfate, and concentrated. Purification via flash chromatography (gradient solution with 0-100% EtOAc/Hexanes) afforded 4-chloro-7-fluoro-2-(((1R,3S)-3-((6-oxo-5-(trifluoromethyl)-1-((2-(trimethylsilyl)ethoxy)methyl)-1,6-dihydropyridazin-4-yl)amino)cyclohexyl)methyl)-6-(5-(trifluoromethyl)pyrimidin-2-yl)isoquinolin-1(2H)-one. ES/MS m/z: 747.18 [M+H].

Step 3. TFA (0.292 mL, 3.81 mmol) was added to a solution of 4-chloro-7-fluoro-2-(((1R,3S)-3-((6-oxo-5-(trifluoromethyl)-1-((2-(trimethylsilyl)ethoxy)methyl)-1,6-dihydropyridazin-4-yl)amino)cyclohexyl)methyl)-6-(5-(trifluoromethyl)pyrimidin-2-yl)isoquinolin-1(2H)-one (19.0 mg, 0.025 mmol) in DCM (2.0 mL). The resulting solution was stirred at room temperature for 1 hr, then concentrated under reduced pressure. The resulting crude oil was taken up in MeOH (1.0 mL) followed by the addition of ethylenediamine (0.59 mL, 0.89 mmol). After stirring at room temperature for 5 minutes the reaction mixture was concentrated in vacuo and purified via reverse phase prep-HPLC (5-100% MeCN in water, 0.1% TFA) to afford 4-chloro-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one. $^1$H NMR (400 MHz, DMSO-d6) δ 12.42 (s, 1H), 9.51 (s, 2H), 8.57 (d, J=6.8 Hz, 1H), 8.13 (d, J=11.0 Hz, 1H), 7.95 (s, 1H), 7.92 (s, 1H), 6.38-6.27 (m, 1H), 3.96-3.85 (m, 2H), 3.73 (d, J=10.1 Hz, 1H), 2.03 (qd, J=7.3, 4.2, 3.7 Hz, 1H), 1.90-1.76 (m, 2H), 1.76-1.67 (m, 1H), 1.59 (d, J=12.7 Hz, 1H), 1.46-1.20 (m, 3H), 1.03-0.88 (m, 1H). ES/MS m/z: 617.00 [M+H].

Example 485: 7-fluoro-4-methyl-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one

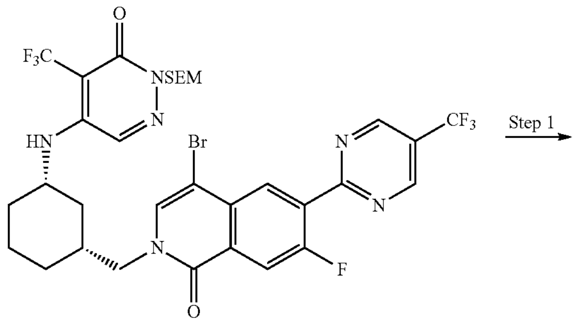

-continued

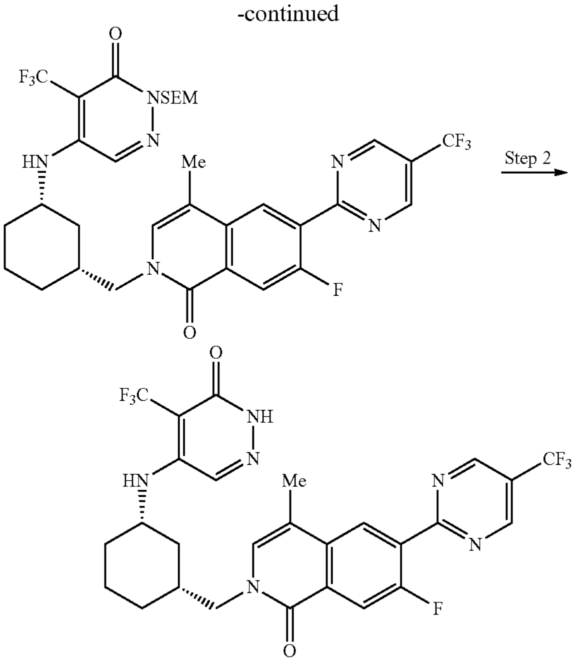

Example 485

Step 1. In a vial was added 4-bromo-7-fluoro-2-[[(1R,3S)-3-[[6-oxo-5-(trifluoromethyl)-1-(2-trimethylsilylethoxymethyl)pyridazin-4-yl]amino]cyclohexyl]methyl]-6-[5-(trifluoromethyl)pyrimidin-2-yl]isoquinolin-1-one (120 mg, 0.15 mmol), trimethylboroxine (0.064 mL, 0.45 mmol), 2M aqueous potassium carbonate (0.23 mL, 0.45 mmol), and cataCXium Pd G4 (23 mg, 0.03 mmol) in dioxane (1.50 mL). The mixture was degassed for 15 minutes with nitrogen gas, heated to 80° C. for 1 hr, cooled to room temperature, filtered through Celite©, and concentrated. The resulting crude material was purified by flash chromatography (0-100% EtOAc in Hexane) to give 7-fluoro-4-methyl-2-(((1R,3S)-3-((6-oxo-5-(trifluoromethyl)-1-((2-(trimethylsilyl)ethoxy)methyl)-1,6-dihydropyridazin-4-yl)amino)cyclohexyl)methyl)-6-(5-(trifluoromethyl)pyrimidin-2-yl)isoquinolin-1(2H)-one.

Step 2. TFA (1.17 mL, 15.2 mmol) was added to a solution of 7-fluoro-4-methyl-2-(((1R,3S)-3-((6-oxo-5-(trifluoromethyl)-1-((2-(trimethylsilyl)ethoxy)methyl)-1,6-dihydropyridazin-4-yl)amino)cyclohexyl)methyl)-6-(5-(trifluoromethyl)pyrimidin-2-yl)isoquinolin-1(2H)-one (110 mg, 0.151 mmol) in DCM (5.0 mL). The resulting solution was stirred at room temperature for 1 hr, then concentrated under reduced pressure. The resulting crude oil was taken up in MeOH (5.0 mL) followed by the addition of ethylenediamine (0.17 mL, 2.54 mmol). After stirring at room temperature for 5 minutes the reaction mixture was concentrated in vacuo and purified via reverse phase prep-HPLC (5-100% MeCN in water, 0.1% TFA) to afford 7-fluoro-4-methyl-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one. $^1$H NMR (400 MHz, DMSO-d6) δ 12.42 (s, 1H), 9.50 (s, 2H), 8.37 (d, J=7.0 Hz, 1H), 8.08 (d, J=11.3 Hz, 1H), 7.91 (s, 1H), 7.38 (s, 1H), 6.40-6.22 (m, 1H), 3.93-3.78 (m, 2H), 3.78-3.68 (m, 1H), 2.31 (s, 3H), 2.09-1.95 (m, 1H), 1.84-1.76 (m, 2H), 1.76-1.68 (m, 1H), 1.63-1.51 (m, 1H), 1.45-1.20 (m, 3H), 1.03-0.88 (m, 1H). one methylene peak in obstructed by the water signal. ES/MS m/z: 597.100 [M+H].

Example 486: 4-amino-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one

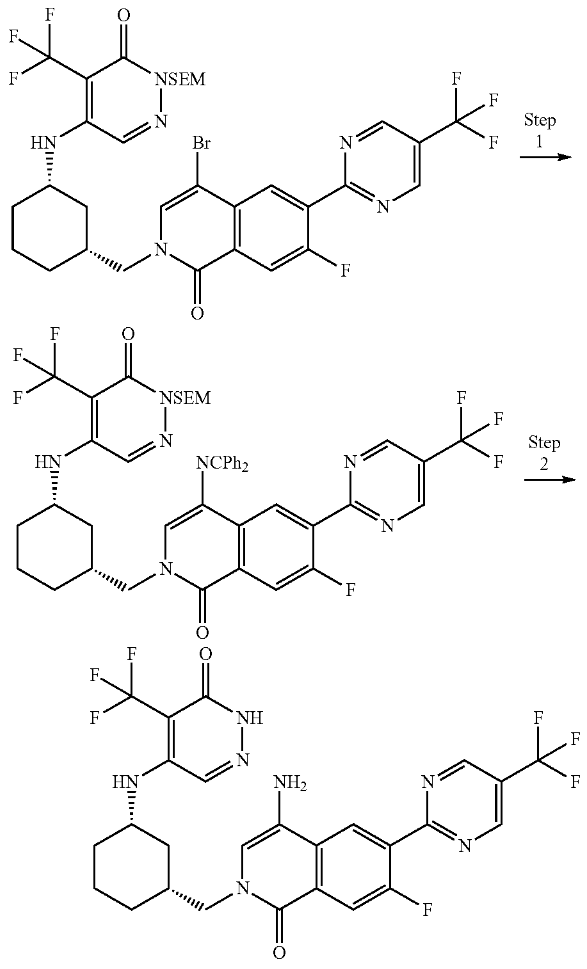

Example 486

Step 1. In a vial is combined 4-bromo-7-fluoro-2-[[(1R,3S)-3-[[6-oxo-5-(trifluoromethyl)-1-(2-trimethylsilylethoxymethyl)pyridazin-4-yl]amino]cyclohexyl]methyl]-6-[5-(trifluoromethyl)pyrimidin-2-yl]isoquinolin-1-one (111 mg, 0.140 mmol), diphenylmethanimine (0.047 mL, 0.280 mmol), $Cs_2CO_3$ (137 mg, 0.42 mmol), XantPhos Pd G4 (13.5 mg, 0.014 mmol), and dioxane (1.0 mL). The suspension is degassed with $N_2$ gas and heated to 75° C. for 8 hrs. The reaction is cooled, filtered over Celite©, concentrated, and purified by flash chromatography (0-100% EtOAc in Hexane) to give 4-((diphenylmethylene)amino)-7-fluoro-2-(((1R,3S)-3-((6-oxo-5-(trifluoromethyl)-1-((2-(trimethylsilyl)ethoxy)methyl)-1,6-dihydropyridazin-4-yl)amino)cyclohexyl)methyl)-6-(5-(trifluoromethyl)pyrimidin-2-yl)isoquinolin-1(2H)-one.

Step 2. In a vial is added 4-((diphenylmethylene)amino)-7-fluoro-2-(((1R,3S)-3-((6-oxo-5-(trifluoromethyl)-1-((2-(trimethylsilyl)ethoxy)methyl)-1,6-dihydropyridazin-4-yl)amino)cyclohexyl)methyl)-6-(5-(trifluoromethyl)pyrimidin-2-yl)isoquinolin-1(2H)-one (125 mg, 0.140 mmol), TFA (1.17 mL, 15.2 mmol), and DCM (5.0 mL).

After 2 hrs LCMS shows cleavage of the SEM group, but the benzephenone imine remains. 5 drops of concentrated HCl is added, and the reaction is stirred for 72 hrs. The reaction is concentrated, treated with 2M $NH_3$ in MeOH (5.0 mL), and concentrated again. Purification via reverse phase prep-HPLC (5-100% MeCN in water, 0.1% TFA) to afford 4-amino-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one. $^1$H NMR (400 MHz, DMSO-d6) 1H NMR (400 MHz, DMSO-d6) δ 12.43 (s, 1H), 9.52 (s, 2H), 8.55 (d, J=6.9 Hz, 1H), 8.09 (d, J=11.2 Hz, 1H), 7.92 (s, 1H), 7.03 (s, 1H), 6.33 (s, 1H), 2.08-1.89 (m, 1H), 1.87-1.78 (m, 2H), 1.78-1.69 (m, 1H), 1.65-1.54 (m, 1H), 1.47-1.21 (m, 3H), 1.02-0.88 (m, 1H). ES/MS m/z: 598.100 [M+H].

Example 487: 7-([1,2,4]triazolo[1,5-a]pyridin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one Example 487

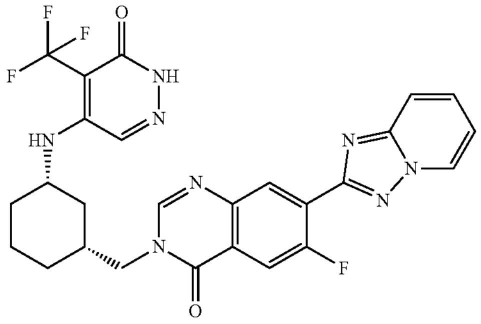

The Following compound was synthesized using the procedure as described in Example 226, using 2-bromo-[1,2,4]triazolo[1,5-a]pyridine instead of 2-chloro-5-trifluoromethyl pyrimidine. 1H NMR (400 MHz, DMSO-d6) δ 12.42 (s, 1H), 9.09 (d, J=6.9 Hz, 1H), 8.66-8.22 (m, 2H), 8.06-7.86 (m, 3H), 7.77 (m, 1H), 7.30 (m, 1H), 6.32 (m, 1H), 4.15-3.59 (m, 3H), 2.02 (s, 1H), 1.86-1.67 (m, 3H), 1.61 (m, 1H), 1.29 (m, 3H), 1.01-0.83 (m, 1H). ES/MS m/z: 555.1 [M+H].

Example 488: 6-([1,2,4]triazolo[1,5-a]pyridin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one Example 488

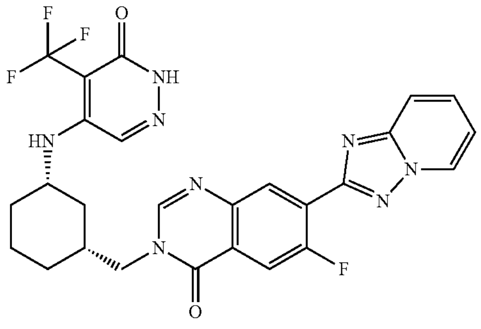

The Following compound was synthesized using the procedure as described in Example 226, using 2-bromo-[1,2,4]triazolo[1,5-a]pyridine instead of 2-chloro-5-trifluoromethyl pyrimidine. 1H NMR (400 MHz, DMSO-d6) δ 12.42 (s, 1H), 9.08 (d, J=6.9 Hz, 1H), 8.58 (d, J=6.9 Hz, 1H), 8.03 (d, J=11.3 Hz, 1H), 8.01-7.86 (m, 2H), 7.83-7.66 (m, 1H), 7.49 (d, J=7.4 Hz, 1H), 7.29 (m, 1H), 6.84 (d, J=7.4 Hz, 1H), 6.33 (m, 1H), 3.89 (m, 3H), 2.02 (m, 1H), 1.77 (m, 3H), 1.58 (m, 1H), 1.32 (m, 3H), 1.11-0.86 (m, 1H). ES/MS m/z: 554.1 [M+H].

Example 489: (R)-6-([1,2,4]triazolo[1,5-a]pyridin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one Example 489

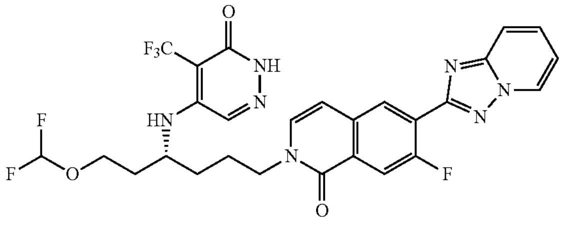

The Following compound was synthesized using the procedure as described in Example 168, using 2-bromo-[1,2,4]triazolo[1,5-a]pyridine instead of 2-chloro-5-trifluoromethyl pyrimidine. 1H NMR (400 MHz, DMSO-d6) δ 12.48 (s, 1H), 9.08 (d, J=6.8 Hz, 1H), 8.57 (d, J=6.9 Hz, 1H), 8.16-7.89 (m, 3H), 7.83-7.68 (m, 1H), 7.51 (d, J=7.3 Hz, 1H), 7.29 (m, 1H), 7.00-6.27 (m, 3H), 4.27 (m, 1H), 4.12-3.83 (m, 4H), 1.77 (m, 2H), 1.62 (m, 2H). ES/MS m/z: 594.0 [M+H].

Example 490: (R)-7-([1,2,4]triazolo[1,5-a]pyridin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one Example 490

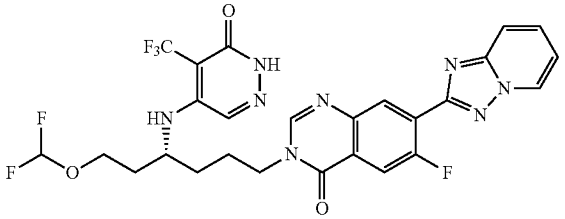

The Following compound was synthesized using the procedure as described in Example 168, using 2-bromo-[1,2,4]triazolo[1,5-a]pyridine instead of 2-chloro-5-trifluoromethyl pyrimidine. 1H NMR (400 MHz, DMSO-d6) δ 12.49 (s, 1H), 9.09 (d, J=6.9 Hz, 1H), 8.54-8.39 (m, 2H), 8.12-7.93 (m, 3H), 7.87-7.68 (m, 1H), 7.30 (m, 1H), 6.95-6.30 (m, 2H), 4.27 (m, 1H), 4.06-3.76 (m, 4H), 1.71 (m, 4H). ES/MS m/z: 595.0 [M+H].

Example 491: 7-fluoro-6-[1-methyl-5-(trifluoromethyl)pyrazol-3-yl]-2-[[(1R,3S)-3-[[6-oxo-5-(trifluoromethyl)-1H-pyridazin-4-yl]amino]cyclohexyl]methyl]isoquinolin-1-one Example 491

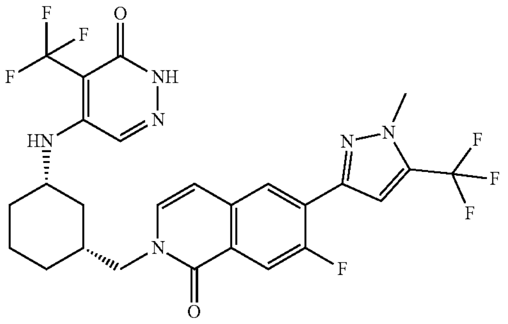

The Following compound was synthesized using the procedure as described in Example 226, using 2-3-chloro-1-methyl-5-(trifluoromethyl)pyrazole instead of 2-chloro-5-trifluoromethyl pyrimidine. 1H NMR (400 MHz, DMSO-d6) δ 12.42 (s, 1H), 8.27 (d, J=7.1 Hz, 1H), 7.97 (d, J=11.6 Hz, 1H), 7.90 (s, 1H), 7.44 (d, J=7.4 Hz, 1H), 7.32 (d, J=3.1 Hz, 1H), 6.75 (d, J=7.4 Hz, 1H), 6.37-6.28 (m, 1H), 4.09 (s, 3H), 3.86 (d, J=7.0 Hz, 2H), 3.79-3.66 (m, 1H), 2.08-1.93 (m, 1H), 1.85-1.67 (m, 3H), 1.56 (d, J=12.4 Hz, 1H), 1.45-1.20 (m, 3H), 1.01-0.87 (m, 1H). ES/MS m/z: 585.10 [M+H].

Example 492: 7-fluoro-6-(5-methoxypyrimidin-2-yl)-2-[[(1R,3S)-3-[[6-oxo-5-(trifluoromethyl)-1H-pyridazin-4-yl]amino]cyclohexyl]methyl]isoquinolin-1-one Example 492

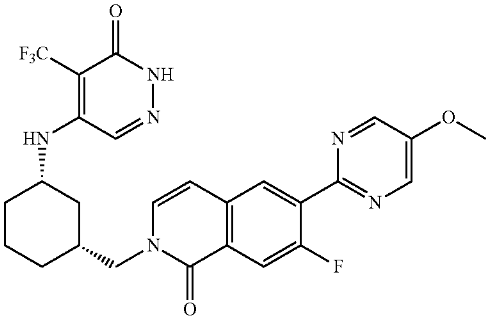

The Following compound was synthesized using the procedure as described in Example 226, using 2-bromo-5-methoxy-pyrimidine instead of 2-chloro-5-trifluoromethyl pyrimidine. 1H NMR (400 MHz, DMSO-d6) δ 12.42 (s, 1H), 8.75 (s, 2H), 8.28 (d, J=7.3 Hz, 1H), 7.96 (d, J=11.4 Hz, 1H), 7.91 (s, 1H), 7.48-7.43 (m, 1H), 6.78 (d, J=7.4 Hz, 1H), 6.32 (dd, J=7.9, 3.5 Hz, 1H), 4.00 (s, 3H), 3.88 (d, J=6.8 Hz, 2H), 3.78-3.68 (m, 1H), 2.09-1.98 (m, 1H), 1.76 (dd, J=30.9, 8.7 Hz, 3H), 1.57 (d, J=12.6 Hz, 1H), 1.43-1.20 (m, 3H), 0.95 (q, J=12.3, 11.0 Hz, 1H). ES/MS m/z: 545.20 [M+H].

Example 493: 7,8-difluoro-6-(5-methoxypyrimidin-2-yl)-2-[[(1R,3S)-3-[[6-oxo-5-(trifluoromethyl)-1H-pyridazin-4-yl]amino]cyclohexyl]methyl]isoquinolin-1-one Example 493

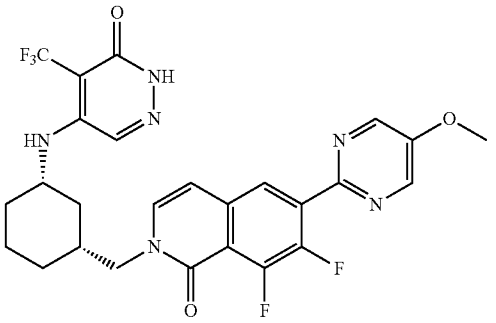

The Following compound was synthesized using the procedure as described in Example 226, using 2-bromo-5-methoxy-pyrimidine instead of 2-chloro-5-trifluoromethyl pyrimidine. 1H NMR (400 MHz, DMSO-d6) δ 12.42 (s, 1H), 8.77 (s, 2H), 8.09 (d, J=6.6 Hz, 1H), 7.92 (s, 1H), 7.48 (d, J=7.4 Hz, 1H), 6.75 (d, J=7.3 Hz, 1H), 6.36-6.28 (m, 1H), 4.01 (s, 3H), 3.83 (dd, J=7.2, 3.1 Hz, 2H), 3.73 (d, J=5.1 Hz, 1H), 2.01 (m, 1H), 1.80 (m, 2H), 1.73 (d, J=11.0 Hz, 1H), 1.57 (d, J=12.7 Hz, 1H), 1.31 (m, 4H), 0.94 (m, 1H). ES/MS m/z: 563.20 [M+H].

Example 494: 7-fluoro-6-(6-fluoro-[1,2,4]triazolo[1,5-a]pyridin-2-yl)-2-(((1R,3S)-3-((6-oxo-5-(trifluoromethyl)-1,6-dihydropyridazin-4-yl)amino)cyclohexyl)methyl)isoquinolin-1(2H)-one Example 494

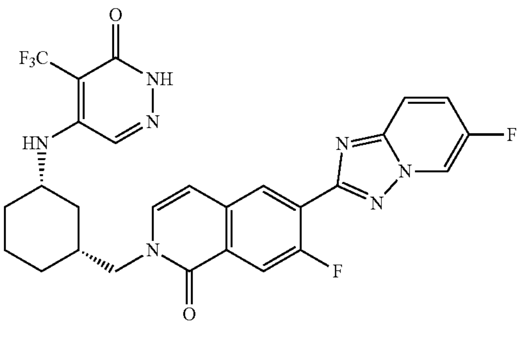

The Following compound was synthesized using the procedure as described in Example 226, using 2-bromo-6-fluoro-[1,2,4]triazolo[1,5-a]pyridine instead of 2-chloro-5-trifluoromethyl pyrimidine. 1H NMR (400 MHz, DMSO-d6) δ 1H NMR (400 MHz, DMSO-d6) δ 12.42 (s, 1H), 9.46 (m, 1H), 8.55 (d, J=6.9 Hz, 1H), 8.12-7.69 (m, 3H), 7.49 (d, J=7.4 Hz, 1H), 6.84 (d, J=7.4 Hz, 1H), 6.33 (m, 1H), 3.89 (m, 2H), 2.05 (m, 1H), 1.77 (m, 4H), 1.58 (m, 1H), 1.32 (m, 4H), 0.94 (m, 1H). ES/MS m/z: 572.20 [M+H].

Example 495: 7-fluoro-6-[5-(2-hydroxyethoxy)pyrimidin-2-yl]-2-[[(1R,3S)-3-[[6-oxo-5-(trifluoromethyl)-1H-pyridazin-4-yl]amino]cyclohexyl]methyl]isoquinolin-1-one Example 495

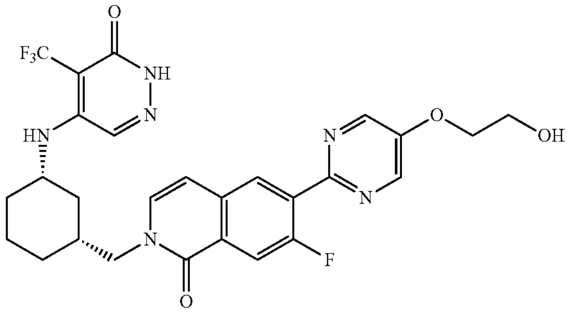

The Following compound was synthesized using the procedure as described in Example 226, using tert-butyl-[2-(2-chloropyrimidin-5-yl)oxyethoxy]-dimethyl-silane instead of 2-chloro-5-trifluoromethyl pyrimidine. 1H NMR (400 MHz, DMSO-d6) δ 12.42 (s, 1H), 8.75 (s, 2H), 8.29 (d, J=7.3 Hz, 1H), 7.96 (d, J=11.4 Hz, 1H), 7.91 (s, 1H), 7.46 (d, J=7.4 Hz, 1H), 6.78 (d, J=7.4 Hz, 1H), 6.32 (dd, J=8.4, 4.2 Hz, 1H), 4.27 (t, J=4.8 Hz, 2H), 3.88 (d, J=7.0 Hz, 2H), 3.78 (t, J=4.8 Hz, 2H), 2.05 (d, J=22.9 Hz, 1H), 1.85-1.67 (m, 3H), 1.57 (d, J=12.6 Hz, 1H), 1.31 (dq, J=34.7, 11.8 Hz, 3H), 0.95 (q, J=12.0 Hz, 1H). ES/MS m/z: 575.20 [M+H].

Example 496: 6-(7,7-difluoro-5,6-dihydrocyclopenta[c]pyridin-3-yl)-7-fluoro-2-[[(1R,3S)-3-[[6-oxo-5-(trifluoromethyl)-1H-pyridazin-4-yl]amino]cyclohexyl]methyl]isoquinolin-1-one Example 496

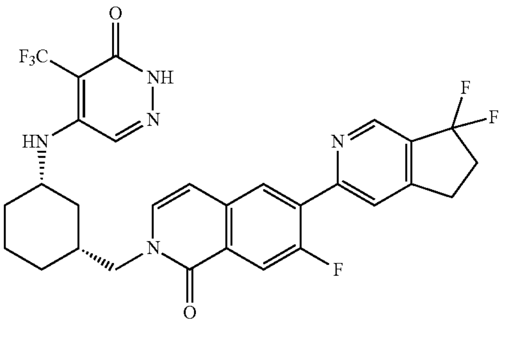

The Following compound was synthesized using the procedure as described in Example 226, using 3-chloro-7,7-difluoro-5,6-dihydrocyclopenta[c]pyridine instead of 2-chloro-5-trifluoromethyl pyrimidine. 1H NMR (400 MHz, DMSO-d6) δ 12.42 (s, 1H), 9.00 (s, 1H), 8.25 (d, J=7.3 Hz, 1H), 8.01 (d, J=11.6 Hz, 1H), 7.95 (s, 1H), 7.91 (s, 1H), 7.47 (d, J=7.4 Hz, 1H), 6.78 (d, J=7.3 Hz, 1H), 6.37-6.28 (m, 1H), 3.89 (d, J=7.0 Hz, 2H), 3.79-3.66 (m, 1H), 3.25-3.15 (m, 2H), 2.71 (tt, J=14.4, 6.8 Hz, 2H), 2.10-1.95 (m, 1H), 1.84-1.66 (m, 3H), 1.57 (d, J=12.7 Hz, 1H), 1.46-1.20 (m, 3H), 1.03-0.88 (m, 1H). ES/MS m/z: 590.2 [M+H].

Example 497: 6-fluoro-7-(5-methoxypyrimidin-2-yl)-3-[[(1R,3S)-3-[[6-oxo-5-(trifluoromethyl)-1H-pyridazin-4-yl]amino]cyclohexyl]methyl]quinazolin-4-one Example 497

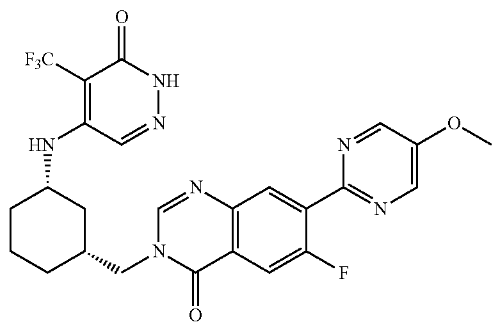

The Following compound was synthesized using the procedure as described in Example 226, using 2-bromo-5-methoxy-pyrimidine instead of 2-chloro-5-trifluoromethyl pyrimidine. 1H NMR (400 MHz, DMSO-d6) δ 12.42 (s, 1H), 8.76 (s, 2H), 8.39 (s, 2H), 8.22 (d, J=11.4 Hz, 1H), 7.93 (d, J=9.4 Hz, 2H), 6.37-6.27 (m, 1H), 4.00 (s, 3H), 3.90 (d, J=6.8 Hz, 2H), 3.71 (s, 1H), 2.09-1.95 (m, 1H), 1.82 (d, J=12.9 Hz, 2H), 1.66 (dd, J=52.9, 11.6 Hz, 2H), 1.43-1.18 (m, 3H), 1.02-0.88 (m, 1H). ES/MS m/z: 546.20 [M+H].

Example 498: 6-fluoro-7-(5-methoxypyrimidin-2-yl)-3-[[(1R,3S)-3-[[6-oxo-5-(trifluoromethyl)-1H-pyridazin-4-yl]amino]cyclohexyl]methyl]quinazolin-4-one Example 498

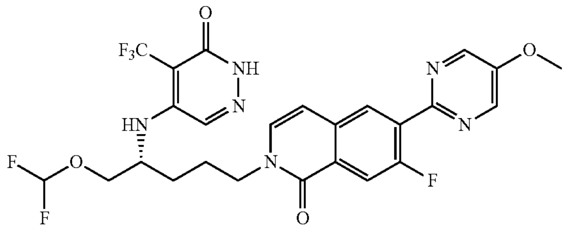

The Following compound was synthesized using the procedure as described in Example 226, using 2-bromo-5-methoxy-pyrimidine instead of 2-chloro-5-trifluoromethyl pyrimidine. 1H NMR (400 MHz, DMSO-d6) δ 1H NMR (400 MHz, DMSO-d6) δ 12.49 (s, 1H), 8.75 (s, 2H), 8.28 (d, J=7.3 Hz, 1H), 8.00-7.91 (m, 2H), 7.48 (d, J=7.4 Hz, 1H), 6.80 (d, J=7.3 Hz, 1H), 6.66 (t, J=75.5 Hz, 1H), 6.44-6.37 (m, 1H), 4.34-4.20 (m, 1H), 4.05-3.95 (m, 5H), 3.96-3.90 (m, 2H), 1.84-1.68 (m, 2H), 1.68-1.52 (m, 2H). ES/MS m/z: 585.1 [M+H].

a.

VII. Compound Table b. The following compounds were prepared according to the Examples and Procedures described herein (and indicated in Table 1 under Example/Procedure) using the appropriate starting material(s) and appropriate protecting group chemistry as needed.

| Example | Name |
|---|---|
| 1 | 2-[4-[[6-oxo-5-(trifluoromethyl)-1H-pyridazin-4-yl]amino]pentyl]-6-[5-(trifluoromethyl)pyridin-2-yl]isoquinolin-1-one |
| 2 | 2-[(4R)-4-[[6-oxo-5-(trifluoromethyl)-1H-pyridazin-4-yl]amino]pentyl]-6-[5-(trifluoromethyl)pyridin-2-yl]isoquinolin-1-one |
| 3 | 2-[(4S)-4-[[6-oxo-5-(trifluoromethyl)-1H-pyridazin-4-yl]amino]pentyl]-6-[5-(trifluoromethyl)pyridin-2-yl]isoquinolin-1-one |
| 4 | 2-[(4S)-4-[[6-oxo-5-(trifluoromethyl)-1H-pyridazin-4-yl]amino]pentyl]-6-[5-(trifluoromethyl)pyridin-2-yl]phthalazin-1-one |
| 5 | 2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one |
| 6 | 5-fluoro-2-[(4S)-4-[6-oxo-5-(trifluoromethyl)-1H-pyridazin-4-yl]amino]pentyl]-6-[5-(trifluoromethyl)pyrimidin-2-yl]isoquinolin-1-one |
| 7 | 8-fluoro-2-[(4S)-4-[6-oxo-5-(trifluoromethyl)-1H-pyridazin-4-yl]amino]pentyl]-6-[5-(trifluoromethyl)pyrimidin-2-yl]isoquinolin-1-one |
| 8 | 7-fluoro-2-[(4S)-4-[6-oxo-5-(trifluoromethyl)-1H-pyridazin-4-yl]amino]pentyl]-6-[5-(trifluoromethyl)pyrimidin-2-yl]isoquinolin-1-one |
| 9 | 7-fluoro-2-[(4S)-4-[6-oxo-5-(trifluoromethyl)-1H-pyridazin-4-yl]amino]pentyl]-6-[5-(trifluoromethyl)pyridin-2-yl]isoquinolin-1-one |
| 10 | 5-fluoro-2-[(4S)-4-[[6-oxo-5-(trifluoromethyl)-1H-pyridazin-4-yl]amino]pentyl]-6-[5-(trifluoromethyl)pyridin-2-yl]isoquinolin-1-one |
| 11 | 8-fluoro-2-[(4S)-4-[[6-oxo-5-(trifluoromethyl)-1H-pyridazin-4-yl]amino]pentyl]-6-[5-(trifluoromethyl)pyridin-2-yl]isoquinolin-1-one |
| 12 | 7-[(4S)-4-[[6-oxo-5-(trifluoromethyl)-1H-pyridazin-4-yl]amino]pentyl]-3-[5-(trifluoromethyl)pyrimidin-2-yl]-1,7-naphthyridin-8-one |
| 13 | 2-[(4S)-4-[6-oxo-5-(trifluoromethyl)-1H-pyridazin-4-yl]amino]pentyl]-6-[5-(trifluoromethyl)pyridin-2-yl]-2,7-naphthyridin-1-one |
| 14 | 6-[(4S)-4-[[6-oxo-5-(trifluoromethyl)-1H-pyridazin-4-yl]amino]pentyl]-2-[5-(trifluoromethyl)pyridin-2-yl]-1,6-naphthyridin-5-one |
| 15 | 2-[(4S)-4-[(5-acetyl-6-oxo-1H-pyridazin-4-yl)amino]pentyl]-6-[5-(trifluoromethyl)pyrimidin-2-yl]isoquinolin-1-one |
| 16 | 2-[(4S)-4-[(5-acetyl-6-oxo-1H-pyridazin-4-yl)amino]pentyl]-7-fluoro-6-[5-(trifluoromethyl)pyrimidin-2-yl]isoquinolin-1-one |

-continued

| Example | Name |
|---|---|
| 17 | 6-[5-(difluoromethoxy)pyridin-2-yl]-8-fluoro-2-[(4S)-4-[[6-oxo-5-(trifluoromethyl)-1H-pyridazin-4-yl]amino]pentyl]isoquinolin-1-one |
| 18 | 6-[8-fluoro-1-oxo-2-[(4S)-4-[[6-oxo-5-(trifluoromethyl)-1H-pyridazin-4-yl]amino]pentyl]isoquinolin-6-yl]pyridine-3-carbonitrile |
| 19 | 8-fluoro-6-(5-fluoropyridin-2-yl)-2-[(4S)-4-[[6-oxo-5-(trifluoromethyl)-1H-pyridazin-4-yl]amino]pentyl]isoquinolin-1-one |
| 20 | 7,8-difluoro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one |
| 21 | 7-fluoro-2-[(4S)-4-[6-oxo-5-(trifluoromethyl)-1H-pyridazin-4-yl]amino]pentyl]-6-[5-(trifluoromethyl)pyrazin-2-yl]isoquinolin-1-one |
| 22 | 7-fluoro-6-(5-methoxypyrimidin-2-yl)-2-[(4S)-4-[[6-oxo-5-(trifluoromethyl)-1H-pyridazin-4-yl]amino]pentyl]isoquinolin-1-one |
| 23 | 5-[7-fluoro-1-oxo-2-[(4S)-4-[[6-oxo-5-(trifluoromethyl)-1H-pyridazin-4-yl]amino]pentyl]isoquinolin-6-yl]pyrazine-2-carbonitrile |
| 24 | 2-[7-fluoro-1-oxo-2-[(4S)-4-[6-oxo-5-(trifluoromethyl)-1H-pyridazin-4-yl]amino]pentyl]isoquinolin-6-yl]pyrimidine-5-carbonitrile |
| 25 | 6-[7-fluoro-1-oxo-2-[(4S)-4-[[6-oxo-5-(trifluoromethyl)-1H-pyridazin-4-yl]amino]pentyl]isoquinolin-6-yl]pyridine-3-carbonitrile |
| 26 | 6-(2,3-dihydro-1-benzofuran-7-yl)-7-fluoro-2-[(4S)-4-[6-oxo-5-(trifluoromethyl)-1H-pyridazin-4-yl]amino]pentyl]isoquinolin-1-one |
| 27 | 6-(2,3-dihydro-1,4-benzodioxin-5-yl)-7-fluoro-2-[(4S)-4-[[6-oxo-5-(trifluoromethyl)-1H-pyridazin-4-yl]amino]pentyl]isoquinolin-1-one |
| 28 | 6-(2,3-dihydro-1,4-benzodioxin-6-yl)-7-fluoro-2-[(4S)-4-[6-oxo-5-(trifluoromethyl)-1H-pyridazin-4-yl]amino]pentyl]isoquinolin-1-one |
| 29 | 6-fluoro-3-[(4S)-4-[[6-oxo-5-(trifluoromethyl)-1H-pyridazin-4-yl]amino]pentyl]-7-[5-(trifluoromethyl)pyrimidin-2-yl]quinazolin-4-one |
| 30 | 6-fluoro-3-[(4S)-4-[[6-oxo-5-(trifluoromethyl)-1H-pyridazin-4-yl]amino]pentyl]-7-[5-(trifluoromethyl)pyrimidin-2-yl]-1H-quinazoline-2,4-dione |
| 31 | 7-fluoro-2-[(4S)-4-[6-oxo-5-(trifluoromethyl)-1H-pyridazin-4-yl]amino]pentyl]-6-pyridin-2-ylisoquinolin-1-one |
| 32 | 7-fluoro-2-[(4S)-4-[6-oxo-5-(trifluoromethyl)-1H-pyridazin-4-yl]amino]pentyl]-6-[5-(trifluoromethoxy)pyridin-2-yl]isoquinolin-1-one |
| 33 | 6-[5-(difluoromethyl)pyridin-2-yl]-7-fluoro-2-[(4S)-4-[6-oxo-5-(trifluoromethyl)-1H-pyridazin-4-yl]amino]pentyl]isoquinolin-1-one |
| 34 | 7-fluoro-6-(5-fluoropyrimidin-2-yl)-2-[(4S)-4-[[6-oxo-5-(trifluoromethyl)-1H-pyridazin-4-yl]amino]pentyl]isoquinolin-1-one |
| 35 | 7-fluoro-6-(5-fluoropyridin-2-yl)-2-[(4S)-4-[6-oxo-5-(trifluoromethyl)-1H-pyridazin-4-yl]amino]pentyl]isoquinolin-1-one |
| 36 | 2-[(4R)-4-cyclopropyl-4-[[6-oxo-5-(trifluoromethyl)-1H-pyridazin-4-yl]amino]butyl]-7-fluoro-6-[5-(trifluoromethyl)pyrimidin-2-yl]isoquinolin-1-one |
| 37 | 7-fluoro-2-[(4S)-4-[6-oxo-5-(trifluoromethyl)-1H-pyridazin-4-yl]amino]hexyl]-6-[5-(trifluoromethyl)pyrimidin-2-yl]isoquinolin-1-one |
| 38 | 1-[6-[8-fluoro-1-oxo-2-[(4S)-4-[[6-oxo-5-(trifluoromethyl)-1H-pyridazin-4-yl]amino]pentyl]isoquinolin-6-yl]pyridin-3-yl]cyclopropane-1-carbonitrile |
| 39 | 8-fluoro-2-[rac-(4R)-4-[[6-oxo-5-(trifluoromethyl)-1H-pyridazin-4-yl]amino]pentyl]-6-[5-[1-(trifluoromethyl)cyclopropyl]pyridin-2-yl]isoquinolin-1-one |
| 40 | 8-fluoro-6-[5-(methylsulfonimidoyl)pyridin-2-yl]-2-[(4S)-4-[[6-oxo-5-(trifluoromethyl)-1H-pyridazin-4-yl]amino]pentyl]isoquinolin-1-one |
| 41 | 8-fluoro-2-[(4S)-4-[6-oxo-5-(trifluoromethyl)-1H-pyridazin-4-yl]amino]pentyl]-6-[5-(2,2,2-trifluoroethyl)pyridin-2-yl]isoquinolin-1-one |
| 42 | 6-[5-(difluoromethoxy)pyrimidin-2-yl]-7-fluoro-2-[(4S)-4-[6-oxo-5-(trifluoromethyl)-1H-pyridazin-4-yl]amino]pentyl]isoquinolin-1-one |
| 43 | 6-[5-(difluoromethoxy)pyridin-2-yl]-7-fluoro-2-[(4S)-4-[[6-oxo-5-(trifluoromethyl)-1H-pyridazin-4-yl]amino]pentyl]isoquinolin-1-one |
| 44 | 7-chloro-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one |
| 45 | 3-methyl-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one |
| 46 | 4-methyl-2-[(4S)-4-[[6-oxo-5-(trifluoromethyl)-1H-pyridazin-4-yl]amino]pentyl]-6-[5-(trifluoromethyl)pyrimidin-2-yl]isoquinolin-1-one |
| 47 | 6-[3-[(1R,2R,5S)-3-[6-oxo-5-(trifluoromethyl)-1H-pyridazin-4-yl]-3-azabicyclo[3.1.0]hexan-2-yl]propyl]-2-[5-(trifluoromethyl)pyridin-2-yl]-1,6-naphthyridin-5-one |
| 48 | 8-fluoro-2-[3-[(1R,2R,5S)-3-[6-oxo-5-(trifluoromethyl)-1H-pyridazin-4-yl]-3-azabicyclo[3.1.0]hexan-2-yl]propyl]-6-[5-(trifluoromethyl)pyridin-2-yl]isoquinolin-1-one |
| 49 | 6-[4-amino-5-(trifluoromethyl)pyridin-2-yl]-7-fluoro-2-[(4S)-4-[[6-oxo-5-(trifluoromethyl)-1H-pyridazin-4-yl]amino]pentyl]isoquinolin-1-one |
| 50 | 6-[5-(1-amino-2,2,2-trifluoroethyl)pyridin-2-yl]-7-fluoro-2-[(4S)-4-[6-oxo-5-(trifluoromethyl)-1H-pyridazin-4-yl]amino]pentyl]isoquinolin-1-one |
| 51 | 6-[5-(difluoromethyl)pyridin-2-yl]-7,8-difluoro-2-[(4S)-4-[[6-oxo-5-(trifluoromethyl)-1H-pyridazin-4-yl]amino]pentyl]isoquinolin-1-one |
| 52 | 7,8-difluoro-6-(5-fluoropyridin-2-yl)-2-[(4S)-4-[[6-oxo-5-(trifluoromethyl)-1H-pyridazin-4-yl]amino]pentyl]isoquinolin-1-one |
| 53 | 6-[5-(difluoromethyl)pyrimidin-2-yl]-7,8-difluoro-2-[(4S)-4-[6-oxo-5-(trifluoromethyl)-1H-pyridazin-4-yl]amino]pentyl]isoquinolin-1-one |
| 54 | 7,8-difluoro-6-(5-fluoropyrimidin-2-yl)-2-[(4S)-4-[[6-oxo-5-(trifluoromethyl)-1H-pyridazin-4-yl]amino]pentyl]isoquinolin-1-one |

-continued

| Example | Name |
|---|---|
| 55 | 7,8-difluoro-2-[(4S)-4-[6-oxo-5-(trifluoromethyl)-1H-pyridazin-4-yl]amino]pentyl]-6-[5-(trifluoromethyl)pyridin-2-yl]isoquinolin-1-one |
| 56 | 6-[5-(difluoromethoxy)pyrimidin-2-yl]-7,8-difluoro-2-[(4S)-4-[[6-oxo-5-(trifluoromethyl)-1H-pyridazin-4-yl]amino]pentyl]isoquinolin-1-one |
| 57 | 6-[5-(difluoromethoxy)pyridin-2-yl]-7,8-difluoro-2-[(4S)-4-[6-oxo-5-(trifluoromethyl)-1H-pyridazin-4-yl]amino]pentyl]isoquinolin-1-one |
| 58 | 6-fluoro-3-[(4S)-4-[[6-oxo-5-(trifluoromethyl)-1H-pyridazin-4-yl]amino]pentyl]-7-[5-(trifluoromethyl)pyridin-2-yl]quinazolin-4-one |
| 59 | 6-fluoro-7-(5-fluoropyridin-2-yl)-3-[(4S)-4-[[6-oxo-5-(trifluoromethyl)-1H-pyridazin-4-yl]amino]pentyl]quinazolin-4-one |
| 60 | 6-fluoro-7-(5-fluoropyrimidin-2-yl)-3-[(4S)-4-[[6-oxo-5-(trifluoromethyl)-1H-pyridazin-4-yl]amino]pentyl]quinazolin-4-one |
| 61 | 7-fluoro-2-[3-[1-[[6-oxo-5-(trifluoromethyl)-1H-pyridazin-4-yl]amino]cyclopropyl]propyl]-6-[5-(trifluoromethyl)pyrimidin-2-yl]isoquinolin-1-one |
| 62 | 6-fluoro-3-[(4S)-4-[[6-oxo-5-(trifluoromethyl)-1H-pyridazin-4-yl]amino]pentyl]-7-(7H-pyrrolo[2,3-d]pyrimidin-2-yl)quinazolin-4-one |
| 63 | 6-fluoro-7-(5-methyl-7H-pyrrolo[2,3-d]pyrimidin-2-yl)-3-[(4S)-4-[6-oxo-5-(trifluoromethyl)-1H-pyridazin-4-yl]amino]pentyl]quinazolin-4-one |
| 64 | 6-fluoro-7-(5-fluoro-7H-pyrrolo[2,3-d]pyrimidin-2-yl)-3-[(4S)-4-[[6-oxo-5-(trifluoromethyl)-1H-pyridazin-4-yl]amino]pentyl]quinazolin-4-one |
| 65 | 7-(4-amino-5-cyclopropylpyrimidin-2-yl)-6-fluoro-3-[(4S)-4-[[6-oxo-5-(trifluoromethyl)-1H-pyridazin-4-yl]amino]pentyl]quinazolin-4-one |
| 66 | 7-(4-amino-5-methoxypyrimidin-2-yl)-6-fluoro-3-[(4S)-4-[6-oxo-5-(trifluoromethyl)-1H-pyridazin-4-yl]amino]pentyl]quinazolin-4-one |
| 67 | 7-(4-amino-5-fluoropyrimidin-2-yl)-6-fluoro-3-[(4S)-4-[[6-oxo-5-(trifluoromethyl)-1H-pyridazin-4-yl]amino]pentyl]quinazolin-4-one |
| 68 | 7-fluoro-2-[(1R,2R)-2-[(1S)-1-[[6-oxo-5-(trifluoromethyl)-1H-pyridazin-4-yl]amino]ethyl]cyclopropyl]methyl]-6-[5-(trifluoromethyl)pyrimidin-2-yl]isoquinolin-1-one |
| 69 | 7-fluoro-6-[5-[3-hydroxy-3-(trifluoromethyl)azetidin-1-yl]pyrimidin-2-yl]-2-[(4S)-4-[[6-oxo-5-(trifluoromethyl)-1H-pyridazin-4-yl]amino]pentyl]isoquinolin-1-one |
| 70 | 4-amino-2-[7-fluoro-1-oxo-2-[(4S)-4-[6-oxo-5-(trifluoromethyl)-1H-pyridazin-4-yl]amino]hexyl]isoquinolin-6-yl]pyrimidine-5-carbonitrile |
| 71 | 6-[4-amino-5-(trifluoromethyl)pyrimidin-2-yl]-7-fluoro-2-[(4S)-4-[[6-oxo-5-(trifluoromethyl)-1H-pyridazin-4-yl]amino]hexyl]isoquinolin-1-one |
| 72 | 7-fluoro-2-[3-[1-[6-oxo-5-(trifluoromethyl)-1H-pyridazin-4-yl]azetidin-2-yl]propyl]-6-[5-(trifluoromethyl)pyrimidin-2-yl]isoquinolin-1-one |
| 73 | 7-fluoro-2-[(4R)-5-hydroxy-5-methyl-4-[[6-oxo-5-(trifluoromethyl)-1H-pyridazin-4-yl]amino]hexyl]-6-[5-(trifluoromethyl)pyrimidin-2-yl]isoquinolin-1-one |
| 74 | 7-fluoro-6-[5-(2-hydroxypropan-2-yl)pyrimidin-2-yl]-2-[(4S)-4-[6-oxo-5-(trifluoromethyl)-1H-pyridazin-4-yl]amino]pentyl]isoquinolin-1-one |
| 75 | 6-[5-(1,1-difluoro-2-hydroxyethyl)pyridin-2-yl]-7-fluoro-2-[(4S)-4-[[6-oxo-5-(trifluoromethyl)-1H-pyridazin-4-yl]amino]pentyl]isoquinolin-1-one |
| 76 | 6-[5-(difluoromethyl)pyrimidin-2-yl]-7-fluoro-2-[(4S)-4-[6-oxo-5-(trifluoromethyl)-1H-pyridazin-4-yl]amino]pentyl]isoquinolin-1-one |
| 77 | 6-(4-amino-5-methylpyrimidin-2-yl)-7,8-difluoro-2-[(4S)-4-[[6-oxo-5-(trifluoromethyl)-1H-pyridazin-4-yl]amino]pentyl]isoquinolin-1-one |
| 78 | 7-(4-amino-5-methylpyrimidin-2-yl)-6-fluoro-3-[(4S)-4-[[6-oxo-5-(trifluoromethyl)-1H-pyridazin-4-yl]amino]pentyl]quinazolin-4-one |
| 79 | 7-(2-amino-5-methylpyrimidin-4-yl)-6-fluoro-3-[(4S)-4-[[6-oxo-5-(trifluoromethyl)-1H-pyridazin-4-yl]amino]pentyl]quinazolin-4-one |
| 80 | 6-(2-amino-5-methylpyrimidin-4-yl)-7,8-difluoro-2-[(4S)-4-[[6-oxo-5-(trifluoromethyl)-1H-pyridazin-4-yl]amino]pentyl]isoquinolin-1-one |
| 81 | 6-[4-amino-5-(trifluoromethyl)pyrimidin-2-yl]-7,8-difluoro-2-[(4S)-4-[6-oxo-5-(trifluoromethyl)-1H-pyridazin-4-yl]amino]pentyl]isoquinolin-1-one |
| 82 | 7-[5-(difluoromethyl)pyrimidin-2-yl]-6-fluoro-3-[(4S)-4-[[6-oxo-5-(trifluoromethyl)-1H-pyridazin-4-yl]amino]pentyl]quinazolin-4-one |
| 83 | 7-(5-cyclopropylpyrimidin-2-yl)-6-fluoro-3-[(4S)-4-[[6-oxo-5-(trifluoromethyl)-1H-pyridazin-4-yl]amino]pentyl]quinazolin-4-one |
| 84 | 7-fluoro-6-(5-methylsulfonylpyrimidin-2-yl)-2-[(4S)-4-[[6-oxo-5-(trifluoromethyl)-1H-pyridazin-4-yl]amino]pentyl]isoquinolin-1-one |
| 85 | 7,8-difluoro-2-[4-[6-oxo-5-(trifluoromethyl)-1H-pyridazin-4-yl]amino]butyl]-6-[5-(trifluoromethyl)pyrimidin-2-yl]isoquinolin-1-one |
| 86 | 2-[(4R)-4-deuterio-4-[[6-oxo-5-(trifluoromethyl)-1H-pyridazin-4-yl]amino]pentyl]-7,8-difluoro-6-[5-(trifluoromethyl)pyrimidin-2-yl]isoquinolin-1-one |
| 87 | 2-[(4S)-4-deuterio-4-[[6-oxo-5-(trifluoromethyl)-1H-pyridazin-4-yl]amino]pentyl]-7,8-difluoro-6-[5-(trifluoromethyl)pyrimidin-2-yl]isoquinolin-1-one |
| 88 | 7-fluoro-2-[(4R)-5-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one |
| 89 | (S)-2-(2,2-difluoro-4-((6-oxo-5-(trifluoromethyl)-1,6-dihydropyridazin-4-yl)amino)pentyl)-7-fluoro-6-(5-(trifluoromethyl)pyrimidin-2-yl)isoquinolin-1(2H)-one |
| 90 | (S)-7-fluoro-2-(2-oxo-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one |
| 91 | 7-fluoro-2-(3-((6-oxo-5-(trifluoromethyl)-1,6-dihydropyridazin-4-yl)amino)benzyl)-6-(5-(trifluoromethyl)pyrimidin-2-yl)isoquinolin-1(2H)-one |
| 92 | 6-[5-(dimethylamino)pyrimidin-2-yl]-7-fluoro-2-[(4S)-4-[6-oxo-5-(trifluoromethyl)-1H-pyridazin-4-yl]amino]pentyl]isoquinolin-1-one |

-continued

| Example | Name |
|---|---|
| 93 | 7-fluoro-6-[1-methyl-5-(trifluoromethyl)pyrazol-3-yl]-2-[(4S)-4-[[6-oxo-5-(trifluoromethyl)-1H-pyridazin-4-yl]amino]pentyl]isoquinolin-1-one |
| 94 | 6-(6,7-dihydro-5H-cyclopenta[d]pyrimidin-2-yl)-7-fluoro-2-[(4S)-4-[[6-oxo-5-(trifluoromethyl)-1H-pyridazin-4-yl]amino]pentyl]isoquinolin-1-one |
| 95 | 6-fluoro-7-(5-methylpyrimidin-2-yl)-3-[(4S)-4-[[6-oxo-5-(trifluoromethyl)-1H-pyridazin-4-yl]amino]pentyl]quinazolin-4-one |
| 96 | 6-(5-amino-4-fluoropyridin-2-yl)-7-fluoro-2-[(4S)-4-[[6-oxo-5-(trifluoromethyl)-1H-pyridazin-4-yl]amino]pentyl]isoquinolin-1-one |
| 97 | 6-[5-amino-4-(trifluoromethyl)pyridin-2-yl]-7-fluoro-2-[(4S)-4-[[6-oxo-5-(trifluoromethyl)-1H-pyridazin-4-yl]amino]pentyl]isoquinolin-1-one |
| 98 | 6-(5-chloropyrimidin-2-yl)-7-fluoro-2-[(4S)-4-[[6-oxo-5-(trifluoromethyl)-1H-pyridazin-4-yl]amino]pentyl]isoquinolin-1-one |
| 99 | 7-fluoro-6-[5-(2-oxa-6-azaspiro[3.3]heptan-6-yl)pyrimidin-2-yl]-2-[(4S)-4-[6-oxo-5-(trifluoromethyl)-1H-pyridazin-4-yl]amino]pentyl]isoquinolin-1-one |
| 100 | 6-[4-amino-5-(trifluoromethyl)pyrimidin-2-yl]-7-fluoro-2-[(4S)-4-[[6-oxo-5-(trifluoromethyl)-1H-pyridazin-4-yl]amino]pentyl]isoquinolin-1-one |
| 101 | 4-amino-2-[7-fluoro-1-oxo-2-[(4S)-4-[[6-oxo-5-(trifluoromethyl)-1H-pyridazin-4-yl]amino]pentyl]isoquinolin-6-yl]pyrimidine-5-carbonitrile |
| 102 | 6-(4-amino-5-methoxypyrimidin-2-yl)-7-fluoro-2-[(4S)-4-[[6-oxo-5-(trifluoromethyl)-1H-pyridazin-4-yl]amino]pentyl]isoquinolin-1-one |
| 103 | 6-(4-amino-5-fluoropyrimidin-2-yl)-7-fluoro-2-[(4S)-4-[[6-oxo-5-(trifluoromethyl)-1H-pyridazin-4-yl]amino]pentyl]isoquinolin-1-one |
| 104 | 6-[4-amino-5-(difluoromethyl)pyrimidin-2-yl]-7-fluoro-2-[(4S)-4-[[6-oxo-5-(trifluoromethyl)-1H-pyridazin-4-yl]amino]pentyl]isoquinolin-1-one |
| 105 | 6-[2-amino-5-(difluoromethyl)pyrimidin-4-yl]-7-fluoro-2-[(4S)-4-[[6-oxo-5-(trifluoromethyl)-1H-pyridazin-4-yl]amino]pentyl]isoquinolin-1-one |
| 106 | 7-fluoro-6-[4-(methylamino)-5-(trifluoromethyl)pyrimidin-2-yl]-2-[(4S)-4-[6-oxo-5-(trifluoromethyl)-1H-pyridazin-4-yl]amino]pentyl]isoquinolin-1-one |
| 107 | 6-(4-amino-5-cyclopropylpyrimidin-2-yl)-7-fluoro-2-[(4S)-4-[[6-oxo-5-(trifluoromethyl)-1H-pyridazin-4-yl]amino]pentyl]isoquinolin-1-one |
| 108 | 7-[4-amino-5-(difluoromethyl)pyrimidin-2-yl]-6-fluoro-3-[(4S)-4-[[6-oxo-5-(trifluoromethyl)-1H-pyridazin-4-yl]amino]pentyl]quinazolin-4-one |
| 109 | 6-(4-amino-5-methoxypyrimidin-2-yl)-7,8-difluoro-2-[(4S)-4-[6-oxo-5-(trifluoromethyl)-1H-pyridazin-4-yl]amino]pentyl]isoquinolin-1-one |
| 110 | 4-amino-2-[7,8-difluoro-1-oxo-2-[(4S)-4-[6-oxo-5-(trifluoromethyl)-1H-pyridazin-4-yl]amino]pentyl]isoquinolin-6-yl]pyrimidine-5-carbonitrile |
| 111 | 6-(4-amino-5-nitropyrimidin-2-yl)-7-fluoro-2-[(4S)-4-[[6-oxo-5-(trifluoromethyl)-1H-pyridazin-4-yl]amino]pentyl]isoquinolin-1-one |
| 112 | 6-(5,5-dimethyl-6,7-dihydropyrrolo[2,3-d]pyrimidin-2-yl)-7-fluoro-2-[(4S)-4-[6-oxo-5-(trifluoromethyl)-1H-pyridazin-4-yl]amino]pentyl]isoquinolin-1-one |
| 113 | 6-[4-amino-5-(difluoromethyl)pyrimidin-2-yl]-7,8-difluoro-2-[(4S)-4-[6-oxo-5-(trifluoromethyl)-1H-pyridazin-4-yl]amino]pentyl]isoquinolin-1-one |
| 114 | 6-[2-amino-5-(difluoromethyl)pyrimidin-4-yl]-7,8-difluoro-2-[(4S)-4-[[6-oxo-5-(trifluoromethyl)-1H-pyridazin-4-yl]amino]pentyl]isoquinolin-1-one |
| 115 | 6-fluoro-7-[4-(methylamino)-5-(trifluoromethyl)pyrimidin-2-yl]-3-[(4S)-4-[[6-oxo-5-(trifluoromethyl)-1H-pyridazin-4-yl]amino]pentyl]quinazolin-4-one |
| 116 | 7-[4-(cyclopropylamino)-5-(trifluoromethyl)pyrimidin-2-yl]-6-fluoro-3-[(4S)-4-[6-oxo-5-(trifluoromethyl)-1H-pyridazin-4-yl]amino]pentyl]quinazolin-4-one |
| 117 | 7-[4-(ethylamino)-5-(trifluoromethyl)pyrimidin-2-yl]-6-fluoro-3-[(4S)-4-[6-oxo-5-(trifluoromethyl)-1H-pyridazin-4-yl]amino]pentyl]quinazolin-4-one |
| 118 | 6-(7,8-dihydro-6H-pyrimido[5,4-b][1,4]oxazin-2-yl)-7-fluoro-2-[(4S)-4-[[6-oxo-5-(trifluoromethyl)-1H-pyridazin-4-yl]amino]pentyl]isoquinolin-1-one |
| 119 | 1-[2-[7-fluoro-1-oxo-2-[(4S)-4-[6-oxo-5-(trifluoromethyl)-1H-pyridazin-4-yl]amino]pentyl]isoquinolin-6-yl]-5-(trifluoromethyl)pyrimidin-4-yl]azetidine-3-carbonitrile |
| 120 | 7-fluoro-2-[3-[(2S)-1-[6-oxo-5-(trifluoromethyl)-1H-pyridazin-4-yl]pyrrolidin-2-yl]propyl]-6-[5-(trifluoromethyl)pyrimidin-2-yl]isoquinolin-1-one |
| 121 | 6-[4-amino-5-(trifluoromethyl)pyrimidin-2-yl]-7-fluoro-2-[3-[(2S)-1-[6-oxo-5-(trifluoromethyl)-1H-pyridazin-4-yl]pyrrolidin-2-yl]propyl]isoquinolin-1-one |
| 122 | 6-(4-amino-5-methoxypyrimidin-2-yl)-7-fluoro-2-[3-[(2S)-1-[6-oxo-5-(trifluoromethyl)-1H-pyridazin-4-yl]pyrrolidin-2-yl]propyl]isoquinolin-1-one |
| 123 | 6-[4-amino-5-(trifluoromethyl)pyrimidin-2-yl]-7-fluoro-2-[2-[(1R,2S)-2-[[6-oxo-5-(trifluoromethyl)-1H-pyridazin-4-yl]amino]cyclobutyl]ethyl]isoquinolin-1-one |
| 124 | 6-fluoro-7-[4-(3-hydroxyazetidin-1-yl)-5-(trifluoromethyl)pyrimidin-2-yl]-3-[(4S)-4-[[6-oxo-5-(trifluoromethyl)-1H-pyridazin-4-yl]amino]pentyl]quinazolin-4-one |
| 125 | 4-amino-2-[6-fluoro-4-oxo-3-[(4S)-4-[[6-oxo-5-(trifluoromethyl)-1H-pyridazin-4-yl]amino]pentyl]quinazolin-7-yl]pyrimidine-5-carbonitrile |
| 126 | 6-fluoro-7-(5-methylsulfonylpyrimidin-2-yl)-3-[(4S)-4-[[6-oxo-5-(trifluoromethyl)-1H-pyridazin-4-yl]amino]pentyl]quinazolin-4-one |
| 127 | 6-fluoro-7-[5-(2-hydroxyethoxy)pyrimidin-2-yl]-3-[(4S)-4-[[6-oxo-5-(trifluoromethyl)-1H-pyridazin-4-yl]amino]pentyl]quinazolin-4-one |
| 128 | 7-[4-amino-5-(trifluoromethyl)pyrimidin-2-yl]-6-fluoro-3-[(4S)-4-[[6-oxo-5-(trifluoromethyl)-1H-pyridazin-4-yl]amino]pentyl]quinazolin-4-one |
| 129 | 7-fluoro-6-[5-(2-hydroxyethoxy)pyrimidin-2-yl]-2-[(4S)-4-[[6-oxo-5-(trifluoromethyl)-1H-pyridazin-4-yl]amino]pentyl]isoquinolin-1-one |

-continued

| Example | Name |
|---|---|
| 130 | 7,8-difluoro-2-[[3-[[[6-oxo-5-(trifluoromethyl)-1H-pyridazin-4-yl]amino]methyl]cyclobutyl]methyl]-6-[5-(trifluoromethyl)pyrimidin-2-yl]isoquinolin-1-one |
| 131 | 7,8-difluoro-2-[(Z,4R)-3-fluoro-4-[[6-oxo-5-(trifluoromethyl)-1H-pyridazin-4-yl]amino]pent-2-enyl]-6-[5-(trifluoromethyl)pyrimidin-2-yl]isoquinolin-1-one |
| 132 | 7,8-difluoro-2-[(Z,4S)-3-fluoro-4-[[6-oxo-5-(trifluoromethyl)-1H-pyridazin-4-yl]amino]pent-2-enyl]-6-[5-(trifluoromethyl)pyrimidin-2-yl]isoquinolin-1-one |
| 133 | 7,8-difluoro-2-[(E,4S)-4-[6-oxo-5-(trifluoromethyl)-1H-pyridazin-4-yl]amino]pent-2-enyl]-6-[5-(trifluoromethyl)pyrimidin-2-yl]isoquinolin-1-one |
| 134 | 6-(4-amino-5-methoxypyrimidin-2-yl)-7-fluoro-2-[(E,4S)-4-[6-oxo-5-(trifluoromethyl)-1H-pyridazin-4-yl]amino]pent-2-enyl]isoquinolin-1-one |
| 135 | 7-fluoro-2-[(4R)-5-methoxy-4-[[6-oxo-5-(trifluoromethyl)-1H-pyridazin-4-yl]amino]pentyl]-6-[5-(trifluoromethyl)pyrimidin-2-yl]isoquinolin-1-one |
| 136 | 7-fluoro-2-[4-[[6-oxo-5-(trifluoromethyl)-1H-pyridazin-4-yl]oxy]pentyl]-6-[5-(trifluoromethyl)pyrimidin-2-yl]isoquinolin-1-one |
| 137 | 6-[4-amino-5-(trifluoromethyl)pyrimidin-2-yl]-7-fluoro-2-[4-methyl-4-[[6-oxo-5-(trifluoromethyl)-1H-pyridazin-4-yl]amino]pentyl]isoquinolin-1-one |
| 138 | 7-fluoro-2-[3-[(2R,4S)-4-hydroxy-1-[6-oxo-5-(trifluoromethyl)-1H-pyridazin-4-yl]pyrrolidin-2-yl]propyl]-6-[5-(trifluoromethyl)pyrimidin-2-yl]isoquinolin-1-one |
| 139 | 2-[3-[(2R)-4,4-difluoro-1-[6-oxo-5-(trifluoromethyl)-1H-pyridazin-4-yl]pyrrolidin-2-yl]propyl]-7-fluoro-6-[5-(trifluoromethyl)pyrimidin-2-yl]isoquinolin-1-one |
| 140 | 7-fluoro-2-[3-[(2R,4R)-4-fluoro-1-[6-oxo-5-(trifluoromethyl)-1H-pyridazin-4-yl]pyrrolidin-2-yl]propyl]-6-[5-(trifluoromethyl)pyrimidin-2-yl]isoquinolin-1-one |
| 141 | 7-fluoro-2-[3-[(2R,4S)-4-fluoro-1-[6-oxo-5-(trifluoromethyl)-1H-pyridazin-4-yl]pyrrolidin-2-yl]propyl]-6-[5-(trifluoromethyl)pyrimidin-2-yl]isoquinolin-1-one |
| 142 | 7-fluoro-2-[3-[(6R)-5-[6-oxo-5-(trifluoromethyl)-1H-pyridazin-4-yl]-5-azaspiro[2.4]heptan-6-yl]propyl]-6-[5-(trifluoromethyl)pyrimidin-2-yl]isoquinolin-1-one |
| 143 | 6-[4-amino-5-(difluoromethyl)pyrimidin-2-yl]-7-fluoro-2-[3-[(6R)-5-[6-oxo-5-(trifluoromethyl)-1H-pyridazin-4-yl]-5-azaspiro[2.4]heptan-6-yl]propyl]isoquinolin-1-one |
| 144 | 6-[4-amino-5-(trifluoromethyl)pyrimidin-2-yl]-2-[(4R)-4-cyclopropyl-4-[[6-oxo-5-(trifluoromethyl)-1H-pyridazin-4-yl]amino]butyl]-7-fluoroisoquinolin-1-one |
| 145 | 4-amino-2-[2-[(4R)-4-cyclopropyl-4-[[6-oxo-5-(trifluoromethyl)-1H-pyridazin-4-yl]amino]butyl]-7-fluoro-1-oxoisoquinolin-6-yl]pyrimidine-5-carbonitrile |
| 146 | 6-(4-amino-5-methoxypyrimidin-2-yl)-2-[(4R)-4-cyclopropyl-4-[[6-oxo-5-(trifluoromethyl)-1H-pyridazin-4-yl]amino]butyl]-7-fluoroisoquinolin-1-one |
| 147 | 6-[4-amino-5-(difluoromethyl)pyrimidin-2-yl]-2-[(4R)-4-cyclopropyl-4-[6-oxo-5-(trifluoromethyl)-1H-pyridazin-4-yl]amino]butyl]-7-fluoroisoquinolin-1-one |
| 148 | 7-fluoro-2-[3-[(2S)-1-[6-oxo-5-(trifluoromethyl)-1H-pyridazin-4-yl]azetidin-2-yl]propyl]-6-[5-(trifluoromethyl)pyrimidin-2-yl]isoquinolin-1-one |
| 149 | 7-fluoro-2-[3-[(2R)-1-[6-oxo-5-(trifluoromethyl)-1H-pyridazin-4-yl]azetidin-2-yl]propyl]-6-[5-(trifluoromethyl)pyrimidin-2-yl]isoquinolin-1-one |
| 150 | 6-fluoro-3-[3-[1-[6-oxo-5-(trifluoromethyl)-1H-pyridazin-4-yl]azetidin-2-yl]propyl]-7-[5-(trifluoromethyl)pyrimidin-2-yl]quinazolin-4-one |
| 151 | 6-fluoro-3-[3-[(2S)-1-[6-oxo-5-(trifluoromethyl)-1H-pyridazin-4-yl]azetidin-2-yl]propyl]-7-[5-(trifluoromethyl)pyrimidin-2-yl]quinazolin-4-one |
| 152 | 6-fluoro-3-[3-[(2R)-1-[6-oxo-5-(trifluoromethyl)-1H-pyridazin-4-yl]azetidin-2-yl]propyl]-7-[5-(trifluoromethyl)pyrimidin-2-yl]quinazolin-4-one |
| 153 | 6-(4-amino-5-methoxypyrimidin-2-yl)-7-fluoro-2-[3-[1-[6-oxo-5-(trifluoromethyl)-1H-pyridazin-4-yl]azetidin-2-yl]propyl]isoquinolin-1-one |
| 154 | 7-fluoro-2-[3-[2-[6-oxo-5-(trifluoromethyl)-1H-pyridazin-4-yl]pyrazolidin-1-yl]propyl]-6-[5-(trifluoromethyl)pyrimidin-2-yl]isoquinolin-1-one |
| 155 | 6-fluoro-3-[(4S)-4-[[6-oxo-5-(trifluoromethyl)-1H-pyridazin-4-yl]amino]hexyl]-7-[5-(trifluoromethyl)pyrimidin-2-yl]quinazolin-4-one |
| 156 | 7-[5-(difluoromethyl)pyrimidin-2-yl]-6-fluoro-3-[(4S)-4-[[6-oxo-5-(trifluoromethyl)-1H-pyridazin-4-yl]amino]hexyl]quinazolin-4-one |
| 157 | 7-(5-chloropyrimidin-2-yl)-6-fluoro-3-[(4S)-4-[[6-oxo-5-(trifluoromethyl)-1H-pyridazin-4-yl]amino]hexyl]quinazolin-4-one |
| 158 | 6-[4-(2,2-difluoroethylamino)-5-methoxypyrimidin-2-yl]-7-fluoro-2-[(4S)-4-[[6-oxo-5-(trifluoromethyl)-1H-pyridazin-4-yl]amino]pentyl]isoquinolin-1-one |
| 159 | 7-[4-(2,2-difluoroethylamino)-5-methoxypyrimidin-2-yl]-6-fluoro-3-[(4S)-4-[[6-oxo-5-(trifluoromethyl)-1H-pyridazin-4-yl]amino]pentyl]quinazolin-4-one |
| 160 | (3R)-6-[7-fluoro-1-oxo-6-[5-(trifluoromethyl)pyrimidin-2-yl]isoquinolin-2-yl]-3-[[6-oxo-5-(trifluoromethyl)-1H-pyridazin-4-yl]amino]hexanenitrile |
| 161 | 7,8-difluoro-2-[(4R)-4-[[6-oxo-5-(trifluoromethyl)-1H-pyridazin-4-yl]amino]hept-5-ynyl]-6-[5-(trifluoromethyl)pyrimidin-2-yl]isoquinolin-1-one |
| 162 | (2R)-5-[7-fluoro-1-oxo-6-[5-(trifluoromethyl)pyrimidin-2-yl]isoquinolin-2-yl]-2-[6-oxo-5-(trifluoromethyl)-1H-pyridazin-4-yl]amino]pentanenitrile |
| 163 | 7,8-difluoro-2-[(4R)-5-hydroxy-4-[[6-oxo-5-(trifluoromethyl)-1H-pyridazin-4-yl]amino]pentyl]-6-[5-(trifluoromethyl)pyrimidin-2-yl]isoquinolin-1-one |
| 164 | 6-fluoro-3-[(4R)-5-hydroxy-4-[[6-oxo-5-(trifluoromethyl)-1H-pyridazin-4-yl]amino]pentyl]-7-[5-(trifluoromethyl)pyrimidin-2-yl]quinazolin-4-one |
| 165 | 6-[5-(difluoromethyl)pyrimidin-2-yl]-7-fluoro-2-[(4R)-5-hydroxy-4-[6-oxo-5-(trifluoromethyl)-1H-pyridazin-4-yl]amino]pentyl]isoquinolin-1-one |
| 166 | 6-(5-chloropyrimidin-2-yl)-7-fluoro-2-[(4R)-5-hydroxy-4-[[6-oxo-5-(trifluoromethyl)-1H-pyridazin-4-yl]amino]pentyl]isoquinolin-1-one |
| 167 | 6-[6-amino-5-(trifluoromethyl)pyridin-2-yl]-7-fluoro-2-[(4R)-5-hydroxy-4-[[6-oxo-5-(trifluoromethyl)-1H-pyridazin-4-yl]amino]pentyl]isoquinolin-1-one |

-continued

| Example | Name |
|---|---|
| 168 | 2-[(4R)-5-(difluoromethoxy)-4-[[6-oxo-5-(trifluoromethyl)-1H-pyridazin-4-yl]amino]pentyl]-7-fluoro-6-[5-(trifluoromethyl)pyrimidin-2-yl]isoquinolin-1-one |
| 169 | 7-fluoro-2-[(4R)-4-(5-methyl-1,3,4-oxadiazol-2-yl)-4-[6-oxo-5-(trifluoromethyl)-1H-pyridazin-4-yl]amino]butyl]-6-[5-(trifluoromethyl)pyrimidin-2-yl]isoquinolin-1-one |
| 170 | 7-fluoro-2-[(4R)-4-[[6-oxo-5-(trifluoromethyl)-1H-pyridazin-4-yl]amino]hex-5-ynyl]-6-[5-(trifluoromethyl)pyrimidin-2-yl]isoquinolin-1-one |
| 171 | 7,8-difluoro-2-[(4S)-4-[[6-oxo-5-(trifluoromethyl)-1H-pyridazin-4-yl]amino]hex-5-ynyl]-6-[5-(trifluoromethyl)pyrimidin-2-yl]isoquinolin-1-one |
| 172 | 7-fluoro-2-[3-[methyl-[[6-oxo-5-(trifluoromethyl)-1H-pyridazin-4-yl]amino]amino]propyl]-6-[5-(trifluoromethyl)pyrimidin-2-yl]isoquinolin-1-one |
| 173 | 2-[(4S)-4-[[6-oxo-5-(trifluoromethyl)-1H-pyridazin-4-yl]amino]pentyl]-6-[4-(trifluoromethyl)pyrazol-1-yl]isoquinolin-1-one |
| 174 | 7-fluoro-2-[3-[(2R,4R)-4-methyl-1-[6-oxo-5-(trifluoromethyl)-1H-pyridazin-4-yl]pyrrolidin-2-yl]propyl]-6-[5-(trifluoromethyl)pyrimidin-2-yl]isoquinolin-1-one |
| 175 | 6-(4-amino-5-methoxypyrimidin-2-yl)-7-fluoro-2-[3-[(2R,4R)-4-methyl-1-[6-oxo-5-(trifluoromethyl)-1H-pyridazin-4-yl]pyrrolidin-2-yl]propyl]isoquinolin-1-one |
| 176 | 6-fluoro-3-[3-[(2R,4R)-4-methyl-1-[6-oxo-5-(trifluoromethyl)-1H-pyridazin-4-yl]pyrrolidin-2-yl]propyl]-7-[5-(trifluoromethyl)pyrimidin-2-yl]quinazolin-4-one |
| 177 | 7-(4-amino-5-methoxypyrimidin-2-yl)-6-fluoro-3-[3-[(2R,4R)-4-methyl-1-[6-oxo-5-(trifluoromethyl)-1H-pyridazin-4-yl]pyrrolidin-2-yl]propyl]quinazolin-4-one |
| 178 | 6-[4-amino-5-(trifluoromethyl)pyrimidin-2-yl]-7-fluoro-2-[2-[(1R,2S)-2-[[6-oxo-5-(trifluoromethyl)-1H-pyridazin-4-yl]amino]cyclopentyl]ethyl]isoquinolin-1-one |
| 179 | 7-fluoro-2-[2-[(1R,2S)-2-[[6-oxo-5-(trifluoromethyl)-1H-pyridazin-4-yl]amino]cyclopentyl]ethyl]-6-[5-(trifluoromethyl)pyrimidin-2-yl]isoquinolin-1-one |
| 180 | 2-[(4R)-5-ethoxy-4-[[6-oxo-5-(trifluoromethyl)-1H-pyridazin-4-yl]amino]pentyl]-7-fluoro-6-[5-(trifluoromethyl)pyrimidin-2-yl]isoquinolin-1-one |
| 181 | 7-fluoro-2-[(4R)-4-[[6-oxo-5-(trifluoromethyl)-1H-pyridazin-4-yl]amino]-5-(trideuteriomethoxy)pentyl]-6-[5-(trifluoromethyl)pyrimidin-2-yl]isoquinolin-1-one |
| 182 | (R)-7-fluoro-2-(3-(2-(6-oxo-5-(trifluoromethyl)-1,6-dihydropyridazin-4-yl)isoindolin-1-yl)propyl)-6-(5-(trifluoromethyl)pyrimidin-2-yl)isoquinolin-1(2H)-one |
| 183 | 7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 184 | 6-(4-amino-5-(trifluoromethyl)pyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 185 | (S)-2-(7-fluoro-1-oxo-2-(4-((6-oxo-5-(trifluoromethyl)-1,6-dihydropyridazin-4-yl)amino)pentyl)-1,2-dihydroisoquinolin-6-yl)-6H-pyrimido[5,4-b][1,4]oxazin-7(8H)-one |
| 186 | (S)-6-(4-(azetidin-1-yl)-5-methoxypyrimidin-2-yl)-7-fluoro-2-(4-((6-oxo-5-(trifluoromethyl)-1,6-dihydropyridazin-4-yl)amino)pentyl)isoquinolin-1(2H)-one |
| 187 | (S)-6-(4-(azetidin-1-yl)-5-(trifluoromethyl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 188 | (S)-7-(4-(azetidin-1-yl)-5-methoxypyrimidin-2-yl)-6-fluoro-3-(4-((6-oxo-5-(trifluoromethyl)-1,6-dihydropyridazin-4-yl)amino)pentyl)quinazolin-4(3H)-one |
| 189 | (S)-7-(4-(azetidin-1-yl)-5-(trifluoromethyl)pyrimidin-2-yl)-6-fluoro-3-(4-((6-oxo-5-(trifluoromethyl)-1,6-dihydropyridazin-4-yl)amino)pentyl)quinazolin-4(3H)-one |
| 190 | (S)-6-fluoro-7-(4-(3-hydroxy-3-methylazetidin-1-yl)-5-(trifluoromethyl)pyrimidin-2-yl)-3-(4-((6-oxo-5-(trifluoromethyl)-1,6-dihydropyridazin-4-yl)amino)pentyl)quinazolin-4(3H)-one |
| 191 | (S)-7-fluoro-6-(4-(3-hydroxy-3-methylazetidin-1-yl)-5-(trifluoromethyl)pyrimidin-2-yl)-2-(4-((6-oxo-5-(trifluoromethyl)-1,6-dihydropyridazin-4-yl)amino)pentyl)isoquinolin-1(2H)-one |
| 192 | (S)-6-(4-amino-5-ethoxypyrimidin-2-yl)-7-fluoro-2-(4-((6-oxo-5-(trifluoromethyl)-1,6-dihydropyridazin-4-yl)amino)pentyl)isoquinolin-1(2H)-one |
| 193 | (S)-6-(6-amino-5-ethoxypyridin-2-yl)-7-fluoro-2-(4-((6-oxo-5-(trifluoromethyl)-1,6-dihydropyridazin-4-yl)amino)pentyl)isoquinolin-1(2H)-one |
| 194 | (S)-6-(4-amino-5-(difluoromethoxy)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 195 | (S)-6-(6-amino-5-methoxypyridin-2-yl)-7-fluoro-2-(4-((6-oxo-5-(trifluoromethyl)-1,6-dihydropyridazin-4-yl)amino)pentyl)isoquinolin-1(2H)-one |
| 196 | 6-[4-amino-5-(trideuteriomethoxy)pyrimidin-2-yl]-7-fluoro-2-[(4S)-4-[[6-oxo-5-(trifluoromethyl)-1H-pyridazin-4-yl]amino]pentyl]isoquinolin-1-one |
| 197 | (S)-6-(4-(difluoromethyl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 198 | (S)-6-(4-aminopyrimidin-2-yl)-7-fluoro-2-(4-((6-oxo-5-(trifluoromethyl)-1,6-dihydropyridazin-4-yl)amino)pentyl)isoquinolin-1(2H)-one |
| 199 | (S)-6-(5-aminopyrimidin-2-yl)-7-fluoro-2-(4-((6-oxo-5-(trifluoromethyl)-1,6-dihydropyridazin-4-yl)amino)pentyl)isoquinolin-1(2H)-one |
| 200 | (S)-7-(5-chloropyrimidin-2-yl)-6-fluoro-3-(4-((6-oxo-5-(trifluoromethyl)-1,6-dihydropyridazin-4-yl)amino)pentyl)quinazolin-4(3H)-one |
| 201 | (S)-6-fluoro-7-(4-morpholino-5-(trifluoromethyl)pyrimidin-2-yl)-3-(4-((6-oxo-5-(trifluoromethyl)-1,6-dihydropyridazin-4-yl)amino)pentyl)quinazolin-4(3H)-one |
| 202 | (S)-6-(4-amino-5-chloropyrimidin-2-yl)-7-fluoro-2-(4-((6-oxo-5-(trifluoromethyl)-1,6-dihydropyridazin-4-yl)amino)pentyl)isoquinolin-1(2H)-one |
| 203 | (S)-6-(4-(difluoromethyl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 204 | (S)-6-(4-aminopyrimidin-2-yl)-7-fluoro-2-(4-((6-oxo-5-(trifluoromethyl)-1,6-dihydropyridazin-4-yl)amino)pentyl)isoquinolin-1(2H)-one |

-continued

| Example | Name |
|---|---|
| 205 | (S)-6-(5-aminopyrimidin-2-yl)-7-fluoro-2-(4-((6-oxo-5-(trifluoromethyl)-1,6-dihydropyridazin-4-yl)amino)pentyl)isoquinolin-1(2H)-one |
| 206 | (S)-7-(5-chloropyrimidin-2-yl)-6-fluoro-3-(4-((6-oxo-5-(trifluoromethyl)-1,6-dihydropyridazin-4-yl)amino)pentyl)quinazolin-4(3H)-one |
| 207 | (S)-6-fluoro-7-(4-morpholino-5-(trifluoromethyl)pyrimidin-2-yl)-3-(4-((6-oxo-5-(trifluoromethyl)-1,6-dihydropyridazin-4-yl)amino)pentyl)quinazolin-4(3H)-one |
| 208 | (S)-6-(4-amino-5-chloropyrimidin-2-yl)-7-fluoro-2-(4-((6-oxo-5-(trifluoromethyl)-1,6-dihydropyridazin-4-yl)amino)pentyl)isoquinolin-1(2H)-one |
| 209 | (S)-6-(4-(difluoromethyl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 210 | (S)-6-(4-aminopyrimidin-2-yl)-7-fluoro-2-(4-((6-oxo-5-(trifluoromethyl)-1,6-dihydropyridazin-4-yl)amino)pentyl)isoquinolin-1(2H)-one |
| 211 | (S)-6-(5-aminopyrimidin-2-yl)-7-fluoro-2-(4-((6-oxo-5-(trifluoromethyl)-1,6-dihydropyridazin-4-yl)amino)pentyl)isoquinolin-1(2H)-one |
| 212 | (S)-7-(5-chloropyrimidin-2-yl)-6-fluoro-3-(4-((6-oxo-5-(trifluoromethyl)-1,6-dihydropyridazin-4-yl)amino)pentyl)quinazolin-4(3H)-one |
| 213 | (S)-6-fluoro-7-(4-morpholino-5-(trifluoromethyl)pyrimidin-2-yl)-3-(4-((6-oxo-5-(trifluoromethyl)-1,6-dihydropyridazin-4-yl)amino)pentyl)quinazolin-4(3H)-one |
| 214 | (S)-6-(4-amino-5-chloropyrimidin-2-yl)-7-fluoro-2-(4-((6-oxo-5-(trifluoromethyl)-1,6-dihydropyridazin-4-yl)amino)pentyl)isoquinolin-1(2H)-one |
| 215 | (S)-6-(4-(ethylamino)-5-methoxypyrimidin-2-yl)-7-fluoro-2-(4-((6-oxo-5-(trifluoromethyl)-1,6-dihydropyridazin-4-yl)amino)pentyl)isoquinolin-1(2H)-one |
| 216 | (S)-6-(4-(cyclopropylamino)-5-methoxypyrimidin-2-yl)-7-fluoro-2-(4-((6-oxo-5-(trifluoromethyl)-1,6-dihydropyridazin-4-yl)amino)pentyl)isoquinolin-1(2H)-one |
| 217 | (S)-7-fluoro-6-(5-methoxy-4-(oxetan-3-ylamino)pyrimidin-2-yl)-2-(4-((6-oxo-5-(trifluoromethyl)-1,6-dihydropyridazin-4-yl)amino)pentyl)isoquinolin-1(2H)-one |
| 218 | (S)-7-fluoro-6-(4-((2-hydroxyethyl)amino)-5-methoxypyrimidin-2-yl)-2-(4-((6-oxo-5-(trifluoromethyl)-1,6-dihydropyridazin-4-yl)amino)pentyl)isoquinolin-1(2H)-one |
| 219 | (S)-6-(4-((1-(difluoromethyl)cyclopropyl)amino)-5-methoxypyrimidin-2-yl)-7-fluoro-2-(4-((6-oxo-5-(trifluoromethyl)-1,6-dihydropyridazin-4-yl)amino)pentyl)isoquinolin-1(2H)-one |
| 220 | (S)-7-(4-(cyclopropylamino)-5-methoxypyrimidin-2-yl)-6-fluoro-3-(4-((6-oxo-5-(trifluoromethyl)-1,6-dihydropyridazin-4-yl)amino)pentyl)quinazolin-4(3H)-one |
| 221 | (S)-6-(4-(cyclopropylamino)-5-(difluoromethyl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 222 | (S)-6-(5-(difluoromethyl)-4-((2-hydroxyethyl)amino)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 223 | 6-(5-(difluoromethyl)-4-(((1R,2S)-2-fluorocyclopropyl)amino)pyrimidin-2-yl)-7-fluoro-2-((S)-4-((6-oxo-5-(trifluoromethyl)-1,6-dihydropyridazin-4-yl)amino)pentyl)isoquinolin-1(2H)-one |
| 224 | (S)-6-(6-amino-5-(difluoromethyl)pyridin-2-yl)-7-fluoro-2-(4-((6-oxo-5-(trifluoromethyl)-1,6-dihydropyridazin-4-yl)amino)pentyl)isoquinolin-1(2H)-one |
| 22.5 | (S)-6-(6,6-dioxido-5,7-dihydrothieno[3,4-d]pyrimidin-2-yl)-7-fluoro-2-(4-((6-oxo-5-(trifluoromethyl)-1,6-dihydropyridazin-4-yl)amino)pentyl)isoquinolin-1(2H)-one |
| 226 | 6-(5-(difluoromethyl)pyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 227 | 6-(4-amino-5-(trifluoromethyl)pyrimidin-2-yl)-7-fluoro-2-(((1S,3S)-3-((6-oxo-5-(trifluoromethyl)-1,6-dihydropyridazin-4-yl)amino)cyclohexyl)methyl)isoquinolin-1(2H)-one |
| 228 | 7-fluoro-2-(((1S,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 229 | 7-fluoro-2-(((3R,5R)-5-((6-oxo-5-(trifluoromethyl)-1,6-dihydropyridazin-4-yl)amino)tetrahydro-2H-pyran-3-yl)methyl)-6-(5-(trifluoromethyl)pyrimidin-2-yl)isoquinolin-1(2H)-one |
| 230 | 6-(4-amino-5-(trifluoromethyl)pyrimidin-2-yl)-7-fluoro-2-(((3R,5R)-5-((6-oxo-5-(trifluoromethyl)-1,6-dihydropyridazin-4-yl)amino)tetrahydro-2H-pyran-3-yl)methyl)isoquinolin-1(2H)-one |
| 231 | 6-(4-amino-5-(difluoromethyl)pyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 232 | 7,8-difluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 235 | 6-(5-(difluoromethyl)pyrimidin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 236 | 6-(4-amino-5-(trifluoromethyl)pyrimidin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 237 | 6-fluoro-3-(((1R,3S)-3-((6-oxo-5-(trifluoromethyl)-1,6-dihydropyridazin-4-yl)amino)cyclohexyl)methyl)-7-(5-(trifluoromethyl)pyrimidin-2-yl)quinazolin-4(3H)-one |
| 238 | 7-(4-amino-5-(difluoromethyl)pyrimidin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one |
| 239 | 7-fluoro-2-(((1S,3R)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |

-continued

| Example | Name |
|---|---|
| 240 | 6-(4-amino-5-(trifluoromethyl)pyrimidin-2-yl)-7-fluoro-2-(((1S,3R)-3-((6-oxo-5-(trifluoromethyl)-1,6-dihydropyridazin-4-yl)amino)cyclohexyl)methyl)isoquinolin-1(2H)-one |
| 241 | 6-(4-amino-5-(difluoromethyl)pyrimidin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 242 | 7-fluoro-6-(5-methylpyrimidin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 243 | 6-(4-amino-5-chloropyrimidin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 244 | 7-(5-(difluoromethyl)pyrimidin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one |
| 245 | 6-(4-amino-5-(difluoromethoxy)pyrimidin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 246 | 6-(5-chloropyrimidin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 247 | 7-(5-chloropyrimidin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one |
| 248 | 6-(5-chloropyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 249 | 6-(6-amino-5-(trifluoromethyl)pyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 250 | 6-(4-amino-5-chloropyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 251 | 6-(6-amino-5-(trifluoromethyl)pyridin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 252 | 6-(6-amino-5-(trifluoromethyl)pyridin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 253 | 6-(5-(difluoromethyl)pyrazin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 254 | 7-(6-amino-5-(trifluoromethyl)pyrazin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one |
| 255 | 6-(4-amino-5-methoxypyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 256 | 7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrazin-2-yl)isoquinolin-1(2H)-one |
| 257 | 6-(6-amino-5-(trifluoromethyl)pyrazin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 258 | 6-(5-(difluoromethyl)pyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 259 | 6-(5-(difluoromethoxy)pyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 260 | 6-(4-amino-5-(difluoromethoxy)pyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 261 | 7-(4-amino-5-chloropyrimidin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one |
| 262 | 6-(6-amino-5-methylpyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 263 | 6-(6-amino-5-methoxypyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 264 | 6-(6-amino-5-(difluoromethyl)pyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 265 | 7-(4-amino-5-(difluoromethoxy)pyrimidin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one |
| 266 | 7-fluoro-6-(5-(oxetan-3-yl)pyrazin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 267 | 7-fluoro-6-(5-(2-hydroxypropan-2-yl)pyrazin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 268 | 7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyridin-2-yl)isoquinolin-1(2H)-one |
| 269 | 6-(6-amino-5-(difluoromethyl)pyridin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |

-continued

| Example | Name |
|---|---|
| 270 | 6-(5-cyclopropylpyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 271 | 6-(5-amino-6-(trifluoromethyl)pyridin-3-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 272 | 7-fluoro-2-(((1R,3S)-3-((6-oxo-5-(trifluoromethyl)-1,6-dihydropyridazin-4-yl)amino)cyclohexyl)methyl)-6-(4-(trifluoromethyl)pyrimidin-2-yl)isoquinolin-1(2H)-one |
| 273 | 6-(((1R,3S)-3-((6-oxo-5-(trifluoromethyl)-1,6-dihydropyridazin-4-yl)amino)cyclohexyl)methyl)-2-(5-(trifluoromethyl)pyridin-2-yl)-1,6-naphthyridin-5(6H)-one |
| 274 | 7-fluoro-6-(5-(methylamino)pyrazin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 275 | 6-(5-(3-aminooxetan-3-yl)pyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 276 | 6-(4-amino-5-chloro-6-methylpyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 277 | 6-(5-(ethylamino)pyrazin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 278 | 6-(4-amino-5-methoxypyrimidin-2-yl)-7,8-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 279 | 6-(5-(1,1-difluoro-2-hydroxyethyl)pyridin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 280 | 6-(5-chloropyridin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 281 | 6-fluoro-3-(((1R,3S)-3-((6-oxo-5-(trifluoromethyl)-1,6-dihydropyridazin-4-yl)amino)cyclohexyl)methyl)-7-(5-(trifluoromethyl)pyrimidin-2-yl)quinazoline-2,4(1H,3H)-dione |
| 282 | 6-(4-amino-5-chloro-6-cyclopropylpyrimidin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 283 | 7-fluoro-6-(5-(2-hydroxypropan-2-yl)pyridin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 284 | 7-fluoro-6-(5-(2-hydroxypropan-2-yl)pyrimidin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 285 | 8-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 286 | (S)-7-fluoro-6-(4-(3-hydroxy-3-(trifluoromethyl)azetidin-1-yl)-5-methoxypyrimidin-2-yl)-2-(4-((6-oxo-5-(trifluoromethyl)-1,6-dihydropyridazin-4-yl)amino)pentyl)isoquinolin-1(2H)-one |
| 287 | (S)-6-fluoro-7-(4-(3-hydroxy-3-(trifluoromethyl)azetidin-1-yl)-5-methoxypyrimidin-2-yl)-3-(4-((6-oxo-5-(trifluoromethyl)-1,6-dihydropyridazin-4-yl)amino)pentyl)quinazolin-4(3H)-one |
| 288 | 6-fluoro-7-(4-((2R,3R)-3-hydroxy-2-methylazetidin-1-yl)-5-(trifluoromethyl)pyrimidin-2-yl)-3-((S)-4-((6-oxo-5-(trifluoromethyl)-1,6-dihydropyridazin-4-yl)amino)pentyl)quinazolin-4(3H)-one |
| 289 | (S)-2-(7-fluoro-1-oxo-2-(4-((6-oxo-5-(trifluoromethyl)-1,6-dihydropyridazin-4-yl)amino)pentyl)-1,2-dihydroisoquinolin-6-yl)-5-(trifluoromethyl)nicotinonitrile |
| 290 | (S)-6-amino-2-(7-fluoro-1-oxo-2-(4-((6-oxo-5-(trifluoromethyl)-1,6-dihydropyridazin-4-yl)amino)pentyl)-1,2-dihydroisoquinolin-6-yl)-5-(trifluoromethyl)nicotinonitrile |
| 291 | (S)-6-amino-2-(7-fluoro-1-oxo-2-(4-((6-oxo-5-(trifluoromethyl)-1,6-dihydropyridazin-4-yl)amino)pentyl)-1,2-dihydroisoquinolin-6-yl)nicotinonitrile |
| 292 | (S)-7-fluoro-2-(4-((6-oxo-5-(trifluoromethyl)-1,6-dihydropyridazin-4-yl)amino)pentyl)-6-(thieno[2,3-d]pyrimidin-2-yl)isoquinolin-1(2H)-one |
| 293 | (S)-6-(6-amino-5-chloropyridin-2-yl)-7-fluoro-2-(4-((6-oxo-5-(trifluoromethyl)-1,6-dihydropyridazin-4-yl)amino)pentyl)isoquinolin-1(2H)-one |
| 294 | (S)-7-(6-amino-5-chloropyridin-2-yl)-6-fluoro-3-(4-((6-oxo-5-(trifluoromethyl)-1,6-dihydropyridazin-4-yl)amino)pentyl)quinazolin-4(3H)-one |
| 295 | (S)-6-(7-fluoro-1-oxo-2-(4-((6-oxo-5-(trifluoromethyl)-1,6-dihydropyridazin-4-yl)amino)pentyl)-1,2-dihydroisoquinolin-6-yl)-2-(trifluoromethyl)nicotinonitrile |
| 296 | (S)-7-fluoro-6-(5-methyl-6-(trifluoromethyl)pyridin-2-yl)-2-(4-((6-oxo-5-(trifluoromethyl)-1,6-dihydropyridazin-4-yl)amino)pentyl)isoquinolin-1(2H)-one |
| 297 | (S)-6-(4-amino-5-(difluoromethyl)pyrimidin-2-yl)-7-fluoro-2-(4-((6-oxo-5-(trifluoromethyl)-1,6-dihydropyridazin-4-yl)amino)hexyl)isoquinolin-1(2H)-one |
| 298 | (S)-7-fluoro-6-(4-morpholinothieno[3,2-d]pyrimidin-2-yl)-2-(4-((6-oxo-5-(trifluoromethyl)-1,6-dihydropyridazin-4-yl)amino)pentyl)isoquinolin-1(2H)-one |
| 299 | (S)-7-fluoro-2-(4-((6-oxo-5-(trifluoromethyl)-1,6-dihydropyridazin-4-yl)amino)pentyl)-6-(1H-pyrazolo[3,4-d]pyrimidin-6-yl)isoquinolin-1(2H)-one |
| 300 | (S)-7-fluoro-6-(1-methyl-5-(trifluoromethyl)-1H-1,2,4-triazol-3-yl)-2-(4-((6-oxo-5-(trifluoromethyl)-1,6-dihydropyridazin-4-yl)amino)pentyl)isoquinolin-1(2H)-one |
| 301 | (S)-6-(4-(difluoromethyl)thiazol-2-yl)-7-fluoro-2-(4-((6-oxo-5-(trifluoromethyl)-1,6-dihydropyridazin-4-yl)amino)pentyl)isoquinolin-1(2H)-one |

-continued

| Example | Name |
|---|---|
| 302 | (S)-6-(5-(aminomethyl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 303 | (S)-6-(4-amino-5-chloropyrimidin-2-yl)-7-fluoro-2-(4-((6-oxo-5-(trifluoromethyl)-1,6-dihydropyridazin-4-yl)amino)hexyl)isoquinolin-1(2H)-one |
| 304 | (S)-7-fluoro-2-(4-((6-oxo-5-(trifluoromethyl)-1,6-dihydropyridazin-4-yl)amino)pentyl)-6-(pyrazolo[1,5-a]pyridin-2-yl)isoquinolin-1(2H)-one |
| 305 | (S)-7-fluoro-6-(imidazo[1,2-a]pyridin-2-yl)-2-(4-((6-oxo-5-(trifluoromethyl)-1,6-dihydropyridazin-4-yl)amino)pentyl)isoquinolin-1(2H)-one |
| 306 | (S)-6-([1,2,4]triazolo[1,5-a]pyridin-2-yl)-7-fluoro-2-(4-((6-oxo-5-(trifluoromethyl)-1,6-dihydropyridazin-4-yl)amino)pentyl)isoquinolin-1(2H)-one |
| 307 | (S)-6-(benzo[d]oxazol-2-yl)-7-fluoro-2-(4-((6-oxo-5-(trifluoromethyl)-1,6-dihydropyridazin-4-yl)amino)pentyl)isoquinolin-1(2H)-one |
| 308 | (S)-6-(benzo[d]thiazol-2-yl)-7-fluoro-2-(4-((6-oxo-5-(trifluoromethyl)-1,6-dihydropyridazin-4-yl)amino)pentyl)isoquinolin-1(2H)-one |
| 309 | (S)-7-fluoro-2-(4-((6-oxo-5-(trifluoromethyl)-1,6-dihydropyridazin-4-yl)amino)pentyl)-6-(5-(trifluoromethyl)thiazol-2-yl)isoquinolin-1(2H)-one |
| 310 | (S)-6-(4-(cyclopropylamino)-6-methylpyrimidin-2-yl)-7-fluoro-2-(4-((6-oxo-5-(trifluoromethyl)-1,6-dihydropyridazin-4-yl)amino)pentyl)isoquinolin-1(2H)-one |
| 311 | 7-fluoro-6-(4-((2S,3R)-3-hydroxy-2-methylazetidin-1-yl)-5-(trifluoromethyl)pyrimidin-2-yl)-2-((S)-4-((6-oxo-5-(trifluoromethyl)-1,6-dihydropyridazin-4-yl)amino)pentyl)isoquinolin-1(2H)-one |
| 312 | 7-fluoro-6-(4-((2S,4S)-4-hydroxy-2-methylpyrrolidin-1-yl)-5-(trifluoromethyl)pyrimidin-2-yl)-2-((S)-4-((6-oxo-5-(trifluoromethyl)-1,6-dihydropyridazin-4-yl)amino)pentyl)isoquinolin-1(2H)-one |
| 313 | 7-fluoro-6-(4-((2S,4R)-4-hydroxy-2-methylpyrrolidin-1-yl)-5-(trifluoromethyl)pyrimidin-2-yl)-2-((S)-4-((6-oxo-5-(trifluoromethyl)-1,6-dihydropyridazin-4-yl)amino)pentyl)isoquinolin-1(2H)-one |
| 314 | 6-fluoro-7-(4-((2S,3R)-3-hydroxy-2-methylazetidin-1-yl)-5-(trifluoromethyl)pyrimidin-2-yl)-3-((S)-4-((6-oxo-5-(trifluoromethyl)-1,6-dihydropyridazin-4-yl)amino)pentyl)quinazolin-4(3H)-one |
| 315 | (S)-6-(4-amino-6-methylpyrimidin-2-yl)-7-fluoro-2-(4-((6-oxo-5-(trifluoromethyl)-1,6-dihydropyridazin-4-yl)amino)pentyl)isoquinolin-1(2H)-one |
| 316 | (S)-6-(6-amino-5-(trifluoromethyl)pyrazin-2-yl)-7-fluoro-2-(4-((6-oxo-5-(trifluoromethyl)-1,6-dihydropyridazin-4-yl)amino)pentyl)isoquinolin-1(2H)-one |
| 317 | (S)-6-(4-(1,1-dioxidothiazolidin-3-yl)-5-(trifluoromethyl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 318 | 6-(4-((2R,4S)-2,4-dimethylazetidin-1-yl)-5-(trifluoromethyl)pyrimidin-2-yl)-7-fluoro-2-((S)-4-((6-oxo-5-(trifluoromethyl)-1,6-dihydropyridazin-4-yl)amino)pentyl)isoquinolin-1(2H)-one |
| 319 | (S)-6-(4-amino-5-chloro-6-methylpyrimidin-2-yl)-7-fluoro-2-(4-((6-oxo-5-(trifluoromethyl)-1,6-dihydropyridazin-4-yl)amino)pentyl)isoquinolin-1(2H)-one |
| 320 | (S)-7-(4-amino-5-(difluoromethyl)pyrimidin-2-yl)-6-fluoro-3-(4-((6-oxo-5-(trifluoromethyl)-1,6-dihydropyridazin-4-yl)amino)hexyl)quinazolin-4(3H)-one |
| 321 | (S)-7-(4-amino-5-(trifluoromethyl)pyrimidin-2-yl)-6-fluoro-3-(4-((6-oxo-5-(trifluoromethyl)-1,6-dihydropyridazin-4-yl)amino)hexyl)quinazolin-4(3H)-one |
| 322 | (S)-7-fluoro-6-(6-fluoroquinazolin-2-yl)-2-(4-((6-oxo-5-(trifluoromethyl)-1,6-dihydropyridazin-4-yl)amino)pentyl)isoquinolin-1(2H)-one |
| 323 | (S)-7-fluoro-2-(4-((6-oxo-5-(trifluoromethyl)-1,6-dihydropyridazin-4-yl)amino)pentyl)-6-(4-(trifluoromethyl)oxazol-2-yl)isoquinolin-1(2H)-one |
| 324 | (S)-6-(6-amino-5-(difluoromethyl)pyrazin-2-yl)-7-fluoro-2-(4-((6-oxo-5-(trifluoromethyl)-1,6-dihydropyridazin-4-yl)amino)pentyl)isoquinolin-1(2H)-one |
| 325 | (S)-6-(4-amino-5-isopropylpyrimidin-2-yl)-7-fluoro-2-(4-((6-oxo-5-(trifluoromethyl)-1,6-dihydropyridazin-4-yl)amino)pentyl)isoquinolin-1(2H)-one |
| 326 | (S)-6-(3-chloro-5-(trifluoromethyl)pyridin-2-yl)-7-fluoro-2-(4-((6-oxo-5-(trifluoromethyl)-1,6-dihydropyridazin-4-yl)amino)pentyl)isoquinolin-1(2H)-one |
| 327 | (S)-6-(4-amino-6-methyl-5-(trifluoromethyl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 328 | (S)-6-(3-amino-5-(trifluoromethyl)pyridin-2-yl)-7-fluoro-2-(4-((6-oxo-5-(trifluoromethyl)-1,6-dihydropyridazin-4-yl)amino)pentyl)isoquinolin-1(2H)-one |
| 329 | (S)-6-(5-(difluoromethyl)pyrazin-2-yl)-7-fluoro-2-(4-((6-oxo-5-(trifluoromethyl)-1,6-dihydropyridazin-4-yl)amino)pentyl)isoquinolin-1(2H)-one |
| 330 | (S)-6-(6-(difluoromethyl)-5-fluoropyridin-2-yl)-7-fluoro-2-(4-((6-oxo-5-(trifluoromethyl)-1,6-dihydropyridazin-4-yl)amino)pentyl)isoquinolin-1(2H)-one |
| 331 | (S)-7-fluoro-6-(4-methoxy-5-(trifluoromethyl)pyridin-2-yl)-2-(4-((6-oxo-5-(trifluoromethyl)-1,6-dihydropyridazin-4-yl)amino)pentyl)isoquinolin-1(2H)-one |
| 332 | (S)-6-(8-aminoimidazo[1,2-a]pyrazin-6-yl)-7-fluoro-2-(4-((6-oxo-5-(trifluoromethyl)-1,6-dihydropyridazin-4-yl)amino)pentyl)isoquinolin-1(2H)-one |
| 333 | (S)-7-fluoro-2-(4-((6-oxo-5-(trifluoromethyl)-1,6-dihydropyridazin-4-yl)amino)pentyl)-6-(thiazolo[5,4-b]pyridin-5-yl)isoquinolin-1(2H)-one |
| 334 | (S)-6-([1,2,4]triazolo[1,5-a]pyrazin-2-yl)-7-fluoro-2-(4-((6-oxo-5-(trifluoromethyl)-1,6-dihydropyridazin-4-yl)amino)pentyl)isoquinolin-1(2H)-one |
| 335 | (S)-7-fluoro-6-(7-fluoro-[1,2,4]triazolo[1,5-a]pyridin-2-yl)-2-(4-((6-oxo-5-(trifluoromethyl)-1,6-dihydropyridazin-4-yl)amino)pentyl)isoquinolin-1(2H)-one |

-continued

| Example | Name |
|---|---|
| 336 | (S)-7-fluoro-6-(5-(2-fluorophenyl)pyrimidin-2-yl)-2-(4-((6-oxo-5-(trifluoromethyl)-1,6-dihydropyridazin-4-yl)amino)pentyl)isoquinolin-1(2H)-one |
| 337 | (S)-7-(6-amino-5-(trifluoromethyl)pyrazin-2-yl)-6-fluoro-3-(4-((6-oxo-5-(trifluoromethyl)-1,6-dihydropyridazin-4-yl)amino)pentyl)quinazolin-4(3H)-one |
| 338 | (S)-7-(5-(difluoromethyl)pyridin-2-yl)-6-fluoro-3-(4-((6-oxo-5-(trifluoromethyl)-1,6-dihydropyridazin-4-yl)amino)hexyl)quinazolin-4(3H)-one |
| 339 | (S)-6-(6-amino-5-(trifluoromethyl)pyrazin-2-yl)-7-fluoro-2-(4-((6-oxo-5-(trifluoromethyl)-1,6-dihydropyridazin-4-yl)amino)hexyl)isoquinolin-1(2H)-one |
| 340 | (S)-7-(5-(difluoromethoxy)pyridin-2-yl)-6-fluoro-3-(4-((6-oxo-5-(trifluoromethyl)-1,6-dihydropyridazin-4-yl)amino)hexyl)quinazolin-4(3H)-one |
| 341 | (S)-6-(4-amino-5-chloropyrimidin-2-yl)-7,8-difluoro-2-(4-((6-oxo-5-(trifluoromethyl)-1,6-dihydropyridazin-4-yl)amino)pentyl)isoquinolin-1(2H)-one |
| 342 | (S)-7-(4-amino-5-chloropyrimidin-2-yl)-6-fluoro-3-(4-((6-oxo-5-(trifluoromethyl)-1,6-dihydropyridazin-4-yl)amino)hexyl)quinazolin-4(3H)-one |
| 343 | (S)-6-(4-amino-5-methoxypyrimidin-2-yl)-7-fluoro-2-(4-((6-oxo-5-(trifluoromethyl)-1,6-dihydropyridazin-4-yl)amino)hexyl)isoquinolin-1(2H)-one |
| 344 | (S)-6-(4-amino-5-(3-fluorooxetan-3-yl)pyrimidin-2-yl)-7-fluoro-2-(4-((6-oxo-5-(trifluoromethyl)-1,6-dihydropyridazin-4-yl)amino)pentyl)isoquinolin-1(2H)-one |
| 345 | (S)-6-(5-(difluoromethyl)pyrimidin-2-yl)-7-fluoro-2-(4-((6-oxo-5-(trifluoromethyl)-1,6-dihydropyridazin-4-yl)amino)hexyl)isoquinolin-1(2H)-one |
| 346 | (S)-7-(5-(difluoromethyl)pyrazin-2-yl)-6-fluoro-3-(4-((6-oxo-5-(trifluoromethyl)-1,6-dihydropyridazin-4-yl)amino)hexyl)quinazolin-4(3H)-one |
| 347 | (S)-7-(6-amino-5-(trifluoromethyl)pyrazin-2-yl)-6-fluoro-3-(4-((6-oxo-5-(trifluoromethyl)-1,6-dihydropyridazin-4-yl)amino)hexyl)quinazolin-4(3H)-one |
| 348 | (S)-6-(4-amino-5-(trifluoromethyl)pyrimidin-2-yl)-7,8-difluoro-2-(4-((6-oxo-5-(trifluoromethyl)-1,6-dihydropyridazin-4-yl)amino)hexyl)isoquinolin-1(2H)-one |
| 349 | (S)-6-(6-amino-5-(trifluoromethyl)pyrazin-2-yl)-7,8-difluoro-2-(4-((6-oxo-5-(trifluoromethyl)-1,6-dihydropyridazin-4-yl)amino)pentyl)isoquinolin-1(2H)-one |
| 350 | (S)-6-(4-amino-5-methoxypyrimidin-2-yl)-7,8-difluoro-2-(4-((6-oxo-5-(trifluoromethyl)-1,6-dihydropyridazin-4-yl)amino)hexyl)isoquinolin-1(2H)-one |
| 351 | (S)-6-(6-amino-5-chloropyrazin-2-yl)-7-fluoro-2-(4-((6-oxo-5-(trifluoromethyl)-1,6-dihydropyridazin-4-yl)amino)pentyl)isoquinolin-1(2H)-one |
| 352 | (S)-7-(6-amino-5-chloropyrazin-2-yl)-6-fluoro-3-(4-((6-oxo-5-(trifluoromethyl)-1,6-dihydropyridazin-4-yl)amino)pentyl)quinazolin-4(3H)-one |
| 353 | (S)-7,8-difluoro-2-(4-((6-oxo-5-(trifluoromethyl)-1,6-dihydropyridazin-4-yl)amino)hexyl)-6-(5-(trifluoromethyl)pyrimidin-2-yl)isoquinolin-1(2H)-one |
| 354 | (S)-4-amino-6’-fluoro-3’-(4-((6-oxo-5-(trifluoromethyl)-1,6-dihydropyridazin-4-yl)amino)pentyl)-[2,7’-biquinazolin]-4’(3’H)-one |
| 355 | (S)-6-(5-(difluoromethyl)pyrimidin-2-yl)-7,8-difluoro-2-(4-((6-oxo-5-(trifluoromethyl)-1,6-dihydropyridazin-4-yl)amino)hexyl)isoquinolin-1(2H)-one |
| 356 | (S)-6-(4-amino-5-(difluoromethyl)pyrimidin-2-yl)-7,8-difluoro-2-(4-((6-oxo-5-(trifluoromethyl)-1,6-dihydropyridazin-4-yl)amino)hexyl)isoquinolin-1(2H)-one |
| 357 | (S)-6-(4-amino-5,7-dihydrofuro[3,4-d]pyrimidin-2-yl)-7-fluoro-2-(4-((6-oxo-5-(trifluoromethyl)-1,6-dihydropyridazin-4-yl)amino)pentyl)isoquinolin-1(2H)-one |
| 358 | (S)-6-(4-amino-7,7-dimethyl-5,7-dihydrofuro[3,4-d]pyrimidin-2-yl)-7-fluoro-2-(4-((6-oxo-5-(trifluoromethyl)-1,6-dihydropyridazin-4-yl)amino)pentyl)isoquinolin-1(2H)-one |
| 359 | (S)-6-(4-amino-5-chloropyrimidin-2-yl)-7,8-difluoro-2-(4-((6-oxo-5-(trifluoromethyl)-1,6-dihydropyridazin-4-yl)amino)hexyl)isoquinolin-1(2H)-one |
| 360 | (S)-6-(4-amino-5-(difluoromethoxy)pyrimidin-2-yl)-7-fluoro-2-(4-((6-oxo-5-(trifluoromethyl)-1,6-dihydropyridazin-4-yl)amino)hexyl)isoquinolin-1(2H)-one |
| 361 | (S)-6-(4-amino-5-(difluoromethoxy)pyrimidin-2-yl)-7,8-difluoro-2-(4-((6-oxo-5-(trifluoromethyl)-1,6-dihydropyridazin-4-yl)amino)hexyl)isoquinolin-1(2H)-one |
| 362 | (S)-6-(6-amino-5-(trifluoromethyl)pyrazin-2-yl)-7,8-difluoro-2-(4-((6-oxo-5-(trifluoromethyl)-1,6-dihydropyridazin-4-yl)amino)hexyl)isoquinolin-1(2H)-one |
| 363 | (S)-6-(4-aminoquinazolin-2-yl)-7-fluoro-2-(4-((6-oxo-5-(trifluoromethyl)-1,6-dihydropyridazin-4-yl)amino)pentyl)isoquinolin-1(2H)-one |
| 364 | (S)-7-(4-amino-5-(difluoromethoxy)pyrimidin-2-yl)-6-fluoro-3-(4-((6-oxo-5-(trifluoromethyl)-1,6-dihydropyridazin-4-yl)amino)hexyl)quinazolin-4(3H)-one |
| 365 | (S)-6-(4-amino-1,3,5-triazin-2-yl)-7-fluoro-2-(4-((6-oxo-5-(trifluoromethyl)-1,6-dihydropyridazin-4-yl)amino)pentyl)isoquinolin-1(2H)-one |
| 366 | (S)-6-(4-amino-6-methyl-1,3,5-triazin-2-yl)-7-fluoro-2-(4-((6-oxo-5-(trifluoromethyl)-1,6-dihydropyridazin-4-yl)amino)pentyl)isoquinolin-1(2H)-one |
| 367 | (S)-7-(4-amino-5-(difluoromethoxy)pyrimidin-2-yl)-6-fluoro-3-(4-((6-oxo-5-(trifluoromethyl)-1,6-dihydropyridazin-4-yl)amino)pentyl)quinazolin-4(3H)-one |
| 368 | (R)-6-(6-amino-5-(difluoromethyl)pyridin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 369 | (R)-6-(4-amino-5-(difluoromethoxy)pyrimidin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 370 | (R)-6-(4-amino-5-methoxypyrimidin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 371 | (R)-2-(5-(difluoromethoxy)-4-((6-oxo-5-(trifluoromethyl)-1,6-dihydropyridazin-4-yl)amino)pentyl)-6-(5-(difluoromethoxy)pyrazin-2-yl)-7-fluoroisoquinolin-1(2H)-one |
| 372 | (R)-3-(5-(difluoromethoxy)-4-((6-oxo-5-(trifluoromethyl)-1,6-dihydropyridazin-4-yl)amino)pentyl)-7-(5-(difluoromethyl)pyrazin-2-yl)-6-fluoroquinazolin-4(3H)-one |
| 373 | (R)-3-(5-(difluoromethoxy)-4-((6-oxo-5-(trifluoromethyl)-1,6-dihydropyridazin-4-yl)amino)pentyl)-7-(5-(difluoromethoxy)pyrazin-2-yl)-6-fluoroquinazolin-4(3H)-one |

-continued

| Example | Name |
|---|---|
| 374 | (R)-7-(4-amino-5-(difluoromethoxy)pyrimidin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 375 | (R)-2-(5-(difluoromethoxy)-4-((6-oxo-5-(trifluoromethyl)-1,6-dihydropyridazin-4-yl)amino)pentyl)-7,8-difluoro-6-(5-(trifluoromethyl)pyrimidin-2-yl)isoquinolin-1(2H)-one |
| 376 | (R)-6-(4-amino-5-(difluoromethyl)pyrimidin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 377 | (R)-2-(5-(difluoromethoxy)-4-((6-oxo-5-(trifluoromethyl)-1,6-dihydropyridazin-4-yl)amino)pentyl)-6-(5-(difluoromethyl)pyrimidin-2-yl)-7-fluoroisoquinolin-1(2H)-one |
| 378 | (R)-6-(4-amino-5-chloropyrimidin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 379 | (R)-6-(4-amino-5-(trifluoromethyl)pyrimidin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 380 | (R)-6-(6-amino-5-(trifluoromethyl)pyridin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 381 | (R)-6-(5-chloropyrimidin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 382 | (R)-3-(5-(difluoromethoxy)-4-((6-oxo-5-(trifluoromethyl)-1,6-dihydropyridazin-4-yl)amino)pentyl)-6-fluoro-7-(5-(trifluoromethyl)pyrimidin-2-yl)quinazolin-4(3H)-one |
| 383 | (R)-7-(4-amino-5-(difluoromethyl)pyrimidin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 384 | (R)-3-(5-(difluoromethoxy)-4-((6-oxo-5-(trifluoromethyl)-1,6-dihydropyridazin-4-yl)amino)pentyl)-7-(5-(difluoromethyl)pyrimidin-2-yl)-6-fluoroquinazolin-4(3H)-one |
| 385 | (R)-7-(4-amino-5-(trifluoromethyl)pyrimidin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 386 | (R)-6-(5-(difluoromethoxy)-4-((6-oxo-5-(trifluoromethyl)-1,6-dihydropyridazin-4-yl)amino)pentyl)-2-(5-(trifluoromethyl)pyridin-2-yl)-1,6-naphthyridin-5(6H)-one |
| 387 | (R)-6-(4-amino-5-(difluoromethyl)pyrimidin-2-yl)-2-(5-(difluoromethoxy)-4-((6-oxo-5-(trifluoromethyl)-1,6-dihydropyridazin-4-yl)amino)pentyl)-7,8-difluoroisoquinolin-1(2H)-one |
| 388 | (R)-2-(5-(difluoromethoxy)-4-((6-oxo-5-(trifluoromethyl)-1,6-dihydropyridazin-4-yl)amino)pentyl)-6-(5-(difluoromethyl)pyrimidin-2-yl)-7,8-difluoroisoquinolin-1(2H)-one |
| 389 | (R)-6-(4-amino-5-(trifluoromethyl)pyrimidin-2-yl)-2-(5-(difluoromethoxy)-4-((6-oxo-5-(trifluoromethyl)-1,6-dihydropyridazin-4-yl)amino)pentyl)-7,8-difluoroisoquinolin-1(2H)-one |
| 390 | (R)-7-(6-amino-5-(trifluoromethyl)pyridin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 391 | (R)-6-(4-amino-5-chloropyrimidin-2-yl)-2-(5-(difluoromethoxy)-4-((6-oxo-5-(trifluoromethyl)-1,6-dihydropyridazin-4-yl)amino)pentyl)-7,8-difluoroisoquinolin-1(2H)-one |
| 392 | (R)-6-(5-chloropyrimidin-2-yl)-2-(5-(difluoromethoxy)-4-((6-oxo-5-(trifluoromethyl)-1,6-dihydropyridazin-4-yl)amino)pentyl)-7,8-difluoroisoquinolin-1(2H)-one |
| 393 | (R)-7-(4-amino-5-methoxypyrimidin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 394 | (R)-7-(5-chloropyrimidin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 395 | (R)-7-(6-amino-5-(difluoromethyl)pyridin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 396 | (R)-2-(5-(difluoromethoxy)-4-((6-oxo-5-(trifluoromethyl)-1,6-dihydropyridazin-4-yl)amino)pentyl)-7-fluoro-6-(5-(trifluoromethyl)thiazol-2-yl)isoquinolin-1(2H)-one |
| 397 | (R)-6-(4-amino-5-(difluoromethoxy)pyrimidin-2-yl)-2-(5-(difluoromethoxy)-4-((6-oxo-5-(trifluoromethyl)-1,6-dihydropyridazin-4-yl)amino)pentyl)-7,8-difluoroisoquinolin-1(2H)-one |
| 398 | (R)-3-(5-(difluoromethoxy)-4-((6-oxo-5-(trifluoromethyl)-1,6-dihydropyridazin-4-yl)amino)pentyl)-7-(3,4-dihydro-2H-pyran-6-yl)-6-fluoroquinazolin-4(3H)-one |
| 399 | (R)-2-(5-(difluoromethoxy)-4-((6-oxo-5-(trifluoromethyl)-1,6-dihydropyridazin-4-yl)amino)pentyl)-7-fluoro-6-(5-(trifluoromethyl)pyridin-2-yl)isoquinolin-1(2H)-one |
| 400 | (R)-6-(5-amino-6-(trifluoromethyl)pyridin-3-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 401 | (R)-2-(5-(difluoromethoxy)-4-((6-oxo-5-(trifluoromethyl)-1,6-dihydropyridazin-4-yl)amino)pentyl)-6-(5-(difluoromethyl)pyridin-2-yl)-7-fluoroisoquinolin-1(2H)-one |
| 402 | (R)-3-(5-(difluoromethoxy)-4-((6-oxo-5-(trifluoromethyl)-1,6-dihydropyridazin-4-yl)amino)pentyl)-7-(5-(difluoromethyl)pyridin-2-yl)-6-fluoroquinazolin-4(3H)-one |
| 403 | (R)-3-(5-(difluoromethoxy)-4-((6-oxo-5-(trifluoromethyl)-1,6-dihydropyridazin-4-yl)amino)pentyl)-6-fluoro-7-(5-(trifluoromethyl)pyridin-2-yl)quinazolin-4(3H)-one |
| 404 | (R)-3-(5-(difluoromethoxy)-4-((6-oxo-5-(trifluoromethyl)-1,6-dihydropyridazin-4-yl)amino)pentyl)-7-(5-(trifluoromethyl)pyridin-2-yl)pyrido[2,3-d]pyrimidin-4(3H)-one |
| 405 | (R)-2-(6-amino-5-(trifluoromethyl)pyridin-2-yl)-6-(5-(difluoromethoxy)-4-((6-oxo-5-(trifluoromethyl)-1,6-dihydropyridazin-4-yl)amino)pentyl)-1,6-naphthyridin-5(6H)-one |
| 406 | (R)-2-(5-(difluoromethoxy)-4-((6-oxo-5-(trifluoromethyl)-1,6-dihydropyridazin-4-yl)amino)pentyl)-6-(5-(difluoromethyl)pyridin-2-yl)-7,8-difluoroisoquinolin-1(2H)-one |
| 407 | (R)-2-(5-(difluoromethoxy)-4-((6-oxo-5-(trifluoromethyl)-1,6-dihydropyridazin-4-yl)amino)pentyl)-7,8-difluoro-6-(5-(trifluoromethyl)pyridin-2-yl)isoquinolin-1(2H)-one |
| 408 | (R)-6-(5-(difluoromethoxy)-4-((6-oxo-5-(trifluoromethyl)-1,6-dihydropyridazin-4-yl)amino)pentyl)-2-(5-(difluoromethyl)pyridin-2-yl)-1,6-naphthyridin-5(6H)-one |
| 409 | (R)-6-(6-amino-5-fluoropyridin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |

-continued

| Example | Name |
|---|---|
| 410 | (R)-6-(6-amino-5-chloropyridin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 411 | (R)-2-amino-6-(2-(5-(difluoromethoxy)-4-((6-oxo-5-(trifluoromethyl)-1,6-dihydropyridazin-4-yl)amino)pentyl)-7-fluoro-1-oxo-1,2-dihydroisoquinolin-6-yl)nicotinonitrile |
| 412 | (R)-6-(6-amino-5-methylpyridin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 413 | (R)-7-(5-cyclopropylpyrazin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 414 | (R)-7-(4-amino-5-chloro-6-cyclopropylpyrimidin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 415 | (R)-6-(6-amino-5-methoxypyrazin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 416 | (R)-6-(6-amino-5-(trifluoromethyl)pyrazin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 417 | (R)-2-(5-(difluoromethoxy)-4-((6-oxo-5-(trifluoromethyl)-1,6-dihydropyridazin-4-yl)amino)pentyl)-7-fluoro-6-(5-(trifluoromethyl)pyrazin-2-yl)isoquinolin-1(2H)-one |
| 418 | (R)-6-(6-amino-5-(trifluoromethyl)pyrazin-2-yl)-2-(5-(difluoromethoxy)-4-((6-oxo-5-(trifluoromethyl)-1,6-dihydropyridazin-4-yl)amino)pentyl)-7,8-difluoroisoquinolin-1(2H)-one |
| 419 | (R)-7-(6-amino-5-(trifluoromethyl)pyrazin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 420 | (R)-3-(5-(difluoromethoxy)-4-((6-oxo-5-(trifluoromethyl)-1,6-dihydropyridazin-4-yl)amino)pentyl)-6-fluoro-7-(5-(trifluoromethyl)pyrazin-2-yl)quinazolin-4(3H)-one |
| 421 | (R)-6-(5-amino-1H-1,2,4-triazol-3-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 422 | (R)-2-(5-(difluoromethoxy)-4-((6-oxo-5-(trifluoromethyl)-1,6-dihydropyridazin-4-yl)amino)pentyl)-7-fluoro-6-(5-morpholinopyrazin-2-yl)isoquinolin-1(2H)-one |
| 423 | (R)-2-(5-(difluoromethoxy)-4-((6-oxo-5-(trifluoromethyl)-1,6-dihydropyridazin-4-yl)amino)pentyl)-7-fluoro-6-(5-(piperazin-1-yl)pyrazin-2-yl)isoquinolin-1(2H)-one |
| 424 | (R)-2-(5-(difluoromethoxy)-4-((6-oxo-5-(trifluoromethyl)-1,6-dihydropyridazin-4-yl)amino)pentyl)-6-(5-(difluoromethyl)pyrazin-2-yl)-7-fluoroisoquinolin-1(2H)-one |
| 425 | (R)-3-(5-(difluoromethoxy)-4-((6-oxo-5-(trifluoromethyl)-1,6-dihydropyridazin-4-yl)amino)pentyl)-7-(3,4-dihydro-2H-pyrido[3,2-b][1,4]oxazin-6-yl)-6-fluoroquinazolin-4(3H)-one |
| 426 | (R)-7-(4-amino-5-chloropyrimidin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 427 | 6-[4-amino-5-(trifluoromethyl)pyrimidin-2-yl]-7-fluoro-2-[(4R)-4-[[6-oxo-5-(trifluoromethyl)-1H-pyridazin-4-yl]amino]-5-(trideuteriomethoxy)pentyl]isoquinolin-1-one |
| 428 | 6-[5-(difluoromethyl)pyrimidin-2-yl]-7-fluoro-2-[(4R)-4-[[6-oxo-5-(trifluoromethyl)-1H-pyridazin-4-yl]amino]-5-(trideuteriomethoxy)pentyl]isoquinolin-1-one |
| 429 | 6-[4-amino-5-(difluoromethyl)pyrimidin-2-yl]-7-fluoro-2-[(4R)-4-[[6-oxo-5-(trifluoromethyl)-1H-pyridazin-4-yl]amino]-5-(trideuteriomethoxy)pentyl]isoquinolin-1-one |
| 430 | 6-fluoro-3-[(4R)-4-[[6-oxo-5-(trifluoromethyl)-1H-pyridazin-4-yl]amino]-5-(trideuteriomethoxy)pentyl]-7-[5-(trifluoromethyl)pyrimidin-2-yl]quinazolin-4-one |
| 431 | 7-[5-(difluoromethyl)pyrimidin-2-yl]-6-fluoro-3-[(4R)-4-[6-oxo-5-(trifluoromethyl)-1H-pyridazin-4-yl]amino]-5-(trideuteriomethoxy)pentyl]quinazolin-4-one |
| 432 | 7-[4-amino-5-(trifluoromethyl)pyrimidin-2-yl]-6-fluoro-3-[(4R)-4-[[6-oxo-5-(trifluoromethyl)-1-(2-trimethylsilylethoxymethyl)pyridazin-4-yl]amino]-5-(trideuteriomethoxy)pentyl]quinazolin-4-one |
| 433 | 7-[4-amino-5-(difluoromethyl)pyrimidin-2-yl]-6-fluoro-3-[(4R)-4-[6-oxo-5-(trifluoromethyl)-1-(2-trimethylsilylethoxymethyl)pyridazin-4-yl]amino]-5-(trideuteriomethoxy)pentyl]quinazolin-4-one |
| 434 | 7-fluoro-2-[(4R)-4-[[6-oxo-5-(trifluoromethyl)-1-(2-trimethylsilylethoxymethyl)pyridazin-4-yl]amino]-5-(trideuteriomethoxy)pentyl]-6-[5-(trifluoromethyl)-2-pyridyl]isoquinolin-1-one |
| 435 | (R)-7-fluoro-2-(4-((6-oxo-5-(trifluoromethyl)-1,6-dihydropyridazin-4-yl)amino)-5-(trifluoromethoxy)pentyl)-6-(5-(trifluoromethyl)pyrimidin-2-yl)isoquinolin-1(2H)-one |
| 436 | 7-fluoro-2-(2-((1S,2S)-2-((6-oxo-5-(trifluoromethyl)-1,6-dihydropyridazin-4-yl)amino)cyclohexyl)ethyl)-6-(5-(trifluoromethyl)pyrimidin-2-yl)isoquinolin-1(2H)-one |
| 437 | 7-fluoro-2-(2-((1S,2S)-2-((6-oxo-5-(trifluoromethyl)-1,6-dihydropyridazin-4-yl)amino)cyclopentyl)ethyl)-6-(5-(trifluoromethyl)pyrimidin-2-yl)isoquinolin-1(2H)-one |
| 438 | 6-(4-amino-5-(trifluoromethyl)pyrimidin-2-yl)-7-fluoro-2-(3-((6-oxo-5-(trifluoromethyl)-1,6-dihydropyridazin-4-yl)amino)benzyl)isoquinolin-1(2H)-one |
| 439 | (R)-2-(5-(difluoromethoxy)-4-((6-oxo-5-(trifluoromethyl)-1,6-dihydropyridazin-4-yl)amino)pentyl)-7-fluoro-6-(5,6,7,8-tetrahydro-[1,2,4]triazolo[1,5-a]pyrazin-2-yl)isoquinolin-1(2H)-one |
| 440 | 7-fluoro-2-(2-((2R,3S)-3-((6-oxo-5-(trifluoromethyl)-1,6-dihydropyridazin-4-yl)amino)pyrrolidin-2-yl)ethyl)-6-(5-(trifluoromethyl)pyrimidin-2-yl)isoquinolin-1(2H)-one |

-continued

| Example | Name |
|---|---|
| 441 | 6-(4-amino-5-(trifluoromethyl)pyrimidin-2-yl)-7-fluoro-2-(2-((3R,4R)-4-((6-oxo-5-(trifluoromethyl)-1,6-dihydropyridazin-4-yl)amino)tetrahydrofuran-3-yl)ethyl)isoquinolin-1(2H)-one |
| 442 | 7-fluoro-2-((3S,4S)-3-hydroxy-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one |
| 443 | 7-fluoro-2-(((1R,3S)-3-((6-oxo-5-(trifluoromethyl)-1,6-dihydropyridazin-4-yl)amino)cyclopentyl)methyl)-6-(5-(trifluoromethyl)pyrimidin-2-yl)isoquinolin-1(2H)-one |
| 444 | 6-(4-amino-5-(trifluoromethyl)pyrimidin-2-yl)-7-fluoro-2-(((1R,3S)-3-((6-oxo-5-(trifluoromethyl)-1,6-dihydropyridazin-4-yl)amino)cyclopentyl)methyl)isoquinolin-1(2H)-one |
| 445 | 7-fluoro-2-((3R,4S)-3-hydroxy-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one |
| 446 | 7-fluoro-2-(((1S,3R)-3-((6-oxo-5-(trifluoromethyl)-1,6-dihydropyridazin-4-yl)amino)cyclopentyl)methyl)-6-(5-(trifluoromethyl)pyrimidin-2-yl)isoquinolin-1(2H)-one |
| 447 | 6-(4-amino-5-(trifluoromethyl)pyrimidin-2-yl)-7-fluoro-2-(((1S,3R)-3-((6-oxo-5-(trifluoromethyl)-1,6-dihydropyridazin-4-yl)amino)cyclopentyl)methyl)isoquinolin-1(2H)-one |
| 448 | 7-(5-chloropyrimidin-2-yl)-6-fluoro-3-(2-((1R,2S)-2-((6-oxo-5-(trifluoromethyl)-1,6-dihydropyridazin-4-yl)amino)cyclopentyl)ethyl)quinazolin-4(3H)-one |
| 449 | 7-(4-amino-5-chloropyrimidin-2-yl)-6-fluoro-3-(2-((1R,2S)-2-((6-oxo-5-(trifluoromethyl)-1,6-dihydropyridazin-4-yl)amino)cyclopentyl)ethyl)quinazolin-4(3H)-one |
| 450 | 7-fluoro-2-(2-((1R,2S)-2-((6-oxo-5-(trifluoromethyl)-1,6-dihydropyridazin-4-yl)amino)cyclohexyl)ethyl)-6-(5-(trifluoromethyl)pyrimidin-2-yl)isoquinolin-1(2H)-one |
| 451 | 6-(4-amino-5-(trifluoromethyl)pyrimidin-2-yl)-7-fluoro-2-(2-((1R,2S)-2-((6-oxo-5-(trifluoromethyl)-1,6-dihydropyridazin-4-yl)amino)cyclohexyl)ethyl)isoquinolin-1(2H)-one |
| 452 | 6-fluoro-3-(2-((1R,2S)-2-((6-oxo-5-(trifluoromethyl)-1,6-dihydropyridazin-4-yl)amino)cyclobutyl)ethyl)-7-(5-(trifluoromethyl)pyrimidin-2-yl)quinazolin-4(3H)-one |
| 453 | (R)-7-fluoro-2-(6,6,6-trifluoro-4-((6-oxo-5-(trifluoromethyl)-1,6-dihydropyridazin-4-yl)amino)hexyl)-6-(5-(trifluoromethyl)pyrimidin-2-yl)isoquinolin-1(2H)-one |
| 454 | 7-fluoro-2-(((1R,3S)-3-((6-oxo-5-(trifluoromethyl)-1,6-dihydropyridazin-4-yl)oxy)cyclohexyl)methyl)-6-(5-(trifluoromethyl)pyrimidin-2-yl)isoquinolin-1(2H)-one |
| 455 | 6-(4-amino-5-(trifluoromethyl)pyrimidin-2-yl)-7-fluoro-2-(((1R,3S)-3-((6-oxo-5-(trifluoromethyl)-1,6-dihydropyridazin-4-yl)oxy)cyclohexyl)methyl)isoquinolin-1(2H)-one |
| 456 | 6-(5-(difluoromethyl)pyrimidin-2-yl)-7-fluoro-2-(((1R,3S)-3-((6-oxo-5-(trifluoromethyl)-1,6-dihydropyridazin-4-yl)oxy)cyclohexyl)methyl)isoquinolin-1(2H)-one |
| 457 | 7-(5-(difluoromethyl)pyrimidin-2-yl)-6-fluoro-3-(((1R,3S)-3-((6-oxo-5-(trifluoromethyl)-1,6-dihydropyridazin-4-yl)oxy)cyclohexyl)methyl)quinazolin-4(3H)-one |
| 458 | 7-(4-bromo-5-(trifluoromethyl)pyrimidin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one |
| 459 | 4-bromo-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 460 | (R)-7-(6-amino-5-(trifluoromethyl)pyrazin-2-yl)-3-(4-cyclopropyl-4-((6-oxo-5-(trifluoromethyl)-1,6-dihydropyridazin-4-yl)amino)butyl)-6-fluoroquinazolin-4(3H)-one |
| 461 | (R)-7-(4-amino-5-chloropyrimidin-2-yl)-3-(4-cyclopropyl-4-((6-oxo-5-(trifluoromethyl)-1,6-dihydropyridazin-4-yl)amino)butyl)-6-fluoroquinazolin-4(3H)-one |
| 462 | (R)-7-(4-amino-5-(difluoromethyl)pyrimidin-2-yl)-3-(4-cyclopropyl-4-((6-oxo-5-(trifluoromethyl)-1,6-dihydropyridazin-4-yl)amino)butyl)-6-fluoroquinazolin-4(3H)-one |
| 463 | 6-fluoro-3-(2-((1R,2S)-2-((6-oxo-5-(trifluoromethyl)-1,6-dihydropyridazin-4-yl)amino)cyclopentyl)ethyl)-7-(5-(trifluoromethyl)pyrimidin-2-yl)quinazolin-4(3H)-one |
| 464 | 7-(4-amino-5-(trifluoromethyl)pyrimidin-2-yl)-6-fluoro-3-(2-((1R,2S)-2-((6-oxo-5-(trifluoromethyl)-1,6-dihydropyridazin-4-yl)amino)cyclopentyl)ethyl)quinazolin-4(3H)-one |
| 465 | 7-(6-amino-5-(trifluoromethyl)pyrazin-2-yl)-6-fluoro-3-(2-((1R,2S)-2-((6-oxo-5-(trifluoromethyl)-1,6-dihydropyridazin-4-yl)amino)cyclopentyl)ethyl)quinazolin-4(3H)-one |
| 466 | (R)-2-(6-(difluoromethoxy)-4-((6-oxo-5-(trifluoromethyl)-1,6-dihydropyridazin-4-yl)amino)hexyl)-7-fluoro-6-(5-(trifluoromethyl)pyrimidin-2-yl)isoquinolin-1(2H)-one |
| 467 | (R)-6-(4-amino-5-(trifluoromethyl)pyrimidin-2-yl)-2-(6-(difluoromethoxy)-4-((6-oxo-5-(trifluoromethyl)-1,6-dihydropyridazin-4-yl)amino)hexyl)-7-fluoroisoquinolin-1(2H)-one |
| 468 | (R)-3-(4-cyclopropyl-4-((6-oxo-5-(trifluoromethyl)-1,6-dihydropyridazin-4-yl)amino)butyl)-7-(5-(difluoromethyl)pyrimidin-2-yl)-6-fluoroquinazolin-4(3H)-one |
| 469 | (R)-7-(4-amino-5-(trifluoromethyl)pyrimidin-2-yl)-3-(4-cyclopropyl-4-((6-oxo-5-(trifluoromethyl)-1,6-dihydropyridazin-4-yl)amino)butyl)-6-fluoroquinazolin-4(3H)-one |
| 470 | (R)-7-(5-chloropyrimidin-2-yl)-3-(4-cyclopropyl-4-((6-oxo-5-(trifluoromethyl)-1,6-dihydropyridazin-4-yl)amino)butyl)-6-fluoroquinazolin-4(3H)-one |
| 471 | (R)-3-(4-cyclopropyl-4-((6-oxo-5-(trifluoromethyl)-1,6-dihydropyridazin-4-yl)amino)butyl)-6-fluoro-7-(5-(trifluoromethyl)pyrimidin-2-yl)quinazolin-4(3H)-one |
| 472 | (R)-7-(4-amino-5-(difluoromethoxy)pyrimidin-2-yl)-3-(4-cyclopropyl-4-((6-oxo-5-(trifluoromethyl)-1,6-dihydropyridazin-4-yl)amino)butyl)-6-fluoroquinazolin-4(3H)-one |
| 473 | (R)-2-(5-(dimethylamino)-4-((6-oxo-5-(trifluoromethyl)-1,6-dihydropyridazin-4-yl)amino)pentyl)-7-fluoro-6-(5-(trifluoromethyl)pyrimidin-2-yl)isoquinolin-1(2H)-one |
| 474 | (R)-7,8-difluoro-2-(4-(5-methyl-1,3,4-oxadiazol-2-yl)-4-((6-oxo-5-(trifluoromethyl)-1,6-dihydropyridazin-4-yl)amino)butyl)-6-(5-(trifluoromethyl)pyrimidin-2-yl)isoquinolin-1(2H)-one |

-continued

| Example | Name |
|---|---|
| 475 | (R)-2-(4-(5-cyclopropyl-1,3,4-oxadiazol-2-yl)-4-((6-oxo-5-(trifluoromethyl)-1,6-dihydropyridazin-4-yl)amino)butyl)-7,8-difluoro-6-(5-(trifluoromethyl)pyrimidin-2-yl)isoquinolin-1(2H)-one |
| 476 | (R)-2-(4-(5-cyclopropyl-1,3,4-oxadiazol-2-yl)-4-((6-oxo-5-(trifluoromethyl)-1,6-dihydropyridazin-4-yl)amino)butyl)-7-fluoro-6-(5-(trifluoromethyl)pyrimidin-2-yl)isoquinolin-1(2H)-one |
| 477 | (R)-2-(4-(5-(difluoromethyl)-1,3,4-oxadiazol-2-yl)-4-((6-oxo-5-(trifluoromethyl)-1,6-dihydropyridazin-4-yl)amino)butyl)-7-fluoro-6-(5-(trifluoromethyl)pyrimidin-2-yl)isoquinolin-1(2H)-one |
| 478 | 7-fluoro-2-((4S)-2-hydroxy-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one |
| 479 | 7-fluoro-2-((2S,4S)-2-hydroxy-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one |
| 480 | 7-fluoro-2-((2R,4S)-2-hydroxy-4-((6-oxo-5-(trifluoromethyl)-1,6-dihydropyridazin-4-yl)amino)pentyl)-6-(5-(trifluoromethyl)pyrimidin-2-yl)isoquinolin-1(2H)-one |
| 481 | 4,7-difluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 482 | 6-(5-(difluoromethyl)pyrimidin-2-yl)-4,7-difluoro-2-(((1R,3S)-3-((6-oxo-5-(trifluoromethyl)-1,6-dihydropyridazin-4-yl)amino)cyclohexyl)methyl)isoquinolin-1(2H)-one |
| 483 | 7-fluoro-1-oxo-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)-1,2-dihydroisoquinoline-4-carbonitrile |
| 484 | 4-chloro-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 485 | 7-fluoro-4-methyl-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 486 | 4-amino-7-fluoro-2-(((1R,3S)-3-((6-oxo-5-(trifluoromethyl)-1,6-dihydropyridazin-4-yl)amino)cyclohexyl)methyl)-6-(5-(trifluoromethyl)pyrimidin-2-yl)isoquinolin-1(2H)-one |
| 487 | 7-([1,2,4]triazolo[1,5-a]pyridin-2-yl)-6-fluoro-3-(((1R,3S)-3-((6-oxo-5-(trifluoromethyl)-1,6-dihydropyridazin-4-yl)amino)cyclohexyl)methyl)quinazolin-4(3H)-one |
| 488 | 6-([1,2,4]triazolo[1,5-a]pyridin-2-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 489 | (R)-6-([1,2,4]triazolo[1,5-a]pyridin-2-yl)-2-(5-(difluoromethoxy)-4-((6-oxo-5-(trifluoromethyl)-1,6-dihydropyridazin-4-yl)amino)pentyl)-7-fluoroisoquinolin-1(2H)-one |
| 490 | (R)-7-([1,2,4]triazolo[1,5-a]pyridin-2-yl)-3-(5-(difluoromethoxy)-4-((6-oxo-5-(trifluoromethyl)-1,6-dihydropyridazin-4-yl)amino)pentyl)-6-fluoroquinazolin-4(3H)-one |
| 491 | 7-fluoro-6-(1-methyl-5-(trifluoromethyl)-1H-pyrazol-3-yl)-2-(((1R,3S)-3-((6-oxo-5-(trifluoromethyl)-1,6-dihydropyridazin-4-yl)amino)cyclohexyl)methyl)isoquinolin-1(2H)-one |
| 492 | 7-fluoro-6-(5-methoxypyrimidin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 493 | 7,8-difluoro-6-(5-methoxypyrimidin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 494 | 7-fluoro-6-(6-fluoro-[1,2,4]triazolo[1,5-a]pyridin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 495 | 7-fluoro-6-(5-(2-hydroxyethoxy)pyrimidin-2-yl)-2-(((1R,3S)-3-((6-oxo-5-(trifluoromethyl)-1,6-dihydropyridazin-4-yl)amino)cyclohexyl)methyl)isoquinolin-1(2H)-one |
| 496 | 6-(7,7-difluoro-6,7-dihydro-5H-cyclopenta[c]pyridin-3-yl)-7-fluoro-2-(((1R,3S)-3-((6-oxo-5-(trifluoromethyl)-1,6-dihydropyridazin-4-yl)amino)cyclohexyl)methyl)isoquinolin-1(2H)-one |
| 497 | 6-fluoro-7-(5-methoxypyrimidin-2-yl)-3-[[(1R,3S)-3-[6-oxo-5-(trifluoromethyl)-1H-pyridazin-4-yl]amino]cyclohexyl]methyl]quinazolin-4-one |
| 498 | 6-fluoro-7-(5-methoxypyrimidin-2-yl)-3-[[(1R,3S)-3-[[6-oxo-5-(trifluoromethyl)-1H-pyridazin-4-yl]amino]cyclohexyl]methyl]quinazolin-4-one |

VIII. Biological Data

Probe Displacement Assay for PARP7 c. Displacement of a biotinylated probe (RBNO11147; Wigle et al., Cell Chemical Biology, 2020, pp. 877-887) from the PARP7 NAD+-binding site was measured in vitro using a Mesoscale Discovery electrochemiluminescent assay. Twenty microliters of the biotinylated probe (78 nM, 2× Kd) in PBS buffer was incubated for 1 hour at room temperature in MSD streptavidin-coated plates (CAT #L21SA). The plates were then washed 3× with PBS and subsequently blocked overnight in PBS buffer containing 1% BSA. The BSA is removed with 3×PBS washes, the remaining PBS is flicked out of the plate, and 10 ml of PARP7 assay buffer (20 mM Hepes pH 7.4, 100 mM NaCl, 0.1% BSA, 1 mM DTT, 0.002% Tween-20) is added to each well of the 384-well MSD plate. Next, 10 ml of 10 nM PARP7 protein incubated for 1 hour at room temperature with a dose response curve of each test compound in a Greiner LDV polypropylene plate (#781201) is added to the MSD plate containing the immobilized probe. The interaction is allowed to reach equilibrium for 1.5 hours, and then 10 ml of SULFO-TAG labeled anti-GST antibody (Cat #R32AA-1) is added to each well and allowed to incubate for an additional 1.5 hours at room temperature. Finally, 10 ml of MSD read buffer T (4×, Cat. #R92C-1) is added to each well using a Bravo liquid handler to prevent air bubbles in the wells, and the plates are subsequently read in an MSD instrument. Light intensity is then measured to quantify the amount of PARP7 bound to the immobilized probe on the plate. Therefore, the ability of a compound to displace the PARP7/probe interaction results in decreased light emission. Control wells containing a DMSO (negative) and 10 mM GS-11154611 (positive) were used to calculate the % inhibition, and the values were then plotted as a function of compound concentration and a 4-parameter fit was applied to derive the $IC_{50}$ values.

Phospho-STAT1 (Tyr701 LANCE Ultra TR-FRET Detection Assay d. LANCE Ultra phospho-STAT1 (Tyr701) kits are designed for the detection of phosphorylated STAT1 in cell lysates using a simple, homogeneous LANCE Ultra sandwich assay (Cat. #TRF4028M). This assay is intended for assessing compound induction of endogenous levels of cellular STAT1 (phosphorylated at Tyr701) in NCI-H1373 cells. The NCI-H1373 cells are cultured in RPMI 1640 media containing 10% heat inactivated FBS, GlutaMAX, 1% Penicillin-Streptomycin. An Echo acoustic liquid handler is used to transfer 60 nanoliters of compound dilutions using the Echo Qualified, 384-well polypropylene microplate clear flat bottom source plates into a Greiner (#781080) cell culture microplate. NCI-H1373 cells are seeded into these compound-spotted culture plates at 30,000 cells/well in a 60 uL volume in growth media. The plates are incubated in a 5% $CO_2$ humidified incubator at 37° C. for 48 hours. The media is removed and the cells are processed according to the manufacturer's suggested protocol. Briefly, 20 mL of supplemented lysis buffer is added to each well and allowed to shake for 1 hour at 400 rpm. Next, 5 ul of remixed antibody solutions (vol/vol) prepared in detection buffer are added to each well and allowed to incubate at room temperature overnight. After spinning the plate down at 300 rpm for 1 min, the plate is read on an EnVision plate reader set up for Eu3+ Cryptate and fluorescence emission is measured at two different wavelengths (665 nm and 620 nm). The HTRF ratio is then calculated (665 nM/620 nM) for each well to determine the amount of pSTAT1 in the cell lysate, and the data is then normalized to 10 uM GS-1154611 positive and DMSO negative controls. The values were then plotted as a function of compound concentration and a 4-parameter fit was applied to derive the $EC_{50}$ values.

VIII. Biological Data

| Example | MSD ProbeDisp PARP7 $IC_{50}$ (nM) | NH1373 pSTAT1 $EC_{50}$ (nM) |
|---|---|---|
| 1 | 0.5 | 97.808 |
| 2 | 33 | 10000 |
| 3 | 0.3 | 107.6 |
| 4 | 0.2 | 95.638 |
| 5 | 0.3 | 142.67 |
| 6 | 0.7 | 433.96 |
| 7 | 0.3 | 61.263 |
| 8 | 0.2 | 19.241 |
| 9 | 0.4 | 92.097 |
| 10 | 0.7 | 290.74 |
| 11 | 0.2 | 32.387 |
| 12 | 23 | 10000 |
| 13 | 3.7 | 10000 |
| 14 | 0.5 | 94.346 |
| 15 | 0.3 | 575.88 |
| 16 | 0.2 | 25.17 |
| 17 | 0.4 | 117.3 |
| 18 | 0.4 | 163.9 |
| 19 | 0.3 | 74.093 |
| 20 | 0.3 | 14.632 |
| 21 | 0.3 | 136.01 |
| 22 | 0.4 | 71.264 |
| 23 | 0.4 | 2299.9 |

-continued

VIII. Biological Data

| Example | MSD ProbeDisp PARP7 $IC_{50}$ (nM) | NH1373 pSTAT1 $EC_{50}$ (nM) |
|---|---|---|
| 24 | 0.9 | 219.67 |
| 25 | 0.6 | 135.85 |
| 26 | 0.4 | 10000 |
| 27 | 25 | 10000 |
| 28 | >33 | 2182.3 |
| 29 | 1.6 | 31.62 |
| 30 | 0.3 | 18.604 |
| 31 | 0.2 | 2177.8 |
| 32 | 2.6 | 187.39 |
| 33 | 0.5 | 168.22 |
| 34 | 0.6 | 429.41 |
| 35 | 0.5 | 436.06 |
| 36 | 0.7 | 74.083 |
| 37 | 0.4 | 42.73 |
| 38 | 0.3 | 579.38 |
| 39 | 2.5 | 890.3 |
| 40 | 2.7 | 10000 |
| 41 | 3.7 | 143.9 |
| 42 | 1.0 | 132.52 |
| 43 | 0.76 | 311.2 |
| 44 | 0.67 | 10000 |
| 45 | 1.194 | 616.54 |
| 46 | 0.824 | 431.87 |
| 47 | 1.273 | 10000 |
| 48 | 0.897 | 337.57 |
| 49 | 0.413 | 54.056 |
| 50 | 2.134 | 2764.3 |
| 51 | 0.75 | 44.91 |
| 52 | 0.763 | 164.38 |
| 53 | 0.496 | 17.041 |
| 54 | 0.685 | 155.79 |
| 55 | 0.692 | 39.103 |
| 56 | 0.579 | 67.153 |
| 57 | 0.613 | 143.68 |
| 58 | 0.484 | 123.9 |
| 59 | 0.82 | 386.2 |
| 60 | 0.897 | 771.89 |
| 61 | 1.267 | 638.31 |
| 62 | | 31.341 |
| 63 | | 7.148 |
| 64 | | 37.324 |
| 65 | | 29.163 |
| 66 | | 71.498 |
| 67 | | 218.28 |
| 68 | | 10000 |
| 69 | | 147.87 |
| 70 | | 22.068 |
| 71 | | 5.94 |
| 72 | | 5.846 |
| 73 | | 733.62 |
| 74 | | 65.288 |
| 75 | | 54.217 |
| 76 | 0.41 | 21.259 |
| 77 | | 13.512 |
| 78 | | 316.55 |
| 79 | | 1504.3 |
| 80 | | 478.89 |
| 81 | | 4.257 |
| 82 | | 63.362 |
| 83 | | 58.169 |
| 84 | | 263.02 |
| 85 | | 112.86 |
| 86 | | 9.215 |
| 87 | | 10000 |
| 88 | | 86.195 |
| 89 | | 40.5 |
| 90 | | 52.02 |
| 91 | | 290.1 |
| 92 | | 11.055 |
| 93 | | 45.934 |
| 94 | | 22.811 |
| 95 | | 97.052 |
| 96 | | 557.64 |
| 97 | | 67.275 |

-continued

VIII. Biological Data

| Example | MSD ProbeDisp PARP7 $IC_{50}$ (nM) | NH1373 pSTAT1 $EC_{50}$ (nM) |
|---|---|---|
| 98 | | 9.667 |
| 99 | | 1276 |
| 100 | | 4.352 |
| 101 | | 12.633 |
| 102 | | 8.233 |
| 103 | | 39.788 |
| 104 | 0.33 | 4.596 |
| 105 | | 464.8 |
| 106 | | 2.31 |
| 107 | | 2.216 |
| 108 | | 29.386 |
| 109 | | 8.594 |
| 110 | | 13.443 |
| 111 | | 6.672 |
| 112 | | 2.074 |
| 113 | | 6.93 |
| 114 | | 852.46 |
| 115 | | 3.419 |
| 116 | | 6.696 |
| 117 | | 5.206 |
| 118 | | 9.836 |
| 119 | | 3.356 |
| 120 | | 9.727 |
| 121 | | 5.156 |
| 122 | | 8.042 |
| 123 | | 6.29 |
| 124 | | 11.415 |
| 125 | | 84.79 |
| 126 | | 1285.5 |
| 127 | | 474.23 |
| 128 | | 16.726 |
| 129 | | 77.781 |
| 130 | | 1467.3 |
| 131 | | 158.31 |
| 132 | | 3.469 |
| 133 | | 2.835 |
| 134 | | 5.191 |
| 135 | | 17.706 |
| 136 | | 75.94 |
| 137 | | 50.554 |
| 138 | | 55.533 |
| 139 | | 64.841 |
| 140 | | 585.41 |
| 141 | | 16.233 |
| 142 | | 38.626 |
| 143 | | 26.535 |
| 144 | | 3.547 |
| 145 | | 14.126 |
| 146 | | 14.549 |
| 147 | | 39.139 |
| 148 | | 398.86 |
| 149 | | 3.981 |
| 150 | | 19.099 |
| 151 | | 58.698 |
| 152 | | 0.508 |
| 153 | | 10.926 |
| 154 | | 115.34 |
| 155 | 0.2 | 21.228 |
| 156 | 0.29 | 22.112 |
| 157 | | 22.701 |
| 158 | | 109.34 |
| 159 | | 282.62 |
| 160 | | 218.76 |
| 161 | | 28.661 |
| 162 | | 662.32 |
| 163 | 0.341 | 62.773 |
| 164 | | 219.07 |
| 165 | | 159.27 |
| 166 | | 128.24 |
| 167 | | 103.16 |
| 168 | 0.256 | 1.316 |
| 169 | | 61.909 |
| 170 | | 195.3 |
| 171 | | 257.15 |
| 172 | | 1010.1 |
| 173 | | 269.5 |
| 174 | | 286.55 |
| 175 | | 57.544 |
| 176 | | 185.65 |
| 177 | | 537.12 |
| 178 | | 1.8 |
| 179 | | 4.032 |
| 180 | | 1.893 |
| 181 | | 14.228 |
| 182 | | 82.484 |
| 183 | | 6.393 |
| 184 | 0.311 | 1.803 |
| 185 | 0.11 | 1753.6 |
| 186 | | 66.081 |
| 187 | | 20.692 |
| 188 | | 41.951 |
| 189 | | 14.658 |
| 190 | | 29.879 |
| 191 | | 26.947 |
| 192 | | 2.238 |
| 193 | | 22.286 |
| 194 | | 6.604 |
| 195 | | 8.145 |
| 196 | | 6.133 |
| 197 | | 638.14 |
| 198 | | 276.21 |
| 199 | | 316.89 |
| 200 | | 29.138 |
| 201 | | 4.03 |
| 202 | | 1.845 |
| 203 | 0.188 | 11.045 |
| 204 | | 45.121 |
| 205 | | 75.812 |
| 206 | 0.188 | 9.337 |
| 207 | | 157.05 |
| 208 | | 206.04 |
| 209 | | 41.225 |
| 210 | | 132.03 |
| 211 | | 28.251 |
| 212 | | 36.63 |
| 213 | | 11.481 |
| 214 | | 17.871 |
| 215 | | 36.146 |
| 216 | | 39.276 |
| 217 | | 1578.4 |
| 218 | | 1101.4 |
| 219 | | 430.41 |
| 220 | | 194.74 |
| 221 | | 15.255 |
| 222 | | 257.58 |
| 223 | | 33.281 |
| 224 | | 6.144 |
| 225 | | 957.03 |
| 226 | | 5.344 |
| 227 | | 15.689 |
| 228 | | 10000 |
| 229 | | 72.525 |
| 230 | | 115.02 |
| 231 | | 5.925 |
| 232 | | 1.67 |
| 233 | | 1.954 |
| 234 | | 1.554 |
| 235 | | 4.38 |
| 236 | | 32.188 |
| 237 | | 10000 |
| 238 | | 10000 |
| 239 | | 5.367 |
| 240 | | 4.346 |
| 241 | | 6.38 |
| 242 | | 9.438 |
| 243 | | 2.981 |
| 244 | | 5.193 |
| 245 | | 8.132 |

-continued

VIII. Biological Data

| Example | MSD ProbeDisp PARP7 $IC_{50}$ (nM) | NH1373 pSTAT1 $EC_{50}$ (nM) |
|---|---|---|
| 246 | | 3.782 |
| 247 | | 8.797 |
| 248 | | 3.435 |
| 249 | | 32.425 |
| 250 | | 4.712 |
| 251 | | 47.341 |
| 252 | | 16.181 |
| 253 | | 9.413 |
| 254 | | 31.873 |
| 255 | | 9.1 |
| 256 | | 30.185 |
| 257 | | 25.134 |
| 258 | | 31.684 |
| 259 | | 183.4 |
| 260 | | 12.665 |
| 261 | | 6.098 |
| 262 | | 192.9 |
| 263 | | 121.99 |
| 264 | | 76.127 |
| 265 | | 52.257 |
| 266 | | 186.85 |
| 267 | | 80.238 |
| 268 | | 12.996 |
| 269 | | 54.288 |
| 270 | | 148.82 |
| 271 | | 211.39 |
| 272 | | 10000 |
| 273 | | 10000 |
| 274 | | 78.027 |
| 275 | | 200.21 |
| 276 | | 10.26 |
| 277 | | 347.7 |
| 278 | | 4.38 |
| 279 | | 15.5 |
| 280 | | 34.84 |
| 281 | | 2.87 |
| 282 | | 80.1 |
| 283 | | 112.58 |
| 284 | | 51.69 |
| 285 | | 78.71 |
| 286 | | 61.871 |
| 287 | | 136.96 |
| 288 | | 10.478 |
| 289 | | 108.17 |
| 290 | | 21.286 |
| 291 | | 708.74 |
| 292 | | 16.024 |
| 293 | | 5.281 |
| 294 | | 28.789 |
| 295 | | 2018.6 |
| 296 | | 1462.8 |
| 297 | | 3.709 |
| 298 | | 31.961 |
| 299 | 0.221 | 30.958 |
| 300 | 0.413 | 56.051 |
| 301 | 0.508 | 549.48 |
| 302 | 2.062 | 108.41 |
| 303 | 0.273 | 3.428 |
| 304 | 0.199 | 25.591 |
| 305 | 0.387 | 57.044 |
| 306 | 0.21 | 2.178 |
| 307 | 0.352 | 11.176 |
| 308 | 0.387 | 35.778 |
| 309 | 0.258 | 149.03 |
| 310 | 1.302 | 910.02 |
| 311 | 0.258 | 14.042 |
| 312 | 0.623 | 70.035 |
| 313 | 0.192 | 18.4 |
| 314 | 0.185 | 6.078 |
| 315 | | 560.95 |
| 316 | | 15.544 |
| 317 | | 45.078 |
| 318 | | 28.646 |
| 319 | | 2.923 |
| 320 | | 31.246 |
| 321 | | 4.108 |
| 322 | | 5.638 |
| 323 | | 259.78 |
| 324 | | 4.647 |
| 325 | | 10.62 |
| 326 | | 113.33 |
| 327 | | 3.049 |
| 328 | | 78.625 |
| 329 | | 97.709 |
| 330 | | 1210.6 |
| 331 | | 78.121 |
| 332 | | 8.921 |
| 333 | | 502.85 |
| 334 | | 24.137 |
| 335 | | 5.574 |
| 336 | | 95.1 |
| 337 | | 36.579 |
| 338 | | 218.18 |
| 339 | | 17.437 |
| 340 | | 97.147 |
| 341 | | 1.953 |
| 342 | | 9.844 |
| 343 | | 3.556 |
| 344 | | 28.195 |
| 345 | | 6.706 |
| 346 | | 187.37 |
| 347 | | 93.362 |
| 348 | | 6.471 |
| 349 | | 11.778 |
| 350 | | 15.127 |
| 351 | | 8.386 |
| 352 | | 64.416 |
| 353 | | 16.106 |
| 354 | | 65.059 |
| 355 | | 11.422 |
| 356 | | 4.9 |
| 357 | | 142.75 |
| 358 | | 1327.7 |
| 359 | | 1.152 |
| 360 | | 12.72 |
| 361 | | 10.851 |
| 362 | | 15.741 |
| 363 | | 3.283 |
| 364 | | 96.367 |
| 365 | | 55.81 |
| 366 | | 92.522 |
| 367 | | 51.141 |
| 368 | | |
| 369 | | 7.351 |
| 370 | | 8.329 |
| 371 | | 6.776 |
| 372 | | 7.131 |
| 373 | | 16.587 |
| 374 | | 44.817 |
| 375 | | 3.839 |
| 376 | 0.339 | 3.033 |
| 377 | 0.179 | 1.146 |
| 378 | 0.255 | 2.446 |
| 379 | 0.14 | 2.429 |
| 380 | 0.211 | 4.878 |
| 381 | 0.28 | 0.885 |
| 382 | | 2.173 |
| 383 | | 18.537 |
| 384 | | 2.409 |
| 385 | | 13.336 |
| 386 | | 2.956 |
| 387 | | 10.379 |
| 388 | | 2.736 |
| 389 | | 5.137 |
| 390 | | 11.679 |
| 391 | | 6.298 |
| 392 | | 1.501 |
| 393 | | 22.741 |

-continued

| VIII. Biological Data | | |
|---|---|---|
| Example | MSD ProbeDisp PARP7 $IC_{50}$ (nM) | NH1373 pSTAT1 $EC_{50}$ (nM) |
| 394 | | 1.219 |
| 395 | | 30.386 |
| 396 | | 48.788 |
| 397 | | 10.078 |
| 398 | | 423.69 |
| 399 | | 2.98 |
| 400 | | 56.807 |
| 401 | | 1.628 |
| 402 | | 3.131 |
| 403 | | 3.654 |
| 404 | | 1.569 |
| 405 | | 9.67 |
| 406 | | 1.72 |
| 407 | | 1.99 |
| 408 | | 4.11 |
| 409 | | 4.49 |
| 410 | | 0.99 |
| 411 | | 5.28 |
| 412 | | 17.39 |
| 413 | | 4.593 |
| 414 | | 10.88 |
| 415 | | 2.486 |
| 416 | | 6.777 |
| 417 | | 2.281 |
| 418 | | 4.584 |
| 419 | | 14.235 |
| 420 | | 9.408 |
| 421 | | 110.36 |
| 422 | | 87.89 |
| 423 | | 445.63 |
| 424 | | 3.114 |
| 425 | | 9.83 |
| 426 | | 14.177 |
| 427 | | 2.865 |
| 428 | | 4.167 |
| 429 | | 7.212 |
| 430 | | 2.63 |
| 431 | | 6.416 |
| 432 | | 12.703 |
| 433 | | 15.638 |
| 434 | | 12.96 |
| 435 | | 2.831 |
| 436 | | 442.69 |
| 437 | | 101.72 |
| 438 | | 23.139 |
| 439 | | 533.93 |
| 440 | | 1745.8 |
| 441 | | 387.83 |
| 442 | | 1850.7 |
| 443 | | 272.82 |
| 444 | | 25.099 |
| 445 | | 18.481 |
| 446 | | 269.88 |
| 447 | | 25.631 |
| 448 | | 6.82 |
| 449 | | 6.42 |
| 450 | | 11.4 |
| 451 | | 4.757 |
| 452 | | 35.916 |
| 453 | | 215.15 |
| 454 | | 7.482 |
| 455 | | 38.21 |
| 456 | | 48.03 |
| 457 | | 10.6 |
| 458 | | 2943.8 |
| 459 | | 12.187 |
| 460 | | 69.872 |
| 461 | | 15.1 |
| 462 | | 27.556 |
| 463 | | 9.475 |
| 464 | | 3.624 |
| 465 | | 18.037 |
| 466 | | 6.521 |
| 467 | | 4.129 |
| 468 | | 42.525 |
| 469 | | 14.52 |
| 470 | | 39.303 |
| 471 | | 23.201 |
| 472 | | 51.605 |
| 473 | | 969.32 |
| 474 | | 14.772 |
| 475 | | 10.626 |
| 476 | | 20.27 |
| 477 | | 18.429 |
| 478 | | 5.25 |
| 479 | | 82.83 |
| 480 | | 4.14 |
| 481 | | 3.243 |
| 482 | | 1.939 |
| 483 | | 4.71 |
| 484 | | |
| 485 | | 5.459 |
| 486 | | 95.805 |
| 487 | | 0.51 |
| 488 | | 0.51 |
| 489 | | 0.51 |
| 490 | | 1.00 |
| 491 | | 50.5 |
| 492 | | 7 |
| 493 | | |
| 494 | | |
| 495 | | 29 |
| 496 | | 5.5 |
| 497 | | |
| 498 | | |

What is claimed is:

1. A compound, or a pharmaceutically acceptable salt, stereoisomer, mixture of stereoisomers, or deuterated analog thereof, which is:

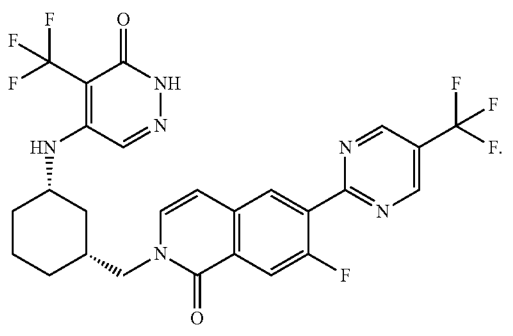 [SMILES: O=c1[nH]ncc(N[C@H]2CCC[C@@H](Cn3ccc4cc(-c5ncc(C(F)(F)F)cn5)c(F)cc4c3=O)C2)c1C(F)(F)F]

2. A compound, or a pharmaceutically acceptable salt, stereoisomer, mixture of stereoisomers, or deuterated analog thereof, which is:

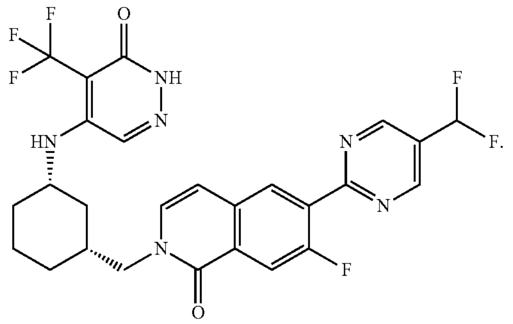 [SMILES: O=c1[nH]ncc(N[C@H]2CCC[C@@H](Cn3ccc4cc(-c5ncc(C(F)F)cn5)c(F)cc4c3=O)C2)c1C(F)(F)F]

3. A compound, or a pharmaceutically acceptable salt, stereoisomer, mixture of stereoisomers, or deuterated analog thereof, which is:

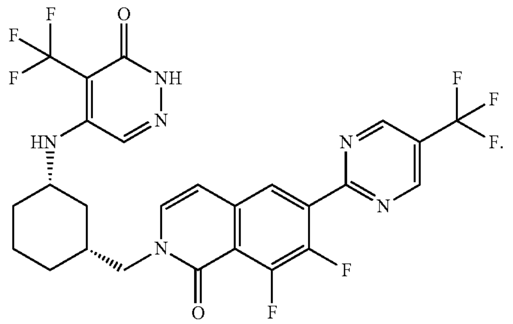 [SMILES: O=c1[nH]ncc(N[C@H]2CCC[C@@H](Cn3ccc4cc(-c5ncc(C(F)(F)F)cn5)c(F)c(F)c4c3=O)C2)c1C(F)(F)F]

4. A compound, or a pharmaceutically acceptable salt, stereoisomer, mixture of stereoisomers, or deuterated analog thereof, which is:

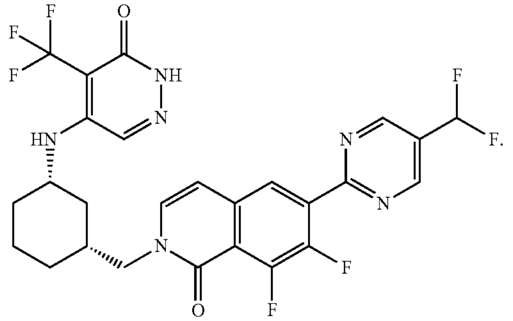 [SMILES: O=c1[nH]ncc(N[C@H]2CCC[C@@H](Cn3ccc4cc(-c5ncc(C(F)F)cn5)c(F)c(F)c4c3=O)C2)c1C(F)(F)F]

5. A compound, or a pharmaceutically acceptable salt, stereoisomer, mixture of stereoisomers, or deuterated analog thereof, which is:

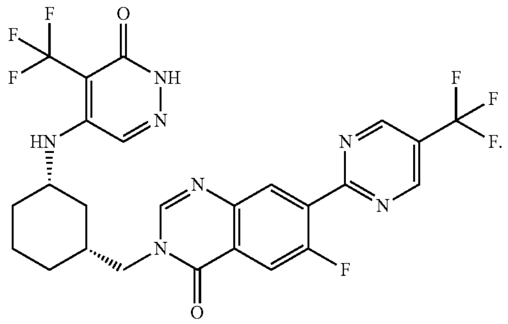 [SMILES: O=c1[nH]ncc(N[C@H]2CCC[C@@H](Cn3cnc4cc(-c5ncc(C(F)(F)F)cn5)c(F)cc4c3=O)C2)c1C(F)(F)F]

6. A compound, or a pharmaceutically acceptable salt, stereoisomer, mixture of stereoisomers, or deuterated analog thereof, which is:

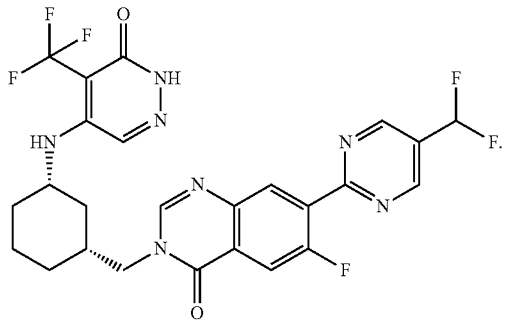 [SMILES: O=c1[nH]ncc(N[C@H]2CCC[C@@H](Cn3cnc4cc(-c5ncc(C(F)F)cn5)c(F)cc4c3=O)C2)c1C(F)(F)F]

7. A compound, or a pharmaceutically acceptable salt, stereoisomer, mixture of stereoisomers, or deuterated analog thereof, which is:

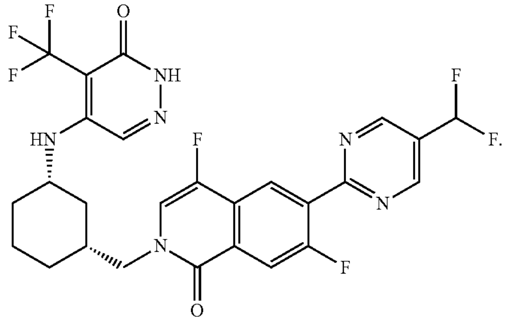 [SMILES: O=c1[nH]ncc(N[C@H]2CCC[C@@H](Cn3cc(F)c4cc(-c5ncc(C(F)F)cn5)c(F)cc4c3=O)C2)c1C(F)(F)F]

8. A compound, or a pharmaceutically acceptable salt, stereoisomer, mixture of stereoisomers, or deuterated analog thereof, which is:

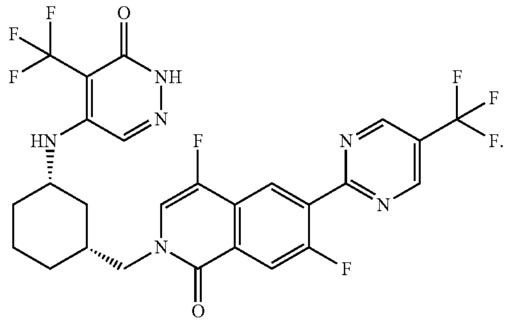 [SMILES: O=c1[nH]ncc(N[C@H]2CCC[C@@H](Cn3cc(F)c4cc(-c5ncc(C(F)(F)F)cn5)c(F)cc4c3=O)C2)c1C(F)(F)F]

9. A compound, or a pharmaceutically acceptable salt, stereoisomer, mixture of stereoisomers, or deuterated analog thereof, which is:

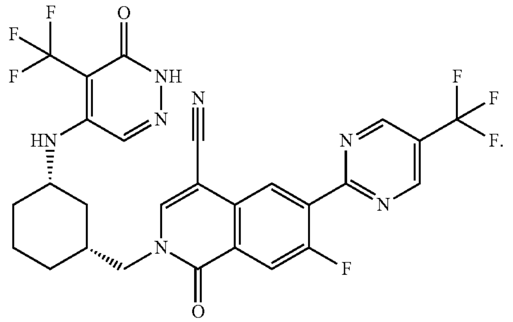 [SMILES: N#Cc1cn(C[C@@H]2CCC[C@H](Nc3cn[nH]c(=O)c3C(F)(F)F)C2)c(=O)c2cc(F)c(-c3ncc(C(F)(F)F)cn3)cc12]

10. A compound, or a pharmaceutically acceptable salt, stereoisomer, mixture of stereoisomers, or deuterated analog thereof, which is:

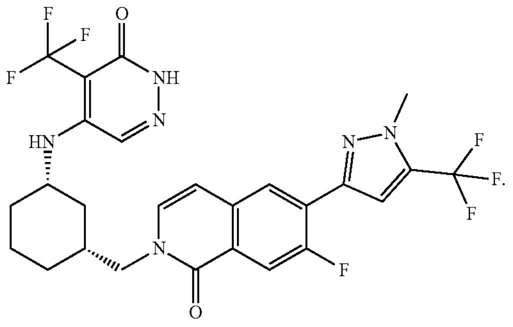 [SMILES: Cn1nc(-c2cc3ccn(C[C@@H]4CCC[C@H](Nc5cn[nH]c(=O)c5C(F)(F)F)C4)c(=O)c3cc2F)cc1C(F)(F)F]

11. A compound, or a pharmaceutically acceptable salt, stereoisomer, mixture of stereoisomers, or deuterated analog thereof, which is:

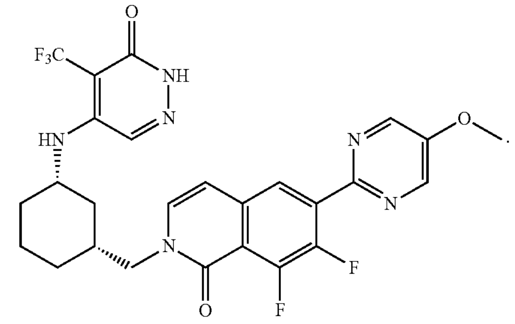 [SMILES: COc1cnc(-c2cc3ccn(C[C@@H]4CCC[C@H](Nc5cn[nH]c(=O)c5C(F)(F)F)C4)c(=O)c3c(F)c2F)nc1]

12. A compound, or a pharmaceutically acceptable salt, stereoisomer, mixture of stereoisomers, or deuterated analog thereof, which is:

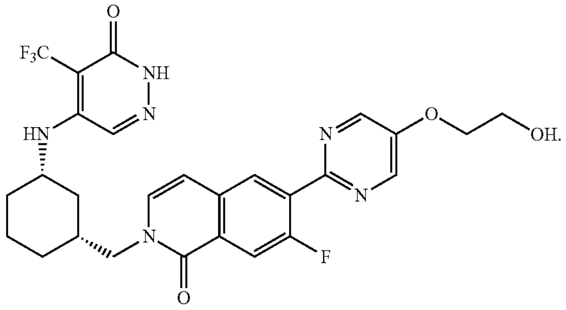 [SMILES: O=c1[nH]ncc(N[C@H]2CCC[C@@H](Cn3ccc4cc(-c5ncc(OCCO)cn5)c(F)cc4c3=O)C2)c1C(F)(F)F]

13. A compound, or a pharmaceutically acceptable salt, stereoisomer, mixture of stereoisomers, or deuterated analog thereof, which is:

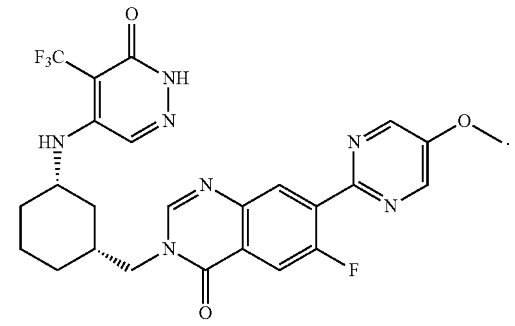 [SMILES: COc1cnc(-c2cc3ncn(C[C@@H]4CCC[C@H](Nc5cn[nH]c(=O)c5C(F)(F)F)C4)c(=O)c3cc2F)nc1]

14. A pharmaceutical composition comprising a compound of any of claims 1-6, 7-10, 11, 12, or 13, or a pharmaceutically acceptable salt, stereoisomer, mixture of stereoisomers, or deuterated analog thereof, and a pharmaceutically acceptable excipient.

15. A compound of any of claims 1-6, 7-10, 11, 12, or 13, or a pharmaceutically acceptable salt, stereoisomer, or mixture of stereoisomers thereof.

16. A pharmaceutical composition comprising a compound of any of claims 1-6, 7-10, 11, 12, or 13, or a pharmaceutically acceptable salt, stereoisomer, or mixture of stereoisomers thereof.

* * * * *